United States Patent
Baxter et al.

(10) Patent No.: US 11,555,040 B2
(45) Date of Patent: Jan. 17, 2023

(54) OXEPINOPYRAZOLE DERIVATIVES AS INHIBITORS OF PI3-KINASE ACTIVITY

(71) Applicant: GLAXOSMITHKLINE INTELLECTUAL PROPERTY DEVELOPMENT LIMITED, Brentford (GB)

(72) Inventors: Andrew Baxter, Stevenage (GB); Sophie Marie Bertrand, Stevenage (GB); Matthew Campbell, Stevenage (GB); Kenneth David Down, Stevenage (GB); Curt Dale Haffner, Collegeville, PA (US); Julie Nicole Hamblin, Stevenage (GB); Zoe Alicia Henley, Stevenage (GB); William Henry Miller, Little Chesterford (GB); Eric Philippe Andre Talbot, Stevenage (GB); Jonathan Andrew Taylor, Stevenage (GB)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 696 days.

(21) Appl. No.: 16/604,605

(22) PCT Filed: Apr. 16, 2018

(86) PCT No.: PCT/EP2018/059612
§ 371 (c)(1),
(2) Date: Oct. 11, 2019

(87) PCT Pub. No.: WO2018/192864
PCT Pub. Date: Oct. 25, 2018

(65) Prior Publication Data
US 2022/0324875 A1     Oct. 13, 2022

(30) Foreign Application Priority Data
Apr. 18, 2017 (GB) .................... 1706102

(51) Int. Cl.
*C07D 491/044* (2006.01)

(52) U.S. Cl.
CPC ................ *C07D 491/044* (2013.01)

(58) Field of Classification Search
CPC .................................. C07D 491/044
See application file for complete search history.

(56) References Cited

FOREIGN PATENT DOCUMENTS

| WO | 2014/023258 A1 | 2/2014 |
| WO | 2017/004500 A1 | 1/2017 |

OTHER PUBLICATIONS

Heffron, T.P. et al., "Rational Design of Phosphoinositide 3-Kinase alpha Inhibitors That Exhibit Selectivity over the Phosphoinositide 3-Kinase beta Isoform" Journal of Medicinal Chemistry; 2011; pp. 7815-7833; vol. 54 (22).

Ndubaku, C.O. et al., "Discovery of 2-{3-[2-(1-Isopropyl-3-methyl-1 H-1,2-4-triazol-5-yl) -5,6-dihydrobenzo[f] imidazo [1,2-d][1,4] oxazepin-9-yl]-1H-pyrazol-1-yl}-2-methylpropanamide {GDC-0032}: A beta-Sparing PHosphoinositide 3-Kinase Inhibitor with High Unbound Exposure and Robust in Vivo Antitumor Activity" Journal of Medicinal Chemistry; 2013; pp. 4597-4610; vol. 56 (11).

*Primary Examiner* — Laura L Stockton
(74) *Attorney, Agent, or Firm* — Robert J. Smith

(57) ABSTRACT

The invention is directed to compounds of formula (I), and salts thereof. The compounds are inhibitors of kinase activity, in particular PI3-kinase activity.

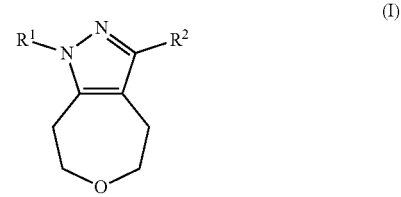

13 Claims, No Drawings

OXEPINOPYRAZOLE DERIVATIVES AS INHIBITORS OF PI3-KINASE ACTIVITY

CROSS-REFERENCE TO RELATED APPLICATIONS

This is the U.S. National Stage application submitted under 35 U.S.C. § 371 for International Application No. PCT/EP2018/059612, filed Apr. 16, 2018, which claims priority to Application No. GB 1706102.9, filed Apr. 18, 2017.

FIELD OF THE INVENTION

The present invention is directed to compounds which are inhibitors of kinase activity, pharmaceutical compositions comprising the compounds, and the use of the compounds or the compositions in the treatment of various disorders. More specifically, the compounds of the invention are inhibitors of the activity or function of the phosphoinositide 3'OH kinase family (hereinafter PI3-kinases), for example PI3K δ, PI3K α, PI3K β and/or PI3K γ.

BACKGROUND OF THE INVENTION

Cellular membranes represent a large store of second messengers that can be enlisted in a variety of signal transduction pathways. In relation to function and regulation of effector enzymes in phospholipids signalling pathways, class I PI3-kinases (e.g. PI3Kdelta) generate second messengers from the membrane phospholipid pools. Class I PI3Ks convert the membrane phospholipid PI(4,5)P2 into PI(3,4,5)P3, which functions as a second messenger. PI and PI(4)P are also substrates of PI3K and can be phosphorylated and converted into PI3P and PI(3,4)P2, respectively. In addition, these phosphoinositides can be converted into other phosphoinositides by 5'-specific and 3'-specific phosphatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate (PI(4,5)P2) to produce phosphatidylinositol-3-phosphate (PI3P), phosphatidylinositol-3,4-bisphosphate (PI(3,4)P2, and phosphatidylinositol-3,4,5-trisphosphate (PI(3,4,5)P3, respectively. Class II PI3Ks can phosphorylate PI and PI4P. Class III PI3Ks can only phosphorylate PI (Vanhaesebroeck et al. (1997), above; Vanhaesebroeck et al. Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of $PI(4,5)P_2$ to $PI(3,4,5)P_3$

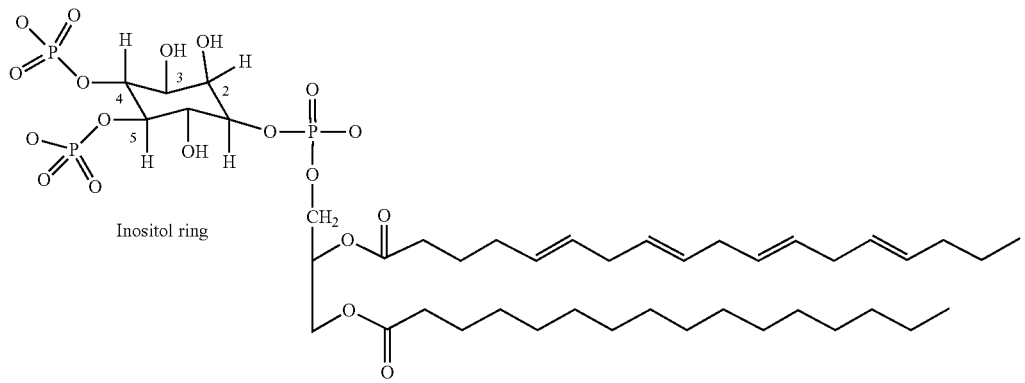

PtdIns(4,5)P$_2$

↓ PI3K

-continued

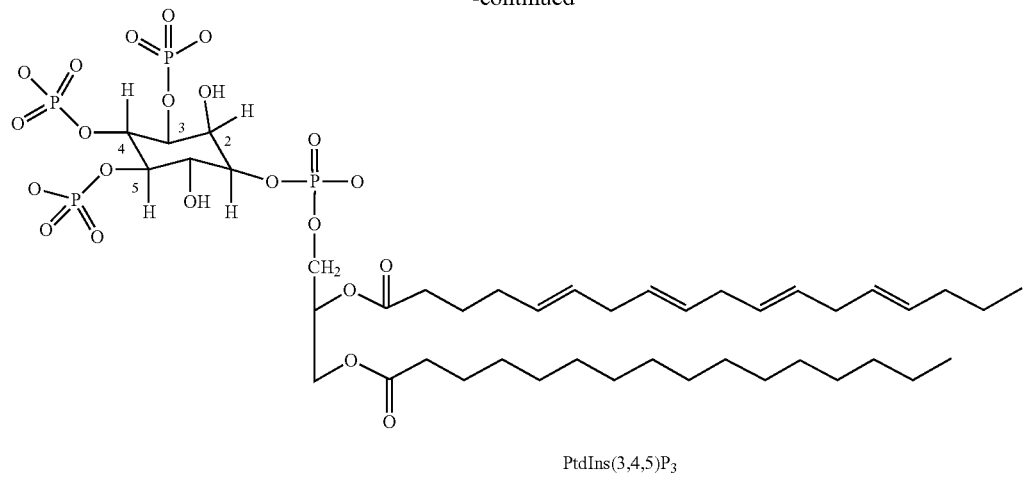

PtdIns(3,4,5)P₃

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P3, PtdIns(3,4)P2 and PtdIns(3)P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, which have been shown to be capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation, is believed to be involved in a wide range of cellular responses including cell growth, differentiation, and apoptosis (Parker, Current Biology 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pagès et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the $IC_{50}$ values of wortmannin against each of the various Class I PI3-kinases are in the range of 1-10 nM. Similarly, the $IC_{50}$ values for LY294002 against each of these PI3-kinases is about 15-20 µM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P3. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

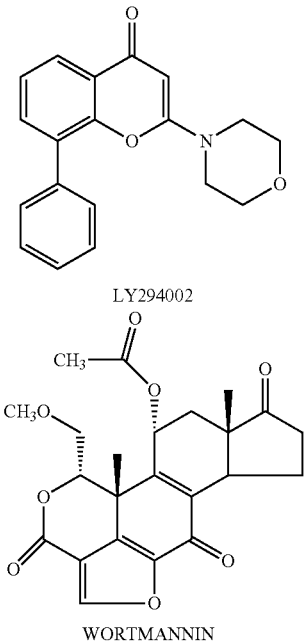

LY294002

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signalling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. 1. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins(3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5)P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonist (LABA) or leukotriene antagonist in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56.). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutical benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; AI-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus (SLE). Therefore PI3K inhibitors may also be of benefit for these indications.

Pharmacological inhibition of PI3K inhibits fMLP-dependent neutrophil chemotaxis on an ICAM coated agarose matrix integrin-dependent biased system (Sadhu et al., J.

Immunol. (2003) 170(5) p. 2647-54.). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

PI3Kδ inhibition may also lead to cancer immunotherapy. For instance, PI3Kδ has a critical signalling role in regulatory T cells (Tregs), which enables their expansion (Patton et al. PLoS One. 2011; 6(3):e17359). Activation of Tregs is one of the key processes that allow cancer cells to build immunological tolerance and escape immune surveillance. Another aspect of cancer immunity where PI3Kδ inhibitors may play a role is in upregulating the expression of PD-L1 (Programmed cell death 1 ligand 1) as has been shown in cultured airway epithelial cells (Kan-O et al. Biochem Biophys Res Commun. 2013; 435(2):195-201). PD-L1, expressed on various cell types such as T and B lymphocytes, NK and DC cells or epithelial cells, is involved in suppressing T cell dependent immunity such as the activation of cytotoxic CD8 T cells. Neutralising antibodies targeting PD-L1 are currently being developed as cancer immuno-therapeutics. Therefore, PI3Kδ inhibition may provide a novel way of enhancing anti-tumour responses. A similar rationale may also be applied to anti-infective immunity where the balance of Tregs and CD8s are known to play an important role in the outcome of the immune response such as viral infections.

The central nervous system (CNS) is also enriched with PI3Kδ expression (Eickholt et al. PLoS One 2007 11; 2(9):e869). A more recent report further uncovered a link between PI3Kδ and the neuregulin NRG-1 and ErbB4 receptor in the CNS with implications for schizophrenia (Law et al. Proc Natl Acad Sci USA. 2012; 109(30):12165-70). It was previously known that increased expression of a splice variant of ErbB4 containing the cytoplasmic portion, Cyt1, resulted in activation of the PI3K pathway as well as increased risk of schizophrenia. The publication by Law et al. indicates that the schizophrenia genetically associated Cyt1 couples preferentially to the PI3Kδ isoform. Furthermore, the PI3Kδ selective inhibitor, IC87114, showed remarkable efficacy in a mouse model of amphetamine-induced psychosis (Law et al. Proc Natl Acad Sci USA. 2012; 109(30):12165-70). Therefore PI3Kδ inhibitors have the potential to form the basis for new schizophrenia therapy approaches.

In addition, there is also good evidence that class IA PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumours such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

A wide variety of retroviruses and DNA based viruses activate the PI3K pathway as a way of preventing host cell death during viral infection and ultimately exploiting the host cell synthesis machinery for its replication (Virology 344(1) p. 131-8 (2006) by Vogt et al.; and Nat. Rev. Microbiol. 6(4) p. 265-75 (2008) by Buchkovich et al.). Therefore PI3K inhibitors may have anti-viral properties in addition to more established oncolytic and anti-inflammatory indications. These antiviral effects raise interesting prospects in viral induced inflammatory exacerbations. For example, the common cold human rhinovirus (HRV) is responsible for more than 50% of respiratory tract infections but complications of these infections can be significant in certain populations. This is particularly the case in respiratory diseases such as asthma or chronic obstruction pulmonary disease (COPD). Rhinoviral infection of epithelial cells leads to a PI3K dependent cytokine and chemokine secretion (J. Biol. Chem. (2005) 280(44) p. 36952 by Newcomb et al.). This inflammatory response correlates with worsening of respiratory symptoms during infection. Therefore PI3K inhibitors may dampen an exaggerated immune response to an otherwise benign virus. The majority of HRV strains infect bronchial epithelial cells by initially binding to the ICAM-1 receptor. The HRV-ICAM-1 complex is then further internalised by endocytosis and it has been shown that this event requires PI3K activity (J. Immunol. (2008) 180(2) p. 870-880 by Lau et al.). Therefore, PI3K inhibitors may also block viral infections by inhibiting viral entry into host cells.

PI3K inhibitors may be useful in reducing other types of respiratory infections including the fungal infection aspergillosis (Mucosal Immunol. (2010) 3(2) p. 193-205 by Bonifazi et al.). In addition, PI3Kδ deficient mice are more resistant towards infections by the protozoan parasite *Leishmania major* (J. Immunol. (2009) 183(3) p. 1921-1933 by Liu et al.) or by the intracellular bacteria *Listeria* (Pearce et al. J. Immunol. (2015) 195(7) p. 3206-17). Taken with effects on viral infections, these reports suggest that PI3K inhibitors may be useful for the treatment of a wide variety of infections. A published report points towards PI3Kδ inhibitors having potential benefits in preventing infections by the common airway bacterial pathogen *S. pneumoniae* (Fallah et al., Mech. Ageing Dev. 2011; 132(6-7): 274-86). In this report PI3Kδ is shown to reduce the macrophage-derived cytokines required to mount an effective antibody response to *S. pneumoniae* in the elderly. The anti-bacterial benefit of PI3Kδ inhibitors may thus be useful in the treatment of bacterial respiratory tract infections and bacterial exacerbations of respiratory conditions and lung damage such as asthma, COPD and cystic fibrosis, and pneumonia.

PI3K inhibition has also been shown to promote regulatory T cell differentiation (Proc. Natl. Acad. Sci. USA (2008) 105(22) p. 7797-7802 by Sauer et al.) suggesting that PI3K inhibitors may serve therapeutic purposes in auto-immune or allergic indications by inducing immuno-tolerance towards self antigen or allergen. The PI3Kδ isoform has also been linked to smoke induced glucocorticoid insensitivity (Am. J. Respir. Crit. Care Med. (2009) 179(7) p. 542-548 by Marwick et al.). This observation suggests that COPD patients, which otherwise respond poorly to corticosteroids, may benefit from the combination of a PI3K inhibitor with a corticosteroid.

PI3K has also been involved in other respiratory conditions such as idiopathic pulmonary fibrosis (IPF). IPF is a fibrotic disease with progressive decline of lung function and increased mortality due to respiratory failure. In IPF, circulating fibrocytes are directed to the lung via the chemokine receptor CXCR4. PI3K is required for both signalling and expression of CXCR4 (Int. J. Biochem. and Cell Biol. (2009) 41 p. 1708-1718 by Mehrad et al.). Therefore, by reducing CXCR4 expression and blocking its effector function, a PI3K inhibitor should inhibit the recruitment of fibrocytes to the lung and consequently slow down the fibrotic process underlying IPF, a disease with high unmet need.

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered compounds which are inhibitors of kinase activity, in particular PI3-kinase activity. Compounds which are PI3-kinase inhibitors may be useful in the treatment of disorders associated with inappropriate kinase activity, in particular inappropriate PI3-kinase activity, for example in the treatment and prevention of disorders mediated by PI3-kinase mechanisms. Such disorders include respiratory diseases including asthma, chronic obstructive pulmonary disease (COPD) and idiopathic pulmonary fibrosis (IPF); ciliopathy including primary ciliary dyskinesia, polycystic liver disease and nephronophthisis; bacterial infections including bacterial respiratory tract infections, for example infections by *S. pneumoniae, H. influenzae, M. catarrhalis* and/or mycobacteria such as *Mycobacterium tuberculosis*, and bacterial exacerbations of respiratory conditions and lung damage such as asthma, COPD and cystic fibrosis; viral infections including viral respiratory tract infections, for example infections by influenza, rhinovirus, respiratory syncytial virus (RSV), human parainfluenza virus (HPIV), adenovirus and/or coronavirus, and viral exacerbation of respiratory conditions and lung damage such as asthma, COPD and cystic fibrosis; other non-viral respiratory infections including aspergillosis and leishmaniasis; allergic diseases including allergic rhinitis; autoimmune diseases including ankylosing spondylitis, Churg-Strauss syndrome, Crohn's disease, Glomerulonephritis, Henoch-Schonlein purpura, idiopathic thrombocytopenic purpura (ITP), interstitial cystitis, pemphigus, primary sclerosing cholangitis, psoriasis, rheumatoid arthritis, sarcoidosis, Sjogren's syndrome, Type 1 diabetes, ulcerative colitis, vasculitis, vitiligo and Wegener's granulomatosis; inflammatory disorders including inflammatory bowel disease, atopic dermatitis, eczema and psoriasis; diabetes; cardiovascular diseases including thrombosis, atherosclerosis and hypertension; hematologic malignancies; neurodegenerative diseases; pancreatitis; multiorgan failure; kidney diseases; platelet aggregation; cancer; sperm motility; transplantation rejection; graft rejection; lung injuries; pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain; fibrotic diseases; depression; psychotic disorders including schizophrenia; bronchiectasis; and activated PI3Kδ syndrome (APDS).

In one embodiment, compounds of the invention may show selectivity for PI3-kinases over other kinases.

In another embodiment, compounds of the invention may be potent inhibitors of PI3Kδ.

In another embodiment, compounds of the invention may show selectivity for PI3Kδ over other PI3-kinases.

In a further embodiment, compounds of the invention may have properties which make them particularly suitable for oral administration.

SUMMARY OF THE INVENTION

The invention is directed to certain novel compounds. Specifically, the invention is directed to compounds of formula (I)

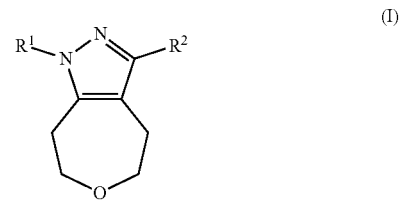

wherein $R^1$ and $R^2$ are as defined below, and salts thereof.

The compounds are inhibitors of kinase activity, in particular PI3-kinase activity. Compounds which are PI3-kinase inhibitors may be useful in the treatment of disorders associated with inappropriate PI3-kinase activity. Accordingly, the invention is further directed to pharmaceutical compositions comprising a compound of formula (I) or a pharmaceutically acceptable salt thereof, and one or more pharmaceutically acceptable excipients. The invention is still further directed to methods of treating disorders mediated by inappropriate PI3-kinase activity comprising administering a safe and effective amount of a compound of formula (I) or a pharmaceutically acceptable salt thereof, to a patient in need thereof.

DETAILED DESCRIPTION OF THE INVENTION

In one embodiment, the invention is directed to compounds of formula (I)

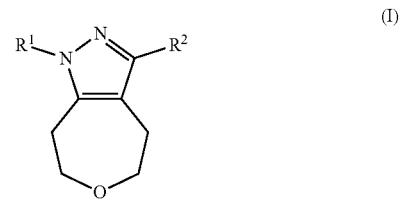

wherein
$R^1$ is 5- or 6-membered heteroaryl wherein the heteroaryl contains from one to three heteroatoms independently selected from oxygen and nitrogen and is substituted by one or two substituents independently selected from halo, cyano, $C_{1-6}$alkoxy, —NHSO$_2$$C_{1-6}$alkyl, —XR$^3$ and $C_{1-6}$alkyl wherein the $C_{1-6}$alkyl is optionally substituted by halo;
$R^2$ is —OR$^4$, —CONHR$^5$, or 5- or 6-membered heteroaryl wherein the heteroaryl contains from one to three heteroatoms independently selected from oxygen and nitrogen and is substituted by one or two substituents independently selected from halo, cyano, $C_{1-6}$alkoxy, —NHSO$_2$$C_{1-6}$alkyl, —CONR$^6$R$^7$, —YR$^8$ and $C_{1-6}$alkyl wherein the $C_{1-6}$alkyl is optionally substituted by one or two substituents independently selected from hydroxy and —NR$^9$R$^{10}$;

R³ is 5- or 6-membered heterocyclyl wherein the heterocyclyl contains one or two heteroatoms independently selected from oxygen and nitrogen and is optionally substituted by from one to three substituents independently selected from $C_{1-6}$alkyl;

R⁴ is $C_{1-6}$alkyl optionally substituted by $C_{3-6}$cycloalkyl or 5- or 6-membered heterocyclyl containing one or two heteroatoms selected from oxygen and nitrogen wherein the $C_{3-6}$cycloalkyl is optionally substituted by —NHCO₂$C_{1-6}$alkyl and the heterocyclyl is optionally substituted by from one to three substituents independently selected from halo, —COC$_{1-6}$alkyl, —CO₂$C_{1-6}$alkyl and $C_{1-6}$alkyl optionally substituted by —OR¹¹;

R⁵ is hydrogen or $C_{1-6}$alkyl optionally substituted by 6-membered heterocyclyl wherein the heterocyclyl contains an oxygen atom or a nitrogen atom and is optionally substituted by $C_{1-6}$alkyl;

R⁶ and R⁷, together with the nitrogen atom to which they are attached, are linked to form a 5- or 6-membered heterocyclyl wherein the heterocyclyl optionally contains an oxygen atom or a further nitrogen atom and is optionally substituted by $C_{1-6}$alkyl;

R⁸ is 5- to 9-membered heterocyclyl wherein the heterocyclyl contains one or two heteroatoms independently selected from oxygen and nitrogen and is substituted by from one to three substituents independently selected from oxo, hydroxy, halo, —COC$_{1-6}$alkyl and $C_{1-6}$alkyl optionally substituted by —OR¹²;

R⁹, R¹⁰, R¹¹ and R¹² are each independently hydrogen or $C_{1-6}$alkyl;

X and Y are each independently —CH₂— or —CH(CH₃)—;

and salts thereof (hereinafter "compounds of the invention").

In one embodiment, R¹ is 5- or 6-membered heteroaryl wherein the heteroaryl contains one or two nitrogen atoms and is substituted by one or two substituents independently selected from halo, cyano, $C_{1-6}$alkoxy, —NHSO₂$C_{1-6}$alkyl, —XR³ and $C_{1-6}$alkyl wherein the $C_{1-6}$alkyl is optionally substituted by halo. In another embodiment, R¹ is 5- or 6-membered heteroaryl wherein the heteroaryl contains one or two nitrogen atoms and is substituted by one or two substituents independently selected from halo, $C_{1-6}$alkoxy, —XR³ and $C_{1-6}$alkyl. In another embodiment, R¹ is 5-membered heteroaryl wherein the heteroaryl contains one or two nitrogen atoms and is substituted by —XR³. In another embodiment, R¹ is pyrazolyl substituted by —XR³. In another embodiment, R¹ is 6-membered heteroaryl wherein the heteroaryl contains one or two nitrogen atoms and is substituted by one or two substituents independently selected from halo, $C_{1-6}$alkoxy and $C_{1-6}$alkyl. In another embodiment, R¹ is pyridinyl substituted by two substituents independently selected from halo, $C_{1-6}$alkoxy and $C_{1-6}$alkyl. In another embodiment, R¹ is pyridinyl substituted by $C_{1-6}$alkoxy. In a further embodiment, R¹ is pyridinyl substituted by methoxy.

In one embodiment, R² is —OR⁴, or 5- or 6-membered heteroaryl wherein the heteroaryl contains from one to three heteroatoms independently selected from oxygen and nitrogen and is substituted by one or two substituents independently selected from halo, cyano, $C_{1-6}$alkoxy, —NHSO₂$C_{1-6}$alkyl, —CONR⁶R⁷, —YR⁸ and $C_{1-6}$alkyl wherein the $C_{1-6}$alkyl is optionally substituted by one or two substituents independently selected from hydroxy and —NR⁹R¹⁰. In another embodiment, R² is 5- or 6-membered heteroaryl wherein the heteroaryl contains one or two nitrogen atoms and is substituted by one or two substituents independently selected from halo, cyano, $C_{1-6}$alkoxy, —NHSO₂$C_{1-6}$alkyl, —CONR⁶R⁷, —YR⁸ and $C_{1-6}$alkyl wherein the $C_{1-6}$alkyl is optionally substituted by one or two substituents independently selected from hydroxy and —NR⁹R¹⁰. In another embodiment, R² is 5- or 6-membered heteroaryl wherein the heteroaryl contains one or two nitrogen atoms and is substituted by one or two substituents independently selected from halo, $C_{1-6}$alkoxy, —YR⁸ and $C_{1-6}$alkyl. In another embodiment, R² is 5-membered heteroaryl wherein the heteroaryl contains one or two nitrogen atoms and is substituted by —YR⁸. In another embodiment, R² is pyrazolyl substituted by —YR⁸. In another embodiment, R² is 6-membered heteroaryl wherein the heteroaryl contains one or two nitrogen atoms and is substituted by one or two substituents independently selected from halo, $C_{1-6}$alkoxy and $C_{1-6}$alkyl. In a further embodiment, R² is pyridinyl substituted by one or two substituents independently selected from halo, $C_{1-6}$alkoxy and $C_{1-6}$alkyl.

In one embodiment, R³ is 6-membered heterocyclyl wherein the heterocyclyl contains one or two nitrogen atoms and is optionally substituted by from one to three substituents independently selected from $C_{1-6}$alkyl. In a further embodiment, R³ is piperidinyl substituted by from one to three substituents independently selected from $C_{1-6}$alkyl.

In one embodiment, R⁴ is $C_{1-6}$alkyl optionally substituted by 5- or 6-membered heterocyclyl containing one or two heteroatoms selected from oxygen and nitrogen wherein the heterocyclyl is optionally substituted by from one to three substituents independently selected from halo, —COC$_{1-6}$alkyl, —CO₂$C_{1-6}$alkyl and $C_{1-6}$alkyl optionally substituted by —OR¹¹. In a further embodiment, R⁴ is methyl substituted by 5- or 6-membered heterocyclyl containing a nitrogen atom wherein the heterocyclyl is optionally substituted by from one to three substituents independently selected from halo, —COC$_{1-6}$alkyl, —CO₂$C_{1-6}$alkyl and $C_{1-6}$alkyl optionally substituted by —OR¹¹.

In one embodiment, R⁵ is hydrogen.

In one embodiment, R⁶ and R⁷, together with the nitrogen atom to which they are attached, are linked to form a piperazinyl optionally substituted by $C_{1-6}$alkyl.

In one embodiment, R⁸ is 5- or 6-membered heterocyclyl wherein the heterocyclyl contains one or two heteroatoms independently selected from oxygen and nitrogen and is substituted by from one to three substituents independently selected from oxo, hydroxy, halo, —COC$_{1-6}$alkyl and $C_{1-6}$alkyl optionally substituted by —OR¹². In another embodiment, R⁸ is 5- or 6-membered heterocyclyl wherein the heterocyclyl contains one or two heteroatoms independently selected from oxygen and nitrogen and is substituted by from one to three substituents independently selected from $C_{1-6}$alkyl. In another embodiment, R⁸ is piperidinyl substituted by from one to three substituents independently selected from $C_{1-6}$alkyl. In another embodiment, R⁸ is piperidinyl substituted by $C_{1-6}$alkyl. In a further embodiment, R⁸ is piperidinyl substituted by methyl.

In one embodiment, R⁹ and R¹⁰ are each independently $C_{1-6}$alkyl. In a further embodiment, R⁹ and R¹⁰ are each methyl.

In one embodiment, R¹¹ is hydrogen.

In one embodiment, R¹² is hydrogen.

In one embodiment, X and Y are each independently —CH₂—. In a further embodiment, Y is —CH(CH₃)—.

It is to be understood that the present invention covers all combinations of substituent groups described hereinabove.

Compounds of the invention include the compounds of Examples 1 to 296 and salts thereof.

In one embodiment, the compound of the invention is:
- 1-(1-(((2R,4r,6S)-2,6-dimethylpiperidin-4-yl)methyl)-1H-pyrazol-4-yl)-3-(5-fluoro-6-methoxypyridin-3-yl)-4,5,7,8-tetrahydro-1H-oxepino[4,5-c]pyrazole;
- 3-(1-(((2R,4r,6S)-2,6-dimethylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;
- N-(2-methoxy-5-(3-(1-methyl-1H-pyrazol-4-yl)-4,5,7,8-tetrahydro-1H-oxepino[4,5-c]pyrazol-1-yl)pyridin-3-yl)methanesulfonamide;
- 1-(6-methoxy-5-methylpyridin-3-yl)-3-(1-methyl-1H-pyrazol-4-yl)-4,5,7,8-tetrahydro-1H-oxepino[4,5-c]pyrazole;
- N-(2-methoxy-5-(1-(1-methyl-1H-pyrazol-4-yl)-4,5,7,8-tetrahydro-1H-oxepino[4,5-c]pyrazol-3-yl)pyridin-3-yl)methanesulfonamide;
- 1-(2-methoxypyrimidin-5-yl)-3-(1-((1-methylpiperidin-4-yl)methyl)-1H-pyrazol-4-yl)-4,5,7,8-tetrahydro-1H-oxepino[4,5-c]pyrazole;
- 3-(1-((1-isopropylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;
- 3-(1-((1-isopropylpiperidin-3-yl)methyl)-1H-pyrazol-4-yl)-1-(6-methoxy-5-methylpyridin-3-yl)-4,5,7,8-tetrahydro-1H-oxepino[4,5-c]pyrazole;
- 1-(6-methoxy-5-methylpyridin-3-yl)-3-(1-((1-methylpiperidin-4-yl)methyl)-1H-pyrazol-4-yl)-4,5,7,8-tetrahydro-1H-oxepino[4,5-c]pyrazole;
- 1-(5-fluoro-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;
- 1-(5-fluoro-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;
- N-(2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)pyridin-3-yl)methanesulfonamide;
- 2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)nicotinonitrile;
- 5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxynicotinonitrile;
- 1-(5-(fluoromethyl)-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;
- 1-(5-(fluoromethyl)-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;
- N-(5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;
- 3-(5-((4-isopropylpiperazin-1-yl)methyl)oxazol-2-yl)-1-(6-methoxy-5-methylpyridin-3-yl)-4,5,7,8-tetrahydro-1H-oxepino[4,5-c]pyrazole;
- 1-(6-methoxy-5-methylpyridin-3-yl)-4,5,7,8-tetrahydro-1H-oxepino[4,5-c]pyrazole-3-carboxamide;
- 1-(6-methoxy-5-methylpyridin-3-yl)-N-((1-methylpiperidin-3-yl)methyl)-4,5,7,8-tetrahydro-1H-oxepino[4,5-c]pyrazole-3-carboxamide;
- 1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;
- (R)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;
- (S)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;
- 3-(1-ethyl-5-methyl-1H-pyrazol-4-yl)-1-(1-methyl-1H-pyrazol-4-yl)-4,5,7,8-tetrahydro-1H-oxepino[4,5-c]pyrazole;
- 1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;
- (R)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;
- (S)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;
- 3-(6-methoxy-5-methylpyridin-3-yl)-1-(1-((1-methylpiperidin-4-yl)methyl)-1H-pyrazol-4-yl)-4,5,7,8-tetrahydro-1H-oxepino[4,5-c]pyrazole;
- 2-(4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol;
- 5-(3-(1-((1-isopropylpiperidin-3-yl)methyl)-1H-pyrazol-4-yl)-4,5,7,8-tetrahydro-1H-oxepino[4,5-c]pyrazol-1-yl)-2-methoxynicotinonitrile;
- 3-(5-fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole;
- 3-(5-fluoro-6-methoxypyridin-3-yl)-1-(1-((1-isopropylpiperidin-4-yl)methyl)-1H-pyrazol-4-yl)-4,5,7,8-tetrahydro-1H-oxepino[4,5-c]pyrazole;
- 1-(1-((1-isopropylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;
- 1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;
- (S)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;
- (R)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;
- 1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;
- (R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;
- (S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;
- 3-(1-((1-isopropylpyrrolidin-3-yl)methyl)-1H-pyrazol-4-yl)-1-(6-methoxy-5-methylpyridin-3-yl)-4,5,7,8-tetrahydro-1H-oxepino[4,5-c]pyrazole;
- 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)-1-methylpiperidin-4-ol;
- 3-(5-fluoro-6-methoxypyridin-3-yl)-1-(1-((1-methylpiperidin-4-yl)methyl)-1H-pyrazol-4-yl)-4,5,7,8-tetrahydro-1H-oxepino[4,5-c]pyrazole;
- 3-(1-((4-fluoro-1-methylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;
- (2R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((R)-3-((4-(1-(5-fluoro-6-methoxypyridin-3-yl)-4,5, 7,8-tetrahydro-1H-oxepino[4,5-c]pyrazol-3-yl)-1H-pyrazol-1-yl)methyl)pyrrolidin-1-yl)propan-2-ol;

(R)-1-((S)-3-((4-(1-(5-fluoro-6-methoxypyridin-3-yl)-4,5,7, 8-tetrahydro-1H-oxepino[4,5-c]pyrazol-3-yl)-1H-pyrazol-1-yl)methyl)pyrrolidin-1-yl)propan-2-ol;

(2S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((R)-3-((4-(1-(5-fluoro-6-methoxypyridin-3-yl)-4,5,7, 8-tetrahydro-1H-oxepino[4,5-c]pyrazol-3-yl)-1H-pyrazol-1-yl)methyl)pyrrolidin-1-yl)propan-2-ol;

(5)-1-((S)-3-((4-(1-(5-fluoro-6-methoxypyridin-3-yl)-4,5,7, 8-tetrahydro-1H-oxepino[4,5-c]pyrazol-3-yl)-1H-pyrazol-1-yl)methyl)pyrrolidin-1-yl)propan-2-ol;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

7-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)-1,1-dimethyltetrahydro-1H-oxazolo[3,4-a]pyridin-3(5H)-one;

1-(5-fluoro-6-methoxypyridin-3-yl)-3-(1-(((2R,4r,6S)-1,2, 6-trimethylpiperidin-4-yl)methyl)-1H-pyrazol-4-yl)-4,5, 7,8-tetrahydro-1H-oxepino[4,5-c]pyrazole;

1-(6-methoxy-5-methylpyridin-3-yl)-3-(3-methyl-1H-pyrazol-5-yl)-4,5,7,8-tetrahydro-1H-oxepino[4,5-c]pyrazole;

1-(5-fluoro-6-methoxypyridin-3-yl)-3-(5-methyl-1H-pyrazol-4-yl)-4,5,7,8-tetrahydro-1H-oxepino[4,5-c]pyrazole;

3-(1,3-dimethyl-1H-pyrazol-5-yl)-1-(6-methoxy-5-methylpyridin-3-yl)-4,5,7,8-tetrahydro-1H-oxepino[4,5-c]pyrazole;

1-(dimethylamino)-3-(4-(1-(5-fluoro-6-methoxypyridin-3-yl)-4,5,7,8-tetrahydro-1H-oxepino[4,5-c]pyrazol-3-yl)-1H-pyrazol-1-yl)propan-2-ol;

3-(1-((3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

3-(1-(((3R,4S)-3-fluoro-1-isopropylpiperidin-4-yl)methyl)-1H-pyrazol-4-yl)-1-(5-fluoro-6-methoxypyridin-3-yl)-4, 5,7,8-tetrahydro-1H-oxepino[4,5-c]pyrazole;

5-(3-(1-((1-isopropylpyrrolidin-3-yl)methyl)-1H-pyrazol-4-yl)-4,5,7,8-tetrahydro-1H-oxepino[4,5-c]pyrazol-1-yl)-2-methoxynicotinonitrile;

1-(4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidin-1-yl)propan-1-one;

1-(1-(((2R,4r,6S)-2,6-dimethylpiperidin-4-yl)methyl)-1H-pyrazol-4-yl)-3-(6-methoxy-5-methylpyridin-3-yl)-4,5,7, 8-tetrahydro-1H-oxepino[4,5-c]pyrazole;

N-(5-(3-(1-(((2R,6S)-2,6-dimethyltetrahydro-2H-pyran-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(1-(((2R,4r,6S)-2,6-dimethylpiperidin-4-yl)methyl)-1H-pyrazol-4-yl)-1-(6-methoxy-5-methylpyridin-3-yl)-4,5,7, 8-tetrahydro-1H-oxepino[4,5-c]pyrazole;

3-(6-methoxy-5-methylpyridin-3-yl)-1-(1-(((2R,4r,6S)-1,2, 6-trimethylpiperidin-4-yl)methyl)-1H-pyrazol-4-yl)-4,5, 7,8-tetrahydro-1H-oxepino[4,5-c]pyrazole;

1-(1-((1-isopropylpiperidin-4-yl)methyl)-1H-pyrazol-4-yl)-3-(6-methoxypyridin-3-yl)-4,5,7,8-tetrahydro-1H-oxepino[4,5-c]pyrazole;

1-(6-methoxy-5-methylpyridin-3-yl)-3-(1-(((2R,4r,6S)-1,2, 6-trimethylpiperidin-4-yl)methyl)-1H-pyrazol-4-yl)-4,5, 7,8-tetrahydro-1H-oxepino[4,5-c]pyrazole;

N-(5-(3-(2-(4-(2-hydroxypropan-2-yl)piperidin-1-yl) ethoxy)-4,5,7,8-tetrahydro-1H-oxepino[4,5-c]pyrazol-1-yl)-2-methoxypyridin-3-yl)methanesulfonamide;

2-(1-(2-((1-(6-methoxy-5-methylpyridin-3-yl)-4,5,7,8-tetrahydro-1H-oxepino[4,5-c]pyrazol-3-yl)oxy)ethyl)piperidin-4-yl)propan-2-ol;

2-(1-(2-((1-(5-(fluoromethyl)-6-methoxypyridin-3-yl)-4,5, 7,8-tetrahydro-1H-oxepino[4,5-c]pyrazol-3-yl)oxy)ethyl) piperidin-4-yl)propan-2-ol;

2-(1-(2-((1-(5-fluoro-6-methoxypyridin-3-yl)-4,5,7,8-tetrahydro-1H-oxepino[4,5-c]pyrazol-3-yl)oxy)ethyl)piperidin-4-yl)propan-2-ol;

5-(3-(2-(4-(2-hydroxypropan-2-yl)piperidin-1-yl)ethoxy)-4, 5,7,8-tetrahydro-1H-oxepino[4,5-c]pyrazol-1-yl)-2-methoxynicotinonitrile;

2-(1-(2-((1-(2-methoxypyrimidin-5-yl)-4,5,7,8-tetrahydro-1H-oxepino[4,5-c]pyrazol-3-yl)oxy)ethyl)piperidin-4-yl) propan-2-ol;

tert-butyl 4-(((1-(6-methoxy-5-methylpyridin-3-yl)-4,5,7,8-tetrahydro-1H-oxepino[4,5-c]pyrazol-3-yl)oxy)methyl) piperidine-1-carboxylate;

1-(6-methoxy-5-methylpyridin-3-yl)-3-(piperidin-4-ylmethoxy)-4,5,7,8-tetrahydro-1H-oxepino[4,5-c]pyrazole;

3-((1-isopropylpiperidin-4-yl)methoxy)-1-(6-methoxy-5-methylpyridin-3-yl)-4,5,7,8-tetrahydro-1H-oxepino[4,5-c]pyrazole;

tert-butyl 3-(((1-(6-methoxy-5-methylpyridin-3-yl)-4,5,7,8-tetrahydro-1H-oxepino[4,5-c]pyrazol-3-yl)oxy)methyl) pyrrolidine-1-carboxylate;

tert-butyl 3-(((1-(6-methoxy-5-methylpyridin-3-yl)-4,5,7,8-tetrahydro-1H-oxepino[4,5-c]pyrazol-3-yl)oxy)methyl) piperidine-1-carboxylate;

1-(6-methoxy-5-methylpyridin-3-yl)-3-(piperidin-3-ylmethoxy)-4,5,7,8-tetrahydro-1H-oxepino[4,5-c]pyrazole;

(S)-tert-butyl 3-(((1-(6-methoxy-5-methylpyridin-3-yl)-4,5, 7,8-tetrahydro-1H-oxepino[4,5-c]pyrazol-3-yl)oxy) methyl)piperidine-1-carboxylate;

(S)-1-(6-methoxy-5-methylpyridin-3-yl)-3-(piperidin-3-ylmethoxy)-4,5,7,8-tetrahydro-1H-oxepino[4,5-c]pyrazole;

(S)-1-(3-(((1-(6-methoxy-5-methylpyridin-3-yl)-4,5,7,8-tetrahydro-1H-oxepino[4,5-c]pyrazol-3-yl)oxy)methyl)piperidin-1-yl)-2-methylpropan-2-ol;

(R)-1-((S)-3-(((1-(6-methoxy-5-methylpyridin-3-yl)-4,5,7, 8-tetrahydro-1H-oxepino[4,5-c]pyrazol-3-yl)oxy)methyl) piperidin-1-yl)propan-2-ol;

(S)-1-((S)-3-(((1-(6-methoxy-5-methylpyridin-3-yl)-4,5,7, 8-tetrahydro-1H-oxepino[4,5-c]pyrazol-3-yl)oxy)methyl) piperidin-1-yl)propan-2-ol;

(R)-tert-butyl 3-(((1-(6-methoxy-5-methylpyridin-3-yl)-4,5, 7,8-tetrahydro-1H-oxepino[4,5-c]pyrazol-3-yl)oxy) methyl)piperidine-1-carboxylate;

(S)-1-(2-(((1-(6-methoxy-5-methylpyridin-3-yl)-4,5,7,8-tetrahydro-1H-oxepino[4,5-c]pyrazol-3-yl)oxy)methyl) morpholino)-2-methylpropan-2-ol;

3-((1-isopropylpyrrolidin-3-yl)methoxy)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-((1-methylpyrrolidin-3-yl)methoxy)-4,5,7,8-tetrahydro-1H-oxepino[4,5-c] pyrazole;

1-(3-(((1-(6-methoxy-5-methylpyridin-3-yl)-4,5,7,8-tetrahydro-1H-oxepino[4,5-c]pyrazol-3-yl)oxy)methyl)pyrrolidin-1-yl)ethanone;

tert-butyl ((1R,2S)-2-(((1-(6-methoxy-5-methylpyridin-3-yl)-4,5,7,8-tetrahydro-1H-oxepino[4,5-c]pyrazol-3-yl)oxy)methyl)cyclopropyl)carbamate;

tert-butyl 3-fluoro-3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;

tert-butyl 4,4-difluoro-3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

3-((1,3-dimethylpiperidin-3-yl)methoxy)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-((1-(2-methoxyethyl)-3-methylpyrrolidin-3-yl)methoxy)-4,5,7,8-tetrahydro-1H-oxepino[4,5-c]pyrazole;

1-(6-methoxy-5-methylpyridin-3-yl)-3-((pyrrolidin-3-yl)methoxy)-4,5,7,8-tetrahydro-1H-oxepino[4,5-c]pyrazole;

1-(6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(2-(1-(4-isopropylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole;

3-(2-(1-(4-isopropylpiperazin-1-yl)ethyl)pyridin-4-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-(2-(1-((3S,5R)-3,4,5-trimethylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(1-((3-fluoropiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-(((3R,4S)-3-fluoropiperidin-4-yl)methyl)-1H-pyrazol-4-yl)-4,5,7,8-tetrahydro-1H-oxepino[4,5-c]pyrazole;

(S)-tert-butyl 2-(((1-(6-methoxy-5-methylpyridin-3-yl)-4,5,7,8-tetrahydro-1H-oxepino[4,5-c]pyrazol-3-yl)oxy)methyl)morpholine-4-carboxylate;

(S)-1-(6-methoxy-5-methylpyridin-3-yl)-3-(morpholin-2-ylmethoxy)-4,5,7,8-tetrahydro-1H-oxepino[4,5-c]pyrazole;

(4-isopropylpiperazin-1-yl)(2-(1-(6-methoxy-5-methylpyridin-3-yl)-4,5,7,8-tetrahydro-1H-oxepino[4,5-c]pyrazol-3-yl)oxazol-5-yl)methanone;

4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-4-ol;

3-(1-((4-fluoropiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

1-(6-methoxypyridin-3-yl)-3-(2-((S)-1-((3S,5R)-3,4,5-trimethylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(2-((S)-1-((3S,5R)-3,4,5-trimethylpiperazin-1-yl)ethyl)pyridin-4-yl)-4,5,7,8-tetrahydro-1H-oxepino[4,5-c]pyrazole;

(S)-1-(6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

(S)-1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

(S)-1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;

(S)-1-(1-(4-(1-(5-fluoro-6-methoxypyridin-3-yl)-4,5,7,8-tetrahydro-1H-oxepino[4,5-c]pyrazol-3-yl)pyridin-2-yl)ethyl)-3-methylimidazolidin-2-one;

3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;

(S)-3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;

(R)-3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;

1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;

(S)-1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;

(R)-1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;

(R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;

3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;

(S)-3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;

(R)-3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;

1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole;

(S)-1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole;

(R)-1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole;

3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole;

(S)-3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole; or (R)-3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole;

or a salt thereof.

In another embodiment, the compound of the invention is:

1-(1-(((2R,4r,6S)-2,6-dimethylpiperidin-4-yl)methyl)-1H-pyrazol-4-yl)-3-(5-fluoro-6-methoxypyridin-3-yl)-4,5,7,8-tetrahydro-1H-oxepino[4,5-c]pyrazole;

3-(1-(((2R,4r,6S)-2,6-dimethylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

N-(2-methoxy-5-(3-(1-methyl-1H-pyrazol-4-yl)-4,5,7,8-tetrahydro-1H-oxepino[4,5-c]pyrazol-1-yl)pyridin-3-yl)methanesulfonamide;

1-(6-methoxy-5-methylpyridin-3-yl)-3-(1-methyl-1H-pyrazol-4-yl)-4,5,7,8-tetrahydro-1H-oxepino[4,5-c]pyrazole;

N-(2-methoxy-5-(1-(1-methyl-1H-pyrazol-4-yl)-4,5,7,8-tetrahydro-1H-oxepino[4,5-c]pyrazol-3-yl)pyridin-3-yl)methanesulfonamide;

1-(2-methoxypyrimidin-5-yl)-3-(1-((1-methylpiperidin-4-yl)methyl)-1H-pyrazol-4-yl)-4,5,7,8-tetrahydro-1H-oxepino[4,5-c]pyrazole;

3-(1-((1-isopropylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

3-(1-((1-isopropylpiperidin-3-yl)methyl)-1H-pyrazol-4-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;

N-(2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)pyridin-3-yl)methanesulfonamide;

2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)nicotinonitrile;

5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxynicotinonitrile;

1-(5-(fluoromethyl)-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-(fluoromethyl)-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;

N-(5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(5-((4-isopropylpiperazin-1-yl)methyl)oxazol-2-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-4,5,7,8-tetrahydro-1H-oxepino[4,5-c]pyrazole-3-carboxamide;

1-(6-methoxy-5-methylpyridin-3-yl)-N-((1-methylpiperidin-3-yl)methyl)-4,5,7,8-tetrahydro-1H-oxepino[4,5-c]pyrazole-3-carboxamide;

1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(R)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(S)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

3-(1-ethyl-5-methyl-1H-pyrazol-4-yl)-1-(1-methyl-1H-pyrazol-4-yl)-4,5,7,8-tetrahydro-1H-oxepino[4,5-c]pyrazole;

1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

(R)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

(S)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

3-(6-methoxy-5-methylpyridin-3-yl)-1-(1-((1-methylpiperidin-4-yl)methyl)-1H-pyrazol-4-yl)-4,5,7,8-tetrahydro-1H-oxepino[4,5-c]pyrazole;

2-(4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol;

5-(3-(1-((1-isopropylpiperidin-3-yl)methyl)-1H-pyrazol-4-yl)-4,5,7,8-tetrahydro-1H-oxepino[4,5-c]pyrazol-1-yl)-2-methoxynicotinonitrile;

3-(5-fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole;

3-(5-fluoro-6-methoxypyridin-3-yl)-1-(1-((1-isopropylpiperidin-4-yl)methyl)-1H-pyrazol-4-yl)-4,5,7,8-tetrahydro-1H-oxepino[4,5-c]pyrazole;

1-(1-((1-isopropylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;

1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

(S)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

(R)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

3-(1-((1-isopropylpyrrolidin-3-yl)methyl)-1H-pyrazol-4-yl)-1-(6-methoxy-5-methylpyridin-3-yl)-4,5,7,8-tetrahydro-1H-oxepino[4,5-c]pyrazole;

4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)-1-methylpiperidin-4-ol;

3-(5-fluoro-6-methoxypyridin-3-yl)-1-(1-((1-methylpiperidin-4-yl)methyl)-1H-pyrazol-4-yl)-4,5,7,8-tetrahydro-1H-oxepino[4,5-c]pyrazole;

3-(1-((4-fluoro-1-methylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

(2R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(2S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

7-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)-1,1-dimethyltetrahydro-1H-oxazolo[3,4-a]pyridin-3(5H)-one;

1-(5-fluoro-6-methoxypyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

1-(6-methoxy-5-methylpyridin-3-yl)-3-(3-methyl-1H-pyrazol-5-yl)-4,5,7,8-tetrahydro-1H-oxepino[4,5-c]pyrazole;

1-(5-fluoro-6-methoxypyridin-3-yl)-3-(5-methyl-1H-pyrazol-4-yl)-4,5,7,8-tetrahydro-1H-oxepino[4,5-c]pyrazole;

3-(1,3-dimethyl-1H-pyrazol-5-yl)-1-(6-methoxy-5-methylpyridin-3-yl)-4,5,7,8-tetrahydro-1H-oxepino[4,5-c]pyrazole;

1-(dimethylamino)-3-(4-(1-(5-fluoro-6-methoxypyridin-3-yl)-4,5,7,8-tetrahydro-1H-oxepino[4,5-c]pyrazol-3-yl)-1H-pyrazol-1-yl)propan-2-ol;

3-(1-((3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

3-(1-(((3R,4S)-3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

5-(3-(1-((1-isopropylpyrrolidin-3-yl)methyl)-1H-pyrazol-4-yl)-4,5,7,8-tetrahydro-1H-oxepino[4,5-c]pyrazol-1-yl)-2-methoxynicotinonitrile;

1-(4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidin-1-yl)propan-1-one;

1-(1-(((2R,4r,6S)-2,6-dimethylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;

N-(5-(3-(1-(((2R,6S)-2,6-dimethyltetrahydro-2H-pyran-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(1-(((2R,4r,6S)-2,6-dimethylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

3-(6-methoxy-5-methylpyridin-3-yl)-1-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

1-(1-((1-isopropylpiperidin-4-yl)methyl)-1H-pyrazol-4-yl)-3-(6-methoxypyridin-3-yl)-4,5,7,8-tetrahydro-1H-oxepino[4,5-c]pyrazole;

1-(6-methoxy-5-methylpyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

N-(5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxypyridin-3-yl)methanesulfonamide;

2-(1-(2-((1-(6-methoxy-5-methylpyridin-3-yl)-4,5,7,8-tetrahydro-1H-oxepino[4,5-c]pyrazol-3-yl)oxy)ethyl)piperidin-4-yl)propan-2-ol;

2-(1-(2-((1-(5-(fluoromethyl)-6-methoxypyridin-3-yl)-4,5,7,8-tetrahydro-1H-oxepino[4,5-c]pyrazol-3-yl)oxy)ethyl)piperidin-4-yl)propan-2-ol;

2-(1-(2-((1-(5-fluoro-6-methoxypyridin-3-yl)-4,5,7,8-tetrahydro-1H-oxepino[4,5-c]pyrazol-3-yl)oxy)ethyl)piperidin-4-yl)propan-2-ol;

5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxynicotinonitrile;

2-(1-(2-((1-(2-methoxypyrimidin-5-yl)-4,5,7,8-tetrahydro-1H-oxepino[4,5-c]pyrazol-3-yl)oxy)ethyl)piperidin-4-yl)propan-2-ol;

tert-butyl 4-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

1-(6-methoxy-5-methylpyridin-3-yl)-3-(piperidin-4-ylmethoxy)-4,5,7,8-tetrahydro-1H-oxepino[4,5-c]pyrazole;

3-((1-isopropylpiperidin-4-yl)methoxy)-1-(6-methoxy-5-methylpyridin-3-yl)-4,5,7,8-tetrahydro-1H-oxepino[4,5-c]pyrazole;

tert-butyl 3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;

tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

1-(6-methoxy-5-methylpyridin-3-yl)-3-(piperidin-3-ylmethoxy)-4,5,7,8-tetrahydro-1H-oxepino[4,5-c]pyrazole;

(S)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

(S)-1-(6-methoxy-5-methylpyridin-3-yl)-3-(piperidin-3-ylmethoxy)-4,5,7,8-tetrahydro-1H-oxepino[4,5-c]pyrazole;

(S)-1-(3-(((1-(6-methoxy-5-methylpyridin-3-yl)-4,5,7,8-tetrahydro-1H-oxepino[4,5-c]pyrazol-3-yl)oxy)methyl)piperidin-1-yl)-2-methylpropan-2-ol;

(R)-1-((S)-3-(((1-(6-methoxy-5-methylpyridin-3-yl)-4,5,7,8-tetrahydro-1H-oxepino[4,5-c]pyrazol-3-yl)oxy)methyl)piperidin-1-yl)propan-2-ol;

(S)-1-((S)-3-(((1-(6-methoxy-5-methylpyridin-3-yl)-4,5,7,8-tetrahydro-1H-oxepino[4,5-c]pyrazol-3-yl)oxy)methyl)piperidin-1-yl)propan-2-ol;

(R)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

(S)-1-(2-(((1-(6-methoxy-5-methylpyridin-3-yl)-4,5,7,8-tetrahydro-1H-oxepino[4,5-c]pyrazol-3-yl)oxy)methyl)morpholino)-2-methylpropan-2-ol;

3-((1-isopropylpyrrolidin-3-yl)methoxy)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-((1-methylpyrrolidin-3-yl)methoxy)-4,5,7,8-tetrahydro-1H-oxepino[4,5-c]pyrazole;

1-(3-(((1-(6-methoxy-5-methylpyridin-3-yl)-4,5,7,8-tetrahydro-1H-oxepino[4,5-c]pyrazol-3-yl)oxy)methyl)pyrrolidin-1-yl)ethanone;

tert-butyl ((1R,2S)-2-(((1-(6-methoxy-5-methylpyridin-3-yl)-4,5,7,8-tetrahydro-1H-oxepino[4,5-c]pyrazol-3-yl)oxy)methyl)cyclopropyl)carbamate;

tert-butyl 3-fluoro-3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;

tert-butyl 4,4-difluoro-3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

3-((1,3-dimethylpiperidin-3-yl)methoxy)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-((1-(2-methoxyethyl)-3-methylpyrrolidin-3-yl)methoxy)-4,5,7,8-tetrahydro-1H-oxepino[4,5-c]pyrazole;

1-(6-methoxy-5-methylpyridin-3-yl)-3-((pyrrolidin-3-yl)methoxy)-4,5,7,8-tetrahydro-1H-oxepino[4,5-c]pyrazole;

1-(6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(2-(1-(4-isopropylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole;

3-(2-(1-(4-isopropylpiperazin-1-yl)ethyl)pyridin-4-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-(2-(1-((3S,5R)-3,4,5-trimethylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(1-((3-fluoropiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-(((3R,4S)-3-fluoropiperidin-4-yl)methyl)-1H-pyrazol-4-yl)-4,5,7,8-tetrahydro-1H-oxepino[4,5-c]pyrazole;

(S)-tert-butyl 2-(((1-(6-methoxy-5-methylpyridin-3-yl)-4,5,7,8-tetrahydro-1H-oxepino[4,5-c]pyrazol-3-yl)oxy)methyl)morpholine-4-carboxylate;

(S)-1-(6-methoxy-5-methylpyridin-3-yl)-3-(morpholin-2-ylmethoxy)-4,5,7,8-tetrahydro-1H-oxepino[4,5-c]pyrazole;

(4-isopropylpiperazin-1-yl)(2-(1-(6-methoxy-5-methylpyridin-3-yl)-4,5,7,8-tetrahydro-1H-oxepino[4,5-c]pyrazol-3-yl)oxazol-5-yl)methanone;

4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-4-ol; or 3-(1-((4-fluoropiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

or a salt thereof.

In another embodiment, the compound of the invention is:

1-(1-(((2R,4r,6S)-2,6-dimethylpiperidin-4-yl)methyl)-1H-pyrazol-4-yl)-3-(5-fluoro-6-methoxypyridin-3-yl)-4,5,7,8-tetrahydro-1H-oxepino[4,5-c]pyrazole;

3-(1-(((2R,4r,6S)-2,6-dimethylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

N-(2-methoxy-5-(3-(1-methyl-1H-pyrazol-4-yl)-4,5,7,8-tetrahydro-1H-oxepino[4,5-c]pyrazol-1-yl)pyridin-3-yl)methanesulfonamide;

1-(6-methoxy-5-methylpyridin-3-yl)-3-(1-methyl-1H-pyrazol-4-yl)-4,5,7,8-tetrahydro-1H-oxepino[4,5-c]pyrazole;

N-(2-methoxy-5-(1-(1-methyl-1H-pyrazol-4-yl)-4,5,7,8-tetrahydro-1H-oxepino[4,5-c]pyrazol-3-yl)pyridin-3-yl)methanesulfonamide;

1-(2-methoxypyrimidin-5-yl)-3-(1-((1-methylpiperidin-4-yl)methyl)-1H-pyrazol-4-yl)-4,5,7,8-tetrahydro-1H-oxepino[4,5-c]pyrazole;

3-(1-((1-isopropylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

3-(1-((1-isopropylpiperidin-3-yl)methyl)-1H-pyrazol-4-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;

N-(2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)pyridin-3-yl)methanesulfonamide;

2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)nicotinonitrile;

5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxynicotinonitrile;

1-(5-(fluoromethyl)-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-(fluoromethyl)-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;

N-(5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(5-((4-isopropylpiperazin-1-yl)methyl)oxazol-2-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-4,5,7,8-tetrahydro-1H-oxepino[4,5-c]pyrazole-3-carboxamide;

1-(6-methoxy-5-methylpyridin-3-yl)-N-((1-methylpiperidin-3-yl)methyl)-4,5,7,8-tetrahydro-1H-oxepino[4,5-c]pyrazole-3-carboxamide;

1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(R)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(S)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

3-(1-ethyl-5-methyl-1H-pyrazol-4-yl)-1-(1-methyl-1H-pyrazol-4-yl)-4,5,7,8-tetrahydro-1H-oxepino[4,5-c]pyrazole;

1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

(R)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

(S)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

3-(6-methoxy-5-methylpyridin-3-yl)-1-(1-((1-methylpiperidin-4-yl)methyl)-1H-pyrazol-4-yl)-4,5,7,8-tetrahydro-1H-oxepino[4,5-c]pyrazole;

2-(4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol;

5-(3-(1-((1-isopropylpiperidin-3-yl)methyl)-1H-pyrazol-4-yl)-4,5,7,8-tetrahydro-1H-oxepino[4,5-c]pyrazol-1-yl)-2-methoxynicotinonitrile;

3-(5-fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole;

3-(5-fluoro-6-methoxypyridin-3-yl)-1-(1-((1-isopropylpiperidin-4-yl)methyl)-1H-pyrazol-4-yl)-4,5,7,8-tetrahydro-1H-oxepino[4,5-c]pyrazole;

1-(1-((1-isopropylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;

1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

(S)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

(R)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

3-(1-((1-isopropylpyrrolidin-3-yl)methyl)-1H-pyrazol-4-yl)-1-(6-methoxy-5-methylpyridin-3-yl)-4,5,7,8-tetrahydro-1H-oxepino[4,5-c]pyrazole;

4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)-1-methylpiperidin-4-ol;

3-(5-fluoro-6-methoxypyridin-3-yl)-1-(1-((1-methylpiperidin-4-yl)methyl)-1H-pyrazol-4-yl)-4,5,7,8-tetrahydro-1H-oxepino[4,5-c]pyrazole;

3-(1-((4-fluoro-1-methylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

(2R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(2S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

7-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)-1,1-dimethyltetrahydro-1H-oxazolo[3,4-a]pyridin-3(5H)-one;

1-(5-fluoro-6-methoxypyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

1-(6-methoxy-5-methylpyridin-3-yl)-3-(3-methyl-1H-pyrazol-5-yl)-4,5,7,8-tetrahydro-1H-oxepino[4,5-c]pyrazole;

1-(5-fluoro-6-methoxypyridin-3-yl)-3-(5-methyl-1H-pyrazol-4-yl)-4,5,7,8-tetrahydro-1H-oxepino[4,5-c]pyrazole;

3-(1,3-dimethyl-1H-pyrazol-5-yl)-1-(6-methoxy-5-methylpyridin-3-yl)-4,5,7,8-tetrahydro-1H-oxepino[4,5-c]pyrazole;

1-(dimethylamino)-3-(4-(1-(5-fluoro-6-methoxypyridin-3-yl)-4,5,7,8-tetrahydro-1H-oxepino[4,5-c]pyrazol-3-yl)-1H-pyrazol-1-yl)propan-2-ol;

3-(1-((3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

3-(1-(((3R,4S)-3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

5-(3-(1-((1-isopropylpyrrolidin-3-yl)methyl)-1H-pyrazol-4-yl)-4,5,7,8-tetrahydro-1H-oxepino[4,5-c]pyrazol-1-yl)-2-methoxynicotinonitrile;

1-(4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidin-1-yl)propan-1-one;

1-(1-(((2R,4r,6S)-2,6-dimethylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;

N-(5-(3-(1-(((2R,6S)-2,6-dimethyltetrahydro-2H-pyran-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(1-(((2R,4r,6S)-2,6-dimethylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

3-(6-methoxy-5-methylpyridin-3-yl)-1-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

1-(1-((1-isopropylpiperidin-4-yl)methyl)-1H-pyrazol-4-yl)-3-(6-methoxypyridin-3-yl)-4,5,7,8-tetrahydro-1H-oxepino[4,5-c]pyrazole;

1-(6-methoxy-5-methylpyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

N-(5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxypyridin-3-yl)methanesulfonamide;

2-(1-(2-((1-(6-methoxy-5-methylpyridin-3-yl)-4,5,7,8-tetrahydro-1H-oxepino[4,5-c]pyrazol-3-yl)oxy)ethyl)piperidin-4-yl)propan-2-ol;

2-(1-(2-((1-(5-(fluoromethyl)-6-methoxypyridin-3-yl)-4,5,7,8-tetrahydro-1H-oxepino[4,5-c]pyrazol-3-yl)oxy)ethyl)piperidin-4-yl)propan-2-ol;
2-(1-(2-((1-(5-fluoro-6-methoxypyridin-3-yl)-4,5,7,8-tetrahydro-1H-oxepino[4,5-c]pyrazol-3-yl)oxy)ethyl)piperidin-4-yl)propan-2-ol;
5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxynicotinonitrile;
2-(1-(2-((1-(2-methoxypyrimidin-5-yl)-4,5,7,8-tetrahydro-1H-oxepino[4,5-c]pyrazol-3-yl)oxy)ethyl)piperidin-4-yl)propan-2-ol;
tert-butyl 4-(((1-(6-methoxy-5-methylpyridin-3-yl)-4,5,7,8-tetrahydro-1H-oxepino[4,5-c]pyrazol-3-yl)oxy)methyl)piperidine-1-carboxylate;
1-(6-methoxy-5-methylpyridin-3-yl)-3-(piperidin-4-ylmethoxy)-4,5,7,8-tetrahydro-1H-oxepino[4,5-c]pyrazole;
3-((1-isopropylpiperidin-4-yl)methoxy)-1-(6-methoxy-5-methylpyridin-3-yl)-4,5,7,8-tetrahydro-1H-oxepino[4,5-c]pyrazole;
tert-butyl 3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;
tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;
1-(6-methoxy-5-methylpyridin-3-yl)-3-(piperidin-3-ylmethoxy)-4,5,7,8-tetrahydro-1H-oxepino[4,5-c]pyrazole;
(S)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;
(S)-1-(6-methoxy-5-methylpyridin-3-yl)-3-(piperidin-3-ylmethoxy)-4,5,7,8-tetrahydro-1H-oxepino[4,5-c]pyrazole;
(S)-1-(3-(((1-(6-methoxy-5-methylpyridin-3-yl)-4,5,7,8-tetrahydro-1H-oxepino[4,5-c]pyrazol-3-yl)oxy)methyl)piperidin-1-yl)-2-methylpropan-2-ol;
(R)-1-((S)-3-(((1-(6-methoxy-5-methylpyridin-3-yl)-4,5,7,8-tetrahydro-1H-oxepino[4,5-c]pyrazol-3-yl)oxy)methyl)piperidin-1-yl)propan-2-ol;
(S)-1-((S)-3-(((1-(6-methoxy-5-methylpyridin-3-yl)-4,5,7,8-tetrahydro-1H-oxepino[4,5-c]pyrazol-3-yl)oxy)methyl)piperidin-1-yl)propan-2-ol;
(R)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;
(S)-1-(2-(((1-(6-methoxy-5-methylpyridin-3-yl)-4,5,7,8-tetrahydro-1H-oxepino[4,5-c]pyrazol-3-yl)oxy)methyl)morpholino)-2-methylpropan-2-ol;
3-((1-isopropylpyrrolidin-3-yl)methoxy)-1-(6-methoxy-5-methylpyridin-3-yl)-4,5,7,8-tetrahydro-1H-oxepino[4,5-c]pyrazole;
1-(6-methoxy-5-methylpyridin-3-yl)-3-((1-methylpyrrolidin-3-yl)methoxy)-4,5,7,8-tetrahydro-1H-oxepino[4,5-c]pyrazole;
1-(3-(((1-(6-methoxy-5-methylpyridin-3-yl)-4,5,7,8-tetrahydro-1H-oxepino[4,5-c]pyrazol-3-yl)oxy)methyl)pyrrolidin-1-yl)ethanone;
tert-butyl ((1R,2S)-2-(((1-(6-methoxy-5-methylpyridin-3-yl)-4,5,7,8-tetrahydro-1H-oxepino[4,5-c]pyrazol-3-yl)oxy)methyl)cyclopropyl)carbamate;
tert-butyl 3-fluoro-3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;
tert-butyl 4,4-difluoro-3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;
3-((1,3-dimethylpiperidin-3-yl)methoxy)-1-(6-methoxy-5-methylpyridin-3-yl)-4,5,7,8-tetrahydro-1H-oxepino[4,5-c]pyrazole;
1-(6-methoxy-5-methylpyridin-3-yl)-3-((1-(2-methoxyethyl)-3-methylpyrrolidin-3-yl)methoxy)-4,5,7,8-tetrahydro-1H-oxepino[4,5-c]pyrazole;
1-(6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;
1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;
1-(5-fluoro-6-methoxypyridin-3-yl)-3-(2-(1-(4-isopropylpiperazin-1-yl)ethyl)pyridin-4-yl)-4,5,7,8-tetrahydro-1H-oxepino[4,5-c]pyrazole;
1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole;
3-(2-(1-(4-isopropylpiperazin-1-yl)ethyl)pyridin-4-yl)-1-(6-methoxy-5-methylpyridin-3-yl)-4,5,7,8-tetrahydro-1H-oxepino[4,5-c]pyrazole;
1-(6-methoxy-5-methylpyridin-3-yl)-3-(2-(1-((3S,5R)-3,4,5-trimethylpiperazin-1-yl)ethyl)pyridin-4-yl)-4,5,7,8-tetrahydro-1H-oxepino[4,5-c]pyrazole; or
(4-isopropylpiperazin-1-yl)(2-(1-(6-methoxy-5-methylpyridin-3-yl)-4,5,7,8-tetrahydro-1H-oxepino[4,5-c]pyrazol-3-yl)oxazol-5-yl)methanone;
or a salt thereof.

In another embodiment, the compound of the invention is:
(R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;
or a salt thereof.

In further embodiment, the compound of the invention is:

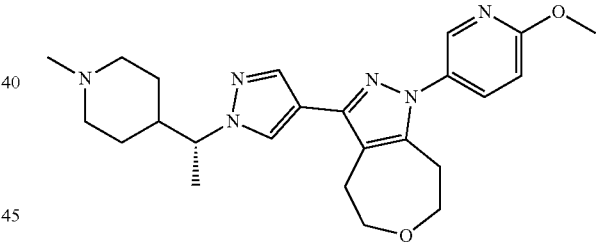

or a salt thereof.

Terms and Definitions

"Alkyl" refers to a saturated hydrocarbon chain having the specified number of member atoms. For example, $C_{1-6}$alkyl refers to an alkyl group having from 1 to 6 member atoms, for example from 1 to 4 member atoms. Alkyl groups may be straight or branched. Representative branched alkyl groups have one, two, or three branches. Alkyl groups may be optionally substituted with one or more substituents as defined herein. Alkyl includes methyl, ethyl, propyl (n-propyl and isopropyl), butyl (n-butyl, isobutyl, and t-butyl), pentyl (n-pentyl, isopentyl, and neopentyl), and hexyl. Alkyl groups may also be part of other groups, for example $C_{1-6}$alkoxy.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, choro, bromo or iodo.

"Heteroatom" refers to a nitrogen or oxygen atom.

"Heterocyclyl", unless otherwise defined, refers to a saturated ring having the specified number of member atoms and containing 1 or 2 heteroatoms as member atoms in the ring.

Heterocyclyl groups may be optionally substituted with one or more substituents as defined herein.

The heterocyclyl groups herein are monocyclic ring systems having 4-, 5- or 6-member atoms or bicyclic ring systems. Monocyclic heterocyclyl includes pyrrolidinyl, piperidinyl, tetrahydropyranyl, piperazinyl and morpholinyl.

"Heteroaryl", unless otherwise defined, refers to an aromatic group containing from 1 to 3 heteroatoms as member atoms. Heteroaryl groups containing more than one heteroatom may contain different heteroatoms. Heteroaryl groups may be optionally substituted as defined herein. The heteroaryl groups herein are monocyclic ring systems. Monocyclic heteroaryl includes pyrazolyl, imidazolyl, oxazolyl, pyridinyl and pyrimidinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group may be unsubstituted or substituted with one or more substituents as defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, salts, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

ACN acetonitrile
AcOH acetic acid
$BF_3OEt_2$ (diethyloxonio)trifluoroborate
Boc tert-butyloxycarbonyl
BuLi butyllithium
$CDCl_3$ deuterochloroform
$Cs_2CO_3$ cesium carbonate
$CHCl_3$ chloroform
MeCN acetonitrile
DCM dichloromethane
DIBAL-H diisobutylaluminum hydride
DIPEA diisopropylethylamine
DMAP 4-dimethylaminopyridine
DMEDA $N^1,N^2$-dimethylethane-1,2-diamine
DMF N,N-dimethylformamide
DMSO dimethylsulfoxide
DMSO-$d_6$ deuterated dimethylsulfoxide
EDTA 2,2',2'',2'''-(ethane-1,2-diylbis(azanetriyl))tetraacetic acid
$Et_3N$ triethylamine
$Et_2O$ diethylether
EtOH ethanol
EtOAc ethyl acetate
GC gas chromatography
h hour(s)
HATU N-[(dimethylamino)-1H-1,2,3-triazolo-[4,5-b]pyridin-1-ylmethylene]-N-methylmethanaminium hexafluorophosphate N-oxide
HCl hydrochloric acid
$HCO_2H$ formic acid
HPLC high performance liquid chromatography
IPA isopropylalcohol
$K_2CO_3$ potassium carbonate
LCMS liquid chromatography-mass spectrometry
LiCl lithium chloride
LiOH lithium hydroxide
M molar (concentration)
MeCN acetonitrile
MeI Methyl iodide
MeOD deuterated methanol
MeOH methanol
2-MeTHF 2-methyltetrahydrofuran
MDAP mass directed autopreparative chromatography
$MgSO_4$ magnesium sulfate
min minute(s)
MS mass spectrometry
$Na_2CO_3$ sodium carbonate
NaH sodium hydride
$NaHCO_3$ sodium hydrogen carbonate
$Na(OAc)_3BH$ sodium triacetoxyborohydride
NaOH sodium hydroxide
$Na_2SO_4$ sodium sulfate NBS N-bromosuccinimide
NEt₃ triethylamine
NH₃ ammonia
NH₄Cl ammonium chloride
NMP N-methyl-2-pyrrolidone
NMR nuclear magnetic resonance
PdCl₂(dppf)DCM [1,1'-bis(diphenylphosphino)ferrocene]dichloropalladium(II) DCM adduct
PdCl₂(dtbpf) [1,1'-bis(di-tert-butylphosphino)ferrocene]dichloropalladium (II)
PPh₃ triphenylphosphine
ppm parts per million
RuCl[(R,R)— [N-[(1R,2R)-2-(Amino-κN)-1,2-diphenylethyl]-4-Tsdpen](p-cymene) methylbenzenesulfonamidato-κN]chloro[(1,2,3,4,5,6-η)-1-methyl-4-(1-methylethyl)benzene]-ruthenium
SCX strong cation exchange
SPE solid phase extraction
STAB sodium triacetoxyborohydride
TBAF tetra-n-butylammonium fluoride
TBDPS tert-butyldiphenylsilyl
TEA triethylamine
TFA trifluoroacetic acid
THF tetrahydrofuran
TMEDA tetramethylethylenediamine
TMS trimethylsilyl
TMSCl trimethylsilylchloride
T₃P 2,4,6-tripropyl-1,3,5,2,4,6-trioxatriphosphinane 2,4,6-trioxide
UPLC ultra performance liquid chromatography
Xphos 2-dicyclohexylphosphino-2',4',6'-triisopropylbiphenyl
Xphos Pd G2 chloro(2-dicyclohexylphosphino-2',4',6'-triisopropyl-1,1'-biphenyl)[2-(2'-amino-1,1'-biphenyl)]palladium(II)

Included within the scope of the "compounds of the invention" are all polymorphs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. The compounds of the invention may exist in solvated and unsolvated form. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of the invention, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^{2}H$, $^{3}H$, $^{11}C$, $^{14}C$ and $^{18}F$.

The compounds of the invention may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of the invention, or in any chemical structure illustrated herein, is not specified the structure is intended to encompass any stereoisomer and all mixtures thereof. Thus, compounds of the invention containing one or more chiral center may be used as racemic mixtures, enantiomerically enriched mixtures, or as enantiomerically pure individual stereoisomers.

Individual stereoisomers of a compound of the invention which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral enviornment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds of the invention may also contain centers of geometric asymmetry. Where the stereochemistry of a center of geometric asymmetry present in a compound of the invention, or in any chemical structure illustrated herein, is not specified, the structure is intended to encompass the trans geometric isomer, the cis geometric isomer, and all mixtures thereof. Likewise, all tautomeric forms are also included whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to a compound of formula (I) as the free acid or free base. In another embodiment, the invention is directed to a compound of formula (I) or a salt thereof. In a further embodiment, the invention is directed to a compound of formula (I) or a pharmaceutically acceptable salt thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts may impart greater stability or solubility to the molecule thereby facilitating formulation into a dosage form.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form, or a non-pharmaceutically acceptable salt, with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic schemes are set out below and then specific compounds of the invention are prepared in the Examples section.

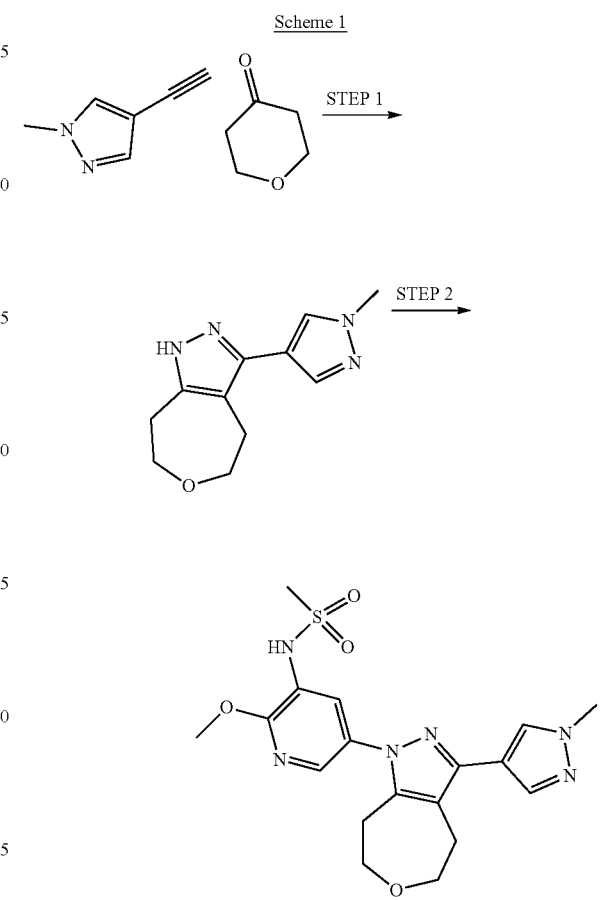

Step 1 may be carried out by treating with p-toluenesulfonhydrazide and a suitable alkyne, such as 4-ethynyl-1-methyl-1H-pyrazole, in the presence of a suitable mixture of solvents, such as MeOH and dioxane, with a suitable base, for example $Cs_2CO_3$, at a suitable temperature, such as 110° C., for a suitable time period, such as 15 h, then isolating using a suitable method, such as column chromatography, dissolving in a suitable solvent, such as dioxane, and treating with a suitable Lewis acid, such as (diethyloxonio)trifluoroborate and stirring for a suitable time period, such as 4 h. Step 2 may be carried out by treating with a suitable boronic acid or a suitable boronate ester, such as N-(2-methoxy-5-(4,4,5,5-tetramethyl-1,3,2-dioxaborolan-2-yl)pyridin-3-yl) methanesulfonamide, and copper (II) acetate and DMAP, in a suitable solvent, such as dry MeCN, heating open to the air at a suitable temperature, such as 50° C., for a suitable time, such as 15 h.

Scheme 2

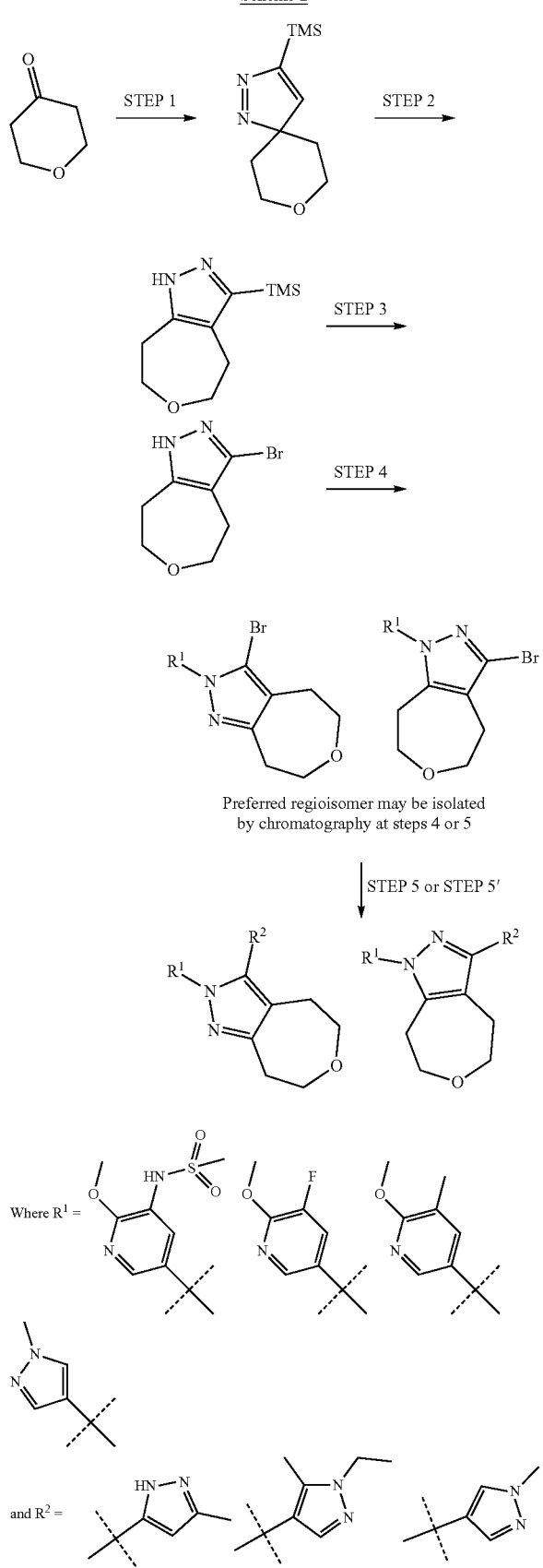

Preferred regioisomer may be isolated by chromatography at steps 4 or 5

STEP 5 or STEP 5'

Where R² =
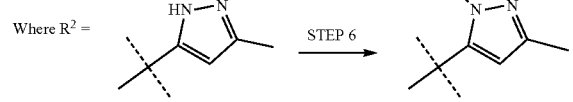

STEP 6

Step 1 may be carried out by treating with p-toluenesulfonhydrazide and ethynyltrimethylsilane, in the presence of a suitable mixture of solvents, such as MeOH and dioxane, with a suitable base, for example $Cs_2CO_3$, at a suitable temperature, such as 110° C., for a suitable time period, such as 15 h.

Step 2 may be carried out by treating with (diethyloxonio) trifluoroborate, in the presence of a suitable solvent, such as dioxane, for a suitable time period, such as 4 h.

Step 3 may be carried out by treating with a suitable brominating agent, such as NBS, in suitable solvent, such as MeCN, at a suitable temperature, such as 25° C., for a suitable time period, such as 4 h.

Step 4 may be carried out by treating with an aryl boronic acid, such as (6-methoxy-5-methylpyridin-3-yl)boronic acid, or an aryl boronate ester, such as 1-methyl-4-(4,4,5,5-tetramethyl-1,3,2-dioxaborolan-2-yl)-1H-pyrazole, in the presence of a suitable base, such as DMAP, and copper (II) acetate, and a suitable solvent, such as MeCN, heating open to the air at a suitable temperature, such as 40° C., for a suitable time period, such as overnight.

Step 5 may be carried out by treating with an aryl boronic acid, such as (1-(tert-butoxycarbonyl)-3-methyl-1H-pyrazol-5-yl)boronic acid, or an aryl boronate ester, such as N-(2-methoxy-5-(4,4,5,5-tetramethyl-1,3,2-dioxaborolan-2-yl)pyridin-3-yl)methanesulfonamide or 3-methyl-4-(4,4,5,5-tetramethyl-1,3,2-dioxaborolan-2-yl)-1H-pyrazole, in the presence of a suitable palladium catalyst and phosphine ligand if required, such as chloro-[2'-(dimethylamino)-2-biphenylyl]-(dinorbornylphosphine)-palladium or XphosPd G2, in the presence of a suitable base, such as tripotassium phosphate, in a suitable solvent or mixture of solvents, such as water and dioxane, and heating at a suitable temperature such as 80° C. or 100° C., using a suitable heating method, such as a microwave, for a suitable time period, such as 60 min or 120 min.

Step 5' may be carried out by treating with a Negishi coupling partner, such as 4-bromo-1-ethyl-5-methyl-1H-pyrazole, that has been separately treated with a solution of nBuLi in hexanes, in the presence of a suitable solvent, such as THF, at a suitable temperature, such as −78° C., for a suitable time period, such as 30 min, then allowing to warm to room temperature, over a suitable period of time, such as 30 min, then treating with a solution of $ZnCl_2$ in a suitable solvent, such as THF, in the presence of a suitable palladium catalyst and phosphine ligand if required, such as $PdCl_2(PPh_3)_2$, and heating at a suitable temperature, such as 80° C., for a suitable time period, such as 7.5 h.

Step 6 may be carried out by treating with a suitable methylating reagent, such as MeI, in the presence of a suitable base, such as a 60% dispersion of NaH on mineral oils, in a suitable solvent, such as THF, at a suitable temperature, such as room temperature, over a suitable time period, such as 2 h.

Scheme 3

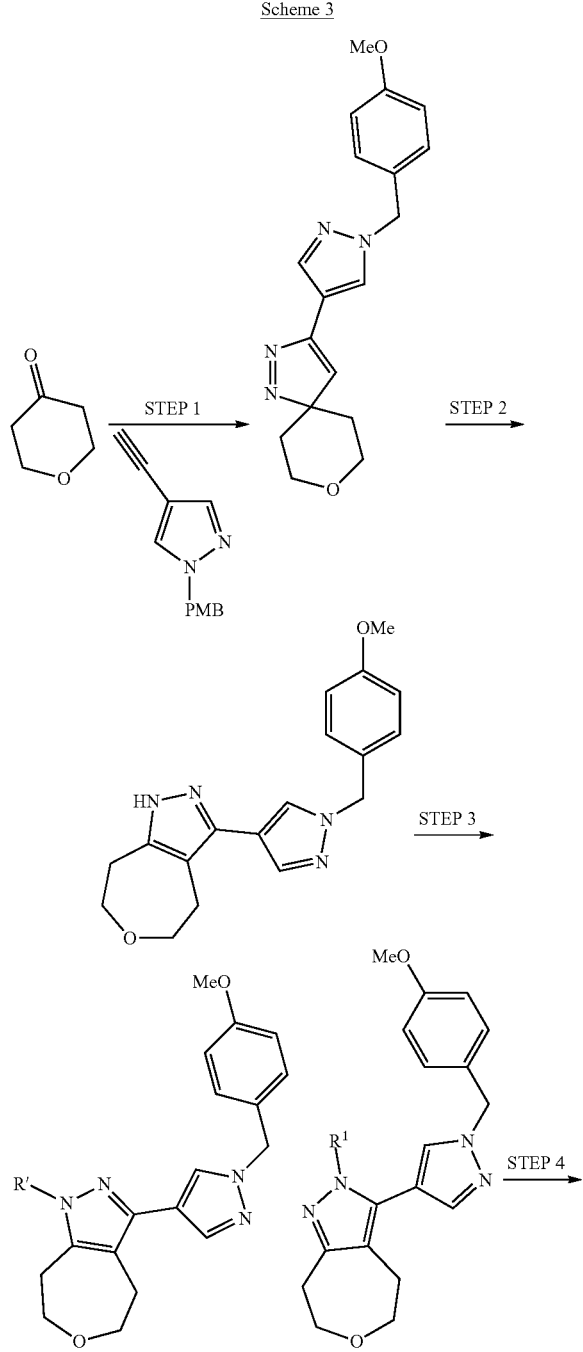

Preferred regioisomer may be isolated by chromatography after Steps 3 or 4.

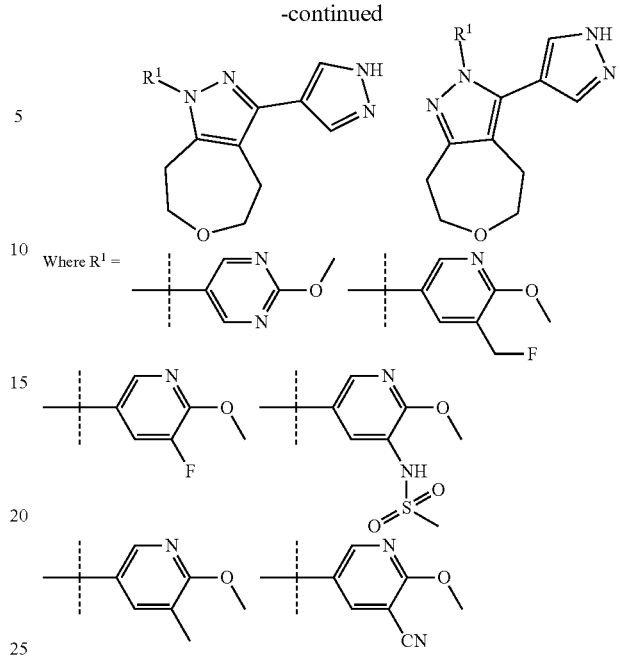

Step 1 may be carried out by treating with p-toluenesulfonhydrazide, in the presence of a suitable mixture of solvents, such MeOH and dioxane, with a suitable base, for example $Cs_2CO_3$, at a suitable temperature, such as 110° C., for a suitable time period, such as 15 h.

Step 2 may be carried out by treating with (diethyloxonio) trifluoroborate, in the presence of a suitable solvent, such as dioxane, for a suitable time period, such as 4 h.

Step 3 may be carried out by treating with an aryl boronic acid, such as (2-methoxypyrimidin-5-yl) boronic acid or (6-methoxy-5-methylpyridin-3-yl)boronic acid or (5-fluoro-6-methoxypyridin-3-yl)boronic acid, or an aryl boronate ester, such as 3-(fluoromethyl)-2-methoxy-5-(4,4,5,5-tetramethyl-1,3,2-dioxaborolan-2-yl)pyridine, N-(2-methoxy-5-(4,4,5,5-tetramethyl-1,3,2-dioxaborolan-2-yl)pyridin-3-yl)methanesulfonamide or 2-methoxy-5-(4,4,5,5-tetramethyl-1,3,2-dioxaborolan-2-yl)nicotinonitrile or N-(2-methoxy-5-(4,4,5,5-tetramethyl-1,3,2-dioxaborolan-2-yl) pyridin-3-yl)methanesulfonamide, in the presence of DMAP and copper (II) acetate, and a suitable solvent, such as MeCN, heating open to the air at a suitable temperature, such as room temperature, or at 40° C., for a suitable time period, such as overnight to four days.

Step 4 may be carried out by treating with a suitable acid, such as TFA, in the presence of a suitable solvent, such as DCM, heating at a suitable temperature, such as 70° C., using a heating method, such as a microwave, for a suitable time period, such as 3 to 6 h.

Scheme 4
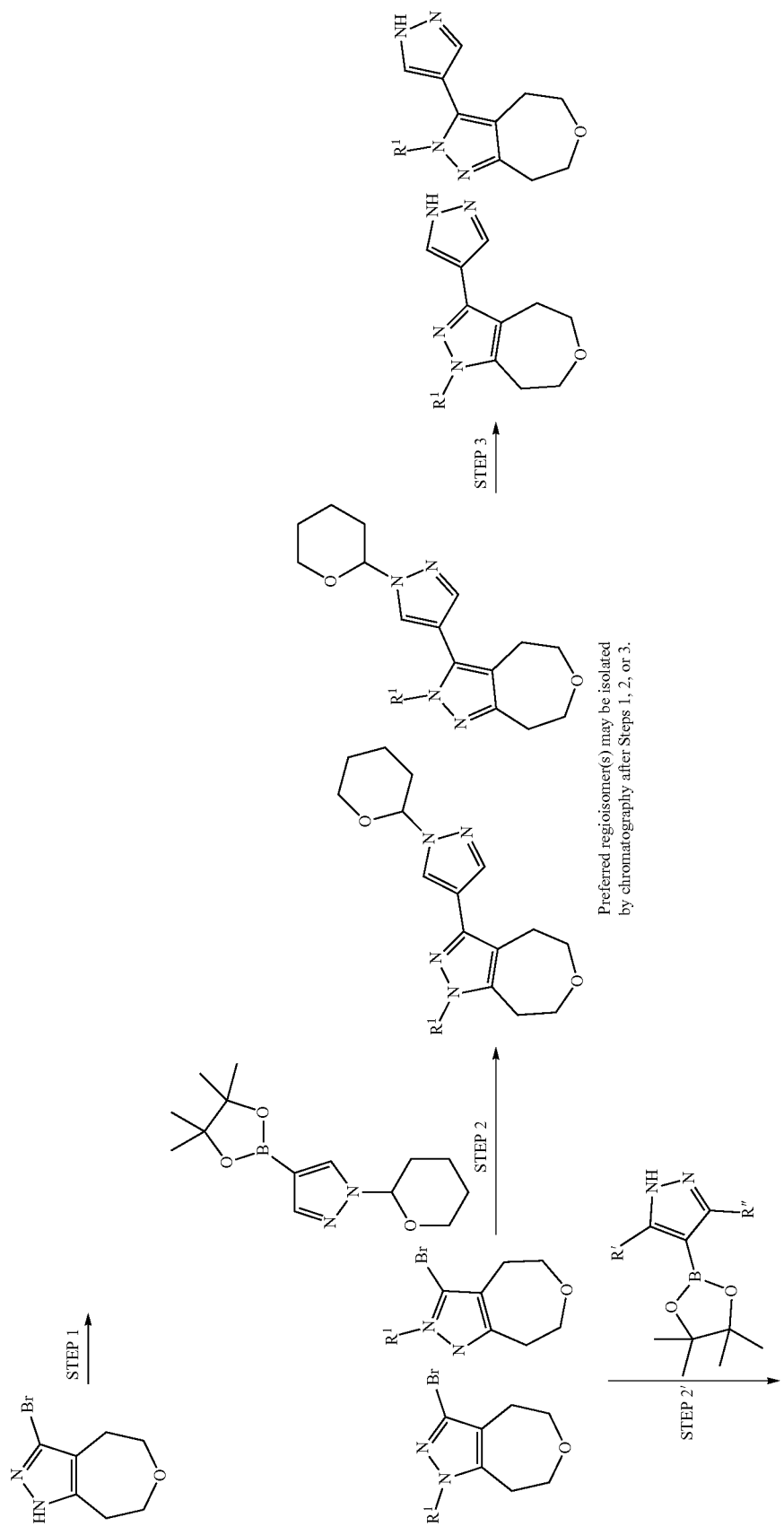

-continued
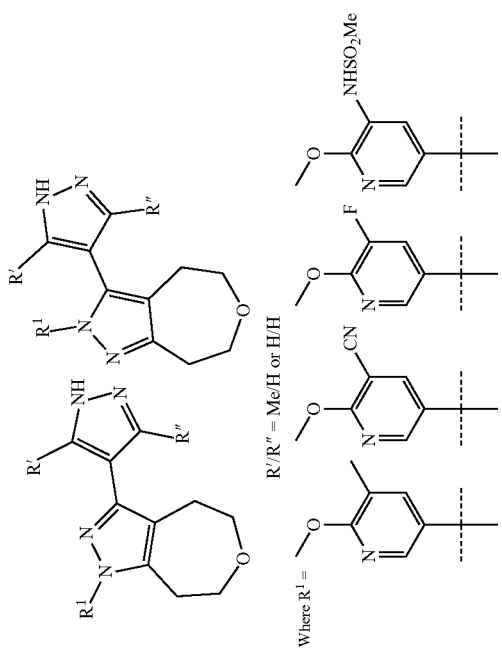

Step 1 may be carried out by treating with an aryl boronic acid, such as (6-methoxy-5-methylpyridin-3-yl)boronic acid, or an aryl boronate ester, such as 1-methyl-4-(4,4,5,5-tetramethyl-1,3,2-dioxaborolan-2-yl)-1H-pyrazole, in the presence of a suitable solvent, such MeCN, in the presence of copper (II) acetate, at a suitable temperature, such as room temperature, or heating at 80° C., for a suitable time period, such as 4 h, or overnight.

Step 2 may be carried out by treating with 1-(tetrahydro-2H-pyran-2-yl)-4-(4,4,5,5-tetramethyl-1,3,2-dioxaborolan-2-yl)-1H-pyrazole, in the presence of a suitable palladium catalyst and phosphine ligand if required, such as Xphos Pd G2, in the presence of a suitable base, such as tripotassium phosphate, in a suitable mixture of solvents, such as water and dioxane, and heating at a suitable temperature, such as 80° C., for a suitable time period, such as 3 h.

Step 2' may be carried out by treating with a suitable boronate ester, such as 3-methyl-4-(4,4,5,5-tetramethyl-1,3,2-dioxaborolan-2-yl)-1H-pyrazole, and a suitable palladium catalyst and ligand system, such as XPhos Pd G2 with added dicyclohexyl(2',4',6'-triisopropyl-[1,1'-biphenyl]-2-yl)phosphine, in the presence of a suitable base, such as potassium phosphate, in a suitable solvent or mixture of solvents, such as EtOH and water, heating at a suitable temperature, such as 100° C., for a suitable time period, such as overnight.

Step 3 may be carried out by treating with a suitable acid, such as HCl, in a suitable solvent, such as MeOH, at a suitable temperature, such as room temperature, for a suitable time period, such as over a weekend.

Scheme 5

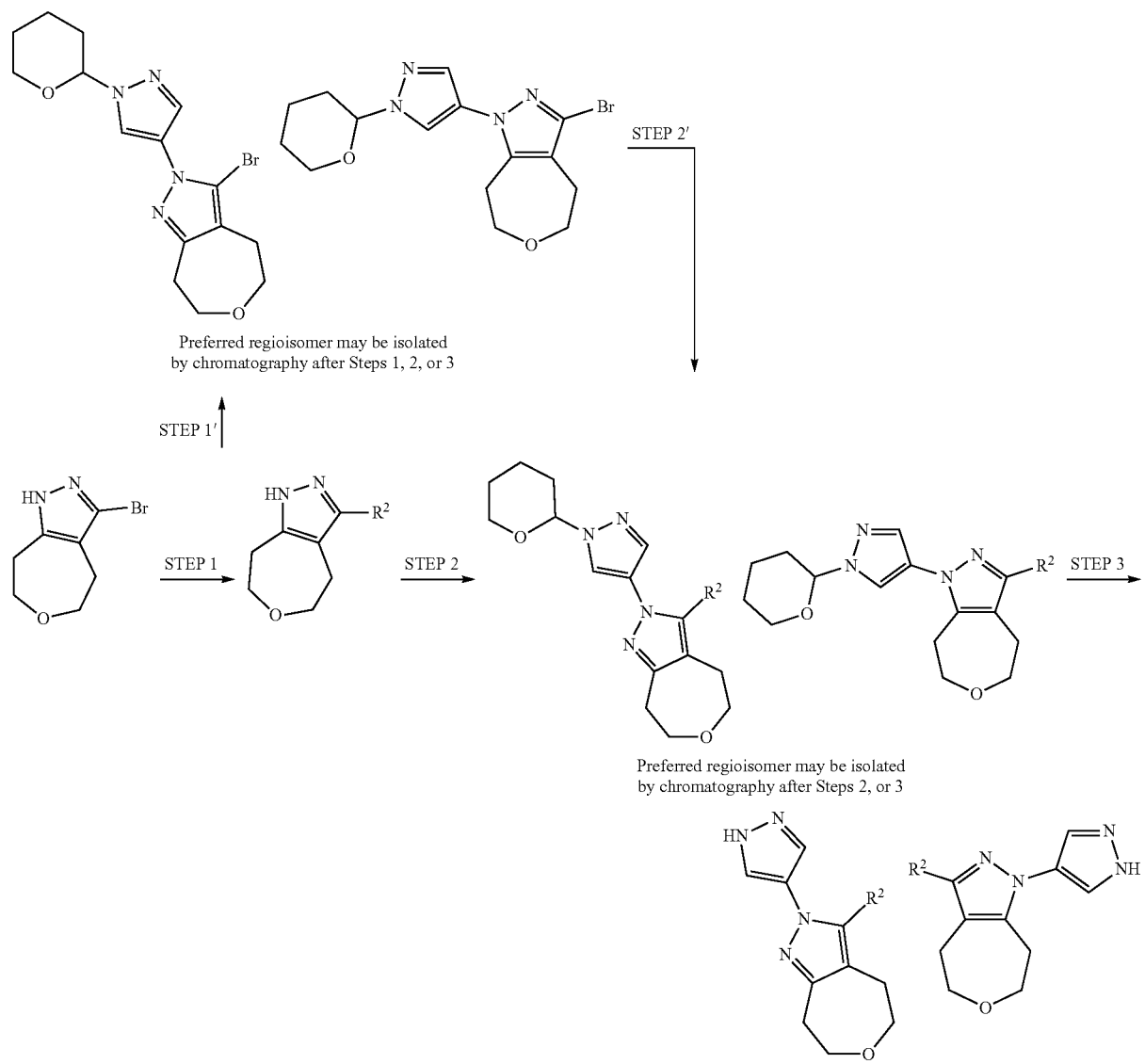

-continued

Where R² = 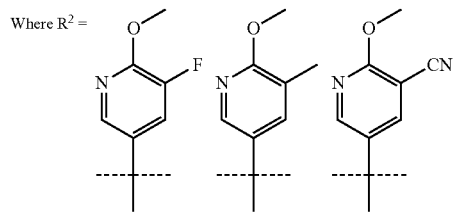

Step 1 may be carried out by treating with an aryl boronic acid, such as (6-methoxy-5-methylpyridin-3-yl)boronic acid, or an aryl boronate ester, in the presence of a suitable palladium catalyst and phosphine ligand if required, such as Xphos Pd G2, in the presence of a suitable base, such as tripotassium phosphate, in a suitable mixture of solvents, such as water and dioxane, and heating at a suitable temperature, such as 80° C., for a suitable time period, such as 2 h.

Step 1' may be carried out by treating with 1-(tetrahydro-2H-pyran-2-yl)-4-(4,4,5,5-tetramethyl-1,3,2-dioxaborolan-2-yl)-1H-pyrazole in the presence of DMAP and copper (II) acetate, and a suitable solvent or mixture of solvents, such as dry MeCN and EtOH, in the presence of powdered molecular sieves, heating open to the air at a suitable temperature, such as 80° C., for a suitable time period, such as up to 72 h.

Step 2 may be carried out by treating with 1-(tetrahydro-2H-pyran-2-yl)-4-(4,4,5,5-tetramethyl-1,3,2-dioxaborolan-2-yl)-1H-pyrazole in the presence of DMAP and copper (II) acetate, and a suitable solvent, such as dry MeCN, or a suitable mixture of solvents, such as IPA and MeCN, heating open to the air at a suitable temperature, such as 40° C., for a suitable time period, such as 48 h.

Step 2' may be carried out by treating with an aryl boronic acid, such as (5-fluoro-6-methoxypyridin-3-yl)boronic acid, or an aryl boronate ester, in the presence of a suitable palladium catalyst and phosphine ligand if required, such as Xphos Pd G2, in the presence of a suitable base, such as tripotassium phosphate, in a suitable mixture of solvents, such as water and dioxane, and heating at a suitable temperature, such as 80° C., for a suitable time period, such as 2 h.

Step 3 may be carried out by treating with a suitable acid, such as 2 M aqueous HCl, in the presence of a suitable solvent, such as MeOH, at a suitable temperature, such as room temperature, for a suitable time period, such as over a weekend.

Scheme 6

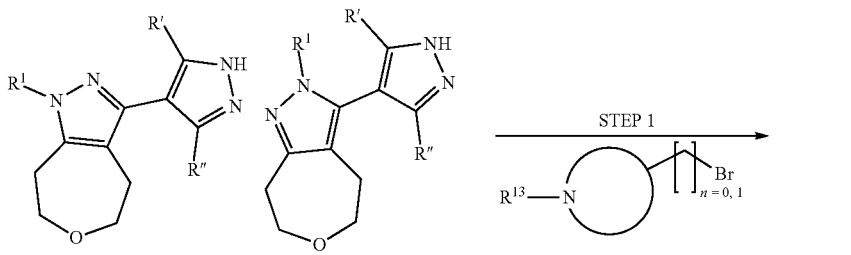

Preferred regioisomer may be isolated by chromatography after Steps 1, 2 or 3.

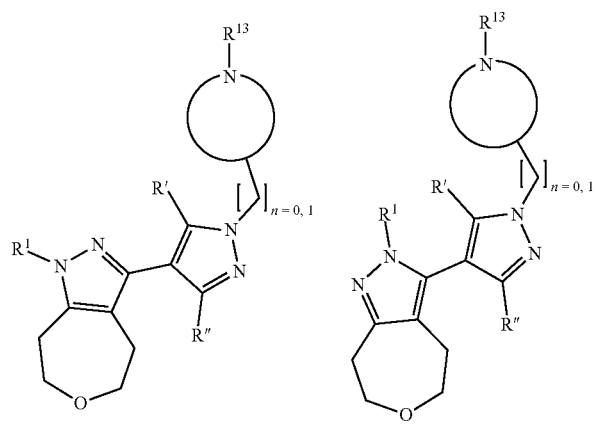

Where R¹³ = Boc | STEP 2

-continued

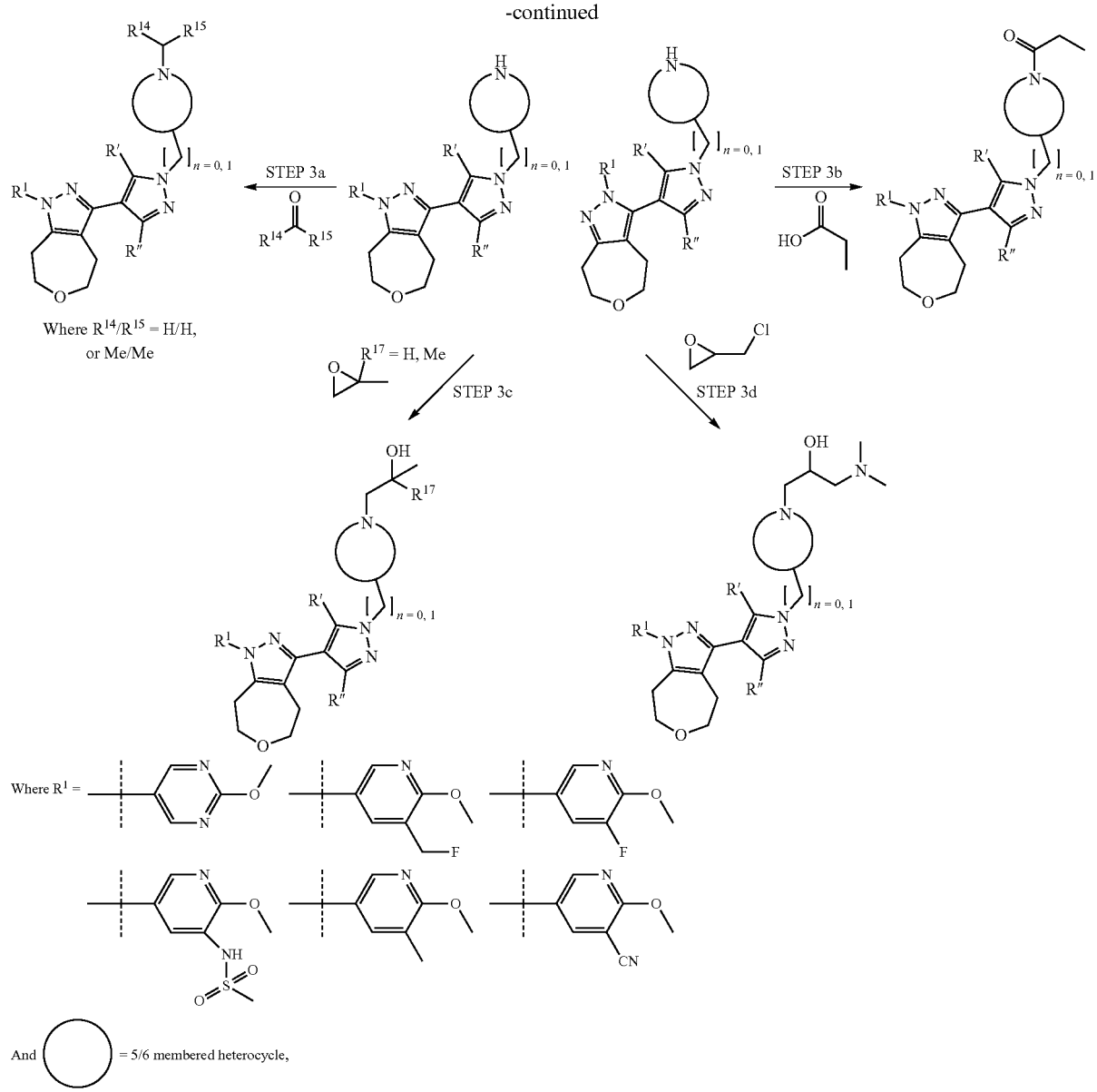

Step 1 may be carried out by treating with a suitable alkylating agent, such as tert-butyl 4-(bromomethyl)piperidine-1-carboxylate or tert-butyl 3-(bromomethyl)piperidine-1-carboxylate or tert-butyl 3-(bromomethyl)pyrrolidine-1-carboxylate or 3-(bromomethyl)-1-isopropylpyrrolidine, in the presence of a suitable base, such as a 600% suspension of NaH on mineral oils or potassium carbonate, in the presence of a suitable solvent, such as DMF, at a suitable temperature, such as room temperature, or heating at 50° C., for a suitable time period, such as 3 h or over a weekend.

Step 2 may be carried out by treating with a suitable acid, such as TFA, in the presence of a suitable solvent, such as DCM, at a suitable temperature, such as room temperature, or 70° C., for a suitable time period, such as 30 min to 15 h, or leaving to stand for up to five days.

Step 3a may be carried out by treating with a suitable aldehyde or ketone, such as formaldehyde or acetone respectively, in a suitable solvent, such as DMF, at a suitable temperature, such as room temperature or heating at 60° C., for a suitable amount of time such as 30 min to over a weekend, before adding a suitable reducing agent, such as STAB, and leaving to stir at a suitable temperature, such as room temperature, in the presence or absence of a suitable base, such as DIPEA, for a suitable time period, such as 2 h or overnight.

Step 3b may be carried out by treating with a suitable carboxylic acid, such as propionic acid, in the presence of a suitable base, such as DIPEA, and a suitable amide coupling reagent, such as HATU, in a suitable solvent, such as DMF, at a suitable temperature, such as room temperature, for a suitable time period, such as 3 h. Alternatively Step 3b may be achieved by treating with a suitable acid chloride, such as propionyl chloride, in the presence of a suitable base, such as triethylamine, in a suitable solvent, such as DCM, at a suitable temperature, such as room temperature, for a suitable time period, such as overnight.

Step 3c may be carried out by treating with a suitable epoxide, such as 2,2-dimethyloxirane, (R)-2-methyloxirane, or (S)-2-methyloxirane, in a suitable solvent, such as EtOH, in the presence of a suitable base, such as DIPEA, at a suitable temperature, such heating at 70° C. or 90° C., for a suitable amount of time such as 1 h or 3 h.

Step 3d may be carried out by treating with a suitable halomethyl oxirane, such as 2-(chloromethyl)oxirane, in the presence of a suitable base, such as $Cs_2CO_3$, in a suitable solvent, such as DMF, heating to a suitable temperature, such as 60° C., using a heating method such as a microwave, for a suitable amount of time, such as 1 h 45 min, then treating with a suitable amine, such as a 2 M solution of dimethylamine in THF, and heating to a suitable temperature, such as 70° C., for a suitable amount of time, such as 7 h.

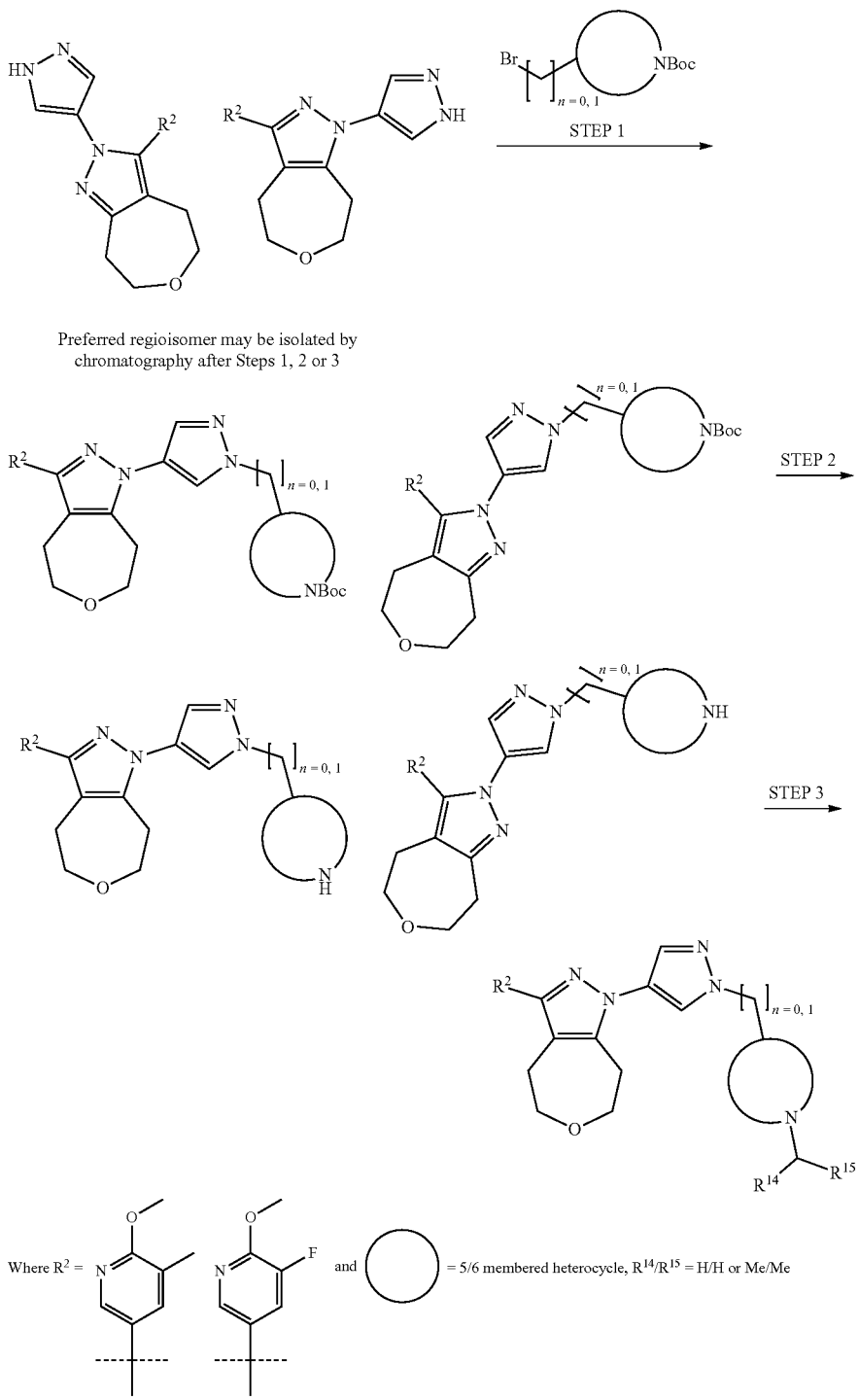

Scheme 7

Step 1 may be carried out by treating with a suitable alkylating agent, such as tert-butyl 4-(bromomethyl)piperidine-1-carboxylate or tert-butyl 3-(bromomethyl)piperidine-1-carboxylate or tert-butyl 3-(bromomethyl)pyrrolidine-1-carboxylate or tert-butyl 3-bromopyrrolidine-1-carboxylate, in the presence of a suitable base, such as NaH or potassium carbonate, in the presence of a suitable solvent, such as DMF, at a suitable temperature, such as room temperature, or heating at 50° C., for a suitable time period, such as 3 to 24 h.

Step 2 may be carried out by treating with a suitable acid, such as TFA, in the presence of a suitable solvent, such as DCM, heating at a suitable temperature such as 70° C., using a suitable method of heating, such as a microwave, for a suitable time period, such as 15 min.

Step 3 may be carried out by treating with a suitable aldehyde or ketone, such as formaldehyde or acetone respectively, in a suitable solvent, such as DMF, at a suitable temperature, such as room temperature or heating at 60° C., for a suitable amount of time such as 30 min to over a weekend, before adding a suitable reducing agent, such as STAB, and leaving to stir at a suitable temperature, such as room temperature, in the presence or absence of a suitable base, such as DIPEA, for a suitable time period, such as 4 h or overnight.

Scheme 8

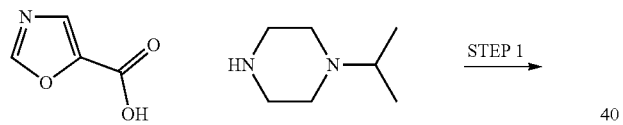

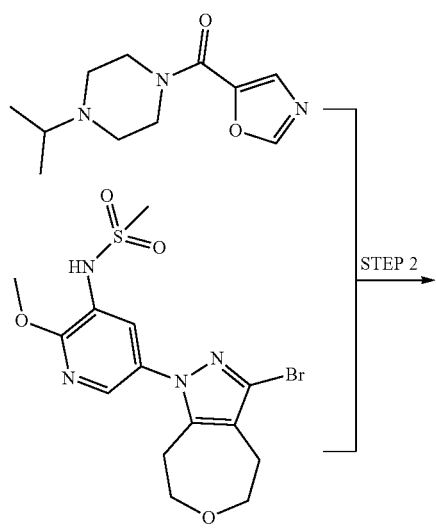

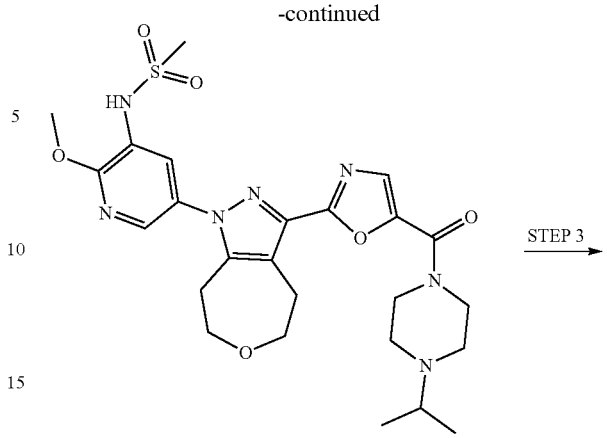

Step 1 may be carried out with a suitable heteroaryl carboxylic acid, such as oxazole-5-carboxylic acid, in the presence of a suitable base, such as DIPEA, with a suitable amine, such as 1-isopropylpiperazine, in the presence of a suitable solvent, such as THF, using a suitable amide coupling reagent, such as T3P, at a suitable temperature, such as room temperature, for a suitable time, such as overnight.

Step 2 may be carried out by treating with pivalic acid, a suitable palladium catalyst and phosphine ligand, such as palladium (II) chloride and Xphos, in the presence of a suitable base, such as potassium carbonate, in the presence of a suitable solvent, such as toluene, and heating in a sealed container, such as a microwave vial, at a suitable temperature, such as 110° C., for a suitable time period, such as 96 h.

Step 3 may be carried out by treating with a suitable reducing agent, such DIBAL-H, in the presence of a suitable solvent, such as THF, at a suitable temperature, such as −78° C., for a suitable time period, such as 5 h, and allowing to warm to a suitable temperature, such as room temperature overnight.

Scheme 9

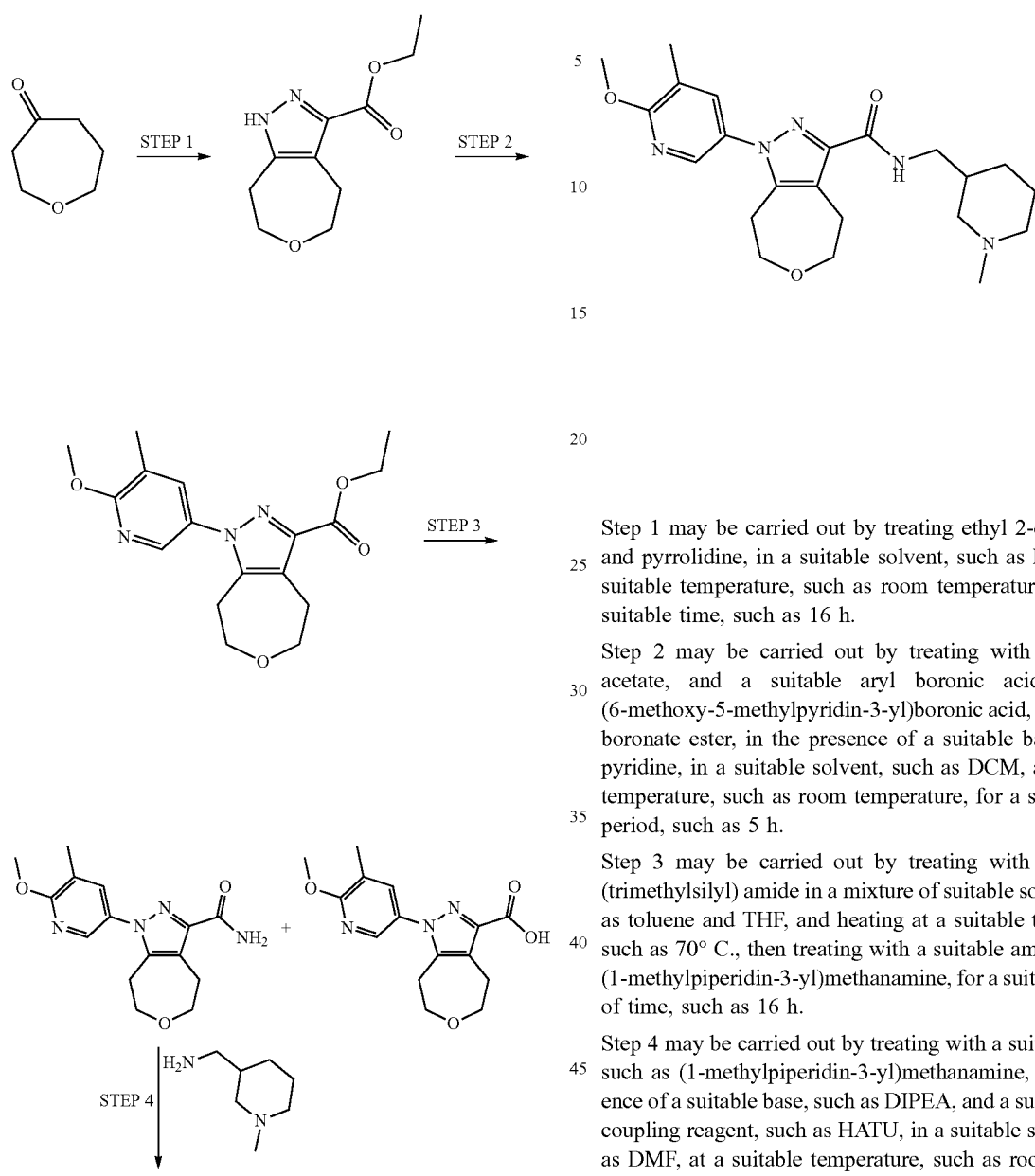

Step 1 may be carried out by treating ethyl 2-diazoacetate and pyrrolidine, in a suitable solvent, such as DMSO, at a suitable temperature, such as room temperature, and for a suitable time, such as 16 h.

Step 2 may be carried out by treating with copper (II) acetate, and a suitable aryl boronic acid, such as (6-methoxy-5-methylpyridin-3-yl)boronic acid, or a suitable boronate ester, in the presence of a suitable base, such as pyridine, in a suitable solvent, such as DCM, at a suitable temperature, such as room temperature, for a suitable time period, such as 5 h.

Step 3 may be carried out by treating with sodium bis(trimethylsilyl) amide in a mixture of suitable solvents, such as toluene and THF, and heating at a suitable temperature, such as 70° C., then treating with a suitable amine, such as (1-methylpiperidin-3-yl)methanamine, for a suitable amount of time, such as 16 h.

Step 4 may be carried out by treating with a suitable amine, such as (1-methylpiperidin-3-yl)methanamine, in the presence of a suitable base, such as DIPEA, and a suitable amide coupling reagent, such as HATU, in a suitable solvent, such as DMF, at a suitable temperature, such as room temperature, for a suitable time period, such as 16 h.

Scheme 10

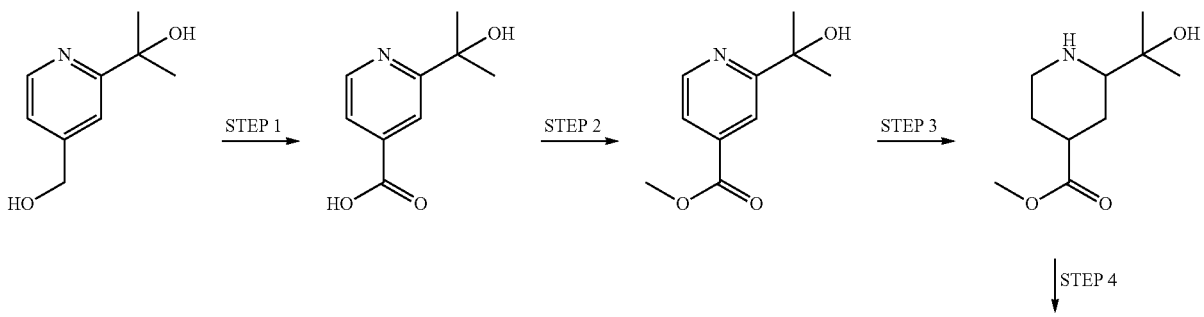

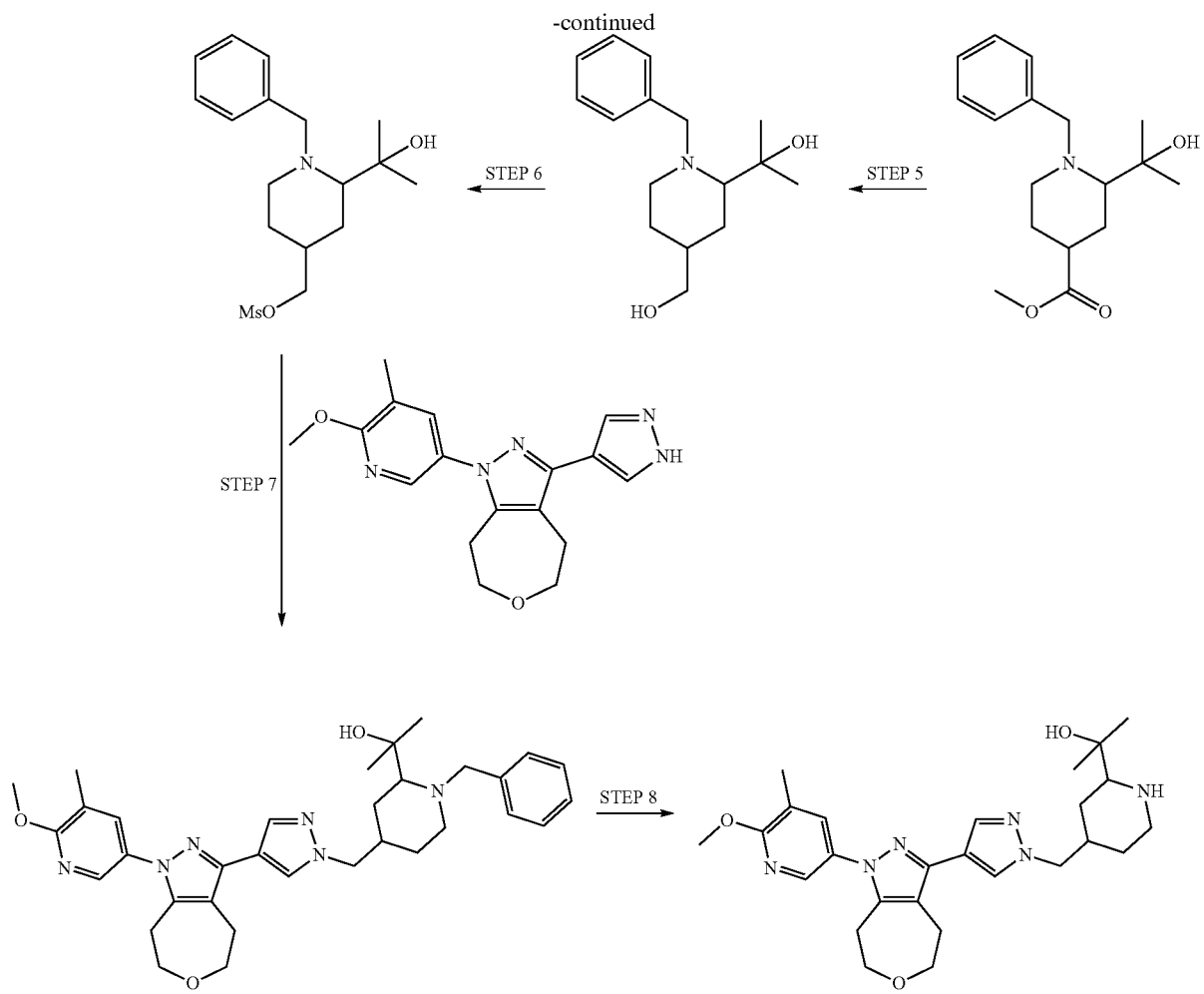

Step 1 may be carried out by treating with a suitable oxidising agent, such as potassium permanganate, in the presence of a suitable solvent, such as water, at a suitable temperature, such as room temperature, for a suitable period of time, such as 1 h. tp 2 may be carried out by treating with a suitable alkylating agent, such as TMS-diazomethane, in the presence of a suitable solvent or mixture of solvents, such as MeOH and toluene, at a suitable temperature, such as room temperature, for a suitable period of time, such as 1 h.

Step 3 may be carried out in the presence of a suitable solvent, such as AcOH, and a suitable hydrogenation catalyst, such as platinum (IV) oxide, in the presence of hydrogen, at a suitable temperature, such as room temperature, and a suitable pressure, such as 4 bar, for a suitable period of time, such as 4 h.

Step 4 may be carried out by treating with for example an alkylating agent, such as benzyl bromide, in the presence of a suitable base, such as potassium carbonate, in a suitable solvent, such as MeCN, at a suitable temperature, such as room temperature, for a suitable period of time, such as overnight.

Step 5 may be carried out by treating with a suitable reducing agent, such as lithium borohydride, in the presence of a suitable solvent, such as THF, at a suitable temperature, such as room temperature, for a suitable period of time, such as 3 h.

Step 6 may be carried out by treating with methanesulfonyl chloride, in the presence of a suitable base, such as TEA, and a suitable solvent, such as THF, at a suitable temperature, such as room temperature, for a suitable period of time, such as 2 h.

Step 7 may be carried out by treating with a suitable alkylating partner, such as 1-(6-methoxy-5-methylpyridin-3-yl)-3-(1H-pyrazol-4-yl)-4,5,7,8-tetrahydro-1H-oxepino[4,5-c]pyrazole, in the presence of a suitable base, such as NaH, in a suitable solvent, such as DMF, at a suitable temperature, such as room temperature, for a suitable period of time, such as 15 h.

Step 8 may be carried out in the presence of a suitable solvent, or mixture of solvents, such as MeOH and EtOAc, and a suitable hydrogenation catalyst, such as palladium hydroxide oxide, using suitable hydrogenation equipment, such as an H-Cube continuous-flow hydrogenation reactor, in the presence of hydrogen, at a suitable temperature, such as 25° C., and a suitable pressure, such as 50 bar.

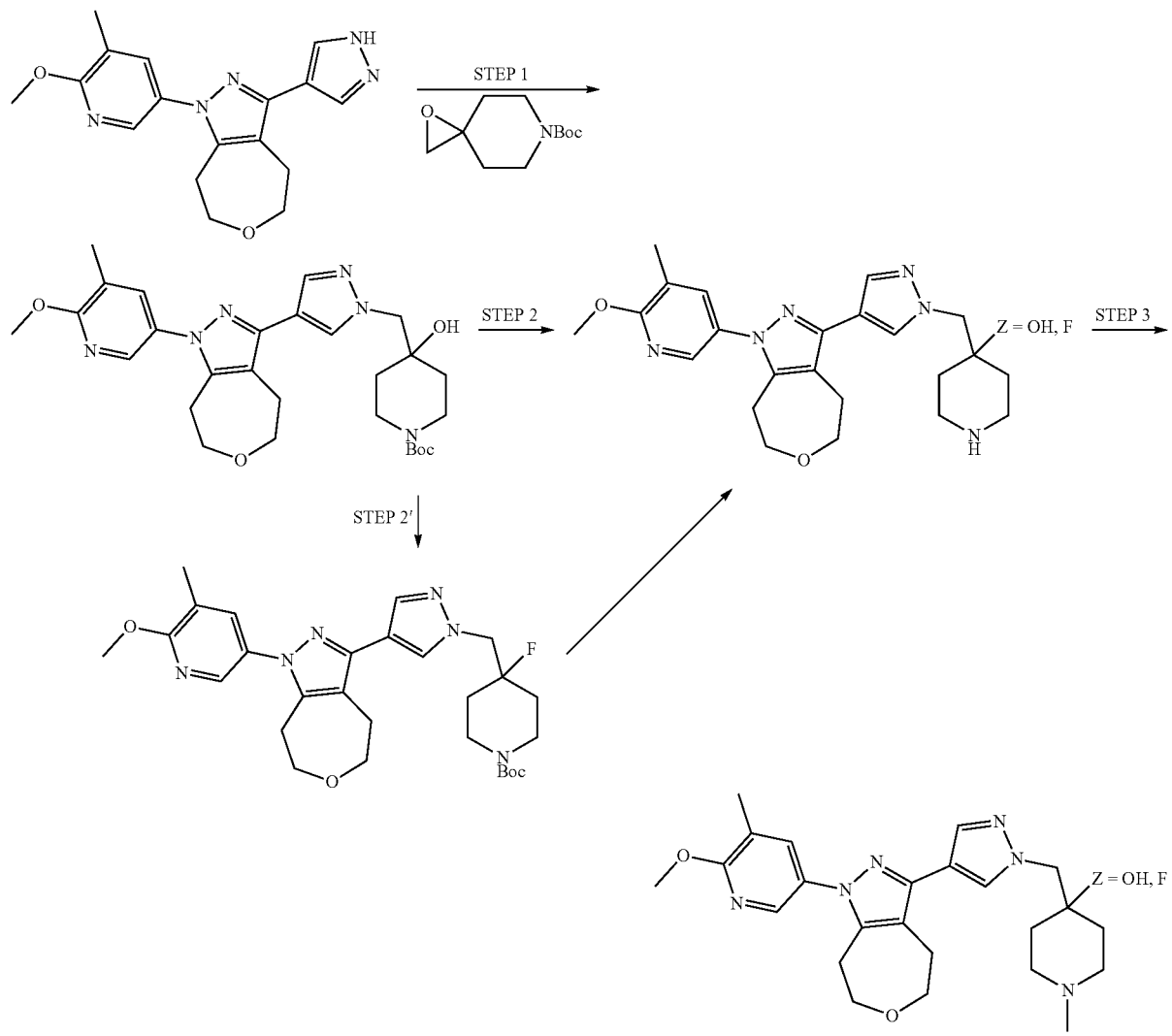

Step 1 may be carried out by treating with a suitable epoxide, such as tert-butyl 1-oxa-6-azaspiro[2.5]octane-6-carboxylate, in the presence of a suitable base, such as cesium carbonate, in a suitable solvent, such as DMF, at a suitable temperature, such as heating at 100° C., using a suitable method of heating, such as a microwave, for a suitable period of time, such as 1 to 1.5 h.

Step 2 may be carried out by treating with a suitable acid, such as TFA, in the presence of a suitable solvent, such as DCM, at a suitable temperature, such as room temperature, for a suitable time period, such as 15 h.

Step 2' may be carried out by treating with a suitable fluorinating reagent, such as a solution of Deoxo-Fluor® in a suitable solvent, such as THF, in the presence of a suitable solvent, such as DCM, at a suitable temperature, such as −78° C., for a suitable time period, such as 24 h.

Step 3 may be carried out by treating with a suitable aldehyde, such as formaldehyde, in a suitable solvent, such as DMF, at a suitable temperature, such as room temperature, for a suitable amount of time such as 1 h, before adding a suitable reducing agent, such as STAB, and leaving to stir at a suitable temperature, such as room temperature, for a suitable time period, such as 3 h.

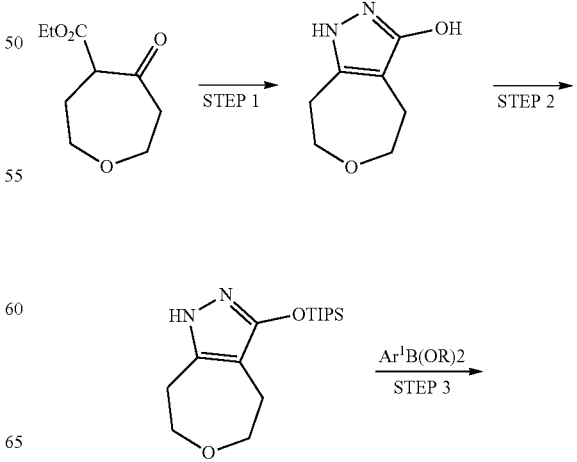

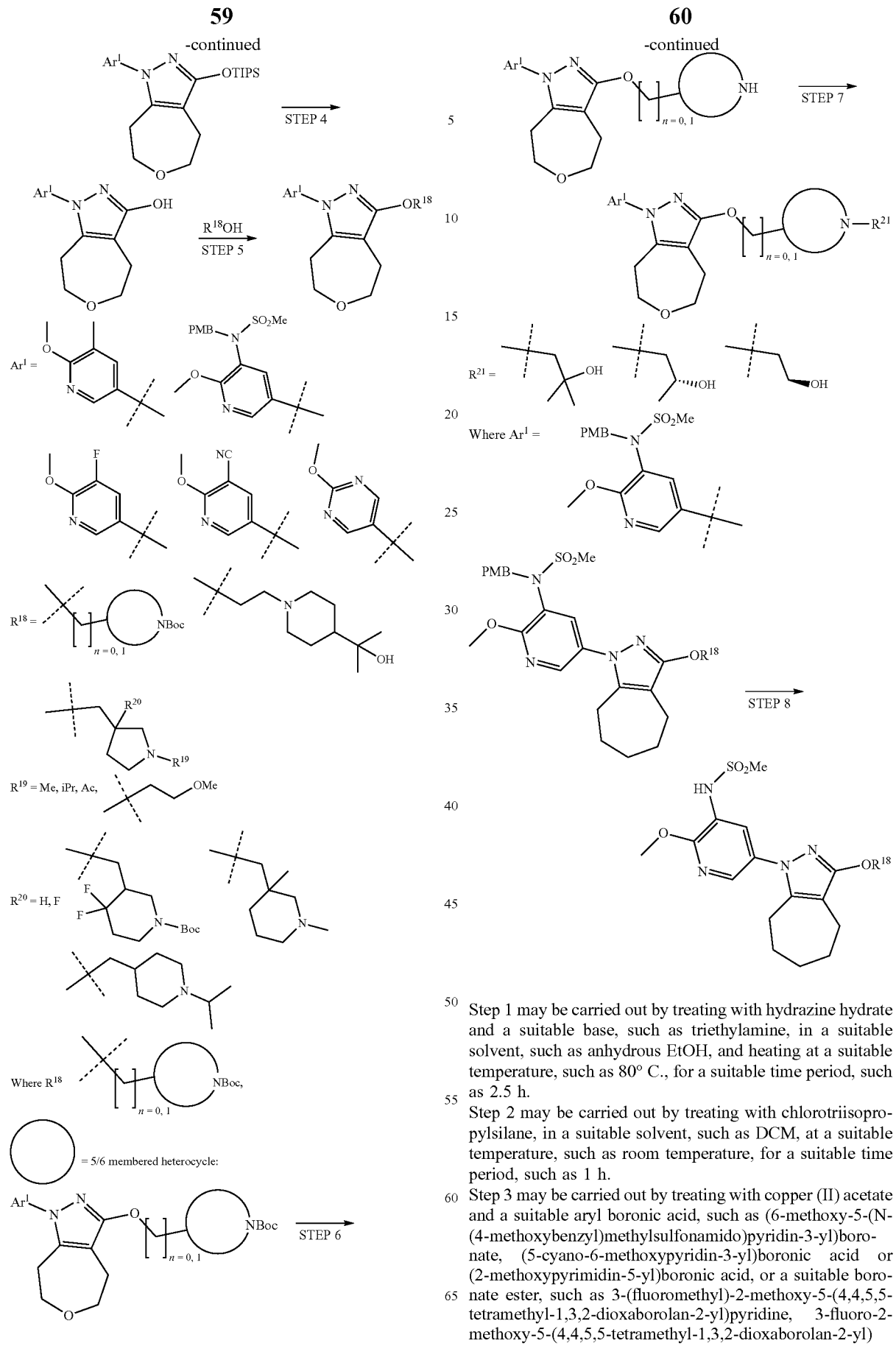

Step 1 may be carried out by treating with hydrazine hydrate and a suitable base, such as triethylamine, in a suitable solvent, such as anhydrous EtOH, and heating at a suitable temperature, such as 80° C., for a suitable time period, such as 2.5 h.

Step 2 may be carried out by treating with chlorotriisopropylsilane, in a suitable solvent, such as DCM, at a suitable temperature, such as room temperature, for a suitable time period, such as 1 h.

Step 3 may be carried out by treating with copper (II) acetate and a suitable aryl boronic acid, such as (6-methoxy-5-(N-(4-methoxybenzyl)methylsulfonamido)pyridin-3-yl)boronate, (5-cyano-6-methoxypyridin-3-yl)boronic acid or (2-methoxypyrimidin-5-yl)boronic acid, or a suitable boronate ester, such as 3-(fluoromethyl)-2-methoxy-5-(4,4,5,5-tetramethyl-1,3,2-dioxaborolan-2-yl)pyridine, 3-fluoro-2-methoxy-5-(4,4,5,5-tetramethyl-1,3,2-dioxaborolan-2-yl)

pyridine or 2-methoxy-3-methyl-5-(4,4,5,5-tetramethyl-1,3,2-dioxaborolan-2-yl)pyridine, in the presence of a suitable base, such as DMAP, in a suitable solvent, such as MeCN, stirring open to the air at a suitable temperature, such as room temperature or 40° C., for a suitable time period, such as 18 h.

Step 4 may be carried out by treating with a solution of TBAF in a suitable solvent, such as THF, and stirring for a suitable period of time, such as 90 min.

Step 5 may be carried out by treating with a suitable Mitsunobu coupling reagent, such as 2-(tributylphosphoranylidene)acetonitrile, and a suitable alcohol, such as 2-(1-(2-hydroxyethyl)piperidin-4-yl)propan-2-ol, tert-butyl 4-(hydroxymethyl)piperidine-1-carboxylate, (1-isopropylpiperidin-4-yl)methanol, tert-butyl 3-(hydroxymethyl)pyrrolidine-1-carboxylate (S)-tert-butyl 2-(hydroxymethyl)morpholine-4-carboxylate or (1-isopropylpyrrolidin-3-yl)methanol, in the presence of a suitable solvent, such as toluene, heating at a suitable temperature, such as 100° C. or 120° C., using a suitable heating method, such as microwave or conventional heating, for a suitable time period, such as 1 h to 4 h.

Step 6 may be carried out by treating with a suitable acid, such as TFA, in the presence of a suitable solvent, such as DCM, and stirring at a suitable temperature, such as room temperature, for a suitable time period, such as 30 min.

Step 7 may be carried out by treating with a suitable alkylating agent, such as 1-chloro-2-methylpropan-2-ol, (R)-2-methyloxirane, (S)-2-methyloxirane or 1-chloro-2-methylpropan-2-ol, in the presence of a suitable base, such as DIPEA, and a suitable solvent, such as EtOH, and heating at a suitable temperature, such as 90° C., using a suitable heating method, such as a microwave, for a suitable time period, such as 1 h to 8 h.

Step 8 may be carried out by treating with a suitable acid, such as TFA, in the presence of a suitable solvent, such as DCM, and heating at a suitable temperature, such as 60° C., using a suitable heating method, such as a microwave, for a suitable time period, such as 105 min.

Scheme 13

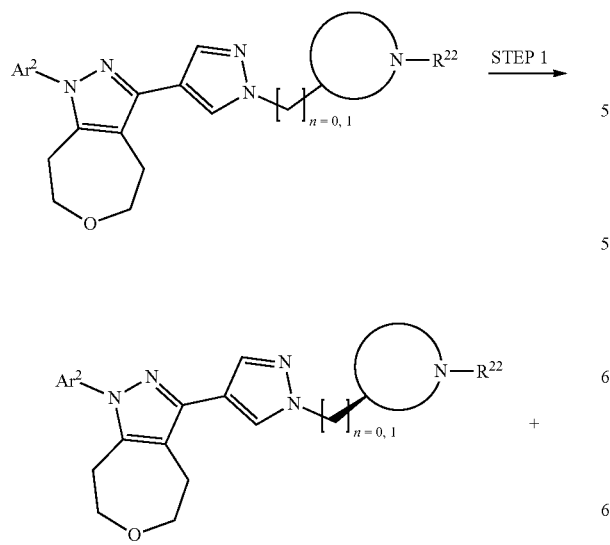

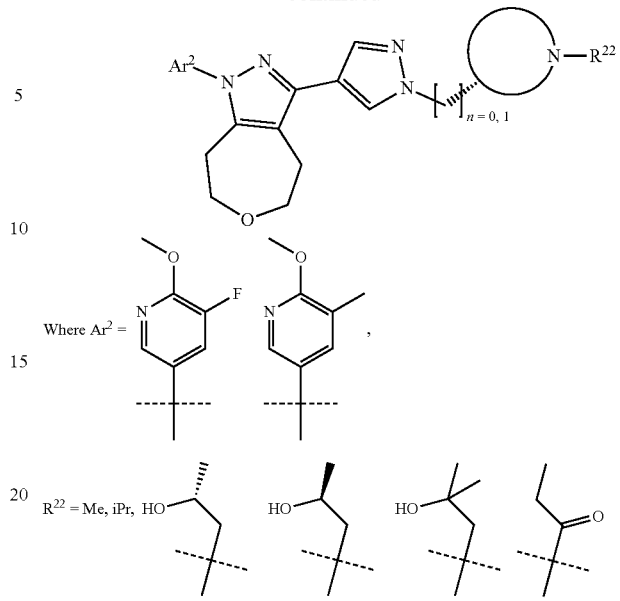

Step 1 may be carried out using suitable chiral HPLC purification conditions, using a suitable chiral column to separate into the constituent enantiomers or diastereomers, such as a 30 mm×25 cm Chiralpak IC column or Chiralpak AD-H column, eluting with a suitable solvent system, such as 40% EtOH (+0.2% isopropylamine)/heptane (+0.2% isopropylamine), with a suitable flow rate, such as 30 mL/min.

Scheme 14

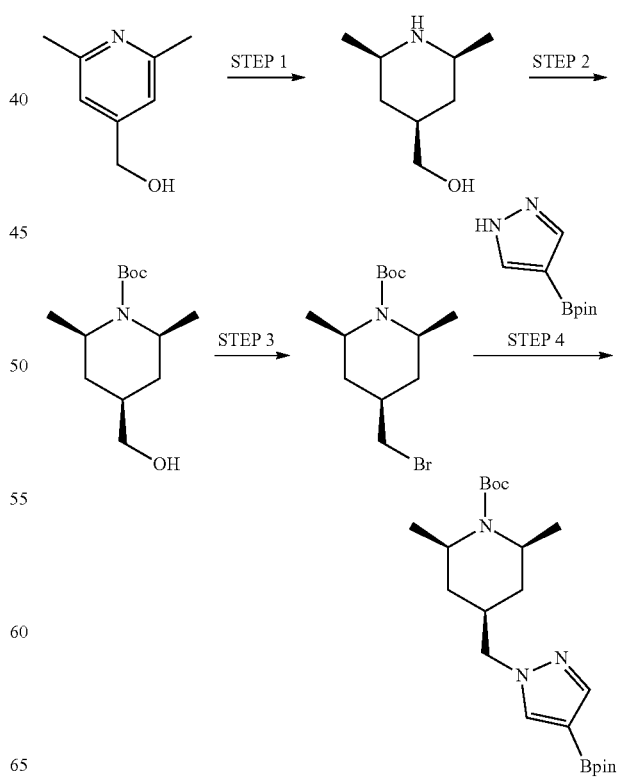

Step 1 may be carried out by stirring in the presence of hydrogen gas at a suitable pressure, such as 70 psi, in the presence of a suitable catalyst, such as Rh on alumina, in a suitable solvent, such as EtOH, in the presence of a suitable acid, such as AcOH, over a suitable time period, such as 48 h.

Step 2 may be carried out by treating with di-tert-butyl dicarbonate in the presence of a suitable base, such as $Na_2CO_3$, in a suitable solvent or mixture of solvents, such as dioxane and water, at a suitable temperature, such as 80° C., for a suitable time period, such as 24 h.

Step 3 may be carried out by treating with a suitable mixture of brominating reagents, such as triphenylphosphine and $CBr_4$, in a suitable solvent, such as DCM, for a suitable time period, such as 4 h.

Step 4 may be carried out by treating with 4-(4,4,5,5-tetramethyl-1,3,2-dioxaborolan-2-yl)-1H-pyrazole in a suitable solvent, such as MeCN, in the presence of a suitable base, such as $Cs_2CO_3$, and stirring at a suitable temperature, such as 60° C., for a suitable period of time, such as 16 h.

Scheme 15

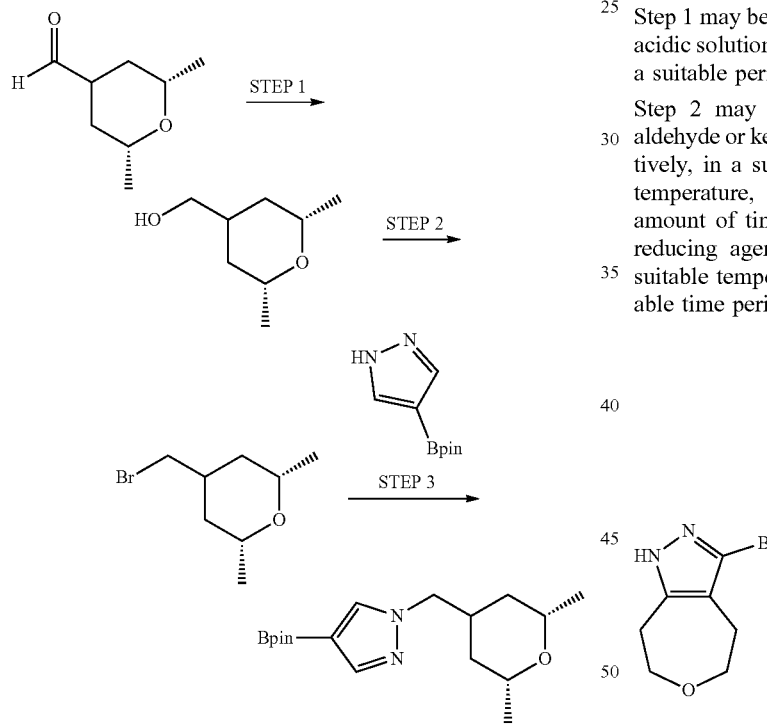

Step 1 may be carried out by treating with a suitable reducing agent, such as $NaBH_4$, in a suitable solvent, such as EtOH, at a suitable temperature, such as 0° C., then allowing to warm to room temperature over a suitable time period, such as 1 h.

Step 2 may be carried out by treating with a suitable brominating agent, such as $PBr_3$, in a suitable solvent, such as DCM, and stirring at a suitable temperature, such as room temperature, for a suitable time period, such as 4 h.

Step 3 may be carried out by treating with a suitable base, such as $Cs_2CO_3$, in a suitable solvent, such as MeCN, heating at a suitable temperature, such as 80° C., for a suitable amount of time, such as 24 h.

Scheme 16

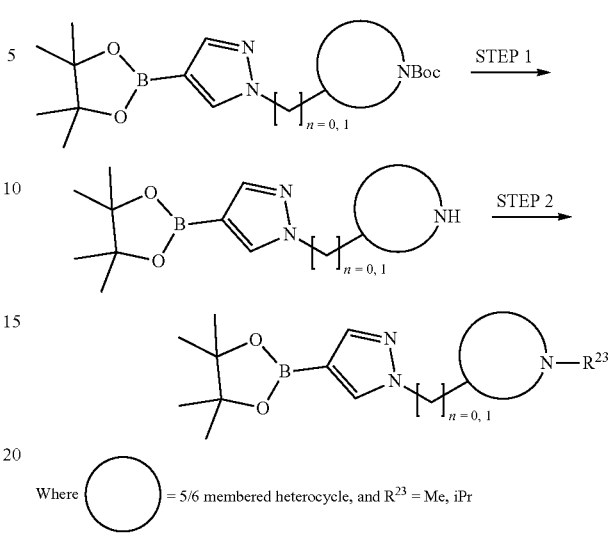

Where ◯ = 5/6 membered heterocycle, and $R^{23}$ = Me, iPr

Step 1 may be carried out by treating with a suitable acid, or acidic solution, such as a 4 M solution of HCl in dioxane, for a suitable period of time, such as 16 h.

Step 2 may be carried out by treating with a suitable aldehyde or ketone, such as formaldehyde or acetone respectively, in a suitable solvent, such as MeCN, at a suitable temperature, such as room temperature, for a suitable amount of time such as 15 min, before adding a suitable reducing agent, such as STAB, and leaving to stir at a suitable temperature, such as room temperature, for a suitable time period, such as 16 h.

Scheme 17

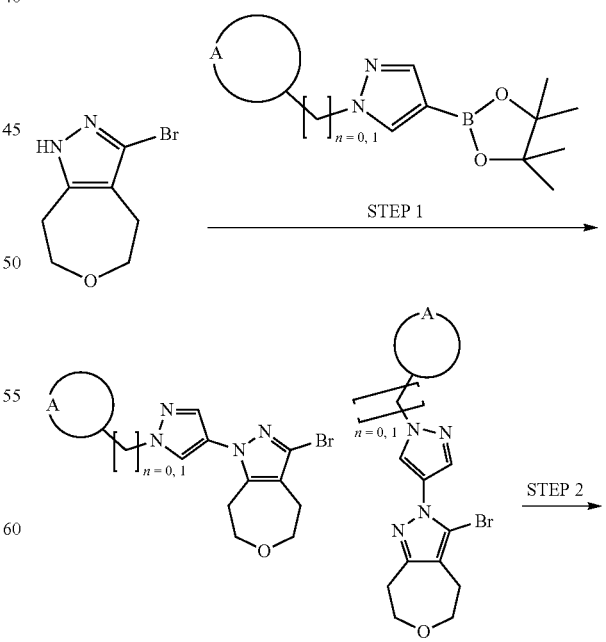

Preferred regioisomer may be isolated by chromotography after Steps 1, 2, 3, or 4

-continued

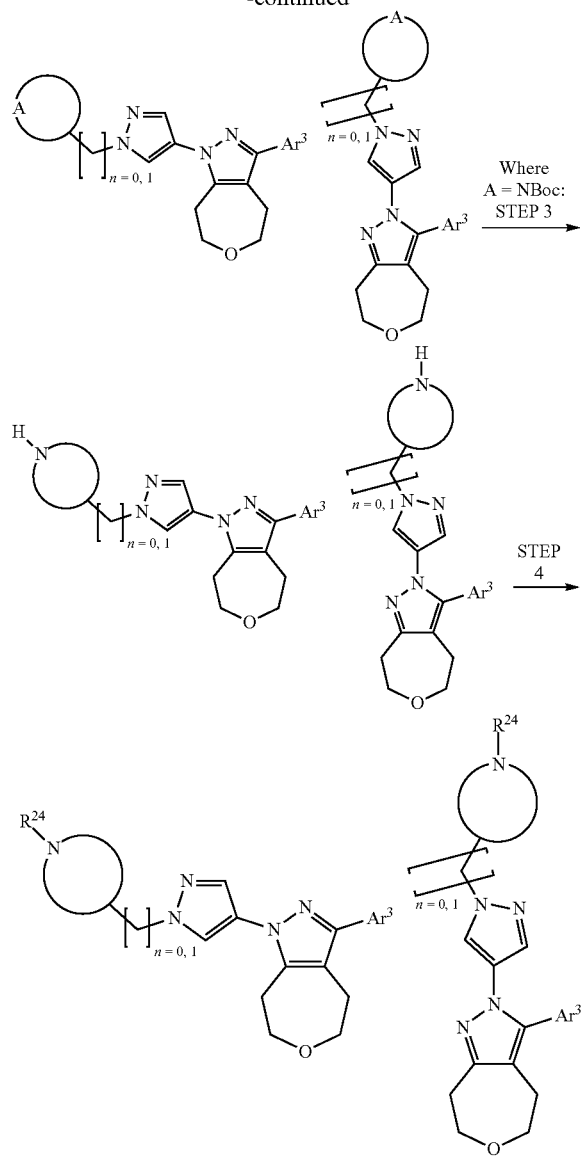

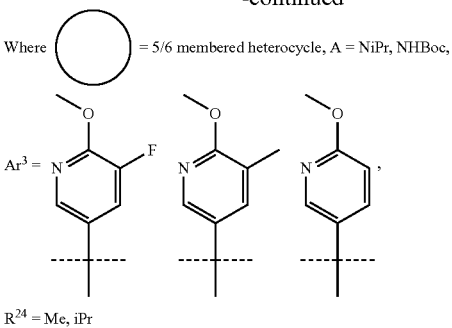

Step 1 may be undertaken by treating with copper (II) acetate, and a suitable boronate ester, such as tert-butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate, or 1-isopropyl-4-((4-(4,4,5,5-tetramethyl-1,3,2-dioxaborolan-2-yl)-1H-pyrazol-1-yl)methyl)piperidine, in the presence of a suitable base, such as DMAP or triethylamine, stirring open to the air, in a suitable solvent, such as MeCN, or mixture of solvents, such as EtOH and MeCN, at a suitable temperature, such as 40° C. or 80° C., for a suitable time period, such as overnight to 4 d.

Step 2 may be undertaken by treating with a suitable boronic acid, such as (5-fluoro-6-methoxypyridin-3-yl)boronic acid or (6-methoxy-5-methylpyridin-3-yl)boronic acid, and a suitable base, such as potassium phosphate, in the presence of a suitable palladium catalyst and ligand system, such as XPhos Pd G2, in a suitable solvent or mixture of solvents, such as 1,4-dioxane and water, heating at a suitable temperature, such as 100° C., using a suitable method of heating, such as a microwave, for a suitable amount of time, such as 1 h.

Step 3 may be carried out by treating with a suitable acid, such as TFA, in the presence of a suitable solvent, such as DCM, at a suitable temperature, such as room temperature, for a suitable time period, such as 15 h.

Step 4 may be carried out by treating with an appropriate alkylating agent, ketone, or aldehyde such as a 37% by weight aqueous solution of formaldehyde, stirring for an appropriate period of time, such as 1 h, then treating with an appropriate reducing agent, such as STAB and stirring for a suitable period of time, such as 3 h.

Scheme 18

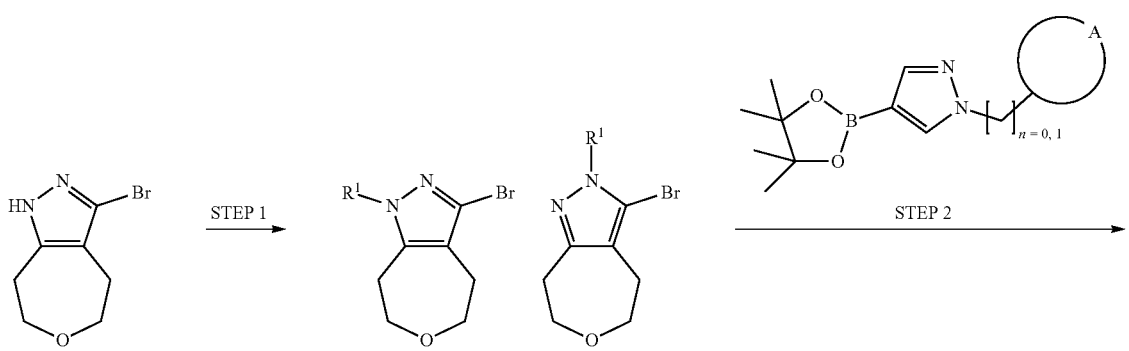

Preferred regioisomer may be isolated
by chromatography after Steps 1, 2, 3, or 4

-continued

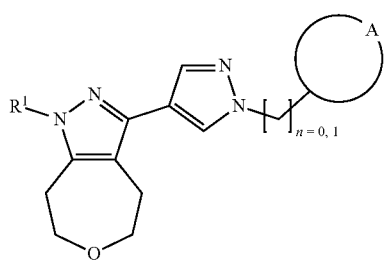 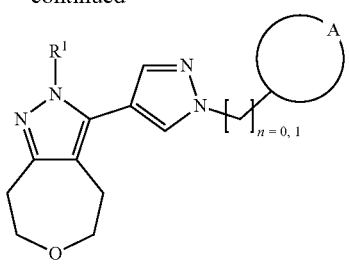

Where A = NBoc
STEP 3

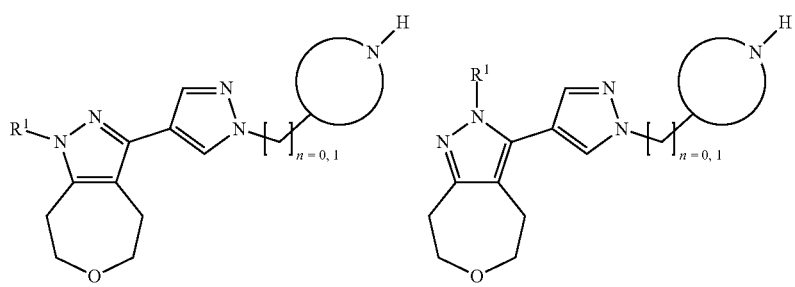

STEP 4

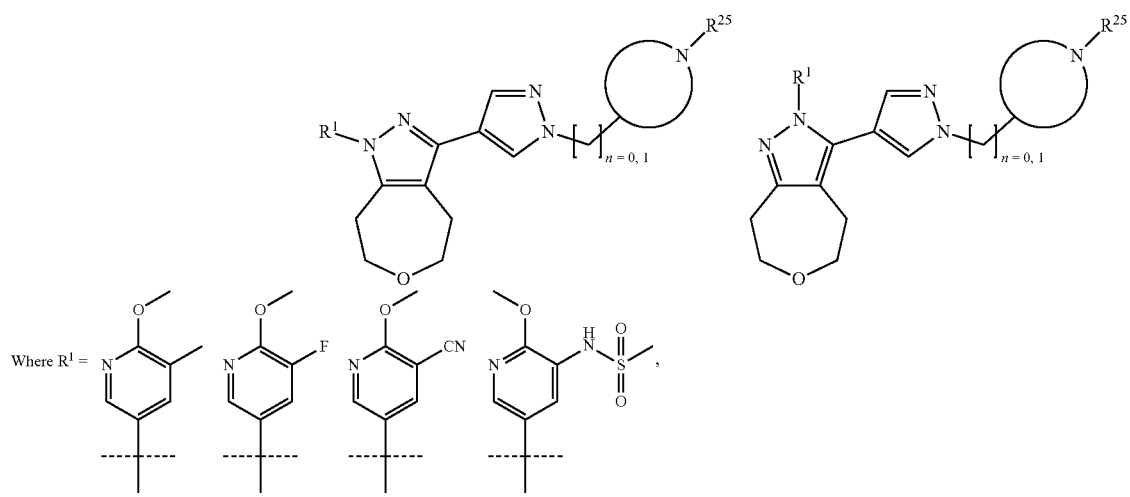

◯ = 5/6 membered heterocycle, E = NHBoc, NiPr, O, $R^{25}$ = Me, iPr

Step 1 may be undertaken by treating with copper (II) acetate, and a suitable boronic acid, such as (6-methoxy-5-methylpyridin-3-yl)boronic acid, in the presence of a suitable base, such as DMAP, stirring open to the air, in a suitable solvent, such as MeCN, at a suitable temperature, such as 80° C., for a suitable time period, such as 4 h.

Step 2 may be carried out by treating with a suitable boronate ester, such as tert-butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate, in the presence of a suitable palladium catalyst and ligand system, such as XPhos Pd G2, using a suitable base, such as potassium phosphate, in a suitable solvent or mixture of solvents, such as 1,4-dioxane and water, heating at a suitable temperature, such as 100° C., using a suitable heating method, such as a microwave, for a suitable amount of time, such as 30 min.

Step 3 may be carried out by treating with a suitable acid, such as TFA, in the presence of a suitable solvent, such as DCM, at a suitable temperature, such as room temperature, for a suitable time period, such as 15 h.

Step 4 may be carried out by treating with an appropriate alkylating agent, ketone, or aldehyde such as a 37% by weight aqueous solution of formaldehyde, stirring for an appropriate period of time, such as 1 h, then treating with an appropriate reducing agent, such as STAB and stirring for a suitable period of time, such as 3 h.

Scheme 19

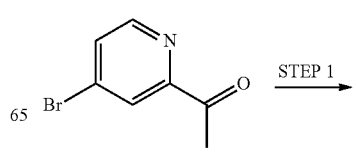

STEP 1

-continued

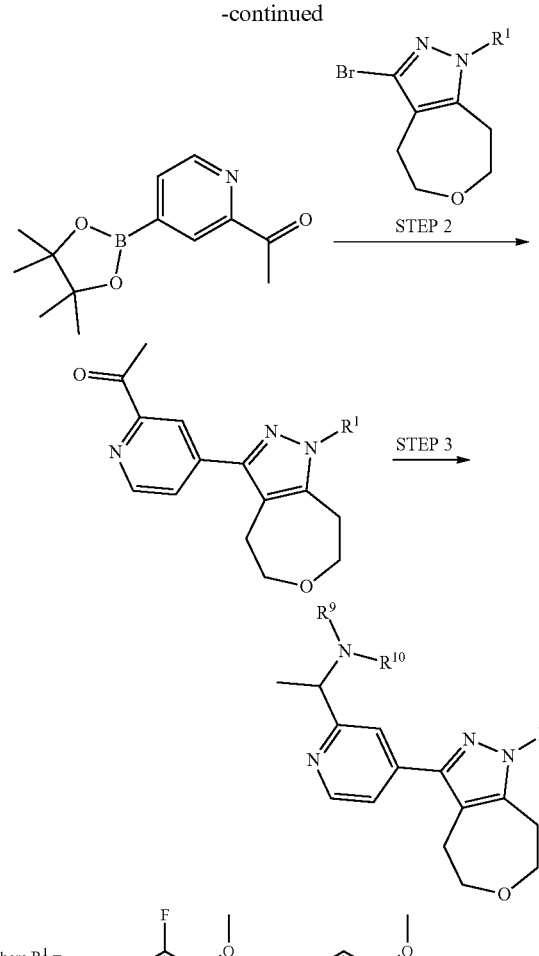

STEP 2

STEP 3

Where R¹ =
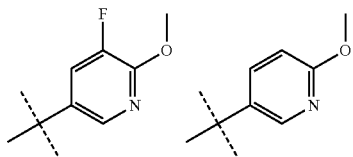
and

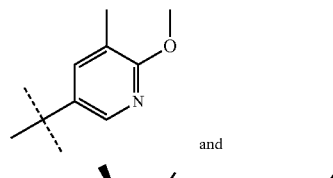

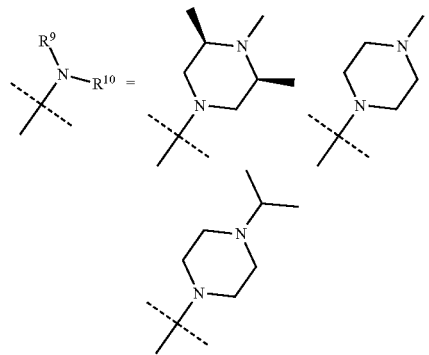

Step 1 may be undertaken by treating with bis(pinacolato)diboron, PdCl₂(dppf)-DCM and potassium acetate in a suitable solvent, such as 1,4-dioxane, at a suitable temperature, such as 100° C., using a suitable heating method, such as a microwave, for a suitable time period, such as 1 h.

Step 2 may be carried out by treating with a suitable bromide, such as 3-bromo-1-(5-fluoro-6-methoxypyridin-3-yl)-4,5,7,8-tetrahydro-1H-oxepino[4,5-c]pyrazole, in the presence of a suitable palladium catalyst and ligand system, such as XPhos Pd G2, using a suitable base, such as tripotassium phosphate, in a suitable solvent or mixture of solvents, such as EtOH and water, heating at a suitable temperature, such as 100° C., using a suitable heating method, such as a microwave, for a suitable amount of time, such as 30 min.

Step 3 may be carried out by treating with a suitable amine, such as 1-methylpiperazine, and titanium(IV) isopropoxide and acetic acid in a suitable solvent, such as THF, at room temperature, followed by treating with a suitable reducing agent, such as sodium triacetoxyborohydride, and heating at a suitable temperature, such as 100° C., using a suitable heating method, such as a microwave, under an atmosphere of nitrogen for a suitable time period, such as 1 h.

Scheme 20

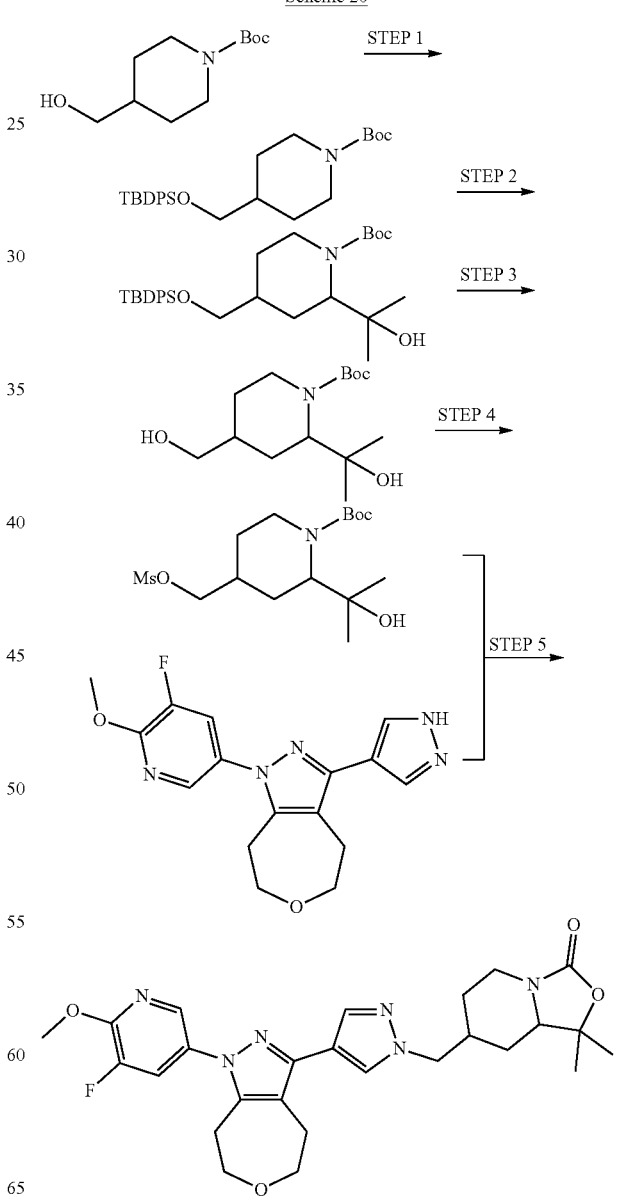

Step 1 may be undertaken by treating with imidazole, in a suitable solvent, such as DMF, and a suitable alkylating agent, such as TBDPS-Cl, stirring at a suitable temperature, such as room temperature, for a suitable time, such as overnight.

Step 2 may be carried out by treating with dry TMEDA, in a suitable solvent, such as diethyl ether, at a suitable temperature, such as −78° C., then by treating with a suitable base, such as sec-butyllithium, and stirring for a suitable time, such as 2 h, followed by acetone, and stirring for a suitable time, such as 2 h.

Step 3 may be undertaken by adding TBAF in a suitable solvent or mixture of solvents, such as DCM and THF, and stirring at a suitable temperature, such as room temperature, for a suitable time, such as 2 h.

Step 4 may be carried out by treating with methanesulfonyl chloride in the presence of a suitable base, such as pyridine, and in a suitable solvent, such as DCM, at a suitable temperature, such as room temperature, for a suitable time, such as 8 h.

Step 5 may be undertaken by treating with a suitable base, such as sodium hydride, in a suitable solvent, such as DMF, at a suitable temperature and time, such as room temperature for 3 h, then 60° C. for 1 h.

Thus, in one embodiment the invention provides a process for preparing a compound of formula (I), or a salt thereof, comprising:

a) reacting a compound of formula (II) or a salt thereof

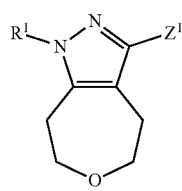

(II)

wherein $R^{1'}$ is $R^1$ as defined above or a group convertable to $R^1$ and $Z^1$ is halo, for example bromo, with a suitable boronic acid or boronate ester, b) reacting a compound of formula (III) or a salt thereof

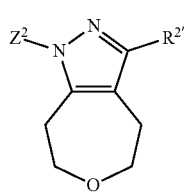

(III)

wherein $R^{2'}$ is $R^2$ as defined above or a group convertable to $R^2$ and $Z^2$ is halo, for example bromo, with a suitable boronic acid or boronate ester, c) when $R^2$ is —$OR^4$, reacting a compound of formula (IV) or a salt thereof

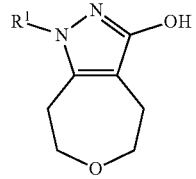

(IV)

wherein $R^1$ is as defined above, with an alcohol of formula $R^4$—OH, or d) when $R^2$ is —$CONHR^5$, reacting a compound of formula (V) or a salt thereof

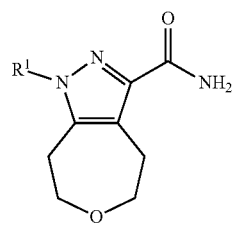

(V)

with an amine of formula $R^5$—$NH_2$.

Methods of Use

The compounds of the invention are inhibitors of kinase activity, in particular PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the PI3-kinase leading to inappropriate or uncontrolled activation. Accordingly, in another aspect the invention is directed to methods of treating such disorders.

Such disorders include respiratory diseases including asthma, chronic obstructive pulmonary disease (COPD) and idiopathic pulmonary fibrosis (IPF); ciliopathy including primary ciliary dyskinesia, polycystic liver disease and nephronophthisis; bacterial infections including bacterial respiratory tract infections, for example infections by *S. pneumoniae, H. influenzae, M. catarrhalis* and/or mycobacteria such as *Mycobacterium tuberculosis*, and bacterial exacerbations of respiratory conditions and lung damage such as asthma, COPD and cystic fibrosis; viral infections including viral respiratory tract infections, for example infections by influenza, rhinovirus, respiratory syncytial virus (RSV), human parainfluenza virus (HPIV), adenovirus and/or coronavirus, and viral exacerbation of respiratory conditions and lung damage such as asthma, COPD and cystic fibrosis; other non-viral respiratory infections including aspergillosis and leishmaniasis; allergic diseases including allergic rhinitis; autoimmune diseases including ankylosing spondylitis, Churg-Strauss syndrome, Crohn's disease, Glomerulonephritis, Henoch-Schonlein purpura, idiopathic thrombocytopenic purpura (ITP), interstitial cystitis, pemphigus, primary sclerosing cholangitis, psoriasis, rheumatoid arthritis, sarcoidosis, Sjogren's syndrome, Type 1 diabetes, ulcerative colitis, vasculitis, vitiligo and Wegener's granulomatosis; inflammatory disorders including inflammatory bowel disease, atopic dermatitis, eczema and psoriasis; diabetes; cardiovascular diseases including thrombosis, atherosclerosis and hypertension; hematologic malignancies; neurodegenerative diseases; pancreatitis; multiorgan failure; kidney diseases; platelet aggregation; cancer; sperm motility; transplantation rejection; graft rejection; lung injuries; pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain; fibrotic diseases; depression; psychotic disorders including schizophrenia; bronchiectasis; and activated PI3Kδ syndrome (APDS).

Such fibrotic diseases may include idiopathic pulmonary fibrosis, interstitial lung diseases, non-specific interstitial pneumonia (NSIP), usual interstitial pneumonia (UIP), endomyocardial fibrosis, mediastinal fibrosis, myelofibrosis, retroperitoneal fibrosis, progressive massive fibrosis (a complication of coal workers' pneumoconiosis), nephrogenic systemic fibrosis, Crohn's disease, old myocardial infarction, scleroderma/systemic sclerosis, neurofibromatosis, Hermansky-Pudlak syndrome, diabetic nephropathy, renal fibrosis, hypertrophic cardiomyopathy (HCM), hypertension-related nephropathy, focal segmental glomerulosclerosis (FSGS), radiation-induced fibrosis, uterine leiomyomas (fibroids), alcoholic liver disease, hepatic steatosis, hepatic fibrosis, hepatic cirrhosis, hepatitis C virus (HCV) infection, chronic organ transplant rejection, fibrotic conditions of the skin, keloid scarring, Dupuytren contracture, Ehlers-Danlos syndrome, epidermolysis bullosa dystrophica, oral submucous fibrosis, and fibro-proliferative disorders.

In one embodiment, the disorder is asthma. In a further embodiment, the disorder is COPD.

Within the context of the present invention, the following terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "depression" includes depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

The compounds of formula (I) or pharmaceutically acceptable salt thereof may also be used for prevention of a disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof. Individual embodiments of the invention include methods of preventing any one of the above-mentioned disorders by administering a safe and effective amount of a compound of formula (I) or a pharmaceutically acceptable salt thereof to a patient in need thereof.

In one embodiment, the methods of the invention are directed to treating a disorder. In another embodiment, the methods of the invention are directed to preventing a disorder.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

In one aspect, the invention thus provides a method of treating a disorder mediated by inappropriate PI3-kinase activity comprising administering a safe and effective amount of a compound of formula (I) or a pharmaceutically acceptable salt thereof to a patient in need thereof. In one embodiment, the invention provides a method of treating a disorder mediated by inappropriate PI3-kinase activity comprising administering a safe and effective amount of (R)-1-(6-methoxypyridin-3-yl)-3-(1-(1-methylpiperidin-4-yl) ethyl)-1H-pyrazol-4-yl)-4,5,7,8-tetrahydro-1H-oxepino[4,5-c]pyrazole or a pharmaceutically acceptable salt thereof to a patient in need thereof.

In one embodiment, the disorder mediated by inappropriate PI3-kinase activity is selected from the group consisting of respiratory diseases (including asthma, chronic obstructive pulmonary disease (COPD) and idiopathic pulmonary fibrosis (IPF)); ciliopathy (including primary ciliary dyskinesia, polycystic liver disease and nephronophthisis); bacterial infections (including bacterial respiratory tract infections, for example infections by *S. pneumoniae, H. influenzae, M. catarrhalis* and/or mycobacteria such as *Mycobacterium tuberculosis*) and bacterial exacerbations of respiratory conditions and lung damage (such as asthma, COPD and cystic fibrosis); viral infections (including viral respiratory tract infections, for example infections by influenza, rhinovirus, respiratory syncytial virus (RSV), human parainfluenza virus (HPIV), adenovirus and/or coronavirus) and viral exacerbation of respiratory conditions and lung damage (such as asthma, COPD and cystic fibrosis); other non-viral respiratory infections (including aspergillosis and leishmaniasis); allergic diseases (including allergic rhinitis); autoimmune diseases (including ankylosing spondylitis, Churg-Strauss syndrome, Crohn's disease, Glomerulonephritis, Henoch-Schonlein purpura, idiopathic thrombocytopenic purpura (ITP), interstitial cystitis, pemphigus, primary sclerosing cholangitis, psoriasis, rheumatoid arthritis, sarcoidosis, Sjogren's syndrome, Type 1 diabetes, ulcerative colitis, vasculitis, vitiligo and Wegener's granulomatosis); inflammatory disorders (including inflammatory bowel disease, atopic dermatitis, eczema and psoriasis); diabetes; cardiovascular diseases (including thrombosis, atherosclerosis and hypertension); hematologic malignancies; neurodegenerative diseases; pancreatitis; multiorgan failure; kidney diseases; platelet aggregation; cancer; sperm motility; transplantation rejection; graft rejection; lung injuries; pain (including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain); fibrotic diseases; depression; psychotic disorders (including schizophrenia); bronchiectasis; and activated PI3Kδ syndrome (APDS).

In one embodiment, the disorder mediated by inappropriate PI3-kinase activity is a respiratory disease. In another embodiment, the disorder mediated by inappropriate PI3-kinase activity is asthma. In a further embodiment, the disorder mediated by inappropriate PI3-kinase activity is chronic obstructive pulmonary disease (COPD).

In one aspect, the invention provides a compound of formula (I) or a pharmaceutically acceptable salt thereof for use in medical therapy. In one embodiment, the invention provides (R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole or a pharmaceutically acceptable salt thereof for use in medical therapy.

In another aspect, the invention provides a compound of formula (I) or a pharmaceutically acceptable salt thereof for use in the treatment of a disorder mediated by inappropriate PI3-kinase activity. In one embodiment, the invention provides (R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole or a pharmaceutically acceptable salt thereof for use in the treatment of a disorder mediated by inappropriate PI3-kinase activity.

In a further aspect, the invention provides the use of a compound of formula (I) or a pharmaceutically acceptable salt thereof in the manufacture of a medicament for use in the treatment of a disorder mediated by inappropriate PI3-kinase activity. In one embodiment, the invention provides the use of (R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole or a pharmaceutically acceptable salt thereof in the manufacture of a medicament for use in the treatment of a disorder mediated by inappropriate PI3-kinase activity.

A number of different genetic variants in PI3Kδ have been observed (Jou et al., International Journal of Immunogenetics, 2006, 33, 361 to 369). One mutation (c.3061G>A, corresponding to m.3256G>A in the mRNA wherein the nucleotide number is based on the sequence data on GenBank: NM_005026) observed in a highly conserved position in the domain responsible for catalytic function results in a glutamic acid to lysine substitution (E1021K). It is believed that this mutation may result in patients being particularly susceptible to developing respiratory infections and/or exacerbations of respiratory infections, and damage to the airway wall, large and small airways, and lung parenchyma (Angulo et al., Science DOI: 10.1125/science. 1243292). Other gain of function mutations identified in the PIK3CD gene and leading to immune deficiencies include the amino acid residue substitution N334K or E525K (Lucas et al. Nat. Immunol. (2014) 15 p. 88-97). Mutations leading to aberrant splicing of PIK3R1 exon 10 and truncation of the p85 a protein result in elevated PI3Kδ activity and to symptoms similar to the gain of function mutations in the PIK3CD gene (Deau et al. J. Clin. Invest. (2014) 124(9) p. 3923-8).

Thus, in one aspect, the invention thus provides a method of treating or preventing a respiratory infection, treating airway damage, and/or preventing airway injury in a patient with a PI3Kδ mutation, or increased PI3Kδ expression or activity, comprising administering a safe and effective amount of a compound of formula (I) or a pharmaceutically acceptable salt thereof to a patient in need thereof.

In one embodiment, the invention thus provides a method of treating or preventing a respiratory infection, treating airway damage (for example bronchiectasis), and/or preventing airway injury in a patient with activated PI3Kδ syndrome (APDS), comprising administering a safe and effective amount of a compound of formula (I) or a pharmaceutically acceptable salt thereof to a patient in need thereof.

In one embodiment, the invention provides a compound of formula (I) or a pharmaceutically acceptable salt thereof for use in the treatment or prevention of a respiratory infection, the treatment of airway damage, and/or the prevention of airway injury in a patient with a PI3Kδ mutation, or increased PI3Kδ expression or activity.

In another embodiment, the invention provides the use of a compound of formula (I) or a pharmaceutically acceptable salt thereof in the manufacture of a medicament for use in the treatment or prevention of a respiratory infection, the treatment of airway damage, and/or the prevention of airway injury in a patient with a PI3Kδ mutation, or increased PI3Kδ expression or activity.

In another embodiment, the present invention provides a compound of formula (I) or a pharmaceutically acceptable salt thereof for use in the treatment or prevention of a respiratory infection, the treatment of airway damage, and/or the prevention of airway injury in a patient, comprising:
  a) assaying a sample from the patient,
  b) determining if the patient has a PI3Kδ mutation, or increased PI3Kδ expression or activity, and
  c) administering a therapeutically effective amount of a compound of formula (I) or a pharmaceutically acceptable salt thereof to the patient if they have a PI3Kδ mutation, or increased PI3Kδ expression or activity.

In another embodiment, the invention provides a compound of formula (I) or a pharmaceutically acceptable salt thereof for use in the treatment or prevention of a respiratory infection, the treatment of airway damage, and/or the prevention of airway injury in a patient classified as a responder, wherein a responder is characterised by the presence of a PI3Kδ mutation, or increased PI3Kδ expression or activity.

In another embodiment, the invention provides use of a compound of formula (I) or a pharmaceutically acceptable salt thereof in the manufacture of a medicament for use in the treatment or prevention of a respiratory infection, the treatment of airway damage, and/or the prevention of airway injury in a patient classified as a responder, wherein a responder is characterised by the presence of a PI3Kδ mutation, or increased PI3Kδ expression or activity.

In a further embodiment, the invention provides a method of evaluating therapy with a compound of formula (I) or a pharmaceutically acceptable salt thereof, comprising:
  a) obtaining a sample from the patient,
  b) testing for a PI3Kδ mutation, or increased PI3Kδ expression or activity, and
  c) determining if the patient should undergo therapy with a compound of formula (I) or a pharmaceutically acceptable salt thereof if a PI3Kδ mutation, or increased PI3Kδ expression or activity, is present.

Such respiratory infections may be the result of bacterial infections including, for example, infections by *S. pneumoniae, H. influenzae, M. catarrhalis* and/or mycobacteria such as *Mycobacterium tuberculosis*; viral infections including, for example, infections by influenza, rhinovirus, respiratory syncytial virus (RSV), human parainfluenza virus (HPIV), adenovirus and/or coronavirus; and other non-viral respiratory infections including aspergillosis and/or leishmaniasis. In one embodiment, patients with a PI3Kδ mutation may be particularly susceptible to developing respiratory infections and/or exacerbations of respiratory infections as a result of bacterial infections by *S. pneumoniae, H. influenzae*, and/or *M. catarrhalis*.

As used herein, the term "airway damage" refers to damage to the airway wall, large and small airways, and/or lung parenchyma which is present at the time a patient commences treatment.

Airway damage, such as inflammation, scarring and/or remodelling, may be caused by, for example, repeated respiratory infections in a patient with a PI3Kδ mutation.

As used herein, the term "airway injury" refers to damage, or further damage, to the airway wall, large and small airways, and/or lung parenchyma which may develop in a patient if treatment does not occur.

As used herein, the term "responder" means someone who is identified (using a particular test or method) to be more likely to derive benefit in response to treatment (e.g. positive response to drug, reduction in adverse events, etc.). It is understood that not all people who have been identified as a responder will necessarily derive benefit, but as a patient class, they are more likely to do so. For example, it may be that out of the total untested diseased population, approximately 80% of that population derive benefit from a drug, but out of the group of "responders" (i.e. those individuals who have been tested, and identified as a responder according to the set criteria) approximately 99% will derive benefit.

As used herein, the term "evaluating therapy" means determining whether therapy with a compound of formula (I), or a pharmaceutically acceptable salt thereof, would be beneficial to a patient.

Patients with a PI3Kδ mutation may be particularly susceptible to an exacerbation of a respiratory infection. As used herein, the term "exacerbation of a respiratory infection" refers to a respiratory infection characterised by the worsening of an underlying persistent respiratory infection, including bacterial infections, viral infections and/or other non-viral respiratory infections. In one embodiment, the present invention thus provides a method of treating or preventing an exacerbation of a respiratory infection in a patient with a PI3Kδ mutation comprising administering a safe and effective amount of a compound of formula (I) or a pharmaceutically acceptable salt thereof to a patient in need thereof.

In one embodiment, the PI3Kδ mutation results in the substitution of glutamic acid for lysine.

In another embodiment, the PI3Kδ mutation results in the substitution of glutamic acid for lysine at codon 1021 (E1021K).

In one embodiment, the PI3Kδ mutation results in a single base-pair missense mutation m.3256G>A in the mRNA (wherein the nucleotide number is based on the sequence data on GenBank: NM_005026).

In one embodiment, the PI3Kδ mutation is c.3061G>A.

Compositions

The compounds of formula (I) and pharmaceutically acceptable salts thereof will normally, but not necessarily, be formulated into pharmaceutical compositions prior to administration to a patient.

Accordingly, in one aspect the invention is directed to pharmaceutical compositions comprising a compound of formula (I) or a pharmaceutically acceptable salt thereof and one or more pharmaceutically acceptable excipients. In one embodiment, the invention is directed to pharmaceutical compositions comprising (R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole or a pharmaceutically acceptable salt thereof and one or more pharmaceutically acceptable excipients.

In another aspect the invention is directed to pharmaceutical compositions comprising 0.05 to 1000 mg of a compound of formula (I) or a pharmaceutically acceptable salt thereof and 0.1 to 2 g of one or more pharmaceutically acceptable excipients.

In a further aspect the invention is directed to a pharmaceutical composition for the treatment or prophylaxis of a disorder mediated by inappropriate PI3-kinase activity comprising a compound of formula (I) or a pharmaceutically acceptable salt thereof.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups.

Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents.

The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In a further embodiment, the invention is directed to a dosage form adapted for administration to a patient by inhalation via a nebulizer.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoro-ethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™)

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents, $\beta_2$-adrenoreceptor agonists, leukotriene antagonists (such as montelukast, zafirlukast or pranlukast), antiinfective agents, antihistamines, antigen immunotherapy, corticosteroids (such as fluticasone propionate, fluticasone furoate, beclomethasone diproprionate, budesonide, ciclesonide, mometasone furoate, triamcinolone or flunisolide), iNOS inhibitors, tryptase inhibitors, IKK2 inhibitors, p38 inhibitors, Syk inhibitors, elastase inhibitors, beta-2 integrin antagonists, adenosine a2a agonists, chemokine antagonists such as CCR3 antagonists or CCR4 antagonists, mediator release inhibitors (such as sodium chromoglycate), 5-lipoxygenase inhibitors (zyflo), DP1 antagonists, DP2 antagonists, PDE4 inhibitors, PI3-kinase inhibitors, P14-kinase inhibitors, ITK inhibitors, LP (lysophosphatidic) inhibitors, FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), DMARDs (disease-modifying anti-rheumatic drugs) (such as methotrexate, leflunomide or azathioprine), monoclonal antibody therapy (such as anti-TSLP, anti-IgE, anti-TNF, anti-IL-5, anti-IL-6, anti-IL-12 or anti-IL-1), receptor therapies (such as etanercept), and/or antigen non-specific immunotherapies (such as interferon or other cytokines/chemokines, cytokine/chemokine receptor modulators, cytokine agonists or antagonists, or TLR agonists).

The invention thus provides, in a further aspect, a combination comprising a compound of formula (I) or a pharmaceutically acceptable salt thereof together with one or more other therapeutically active agents, for example selected from an anti-inflammatory agent, an anticholinergic agent, a $\beta_2$-adrenoreceptor agonist, a leukotriene antagonist, an antiinfective agent, an antihistamine, antigen immunotherapy, a corticosteroid, an iNOS inhibitor, a tryptase inhibitor, an IKK2 inhibitor, a p38 inhibitor, a Syk inhibitor, an elastase inhibitor, a beta-2 integrin antagonist, an adenosine a2a agonist, a chemokine antagonist, a mediator release inhibitor, a 5-lipoxygenase inhibitors, a DPI antagonist, a DP2 antagonist, a PDE4 inhibitor, a PI3-kinase inhibitor, a P14-kinase inhibitor, an ITK inhibitor, a LP (lysophosphatidic) inhibitor, a FLAP (5-lipoxygenase activating protein) inhibitor, a DMARD, monoclonal antibody therapy, receptor therapy, and/or antigen non-specific immunotherapy.

In one embodiment, the invention encompasses a method of treating a disorder mediated by inappropriate PI3-kinase activity comprising administering a safe and effective amount of a combination comprising a compound of formula (I) or a pharmaceutically acceptable salt thereof together with one or more therapeutically active agents.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of p2-adrenoreceptor agonists include:

3-(4-{[6-({(2R)-2-hydroxy-2-[4-hydroxy-3-(hydroxymethyl)phenyl]ethyl}amino) hexyl]oxy}butyl)benzenesulfonamide;

3-(3-{[7-({(2R)-2-hydroxy-2-[4-hydroxy-3-hydroxymethyl)phenyl]ethyl}amino)heptyl]oxy}propyl) benzenesulfonamide;

4-{(1R)-2-[(6-{2-[(2,6-dichlorobenzyl)oxy]ethoxy}hexyl) amino]-1-hydroxyethyl}-2-(hydroxymethyl) phenol;

4-{(1R)-2-[(6-{4-[3-(cyclopentylsulfonyl)phenyl] butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]-ethyl]amino]ethyl] phenyl]formamide;

N-2{2-[4-(3-phenyl-4-methoxyphenyl)aminophenyl] ethyl}-2-hydroxy-2-(8-hydroxy-2(1H)-quinolinon-5-yl) ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

In one embodiment, the invention encompasses a combination comprising a compound of formula (I) or a pharmaceutically acceptable salt thereof together with a leukotriene antagonist. Suitable leukotriene antagonists include, for example, montelukast.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO0/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), tryptase and elastase inhibitors, beta-2 integrin antagonists and adenosine receptor agonists or antagonists (e.g. adenosine 2a agonists), cytokine antagonists, or inhibitors of cytokine synthesis, or 5-lipoxygenase inhibitors.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxy-phenyl)cyclohexan-1-one and cis-[4-cyano-4-(3-cyclopropylmethoxy-4-difluoromethoxy-phenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors.

Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
- (3-endo)-3-(2,2-di-2-thienylethenyl)-8,8-dimethyl-8-azoniabicyclo[3.2.1]octane iodide;
- (3-endo)-3-(2-cyano-2,2-diphenylethyl)-8,8-dimethyl-8-azoniabicyclo[3.2.1]octane bromide;
- 4-[hydroxy(diphenyl)methyl]-1-{2-[(phenylmethyl)oxy] ethyl}-1-azoniabicyclo[2.2.2]octane bromide; and
- (1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
- (3-endo)-3-(2,2-di-2-thienylethenyl)-8,8-dimethyl-8-azoniabicyclo[3.2.1]octane bromide;
- (3-endo)-3-(2,2-diphenylethenyl)-8,8-dimethyl-8-azoniabicyclo[3.2.1]octane bromide;
- (3-endo)-3-(2,2-diphenylethenyl)-8,8-dimethyl-8-azoniabicyclo[3.2.1]octane 4-methyl-benzenesulfonate;
- (3-endo)-8,8-dimethyl-3-[2-phenyl-2-(2-thienyl)ethenyl]-8-azoniabicyclo[3.2.1]octane bromide; and/or
- (3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
- (endo)-3-(2-methoxy-2,2-di-thiophen-2-yl-ethyl)-8,8-dimethyl-8-azonia-bicyclo[3.2.1]octane iodide;
- 3-((endo)-8-methyl-8-aza-bicyclo[3.2.1]oct-3-yl)-2,2-diphenyl-propionitrile;
- (endo)-8-methyl-3-(2,2,2-triphenyl-ethyl)-8-aza-bicyclo [3.2.1]octane;
- 3-((endo)-8-methyl-8-aza-bicyclo[3.2.1]oct-3-yl)-2,2-diphenyl-propionamide;
- 3-((endo)-8-methyl-8-aza-bicyclo[3.2.1]oct-3-yl)-2,2-diphenyl-propionic acid;
- (endo)-3-(2-cyano-2,2-diphenyl-ethyl)-8,8-dimethyl-8-azonia-bicyclo[3.2.1]octane iodide;
- (endo)-3-(2-cyano-2,2-diphenyl-ethyl)-8,8-dimethyl-8-azonia-bicyclo[3.2.1]octane bromide;
- 3-((endo)-8-methyl-8-aza-bicyclo[3.2.1]oct-3-yl)-2,2-diphenyl-propan-1-ol;
- N-benzyl-3-((endo)-8-methyl-8-aza-bicyclo[3.2.1]oct-3-yl)-2,2-diphenyl-propionamide;

(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzene-sulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., J. Med. Chem. 46:3957-3960 (2003).

In one embodiment the invention provides a combination comprising a compound of formula (I) or a pharmaceutically acceptable salt thereof together with an anti-infective agent. The anti-infective agent may be an antibiotic, an antiviral or an antifungal. Examples of suitable antibiotics may include amoxicillin/clavulanate, flucloxacillin, cefalexin, cefixime, erythromycin, ciprofloxacin and tobramycin. Examples of suitable antivirals may include oseltamivir, zanamivir and ribavirin. Examples of suitable antifungals may include fluconazole and itraconazole.

In one embodiment the combination comprising a compound of formula (I) or a pharmaceutically acceptable salt thereof together with an anti-infective agent may be administered by inhalation. Examples of anti-infective agents particularly suitable for inhalation include those that may be inhaled or nebulized, for example, antibiotics such as tobramycin or ciprofloxacin, and antivirals such as zanamivir or ribavirin.

In one embodiment the invention provides a combination comprising a compound of formula (I) or a pharmaceutically acceptable salt thereof together with an anti-infective agent that has a compatible duration of action with the compound of formula (I). By the term "compatible duration of action" as used herein, is meant that the duration of action is such that both compounds may be administered to treat a particular patient, for example, they may be administered the same number of times each day such as once daily or 2, 3, 4 or 8 times.

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a leukotriene antagonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

The invention thus provides, in a further aspect, a combination comprising a compound of formula (I) or a pharmaceutically acceptable salt thereof together with an anti-infective agent.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation.

Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a leukotriene antagonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

The invention thus provides, in a further aspect, a pharmaceutical composition comprising a combination of a compound of formula (I) or a pharmaceutically acceptable salt thereof together with an anti-infective agent.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The names of the Examples have been obtained using a compound naming programme which matches structure to name (e.g. ACD/Name Batch v 9.0).

When the name of a commercial supplier is given after the name of a compound or a reagent, this means that the compound is obtainable from a commercial supplier, such as the commercial supplier named. If not referenced herein the compound or reagent can be purchased from a standard supplier such as Sigma Aldrich, Lancaster, Fluorochem, TCI etc.

General Experimental Details

All temperatures referred to are in ° C.
The names of the following compounds have been generated using ChemBioDraw Ultra v12.0.2d812.
LCMS Methodology
Method A
LC Conditions
The UPLC analysis was conducted on an Acquity UPLC BEH C18 column (50 mm×2.1 mm, i.d. 1.7 µm packing diameter) at 40° C. The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

| MS conditions | | |
|---|---|---|
| MS | : | Waters ZQ |
| Ionisation mode | : | Alternate-scan positive and negative electrospray |
| Scan range | : | 100 to 1000 AMU |
| Scan time | : | 0.27 sec |
| Inter scan delay | : | 0.10 sec |

Method B
LC Conditions
The UPLC analysis was conducted on an Acquity UPLC BEH C18 column (50 mm×2.1 mm, i.d. 1.7 µm packing diameter) at 35° C. The solvents employed were:
A=0.05% v/v solution of formic acid in water
B=0.05% v/v solution of formic acid in acetonitrile
The gradient employed was:

| Time (min) | Flow rate (mL/min) | % A | % B |
|---|---|---|---|
| 0 | 0.6 | 97 | 3 |
| 0.4 | 0.6 | 97 | 3 |
| 3.2 | 0.6 | 2 | 98 |
| 3.8 | 0.6 | 2 | 98 |
| 4.2 | 0.6 | 97 | 3 |
| 4.5 | 0.6 | 97 | 3 |

UV: 190 nm to 400 nm.

Mass spectrometry Method:
MS: Waters SQD—3100 Mass Detector
Ionisation mode: Electrospray Ionisation (ESI)
Polarity Switching: Positive/Negative
Scan range: 100-1000
Scan time: 0.5 (secs)
Inter scan delay: 0.1 (secs)

Method C
LC conditions
The UPLC analysis was conducted on an Acquity UPLC BEH C18 column (50 mm×2.1 mm, i.d. 1.7 μm packing diameter) at 40° C.
The solvents employed were:
A=10 mM ammonium hydrogen carbonate in water adjusted to pH 10 ammonia solution
B=acetonitrile
The gradient employed was:

| Time (min) | Flow rate (mL/min) | % A | % B |
| --- | --- | --- | --- |
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

| MS conditions | |
| --- | --- |
| MS | : Waters ZQ |
| Ionisation mode | : Alternate-scan positive and negative electrospray |
| Scan range | : 100 to 1000 AM U |
| Scan time | : 0.27 sec |
| Inter scan delay | : 0.10 sec |

Method D
LC Conditions
The UPLC analysis was conducted on an Acquity BEH C18 (50 mm×2.1 mm i.d. 1.7 μm packing diameter) at 35° C.
The solvents employed were:
A=0.1% v/v solution of formic acid in water
B=0.1% v/v solution of formic acid in acetonitrile
The gradient employed was:

| Time (min) | Flow (mL/min) | % A | % B |
| --- | --- | --- | --- |
| 0 | 0.6 | 97 | 3 |
| 0.4 | 0.6 | 97 | 3 |
| 2.5 | 0.6 | 2 | 98 |
| 3.4 | 0.6 | 2 | 98 |
| 3.5 | 0.6 | 97 | 3 |
| 4.0 | 0.6 | 97 | 3 |

UV: 190 nm to 400 nm.
Mass spectrometry Method:
MS: Waters SQD—3100 Mass Detector
Ionisation mode: Electrospray Ionisation (ESI)
Polarity Switching: Positive/Negative
Scan range: 100-1000
Scan time: 0.5 (secs)
Inter scan delay: 0.1 (secs)

Method E
LC Conditions
The UPLC analysis was conducted on an Acquity UPLC CSH C18 column (50 mm×2.1 mm, i.d. 1.7 μm packing diameter) at 40° C. The solvents employed were:
A=0.1% v/v solution of TFA in water
B=0.1% v/v solution of TFA in acetonitrile
The gradient employed was:

| Time (min) | Flow rate (mL/min) | % A | % B |
| --- | --- | --- | --- |
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

| MS conditions | |
| --- | --- |
| MS | : Waters Acquity QDa Mass Detector |
| Ionisation mode | : Alternate-scan positive and negative electrospray |
| Scan range | : 100 to 1000 AM U |
| Targeted Sampling Frequency | : 8 Hz |

Method F
LC Conditions
The UPLC analysis was conducted on an Acquity UPLC CSH C18 (100 mm×2.1 mm i.d. 1.7 μm packing diameter) at 50° C.
The solvents employed were:
A=0.1% v/v solution of formic acid in water
B=0.1% v/v solution of formic acid in acetonitrile
The gradient employed was:

| Time (min) | Flow (mL/min) | % A | % B |
| --- | --- | --- | --- |
| 0 | 0.8 | 97 | 3 |
| 0.2 | 0.8 | 97 | 3 |
| 18 | 0.8 | 0 | 100 |
| 19 | 0.8 | 0 | 100 |
| 20.0 | 0.8 | 97 | 3 |

The UV detection was a summed signal from wavelength of 210 nm to 350 nm.
MS Conditions
MS: Waters Acquity QDa Mass Detector
Ionisation mode: Electrospray Ionisation (ESI)
Polarity Switching: Positive/Negative
Scan range: 90-1000
Scan time: 0.2 (secs)
Inter scan delay: 0.05 (secs)
Mass Directed Automated Preparative HPLC Conditions and Eluent
The methods for the Mass Directed Automated Preparative HPLC used for the purification of compounds are described below. Solvent elution gradients of 0 to 99% of Solvent B in Solvent A over a time period of up to 25 min was used.
Method A:
Column: Xselect CSH C18 column (150 mm×30 mm i.d. 5 μm packing diameter) at ambient temperature.
The solvents employed were:
A=10 mM ammonium bicarbonate adjusted to pH 10 with ammonia in water.

B=MeCN.
Flow rate: 40 mL/min.
Or:
Method B:
Column: Xselect CSH C18 column (150 mm×30 mm i.d. 5 μm packing diameter) at ambient temperature.
The solvents employed were:
A=0.1% v/v solution of formic acid in water
B=0.1% v/v solution of formic acid in MeCN.
Flow rate: 40 mL/min.
Or:
Method C:
Column: CSH C18 column (150×30 mm i.d. 5 μm packing diameter) at ambient temperature.
The solvents employed were:
A=0.1% v/v solution of TFA in water
B=0.1% v/v solution of TFA in MeCN
Scan Range: 300 to 1200 AMU
Or:
Method D:
Column: XSelect CSH C18 column (30×150 mm i.d. 5 μm).
The solvents employed were:
A=0.1% v/v solution of formic acid in water
B=0.1% v/v solution of formic acid in MeCN
Flow rate: 20 mL/min.
For Methods A and B:
Injection Volume: 1 mL or 3 mL
For all Methods (unless specified):
The DAD detection was 210 nm to 350 nm.
MS Conditions
MS: Waters ZQ
Ionisation mode: Alternate scan positive/negative Electrospray
Scan Range: 100 to 1000 AMU
Scan Time: 0.2s or 0.50 s
Inter scan Delay: 0.1s or 0.2 s
Preparative Chiral SFC Column, Conditions and Eluent
The methods for the Chiral SFC used for the purification of compounds are described below:
Method A:
Column/dimensions: Chiralcel OX—H (30×250 mm), 5 μm
% CO2: 65.0%
% Co solvent: 35.0% (0.5% diethylamine in Ethanol)
Total Flow: 100.0 g/min
Back Pressure: 90.0 bar
UV: 214 nm
Stack time: 8.0 min
Load/Inj: 60.0 mg
Solubility: 80 ml of Methanol
No of injections: 60
Method B:
Column/dimensions: Chiralpak AD-H (30×250 mm), 5 μm
% CO2: 70.0%
% Co solvent: 30.0% (100% Ethanol)
Total Flow: 100.0 g/min
Back Pressure: 90.0 bar
UV: 214 nm
Stack time: 7.0 min
Load/Inj: 22.0 mg
Solubility: 20 ml of Methanol
No of injections: 25
Preparative HPLC Column, Conditions and Eluent The methods for preparative HPLC used for the purification of compounds are described below:
Method A:
The preparative HPLC was conducted on a Kromasil C18 (250 mm×25 mm, 5 μm packing diameter) at room temperature.
The solvents employed were:
A=10 mM ammonium hydrogen carbonate in water adjusted to pH 10 ammonia solution
B=acetonitrile
The gradient employed was:

| Time (min) | Flow (mL/min) | % A | % B |
| --- | --- | --- | --- |
| 0 | 25 | 80 | 20 |
| 1.0 | 25 | 80 | 20 |
| 12.0 | 25 | 35 | 65 |
| 12.1 | 25 | 0 | 100 |
| 14.0 | 25 | 0 | 100 |
| 14.1 | 25 | 80 | 20 |
| 18.0 | 25 | 80 | 20 |

Method B:
The preparative HPLC was conducted on a CSH C18 column (150 mm×30 mm, i.d. 5 μm packing diameter) at room temperature.
The solvents employed were:
A=0.1% v/v solution of Formic Acid in Water
B=0.1% v/v solution of Formic Acid in Acetonitrile
The gradient employed was:

| Time (min) | Flow (mL/min) | % A | % B |
| --- | --- | --- | --- |
| 0 | 40 | 95 | 5 |
| 4 | 40 | 95 | 5 |
| 4.5 | 40 | 95 | 5 |
| 20 | 40 | 75 | 25 |
| 21 | 40 | 75 | 25 |
| 23 | 40 | 0 | 100 |
| 25 | 40 | 0 | 100 |

Method C:
The preparative HPLC was conducted on a Kromasil C18 (150 mm×25 mm, 10 μm packing diameter) at room temperature.
The solvents employed were:
A=10 mM ammonium hydrogen carbonate in water adjusted to pH 10 ammonia solution
B=acetonitrile
The gradient employed was:

| Time (min) | Flow (mL/min) | % A | % B |
| --- | --- | --- | --- |
| 0 | 25 | 70 | 30 |
| 1 | 25 | 70 | 30 |
| 10 | 25 | 55 | 45 |
| 10.5 | 25 | 0 | 100 |
| 14 | 25 | 0 | 100 |
| 14.5 | 25 | 70 | 30 |

NMR
Spectra were run on a 400 or 600 MHz NMR machine at either 302 K or for VT spectra at 392 to 393 K.

Intermediate 1. 3-(Trimethylsilyl)-8-oxa-1,2-diazaspiro[4.5]deca-1,3-diene

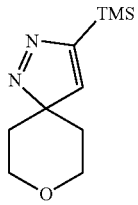

A stirred solution of p-toluenesulfonhydrazide (12.64 g, 67.9 mmol) in MeOH (300 mL) at room temperature and under an atmosphere of argon was treated with tetrahydro-4H-pyran-4-one (6.27 mL, 67.9 mmol). The reaction mixture was stirred in a sealed tube for 5 min at room temperature and concentrated under reduced pressure. The crude material was treated with dioxane (400 mL), cesium carbonate (33.2 g, 102 mmol) and ethynyltrimethylsilane (10 g, 102 mmol) at room temperature and under an atmosphere of argon. The reaction mixture was heated at 110° C. for 15 h then allowed to cool to 25° C. The reaction mixture was diluted with water (100 mL) and partitioned with EtOAc (150 mL). The organic layer was isolated and the aqueous layer re-extracted with EtOAc (150 mL). The combined organic layer was washed with brine (100 mL) and dried over $Na_2SO_4$, filtered and concentrated under reduced pressure. The crude product was purified by silica chromatography, eluting with a 30% solution of EtOAc in hexane to give the title compound as a white solid (4.0 g, 26%).

LCMS (Method B): Rt=2.38 min, $MH^+$ 211.

Intermediate 2. 3-(Trimethylsilyl)-4,5,7,8-tetrahydro-1H-oxepino[4,5-c]pyrazole

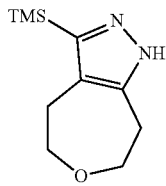 [SMILES: C[Si](C)(C)c1n[nH]c2c1CCOCC2]

A stirred solution of 3-(trimethylsilyl)-8-oxa-1,2-diazaspiro[4.5]deca-1,3-diene (4.0 g, 19.02 mmol) in dioxane (60 mL) at room temperature was treated with (diethyloxonio)trifluoroborate (2.89 mL, 22.82 mmol). The reaction mixture was stirred for 4 h then quenched with a saturated aqueous solution of $NaHCO_3$ (200 mL) and extracted with EtOAc (2×150 mL). The combined organic layers were washed with brine (120 mL), dried over $Na_2SO_4$, filtered and concentrated under reduced pressure to give crude product. The crude material was triturated with diethyl ether (200 mL) and dried under reduced pressure to give the title compound (3.0 g) as white solid.

LCMS (Method B): Rt=1.75 min, $MH^+$ 211.

Crude material was taken forward to the next reaction step without further purification.

Intermediate 3. 3-Bromo-4,5,7,8-tetrahydro-1H-oxepino[4,5-c]pyrazole

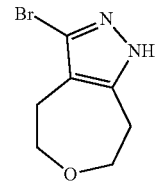 [SMILES: Brc1n[nH]c2c1CCOCC2]

A stirred solution of 3-(trimethylsilyl)-4,5,7,8-tetrahydro-1H-oxepino[4,5-c]pyrazole (2.0 g, 9.51 mmol) in MeCN (40 mL) was treated with N-bromosuccinimide (1.69 g, 9.51 mmol) in MeCN (40 mL) and stirred at 25° C. for 4 h. The reaction mixture was concentrated under reduced pressure and partitioned between DCM (200 mL) and a saturated aqueous solution of sodium hydrogen carbonate (150 mL). The organic layer was isolated, passed through a hydrophobic frit and concentrated under reduced pressure to afford the title compound (2.0 g) as a pale yellow solid.

LCMS (Method B): Rt=1.92 min, $MH^+$ 219.

Crude material was taken forward to the next reaction step without further purification.

Intermediate 4. 3-(6-Methoxy-5-methylpyridin-3-yl)-4,5,7,8-tetrahydro-1H-oxepino[4,5-c]pyrazole

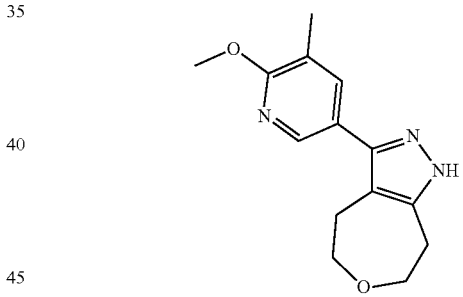

A mixture of 3-bromo-4,5,7,8-tetrahydro-1H-oxepino[4,5-c]pyrazole (500 mg, 2.303 mmol), (6-methoxy-5-methylpyridin-3-yl)boronic acid (764 mg, 4.58 mmol), Xphos Pd G2 (129 mg, 0.164 mmol) and tripotassium phosphate (982 mg, 4.63 mmol) was treated with degassed 1,4-dioxane (15 mL) and degassed water (3.00 mL) with the exclusion of oxygen under a nitrogen atmosphere. The reaction mixture was heated with stirring at 80° C. for 2 h. The reaction mixture was allowed to cool to room temperature and treated with water (20 mL). The reaction mixture was partitioned with EtOAc (15 mL) and the organic layer isolated. The aqueous layer was re-extracted with EtOAc (3×15 mL) and the combined organic layer passed through a hydrophobic frit and concentrated under reduced pressure to give crude product (1.232 g). The crude product was purified by silica column chromatography, eluting with 50 to 100% gradient of EtOAc in cyclohexane to give the title compound (400 mg, 60%).

LCMS (Method C): Rt=0.85 min, $MH^+$ 260.

Intermediate 5. ((2R,4r,6S)-2,6-Dimethylpiperidin-4-yl)methanol

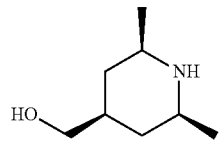

A solution of (2,6-dimethylpyridin-4-yl)methanol (9 g, 65.6 mmol) in EtOH (100 mL) was treated with Rh on alumina (3.37 g, 32.8 mmol) and hydrogen gas at 70 psi. The reaction mixture was stirred for 48 h. The reaction mixture was filtered through a Celite® pad and concentrated under reduced pressure to obtain crude product. The crude product was treated with EtOH (100 mL) followed by fresh Rh on alumina (3.37 g, 32.8 mmol) and AcOH (5 mL) and hydrogen gas at 70 psi in a Parr shaker. The reaction mixture was shaken for 48 h and filtered through a Celite® pad and concentrated under reduced pressure to give crude title compound (6 g).

$^1$H NMR (400 MHz, CDCl$_3$) δ ppm 3.49 (d, J=6 Hz, 2H), 2.83-2.68 (m, 2H), 1.78-1.69 (m, 3H, obscured by residual water peak), 1.15 (d, J=6 Hz, 6H), 0.94-0.76 (m, 2H, obscured by impurity peak).

The crude compound was taken forward into the next reaction step without further purification.

Intermediate 6. (2R,4r,6S)-tert-Butyl 4-(hydroxymethyl)-2,6-dimethylpiperidine-1-carboxylate

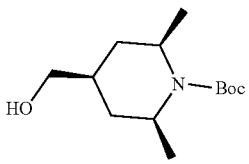 [SMILES: C[C@@H]1C[C@H](CO)C[C@H](C)N1C(=O)OC(C)(C)C]

A solution of ((2R,4r,6S)-2,6-dimethylpiperidin-4-yl)methanol (7 g, 48.9 mmol) in 1,4-dioxane (70 mL) and water (14 mL) was treated with Na$_2$CO$_3$ (7.77 g, 73.3 mmol) followed by di-tert-butyl dicarbonate (11.35 mL, 48.9 mmol). The reaction mixture was stirred at 80° C. for 24 h then diluted with water (50 mL) and extracted with DCM (100 mL×2). The combined organic layer was washed with saturated brine (50 mL×2), dried over sodium sulphate then filtered and concentrated under reduced pressure to give the crude product (5 g) as a colourless oil.

The crude compound purified by neutral alumina chromatography, eluting with a 15% solution of EtOAc in hexane to give the title compound as a colourless liquid (4 g, 33%).

$^1$H NMR (400 MHz, CDCl$_3$) δ ppm 3.49 (d, J=6 Hz, 2H), 2.82-2.70 (m, 2H), 1.78-1.68 (m, 3H, obscured by residual water peak), 1.26 (s, 9H), 1.15 (d, J=6 Hz, 6H), 0.94-0.76 (m, 2H, obscured by impurity peak).

Intermediate 7. (2R,4r,6S)-tert-Butyl 4-(bromomethyl)-2,6-dimethylpiperidine-1-carboxylate

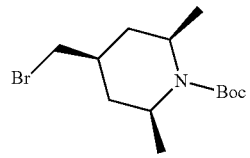 [SMILES: C[C@@H]1C[C@H](CBr)C[C@H](C)N1C(=O)OC(C)(C)C]

A solution of (2R,4r,6S)-tert-butyl 4-(hydroxymethyl)-2,6-dimethylpiperidine-1-carboxylate (4 g, 16.44 mmol) in DCM (40 mL) was treated with triphenylphosphine (5.17 g, 19.73 mmol) and CBr$_4$ (5.45 g, 16.44 mmol). The reaction mixture was stirred 4 h then diluted with water (50 mL) and extracted with DCM (50 mL×3). The organic phase was washed with a saturated brine solution (25 mL), dried over sodium sulphate, filtered and concentrated under reduced pressure the crude product as a yellow oil (4.8 g).

The crude product was purified using neutral alumina column chromatography, eluting with a solution of 15% EtOAc in hexane to give the title compound as a colourless liquid (4 g, 79%).

$^1$H NMR (400 MHz, CDCl$_3$) δ ppm 4.27-4.17 (m, 2H), 3.32 (d, J=6 Hz, 2H), 2.22-2.10 (m, 2H), 1.89-1.76 (m, 1H), 1.46 (s, 9H), 1.24 (d, J=7 Hz, 6H), 1.29-1.09 (m, 2H).

Intermediate 8. tert-Butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate

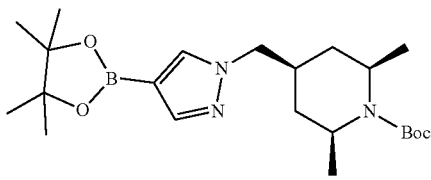 [SMILES: C[C@@H]1C[C@H](Cn2cc(B3OC(C)(C)C(C)(C)O3)cn2)C[C@H](C)N1C(=O)OC(C)(C)C]

A stirred solution of 4-(4,4,5,5-tetramethyl-1,3,2-dioxaborolan-2-yl)-1H-pyrazole (2 g, 10.31 mmol) in MeCN (20 mL) was treated with Cs$_2$CO$_3$ (5.04 g, 15.46 mmol) under an atmosphere of nitrogen followed by (2R,4r,6S)-tert-butyl 4-(bromomethyl)-2,6-dimethylpiperidine-1-carboxylate (3.79 g, 12.37 mmol). The reaction mixture was stirred at 60° C. for 16 h.

The reaction mixture was diluted with water (50 mL) and extracted with EtOAc (50 mL×3). The combined organic layer was dried over sodium sulphate, filtered and concentrated under reduced pressure to give crude product (3.2 g), which was purified by silica column chromatography, eluting with petroleum ether to give the title compound as a white solid (2.65 g, 60%).

LCMS (Method B): Rt=2.76 min, MH$^+$ 420.

General Suzuki Coupling Procedure

Intermediate 9. (2R,4r,6S)-tert-Butyl 4-((4-(3-(5-fluoro-6-methoxypyridin-3-yl)-4,5,7,8-tetrahydro-1H-oxepino[4,5-c]pyrazol-1-yl)-1H-pyrazol-1-yl)methyl)-2,6-dimethylpiperidine-1-carboxylate

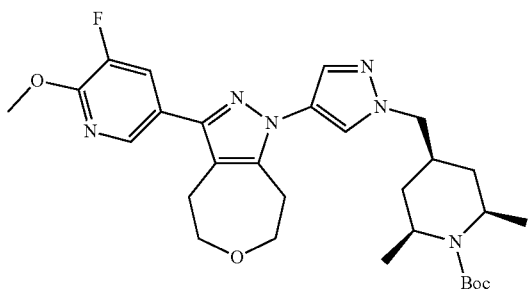

A mixture of (2R,4r,6S)-tert-butyl 4-((4-(3-bromo-4,5,7,8-tetrahydro-1H-oxepino[4,5-c]pyrazol-1-yl)-1H-pyrazol-1-yl)methyl)-2,6-dimethylpiperidine-1-carboxylate (100 mg, 0.197 mmol), (5-fluoro-6-methoxypyridin-3-yl)boronic acid (67.2 mg, 0.393 mmol), potassium phosphate (83 mg, 0.393 mmol) and XPhos Pd G2 (10.83 mg, 0.014 mmol) were treated with 1,4-dioxane (0.4 ml) and water (0.100 ml). The reaction mixture was placed under an atmosphere of nitrogen and heated using a microwave at 100° C. for 1 h. The reaction mixture was concentrated under a stream of nitrogen and the residue was purified by MDAP (Method A) to give the title compound as an orange oil (85 mg, 78%).

LCMS (Method C): Rt=1.37 min, MH+ 555.

Intermediate 10. 3-(1-(4-Methoxybenzyl)-1H-pyrazol-4-yl)-8-oxa-1,2-diazaspiro[4,5]deca-1,3-diene

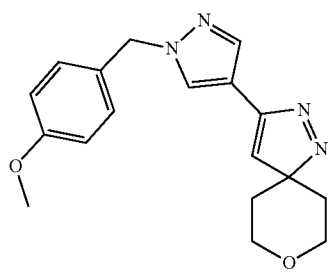 [SMILES: COc1ccc(Cn2cc(C3=CC4(CCOCC4)N=N3)cn2)cc1]

A stirred solution of p-toluenesulfonhydrazide (13.2 g, 70.7 mmol) in MeOH (300 mL) under an atmosphere of argon and at room temperature was treated with tetrahydro-4H-pyran-4-one (6.53 mL, 70.7 mmol). The reaction mixture was stirred for 5 min, concentrated under reduced pressure then treated with dioxane (300 mL), cesium carbonate (34.5 g, 106 mmol) and 4-ethynyl-1-(4-methoxybenzyl)-1H-pyrazole (15 g, 70.7 mmol, synthesis previously described by Chaplin, Jason Hugh et at. In PCT Int. Appl., 2006084338). The reaction mixture was heated under an atmosphere of argon at 110° C. for 15 hr.

The reaction mixture was diluted with water (200 mL) and extracted with EtOAc (300 mL). The organic layer was isolated and the aqueous layer re-extracted with EtOAc (300 mL). The combined organic layer was washed with brine (100 mL), dried over Na2SO4, filtered and concentrated under reduced pressure to afford the crude product. The material was purified by silica chromatography using a 70% solution of EtOAc in hexane to give the title compound as a pale yellow solid (10.0 g, 36%).

LCMS (Method B): Rt=1.89 min, MH+ 325.

Intermediate 11. 3-(1-(4-Methoxybenzyl)-1H-pyrazol-4-yl)-4,5,7,8-tetrahydro-1H-oxepino[4,5-c]pyrazole

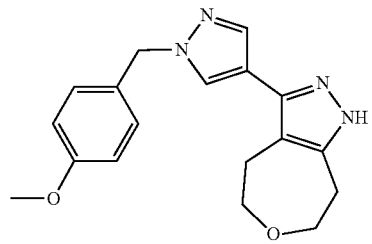 [SMILES: COc1ccc(Cn2cc(-c3n[nH]c4c3CCOCC4)cn2)cc1]

A stirred solution of 3-(1-(4-methoxybenzyl)-1H-pyrazol-4-yl)-8-oxa-1,2-diazaspiro[4.5]deca-1,3-diene (9.8 g, 30.2 mmol) in dioxane (100 mL) at room temperature was treated with (diethyloxonio)trifluoroborate (4.59 mL, 36.3 mmol). The reaction mixture was stirred at room temperature for 4 h then quenched with a saturated aqueous solution of NaHCO3 (100 mL) and partitioned with EtOAc (500 mL). The organic layer was isolated and the aqueous layer was extracted with EtOAc (500 mL) and the combined organic layer washed with brine (250 mL), dried over Na2SO4, filtered and concentrated under reduced pressure to give crude product (11.0 g). The material was purified by silica column chromatography (3% MeOH in DCM) to give the title compound (5.3 g, 52%) as pale yellow solid.

LCMS (Method B): Rt=1.72 min, MH+ 325.

Intermediate 12. 3-(1-(4-Methoxybenzyl)-1H-pyrazol-4-yl)-2-(2-methoxypyrimidin-5-yl)-4,5,7,8-tetrahydro-2H-oxepino[4,5-c]pyrazole and 3-(1-(4-methoxybenzyl)-1H-pyrazol-4-yl)-1-(2-methoxypyrimidin-5-yl)-4,5,7,8-tetrahydro-1H-oxepino[4,5-c]pyrazole

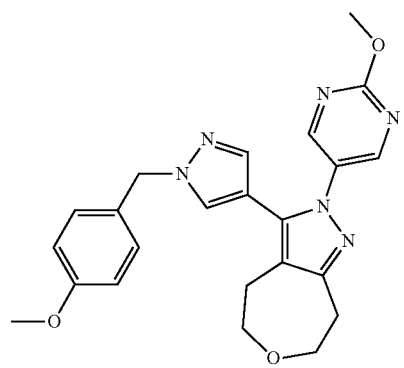

-continued

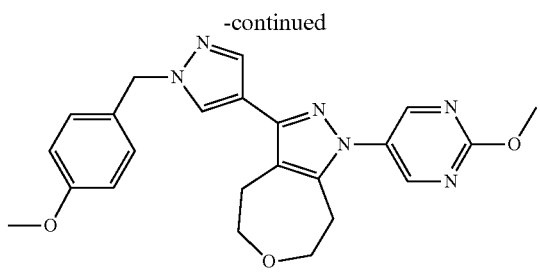

A mixture of (2-methoxypyrimidin-5-yl)boronic acid (48 mg, 0.315 mmol), 3-(1-(4-methoxybenzyl)-1H-pyrazol-4-yl)-4,5,7,8-tetrahydro-1H-oxepino[4,5-c]pyrazole (100 mg) and DMAP (75 mg, 0.617 mmol) were combined in MeCN (1 mL) and treated with copper (II) acetate (84 mg, 0.462 mmol). The reaction mixture was stirred for three days at 40° C., open to air, then allowed to cool to room temperature.

The material was mixed with a batch that had been similarly prepared using (2-methoxypyrimidin-5-yl)boronic acid (131 mg, 0.848 mmol), 3-(1-(4-methoxybenzyl)-1H-pyrazol-4-yl)-4,5,7,8-tetrahydro-1H-oxepino[4,5-c]pyrazole (250 mg, 0.771 mmol), DMAP (188 mg, 1.541 mmol) and copper (II) acetate (210 mg, 1.156 mmol) in MeCN (5 mL).

The combined reaction mixtures were treated with ammonium hydroxide (10 mL), water (10 mL) and partitioned with EtOAc (15 mL). The organic layer was isolated, and the aqueous layer re-extracted with EtOAc (2×15 mL). The combined organic layer was washed with brine (15 mL), passed through a hydrophobic frit and concentrated under reduced pressure, then loaded in MeOH (4 mL) onto an SCX-SPE cartridge that had been pre-conditioned with MeOH. The SCX-SPE cartridge was eluted with MeOH (3×15 mL) and combined eluants concentrated under reduced pressure to give a crude mixture the title compounds (308 mg).

LCMS (Method C): Rt=0.97 min, MH$^+$ 433.

Crude material was taken forward to the next reaction step without further purification.

Intermediate 13. 2-(2-Methoxypyrimidin-5-yl)-3-(1H-pyrazol-4-yl)-4,5,7,8-tetrahydro-2H-oxepino[4,5-c]pyrazole and 1-(2-methoxypyrimidin-5-yl)-3-(1H-pyrazol-4-yl)-4,5,7,8-tetrahydro-1H-oxepino[4,5-c]pyrazole

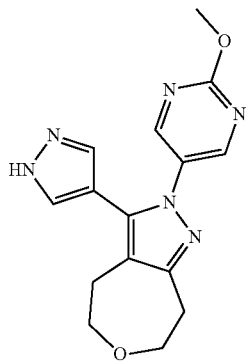

-continued

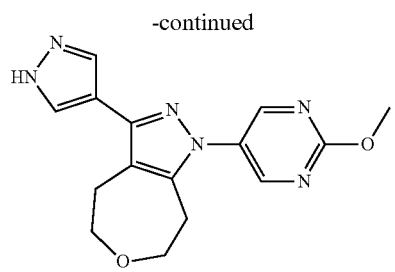

A crude mixture of 3-(1-(4-methoxybenzyl)-1H-pyrazol-4-yl)-2-(2-methoxypyrimidin-5-yl)-4,5,7,8-tetrahydro-2H-oxepino[4,5-c]pyrazole and 3-(1-(4-methoxybenzyl)-1H-pyrazol-4-yl)-1-(2-methoxypyrimidin-5-yl)-4,5,7,8-tetrahydro-1H-oxepino[4,5-c]pyrazole (308 mg) in DCM (2 mL) was treated with TFA (2 mL, 26.0 mmol) and then heated using a microwave at 70° C. for 6 h. The reaction mixture was neutralised to pH 7 using sodium bicarbonate, diluted with water (10 mL) and extracted with EtOAc (15 mL). The organic layer was isolated, and the aqueous layer re-extracted with EtOAc (2×15 mL). The combined organic layer was washed with brine (10 mL), passed through a hydrophobic frit and concentrated under reduced pressure to give a crude mixture of the title compounds (232 mg).

LCMS (Method C): Rt=0.67 min, MH$^+$ 313.

Crude material was taken forward to the next reaction step without further purification.

Intermediate 14. tert-Butyl 4-((4-(2-(2-methoxypyrimidin-5-yl)-4,5,7,8-tetrahydro-2H-oxepino[4,5-c]pyrazol-3-yl)-1H-pyrazol-1-yl)methyl)piperidine-1-carboxylate and tert-butyl 4-((4-(1-(2-methoxypyrimidin-5-yl)-4,5,7,8-tetrahydro-1H-oxepino[4,5-c]pyrazol-3-yl)-1H-pyrazol-1-yl)methyl)piperidine-1-carboxylate

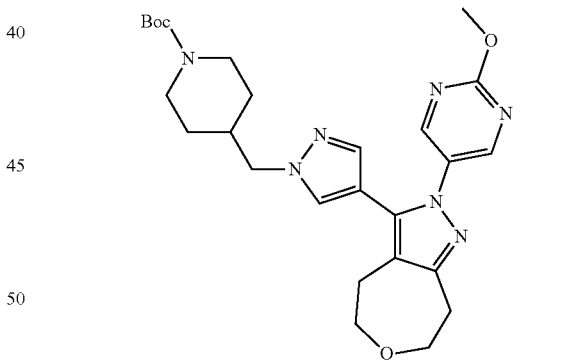

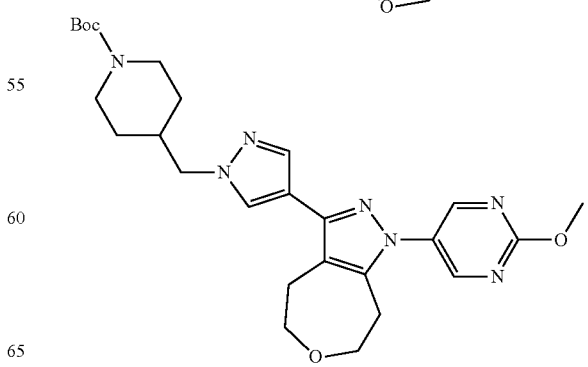

A crude mixture of the 2-(2-methoxypyrimidin-5-yl)-3-(1H-pyrazol-4-yl)-4,5,7,8-tetrahydro-2H-oxepino[4,5-c]pyrazole and 1-(2-methoxypyrimidin-5-yl)-3-(1H-pyrazol-4-yl)-4,5,7,8-tetrahydro-1H-oxepino[4,5-c]pyrazole (232 mg) was dissolved in DMF (2 mL) and placed under an atmosphere of nitrogen. The mixture was treated with NaH (17 mg, 0.423 mmol, 60% suspension in mineral oils) and stirred for 30 min then treated with tert-butyl 4-(bromomethyl)piperidine-1-carboxylate (86 mg, 0.310 mmol) and stirred for a further 24 h. The reaction mixture was acidified to pH 5 using a 2 M solution of HCl and diluted with water (25 mL) then partitioned with EtOAc (25 mL). The organic layer was isolated and the aqueous layer re-extracted with EtOAc (25 mL). The combined organic layer was washed with LiCl (5% solution in water, 2×25 mL) and brine (25 mL), and passed through a hydrophobic frit then concentrated under reduced pressure to give a crude mixture of the title compounds (90 mg).

LCMS (Method A): Rt=1.08 min, MH+ 510.

Crude material was taken forward to the next reaction step without further purification.

Intermediate 15. 2-(2-Methoxypyrimidin-5-yl)-3-(1-(piperidin-4-ylmethyl)-1H-pyrazol-4-yl)-4,5,7,8-tetrahydro-2H-oxepino[4,5-c]pyrazole and 1-(2-methoxypyrimidin-5-yl)-3-(1-(piperidin-4-ylmethyl)-1H-pyrazol-4-yl)-4,5,7,8-tetrahydro-1H-oxepino[4,5-c]pyrazole

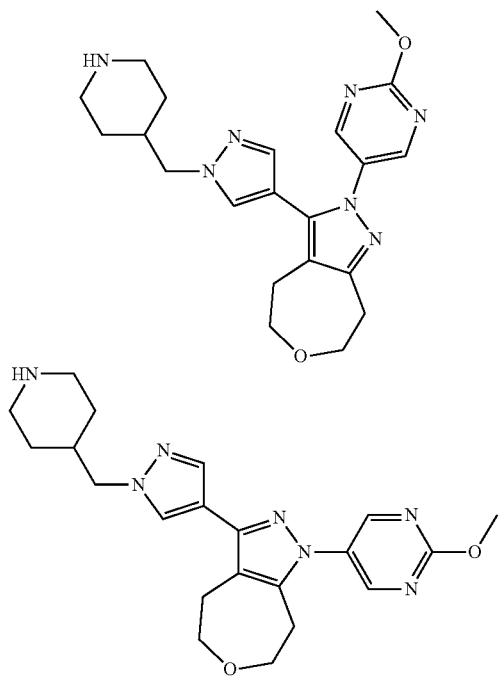

A mixture of tert-butyl 4-((4-(1-(2-methoxypyrimidin-5-yl)-4,5,7,8-tetrahydro-1H-oxepino[4,5-c]pyrazol-3-yl)-1H-pyrazol-1-yl)methyl)piperidine-1-carboxylate and tert-butyl 4-((4-(2-(2-methoxypyrimidin-5-yl)-4,5,7,8-tetrahydro-2H-oxepino[4,5-c]pyrazol-3-yl)-1H-pyrazol-1-yl)methyl)piperidine-1-carboxylate (90 mg) was dissolved in DCM (2 mL). The reaction mixture was placed under an atmosphere of nitrogen and treated with TFA (0.068 mL, 0.883 mmol) then stirred for 1 h. The reaction mixture was treated with saturated aqueous sodium carbonate solution (5 mL) and partitioned with EtOAc (15 mL). The organic layer was isolated and the aqueous layer re-extracted with EtOAc (2×15 mL). The combined organic layer was washed with brine (5 mL), passed through a hydrophobic frit and concentrated under reduced pressure to give a crude mixture of the title compounds (82 mg).

LCMS (Method C): Rt=0.74 min and 0.77 min, MH+ 410.

Crude material was taken forward to the next reaction step without purification.

Intermediate 16. 3-(1-Methyl-1H-pyrazol-4-yl)-4,5,7,8-tetrahydro-1H-oxepino[4,5-c]pyrazole

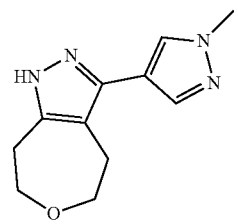 [SMILES: Cn1cc(-c2n[nH]c3c2CCOCC3)cn1]

A solution of dihydro-2H-pyran-4(3H)-one (134 mg, 1.342 mmol) in MeOH (6 mL) was treated with 4-methylbenzenesulfonohydrazide (250 mg, 1.342 mmol) and the reaction mixture stirred for 5 min then concentrated. The crude material was dissolved in anhydrous dioxane (6 mL) and the reaction mixture treated with 4-ethynyl-1-methyl-1H-pyrazole (214 mg, 2.014 mmol) and cesium carbonate (656 mg, 2.014 mmol). The reaction mixture was heated at 110° C. for 15 h. The reaction mixture was diluted with water (10 mL) and partitioned with EtOAc (20 mL). The organic layer was isolated and the aqueous layer re-extracted with EtOAc (2×20 mL). The crude intermediate was purified by silica column chromatography, eluting with a 70 to 100% gradient of a solution of EtOAc in cyclohexanes. The isolated material was dissolved in dioxane (6 mL) and treated with (diethyloxonio)trifluoroborate (0.097 mL, 0.79 mmol) and the reaction mixture was stirred for 4 h. The reaction mixture was treated with a solution of NaHCO3 (20 ml) and partitioned with EtOAc (50 mL). The organic layer was isolated and the aqueous layer re-extracted with EtOAc (2×50 mL). Material was purified by silica column chromatography, eluting with 100% EtOAc, to give the title compound (172 mg, 59%).

LCMS (Method A): Rt=0.58 min, MH+ 219.

Intermediate 17. 3-Bromo-1-(1-methyl-1H-pyrazol-4-yl)-4,5,7,8-tetrahydro-1H-oxepino[4,5-c]pyrazole

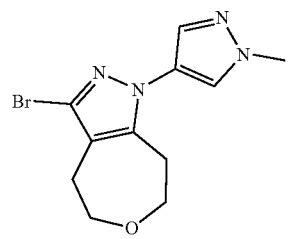 [SMILES: Cn1cc(-n2nc(Br)c3c2CCOCC3)cn1]

A mixture of 1-methyl-4-(4,4,5,5-tetramethyl-1,3,2-dioxaborolan-2-yl)-1H-pyrazole (96 mg, 0.461 mmol), 3-bromo-4,5,7,8-tetrahydro-1H-oxepino[4,5-c]pyrazole (50 mg, 0.230 mmol) and DMAP (56 mg, 0.461 mmol) were combined in MeCN (1 mL). The reaction mixture was treated with copper (II) acetate (63 mg, 0.346 mmol) and stirred overnight at 40° C., open to air. The reaction mixture was allowed to cool to room temperature and treated with ammonium hydroxide (2 mL), diluted with water (5 mL) and partitioned with EtOAc (5 mL). The organic layer was isolated and the aqueous layer re-extracted with EtOAc (2×5 mL). The combined organic layer was washed with brine (5 mL), passed through a hydrophobic frit and concentrated under reduced pressure. The crude product was purified by MDAP (Method B) to give the title compound (10 mg, 15%).

LCMS (Method A): Rt=0.81 min, MH+ 297/299.

Intermediate 18. 3-Bromo-1-(6-methoxy-5-methylpyridin-3-yl)-4,5,7,8-tetrahydro-1H-oxepino[4,5-c]pyrazole

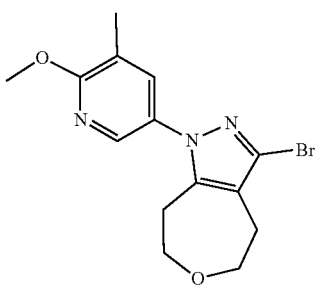 [SMILES: COc1ncc(-n2nc(Br)c3c2CCOCC3)cc1C]

A mixture of 6-methoxy-5-methylpyridin-3-yl)boronic acid (185 mg, 1.106 mmol), 3-bromo-4,5,7,8-tetrahydro-1H-oxepino[4,5-c]pyrazole (200 mg, 0.921 mmol) and DMAP (225 mg, 1.843 mmol) and copper (II) acetate (251 mg, 1.302 mmol) in MeCN (2 mL) was stirred in the open air at 80° C. for 4 h. The reaction mixture was treated with a 5% by weight aqueous solution of TMEDA (20 mL) and partitioned with EtOAc (30 mL). The organic layer was isolated and the aqueous layer re-extracted with EtOAc (2×30 mL). The combined organic layer was passed through a hydrophobic frit then concentrated under reduced pressure to afford a green oil. The crude material was treated with EtOAc (20 mL) and washed with a 1 M aqueous solution of HCl (2×20 mL). The organic layer was isolated and concentrated under reduced pressure to give the crude title compound as a brown oil (191 mg).

LCMS (Method C): Rt=1.17 min, MH+ 338/340

Crude material was taken forward to the next reaction step without purification.

Intermediate 19. 3-Bromo-1-(6-methoxy-5-methylpyridin-3-yl)-4,5,7,8-tetrahydro-1H-oxepino[4,5-c]pyrazole and 3-bromo-2-(6-methoxy-5-methylpyridin-3-yl)-4,5,7,8-tetrahydro-2H-oxepino[4,5-c]pyrazole

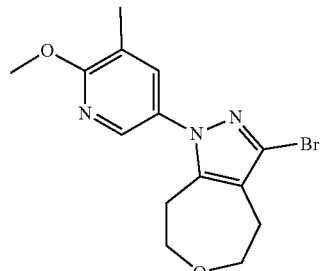

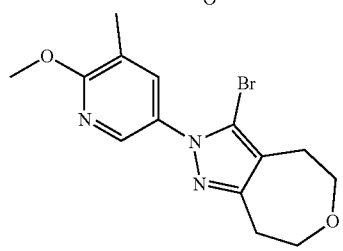

A mixture of (6-methoxy-5-methylpyridin-3-yl)boronic acid (308 mg, 1.843 mmol), 3-bromo-4,5,7,8-tetrahydro-1H-oxepino[4,5-c]pyrazole (400 mg, 1.843 mmol) and DMAP (450 mg, 3.69 mmol) and copper (II) acetate (502 mg, 2.76 mmol) were added to MeCN (6 mL). The reaction mixture was stirred overnight at 40° C., open to air, then allowed to cool to room temperature. The reaction mixture was treated with ammonium hydroxide (20 mL) and water (20 mL) then partitioned with EtOAc (25 mL). The organic layer was isolated and the aqueous layer re-extracted with EtOAc (2×25 mL). The combined organic layer was washed with brine (25 mL) and passed through a hydrophobic frit then concentrated under reduced pressure. The crude material was dissolved in MeOH (2 mL) and loaded onto a SCX-SPE cartridge (5 g) that had been preconditioned with MeOH. The cartridge was eluted with MeOH (20 mL) and the eluant concentrated under reduced pressure to give a crude mixture of the title compounds (535 mg).

LCMS (Method C): Rt=1.15 min, MH+ 338/340.

Crude material was taken forward without further purification.

Intermediate 20. 1-(5-(Fluoromethyl)-6-methoxypyridin-3-yl)-3-(1-(4-methoxybenzyl)-1H-pyrazol-4-yl)-4,5,7,8-tetrahydro-1H-oxepino[4,5-c]pyrazole]

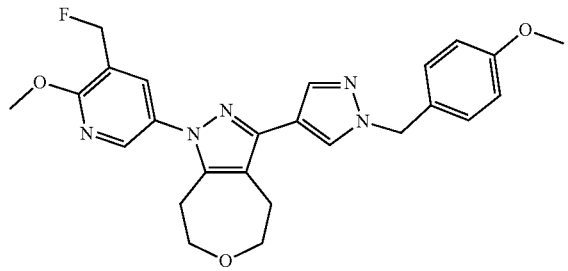

A mixture of copper (II) acetate (53 mg, 0.292 mmol), 3-(1-(4-methoxybenzyl)-1H-pyrazol-4-yl)-4,5,7,8-tetrahydro-1H-oxepino[4,5-c]pyrazole (82 mg, 0.253 mmol), 3-(fluoromethyl)-2-methoxy-5-(4,4,5,5-tetramethyl-1,3,2-dioxaborolan-2-yl)pyridine (72 mg, 0.270 mmol) and DMAP (65 mg, 0.532 mmol) was dissolved in MeCN (2 mL). The reaction mixture was stirred open to air for 1.5 h then heated at 40° C. overnight. The reaction mixture was treated with MeOH (1 mL) and heated at 40° C. for 4 h and allowed to stand at room temperature for 4 d.

Separately, a mixture of copper (II) acetate (123 mg, 0.678 mmol), 3-(1-(4-methoxybenzyl)-1H-pyrazol-4-yl)-4,5,7,8-tetrahydro-1H-oxepino[4,5-c]pyrazole (200 mg, 0.617 mmol), 3-(fluoromethyl)-2-methoxy-5-(4,4,5,5-tetramethyl-1,3,2-dioxaborolan-2-yl)pyridine (181 mg, 0.678 mmol), and DMAP (151 mg, 1.233 mmol) was dissolved in MeCN (5 mL) and treated with MeOH (1 mL). The reaction mixture was stirred at 40° C., open to air, for 24 hours.

The two reaction mixtures were combined and diluted with a 5% by weight aqueous solution of DMEDA (25 mL) and partitioned with EtOAc (25 mL). The organic layer was isolated and the aqueous layer re-extracted with EtOAc (2×25 mL). The combined organic layer was passed through a hydrophobic frit and concentrated under reduced pressure to give crude product as a brown oil (560 mg). The crude product was purified by MDAP (Method A) to give the title compound (191 mg, 64%).

LCMS (Method C): Rt=1.16 min, MH⁺ 464.

Intermediate 21. N-(2-Methoxy-5-(3-(1-(4-methoxybenzyl)-1H-pyrazol-4-yl)-4,5,7,8-tetrahydro-1H-oxepino[4,5-c]pyrazol-1-yl)pyridin-3-yl)methanesulfonamide

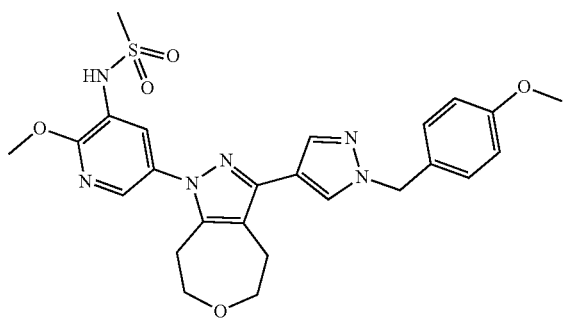

3-(1-(4-Methoxybenzyl)-1H-pyrazol-4-yl)-4,5,7,8-tetrahydro-1H-oxepino[4,5-c]pyrazole (209 mg, 0.644 mmol) was added to a solution of N-(2-methoxy-5-(4,4,5,5-tetramethyl-1,3,2-dioxaborolan-2-yl)pyridin-3-yl)methanesulfonamide (238 mg, 0.725 mmol), copper (II) acetate (126 mg, 0.694 mmol), DMAP (157 mg, 1.289 mmol) in MeCN (5 mL). The reaction mixture was stirred overnight at room temperature open to the air then treated with copper (II) acetate (126 mg, 0.694 mmol). The reaction mixture was heated at 40° C. for 8 h, open to the air. The reaction mixture was partitioned with an aqueous solution of TMEDA (5% by weight, 25 mL) and EtOAc (25 mL). The organic layer was isolated and the aqueous layer re-extracted with EtOAc (2×25 mL). The combined organic layer was passed through a hydrophobic frit and concentrated under reduced pressure. Half the crude material was purified by reverse phase column chromatography using a C18 column, eluting with a 15 to 55% gradient of MeCN in ammonium bicarbonate in water (adjusted to pH 10 with ammonia in water), while the other half was purified by MDAP (Method B) to give the title compound as a beige solid (164 mg).

LCMS (Method C): Rt=0.75, MH⁺ 525

Intermediate 22. (2R,4r,6S)-tert-Butyl 4-((4-(3-bromo-4,5,7,8-tetrahydro-1H-oxepino[4,5-c]pyrazol-1-yl)-1H-pyrazol-1-yl)methyl)-2,6-dimethylpiperidine-1-carboxylate

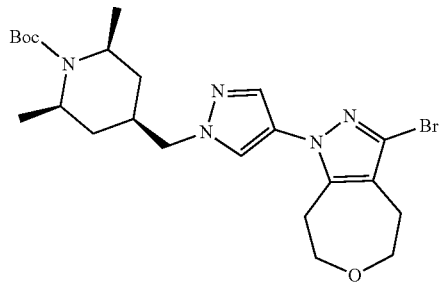 [SMILES: C[C@@H]1C[C@H](Cn2cc(-n3nc(Br)c4c3CCOCC4)cn2)C[C@H](C)N1C(=O)OC(C)(C)C]

A stirred mixture of tert-butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate (1159 mg, 2.76 mmol), 3-bromo-4,5,7,8-tetrahydro-1H-oxepino[4,5-c]pyrazole (500 mg, 2.303 mmol), CuOAc (628 mg, 3.46 mmol) and DMAP (536 mg, 4.61 mmol) in MeCN (5 mL) were heated at 80° C. open to the air for 42 h.

The reaction mixture was quenched with a 5% by weight solution of TMEDA (150 mL) and partitioned with EtOAc (100 mL). The organic layer was isolated and washed with a 5% by weight solution of TMEDA (150 mL). The aqueous layer was extracted with EtOAc (500 mL). The combined organic layer was passed through a hydrophobic frit and concentrated under reduced pressure. The crude product was purified by silica column chromatography using a 0 to 100% gradient of EtOAc in cyclohexane to give the title compound as a white solid (190 mg).

LCMS (Method C): Rt=1.33 min, MH⁺ 508/510

The partially purified product was taken forward into the next synthetic step.

Intermediate 23. 2-Methoxy-5-(3-(1-(4-methoxybenzyl)-1H-pyrazol-4-yl)-4,5,7,8-tetrahydro-1H-oxepino[4,5-c]pyrazol-1-yl)nicotinonitrile and 2-methoxy-5-(3-(1-(4-methoxybenzyl)-1H-pyrazol-4-yl)-4,5,7,8-tetrahydro-2H-oxepino[4,5-c]pyrazol-2-yl)nicotinonitrile

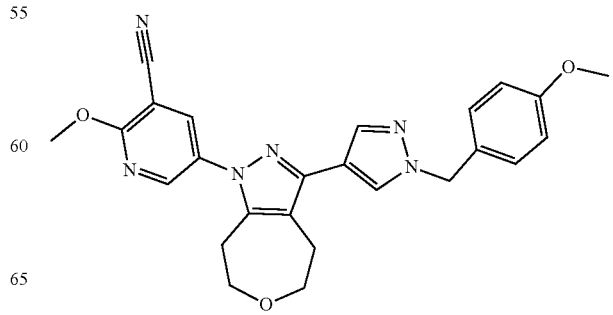

-continued

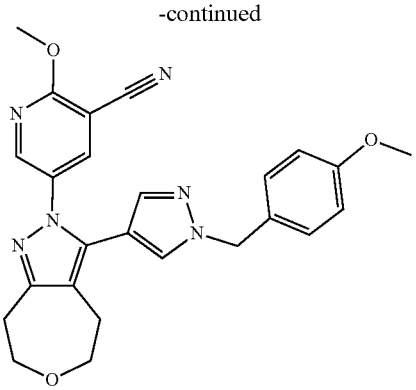

A mixture of copper (II) acetate (140 mg, 0.771 mmol), 2-methoxy-5-(4,4,5,5-tetramethyl-1,3,2-dioxaborolan-2-yl)nicotinonitrile (266 mg, 1.023 mmol), 3-(1-(4-methoxybenzyl)-1H-pyrazol-4-yl)-4,5,7,8-tetrahydro-1H-oxepino[4,5-c]pyrazole (250 mg, 0.771 mmol) and DMAP (188 mg, 1.541 mmol) dissolved in MeCN (6 mL) and stirred at room temperature for 3 h. The reaction mixture was then heated at 40° C. overnight.

The reaction mixture was diluted with a 5% by weight aqueous solution of DMEDA (30 mL) and extracted with three equivalents of EtOAc (30 mL each). The organic phase was passed through a hydrophobic frit and concentrated under reduced pressure to give crude product as a brown gum (660 mg).

The crude product was purified by silica column chromatography using a 0 to 40% gradient of EtOAc and cyclohexane, then 100% EtOAc to give the mixture of title compounds as a white crystalline solid (205 mg).

The partially purified product was taken forward into the next synthetic step.

LCMS (Method C): Rt=1.09 min and 1.10 min, MH$^+$ 457.

Intermediate 24. 3-(6-Methoxy-5-methylpyridin-3-yl)-1-(1H-pyrazol-4-yl)-4,5,7,8-tetrahydro-1H-oxepino[4,5-c]pyrazole

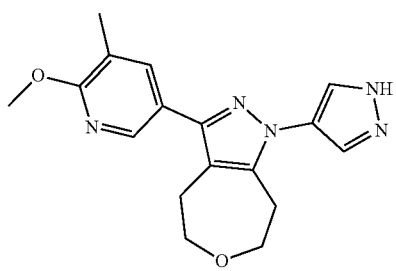 [SMILES: COc1ncc(-c2nn(-c3cn[nH]c3)c3c2CCOCC3)cc1C]

3-(6-Methoxy-5-methylpyridin-3-yl)-1-(1-(tetrahydro-2H-pyran-2-yl)-1H-pyrazol-4-yl)-4,5,7,8-tetrahydro-1H-oxepino[4,5-c]pyrazole (1.8 g, 4.40 mmol) in DCM (30 mL) was treated with TFA (20 mL). The reaction mixture was stirred at room temperature for 5 h. The reaction mixture was concentrated under reduced pressure and neutralised with ammonium bicarbonate solution (50 mL) then extracted with 10% MeOH in DCM (100 mL). The organic layer was dried over sodium sulfate, filtered and concentrated under reduced pressure to give the title compound as an off-white foam (1.5 g).

LCMS (Method B): Rt=2.04 min, MH$^+$ 326.

Intermediate 25. 3-(6-Methoxy-5-methylpyridin-3-yl)-1-(1-(tetrahydro-2H-pyran-2-yl)-1H-pyrazol-4-yl)-4,5,7,8-tetrahydro-1H-oxepino[4,5-c]pyrazole

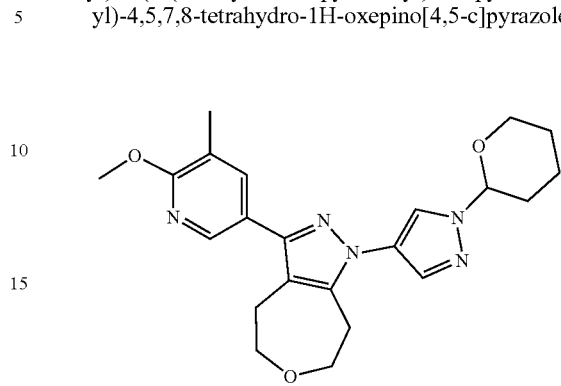

A solution of 3-(6-methoxy-5-methylpyridin-3-yl)-4,5,7,8-tetrahydro-1H-oxepino[4,5-c]pyrazole (260 mg, 1.003 mmol) in dry MeCN (10 mL) was treated with copper (II) acetate (273 mg, 1.504 mmol), 1-(tetrahydro-2H-pyran-2-yl)-4-(4,4,5,5-tetramethyl-1,3,2-dioxaborolan-2-yl)-1H-pyrazole (416 mg, 1.496 mmol) and DMAP (243 mg, 1.989 mmol). The reaction mixture was stirred at 40° C. open to air for 5 h and then treated with a few drops of IPA. The reaction mixture was heated at 40° C. overnight and then treated with 1-(tetrahydro-2H-pyran-2-yl)-4-(4,4,5,5-tetramethyl-1,3,2-dioxaborolan-2-yl)-1H-pyrazole (206 mg, 0.714 mmol) and heated overnight at 60° C. The reaction mixture was heated for a further 6 h and then treated with 1-(tetrahydro-2H-pyran-2-yl)-4-(4,4,5,5-tetramethyl-1,3,2-dioxaborolan-2-yl)-1H-pyrazole (194 mg, 0.697 mmol). The reaction mixture was heated at 60° C. for one day and treated with a 5% by weight solution of TMEDA in water (10 mL). The reaction mixture was partitioned with EtOAc (10 mL), and the organic layer isolated. The aqueous layer was re-extracted with EtOAc (3×10 mL) and the combined organic layers were washed with aqueous HCl (1 M, 20 mL) and then passed through a hydrophobic frit and concentrated under reduced pressure to give crude product (139 mg). The crude product was purified by MDAP (Method A) to give the title compound (44 mg, 8%).

LCMS (Method C): Rt=1.11 min, MH$^+$ 410.

Intermediate 26. 5-(3-Bromo-4,5,7,8-tetrahydro-1H-oxepino[4,5-c]pyrazol-1-yl)-2-methoxynicotinonitrile

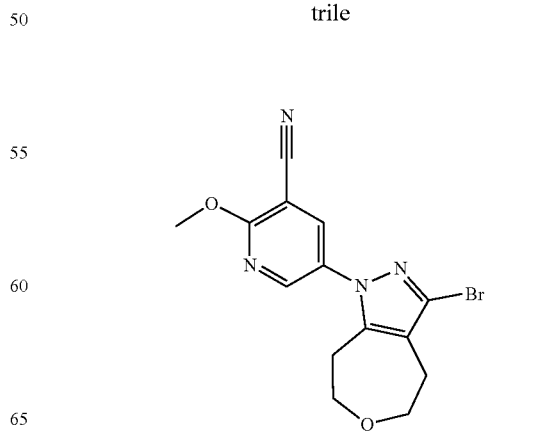

A microwave vial containing molecular sieves (3 Å, 600 mg) was dried overnight in a vacuum oven. The vial was charged with 3-bromo-4,5,7,8-tetrahydro-1H-oxepino[4,5-c]pyrazole (200 mg, 0.921 mmol), 2-methoxy-5-(4,4,5,5-tetramethyl-1,3,2-dioxaborolan-2-yl)nicotinonitrile (394 mg, 1.515 mmol), copper (II) acetate (180 mg, 0.991 mmol), triethylamine (0.257 mL, 1.843 mmol), dry MeCN (2 mL) and dry EtOH (0.100 mL). The reaction mixture was heated at 80° C. for 5 h. The reaction mixture was passed through a 10 g Celite® cartridge, which was washed with methanol (80 mL) and concentrated under reduced pressure to give crude product (432 mg).

The crude product was partially purified using silica column chromatography, eluting with a 0 to 100% gradient of EtOAc and cyclohexane to give the title compounds (67 mg)

LCMS (Method A): Rt=1.09 min, MH+ 349/351.

The partially purified compound was taken forward to the next reaction step.

Intermediate 27. 2-Methoxy-5-(3-(1-(tetrahydro-2H-pyran-2-yl)-1H-pyrazol-4-yl)-4,5,7,8-tetrahydro-1H-oxepino[4,5-c]pyrazol-1-yl)nicotinonitrile

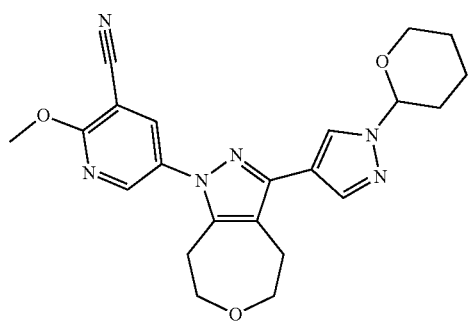 [SMILES: COc1ncc(-n2nc(-c3cnn(C4CCCCO4)c3)c3c2CCOCC3)cc1C#N]

A mixture of 5-(3-bromo-4,5,7,8-tetrahydro-1H-oxepino[4,5-c]pyrazol-1-yl)-2-methoxynicotinonitrile (67 mg), 1-(tetrahydro-2H-pyran-2-yl)-4-(4,4,5,5-tetramethyl-1,3,2-dioxaborolan-2-yl)-1H-pyrazole (80 mg, 0.288 mmol), potassium phosphate (61 mg, 0.287 mmol) and XPhos Pd G2 (8 mg, 10.17 µmol) were added to a microwave vial. The vial was capped and purged with nitrogen. The vial was treated with dioxane (1.2 ml) and water (0.3 ml) and heated at 90° C. for 90 min in a microwave. The reaction mixture was passed through a 2.5 g Celite® cartridge and washed with methanol and concentrated under reduced pressure. The residue was partitioned with EtOAc (10 mL) and water (10 mL). The aqueous layer was extracted with further EtOAc (3×10 mL), and the combined organic layer was passed through a hydrophobic frit and concentrated under reduced pressure to give the crude title compound (104 mg). The crude product was partially purified by MDAP (Method A) to give the title compound (49 mg).

LCMS (Method C): Rt=1.04 min, MH+ 421.

The partially purified compound was taken forward to the next reaction step.

Intermediate 28. 1-(6-Methoxy-5-methylpyridin-3-yl)-3-(1-(4-methoxybenzyl)-1H-pyrazol-4-yl)-4,5,7,8-tetrahydro-1H-oxepino[4,5-c]pyrazole

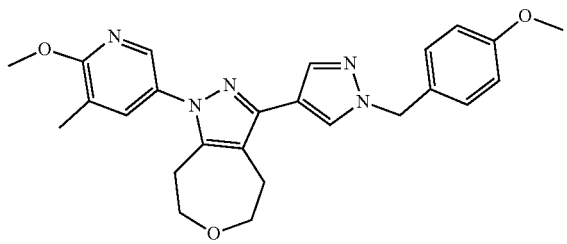

A mixture of copper (II) acetate (560 mg, 3.08 mmol), 3-(1-(4-methoxybenzyl)-1H-pyrazol-4-yl)-4,5,7,8-tetrahydro-1H-oxepino[4,5-c]pyrazole (1000 mg, 3.08 mmol), (6-methoxy-5-methylpyridin-3-yl)boronic acid (515 mg, 3.08 mmol), DMAP (753 mg, 6.17 mmol) and MeCN (30 mL) was stirred over the weekend at room temperature open to the air. The reaction mixture was treated with a 5% solution by weight of DMEDA in water (25 mL), and partially concentrated under reduced pressure. The mixture was partitioned with EtOAc (30 mL) and the organic layer isolated. The aqueous layer was extracted with EtOAc (2×30 mL) and the combined organic layer passed through a hydrophobic frit and concentrated under reduced pressure to afford crude product (approximately 2 g).

A portion of the crude product (340 mg) was purified using C18 silica chromatography on a 30 g cartridge, eluted with a mixture of MeCN and 0.1% ammonium bicarbonate solution in water (30 to 85% gradient), holding the gradient at 35% MeCN and then at 40% MeCN to maximise separation of regioisomers.

The remainder of the crude product was purified using C18 silica chromatography on a 120 g cartridge, eluted with a mixture of MeCN and 0.1% ammonium bicarbonate solution in water (30 to 85% gradient), holding the gradient at 35% MeCN and then at 40% MeCN to maximise separation of regioisomers.

Fractions from both purification batches were combined to give the title compound (595 mg, 40%).

LCMS (Method C): Rt=1.16 min, MH+ 446.

Intermediate 29. 1-(6-Methoxy-5-methylpyridin-3-yl)-3-(1-(tetrahydro-2H-pyran-2-yl)-1H-pyrazol-4-yl)-4,5,7,8-tetrahydro-1H-oxepino[4,5-c]pyrazole

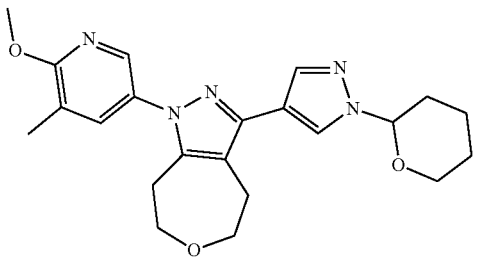 [SMILES: COc1ncc(-n2nc(-c3cnn(C4CCCCO4)c3)c3c2CCOCC3)cc1C]

A mixture of 1-(tetrahydro-2H-pyran-2-yl)-4-(4,4,5,5-tetramethyl-1,3,2-dioxaborolan-2-yl)-1H-pyrazole (314 mg, 1.130 mmol), XPhos Pd G2 (31.1 mg, 0.040 mmol) and potassium phosphate (240 mg, 1.130 mmol) in a microwave vial was put under an atmosphere of nitrogen and treated with a solution of 3-bromo-1-(6-methoxy-5-methylpyridin-3-yl)-4,5,7,8-tetrahydro-1H-oxepino[4,5-c]pyrazole (191 mg, 0.565 mmol) in dioxane (4 ml), followed by water (1.000 ml). The reaction mixture was heated at 80° C. for 3 h and concentrated under reduced pressure to afford a brown gum. The crude product was purified by reverse phase chromatography using a C18 column to afford the title compound as a brown solid (102 mg, 39%).

LCMS (Method C): Rt=1.09 min, MH+ 410.

Intermediate 30. 1-(6-Methoxy-5-methylpyridin-3-yl)-3-(1H-pyrazol-4-yl)-4,5,7,8-tetrahydro-1H-oxepino[4,5-c]pyrazole

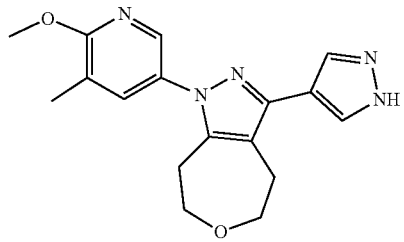 [SMILES: COc1ncc(-n2nc(-c3cn[nH]c3)c3c2CCOCC3)cc1C]

Method 1

A solution of 1-(6-methoxy-5-methylpyridin-3-yl)-3-(1-(4-methoxybenzyl)-1H-pyrazol-4-yl)-4,5,7,8-tetrahydro-1H-oxepino[4,5-c]pyrazole (595 mg, 1.336 mmol) DCM (6 mL) was cautiously treated with TFA (6.00 mL) and heated using a microwave at 70° C. for 3 h and then at 70° C. for a further 3 h. The reaction mixture was cooled to 0° C. and treated with a saturated aqueous solution of sodium bicarbonate (6 mL).

The reaction mixture was stirred vigorously overnight, while allowing to warm to room temperature. The reaction mixture was treated with further saturated aqueous solution of sodium bicarbonate (6 mL) and partitioned with DCM (20 mL). The organic layer was isolated and the aqueous layer was extracted with DCM (2×20 mL). The combined organic layer was passed through a hydrophobic frit and concentrated under reduced pressure to afford crude product.

The crude product was purified by silica chromatography, eluted with a mixture of EtOH and EtOAc (0 to 50% gradient) to give the title compound (269 mg, 56%).

LCMS (Method C): Rt=0.86 min, MH+ 326.

Method 2

A solution of 1-(6-methoxy-5-methylpyridin-3-yl)-3-(1-(tetrahydro-2H-pyran-2-yl)-1H-pyrazol-4-yl)-4,5,7,8-tetrahydro-1H-oxepino[4,5-c]pyrazole (102 mg, 0.249 mmol) in MeOH (2 ml) was treated with a 2 M solution of HCl (0.125 ml, 0.249 mmol) and the reaction stirred at room temperature for 5 h and then left to stand over the weekend.

The reaction mixture was concentrated under a stream of nitrogen and treated with a saturated aqueous solution of sodium bicarbonate solution (10 mL) and partitioned with EtOAc (15 mL). The organic layer was isolated and the aqueous layer re-extracted with EtOAc (2×15 mL). The combined organic layer was passed through a hydrophobic frit and concentrated under reduced pressure to give the crude title compound as a white solid (56 mg).

LCMS (Method C): Rt=0.87 min, MH+ 326.

The aqueous layer was re-extracted with DCM (3×20 mL) and the combined organic layer passed through a hydrophobic frit and concentrated under reduced pressure to afford a second crude batch of the title compound as a white solid (18 mg).

LCMS (Method C): Rt=0.87 min, MH+ 326.

The crude compound was taken forward into the next reaction step.

Intermediate 31. 1-(5-Fluoro-6-methoxypyridin-3-yl)-3-(1-(4-methoxybenzyl)-1H-pyrazol-4-yl)-4,5,7,8-tetrahydro-1H-oxepino[4,5-c]pyrazole

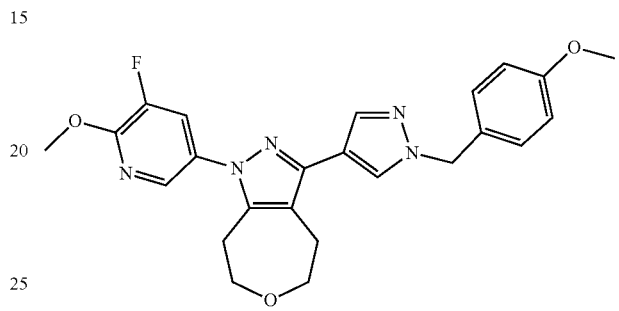

A round bottomed flask was charged with 3-(1-(4-methoxybenzyl)-1H-pyrazol-4-yl)-4,5,7,8-tetrahydro-1H-oxepino[4,5-c]pyrazole (203 mg, 0.626 mmol), (5-fluoro-6-methoxypyridin-3-yl)boronic acid (120 mg, 0.702 mmol), DMAP (153 mg, 1.252 mmol) and MeCN (6 mL). The reaction mixture was then treated with copper (II) acetate (114 mg, 0.626 mmol) and stirred at room temperature open to air for 2 h.

The reaction mixture was diluted with a 5% by weight aqueous solution of TMEDA (25 ml) and partitioned with EtOAc (25 ml). The organic layer was isolated and the aqueous phase washed with two further equivalents of EtOAc (25 ml). The combined organic layer was passed through a hydrophobic frit and concentrated under reduced pressure to give crude product as a brown oil (360 mg). The crude product was purified by MDAP (Method A) to give the title compound as a yellow gum (138 mg, 44%).

LCMS (Method C): Rt=1.13 min, MH+ 450.

Intermediate 32. 1-(5-Fluoro-6-methoxypyridin-3-yl)-3-(1H-pyrazol-4-yl)-4,5,7,8-tetrahydro-1H-oxepino[4,5-c]pyrazole

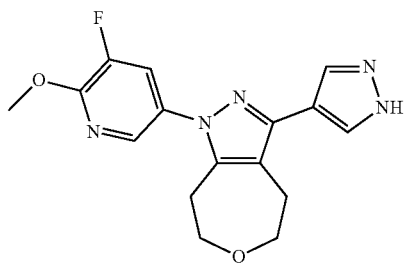 [SMILES: COc1ncc(-n2nc(-c3cn[nH]c3)c3c2CCOCC3)cc1F]

A solution of 1-(5-fluoro-6-methoxypyridin-3-yl)-3-(1-(4-methoxybenzyl)-1H-pyrazol-4-yl)-4,5,7,8-tetrahydro-1H-oxepino[4,5-c]pyrazole (138 mg) in DCM (2 mL) was treated with TFA (0.237 mL, 3.07 mmol) and the reaction mixture was heated at 70° C. using a microwave for 1 h. The reaction mixture was treated with TFA (0.237 mL, 3.07 mmol) and heated at 70° C. using a microwave for 1 h. The reaction mixture was treated with TFA (0.237 mL, 3.07 mmol) and heated at 70° C. using a microwave for 1 h. The reaction mixture was treated with a further portion of TFA (0.237 mL, 3.07 mmol) and heated at 70° C. using a microwave for 1 h. The reaction mixture was treated with a further portion of TFA (0.237 mL, 3.07 mmol) and heated at 70° C. using a microwave for 1 h.

The reaction mixture was treated dropwise with a saturated solution of aqueous sodium bicarbonate (20 mL) to pH 9. The resultant solid was isolated, washed with water (10 mL) and dissolved in a 2:1 mixture of DCM and MeOH (40 mL) then concentrated under reduced pressure to give a batch of product. The basified aqueous layer was partitioned with a 2:1 mixture of DCM and MeOH (30 mL). The organic layer was isolated and the aqueous layer re-extracted with a 2:1 mixture of DCM and MeOH (2×30 mL). The combined organic layer was passed through a hydrophobic frit and concentrated under reduced pressure to give a second batch of product. The two batches of product were combined by dissolving in a 2:1 mixture of DCM and MeOH and concentrating under a stream of nitrogen to give the crude title compound as a beige solid (105 mg).

LCMS (Method C): Rt=0.82 min, MH+ 330.

The crude compound was taken forward into the next reaction step without further purification.

Intermediate 33. N-(5-(3-(1H-Pyrazol-4-yl)-4,5,7,8-tetrahydro-1H-oxepino[4,5-c]pyrazol-1-yl)-2-methoxypyridin-3-yl)methanesulfonamide

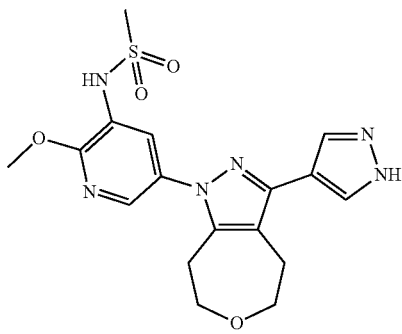 [SMILES: COc1ncc(-n2nc(-c3cn[nH]c3)c3c2CCOCC3)cc1NS(C)(=O)=O]

A solution of N-(2-methoxy-5-(3-(1-(4-methoxybenzyl)-1H-pyrazol-4-yl)-4,5,7,8-tetrahydro-1H-oxepino[4,5-c]pyrazol-1-yl)pyridin-3-yl)methanesulfonamide (140 mg), in DCM (1 mL) was treated with TFA (1 mL) and the mixture was heated at 70° C. using a microwave for a total of 3 h. The reaction mixture was quenched using a saturated aqueous solution of sodium hydrogen carbonate (20 mL) to pH 9. The reaction mixture was extracted with a 1:1 mixture of MeOH and DCM (3×20 mL), and the organic layer isolated, passed through a hydrophobic frit and concentrated under reduced pressure to give the crude title compound (85 mg).

The aqueous layer was concentrated under reduced pressure to remove the majority of organic solvent, then passed through an Isolute 103 Cartridge, washing with water (two column volumes) and MeOH (two column volumes). The solvent was concentrated under reduced pressure and material combined with the previous batch to give crude title compound (137 mg).

LCMS (Method C): Rt=0.53 min, MH+ 405.

The crude compound was taken forward into the next reaction step without further purification.

Intermediate 34. 5-(3-(1H-Pyrazol-4-yl)-4,5,7,8-tetrahydro-1H-oxepino[4,5-c]pyrazol-1-yl)-2-methoxynicotinonitrile

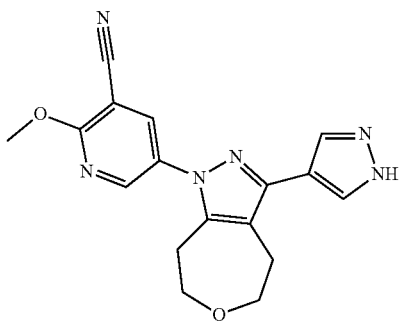 [SMILES: COc1ncc(-n2nc(-c3cn[nH]c3)c3c2CCOCC3)cc1C#N]

To a mixture of 2-methoxy-5-(3-(1-(tetrahydro-2H-pyran-2-yl)-1H-pyrazol-4-yl)-4,5,7,8-tetrahydro-1H-oxepino[4,5-c]pyrazol-1-yl)nicotinonitrile (49 mg) in MeOH (1.5 mL) was added a 2 M solution of aqueous HCl (0.060 mL, 0.120 mmol). The reaction mixture was stirred under nitrogen at room temperature overnight and concentrated under reduced pressure.

The residue was partitioned between sodium bicarbonate (10 mL) and EtOAc (10 mL). The aqueous layer was extracted with further EtOAc (3×10 mL), and the combined organic layer was passed through a hydrophobic frit and concentrated under reduced pressure to give the crude title compound (41 mg).

LCMS (Method C): Rt=0.82 min and Rt 0.80 min, MH+ 337.

The crude mixture of compounds was carried through to the next synthetic step without further purification.

Intermediate 35. 1-(5-(Fluoromethyl)-6-methoxypyridin-3-yl)-3-(1H-pyrazol-4-yl)-4,5,7,8-tetrahydro-1H-oxepino[4,5-c]pyrazole

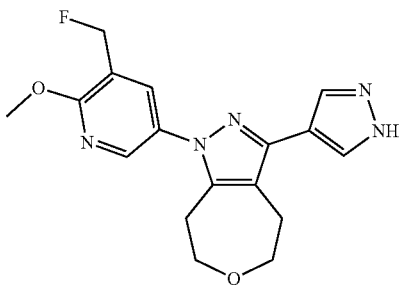 [SMILES: COc1ncc(-n2nc(-c3cn[nH]c3)c3c2CCOCC3)cc1CF]

1-(5-(fluoromethyl)-6-methoxypyridin-3-yl)-3-(1-(4-methoxybenzyl)-1H-pyrazol-4-yl)-4,5,7,8-tetrahydro-1H-oxepino[4,5-c]pyrazole (191 mg, 0.412 mmol) in DCM (1.4 mL) was treated with TFA (1.4 mL, 18.17 mmol) and heated using a microwave at 70° C. for 4 h.

The reaction mixture was treated with a saturated aqueous solution of sodium bicarbonate (20 mL) in a dropwise manner and partitioned with DCM (25 mL). The organic layer was isolated and the aqueous layer re-extracted with DCM (2×25 mL). The combined organic layer was passed through a hydrophobic frit and concentrated under reduced pressure, to give the crude title compound as an off white solid (177 mg).

LCMS (Method C): Rt=0.83 min, MH+ 344.

The crude compound was taken forward into the next reaction step without further purification.

General Alkylation Procedure

Intermediate 36. tert-Butyl 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate

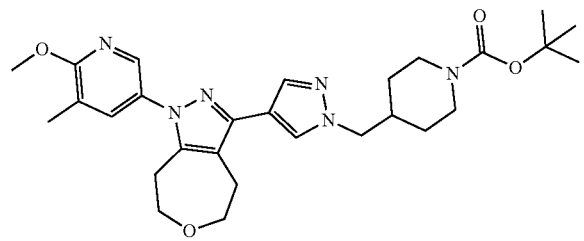 [SMILES: COc1ncc(-n2nc(-c3cnn(CC4CCN(C(=O)OC(C)(C)C)CC4)c3)c3c2CCOCC3)cc1C]

1-(6-Methoxy-5-methylpyridin-3-yl)-3-(1H-pyrazol-4-yl)-4,5,7,8-tetrahydro-1H-oxepino[4,5-c]pyrazole (400 mg, 1.229 mmol) in DMF (5 mL) under nitrogen was treated with NaH (155 mg, 3.88 mmol, 60% by weight as a suspension in mineral oils). The reaction mixture was stirred for 30 min at room temperature and treated with tert-butyl 4-(bromomethyl)piperidine-1-carboxylate (460 mg, 1.654 mmol). The reaction mixture was stirred at room temperature for a further 15 h.

The reaction mixture was treated with a saturated aqueous solution of sodium bicarbonate (10 mL) in a dropwise manner and stirred for 30 min. The reaction mixture was diluted with water (20 mL) and partitioned with EtOAc (30 mL). The organic layer was isolated and the aqueous layer re-extracted with EtOAc (2×30 mL). Each extract was washed with a 5% by weight solution of LiCl (2×20 mL). The combined organic layer passed through a hydrophobic frit and concentrated under reduced pressure and dried to give the crude title compound as a brown oil (726 mg).

LCMS (Method C): Rt=1.25 min, MH+ 523.

The crude compound was taken forward into the next reaction step without further purification.

Intermediate 37. tert-Butyl 3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate

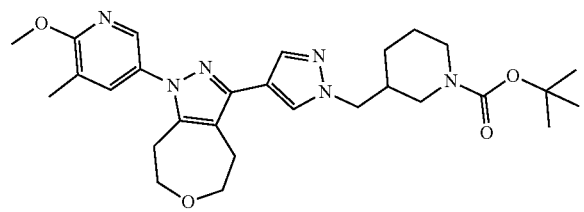 [SMILES: COc1ncc(-n2nc(-c3cnn(CC4CCCN(C(=O)OC(C)(C)C)C4)c3)c3c2CCOCC3)cc1C]

1-(6-Methoxy-5-methylpyridin-3-yl)-3-(1H-pyrazol-4-yl)-4,5,7,8-tetrahydro-1H-oxepino[4,5-c]pyrazole (73 mg, 0.112 mmol) and potassium carbonate (46.5 mg, 0.337 mmol) were combined in DMF (1 mL) and stirred under nitrogen at room temperature for 30 min. The reaction mixture was treated with tert-butyl 3-(bromomethyl)piperidine-1-carboxylate (94 mg, 0.337 mmol) and stirred over the weekend.

The reaction mixture was treated with potassium carbonate (46.5 mg, 0.337 mmol) and tert-butyl 3-(bromomethyl)piperidine-1-carboxylate (94 mg, 0.337 mmol) and heated at 50° C. for 3 h then at room temperature overnight.

The reaction mixture was heated at 50° C. for 7 h and treated with one equivalent of tert-butyl 3-(bromomethyl)piperidine-1-carboxylate (0.112 mmol) and heated at 50° C. for 1 h. The reaction mixture was then heated using a microwave at 50° C. for 1 h, then at 60° C. for 1 h, then at 70° C. for 1 h, then at 80° C. for 1 h, then at 90° C. for 7 h, then at 100° C. for 1 h.

The reaction mixture was treated with saturated ammonium chloride solution (5 mL) and partitioned with EtOAc (10 mL). The organic layer was isolated and the aqueous layer re-extracted with EtOAc (2×10 mL). The combined organic layer was washed with a 5% by weight solution of LiCl. The organic layer was passed through a hydrophobic frit and concentrated to give crude title compound (100 mg).

LCMS (Method C): Rt=1.26 min, MH+ 523.

The crude compound was taken forward into the next reaction step without further purification.

Intermediate 38. tert-Butyl 4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidine-1-carboxylate

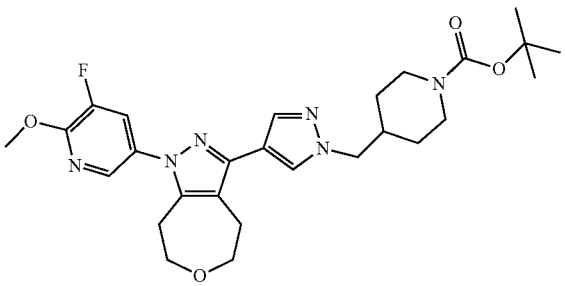 [SMILES: COc1ncc(-n2nc(-c3cnn(CC4CCN(C(=O)OC(C)(C)C)CC4)c3)c3c2CCOCC3)cc1F]

A solution of 1-(5-fluoro-6-methoxypyridin-3-yl)-3-(1H-pyrazol-4-yl)-4,5,7,8-tetrahydro-1H-oxepino[4,5-c]pyrazole (105 mg, 0.319 mmol) in DMF (2 mL) was purged with nitrogen then cooled using ice. The reaction mixture was treated with a 60% suspension of NaH in mineral oils (31.9 mg, 0.797 mmol) and allowed to warm to room temperature. The reaction mixture was stirred for 30 min and treated with tert-butyl 4-(bromomethyl)piperidine-1-carboxylate (266 mg, 0.956 mmol). The reaction was stirred at room temperature under nitrogen for 3 h.

The reaction mixture was cooled using ice and treated dropwise with an aqueous solution of ammonium chloride (6 mL). The mixture was stirred for 30 min and diluted with water (15 mL). The reaction mixture was partitioned with EtOAc (25 mL) and the organic layer isolated. The aqueous layer was re-extracted with EtOAc (2×25 mL). The combined organic layer was isolated and washed with three equivalents of a 5% by weight solution of LiCl (30 mL each). The organic layer was passed through a hydrophobic frit and concentrated under reduced pressure to afford crude product as a yellow oil (335 mg).

The crude product was purified by MDAP (Method B) to give the title compound as a yellow gum (100 mg, 54%).

LCMS (Method C): Rt=1.22 min, MH+ 527.

Intermediate 39. tert-Butyl 4-((4-(1-(6-methoxy-5-(methylsulfonamido)pyridin-3-yl)-4,5,7,8-tetrahydro-1H-oxepino[4,5-c]pyrazol-3-yl)-1H-pyrazol-1-yl)methyl)piperidine-1-carboxylate

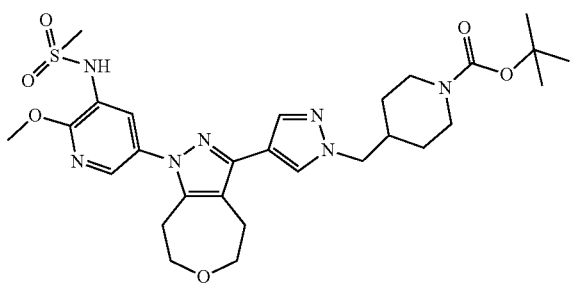 [SMILES: COc1ncc(-n2nc(-c3cnn(CC4CCN(C(=O)OC(C)(C)C)CC4)c3)c3c2CCOCC3)cc1NS(C)(=O)=O]

Prepared using the general alkylation procedure using N-(5-(3-(1H-pyrazol-4-yl)-4,5,7,8-tetrahydro-1H-oxepino[4,5-c]pyrazol-1-yl)-2-methoxypyridin-3-yl)methanesulfonamide (115 mg, 0.284 mmol), NaH (40 mg, 60% by weight in mineral oils), DMF (2 mL), and tert-butyl 4-(bromomethyl)piperidine-1-carboxylate (87 mg, 0.313 mmol), with the exception the reaction was quenched with a saturated aqueous solution of ammonium chloride (10 mL) instead of a saturated aqueous solution of sodium bicarbonate. Crude product was isolated as a beige oil (180 mg) and purified by MDAP (Method A) to give the title compound as a white solid (103 mg, 57%).

LCMS (Method C): Rt=0.86 min, MH+ 602.

Intermediate 40. tert-Butyl 3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidine-1-carboxylate

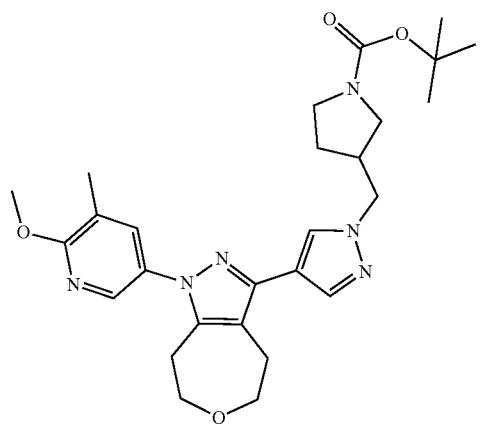 [SMILES: COc1ncc(-n2nc(-c3cnn(CC4CCN(C(=O)OC(C)(C)C)C4)c3)c3c2CCOCC3)cc1C]

Prepared using the general alkylation procedure from 1-(6-methoxy-5-methylpyridin-3-yl)-3-(1H-pyrazol-4-yl)-4,5,7,8-tetrahydro-1H-oxepino[4,5-c]pyrazole (150 mg, 0.461 mmol), NaH (50 mg, 60% by weight suspension on mineral oils), DMF (2.5 mL) and tert-butyl 3-(bromomethyl)pyrrolidine-1-carboxylate (170 mg, 0.645 mmol), except the product was, not purified by MDAP. The crude title compound was isolated as a brown gum (294 mg, >99%).

LCMS (Method C): Rt=1.20 min, MH+ 509.

Intermediate 41. 1-(6-Methoxy-5-methylpyridin-3-yl)-3-(1-(pyrrolidin-3-ylmethyl)-1H-pyrazol-4-yl)-4,5,7,8-tetrahydro-1H-oxepino[4,5-c]pyrazole

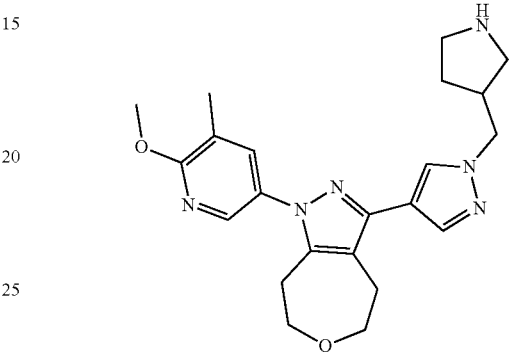

tert-Butyl 3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidine-1-carboxylate (294 mg, 0.578 mmol) in DCM (3 mL) was treated with TFA (1.4 mL, 18.17 mmol) and the mixture was stirred for 2 h at room temperature, then allowed to stand over the weekend. The reaction mixture was treated by dropwise addition of a saturated aqueous solution of sodium bicarbonate (10 mL), until pH 9 was reached. The mixture was diluted with water (10 mL), and partitioned with DCM (20 mL). The organic layer was isolated and the aqueous layer re-extracted with DCM (2×20 mL) The combined organic layer was passed through a hydrophobic frit and concentrated under reduced pressure to give the crude title compound as a brown gum (236 mg, 85%).

LCMS (Method C): Rt=1.03 min, MH+ 409.

Intermediate 42. 5-(3-(1H-Pyrazol-4-yl)-4,5,7,8-tetrahydro-1H-oxepino[4,5-c]pyrazol-1-yl)-2-methoxynicotinonitrile and 5-(3-(1H-pyrazol-4-yl)-4,5,7,8-tetrahydro-2H-oxepino[4,5-c]pyrazol-2-yl)-2-methoxynicotinonitrile

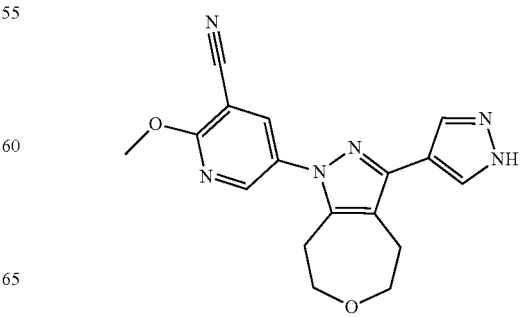

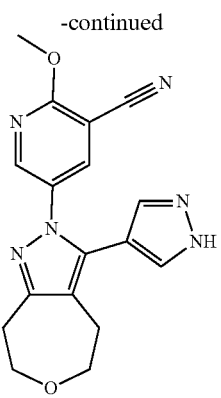

A mixture of 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile and 2-methoxy-5-(3-(1-(4-methoxybenzyl)-1H-pyrazol-4-yl)-4,5,7,8-tetrahydro-2H-oxepino[4,5-c]pyrazol-2-yl)nicotinonitrile (20 mg) was treated with DCM (0.1 mL) and TFA (0.1 mL, 1.298 mmol). The reaction mixture was heated 70° C. using a microwave for 2 h. The reaction mixture was treated with more 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile and 2-methoxy-5-(3-(1-(4-methoxybenzyl)-1H-pyrazol-4-yl)-4,5,7,8-tetrahydro-2H-oxepino[4,5-c]pyrazol-2-yl)nicotinonitrile (183 mg) in DCM (0.5 mL) followed by TFA (0.62 mL) and heated at 70° C. using a microwave for 5 h.

The reaction mixture was diluted with DCM (10 mL) and treated with a saturated aqueous solution of sodium bicarbonate in a dropwise manner until the reaction mixture was pH 9. The reaction mixture was stirred for 30 min then partitioned with DCM (20 mL). The organic layer was isolated and the aqueous layer reextracted with DCM (2×20 mL). The combined organic layer was passed through a hydrophobic frit and concentrated under reduced pressure, to give a crude mixture of the title compounds as a light brown gum (240 mg).

LCMS (Method C): Rt=0.79 min and 0.81 min, MH+ 337.

The crude mixture of compounds was taken forward into the next reaction step without further purification.

Intermediate 43. tert-Butyl 4-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate and tert-butyl 4-((4-(2-(5-cyano-6-methoxypyridin-3-yl)-4,5,7,8-tetrahydro-2H-oxepino[4,5-c]pyrazol-3-yl)-1H-pyrazol-1-yl)methyl)piperidine-1-carboxylate

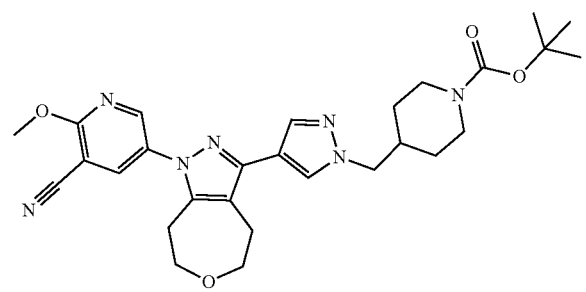 [SMILES: COc1ncc(-n2nc(-c3cnn(CC4CCN(C(=O)OC(C)(C)C)CC4)c3)c3c2CCOCC3)cc1C#N]

A mixture of 5-(3-(1H-pyrazol-4-yl)-4,5,7,8-tetrahydro-1H-oxepino[4,5-c]pyrazol-1-yl)-2-methoxynicotinonitrile and 5-(3-(1H-pyrazol-4-yl)-4,5,7,8-tetrahydro-2H-oxepino[4,5-c]pyrazol-2-yl)-2-methoxynicotinonitrile (200 mg) in DMF (2 mL) was treated with NaH (20 mg of a 60% suspension by weight in mineral oils, 1.682 mmol). The reaction mixture was stirred at room temperature under an atmosphere of nitrogen for 30 min. The reaction mixture was then treated with tert-butyl 4-(bromomethyl)piperidine-1-carboxylate (250 mg, 0.899 mmol) and stirred overnight.

The reaction mixture was treated with a saturated aqueous solution of ammonium chloride (5 mL) in a dropwise manner. The reaction mixture was diluted with water (15 mL) and partitioned with EtOAc (25 mL). The organic layer was isolated and the aqueous layer re-extracted with EtOAc (2×25 mL). The combined organic layer was washed with a 5% solution of LiCl (2×30 mL) and passed through a hydrophobic frit then concentrated under reduced pressure to give the crude product (340 mg). The crude product was purified by MDAP (Method A) to give the title compound as an off-white solid (61 mg, 31%).

LCMS (Method C): Rt=1.22 min, MH+ 534.

Intermediate 44. tert-Butyl 4-((4-(1-(5-(fluoromethyl)-6-methoxypyridin-3-yl)-4,5,7,8-tetrahydro-1H-oxepino[4,5-c]pyrazol-3-yl)-1H-pyrazol-1-yl)methyl)piperidine-1-carboxylate

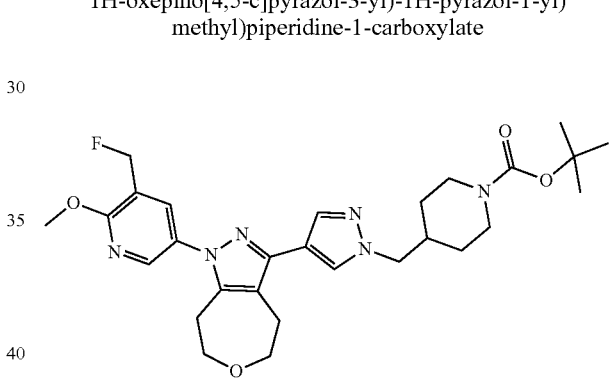

1-(5-(Fluoromethyl)-6-methoxypyridin-3-yl)-3-(1H-pyrazol-4-yl)-4,5,7,8-tetrahydro-1H-oxepino[4,5-c]pyrazole (60 mg, 0.175 mmol) was treated with a 60% by weight suspension of NaH in mineral oils (13 mg, 0.325 mmol) DMF (1 mL). The reaction mixture was stirred under nitrogen for 30 min and treated with tert-butyl 4-(bromomethyl)piperidine-1-carboxylate (146 mg, 0.524 mmol). The reaction mixture was stirred at room temperature under nitrogen for 18 h.

Separately a batch of 1-(5-(fluoromethyl)-6-methoxypyridin-3-yl)-3-(1H-pyrazol-4-yl)-4,5,7,8-tetrahydro-1H-oxepino[4,5-c]pyrazole (117 mg, 0.341 mmol) was dissolved in DMF (2 mL) and treated with a 60% by weight suspension of NaH in mineral oils (28.0 mg, 0.699 mmol). The reaction mixture was stirred under nitrogen for 30 min then treated with tert-butyl 4-(bromomethyl)piperidine-1-carboxylate (300 mg, 1.078 mmol). The reaction mixture was stirred at room temperature under nitrogen for 3 hours.

The two reaction mixtures were quenched with a saturated aqueous solution of ammonium chloride (5 mL) and combined. The reaction combined reaction mixture was partitioned with EtOAc (25 mL). The organic layer was isolated and the aqueous layer re-extracted with EtOAc (2×25 mL). The combined organic layer was washed with a 5% by weight solution of LiCl (2×25 mL) and passed through a hydrophobic frit then concentrated under reduced pressure then dried. The resulting solid was partitioned between EtOAc (25 mL) and water (25 mL). The organic layer was isolated and the aqueous layer re-extracted with EtOAc (2×25 mL). The combined organic layer was washed with a 5% by weight solution of LiCl (25 mL) and passed through a hydrophobic frit then concentrated under reduced pressure to give the crude product as a brown gum (454 mg).

LCMS (Method C): Rt=1.25 min, MH+ 541.

The crude compound was taken forward into the next reaction step without further purification.

Intermediate 45. Ethyl 4,5,7,8-tetrahydro-1H-oxepino[4,5-c]pyrazole-3-carboxylate

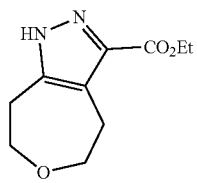 [SMILES: CCOC(=O)c1n[nH]c2c1CCOCC2]

A stirred solution of ethyl 2-diazoacetate (1.4 g, 12.27 mmol) in DMSO (50 mL) at room temperature and under an atmosphere of nitrogen was treated with pyrrolidine (0.101 mL, 1.227 mmol) and oxepan-4-one (2.80 g, 24.54 mmol, see Baldwin, John J. et al. from PCT Int. Appl., 2007070201 for preparation). The reaction mixture was stirred at room temperature for 16 h.

The reaction mixture was diluted with water (500 mL) and partitioned with EtOAc (250 mL). The organic layer was isolated and the aqueous layer re-extracted with EtOAc (250 mL). The combined organic layer was washed with brine (50 mL), dried over sodium sulphate, filtered and concentrated under reduced pressure to give crude product. The compound was purified by silica column chromatography, eluting with a 20% solution of EtOAc in petroleum ether and then a 25% solution of EtOAc in petroleum ether to give the title compound as an off-white solid (200 mg, 7%).

LCMS (Method B): Rt=1.51 min, MH+ 211.

Intermediate 46. Ethyl 1-(6-methoxy-5-methylpyridin-3-yl)-4,5,7,8-tetrahydro-1H-oxepino[4,5-c]pyrazole-3-carboxylate

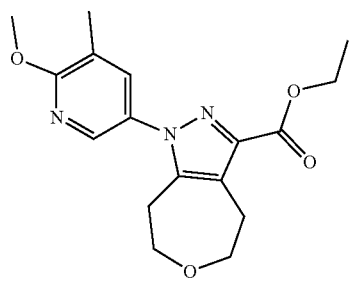 [SMILES: CCOC(=O)c1nn(-c2cnc(OC)c(C)c2)c2c1CCOCC2]

A stirred solution of ethyl 4,5,7,8-tetrahydro-1H-oxepino[4,5-c]pyrazole-3-carboxylate (200 mg, 0.951 mmol) in DCM (20 mL) at room temperature and under an atmosphere of oxygen was treated with (6-methoxy-5-methylpyridin-3-yl)boronic acid (238 mg, 1.427 mmol), copper (II) acetate (259 mg, 1.427 mmol) and pyridine (0.154 mL, 1.903 mmol). The reaction mixture was stirred at room temperature for 5 h then concentrated under reduced pressure. The crude compound was purified by silica column chromatography, eluting with a 15% solution of EtOAc in hexane to give crude product as an off white solid (220 mg). The crude material was purified by preparative HPLC (Method A) to give the title compound as an off white solid (14 mg, 12%).

LCMS (Method B): Rt=2.19 min, MH+ 332.

Intermediate 47.
(4-Isopropylpiperazin-1-yl)(oxazol-5-yl)methanone

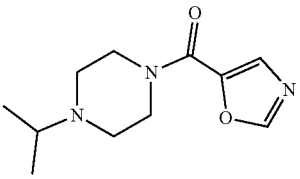 [SMILES: CC(C)N1CCN(C(=O)c2cnco2)CC1]

A mixture of oxazole-5-carboxylic acid (80 mg, 0.708 mmol), DIPEA (0.124 mL, 0.708 mmol), and 1-isopropylpiperazine (0.111 mL, 0.778 mmol) in THF (5 mL) was treated with a 50% by weight solution of 2,4,6-tripropyl-1,3,5,2,4,6-trioxatriphosphinane 2,4,6-trioxide (0.463 mL, 0.778 mmol) and stirred at room temperature overnight. The reaction mixture was diluted with a small amount of MeOH and poured directly onto an SCX-SPE cartridge (5 g) that had been preconditioned with MeOH. The cartridge was washed with MeOH and the product eluted using a 2 M solution of ammonia in MeOH to give the title compound (126 mg, 72%).

LCMS (Method C): Rt=0.59 min, MH+ 224.

The crude compound was taken forward into the next reaction step without further purification.

Intermediate 48.
2-(2-Hydroxypropan-2-yl)isonicotinic acid

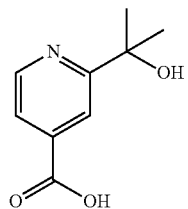

A solution of 2-(4-(hydroxymethyl)pyridin-2-yl)propan-2-ol (50 mg, 0.299 mmol) dissolved in water (2 mL) was treated with a solution of potassium permanganate (0.5 mL, 0.500 mmol) in water (1 mL). The reaction mixture was stirred at room temperature for 1 h and treated with an aqueous solution of NaHSO3 then acidified with a 2 M aqueous solution of HCl. The reaction mixture was partitioned with EtOAc (20 mL) and the organic layer isolated. The aqueous layer was re-extracted with EtOAc (20 mL) and the combined organic layer passed through a hydrophobic frit and concentrated under reduced pressure to give the crude title compound as a white solid (35 mg).

LCMS (Method C) Rt=0.32 min, MH+=182.

The crude compound was taken forward into the next reaction step without further purification.

Intermediate 49. Methyl 2-(2-hydroxypropan-2-yl)isonicotinate

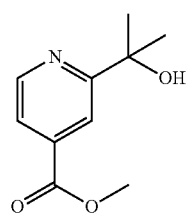

A solution of 2-(2-hydroxypropan-2-yl)isonicotinic acid (35 mg, 0.193 mmol) in a mixture of toluene (1 mL) and MeOH (0.500 mL) under an atmosphere of nitrogen was treated dropwise with a 2 M solution of TMS-diazomethane in hexane (0.2 mL, 0.400 mmol). The reaction mixture was stirred at room temperature for 1 h and treated with a few drops of AcOH and concentrated under reduced pressure to give the crude title compound as a yellow oil (33 mg).

LCMS (Method C) Rt=0.67 min, MH$^+$=196.

The crude compound was taken forward into the next reaction step without further purification.

Intermediate 50. Methyl 2-(2-hydroxypropan-2-yl)piperidine-4-carboxylate

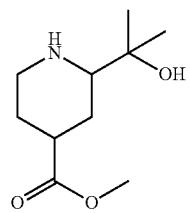

Methyl 2-(2-hydroxypropan-2-yl)isonicotinate (33 mg, 0.169 mmol) in AcOH (2.5 mL) was treated with platinum (IV) oxide (8 mg, 0.035 mmol) and stirred at room temperature under an atmosphere of hydrogen at 4 bar for 2 h and then concentrated under reduced pressure to give the crude title compound as a pale yellow gum (44 mg, 99%).

$^1$H NMR (400 MHz, DMSO-d$_6$) δ-ppm 3.11-2.98 (m, 1H), 2.40-2.22 (m, 2H), 1.89 (s, 6H), 1.85-1.65 (m, 2H), 1.40-1.20 (m, 1H), 1.14-0.97 (m, 7H).

The crude compound was taken forward into the next reaction step without further purification.

Intermediate 51. Methyl 1-benzyl-2-(2-hydroxypropan-2-yl)piperidine-4-carboxylate

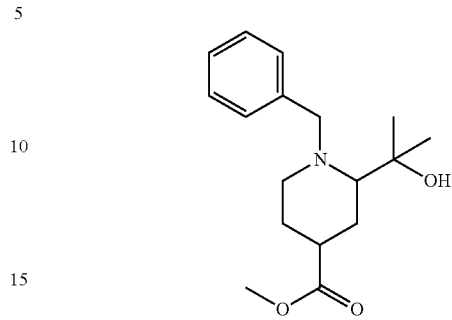

A solution of methyl 2-(2-hydroxypropan-2-yl)piperidine-4-carboxylate (165 mg, 0.820 mmol) in MeCN (5 mL) under an atmosphere of nitrogen was treated with potassium carbonate (250 mg, 1.809 mmol) followed by benzyl bromide (0.2 mL, 1.682 mmol) and stirred at room temperature overnight.

The reaction mixture was treated with water (20 mL) and partitioned with EtOAc (50 mL). The organic layer was isolated and the aqueous layer re-extracted with EtOAc (50 mL). The combined organic layer was passed through a hydrophobic frit and concentrated under reduced pressure. The crude residue was dissolved in the minimum volume of MeOH and loaded onto an SPE-SCX cartridge that had been preconditioned with MeOH. The cartridge was washed with MeOH and product eluted with a 2 M solution of ammonia in MeOH to give the crude title compound as a pale yellow gum (216 mg, 90%).

LCMS (Method C) Rt=1.08 min, MH$^+$=292.

The crude compound was taken forward into the next reaction step without further purification.

Intermediate 52. 2-(1-Benzyl-4-(hydroxymethyl)piperidin-2-yl)propan-2-ol

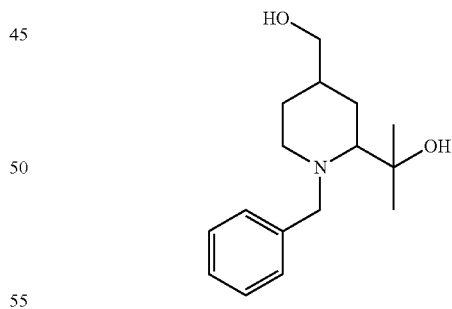

A solution of methyl 1-benzyl-2-(2-hydroxypropan-2-yl)piperidine-4-carboxylate (210 mg, 0.721 mmol) in THF (4 mL) under an atmosphere of nitrogen was treated with lithium borohydride (68 mg, 3.12 mmol) and stirred at room temperature for 2 h. The reaction mixture was treated with a further portion of lithium borohydride (16 mg, 0.734 mmol) and stirred at room temperature for 3 h.

The reaction mixture was treated with water (20 mL) and stirred for 10 min and partitioned with EtOAc (30 mL). The organic layer was isolated and the aqueous layer re-extracted with EtOAc (30 mL). The combined organic layer was passed through a hydrophobic frit and concentrated under reduced pressure to give the crude product as a white solid (219 mg).

The material was dissolved in a minimum volume of EtOAc and passed through an SPE-SCX cartridge that had been preconditioned with MeOH. The cartridge was washed with MeOH and eluted with a 2 M solution of ammonia in MeOH. The solvent was concentrated under reduced pressure to give the crude title compound as a white solid (140 mg, 63%).

LCMS (Method C) Rt=0.83 min, MH$^+$=264.

The crude compound was taken forward into the next reaction step without further purification.

Intermediate 53. (1-Benzyl-2-(2-hydroxypropan-2-yl)piperidin-4-yl)methyl methanesulfonate

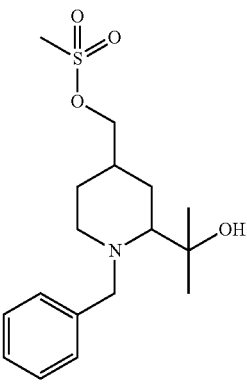 [SMILES: CC(C)(O)C1CC(COS(C)(=O)=O)CCN1Cc1ccccc1]

A solution of 2-(1-benzyl-4-(hydroxymethyl)piperidin-2-yl)propan-2-ol (60 mg, 0.228 mmol) in THF (2 mL) was treated with TEA (0.064 mL, 0.456 mmol) and methanesulfonyl chloride (0.027 mL, 0.342 mmol) and stirred at room temperature under an atmosphere of nitrogen for 2 h.

The reaction mixture was cooled on ice and treated with a saturated solution of sodium bicarbonate in water (5 mL). The solution was partitioned with EtOAc (15 mL) and the organic layer isolated. The aqueous layer was re-extracted with EtOAc (2×15 mL) and the combined organic layer passed through a hydrophobic frit and concentrated under reduced pressure to give the crude title compound as a colourless gum (79 mg).

LCMS (Method C) Rt=1.07 min, MH$^+$=342.

The crude compound was taken forward into the next reaction step.

Intermediate 54. 2-(1-Benzyl-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol

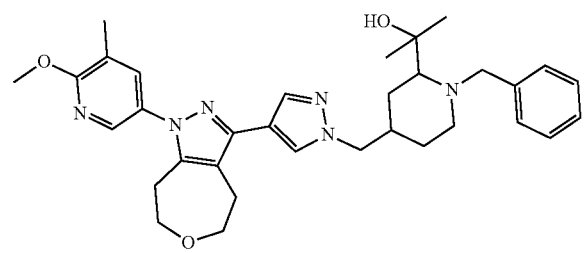 [SMILES: COc1ncc(-n2nc(-c3cnn(CC4CCN(Cc5ccccc5)C(C(C)(C)O)C4)c3)c3c2CCOCC3)cc1C]

Prepared using the general alkylation procedure using 1-(6-methoxy-5-methylpyridin-3-yl)-3-(1H-pyrazol-4-yl)-4,5,7,8-tetrahydro-1H-oxepino[4,5-c]pyrazole (160 mg, 0.418 mmol), NaH (60% by weight dispersion on mineral oils, 50 mg), DMF (3 mL) and (1-benzyl-2-(2-hydroxypropan-2-yl)piperidin-4-yl)methyl methanesulfonate (144 mg, 0.422 mmol), except the material was not purified by MDAP. The crude title compound was isolated as a brown gum (18 mg, 5%).

LCMS (Method C) Rt=1.29 min, MH$^+$=571.

The crude compound was taken forward into the next reaction step without further purification.

Intermediate 55

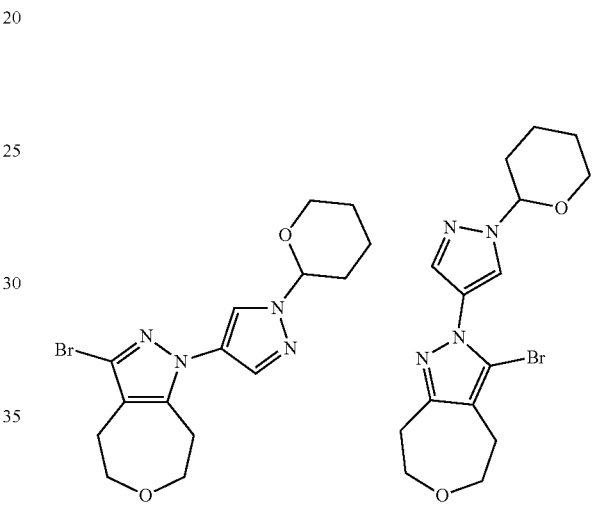

Heat dried powdered molecular sieves (3 Å) were added to a mixture of 3-bromo-4,5,7,8-tetrahydro-1H-oxepino[4,5-c]pyrazole (200 mg, 0.921 mmol) and 1-(tetrahydro-2H-pyran-2-yl)-4-(4,4,5,5-tetramethyl-1,3,2-dioxaborolan-2-yl)-1H-pyrazole (513 mg, 1.843 mmol), triethylamine (0.257 mL, 1.843 mmol) and copper (II) acetate (167 mg, 0.921 mmol). The reaction mixture was treated with MeCN (8 mL) and EtOH (0.400 mL) and heated with stirring at 80° C. overnight and then over a weekend.

The reaction mixture was allowed to cool to room temperature and passed through a Celite® cartridge. The cartridge was washed with MeOH and the filtrate was concentrated under reduced pressure to afford a dark green oil (687 mg). The crude material was purified by silica chromatography, eluting with a 30 to 100% gradient of cyclohexane in EtOAc to give a (presumed) mixture of the title compounds as a yellow oil (104 mg).

LCMS (Method C) Rt=1.00 min, MH$^+$=367/369.

The mixture of compounds was taken forward into the next reaction step.

Intermediate 56. 3-(5-Fluoro-6-methoxypyridin-3-yl)-1-(1-(tetrahydro-2H-pyran-2-yl)-1H-pyrazol-4-yl)-4,5,7,8-tetrahydro-1H-oxepino[4,5-c]pyrazole

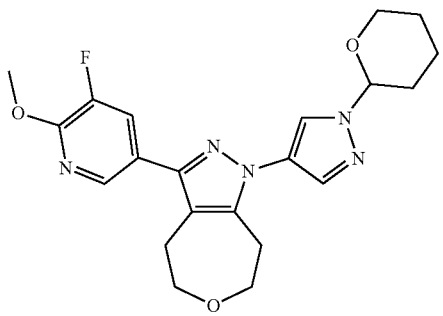 [SMILES: COc1ncc(-c2nn(-c3cnn(C4CCCCO4)c3)c3c2CCOCC3)cc1F]

A mixture of (5-fluoro-6-methoxypyridin-3-yl)boronic acid (624 mg, 3.65 mmol), XPhos Pd G2 (100 mg, 0.128 mmol) and potassium phosphate (775 mg, 3.65 mmol) under an atmosphere of nitrogen was treated with a solution of a mixture of 3-bromo-1-(1-(tetrahydro-2H-pyran-2-yl)-1H-pyrazol-4-yl)-4,5,7,8-tetrahydro-1H-oxepino[4,5-c]pyrazole and 3-bromo-2-(1-(tetrahydro-2H-pyran-2-yl)-1H-pyrazol-4-yl)-4,5,7,8-tetrahydro-2H-oxepino[4,5-c]pyrazole (670 mg) in degassed dioxane (15 mL). The reaction mixture was treated with water (3 mL) and heated at 80° C. for 2 h.

The reaction mixture was concentrated under reduced pressure and treated with water (15 mL) and partitioned with EtOAc (25 mL). The organic layer was isolated and the aqueous later re-extracted with EtOAc (2×25 mL). The combined organic layer was passed through a hydrophobic frit and concentrated under reduced pressure to afford crude product as a brown oil. The crude product was purified by reverse phase chromatography on a C18 cartridge that was eluted with a gradient of 40 to 95% of a solution of ammonium bicarbonate in MeCN and water to give the title compound (247 mg, 32%).

LCMS (Method C) Rt=1.11 min, MH$^+$=414.

Intermediate 57. 3-(5-Fluoro-6-methoxypyridin-3-yl)-1-(1H-pyrazol-4-yl)-4,5,7,8-tetrahydro-1H-oxepino[4,5-c]pyrazole

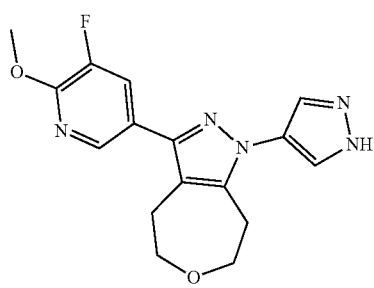 [SMILES: COc1ncc(-c2nn(-c3cn[nH]c3)c3c2CCOCC3)cc1F]

A solution of 3-(5-fluoro-6-methoxypyridin-3-yl)-1-(1-(tetrahydro-2H-pyran-2-yl)-1H-pyrazol-4-yl)-4,5,7,8-tetrahydro-1H-oxepino[4,5-c]pyrazole (247 mg, 0.597 mmol) in MeOH (4 mL) was treated with a 2 M aqueous solution of HCl (0.299 mL, 0.597 mmol) and stirred at room temperature overnight.

The reaction mixture was concentrated under a stream of nitrogen and treated with a saturated aqueous solution of sodium bicarbonate (10 mL) and partitioned with EtOAc (10 mL). The organic layer was isolated and the aqueous layer re-extracted with EtOAc (2×10 mL). The combined organic layer was concentrated under reduced pressure to afford the crude title compound as a white solid (172 mg).

LCMS (Method C) Rt=0.87 min, MH$^+$=330.

The crude material was taken forward into the next reaction step without further purification.

Intermediate 58. tert-Butyl 4-((4-(3-(5-fluoro-6-methoxypyridin-3-yl)-4,5,7,8-tetrahydro-1H-oxepino[4,5-c]pyrazol-1-yl)-1H-pyrazol-1-yl)methyl)piperidine-1-carboxylate

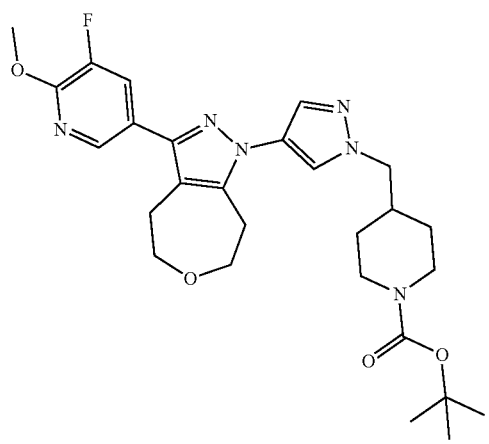 [SMILES: COc1ncc(-c2nn(-c3cnn(CC4CCN(C(=O)OC(C)(C)C)CC4)c3)c3c2CCOCC3)cc1F]

Prepared using the general alkylation procedure from 3-(5-fluoro-6-methoxypyridin-3-yl)-1-(1H-pyrazol-4-yl)-4,5,7,8-tetrahydro-1H-oxepino[4,5-c]pyrazole (110 mg, 0.332 mmol), NaH (33 mg, 60% dispersion on mineral oils), DMF (4 mL), and tert-butyl 4-(bromomethyl)piperidine-1-carboxylate (231 mg, 0.830 mmol), except a saturated aqueous solution of ammonium chloride was used to quench the reaction instead of a saturated aqueous solution sodium bicarbonate. The title compound was isolated as brown solid after MDAP (Method A) (191 mg, 98%).

LCMS (Method C) Rt=1.27 min, MH$^+$=527.

Intermediate 59. 1-(5-Fluoro-6-methoxypyridin-3-yl)-3-(1-(4-methoxybenzyl)-1H-pyrazol-4-yl)-4,5,7,8-tetrahydro-1H-oxepino[4,5-c]pyrazole and 2-(5-fluoro-6-methoxypyridin-3-yl)-3-(1-(4-methoxybenzyl)-1H-pyrazol-4-yl)-4,5,7,8-tetrahydro-2H-oxepino[4,5-c]pyrazole

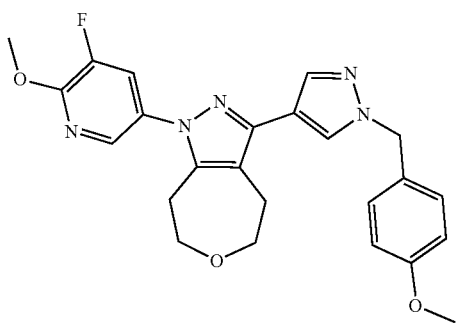

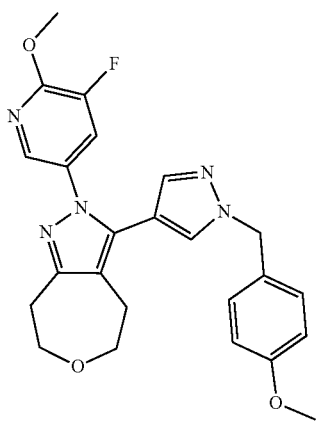

A mixture of 3-(1-(4-methoxybenzyl)-1H-pyrazol-4-yl)-4,5,7,8-tetrahydro-1H-oxepino[4,5-c]pyrazole (1.006 g, 3.10 mmol), (5-fluoro-6-methoxypyridin-3-yl)boronic acid (0.585 g, 3.42 mmol), CuOAc (0.563 g, 3.10 mmol) and DMAP (0.758 g, 6.20 mmol) in MeCN (30 mL) was stirred at room temperature overnight, open to the air. The reaction mixture was treated with a 5% by weight aqueous solution of DMEDA (30 mL) and partitioned with EtOAc (30 mL). The aqueous layer was re-extracted with EtOAc (30 mL) and the combined organic layer passed through a hydrophobic frit then concentrated under reduced pressure to give crude product. The crude product was purified by silica column chromatography, eluting with a 30 to 60% gradient of EtOAc in cyclohexane to afford a mixture of the title compounds (1.2 g).

LCMS (Method C) Rt=1.11 min and 1.14 min, MH$^+$=450.

The partially purified mixture of compounds was taken forward into the next reaction step.

Intermediate 60. 1-(5-Fluoro-6-methoxypyridin-3-yl)-3-(1H-pyrazol-4-yl)-4,5,7,8-tetrahydro-1H-oxepino[4,5-c]pyrazole and 2-(5-fluoro-6-methoxypyridin-3-yl)-3-(1H-pyrazol-4-yl)-4,5,7,8-tetrahydro-2H-oxepino[4,5-c]pyrazole

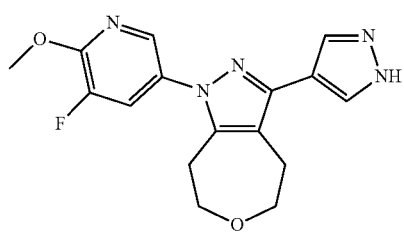

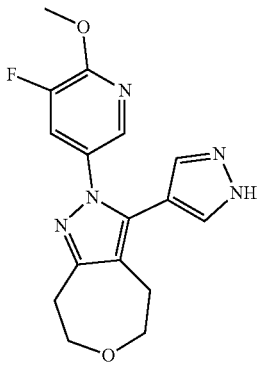

A solution of a mixture of 1-(5-fluoro-6-methoxypyridin-3-yl)-3-(1-(4-methoxybenzyl)-1H-pyrazol-4-yl)-4,5,7,8-tetrahydro-1H-oxepino[4,5-c]pyrazole and 2-(5-fluoro-6-methoxypyridin-3-yl)-3-(1-(4-methoxybenzyl)-1H-pyrazol-4-yl)-4,5,7,8-tetrahydro-2H-oxepino[4,5-c]pyrazole (1.2 g, 2.67 mmol) in DCM (8 mL) was treated with TFA (8.00 mL) and heated using a microwave for 3 h at 70° C.

The reaction mixture was treated with a saturated aqueous solution of sodium bicarbonate (20 mL) and stirred at room temperature for 1 h. The mixture was partitioned using DCM (30 mL) and the organic layer isolated. The aqueous layer was re-extracted with DCM (5×20 mL) and the combined organic layer passed through a hydrophobic frit and concentrated under reduced pressure to afford the crude mixture of products.

The crude product was purified by silica column chromatography, eluting with a 0 to 50% gradient of a 3:1 solution of EtOAc in EtOH and cyclohexane to afford a mixture of the title compounds (698 mg).

LCMS (Method C) Rt=0.79 min and 0.83 min, MH$^+$=330.

The mixture of compounds was taken forward into the next reaction step.

Intermediate 61. tert-Butyl 3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidine-1-carboxylate and tert-butyl 3-((4-(2-(5-fluoro-6-methoxypyridin-3-yl)-4,5,7,8-tetrahydro-2H-oxepino[4,5-c]pyrazol-3-yl)-1H-pyrazol-1-yl)methyl)pyrrolidine-1-carboxylate

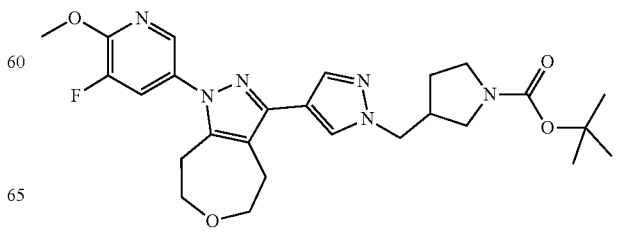

139
-continued

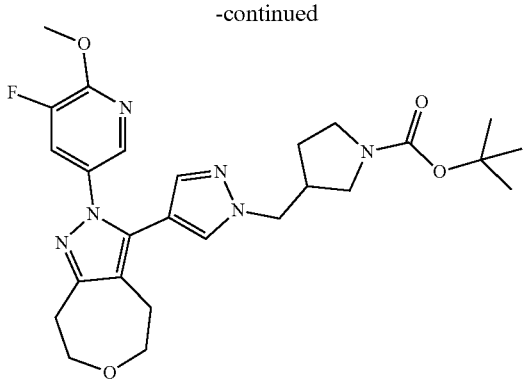

Prepared using the general alkylation procedure from a mixture of 1-(5-fluoro-6-methoxypyridin-3-yl)-3-(1H-pyrazol-4-yl)-4,5,7,8-tetrahydro-1H-oxepino[4,5-c]pyrazole and 2-(5-fluoro-6-methoxypyridin-3-yl)-3-(1H-pyrazol-4-yl)-4,5,7,8-tetrahydro-2H-oxepino[4,5-c]pyrazole (461 mg), NaH (112 mg, 60% dispersion on mineral oils), DMF (10 mL), and tert-butyl 3-(bromomethyl)pyrrolidine-1-carboxylate (924 mg, 3.50 mmol), except the crude material was purified by silica column chromatography using a gradient of 0 to 100% EtOAc in cyclohexane to give a mixture of the title compounds as a white solid (658 mg).

LCMS (Method C) Rt=1.17 min and 1.19 min, MH$^+$=513.

The mixture of compounds was taken forward into the next reaction step.

General Boc-Deprotection Procedure

Intermediate 62. 1-(6-Methoxy-5-methylpyridin-3-yl)-3-(1-(piperidin-4-ylmethyl)-1H-pyrazol-4-yl)-4,5,7,8-tetrahydro-1H-oxepino[4,5-c]pyrazole

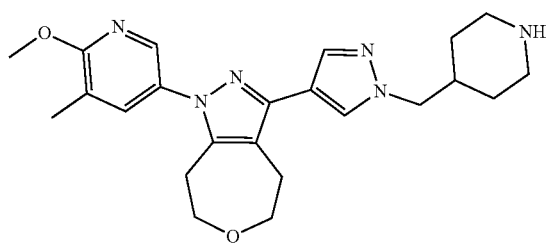 [SMILES: COc1ncc(-n2nc(-c3cnn(CC4CCNCC4)c3)c3c2CCOCC3)cc1C]

tert-Butyl 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate (726 mg, 1.389 mmol) was treated with DCM (5 mL) and TFA (2.140 mL). The reaction mixture was stirred at room temperature for 15 h.

The reaction mixture was treated with an aqueous saturated sodium bicarbonate solution (20 mL) to reach pH 9 and partitioned with DCM (25 mL). The organic layer was isolated, and the aqueous layer re-extracted with DCM (2×15 mL). The combined organic layer was passed through a hydrophobic frit and concentrated under reduced pressure to give the crude title compound as a brown solid (642 mg).

LCMS (Method C): Rt=1.06 min, MH$^+$ 423.

The crude compound was taken forward into the next reaction step without further purification.

140

Intermediate 63. 1-(5-Fluoro-6-methoxypyridin-3-yl)-3-(1-(pyrrolidin-3-ylmethyl)-1H-pyrazol-4-yl)-4,5,7,8-tetrahydro-1H-oxepino[4,5-c]pyrazole and 2-(5-fluoro-6-methoxypyridin-3-yl)-3-(1-(pyrrolidin-3-ylmethyl)-1H-pyrazol-4-yl)-4,5,7,8-tetrahydro-2H-oxepino[4,5-c]

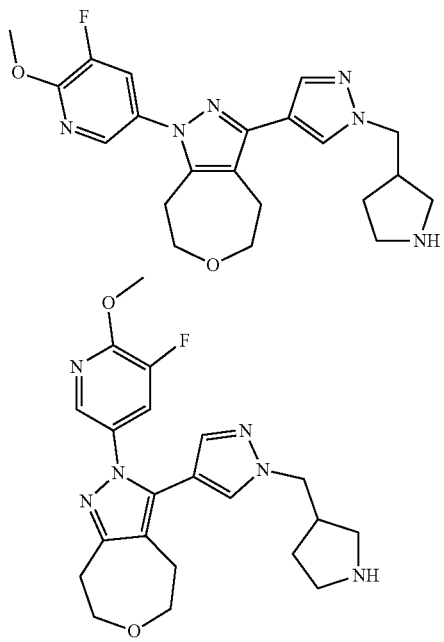

Prepared using the general Boc-deprotection procedure from a mixture of tert-butyl 3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidine-1-carboxylate and tert-butyl 3-((4-(2-(5-fluoro-6-methoxypyridin-3-yl)-4,5,7,8-tetrahydro-2H-oxepino[4,5-c]pyrazol-3-yl)-1H-pyrazol-1-yl)methyl)pyrrolidine-1-carboxylate (658 mg), DCM (7 mL) and TFA (3.96 mL), except the reaction was left for 3 h. A mixture of the title compounds was isolated as a pale yellow glassy solid (483 mg).

LCMS (Method C) Rt=0.84 min and 0.91 min, MH$^+$=413.

The crude mixture of compounds was taken forward into the next reaction step without further purification.

Intermediate 64. tert-Butyl 4-hydroxy-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate

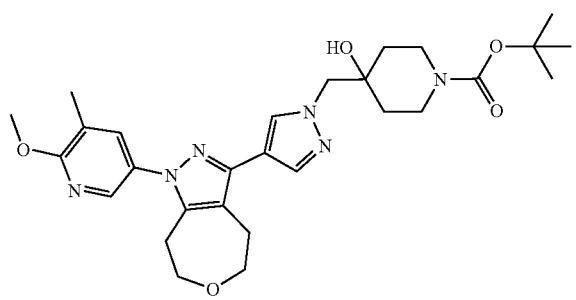 [SMILES: COc1ncc(-n2nc(-c3cnn(CC4(O)CCN(C(=O)OC(C)(C)C)CC4)c3)c3c2CCOCC3)cc1C]

A mixture of tert-butyl 1-oxa-6-azaspiro[2.5]octane-6-carboxylate (53 mg, 0.249 mmol), 1-(6-methoxy-5-methylpyridin-3-yl)-3-(1H-pyrazol-4-yl)-4,5,7,8-tetrahydro-1H-oxepino[4,5-c]pyrazole (53 mg, 0.163 mmol) and cesium carbonate (83 mg, 0.255 mmol) under an atmosphere of nitrogen was treated with DMF (1 mL). The reaction mixture was heated at 100° C. using a microwave for 1 h.

The reaction mixture was treated with a saturated aqueous solution of sodium bicarbonate (15 mL) and partitioned with EtOAc (15 mL). The organic layer was isolated and the aqueous layer re-extracted with EtOAc (2×15 mL). The combined organic layer was washed with a 5% solution of LiCl (15 mL) and passed through a hydrophobic frit and concentrated under reduced pressure to give the crude product as a brown gum (245 mg).

Separately a mixture of tert-butyl 1-oxa-6-azaspiro[2.5]octane-6-carboxylate (420 mg, 1.969 mmol), 1-(6-methoxy-5-methylpyridin-3-yl)-3-(1H-pyrazol-4-yl)-4,5,7,8-tetrahydro-1H-oxepino[4,5-c]pyrazole (449 mg, 1.379 mmol) and cesium carbonate (642 mg, 1.969 mmol) under an atmosphere of nitrogen was treated with DMF (10 mL). The reaction mixture was heated at 100° C. using a microwave for 1.5 h.

The reaction mixture was treated with a saturated aqueous solution of sodium bicarbonate (30 mL) and partitioned with EtOAc (30 mL). The organic layer was isolated and the aqueous layer re-extracted with EtOAc (2×30 mL). The combined organic layer was washed with a 5% solution of LiCl (30 mL) and passed through a hydrophobic frit and concentrated under reduced pressure to give a further batch of the crude product (817 mg).

The two batches of crude material were combined and purified by silica column chromatography using a 0 to 100% gradient of EtOAc in cyclohexane to give the title compound as a white solid (501 mg, 45%).

LCMS (Method C): Rt=1.14 min, MH+ 539.

Intermediate 65. tert-Butyl 4-fluoro-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate

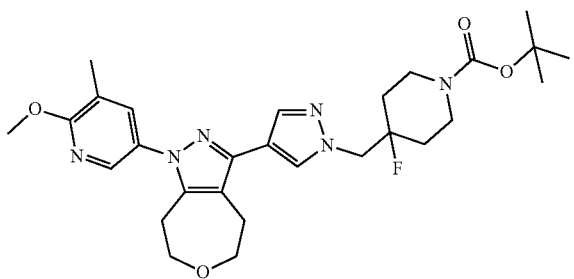 [SMILES: COc1ncc(-n2nc(-c3cnn(CC4(F)CCN(C(=O)OC(C)(C)C)CC4)c3)c3c2CCOCC3)cc1C]

A mixture of tert-butyl 4-hydroxy-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate (166 mg, 0.308 mmol) in DCM (2 mL) was cooled to −78° C. using a dry ice/acetone bath. A 50% solution of Deoxo-Fluor® in THF (0.159 mL, 0.370 mmol) was diluted with DCM (2 mL) and was added to the stirred reaction mixture under an atmosphere of nitrogen. The reaction mixture was stirred for 24 h.

The reaction mixture was treated dropwise with water (10 mL) and stirred over the weekend. The reaction mixture was then extracted with DCM (4×15 mL), passed through a hydrophobic frit and concentrated under reduced pressure to give the crude title compound as a brown gum (153 mg).

LCMS (Method C): Rt=1.25 min, MH+ 541.

The crude compound was taken forward into the next reaction step without further purification.

Intermediate 66. 1-(6-Methoxy-5-methylpyridin-3-yl)-3-(trimethylsilyl)-4,5,7,8-tetrahydro-1H-oxepino[4,5-c]pyrazole

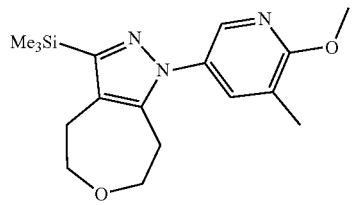 [SMILES: COc1ncc(-n2nc([Si](C)(C)C)c3c2CCOCC3)cc1C]

A mixture of 3-(trimethylsilyl)-4,5,7,8-tetrahydro-1H-oxepino[4,5-c]pyrazole (500 mg, 2.377 mmol), (6-methoxy-5-methylpyridin-3-yl)boronic acid (595 mg, 3.57 mmol), DMAP (581 mg, 4.75 mmol), copper (II) acetate (648 mg, 3.57 mmol) and MeCN (25 mL) was stirred at 40° C. open to air for 3 h.

The reaction mixture was treated with a 5% by weight aqueous solution of DMEDA (50 mL) and extracted with EtOAc (3×50 mL). The combined organic layer was concentrated under reduced pressure to afford an orange oil. The crude material was dissolved in EtOAc (15 mL) and washed with a 2 M aqueous solution of HCl (2×15 mL). The organic layer was isolated and passed through a hydrophobic frit and concentrated under reduced pressure to afford the title compound as an orange solid (743 mg).

LCMS (Method C): Rt=1.35 min, MH+ 332.

The compound was taken forward into the next reaction step without further purification.

Intermediate 67. 3-Bromo-1-(5-fluoro-6-methoxypyridin-3-yl)-4,5,7,8-tetrahydro-1H-oxepino[4,5-c]pyrazole

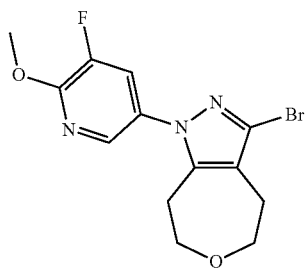 [SMILES: COc1ncc(-n2nc(Br)c3c2CCOCC3)cc1F]

A mixture of 3-bromo-4,5,7,8-tetrahydro-1H-oxepino[4,5-c]pyrazole (500 mg, 2.303 mmol), (5-fluoro-6-methoxypyridin-3-yl)boronic acid (472 mg, 2.76 mmol), copper (II) acetate (628 mg, 3.46 mmol) and DMAP (563 mg, 4.61 mmol) in MeCN (5 ml) was stirred open to the air at 80° C. for 5 h.

The reaction was quenched with an aqueous 5% by weight solution of TMEDA (150 mL) and extracted with EtOAc (2×100 mL). The combined organic layer was washed with brine (100 ml) and a 0.5 M solution of HCl (2×100 mL). The organic layer was passed through a hydrophobic frit and concentrated under reduced pressure. The residue was redissolved in EtOAc (50 mL) and washed with a saturated aqueous solution of sodium hydrogen carbonate (2×100 mL). The organic layer was passed through a hydrophobic frit and concentrated under reduced pressure to give the crude product as a yellow solid (706 mg). The crude product was purified by silica column chromatography, eluting with a 0 to 100% gradient of EtOAc in cyclohexane to give the title compound as a white solid (222 mg).

LCMS (Method C): Rt=1.12 min, MH+ 342/344.

Intermediate 68. 4-((4-(4,4,5,5-Tetramethyl-1,3,2-dioxaborolan-2-yl)-1H-pyrazol-1-yl)methyl)piperidine

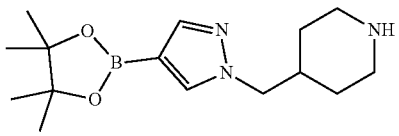 [SMILES: CC1(C)OB(c2cnn(CC3CCNCC3)c2)OC1(C)C]

A stirred solution of tert-butyl 4-((4-(4,4,5,5-tetramethyl-1,3,2-dioxaborolan-2-yl)-1H-pyrazol-1-yl)methyl)piperidine-1-carboxylate (5 g, 12.78 mmol) in 1,4-dioxane (50 mL) under an atmosphere of nitrogen was cooled to 0° C. and treated with a 4 M solution of HCl in dioxane (11.18 mL, 44.7 mmol) in a dropwise fashion over 5 min. The reaction mixture was stirred at 25° C. for 16 h and concentrated under reduced pressure. The resulting residue was treated with DCM (50 mL) and concentrated under reduced pressure twice to give the title compound as a colourless gum (6 g).

LCMS (Method B): Rt=1.41 min, MH+ 292.

The crude compound was taken forward into the next reaction step without further purification.

Intermediate 69. 1-Isopropyl-4-((4-(4,4,5,5-tetramethyl-1,3,2-dioxaborolan-2-yl)-1H-pyrazol-1-yl)methyl)piperidine

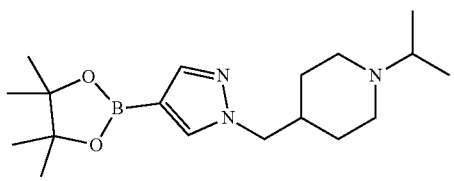 [SMILES: CC(C)N1CCC(Cn2cc(B3OC(C)(C)C(C)(C)O3)cn2)CC1]

A stirred solution of 4-((4-(4,4,5,5-tetramethyl-1,3,2-dioxaborolan-2-yl)-1H-pyrazol-1-yl)methyl)piperidine (1 g, 3.43 mmol) in anhydrous MeCN (12 mL) under an atmosphere of nitrogen was treated with STAB (1.092 g, 5.15 mmol). After 15 min, acetone (0.399 g, 6.87 mmol) was added and the reaction was stirred for 16 h.

The reaction mixture was filtered through a pad of Celite® and washed through with MeCN (10 mL). The filtrate was dried over sodium sulphate and concentrated to obtain crude product as a yellow liquid (700 mg).

Separately a second stirred solution of 4-((4-(4,4,5,5-tetramethyl-1,3,2-dioxaborolan-2-yl)-1H-pyrazol-1-yl)methyl)piperidine (5 g, 17.17 mmol) in anhydrous MeCN (60 mL) under an atmosphere of nitrogen was treated with STAB (5.46 g, 25.8 mmol). After 15 min the reaction mixture was treated with acetone (1.994 g, 34.3 mmol). The reaction mixture was stirred at room temperature for 16 h.

The reaction mixture was filtered through a pad of Celite® and washed through with MeCN (10 mL). The filtrate was dried over sodium sulphate and concentrated to obtain crude product as a yellow liquid (4.1 g).

Separately a third stirred solution of 4-((4-(4,4,5,5-tetramethyl-1,3,2-dioxaborolan-2-yl)-1H-pyrazol-1-yl)methyl)piperidine (5 g, 17.17 mmol) in anhydrous MeCN (60 mL) under an atmosphere of nitrogen was treated with sodium triacetoxyborohydride (5.46 g, 25.8 mmol). After 15 min the reaction mixture was treated with acetone (1.994 g, 34.3 mmol) and stirred for 16 h.

The reaction mixture was filtered through a pad of Celite® and washed through with MeCN (10 mL). The filtrate was dried over sodium sulphate and concentrated to obtain crude product as a yellow liquid (5 g).

A 9 g portion of the three batches of crude material was purified by trituration with n-hexane (100 mL) and dried under vacuum to give the title compound as a pale yellow liquid (6.05 g).

LCMS (Method B): Rt=1.40 min, MH+ 334.

Intermediate 70. 3-Bromo-1-(1-((1-isopropylpiperidin-4-yl)methyl)-1H-pyrazol-4-yl)-4,5,7,8-tetrahydro-1H-oxepino[4,5-c]pyrazole

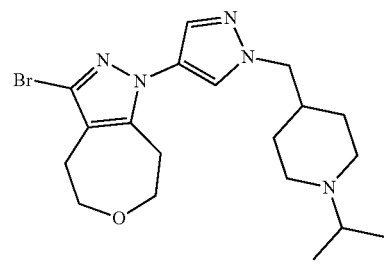 [SMILES: CC(C)N1CCC(Cn2cc(-n3nc(Br)c4c3CCOCC4)cn2)CC1]

A microwave vial was treated with 3-bromo-4,5,7,8-tetrahydro-1H-oxepino[4,5-c]pyrazole (0.5 g, 2.303 mmol), 1-isopropyl-4-((4-(4,4,5,5-tetramethyl-1,3,2-dioxaborolan-2-yl)-1H-pyrazol-1-yl)methyl)piperidine (1.535 g, 4.61 mmol), copper (II) acetate (0.418 g, 2.303 mmol) and triethylamine (0.642 ml, 4.61 mmol), followed by MeCN (22 ml) and EtOH (1.10 ml). The reaction vessel was sealed, and heated at 80° C. overnight.

The reaction mixture was diluted with EtOAc (200 mL) and an aqueous solution of TMEDA solution (5% by weight, 100 mL). The mixture was filtered through a Celite® cartridge and the cartridge washed with further EtAc to remove the remaining precipitate. The organic layer was isolated and the aqueous layer extracted with EtOAc (50 mL). The combined organic layer was passed through a hydrophobic frit and concentrated under reduced pressure.

The crude product purified by silica column chromatography, eluting with a 3:1 mixture of EtOAc/EtOH with triethylamine (1%) and cyclohexane using a 0 to 100% gradient to give the title compound as a brown oil (158 mg, 16%).

LCMS (Method C): Rt=1.01 min, MH+ 422/424.

Intermediate 71. (2R,4r,6S)-tert-Butyl 4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)-2,6-dimethylpiperidine-1-carboxylate

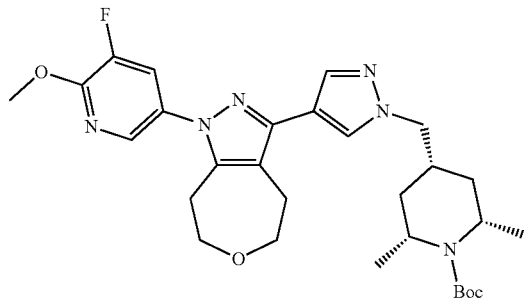

Prepared using the general Suzuki coupling procedure from 3-bromo-1-(5-fluoro-6-methoxypyridin-3-yl)-4,5,7,8-tetrahydro-1H-oxepino[4,5-c]pyrazole (222 mg, 0.649 mmol), tert-butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate (408 mg, 0.973 mmol), XPhos Pd G2 (35.7 mg, 0.045 mmol), 1,4-dioxane (0.4 ml) and water (0.1 ml), except the material was filtered through Celite®, treated with EtOAc (100 mL) and washed with a solution of sodium hydrogen carbonate (100 mL) and brine (100 mL), before purifying by MDAP (Method A) to give the title compound (280 mg, 39%) as a white solid.

LCMS (Method C): Rt=1.33 min, MH-Boc+455.

Intermediate 72. (2R,4r,6S)-tert-Butyl 4-((4-(3-(6-methoxy-5-methylpyridin-3-yl)-4,5,7,8-tetrahydro-1H-oxepino[4,5-c]pyrazol-1-yl)-1H-pyrazol-1-yl)methyl)-2,6-dimethylpiperidine-1-carboxylate

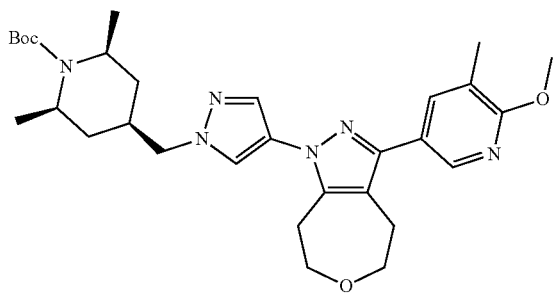

Prepared using the general Suzuki coupling procedure using (2R,4r,6S)-tert-butyl 4-((4-(3-bromo-4,5,7,8-tetrahydro-1H-oxepino[4,5-c]pyrazol-1-yl)-1H-pyrazol-1-yl)methyl)-2,6-dimethylpiperidine-1-carboxylate (100 mg, 0.197 mmol), (6-methoxy-5-methylpyridin-3-yl)boronic acid (65.7 mg, 0.393 mmol), potassium phosphate (83 mg, 0.393 mmol), XPhos Pd G2 (10.83 mg, 0.014 mmol), 1,4-dioxane (0.4 ml) and water (0.100 ml), except the crude product was purified by MDAP (Method A) to give the title compound as a clear, glassy oil (33 mg, 31%).

LCMS (Method C): Rt=1.39 min, MH+ 551.

Intermediate 73. (2R,4r,6S)-tert-Butyl 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)-2,6-dimethylpiperidine-1-carboxylate

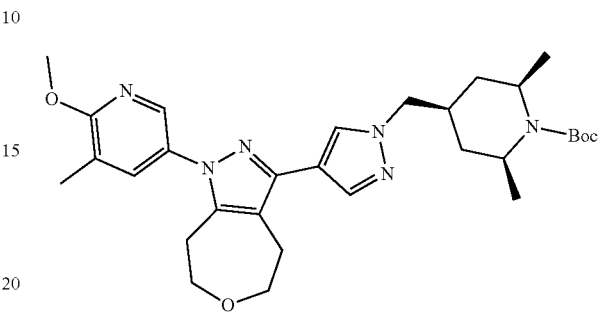

A mixture of tert-butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate (84 mg, 0.200 mmol), XPhos Pd G2 (5 mg, 0.006 mmol), 3-bromo-1-(6-methoxy-5-methylpyridin-3-yl)-4,5,7,8-tetrahydro-1H-oxepino[4,5-c]pyrazole (54 mg, 0.128 mmol), and potassium phosphate (170 mg, 0.801 mmol) was treated with 1,4-dioxane (1 mL) and water (0.43 mL). The reaction mixture was placed under an atmosphere of nitrogen and heated using a microwave at 100° C. for 30 min.

The reaction mixture was filtered through a Celite® cartridge, washed with EtOAc (10 mL), and the filtrate was washed with saturated sodium hydrogencarbonate solution (10 mL) and brine (10 mL). The organic layer was passed through a hydrophobic frit and concentrated under reduced pressure to give 124 mg of crude product.

Separately a mixture of tert-butyl (2R,4r,6S)-2,6-dimethyl-4-((4-(4,4,5,5-tetramethyl-1,3,2-dioxaborolan-2-yl)-1H-pyrazol-1-yl)methyl)piperidine-1-carboxylate (273 mg, 0.651 mmol), XPhos Pd G2 (25 mg, 0.032 mmol), 3-bromo-1-(6-methoxy-5-methylpyridin-3-yl)-4,5,7,8-tetrahydro-1H-oxepino[4,5-c]pyrazole (186 mg, 0.440 mmol), and potassium phosphate (185 mg, 0.872 mmol) was treated with 1,4-dioxane (3 mL) and water (1.3 mL). The reaction mixture was placed under an atmosphere of nitrogen and heated using a microwave at 100° C. for 30 minutes.

The reaction mixture was filtered through a Celite® cartridge, washed with EtOAc (50 mL), and the filtrate was washed with saturated sodium hydrogencarbonate solution (50 mL) and brine (50 mL). The organic layer was passed through a hydrophobic frit and concentrated under reduced pressure to give 406 mg of crude product.

The two batches of crude product were combined and purified by silica column chromatography using a 0 to 100% gradient of a solution of 3:1 EtOAc in EtOH and EtOAc to give the title compound as a brown oil (447 mg).

LCMS (Method C): Rt=1.37 min, MH+=551.

Intermediate 74. tert-Butyl 3-(4-(1-(5-fluoro-6-methoxypyridin-3-yl)-4,5,7,8-tetrahydro-1H-oxepino[4,5-c]pyrazol-3-yl)-1H-pyrazol-1-yl)pyrrolidine-1-carboxylate

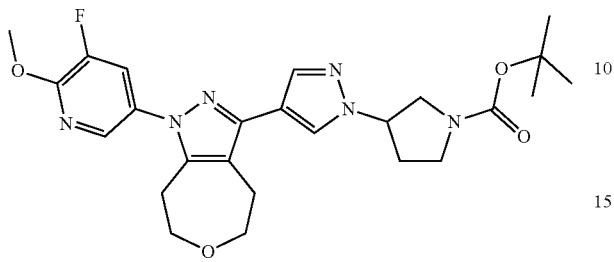

Prepared using the general alkylation procedure using 1-(5-fluoro-6-methoxypyridin-3-yl)-3-(1H-pyrazol-4-yl)-4,5,7,8-tetrahydro-1H-oxepino[4,5-c]pyrazole (250 mg, 0.759 mmol), NaH (76 mg, 60% dispersion on mineral oils), DMF (5 mL) and tert-butyl 3-bromopyrrolidine-1-carboxylate (380 mg, 1.518 mmol), except the material was purified using reverse phase chromatography, eluting with a 40 to 95% gradient of a solution of 10 mM ammonium bicarbonate adjusted to pH 10 with ammonia in water and acetonitrile. The title compound was isolated as a colourless oil (100 mg, 21%).

LCMS (Method C): Rt=1.18 min, MH+ 499.

Intermediate 75. 1-(5-Fluoro-6-methoxypyridin-3-yl)-3-(1-(pyrrolidin-3-yl)-1H-pyrazol-4-yl)-4,5,7,8-tetrahydro-1H-oxepino[4,5-c]pyrazole

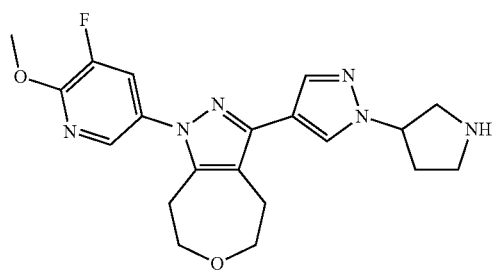 [SMILES: COc1ncc(-n2nc(-c3cnn(C4CCNC4)c3)c3c2CCOCC3)cc1F]

Prepared using the general Boc-deprotection procedure from tert-butyl 3-(4-(1-(5-fluoro-6-methoxypyridin-3-yl)-4,5,7,8-tetrahydro-1H-oxepino[4,5-c]pyrazol-3-yl)-1H-pyrazol-1-yl)pyrrolidine-1-carboxylate (100 mg, 0.201 mmol), DCM (2 mL) and TFA (0.6 mL), except the reaction was complete after stirring at room temperature for 1 h. The crude title compound was isolated as colourless gum (74 mg).

LCMS (Method C): Rt=0.86 min, MH+ 399.

The crude compound was taken forward into the next reaction step without further purification.

Intermediate 76. tert-Butyl 3-fluoro-4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidine-1-carboxylate

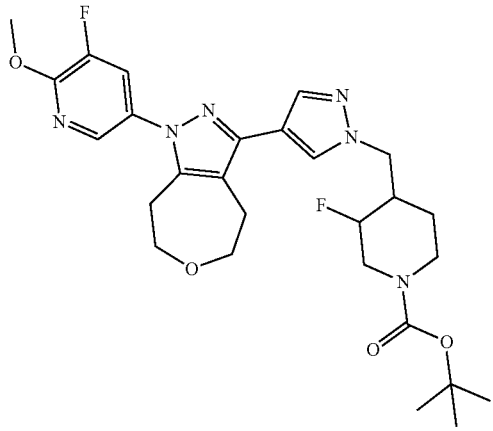 [SMILES: COc1ncc(-n2nc(-c3cnn(CC4CCN(C(=O)OC(C)(C)C)CC4F)c3)c3c2CCOCC3)cc1F]

Prepared using the general alkylation procedure from 1-(5-fluoro-6-methoxypyridin-3-yl)-3-(1H-pyrazol-4-yl)-4,5,7,8-tetrahydro-1H-oxepino[4,5-c]pyrazole (85 mg, 0.258 mmol), NaH (26 mg, 60% suspension in mineral oils), DMF (2 mL) and tert-butyl 3-fluoro-4-(((methylsulfonyl)oxy)methyl)piperidine-1-carboxylate (201 mg, 0.645 mmol), except the material was purified by reverse phase chromatography using a C18 column, eluting with a gradient of 50 to 95% of a solution of ammonium bicarbonate in MeCN to give the title compound as an off white solid (75 mg).

LCMS (Method C): Rt=1.21 min, MH+ 545.

Intermediate 77. tert-Butyl (3R,4S)-3-fluoro-4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidine-1-carboxylate

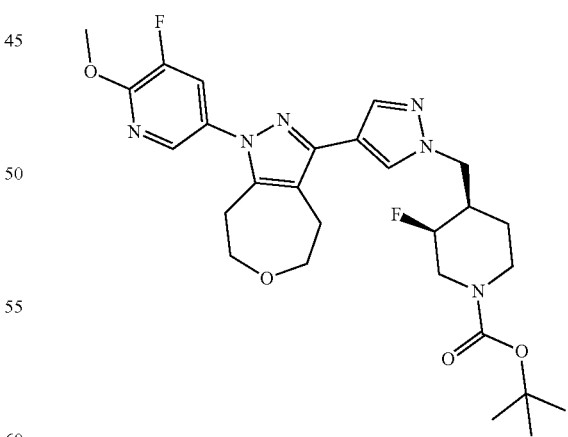

Prepared using the general alkylation procedure from 1-(5-fluoro-6-methoxypyridin-3-yl)-3-(1H-pyrazol-4-yl)-4,5,7,8-tetrahydro-1H-oxepino[4,5-c]pyrazole (85 mg, 0.258 mmol), NaH (26 mg, 60% suspension by weight in mineral oils), DMF (2.5 mL) and tert-butyl (3R,4S)-3-fluoro-4-(((methylsulfonyl)oxy)methyl)piperidine-1-carboxylate (241 mg, 0.774 mmol), except the material was purified by reverse phase chromatography using a C18 column, eluting with a 50 to 95% gradient of ammonium bicarbonate in MeCN to give the title compound as an off-white solid (103 mg, 59%).

LCMS (Method C): Rt=1.24 min, MH+ 545.

Intermediate 78. tert-Butyl 4-(((tert-butyldiphenylsilyl)oxy)methyl)piperidine-1-carboxylate

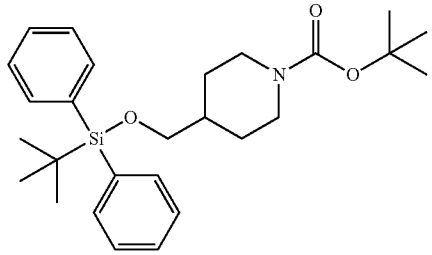 [SMILES: CC(C)(C)OC(=O)N1CCC(CO[Si](c2ccccc2)(c2ccccc2)C(C)(C)C)CC1]

A solution of imidazole (0.696 g, 10.22 mmol) in DMF (20 mL) was treated with tert-butyl 4-(hydroxymethyl)piperidine-1-carboxylate (2.0 g, 9.29 mmol) and TBDPS-Cl (2.386 mL, 9.29 mmol). The reaction mixture was stirred for overnight at room temperature. The reaction was cooled using an ice bath and quenched with a saturated aqueous solution of ammonium chloride (30 mL) and sodium bicarbonate (15 mL). The reaction mixture was partitioned with EtOAc (50 mL) and the aqueous layer extracted with EtOAc (2×50 mL). The combined organic layer was washed with a 5% aqueous solution of LiCl (3×20 mL), passed through a hydrophobic frit and concentrated under reduced pressure to give crude product (4.35 g). The crude product was purified by reverse phase chromatography using a C18 silica column, eluting with a 50 to 95% gradient of MeCN and a solution of 10 mM ammonium bicarbonate in water to give the title compound as a colourless oil (3.444 g, 82%).

LCMS (Method C): Rt=1.81 min, MH+-Boc 354.

Intermediate 79. tert-Butyl 4-(((tert-butyldiphenylsilyl)oxy)methyl)-2-(2-hydroxypropan-2-yl)piperidine-1-carboxylate

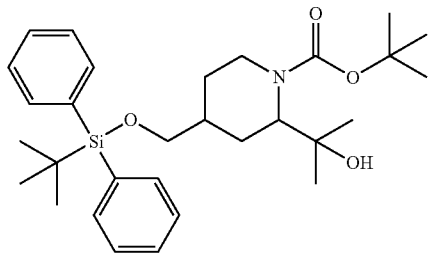 [SMILES: CC(C)(C)OC(=O)N1CCC(CO[Si](c2ccccc2)(c2ccccc2)C(C)(C)C)CC1C(C)(C)O]

A solution of tert-butyl 4-(((tert-butyldiphenylsilyl)oxy)methyl)piperidine-1-carboxylate (2745 mg, 6.05 mmol) and dry TMEDA (1.278 mL, 8.47 mmol) in dry diethyl ether (50 mL) was cooled to −78° C. and slowly treated with sec-butyllithium (7.78 mL, 10.89 mmol). The reaction mixture was stirred for 2 h at −78° C. and treated with dry acetone (1.333 mL, 18.15 mmol) and stirred at −78° C. for 2 h. The reaction mixture was treated with water (20 ml) and extracted with EtOAc (3×20 ml). The reaction mixture was concentrated and purified by silica column chromatography using a 0 to 100% gradient of EtOAc in cyclohexane to give the title compound (1585 mg, 51%).

LCMS (Method C): Rt=1.76 min, MH+-Boc 412.

Intermediate 80. tert-Butyl 3-((4-(1-(5-cyano-6-methoxypyridin-3-yl)-4,5,7,8-tetrahydro-1H-oxepino[4,5-c]pyrazol-3-yl)-1H-pyrazol-1-yl)methyl)pyrrolidine-1-carboxylate

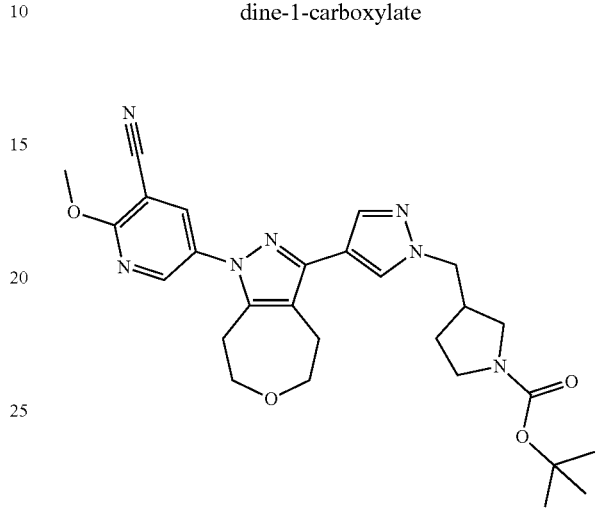

Prepared using the general alkylation procedure from 5-(3-(1H-pyrazol-4-yl)-4,5,7,8-tetrahydro-1H-oxepino[4,5-c]pyrazol-1-yl)-2-methoxynicotinonitrile (41 mg), NaH (12 mg, 60% suspension by weight in mineral oils, 0.300 mmol), DMF (2.3 mL), and tert-butyl 3-(bromomethyl)pyrrolidine-1-carboxylate (101 mg, 0.382 mmol) to give the title compound (26 mg, 41%).

LCMS (Method C): Rt=1.15 min, MH+ 520.

The material was taken forward to the next reaction step.

Intermediate 81. 2-Methoxy-5-(3-(1-(pyrrolidin-3-ylmethyl)-1H-pyrazol-4-yl)-4,5,7,8-tetrahydro-1H-oxepino[4,5-c]pyrazol-1-yl)nicotinonitrile

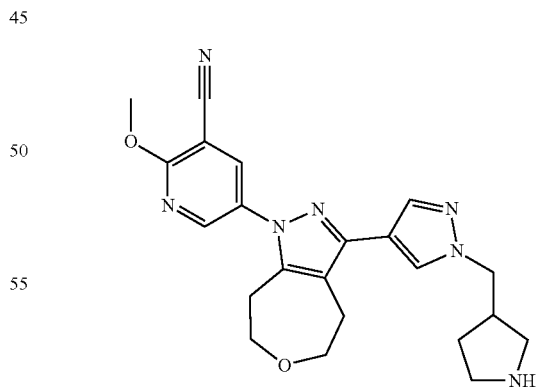

Prepared using the general Boc-deprotection procedure from tert-butyl 3-((4-(1-(5-cyano-6-methoxypyridin-3-yl)-4,5,7,8-tetrahydro-1H-oxepino[4,5-c]pyrazol-3-yl)-1H-pyrazol-1-yl)methyl)pyrrolidine-1-carboxylate (26 mg), DCM (0.75 mL), TFA (0.25 mL), except the reaction mixture was heated using a microwave at 70° C. for 30 min. The title compound was isolated crude (35 mg).

LCMS (Method C): Rt=0.90 min, MH+ 420.

The crude material was taken forward to the next synthetic step without further purification.

Intermediate 82. Ethyl 5-oxooxepane-4-carboxylate

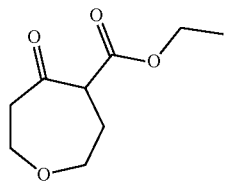

To a stirred solution of dihydro-2H-pyran-4(3H)-one (0.923 mL, 9.99 mmol) in dry diethyl ether (50 mL) under an atmosphere of nitrogen at −30° C. was added slowly BF$_3$OEt$_2$ (1.899 mL, 14.98 mmol) followed by a solution of ethyl 2-diazoacetate (1.328 mL, 10.99 mmol) in diethylether (10 mL). The reaction mixture was stirred at −10° C. for 5.5 h. The reaction was quenched with saturated sodium hydrogenocarbonate (60 mL). The solution was then partitioned with ethyl acetate (60 mL) and the aqueous layer was extracted with further ethyl acetate (2×60 mL). The organic layers were combined, washed with brine (2×50 mL), passed through a hydrophobic frit and then concentrated under reduced pressure. The crude product was purified by silica column chromatography eluting with a gradient of cyclohexane/EtOAc (0 to 80%) to give the title compound (1.139 g, 52%).

$^1$H NMR (400 MHz, CDCl$_3$) δ ppm 12.76 (s, 0.16H, enol), 4.13-4.29 (m, 2H), 4.02 (ddd, J=13, 6, 3 Hz, 1H), 3.92 (ddd, J=13, 6, 4 Hz, 1H), 3.61-3.79 (m, 3H), 2.80-2.95 (m, 1H), 2.61-2.75 (m, 1H), 2.01-2.20 (m, 2H), 1.20-1.31 (m, 3H).

Intermediate 83. ((2R,6S)-2,6-Dimethyltetrahydro-2H-pyran-4-yl)methanol

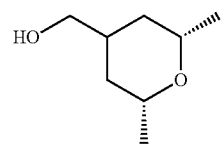

A stirred solution of NaBH$_4$ (3.25 g, 86 mmol) in EtOH (150 mL) at 0° C. was treated with (2R,6S)-2,6-dimethyltetrahydro-2H-pyran-4-carbaldehyde (12.2 g, 86 mmol) and stirred at room temperature for 1 h. The reaction mixture was concentrated under reduced pressure, neutralized 1 N HCl (30 mL), extracted with DCM (2×200 mL), and the combined organic layer was washed with brine and dried over Na$_2$SO$_4$, filtered and concentrated under reduced pressure to give crude product.

The crude product was purified by silica column chromatography, eluting with a 20% solution of EtOAc in hexane to give the title compound as a pale yellow liquid (4.3 g, 26%).

$^1$H NMR (400 MHz, DMSO-d$_6$) δ-ppm 3.54-3.32 (m, 3H), 3.25-3.17 (m, 2H), 1.66-1.50 (m, 3H), 1.07 (d, J=6 Hz, 6H), 0.77-0.64 (m, 2H).

Intermediate 84. (2R,6S)-4-(Bromomethyl)-2,6-dimethyltetrahydro-2H-pyran

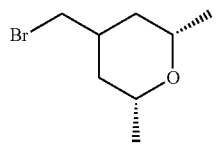

A solution of ((2R,6S)-2,6-dimethyltetrahydro-2H-pyran-4-yl)methanol (1 g, 6.93 mmol) in DCM (10 mL) was treated with PBr$_3$ (0.654 mL, 6.93 mmol). The reaction mixture was stirred at room temperature for 4 h. The reaction mixture was diluted with water (50 mL) and extracted with DCM (50 mL×3). The organic layer was isolated and washed with a saturated solution of sodium bicarbonate (30 mL), dried over sodium sulphate and concentrated under reduced pressure to give the crude product as a yellow oil (650 mg).

$^1$H NMR (400 MHz, CDCl$_3$) δ-ppm 3.95-3.77 (m, 2H), 3.54-3.43 (m, 2H) 2.07-1.89 (m, 1H), 1.72-1.64 (m, 2H), 1.23 (d, J=6 Hz, 6H), 1.00-0.87 (m, 2H).

Intermediate 85. 1-(((2R,6S)-2,6-Dimethyltetrahydro-2H-pyran-4-yl)methyl)-4-(4,4,5,5-tetramethyl-1,3,2-dioxaborolan-2-yl)-1H-pyrazole

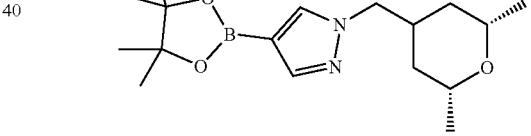

A solution of 4-(4,4,5,5-tetramethyl-1,3,2-dioxaborolan-2-yl)-1H-pyrazole (600 mg, 3.09 mmol), Cs$_2$CO$_3$ (1511 mg, 4.64 mmol) in MeCN (20 mL) under an atmosphere of nitrogen was treated with (2R,6S)-4-(bromomethyl)-2,6-dimethyltetrahydro-2H-pyran (640 mg, 3.09 mmol). The reaction mixture was stirred at 80° C. for 24 h.

The reaction mixture was diluted with water (50 mL) and extracted with DCM (50 mL×3). The combined organic layer was washed with a saturated solution of sodium bicarbonate (25 mL), dried over sodium sulphate then filtered and evaporated under reduced pressure to give the crude product as a yellow oil. The crude product was purified by silica column chromatography, eluting with petroleum ether to give the title compound as a colourless liquid (300 mg, 25%).

LCMS (Method B): Rt=2.72 min, MH+=321.

Intermediate 86. N-(5-(3-Bromo-4,5,7,8-tetrahydro-1H-oxepino[4,5-c]pyrazol-1-yl)-2-methoxypyridin-3-yl)methanesulfonamide

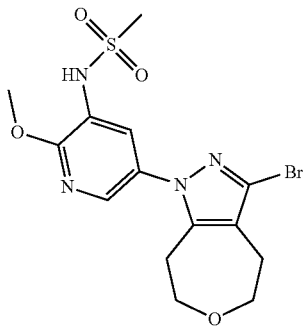 [SMILES: COc1ncc(-n2nc(Br)c3c2CCOCC3)cc1NS(C)(=O)=O]

A mixture of 3-bromo-4,5,7,8-tetrahydro-1H-oxepino[4,5-c]pyrazole (1 g, 4.61 mmol), (6-methoxy-5-(methylsulfonamido)pyridin-3-yl)boronic acid (2.83 g, 11.52 mmol), TEA (1.284 mL, 9.21 mmol) and copper (II) acetate (0.837 g, 4.61 mmol) was stirred at room temperature under an atmosphere of oxygen in the presence of 4 Å molecular sieves (2 g).

The reaction mixture was filtered through Celite® and the Celite® was washed with MeCN (30 mL×2). The filtrate was concentrated under reduced pressure. The crude product (860 mg) was purified using reverse phase chromatography using a C18 column, using a solution of ammonium formate in water (0.01 M) and MeCN. The title compound was isolated as a yellow solid (160 mg, 7%) as a yellow solid.

LCMS (Method B): Rt=1.93 min, MH$^+$=417/419.

Intermediate 87. 4,5,7,8-Tetrahydro-1H-oxepino[4,5-c]pyrazol-3-ol

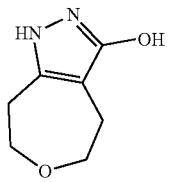 [SMILES: Oc1n[nH]c2c1CCOCC2]

A solution of ethyl 5-oxooxepane-4-carboxylate (1162 mg, 6.24 mmol) in anhydrous EtOH (12 mL) in a sealed vial under a nitrogen atmosphere was treated with triethylamine (1.05 mL, 7.53 mmol) and hydrazine hydrate (1.0 mL, 7.13 mmol). The reaction mixture was stirred at 80° C. over 2.5 h. The reaction mixture was allowed to cool and was quenched with acetone (5 mL), stirred vigorously for 2 h then concentrated under reduced pressure to afford the crude title compound (973 mg, >99%).

LCMS (Method A): Rt=0.32 min, MH$^+$ 155.

The crude material was used for the next reaction step without further purification.

Intermediate 88. 3-((Triisopropylsilyl)oxy)-4,5,7,8-tetrahydro-1H-oxepino[4,5-c]pyrazole

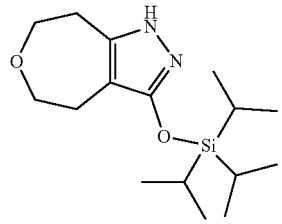 [SMILES: CC(C)[Si](Oc1n[nH]c2c1CCOCC2)(C(C)C)C(C)C]

To a stirred solution of 4,5,7,8-tetrahydro-1H-oxepino[4,5-c]pyrazol-3-ol (417 mg, 2.70 mmol) in anhydrous DCM (20 mL) under an atmosphere of nitrogen was added imidazole (225 mg, 3.31 mmol) and chlorotriisopropylsilane (0.61 mL, 2.85 mmol). The reaction mixture was stirred at room temperature for 1 h. Water (10 mL) was then added to the reaction mixture and the solution stirred for 10 min. The mixture was diluted with water and extracted with DCM. The combined organic layer was passed through a hydrophobic frit, evaporated to dryness and dried further on the high-vac line overnight to give the title compound (785 mg).

LCMS (Method C): Rt=1.44 min, MH$^+$=311.

The crude material was used for the next reaction step without further purification.

Intermediate 89. N-(2-Methoxy-5-(3-((triisopropylsilyl)oxy)-4,5,7,8-tetrahydro-1H-oxepino[4,5-c]pyrazol-1-yl)pyridin-3-yl)-N-(4-methoxybenzyl)methanesulfonamide

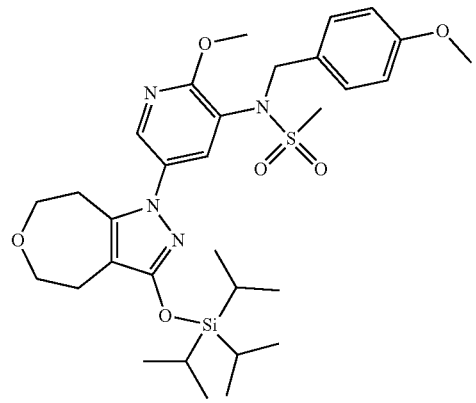 [SMILES: COc1ccc(CN(c2cc(-n3nc(O[Si](C(C)C)(C(C)C)C(C)C)c4c3CCOCC4)cnc2OC)S(C)(=O)=O)cc1]

Copper (II) acetate (62 mg, 0.341 mmol) was added to a solution of 3-((triisopropylsilyl)oxy)-4,5,7,8-tetrahydro-1H-oxepino[4,5-c]pyrazole (90 mg, 0.290 mmol), a mixture of N-(2-methoxy-5-(4,4,5,5-tetramethyl-1,3,2-dioxaborolan-2-yl)pyridin-3-yl)-N-(4-methoxybenzyl)methanesulfonamide and (6-methoxy-5-(N-(4-methoxybenzyl)methylsulfonamido)pyridin-3-yl)boronate (260 mg) and DMAP (70 mg, 0.573 mmol) in dry MeCN (3 mL). The reaction mixture was stirred, open to air, for 18 h at room temperature. The reaction mixture was quenched with water (5 mL, 5% TMEDA), and the aqueous layer was extracted with EtOAc (4×10 mL). The combined organic layer was passed through a hydrophobic frit and concentrated under reduced pressure. The crude product was purified by silica column chromatography, eluting with a 0 to 50% gradient of EtOAc and cyclohexane to give crude product. The crude product was repurified by reverse phase column chromatography using a C18 silica column, eluting with a 80-95% gradient of MeCN(+0.1% ammonium) in water (10 mM ammonium bicarbonate) to give the title compound (24 mg, 12%).

LCMS (Method C): Rt=1.73 min, MH+ 631.

Intermediate 90. 1-(6-Methoxy-5-methylpyridin-3-yl)-3-((triisopropylsilyl)oxy)-4,5,7,8-tetrahydro-1H-oxepino[4,5-c]pyrazole

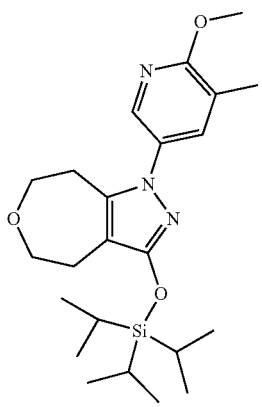 [SMILES: COc1ncc(-n2nc(O[Si](C(C)C)(C(C)C)C(C)C)c3c2CCOCC3)cc1C]

Copper (II) acetate (292 mg, 1.610 mmol) was added to a solution of 3-((triisopropylsilyl)oxy)-4,5,7,8-tetrahydro-1H-oxepino[4,5-c]pyrazole (500 mg, 1.610 mmol), 2-methoxy-3-methyl-5-(4,4,5,5-tetramethyl-1,3,2-dioxaborolan-2-yl)pyridine (505 mg, 2.027 mmol) and DMAP (394 mg, 3.23 mmol) in dry MeCN (7 mL). The reaction mixture was stirred for 24 h at room temperature open to air. The reaction mixture was quenched with water (5 mL, 5% TMEDA), and the aqueous layer was extracted with EtOAC (5×10 mL). The combined organic layer was passed through a hydrophobic frit and concentrated under reduced pressure. The crude product was purified by reverse phase chromatography using a C18 silica column, eluting with a 80-95% gradient of MeCN(+0.1% ammonium) in water (+0.1% ammonium bicarbonate) to give the title compound (571 mg, 74%).

LCMS (Method C): Rt=1.82 min, MH+=432.

Intermediate 91. 1-(5-(Fluoromethyl)-6-methoxypyridin-3-yl)-3-((triisopropylsilyl)oxy)-4,5,7,8-tetrahydro-1H-oxepino[4,5-c]pyrazole

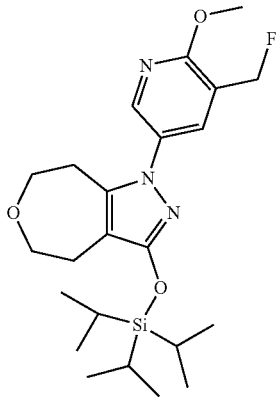 [SMILES: COc1ncc(-n2nc(O[Si](C(C)C)(C(C)C)C(C)C)c3c2CCOCC3)cc1CF]

Copper (II) acetate (36 mg, 0.198 mmol) was added to a solution of 3-((triisopropylsilyl)oxy)-4,5,7,8-tetrahydro-1H-oxepino[4,5-c]pyrazole (50 mg, 0.161 mmol), 3-(fluoromethyl)-2-methoxy-5-(4,4,5,5-tetramethyl-1,3,2-dioxaborolan-2-yl)pyridine (48 mg, 0.180 mmol) and DMAP (43 mg, 0.352 mmol) in dry MeCN (1.5 mL). The reaction mixture was stirred for 18 h at room temperature open to air. The reaction mixture was quenched with water (2 mL, 5% TMEDA), and the aqueous layer was extracted with EtOAc (4×5 mL). The combined organic layer was passed through a hydrophobic frit and concentrated under reduced pressure. The crude product was purified by MDAP (Method A) to give the title compound (35 mg, 46%).

LCMS (Method C): Rt=1.80 min, MH+=450.

Intermediate 92. 1-(5-Fluoro-6-methoxypyridin-3-yl)-3-((triisopropylsilyl)oxy)-4,5,7,8-tetrahydro-1H-oxepino[4,5-c]pyrazole Copper (II) acetate (31 mg, 0.171 mmol) was added to a solution of 3-((triisopropylsilyl)oxy)-4,5,7,8-tetrahydro-1H-oxepino[4,5-c]pyrazole (50 mg, 0.161 mmol), 3-fluoro-2-methoxy-5-(4,4,5,5-tetramethyl-1,3,2-dioxaborolan-2-yl)pyridine (59 mg, 0.233 mmol) and DMAP (43 mg, 0.352 mmol) in dry MeCN (1 mL). The reaction mixture was stirred for 15 h at room temperature open to air. The reaction mixture was quenched with water (2 mL, 5% TMEDA), and the aqueous layer was extracted with EtOAc (4×5 mL). The combined organic layer was passed through a hydrophobic frit and concentrated under reduced pressure. The crude product was purified by MDAP (Method A) to give the title compound (35 mg, 47%).

LCMS (Method C): Rt=1.78 min, MH$^+$=436.

Intermediate 93. 2-Methoxy-5-(3-((triisopropylsilyl)oxy)-4,5,7,8-tetrahydro-1H-oxepino[4,5-c]pyrazol-1-yl)nicotinonitrile

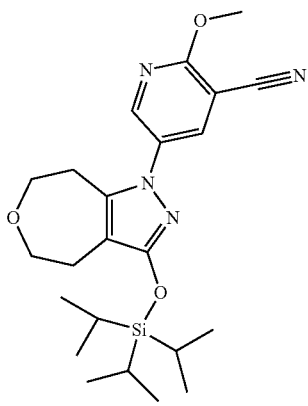 [SMILES: COc1ncc(-n2nc(O[Si](C(C)C)(C(C)C)C(C)C)c3c2CCOCC3)cc1C#N]

Copper (II) acetate (29.2 mg, 0.161 mmol) was added to a solution of 3-((triisopropylsilyl)oxy)-4,5,7,8-tetrahydro-1H-oxepino[4,5-c]pyrazole (50 mg, 0.161 mmol), (5-cyano-6-methoxypyridin-3-yl)boronic acid (40.1 mg, 0.225 mmol) and DMAP (39.3 mg, 0.322 mmol) in dry Acetonitrile (1 mL). The reaction mixture was stirred for 15 h at room temperature open to air. The reaction mixture was quenched with water (2 mL, 5% TMEDA), and the aqueous layer was extracted with EtOAc (5×10 mL). The combined organic layer was passed through a hydrophobic frit, concentrated under reduced pressure and purified by MDAP (Method A) to give the title compound (15 mg, 20%).

LCMS (Method C): Rt=1.76 min, MH$^+$=443.

Intermediate 94. 1-(2-Methoxypyrimidin-5-yl)-3-((triisopropylsilyl)oxy)-4,5,7,8-tetrahydro-1H-oxepino[4,5-c]pyrazole

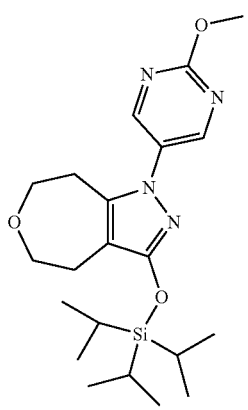 [SMILES: COc1ncc(-n2nc(O[Si](C(C)C)(C(C)C)C(C)C)c3c2CCOCC3)cn1]

A mixture of (2-methoxypyrimidin-5-yl)boronic acid (50 mg, 0.325 mmol), 3-((triisopropylsilyl)oxy)-4,5,7,8-tetrahydro-1H-oxepino[4,5-c]pyrazole (100 mg, 0.322 mmol) and DMAP (79 mg, 0.644 mmol) were combined in MeCN (1 mL). The reaction mixture was treated with copper (II) acetate (88 mg, 0.483 mmol) and stirred overnight at 40° C. open to air. The reaction mixture was cooled to room temperature, diluted with ammonium hydroxide (2 mL), treated with water (5 mL) and extracted with ethyl acetate (3×5 mL). The organic layer was washed with brine (5 mL), passed through a hydrophobic frit and the solvent removed under reduced pressure. The residue was absorbed onto fluorisil and purified by silica column chromatography using a 10 to 40% gradient of ethyl acetate in cyclohexane to give the title compound (45 mg, 33%).

LCMS (Method A): Rt=1.70 min, MH$^+$=419.

Intermediate 95. N-(5-(3-Hydroxy-4,5,7,8-tetrahydro-1H-oxepino[4,5-c]pyrazol-1-yl)-2-methoxypyridin-3-yl)-N-(4-methoxybenzyl)methanesulfonamide

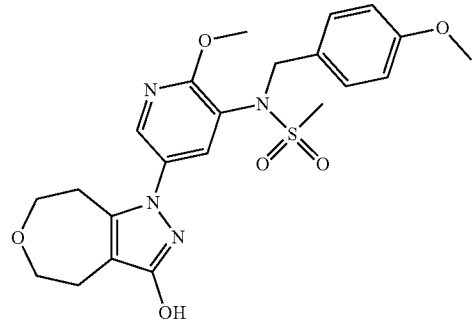 [SMILES: COc1ccc(CN(c2cc(-n3nc(O)c4c3CCOCC4)cnc2OC)S(C)(=O)=O)cc1]

A stirred solution of N-(2-methoxy-5-(3-((triisopropylsilyl)oxy)-4,5,7,8-tetrahydro-1H-oxepino[4,5-c]pyrazol-1-yl)pyridin-3-yl)-N-(4-methoxybenzyl)methanesulfonamide (100 mg, 0.143 mmol) in anhydrous THF (2 mL) under an atmosphere of nitrogen at 0° C. was treated with a 1 M solution of TBAF in THF (0.143 mL, 0.143 mmol). The reaction mixture was stirred for 90 min. Saturated NaHCO$_3$ (5 mL) was added and the mixture extracted with EtOAc (3×10 mL). The combined organic layer was passed through a hydrophobic frit and concentrated under reduced pressure to give the title compound (18 mg, 73% purity by LCMS).

LCMS (Method C): Rt=0.78 min, MH$^+$=475.

The crude material was used in the next reaction step without further purification.

Intermediate 96. 1-(6-Methoxy-5-methylpyridin-3-yl)-4,5,7,8-tetrahydro-1H-oxepino[4,5-c]pyrazol-3-ol

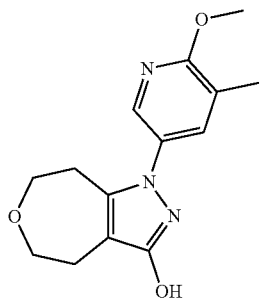 [SMILES: COc1ncc(-n2nc(O)c3c2CCOCC3)cc1C]

A stirred solution of 1-(6-methoxy-5-methylpyridin-3-yl)-3-((triisopropylsilyl)oxy)-4,5,7,8-tetrahydro-1H-oxepino[4,5-c]pyrazole (36 mg, 0.083 mmol) in anhydrous THF (1 mL) under an atmosphere of nitrogen at 0° C. was treated with a 1 M solution of TBAF in THF (0.100 mL, 0.100 mmol). The reaction was stirred for 1.5 hours. Saturated NaHCO$_3$ was added and the mixture transferred to a separating funnel. The aqueous layer was washed with DCM and the combined organic layer combined, passed through a hydrophobic frit and concentrated under reduced pressure. The residue was further dried on the high-vac line for 5 days to afford the title compound (16 mg, 0.058 mmol, 82% purity by LCMS).

LCMS (Method C): Rt=0.64 min, MH$^+$=276.

The crude material was used in the next reaction step without further purification.

Intermediate 97. 1-(5-(Fluoromethyl)-6-methoxypyridin-3-yl)-4,5,7,8-tetrahydro-1H-oxepino[4,5-c]pyrazol-3-ol

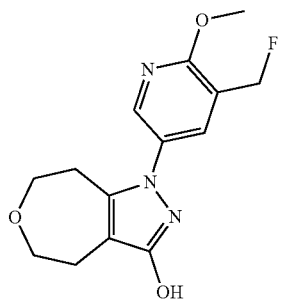 [SMILES: COc1ncc(-n2nc(O)c3c2CCOCC3)cc1CF]

A stirred solution of 1-(5-(fluoromethyl)-6-methoxypyridin-3-yl)-3-((triisopropylsilyl)oxy)-4,5,7,8-tetrahydro-1H-oxepino[4,5-c]pyrazole (71 mg, 0.158 mmol) in anhydrous THF (2 mL) under an atmosphere of nitrogen at 0° C. was treated with a 1 M solution of TBAF in THF (0.160 mL, 0.160 mmol). The reaction mixture was stirred for 2 h. Saturated NaHCO$_3$ (5 mL) was added and the mixture transferred to a separating funnel. The aqueous layer was extracted with EtOAc (4×10 mL), and the combined organic layer was passed through a hydrophobic frit and concentrated under reduced pressure to give the title compound (66 mg, 93% purity by LCMS).

LCMS (Method C): Rt=0.59 min, MH$^+$=294.

The crude material was used in the next step without further purification.

Intermediate 98. 1-(5-Fluoro-6-methoxypyridin-3-yl)-4,5,7,8-tetrahydro-1H-oxepino[4,5-c]pyrazol-3-ol

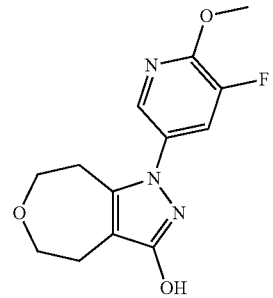 [SMILES: COc1ncc(-n2nc(O)c3c2CCOCC3)cc1F]

A stirred solution of 1-(5-fluoro-6-methoxypyridin-3-yl)-3-((triisopropylsilyl)oxy)-4,5,7,8-tetrahydro-1H-oxepino[4,5-c]pyrazole (198 mg, 0.455 mmol) in anhydrous THF (5 mL) under an atmosphere of nitrogen at 0° C. was treated with a 1 M solution of TBAF in THF (0.455 mL, 0.455 mmol). The reaction mixture was stirred for 2 h. Saturated NaHCO$_3$ (5 mL) was added and the mixture transferred to a separating funnel. The aqueous layer was extracted with EtOAc (4×10 mL), and the combined organic layer was passed through a hydrophobic frit and concentrated under reduced pressure to give the title compound (165 mg, 75% purity by NMR (data not shown)).

LCMS (Method C): Rt=0.57 min, MH$^+$=280.

The crude material was used for the next step without further purification.

Intermediate 99. 5-(3-Hydroxy-4,5,7,8-tetrahydro-1H-oxepino[4,5-c]pyrazol-1-yl)-2-methoxynicotinonitrile

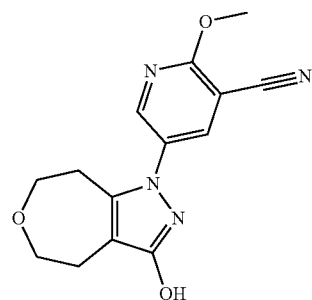 [SMILES: COc1ncc(-n2nc(O)c3c2CCOCC3)cc1C#N]

A stirred solution of 2-methoxy-5-(3-((triisopropylsilyl)oxy)-4,5,7,8-tetrahydro-1H-oxepino[4,5-c]pyrazol-1-yl)nicotinonitrile (59 mg, 0.133 mmol) in anhydrous THF (1 mL) under an atmosphere of nitrogen at 0° C. was treated with a 1 M solution of TBAF in THF (0.133 mL, 0.133 mmol). The reaction mixture was stirred for 2 h. Saturated NaHCO$_3$ (1 mL) was added and the mixture transferred to a separating funnel. The aqueous layer was extracted with EtOAc (4×10 mL), and the combined organic layer was passed through a hydrophobic frit and concentrated under reduced pressure to give the title compound (32 mg, 85% by NMR (data not shown)).

LCMS (Method C): Rt=0.58 min, MH+=287.

The crude material was used in the next reaction step without further purification.

Intermediate 100. 1-(2-Methoxypyrimidin-5-yl)-4,5,7,8-tetrahydro-1H-oxepino[4,5-c]pyrazol-3-ol

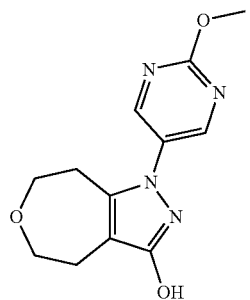 [SMILES: COc1ncc(-n2nc(O)c3c2CCOCC3)cn1]

A 1 M solution of TBAF in THF (0.107 mL, 0.107 mmol) was added to a solution of 1-(2-methoxypyrimidin-5-yl)-3-((triisopropylsilyl)oxy)-4,5,7,8-tetrahydro-1H-oxepino[4,5-c]pyrazole (45 mg, 0.107 mmol) in THF (0.5 mL) at 0° C. for 4 h. The reaction mixture was diluted with water (10 mL), acidified to pH 4 with 2 M hydrochloric acid and extracted with ethyl acetate (3×10 mL). The organic layer was washed with brine (10 mL), passed through a hydrophobic frit and concentrated under reduced pressure to give the title compound (24 mg, 93% purity by LCMS).

LCMS (Method A): Rt=0.58 min, MH+=263.

The crude material was used in the next step without further purification.

Intermediate 101. N-(5-(3-(2-(4-(2-Hydroxypropan-2-yl)piperidin-1-yl)ethoxy)-4,5,7,8-tetrahydro-1H-oxepino[4,5-c]pyrazol-1-yl)-2-methoxypyridin-3-yl)-N-(4-methoxybenzyl)methanesulfonamide

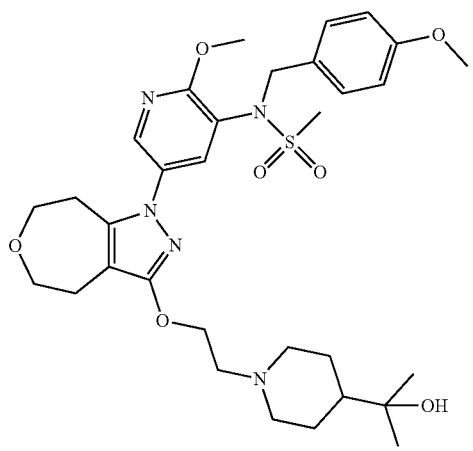 [SMILES: COc1ccc(CN(c2cc(-n3nc(OCCN4CCC(C(C)(C)O)CC4)c4c3CCOCC4)cnc2OC)S(C)(=O)=O)cc1]

A microwave vial was charged with 2-(tributylphosphoranylidene)acetonitrile (0.014 mL, 0.053 mmol) and 2-(1-(2-hydroxyethyl)piperidin-4-yl)propan-2-ol (7 mg, 0.037 mmol). The vial was sealed and purged with nitrogen. The reaction mixture was treated with a solution of N-(5-(3-hydroxy-4,5,7,8-tetrahydro-1H-oxepino[4,5-c]pyrazol-1-yl)-2-methoxypyridin-3-yl)-N-(4-methoxybenzyl)methanesulfonamide (18 mg, 0.027 mmol) in toluene (0.5 mL). The reaction mixture was heated at 100° C. for 2 h then concentrated under a stream of nitrogen. The residue was taken up in water (5 mL) and partitioned with EtOAc (5 mL). The aqueous layer was extracted with further EtOAc (3×5 mL) and the combined organic layer was passed through a hydrophobic frit and concentrated under reduced pressure. The crude product was purified by MDAP (Method A) to give the title compound (8 mg, 44%).

LCMS (Method C): Rt=1.17 min, MH+=644.

Intermediate 102. 2-Methoxy-5-(3-(1-(piperidin-4-ylmethyl)-1H-pyrazol-4-yl)-4,5,7,8-tetrahydro-1H-oxepino[4,5-c]pyrazol-1-yl)nicotinonitrile

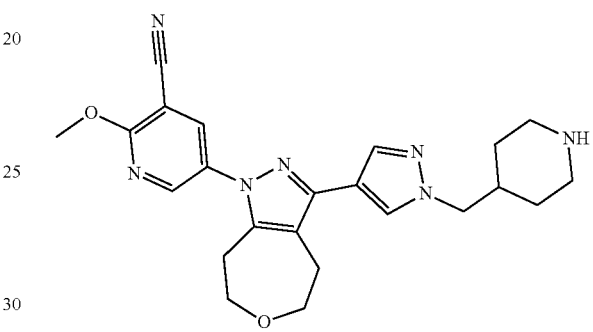

Prepared using the general Boc-deprotection procedure from tert-butyl 4-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate (61 mg, 0.114 mmol), DCM (1 mL) and TFA (0.4 mL), except the reaction was complete after stirring at room temperature for 2 h. The title compound was isolated as a brown solid (47 mg, 74%).

LCMS (Method C): Rt=0.97 min, MH+ 434.

The crude product was taken forward to the next synthetic step without further purification.

Intermediate 103. 1-(6-Methoxy-5-methylpyridin-3-yl)-3-(1-(piperidin-3-ylmethyl)-1H-pyrazol-4-yl)-4,5,7,8-tetrahydro-1H-oxepino[4,5-c]pyrazole

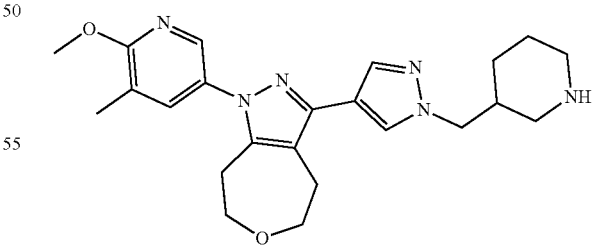

Prepared using the general Boc-deprotection procedure from tert-butyl 3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate (126 mg, 0.241 mmol), DCM (2 mL) and TFA (0.186 mL), to give the title compound (72 mg, 71%).

LCMS (Method C): Rt=0.95 min, MH+ 423.

Intermediate 104. 1-(6-Methoxy-5-methylpyridin-3-yl)-3-(1-(piperidin-4-ylmethyl)-1H-pyrazol-4-yl)-4,5,7,8-tetrahydro-1H-oxepino[4,5-c]pyrazole

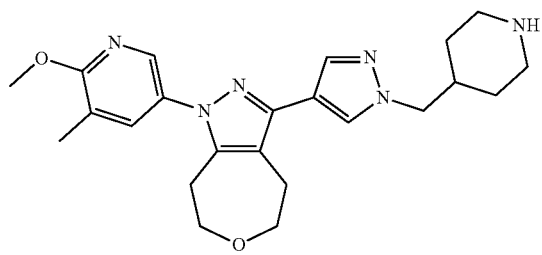 [SMILES: COc1ncc(-n2nc(-c3cnn(CC4CCNCC4)c3)c3c2CCOCC3)cc1C]

Prepared using the general Boc-deprotection procedure from tert-butyl 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate (717 mg, 0.823 mmol), DCM (5 mL), and TFA (0.634 mL) to give the title compound (470 mg, >99%).

LCMS (Method C): Rt=1.00 min, MH$^+$ 423.

The crude product was taken forward to the next synthetic step without further purification.

Intermediate 105. 1-(5-Fluoro-6-methoxypyridin-3-yl)-3-(1-(piperidin-4-ylmethyl)-1H-pyrazol-4-yl)-4,5,7,8-tetrahydro-1H-oxepino[4,5-c]pyrazole

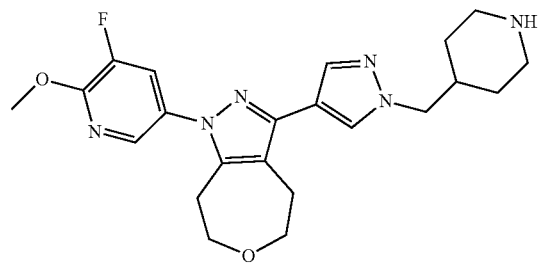 [SMILES: COc1ncc(-n2nc(-c3cnn(CC4CCNCC4)c3)c3c2CCOCC3)cc1F]

Prepared using the general Boc-deprotection procedure from tert-butyl 4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidine-1-carboxylate (96 mg, 0.182 mmol), DCM (1.5 mL) and TFA (0.6 mL), except the reaction was complete after 4 h. The title compound was isolated as a beige oil (92 mg, 89%).

LCMS (Method C): Rt=0.88 min, MH$^+$ 427.

The crude product was taken forward to the next synthetic step without further purification.

Intermediate 106. N-(2-Methoxy-5-(3-(1-(piperidin-4-ylmethyl)-1H-pyrazol-4-yl)-4,5,7,8-tetrahydro-1H-oxepino[4,5-c]pyrazol-1-yl)pyridin-3-yl)methanesulfonamide

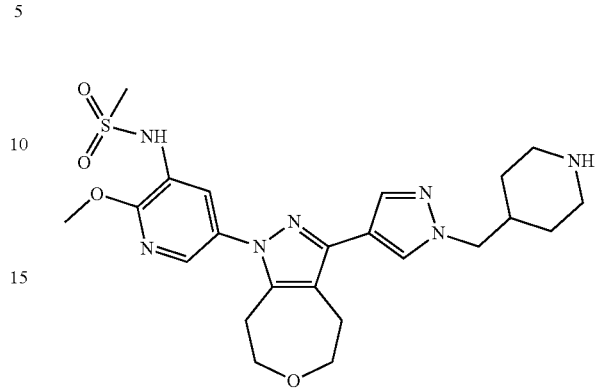

Prepared using the general Boc-deprotection procedure from tert-butyl 4-((4-(1-(6-methoxy-5-(methylsulfonamido)pyridin-3-yl)-4,5,7,8-tetrahydro-1H-oxepino[4,5-c]pyrazol-3-yl)-1H-pyrazol-1-yl)methyl)piperidine-1-carboxylate (103 mg, 0.171 mmol), DCM (1.5 mL) and TFA, (0.6 mL), except a substantial amount of product remained in the aqueous sodium bicarbonate phase. The aqueous phase was therefore passed through an Isolute 103 cartridge (2 g), which was washed with water then MeOH. The residue from the MeOH wash was combined with that obtained from the organic layer to give the title compound as an off white solid (84 mg, 93%).

LCMS (Method C): Rt=0.56 min, MH$^+$ 502.

The crude product was taken forward to the next synthetic step without further purification.

Intermediate 107. 1-(5-(Fluoromethyl)-6-methoxypyridin-3-yl)-3-(1-(piperidin-4-ylmethyl)-1H-pyrazol-4-yl)-4,5,7,8-tetrahydro-1H-oxepino[4,5-c]pyrazole

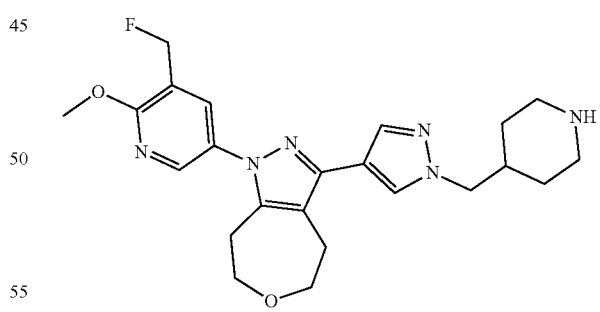

Prepared using the general Boc-deprotection procedure using tert-butyl 4-((4-(1-(5-(fluoromethyl)-6-methoxypyridin-3-yl)-4,5,7,8-tetrahydro-1H-oxepino[4,5-c]pyrazol-3-yl)-1H-pyrazol-1-yl)methyl)piperidine-1-carboxylate (454 mg, 0.840 mmol), DCM (3 mL) and TFA (2 mL) except the reaction was complete after 2 h (257 mg). The title compound was isolated as a brown gum (257 mg, 55%).

LCMS (Method C): Rt=0.92 min, MH$^+$ 441.

The crude product was taken forward to the next synthetic step without further purification.

Intermediate 108. 3-(6-Methoxy-5-methylpyridin-3-yl)-1-(1-(piperidin-4-ylmethyl)-1H-pyrazol-4-yl)-4,5,7,8-tetrahydro-1H-oxepino[4,5-c]pyrazole

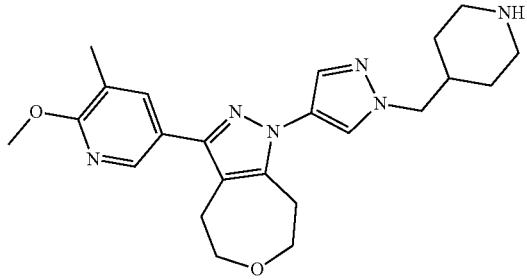 [SMILES: COc1ncc(-c2nn(-c3cnn(CC4CCNCC4)c3)c3c2CCOCC3)cc1C]

Prepared using the general Boc-deprotection procedure from tert-butyl 4-((4-(3-(6-methoxy-5-methylpyridin-3-yl)-4,5,7,8-tetrahydro-1H-oxepino[4,5-c]pyrazol-1-yl)-1H-pyrazol-1-yl)methyl)piperidine-1-carboxylate (55 mg, 0.105 mmol), DCM (1 mL) and TFA (0.5 mL), except the reaction mixture was heated at 70° C. for 15 min, by which time the reaction was complete and gave the title compound (116 mg, >99%).

LCMS (Method C) Rt=0.92 min, MH$^+$=424.

The crude product was taken forward to the next synthetic step without further purification.

Intermediate 109. 1-(6-Methoxypyridin-3-yl)-3-(trimethylsilyl)-4,5,7,8-tetrahydro-1H-oxepino[4,5-c]pyrazole

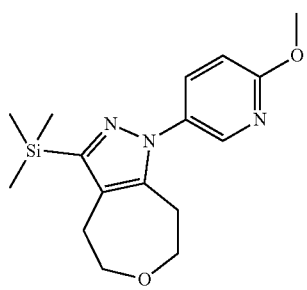

3-(trimethylsilyl)-4,5,7,8-tetrahydro-1H-oxepino[4,5-c]pyrazole (2.0 g, 9.51 mmol), (6-methoxypyridin-3-yl)boronic acid (2.91 g, 19.02 mmol), diacetoxycopper (2.07 g, 11.41 mmol) and DMAP (1.39 g, 11.41 mmol) were combined in MeCN (30 ml) and stirred open to air at 40° C. for 18 h. The reaction mixture was treated with a 5% by weight aqueous solution of TMEDA (150 mL) and partitioned with EtOAc (100 mL). The organic layer was isolated and washed further with a 5% by weight aqueous solution of TMEDA (100 mL). The combined aqueous layers were extracted with EtOAc (2×50 mL). The combined organic extracts were passed through a hydrophobic frit and the solvent removed under reduced pressure. The residue was purified by silica column chromatography, eluting with EtOAc in cyclohexane (0 to 50%) to give the title compound (1.69 g) as a white solid.

LCMS (Method C): Rt=1.23 min, MH$^+$=318.

Intermediate 110. 3-Bromo-1-(6-methoxypyridin-3-yl)-4,5,7,8-tetrahydro-1H-oxepino[4,5-c]pyrazole

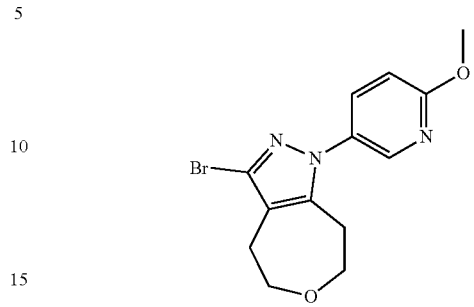

To a solution of 1-(6-methoxypyridin-3-yl)-3-(trimethylsilyl)-4,5,7,8-tetrahydro-1H-oxepino[4,5-c]pyrazole (1.65 g, 5.20 mmol) in MeCN (20 mL) was added N-bromosuccinimide (1.11 g, 6.24 mmol). The mixture was stirred under an atmosphere of nitrogen for 3 h. The reaction mixture was treated with MeOH (12 mL) and concentrated under reduced pressure then dissolved in EtOAc (100 mL). The organic phase was washed with a saturated aqueous solution of sodium hydrogen carbonate (2×100 mL). The combined aqueous phases were extracted with EtOAc (2×50 mL). The combined organic extracts were then passed through a hydrophobic frit and concentrated under reduced pressure to afford the title compound (1.87 g) as an orange solid.

LCMS (Method C): Rt=1.05 min, MH$^+$=324/326.

The crude product was taken forward to the next synthetic step without further purification.

Intermediate 111. 1-(4-(1-(6-Methoxypyridin-3-yl)-4,5,7,8-tetrahydro-1H-oxepino[4,5-c]pyrazol-3-yl)pyridin-2-yl)ethanone

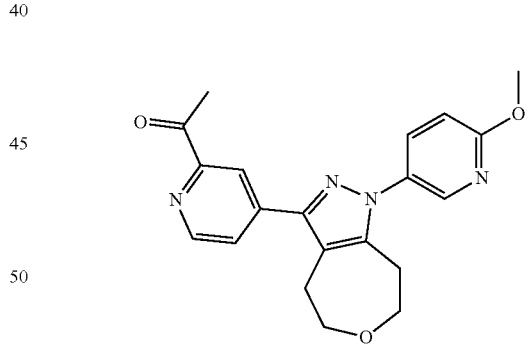

XPhos (11 mg, 0.023 mmol), XPhos Pd G2 (19 mg, 0.024 mmol), tripotassium phosphate (177 mg, 1.018 mmol) and 1-(4-(4,4,5,5-tetramethyl-1,3,2-dioxaborolan-2-yl)pyridin-2-yl)ethan-1-one (201 mg, 0.407 mmol) were added to a microwave vial. A solution of 3-bromo-1-(6-methoxypyridin-3-yl)-4,5,7,8-tetrahydro-1H-oxepino[4,5-c]pyrazole (110 mg, 0.339 mmol) in EtOH (0.8 mL) and water (0.8 mL) was added. The vial was sealed, evacuated and flushed with nitrogen then the reaction mixture was heated using a microwave at 100° C. for 1 h. The reaction mixture was treated with EtOAc (80 mL) and the mixture was extracted with a 2 M aqueous solution of HCl (2×80 mL). The aqueous phase was basified to ~pH 9 by the addition of potassium hydroxide pellets then extracted with EtOAc (2×100 mL). The organic phase was passed through a hydrophobic frit and the solvent was removed under reduced pressure to give the title compound (174 mg).

LCMS (Method C): Rt=1.01 min, MH+=365.

Intermediate 112. 1-(4-(4,4,5,5-Tetramethyl-1,3,2-dioxaborolan-2-yl)pyridin-2-yl)ethan-1-one

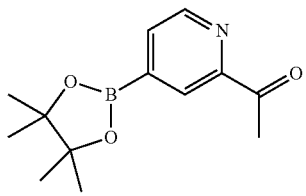 [SMILES: CC(=O)c1cc(B2OC(C)(C)C(C)(C)O2)ccn1]

A microwave vial was charged with 1-(4-bromopyridin-2-yl)ethan-1-one (203 mg, 1.01 mmol), 4,4,4',4',5,5,5',5'-octamethyl-2,2'-bi(1,3,2-dioxaborolane) (335 mg, 1.32 mmol), PdCl₂(dppf)-DCM (48 mg, 0.06 mmol)) and potassium acetate (310 mg, 3.16 mmol) in 1,4-dioxane (6 mL). The vial was sealed, evacuated and flushed with nitrogen then heated using a microwave at 100° C. for 90 min. The solvent was removed under reduced pressure and the residue was partitioned between EtOAc (50 mL) and water (50 mL). The aqueous phase was separated and extracted with EtOAc (3×50 mL). The combined organic extracts were passed through a hydrophobic frit and the solvent was removed under reduced pressure to give the title compound (319 mg).

LCMS (Method C): Rt=0.52 min, MH+=248.

The crude product was taken forward to the next synthetic step without further purification.

Intermediate 113. 1-(4-(1-(5-Fluoro-6-methoxypyridin-3-yl)-4,5,7,8-tetrahydro-1H-oxepino[4,5-c]pyrazol-3-yl)pyridin-2-yl)ethan-1-one

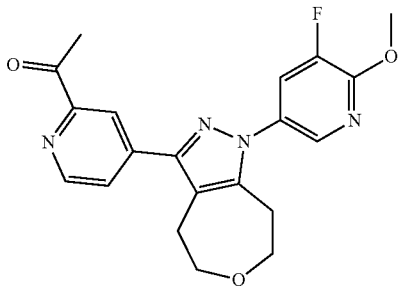 [SMILES: COc1ncc(-n2nc(-c3ccnc(C(C)=O)c3)c3c2CCOCC3)cc1F]

1-(4-(4,4,5,5-Tetramethyl-1,3,2-dioxaborolan-2-yl)pyridin-2-yl)ethan-1-one (542 mg, 2.192 mmol), 3-bromo-1-(5-fluoro-6-methoxypyridin-3-yl)-4,5,7,8-tetrahydro-1H-oxepino[4,5-c]pyrazole (500 mg, 1.461 mmol), tripotassium phosphate (764 mg, 4.38 mmol) and XPhos Pd G2 (80 mg, 0.102 mmol) were added to a microwave vial. EtOH (4 mL) and water (4 mL) were added and the vial was sealed, evacuated and flushed with nitrogen then the reaction mixture was heated using a microwave at 100° C. for 1 h. The reaction mixture was filtered through a silica plug, washing with EtOAc, then diluted with further EtOAc (200 mL). The organic phase was extracted with a 2 M aqueous solution of HCl (2×100 mL). The aqueous phase was basified to ~pH 9 by the addition of sodium hydroxide pellets then extracted with EtOAc (2×100 mL). The organic phase was passed through a hydrophobic frit and the solvent was removed under reduced pressure. The residue was purified by silica column chromatography, eluting with EtOAc in cyclohexane (0 to 100%) to give the title compound in two batches (87 mg and 215 mg) as colourless oils.

LCMS (Method C): Rt=1.09 min, MH+=383.

Intermediate 114. 1-(4-(1-(6-Methoxy-5-methylpyridin-3-yl)-4,5,7,8-tetrahydro-1H-oxepino[4,5-c]pyrazol-3-yl)pyridin-2-yl)ethanone

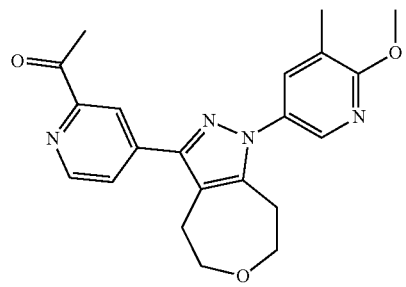 [SMILES: COc1ncc(-n2nc(-c3ccnc(C(C)=O)c3)c3c2CCOCC3)cc1C]

3-bromo-1-(6-methoxy-5-methylpyridin-3-yl)-4,5,7,8-tetrahydro-1H-oxepino[4,5-c]pyrazole (500 mg, 1.478 mmol), 1-(4-(4,4,5,5-tetramethyl-1,3,2-dioxaborolan-2-yl)pyridin-2-yl)ethan-1-one (438 mg, 1.774 mmol), tripotassium phosphate (772 mg, 4.44 mmol) and Xphos Pd G2 (81 mg, 0.103 mmol) were added to a microwave vial. EtOH (4 mL) and water (4 mL) were added and the vial was sealed, evacuated and flushed with nitrogen then the reaction mixture was heated using a microwave at 100° C. for 1 h. The reaction mixture was filtered through a Celite® pad, washing with EtOAc, then diluted with further EtOAc (200 mL). The organic phase was extracted with a 2 M aqueous solution of HCl (2×100 mL). The aqueous phase was basified to ~pH 9 by the addition of sodium hydroxide pellets then extracted with EtOAc (2×100 mL). The organic phase was passed through a hydrophobic frit and the solvent was removed under reduced pressure. The residue was purified by silica column chromatography, eluting with EtOAc in cyclohexane (0 to 100%) to give the title compound in two batches (143 mg and 347 mg) as white solids.

LCMS (Method C): Rt=1.13 min, MH+=379.

Intermediate 115. tert-Butyl 4-((4-(3-(6-methoxy-5-methylpyridin-3-yl)-4,5,7,8-tetrahydro-1H-oxepino[4,5-c]pyrazol-1-yl)-1H-pyrazol-1-yl)methyl)piperidine-1-carboxylate

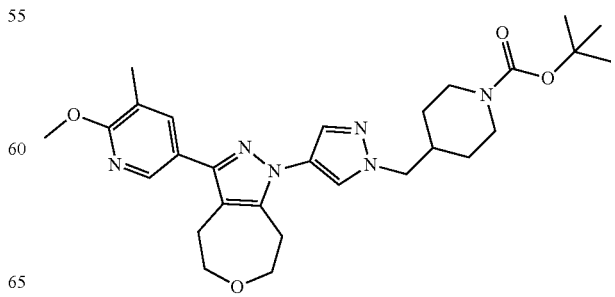

A solution of 3-(6-methoxy-5-methylpyridin-3-yl)-1-(1H-pyrazol-4-yl)-4,5,7,8-tetrahydro-1H-oxepino[4,5-c]pyrazole (19 mg, 0.058 mmol) DMF (0.5 mL) under an atmosphere of nitrogen was cooled on ice then treated with a 60% suspension of NaH in mineral oils (6 mg, 0.150 mmol) and allowed to return to room temperature. The reaction mixture was stirred for 30 min and treated with tert-butyl 4-(bromomethyl)piperidine-1-carboxylate (48 mg, 0.173 mmol). The reaction was stirred at room temperature under an atmosphere of nitrogen for 3 h.

The reaction mixture was cooled on ice and treated dropwise with an aqueous solution of ammonium chloride (5 mL) and stirred for 30 min. The reaction mixture was diluted with water (10 mL) and partitioned with EtOAc (15 mL). The organic layer was isolated and the aqueous layer extracted with EtOAc (2×15 mL). The combined organic layer was washed with a 5% by weight solution of LiCl solution (3×20 mL). The organic layer isolated and passed through a hydrophobic frit and concentrated under reduced pressure to give the crude product (63 mg). The mixture was purified by MDAP (Method A) to give the title compound (21 mg, 62%).

LCMS (Method C) Rt=1.30 min, MH+=523.

Intermediate 116. 5-(3-(1H-Pyrazol-4-yl)-4,5,7,8-tetrahydro-1H-oxepino[4,5-c]pyrazol-1-yl)-2-methoxynicotinonitrile

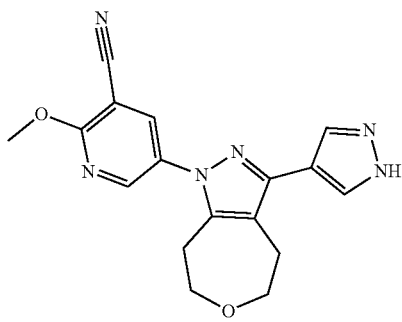 [SMILES: COc1ncc(-n2nc(-c3cn[nH]c3)c3c2CCOCC3)cc1C#N]

Crude 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (174 mg, 0.168 mmol) was dissolved in DCM (4 mL) and treated with TFA (4 mL). The reaction mixture was heated in two portions using a microwave for 3 h at 70° C. The reaction was quenched with sodium bicarbonate (3 mL) and left to stir at room temperature for 1 h and then left overnight. The solutions were combined and extracted with DCM (3×20 mL), making the aqueous phase up to 20 mL. The combined organic layer was passed through a hydrophobic frit and concentrated under reduced pressure to give crude 5-(3-(1H-pyrazol-4-yl)-4,5,7,8-tetrahydro-1H-oxepino[4,5-c]pyrazol-1-yl)-2-methoxynicotinonitrile. The crude material was partially purified by silica column chromatography, eluting with a 0 to 50% gradient of EtOH in EtOAc (3:1) and cyclohexane to give partially purified 5-(3-(1H-pyrazol-4-yl)-4,5,7,8-tetrahydro-1H-oxepino[4,5-c]pyrazol-1-yl)-2-methoxynicotinonitrile.

Intermediate 117. tert-Butyl 4-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate

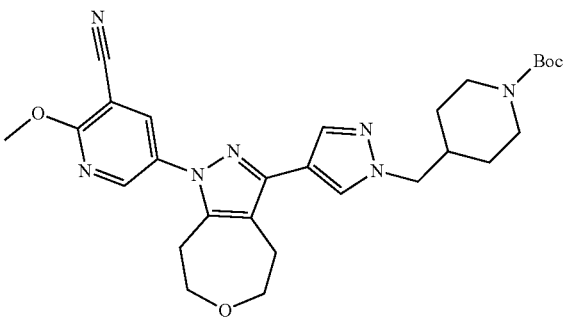 [SMILES: COc1ncc(-n2nc(-c3cnn(CC4CCN(C(=O)OC(C)(C)C)CC4)c3)c3c2CCOCC3)cc1C#N]

Crude 5-(3-(1H-pyrazol-4-yl)-4,5,7,8-tetrahydro-1H-oxepino[4,5-c]pyrazol-1-yl)-2-methoxynicotinonitrile (226 mg) in DMF (4 mL) was stirred overnight. The reaction mixture was cooled to 0° C. and treated carefully with sodium hydride (44.0 mg, 1.834 mmol) then allowed to warm to room temperature under an atmosphere of nitrogen for 30 min. The reaction mixture was treated with tert-butyl 4-(bromomethyl)piperidine-1-carboxylate (510 mg, 1.834 mmol) and stirred at room temperature for 3 h. The reaction mixture was then allowed to stand for 5 d and quenched with a saturated solution of ammonium chloride (3 mL). The mixture was treated with water (10 mL) and extracted with EtOAc (3×15 mL). The combined organic layer was washed with a 5% aqueous solution of LiCl (3×10 mL) then passed through a hydrophobic frit and concentrated under reduced pressure to give crude tert-butyl 4-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate (400 mg).

Intermediate 118. 2-Methoxy-5-(3-(1-(piperidin-4-ylmethyl)-1H-pyrazol-4-yl)-4,5,7,8-tetrahydro-1H-oxepino[4,5-c]pyrazol-1-yl)nicotinonitrile and 2-methoxy-5-(3-(1-(piperidin-4-ylmethyl)-1H-pyrazol-4-yl)-4,5,7,8-tetrahydro-2H-oxepino[4,5-c]pyrazol-2-yl)nicotinonitrile

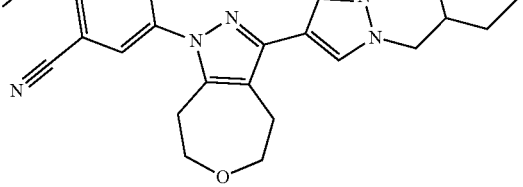

-continued

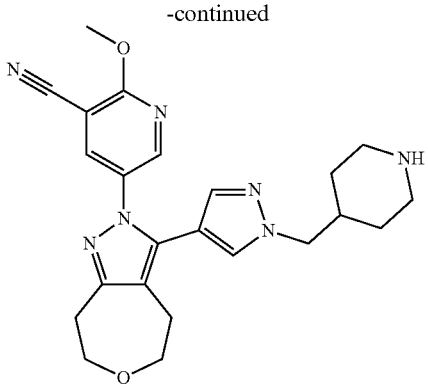

Crude tert-butyl 4-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate (400 mg) in DCM (4 mL) was treated with TFA (0.492 mL, 6.39 mmol) and stirred at room temperature for 1 h then allowed to stand for 5 days. The reaction mixture was treated with a a saturated aqueous solution of sodium bicarbonate until pH 9 was reached. The reaction mixture was extracted with three equivalents of DCM (15 mL each) and the organic layer isolated and passed through a hydrophobic frit and concentrated under reduced pressure to afford a crude product.

An attempt to dissolve the crude product in a 1:1 mixture of DMSO and MeOH 1:1 (2 mL) failed so the mixture was concentrated. The mixture was treated with MeCN (5 mL) and purified by reverse phase chromatography using a C18 silica column, eluting with a solution of MeCN in water, acidified with formic acid (30 to 85% MeCN plus 0.1% formic acid) to give 2-methoxy-5-(3-(1-(piperidin-4-ylmethyl)-1H-pyrazol-4-yl)-4,5,7,8-tetrahydro-1H-oxepino[4,5-c]pyrazol-1-yl)nicotinonitrile (246 mg).

The partially purified mixture of compounds was taken forward into the next reaction step.

Crude 2-methoxy-5-(3-(1-(piperidin-4-ylmethyl)-1H-pyrazol-4-yl)-4,5,7,8-tetrahydro-1H-oxepino[4,5-c]pyrazol-1-yl)nicotinonitrile (123 mg) was dissolved in acetone (1 mL) and stirred at room temperature for 2 h under an atmosphere of nitrogen. The reaction mixture was heated at 60° C. for 2 h and allowed to stand over the weekend. The mixture was carefully treated with sodium triacetoxyborohydride (60.1 mg, 0.284 mmol) and stirred at room temperature under an atmosphere of nitrogen for 4 h. After 2 h, a small amount of DMF was added to improve solubility. The reaction mixture was stirred overnight and further sodium triacetoxyborohydride (60.1 mg, 0.284 mmol) was added. The reaction mixture was stirred for 3 h and treated with an aqueous solution of sodium bicarbonate (2 mL) then stirred overnight at room temperature. The reaction mixture was partitioned with sodium bicarbonate (5 mL) and EtOAc (10 mL). The organic layer was isolated and the aqueous layer re-extracted with EtOAc (2×10 mL). The combined organic layer was passed through a hydrophobic frit and concentrated under reduced pressure to afford the crude product (50 mg). The crude product was purified by MDAP (Method C) to give the title compound (19 mg).

LCMS (Method C): Rt=0.63 min, MH+ 476.

$^1$H NMR (400 MHz, MeCN-$d_3$) δ-ppm 8.46 (d, J=3 Hz, 1H), 8.13 (d, J=3 Hz, 1H), 7.80 (s, 1H), 7.74 (s, 1H), 4.14-4.05 (m, 5H), 3.84 (t, J=5 Hz, 2H), 3.80 (t, J=5 Hz, 2H), 3.49-3.33 (m, 3H), 2.98-2.83 (m, 4H), 2.66-2.51 (m, 2H), 2.29-2.13 (m, 1H), 1.90-1.77 (m, 2H), 1.71-1.53 (m, 2H), 1.27 (d, J=7 Hz, 6H).

Intermediate 119. 2-Methoxy-5-(3-(1-(4-methoxybenzyl)-1H-pyrazol-4-yl)-4,5,7,8-tetrahydro-1H-oxepino[4,5-c]pyrazol-1-yl)nicotinonitrile

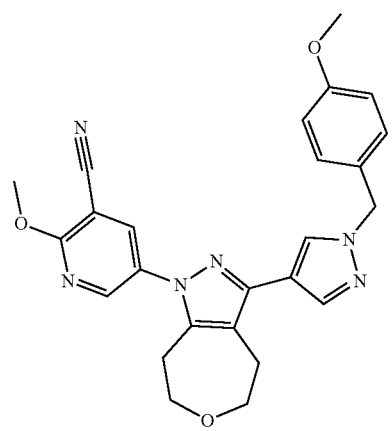 [SMILES: COc1ccc(Cn2cc(-c3nn(-c4cnc(OC)c(C#N)c4)c4c3CCOCC4)cn2)cc1]

A mixture of copper acetate (349 mg, 1.921 mmol), 3-(1-(4-methoxybenzyl)-1H-pyrazol-4-yl)-4,5,7,8-tetrahydro-1H-oxepino[4,5-c]pyrazole (623 mg, 1.921 mmol), 2-methoxy-5-(4,4,5,5-tetramethyl-1,3,2-dioxaborolan-2-yl)nicotinonitrile (500 mg, 1.921 mmol) and DMAP (469 mg, 3.84 mmol) in MeCN (16 mL) was stirred at 40° C. overnight open to air. The reaction was heated for 5 h then left to stand over a weekend. The reaction was diluted with water (25 mL) and reduced in volume by concentrating under reduced pressure. The resulting solution was extracted with EtOAc (3×25 mL) in the presence of a 5% solution of DMEDA. The combined organic layer was passed through a hydrophobic frit and concentrated under reduced pressure. The crude product was treated with DMAP (469 mg, 3.84 mmol), CuOAc (349 mg, 1.921 mmol), 2-methoxy-5-(4,4,5,5-tetramethyl-1,3,2-dioxaborolan-2-yl)nicotinonitrile (500 mg, 1.921 mmol) in MeCN (16 mL). The reaction mixture was heated at 40° C. for 7 h then at room temperature overnight. The reaction mixture was concentrated under reduced pressure and partitioned between water (25 mL) and EtOAc (4×25 mL), in the presence of 5% DMEDA in the aqueous phase. The combined organic layer was passed through a hydrophobic frit and concentrated under reduced pressure. The crude material was partially purified by reverse phase chromatography using a C18 column, eluting with a 30 to 85% gradient of a solution of MeCN (+0.1% formic acid in water) and 0.1% formic acid to give partially purified 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (633 mg). The material was used directly in the next step.

Intermediate 120. 5-(3-(1H-Pyrazol-4-yl)-4,5,7,8-tetrahydro-1H-oxepino[4,5-c]pyrazol-1-yl)-2-methoxynicotinonitrile

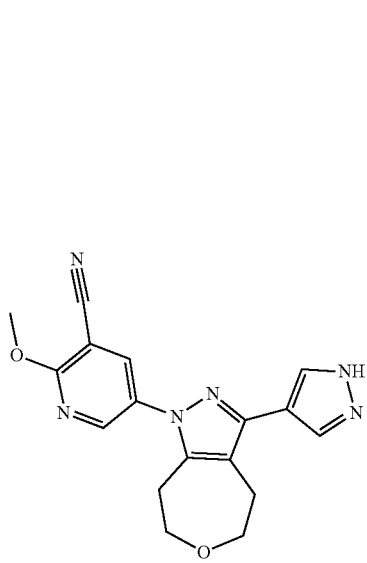 [SMILES: COc1ncc(-n2nc(-c3cn[nH]c3)c3c2CCOCC3)cc1C#N]

Crude 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (20 mg) was treated with DCM (0.1 mL) and TFA (0.1 mL, 1.298 mmol).

The reaction mixture was heated 70° C. using a microwave for 2 h. The reaction mixture was treated with more crude 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (183 mg) in DCM (0.5 mL) followed by TFA (0.62 mL) and heated at 70° C. using a microwave for 5 h.

The reaction mixture was diluted with DCM (10 mL) and treated with a saturated aqueous solution of sodium bicarbonate in a dropwise manner until the reaction mixture was pH 9. The reaction mixture was stirred for 30 min then partitioned with DCM (20 mL). The organic layer was isolated and the aqueous layer re-extracted with DCM (2×20 mL). The combined organic layer was passed through a hydrophobic frit and concentrated under reduced pressure, to give crude 5-(3-(1H-pyrazol-4-yl)-4,5,7,8-tetrahydro-1H-oxepino[4,5-c]pyrazol-1-yl)-2-methoxynicotinonitrile as a light brown gum (240 mg).

The crude material was taken forward into the next reaction step without further purification.

Intermediate 121. tert-Butyl 3-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate

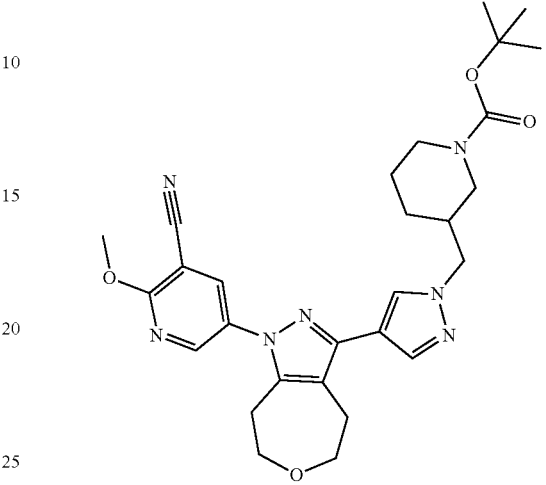

5-(3-(1H-Pyrazol-4-yl)-4,5,7,8-tetrahydro-1H-oxepino[4,5-c]pyrazol-1-yl)-2-methoxynicotinonitrile (100 mg) in DMF (1.4 mL) at 0° C. was treated with a 60% by weight suspension of sodium hydride in mineral oils (14.3 mg, 0.357 mmol) and stirred under an atmosphere of nitrogen for 1 h. The reaction mixture was treated with tert-butyl 3-(bromomethyl)piperidine-1-carboxylate (124 mg, 0.446 mmol) and stirred at room temperature under an atmosphere of nitrogen over the weekend.

The reaction mixture was treated with saturated ammonium chloride solution (5 mL), and extracted into ethyl acetate (3×10 mL). The organic layer was isolated and washed with a 5% by weight solution of LiCl. The solvent was passed through a hydrophobic frit and concentrated to give crude tert-Butyl 3-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate (193 mg).
LCMS (Method C) Rt=1.21 min, MH$^+$=534.

The crude material was taken forward into the next reaction step without further purification.

Intermediate 122. 2-Methoxy-5-(3-(1-(piperidin-3-ylmethyl)-1H-pyrazol-4-yl)-4,5,7,8-tetrahydro-1H-oxepino[4,5-c]pyrazol-1-yl)nicotinonitrile

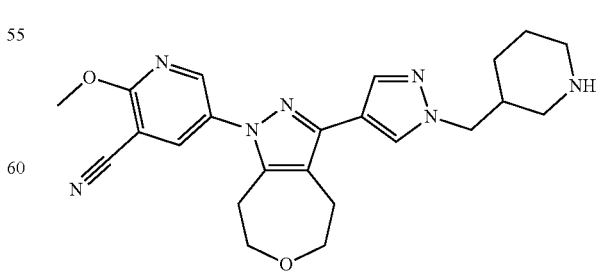

A solution of tert-butyl 3-((4-(1-(5-cyano-6-methoxypyridin-3-yl)-4,5,7,8-tetrahydro-1H-oxepino[4,5-c]pyrazol-3- yl)-1H-pyrazol-1-yl)methyl)piperidine-1-carboxylate in DCM (3 mL) was treated with TFA (0.294 mL, 3.82 mmol). The reaction mixture was stirred at room temperature for 5 h and then overnight.

The reaction mixture was treated with a saturated aqueous solution of sodium bicarbonate (2 mL) and was stirred vigorously for 2 h. An additional 1 mL of a saturated aqueous solution of sodium bicarbonate was added and the mixture was diluted with DCM (15 mL) and more of a saturated aqueous solution of sodium bicarbonate was added to bring the total to 15 mL. The organic layer was isolated and the aqueous layer re-extracted with DCM (2×15 mL). The combined organic layer was passed through a hydrophobic frit and concentrated under reduced pressure to afford a crude product. The crude product was purified by MDAP (Method A) to give 2-methoxy-5-(3-(1-(piperidin-3-ylmethyl)-1H-pyrazol-4-yl)-4,5,7,8-tetrahydro-1H-oxepino[4,5-c]pyrazol-1-yl)nicotinonitrile (73 mg).

A solution of 2-methoxy-5-(3-(1-(piperidin-3-ylmethyl)-1H-pyrazol-4-yl)-4,5,7,8-tetrahydro-1H-oxepino[4,5-c]pyrazol-1-yl)nicotinonitrile (73 mg, 0.168 mmol) in DMF (0.75 mL) and acetone (1 mL) was stirred under an atmosphere of nitrogen in a sealed vial overnight. The reaction mixture was treated with STAB (71.4 mg, 0.337 mmol) and stirred for 3 h. The reaction was quenched with an aqueous solution of sodium bicarbonate (2 mL) and stirred vigorously over a weekend. The mixture was partitioned with sodium bicarbonate in water (10 mL) and EtOAc (10 mL), and extracted with further EtOAc (2×10 mL). The combined organic layer was passed through a hydrophobic frit and concentrated under reduced pressure to give crude product (47 mg). The crude product was placed in a vacuum oven for 3 h then placed under a stream of nitrogen overnight to remove residual DMF. The crude title compound was isolated (47 mg).

LCMS (Method A) Rt=0.65 min, MH+=476.

$^1$H NMR (400 MHz, CDCl$_3$) δ-ppm 8.40 (d, J=3 Hz, 1H), 8.01 (d, J=3 Hz, 1H), 7.74 (s, 1H), 7.66 (s, 1H), 4.15-4.02 (m, 5H), 3.97-3.79 (m, 4H), 2.98-2.90 (m, 4H), 2.32-2.11 (m, 2H), 2.08-1.96 (m, 1H), 1.81-1.47 (m, 7H), 1.13-0.79 (m, 6H).

Intermediate 123. (R)-1-(4-bromopyridin-2-yl)ethan-1-ol

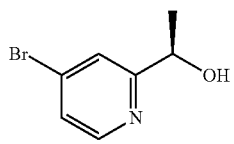

To an EasyMax reaction vessel was added enzyme KRED-P1-F02 (available from Codexis, 60.5 mg, 30.1 mmol), NADP+ (61 mg, 30.1 mmol) and isopropanol (15 mL). The solution was stirred for 10 min at 30° C. A solution of 1-(4-bromopyridin-2-yl)ethan-1-one (6.03 g, 30.1 mmol) in 0.1 M potassium phosphate solution (45 mL) was added and the reaction was stirred at 30° C. for 26 h. EtOAc (40 mL) was added and the layers were separated. The aqueous phase was extracted with further ethyl acetate (2×40 mL). The combined organics were washed with water (20 mL) and dried with MgSO$_4$ before filtering and concentrating under reduced pressure. The residue was taken up in a small amount of DCM and the solvent was removed under reduced pressure to give the title compound (4.88 g).

LCMS (Method C) Rt=0.69 min, MH+=202/204.). Enantiomeric purity by chiral GC=>99.0% e.e.

Intermediate 124. (R)-1-(4-bromopyridin-2-yl)ethyl methanesulfonate

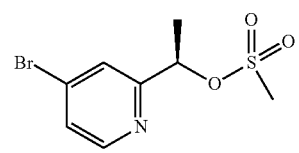

To a solution of (R)-1-(4-bromopyridin-2-yl)ethan-1-ol (4.88 g, 24.15 mmol) in DCM (60 mL) at 0° C. under an atmosphere of nitrogen was added DIPEA (8.44 mL, 48.3 mmol) and methanesulfonic anhydride (6.31 g, 36.2 mmol). The reaction mixture stirred for 1 h then was diluted with DCM (50 mL) and washed with water (50 mL) then saturated aqueous NaHCO$_3$ solution (50 mL). The combined aqueous phases were extracted with DCM (50 mL). The combined organic phases were passed through a hydrophobic frit and solvent removed under reduced pressure to give the title compound (6.897 g).

LCMS (Method C) Rt=0.85 min, MH+=280/282.

Intermediate 125. (2S,6R)-4-((S)-1-(4-bromopyridin-2-yl)ethyl)-1,2,6-trimethylpiperazine

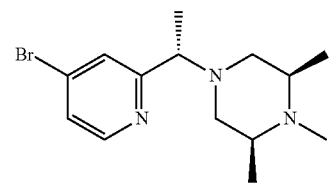 [SMILES: C[C@@H]1CN([C@@H](C)c2cc(Br)ccn2)C[C@H](C)N1C]

A mixture of (R)-1-(4-bromopyridin-2-yl)ethyl methanesulfonate (3.78 g, 13.49 mmol), (2S,6R)-1,2,6-trimethylpiperazine (2.076 g, 16.19 mmol) and DIPEA (2.83 mL, 16.19 mmol) in DCM (40 mL) was stirred at room temperature overnight under an atmosphere of nitrogen. (2S,6R)-1,2,6-trimethylpiperazine (2.076 g, 16.19 mmol) was added and stirring was continued overnight. The mixture was diluted with DCM (50 mL) and washed with saturated aqueous NaHCO$_3$ solution (30 mL). The organic phase was passed through a hydrophobic frit and the solvent was removed under reduced pressure to afford an orange oil. The crude material was purified by chromatography on silica, eluting with 20-100% 3:1 EtOH:EtOAc(+0.1% NEt$_3$) in cyclohexane to give the title compound (3.00 g).

LCMS (Method C) Rt=0.95 min, MH+=312/314.

Intermediate 126. (S)-1-(1-(4-bromopyridin-2-yl)ethyl)-4-methylpiperazine

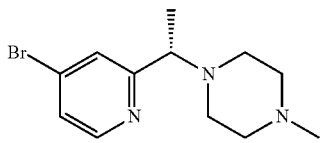

A mixture of (R)-1-(4-bromopyridin-2-yl)ethyl methanesulfonate (488 mg, 1.742 mmol), 1-methylpiperazine (0.290 mL, 2.61 mmol) and DIPEA (0.456 mL, 2.61 mmol) in DCM (10 mL) was stirred at room temperature overnight under an atmosphere of nitrogen. 1-methylpiperazine (0.290 mL, 2.61 mmol) was added and stirring was continued for 6 h. 1-methylpiperazine (0.290 mL, 2.61 mmol) was added and stirring was continued for overnight. 2M aqueous HCl solution was added and the organic phase separated. The aqueous phase was washed with further DCM (3×10 mL). The aqueous phase was taken to pH 12 by the addition of 2M aqueous NaOH solution. The aqueous phase was extracted with DCM (3×30 mL). The combined organic extracts were washed with water (20 mL) then brine (20 mL), dried by passing through a hydrophobic frit and concentrated under reduced pressure to afford a pale orange oil, which was dried on a high vacuum line overnight to give the title compound (351 mg).

LCMS (Method A) Rt=0.38 min, MH+=284/286.

Intermediate 127. (2S,6R)-1,2,6-trimethyl-4-((S)-1-(4-(4,4,5,5-tetramethyl-1,3,2-dioxaborolan-2-yl)pyridin-2-yl)ethyl)piperazine

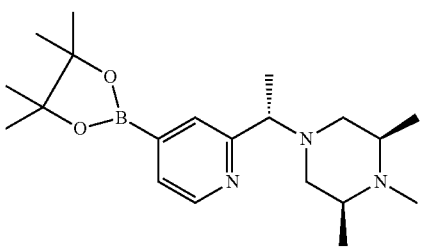

A mixture of (2S,6R)-4-((S)-1-(4-bromopyridin-2-yl)ethyl)-1,2,6-trimethylpiperazine (1.51 g, 4.84 mmol), bis(pinacolato)diboron (1.80 g, 7.09 mmol), potassium acetate (1.40 g, 14.27 mmol) and PdCl2(dppf)-CH2Cl2 adduct (0.191 g, 0.234 mmol) in 1,4-Dioxane (15 mL) was degassed with nitrogen for 15 min with stirring. The reaction mixture was heated in a microwave at 100° C. for 1 h. The reaction mixture was passed through Celite®, washing with EtOAc. The solvent was removed under reduced pressure and the residue taken up in water (50 mL) and EtOAc (50 mL). Brine (20 mL) was added and the layers were separated. The aqueous phase was isolated and the organic phase washed again with water (30 mL). Half of the aqueous phase was loaded onto an ISOLUTE® 103 cartridge (5 g) that had been preconditioned with MeOH then water. The cartridge was eluted with water (1 CV), then MeOH (2 CV). The aqueous fraction was combined with the remaining aqueous phase and split between 2× Isolute 103 cartridges (5 g) that had been preconditioned with MeOH then water. The cartridges were eluted with water (1 CV), then MeOH (2 CV). All the methanolic fractions were combined and concentrated under reduced pressure then dried on a high vacuum line for 30 min to give the title compound (1.78 g).

$^1$H NMR (400 MHz, CDCl$_3$) δ-ppm 8.62 (dd, J=5 Hz, 1 Hz, 1H), 7.62 (s, 1H), 7.53 (dd, J=5 Hz, 1 Hz, 1H), 3.61 (q, J=7 Hz, 1H), 3.07-2.98 (m, 1H), 2.79-2.57 (m, 4H), 2.42 (s, 3H), 2.31-2.19 (m, 2H), 1.43 (d, J=7 Hz, 3H), 1.38 (s, 12H), 1.26 (d, J=6 Hz, 3H), 1.15 (d, J=6 Hz, 3H).

Intermediate 128. (S)-1-methyl-4-(1-(4-(4,4,5,5-tetramethyl-1,3,2-dioxaborolan-2-yl)pyridin-2-yl)ethyl)piperazine

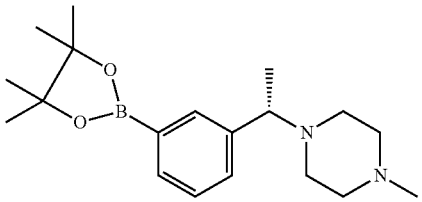

A mixture of (S)-1-(1-(4-bromopyridin-2-yl)ethyl)-4-methylpiperazine (351 mg, 1.235 mmol), 4,4,4',4',5,5,5',5'-octamethyl-2,2'-bi(1,3,2-dioxaborolane) (470 mg, 1.853 mmol), potassium acetate (364 mg, 3.71 mmol) and PdCl2(dppf)-CH2Cl2 adduct (50.4 mg, 0.062 mmol) in 1,4-Dioxane (4 mL) was degassed with nitrogen for 10 min with stirring. The mixture was then heated in a microwave at 100° C. for 1 h. The reaction mixture was passed through Celite®, washing with EtOAc. The solvent was removed under reduced pressure and the residue was dried on a high vacuum line to afford crude title compound (763 mg). The material was used directly in the next step.

Intermediate 129. (R)-1-(4-(1-(6-methoxy-5-methylpyridin-3-yl)-4,5,7,8-tetrahydro-1H-oxepino[4,5-c]pyrazol-3-yl)pyridin-2-yl)ethyl methanesulfonate

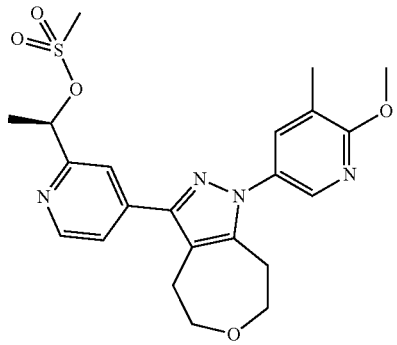 [SMILES: COc1ncc(-n2nc(-c3ccnc([C@@H](C)OS(C)(=O)=O)c3)c3c2CCOCC3)cc1C]

To a stirred solution of (R)-1-(4-(1-(6-methoxy-5-methylpyridin-3-yl)-4,5,7,8-tetrahydro-1H-oxepino[4,5-c]pyrazol-3-yl)pyridin-2-yl)ethanol (2 g, 5.26 mmol) in DCM (20 mL) was added DIPEA (1.836 mL, 10.51 mmol) followed by methanesulfonyl chloride (0.614 mL, 7.89 mmol) at 0° C. The reaction mixture was stirred between 0-10° C. under nitrogen for 3 h. The reaction mixture was quenched with water and extracted into DCM (3×30 mL), dried over sodium sulphate and concentrated under reduced pressure.

The crude product was pre-adsorbed on silicagel (100-200 mesh, 15 g) and purified by normal phase column chromatography on silica, eluting with 100% EtOAc to give the title compound (1.7 g).

LCMS (Method D): Rt=2.33 min, MH+ 459.

Intermediate 130. 1-(4-(1-(5-fluoro-6-methoxypyridin-3-yl)-4,5,7,8-tetrahydro-1H-oxepino[4,5-c]pyrazol-3-yl)pyridin-2-yl)ethyl methanesulfonate

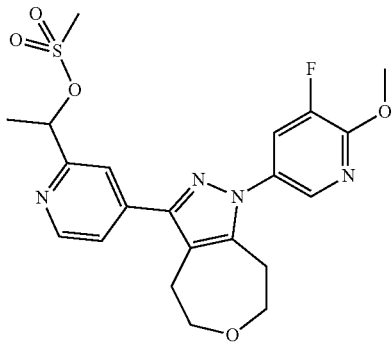 [SMILES: COc1ncc(-n2nc(-c3ccnc(C(C)OS(C)(=O)=O)c3)c3c2CCOCC3)cc1F]

To a stirred solution of 1-(4-(1-(5-fluoro-6-methoxypyridin-3-yl)-4,5,7,8-tetrahydro-1H-oxepino[4,5-c]pyrazol-3-yl)pyridin-2-yl)ethanol (1.97 g, 5.13 mmol) and DIPEA (2.7 mL, 15.4 mmol) in DCM (50 mL) at 0° C. was added methanesulfonyl chloride (0.8 mL, 10.27 mmol) dropwise. The reaction mixture was warmed to room temperature and stirred for 3 h. The reaction mixture was cooled to 0° C. and quenched with saturated aqueous NaHCO$_3$ solution (20 mL). The organic phase was separated and the aqueous phase was extracted further with DCM (20 mL). The combined organic extracts were dried over sodium sulphate and concentrated under reduced pressure. The crude product purified by normal phase column chromatography on silica, eluting with 40-100% EtOAc/hexane then 0-20% MeOH/DCM to give the title compound (1.82 g).

LCMS (Method E): Rt=0.89 min, MH+ 463.

Intermediate 131. tert-butyl 4-(1-hydroxyethyl)piperidine-1-carboxylate

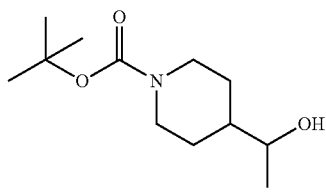 [SMILES: CC(O)C1CCN(C(=O)OC(C)(C)C)CC1]

Di-tert-butyl dicarbonate (1.858 g, 8.51 mmol) was added dropwise to a solution of sodium bicarbonate (0.715 g, 8.51 mmol) and 1-(piperidin-4-yl)ethan-1-ol (1 g, 7.74 mmol) in Water (10 mL) and 1,4-Dioxane (10 mL) at 0° C. under an atmosphere of nitrogen. The reaction was allowed to warm to room temperature and stirred for 18 h. The reaction mixture was diluted with water (100 mL) and extracted with DCM (100 mL). The aqueous layer was extracted with further DCM (3×50 mL) and the combined organic extracts were dried by passing through a hydrophobic frit. The solvent was removed under reduced pressure to afford the crude title compound (1.87 g). The material was used directly in the next step.

Intermediate 132. tert-Butyl 4-(1-((methylsulfonyl)oxy)ethyl)piperidine-1-carboxylate

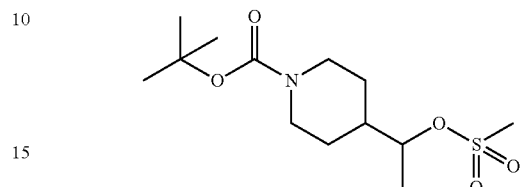

To a solution of tert-butyl 4-(1-hydroxyethyl)piperidine-1-carboxylate (805 mg, 3.51 mmol) and triethylamine (0.979 mL, 3.86 mmol) in DCM (10 mL) was added mesyl-Cl (0.301 mL, 3.86 mmol) at 0° C. under an atmosphere of nitrogen. The reaction mixture was left to stir for 4 h. The reaction mixture was diluted with ether (30 mL) and washed sequentially with 1M aqueous HCl solution (20 mL), saturated aqueous NaHCO$_3$ solution (20 mL) and brine (10 mL). The organic phase was passed through a hydrophobic frit and the solvent removed under reduced pressure to afford the crude title compound (980 mg). The material was used directly in the next step.

Intermediate 133. tert-butyl (S)-4-(1-hydroxyethyl)piperidine-1-carboxylate

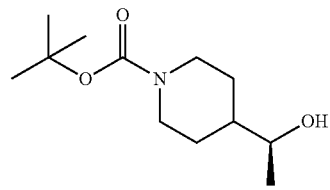 [SMILES: C[C@H](O)C1CCN(C(=O)OC(C)(C)C)CC1]

To a solution of diethylaniline-borane complex (9.39 mL, 52.8 mmol) in THF (15 mL) was added (R)-1-methyl-3,3-diphenyltetrahydro-1H,3H-pyrrolo[1,2-c][1,3,2]oxazaborole (1 M in THF, 4.40 mL, 4.40 mmol). The reaction mixture was stirred at room temperature for 90 mins under an atmosphere of nitrogen. The mixture was cooled to 5° C. in an ice bath then tert-butyl 4-acetylpiperidine-1-carboxylate (10 g, 44.0 mmol) in THF (90 mL) was added dropwise over 20 min. The reaction was stirred in a melting ice bath for 1.5 h, temperature rose to 17° C. The reaction was quenched with MeOH (30 mL) and stirred for 60 min. The solvents were removed under reduced pressure and the residue was left to stand overnight and then taken up in EtOAc (80 mL) and washed with 5% aqueous citric acid solution (2×80 mL) then brine (80 mL). The organic phase was passed through a hydrophobic frit and concentrated under reduced pressure. The crude material was purified by normal phase column chromatography on silica, eluting with 0-100% EtOAc/cyclohexane to afford the title compound (9.68 g).

$^1$H NMR (400 MHz, CDCl$_3$) δ-ppm 4.21-4.14 (m, 2H), 3.61 (q, J=6 Hz, 1H), 2.68 (tt, J=13 Hz, 3 Hz, 2H), 1.87-1.81

(m, 1H), 1.66-1.59 (m, 1H), 1.48 (s, 9H), 1.47-1.39 (m, 2H), 1.32-1.18 (m, 2H), 1.21 (d, J=6 Hz, 3H).

Intermediate 134. tert-butyl (S)-4-(1-((methylsulfonyl)oxy)ethyl)piperidine-1-carboxylate

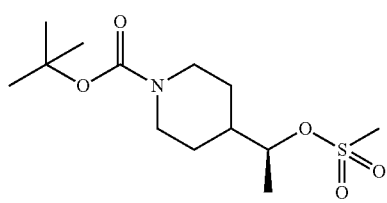 [SMILES: C[C@H](OS(C)(=O)=O)C1CCN(C(=O)OC(C)(C)C)CC1]

To a solution of tert-butyl (S)-4-(1-hydroxyethyl)piperidine-1-carboxylate (10.6 g, 46.2 mmol) in DCM (200 mL) was added methanesulfonic anhydride (8.86 g, 50.8 mmol) and N-ethyl-N-isopropylpropan-2-amine (16.15 mL, 92 mmol) at 0° C. under an atmosphere of nitrogen. The reaction mixture was allowed to warm to room temperature and stirred overnight. The reaction mixture was diluted with ether (750 mL) then washed with a 2 M aqueous solution of HCl (200 mL) then water (200 mL). The organic phase was dried by passing through a hydrophobic frit and the solvent was removed under reduced pressure. The crude material was purified by normal phase column chromatography on silica, eluting with 0-100% EtOAc/cyclohexane to afford the title compound (11.23 g).
$^1$H NMR (400 MHz, CDCl$_3$) δ-ppm 4.71-4.63 (m, 1H), 4.25-4.17 (m, 2H), 3.03 (s, 3H), 2.73-2.66 (m, 2H), 1.83-1.66 (m, 3H), 1.48 (s, 9H), 1.43 (d, J=6 Hz, 3H), 1.35-1.24 (m, 2H).

Intermediate 135. tert-Butyl 4-(1-(4-(3-(5-fluoro-6-methoxypyridin-3-yl)-4,5,7,8-tetrahydro-1H-oxepino[4,5-c]pyrazol-1-yl)-1H-pyrazol-1-yl)ethyl)piperidine-1-carboxylate

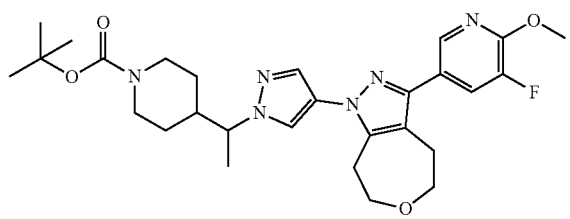 [SMILES: COc1ncc(-c2nn(-c3cnn(C(C)C4CCN(C(=O)OC(C)(C)C)CC4)c3)c3c2CCOCC3)cc1F]

To 3-(5-fluoro-6-methoxypyridin-3-yl)-1-(1H-pyrazol-4-yl)-4,5,7,8-tetrahydro-1H-oxepino[4,5-c]pyrazole (350 mg, 1.063 mmol) and potassium carbonate (441 mg, 3.19 mmol) was added a solution of tert-butyl 4-(1-((methylsulfonyl)oxy)ethyl)piperidine-1-carboxylate (490 mg, 1.594 mmol) in MeCN (7 mL). The reaction mixture was heated in a sealed tube to 100° C. overnight, then for an additional 4 h. The reaction mixture was diluted with EtOAc (100 mL) and washed with saturated aqueous NaHCO$_3$ solution (2×100 mL). The aqueous phase was extracted with EtOAc (50 mL). The combined organic extracts were dried by passing through a hydrophobic frit and the solvent was removed under reduced pressure. The crude product was purified by normal phase column chromatography on silica, eluting with 0-100% EtOAc/cyclohexane to give the title compound (374 mg).
LCMS (Method C): Rt=1.30 min, MH$^+$ 541.

Intermediate 136. 3-(6-methoxypyridin-3-yl)-1-(1-(tetrahydro-2H-pyran-2-yl)-1H-pyrazol-4-yl)-4,5,7,8-tetrahydro-1H-oxepino[4,5-c]pyrazole

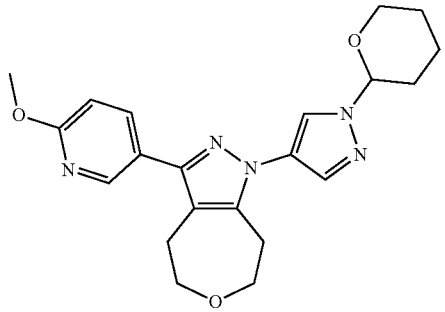 [SMILES: COc1ccc(-c2nn(-c3cnn(C4CCCCO4)c3)c3c2CCOCC3)cn1]

A mixture of 3-bromo-1-(1-(tetrahydro-2H-pyran-2-yl)-1H-pyrazol-4-yl)-4,5,7,8-tetrahydro-1H-oxepino[4,5-c]pyrazole and 3-bromo-2-(1-(tetrahydro-2H-pyran-2-yl)-1H-pyrazol-4-yl)-4,5,7,8-tetrahydro-2H-oxepino[4,5-c]pyrazole (670 mg), (6-methoxypyridin-3-yl)boronic acid (279 mg, 1.824 mmol), XPhos Pd G2 (50 mg, 0.064 mmol) and potassium phosphate (318 mg, 1.824 mmol) in EtOH (4 mL) and water (4 mL) was heated at 100° C. in a microwave. EtOAc (30 mL) and a saturated aqueous solution of NaHCO$_3$ were added (20 mL) and the organic phase was separated. The aqueous layer was extracted with further EtOAc (3×20 mL). The combined organic extracts were was dried by passing through a hydrophobic frit and the solvent was removed under reduced pressure. The crude product was purified by normal phase column chromatography on silica, eluting with 0-100% EtOAc/cyclohexane to give the title compound (356 mg).
LCMS (Method C): Rt=0.99 min, MH$^+$ 396.

Intermediate 137. 3-(6-methoxypyridin-3-yl)-1-(1H-pyrazol-4-yl)-4,5,7,8-tetrahydro-1H-oxepino[4,5-c]pyrazole

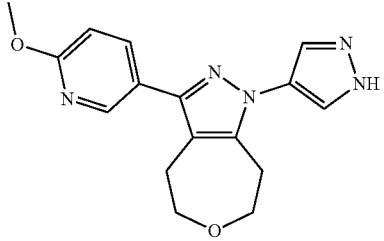 [SMILES: COc1ccc(-c2nn(-c3cn[nH]c3)c3c2CCOCC3)cn1]

A solution of 3-(6-methoxypyridin-3-yl)-1-(1-(tetrahydro-2H-pyran-2-yl)-1H-pyrazol-4-yl)-4,5,7,8-tetrahydro-1H-oxepino[4,5-c]pyrazole (360 mg, 0.910 mmol) in MeOH (6 mL) was treated with a 2 M aqueous solution of HCl (2 mL, 4.0 mmol) and stirred at room temperature under an atmosphere of nitrogen for 4 h. More 2 M aqueous solution of HCl (1 mL, 2.0 mmol) was added and stirring was continued overnight. More 2 M aqueous solution of HCl (0.5 mL, 1.0 mmol) was added and stirring was continued for 3 h. The reaction mixture was treated with a saturated aqueous NaHCO₃ solution and partitioned with EtOAc (10 mL). The organic layer was isolated and the aqueous phase was extracted with EtOAc (2×30 mL). The combined organic extracts were dried by passing through a hydrophobic frit and concentrated under reduced pressure to afford the title compound (287 mg).

LCMS (Method C) Rt=0.77 min, MH⁺=312.

Intermediate 138. tert-Butyl 4-(1-(4-(3-(6-methoxy-pyridin-3-yl)-4,5,7,8-tetrahydro-1H-oxepino[4,5-c]pyrazol-1-yl)-1H-pyrazol-1-yl)ethyl)piperidine-1-carboxylate

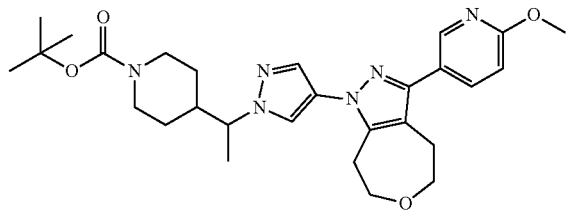 [SMILES: COc1ccc(-c2nn(-c3cnn(C(C)C4CCN(C(=O)OC(C)(C)C)CC4)c3)c3c2CCOCC3)cn1]

Potassium carbonate (381 mg, 2.76 mmol) was added to 3-(6-methoxypyridin-3-yl)-1-(1H-pyrazol-4-yl)-4,5,7,8-tetrahydro-1H-oxepino[4,5-c]pyrazole (286 mg, 0.919 mmol) in MeCN (5 mL) and the reaction mixture was stirred at 100° C. for 1 h. tert-Butyl 4-(1-((methylsulfonyl)oxy)ethyl)piperidine-1-carboxylate (282 mg, 0.919 mmol) was added and string was continued over the weekend. More potassium carbonate (137 mg, 0.92 mmol) was added and stirring was continued at 100° C. for 2 h. The solvent was removed under reduced pressure and the residue was taken up in EtOAc. This was partitioned with saturated aqueous NaHCO₃ solution and the aqueous phase was extracted with EtOAc (3×30 mL). The combined organic phases were passed through a hydrophobic frit and the solvent removed under reduced pressure. The crude product was purified by normal phase column chromatography on silica, eluting with 0-100% 3:1 EtOH:EtOAc(+1% NEt₃)/cyclohexane to give the title compound (248 mg).

LCMS (Method C): Rt=1.22 min, MH⁺ 523.

Intermediate 139. tert-Butyl 4-(1-(4-(1-(6-methoxy-5-methylpyridin-3-yl)-4,5,7,8-tetrahydro-1H-oxepino[4,5-c]pyrazol-3-yl)-1H-pyrazol-1-yl)ethyl)piperidine-1-carboxylate

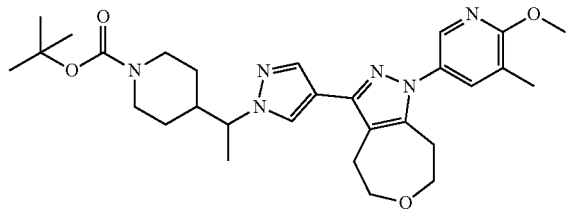 [SMILES: COc1ncc(-n2nc(-c3cnn(C(C)C4CCN(C(=O)OC(C)(C)C)CC4)c3)c3c2CCOCC3)cc1C]

To a solution of 1-(6-methoxy-5-methylpyridin-3-yl)-3-(1H-pyrazol-4-yl)-4,5,7,8-tetrahydro-1H-oxepino[4,5-c]pyrazole (75 mg, 0.231 mmol) and potassium carbonate (63.7 mg, 0.461 mmol) in DMF (0.5 mL) was added tert-butyl 4-(1-((methylsulfonyl)oxy)ethyl)piperidine-1-carboxylate (106 mg, 0.346 mmol) in DMF (0.5 mL) at 0° C. under an atmosphere of nitrogen. The reaction mixture was slowly allowed to warm to room temperature and stirring was continued for 17 h. The reaction mixture was heated to 80° C. stirred for 5 h, then heated to 100° C. and left to stir for 24 h. Further tert-butyl 4-(1-((methylsulfonyl)oxy)ethyl)piperidine-1-carboxylate (106 mg, 0.346 mmol) was added and the reaction mixture was heated to 100° C. for 18 h. The reaction was repeated on 75 mg scale and the combined reaction mixtures were diluted with 5% aqueous LiCl solution (10 mL) and extracted with ethyl acetate (25 mL). The aqueous phase was extracted further with ethyl acetate (2×50 mL). The combined organic extracts were passed through a hydrophobic frit and the solvent removed under reduced pressure. The crude product was purified by normal phase column chromatography on silica, eluting with 0-100% EtOAc/cyclohexane to give the title compound (130 mg).

LCMS (Method C): Rt=1.29 min, MH⁺ 537.

Intermediate 140. 1-(6-methoxy-5-methylpyridin-3-yl)-3-(1-(1-(piperidin-4-yl)ethyl)-1H-pyrazol-4-yl)-4,5,7,8-tetrahydro-1H-oxepino[4,5-c]pyrazole

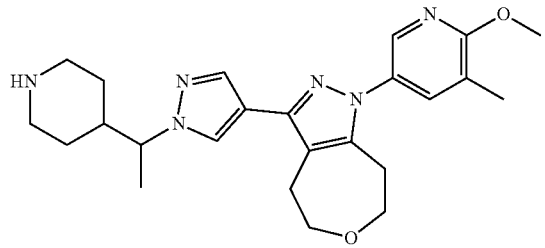 [SMILES: COc1ncc(-n2nc(-c3cnn(C(C)C4CCNCC4)c3)c3c2CCOCC3)cc1C]

tert-Butyl 4-(1-(4-(1-(6-methoxy-5-methylpyridin-3-yl)-4,5,7,8-tetrahydro-1H-oxepino[4,5-c]pyrazol-3-yl)-1H-pyrazol-1-yl)ethyl)piperidine-1-carboxylate (130 mg, 0.242 mmol) was dissolved in DCM (2 mL) and trifluoroacetic acid (0.746 mL, 9.69 mmol) was added. The reaction mixture stirred at room temperature for 1 h. Saturated aqueous NaHCO₃ solution was added dropwise to the reaction mixture until the solution had reached pH 8. The product was extracted with DCM (2×50 mL) and the combined organic extracts were passed through a hydrophobic frit and concentrated under reduced pressure to afford the crude title compound (50 mg). The material was used directly in the next step.

Intermediate 141. 1-(6-methoxypyridin-3-yl)-3-(1H-pyrazol-4-yl)-4,5,7,8-tetrahydro-1H-oxepino[4,5-c]pyrazole

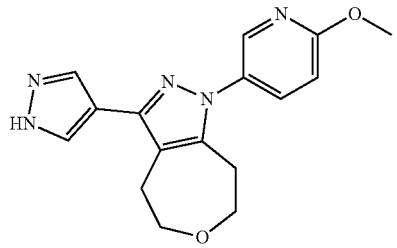 [SMILES: COc1ccc(-n2nc(-c3cn[nH]c3)c3c2CCOCC3)cn1]

3-bromo-1-(6-methoxypyridin-3-yl)-4,5,7,8-tetrahydro-1H-oxepino[4,5-c]pyrazole (4.53 g, 13.97 mmol), 4-(4,4,5,5-tetramethyl-1,3,2-dioxaborolan-2-yl)-1H-pyrazole (3.90 g, 20.10 mmol), potassium phosphate tribasic (7.40 g, 42.5 mmol), XPhos Pd G2 (0.770 g, 0.978 mmol), XPhos (0.466 g, 0.978 mmol), EtOH (15 mL) and water (15 mL) were split between two microwave vials. The vials were sealed and flushed with nitrogen then heated for an initial 60 minutes at 100° C. using a microwave, followed by another 60 minutes at 100° C. using a microwave. The reaction mixtures were filtered through Celite®, washing with EtOAc. The filtrate was concentrated under reduced pressure and the residue was taken up in EtOAc (300 mL). The organic phase was extracted with 2M aqueous HCl (2×300 mL). The aqueous phase was basified to ~pH 12 using sodium hydroxide pellets, cooling the flask in an ice bath. The resulting solid was isolated by vacuum filtration and washed with several portions of water, then dried in the vacuum oven at 40° C. over the weekend to afford the title compound (2.97 g).

LCMS (Method C): Rt=0.76 min, MH⁺ 312.

Intermediate 142. tert-butyl (R)-4-(1-(4-(1-(6-methoxypyridin-3-yl)-4,5,7,8-tetrahydro-1H-oxepino[4,5-c]pyrazol-3-yl)-1H-pyrazol-1-yl)ethyl)piperidine-1-carboxylate

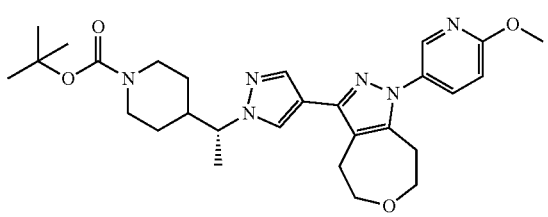 [SMILES: COc1ccc(-n2nc(-c3cnn([C@H](C)C4CCN(C(=O)OC(C)(C)C)CC4)c3)c3c2CCOCC3)cn1]

A solution of tert-butyl (S)-4-(1-((methylsulfonyl)oxy)ethyl)piperidine-1-carboxylate (4.40 g, 14.31 mmol) in DMF (20 mL) was added to flask containing 1-(6-methoxypyridin-3-yl)-3-(1H-pyrazol-4-yl)-4,5,7,8-tetrahydro-1H-oxepino[4,5-c]pyrazole (2.97 g, 9.54 mmol) and cesium carbonate (9.32 g, 28.6 mmol) in DMF (30 mL). The mixture was stirred at 60° C. for 3 h under an atmosphere of nitrogen. The reaction mixture was cooled to room temperature and left to stand overnight. EtOAc (100 mL) was added and the organic phase was washed with saturated aqueous ammonium chloride solution (100 mL). The aqueous phase was extracted with EtOAc (2×100 mL). The combined organic extracts were washed with 5% aqueous LiCl solution (5×20 mL) then dried by passing through a hydrophobic frit. The solvent was removed under reduced pressure. The crude material was purified by reverse phase chromatography using a C18 silica column and a 30 to 75% gradient of MeCN/10 mM ammonium bicarbonate in water. The product-containing fractions were left to stand overnight then combined and the MeCN removed under reduced pressure. The aqueous phase was extracted with EtOAc (3×100 mL). The combined organic extracts were dried by passing through a hydrophobic frit and concentrated under reduced pressure, then the residue was dried on a high vacuum line for 3 h to afford the title compound (3.92 g).

LCMS (Method C): Rt=1.23 min, MH⁺ 523.

Intermediate 143. (R)-1-(6-methoxypyridin-3-yl)-3-(1-(1-(piperidin-4-yl)ethyl)-1H-pyrazol-4-yl)-4,5,7,8-tetrahydro-1H-oxepino[4,5-c]pyrazole

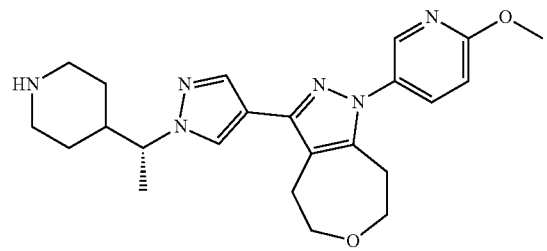 [SMILES: COc1ccc(-n2nc(-c3cnn([C@H](C)C4CCNCC4)c3)c3c2CCOCC3)cn1]

TFA (5 mL, 64.9 mmol) was added to a solution of tert-butyl (R)-4-(1-(4-(1-(6-methoxypyridin-3-yl)-4,5,7,8-tetrahydro-1H-oxepino[4,5-c]pyrazol-3-yl)-1H-pyrazol-1-yl)ethyl)piperidine-1-carboxylate (3.90 g, 7.46 mmol) in DCM (30 mL) and the reaction mixture was stirred overnight at room temperature. The reaction mixture was quenched by slow addition of saturated aqueous NaHCO₃ solution (60 mL) and the mixture was stirred for 15 min until effervescence ceased. The organic phase was isolated and the aqueous phase extracted with further DCM (2×60 mL). The combined organic extracts were passed through a hydrophobic frit and the solvent removed under reduced pressure to afford the title compound (3.69 g).

LCMS (Method C): Rt=0.91 min, MH⁺ 423.

Intermediate 144. 1-(4-(3-bromo-4,5,7,8-tetrahydro-1H-oxepino[4,5-c]pyrazol-1-yl)pyridin-2-yl)ethan-1-one

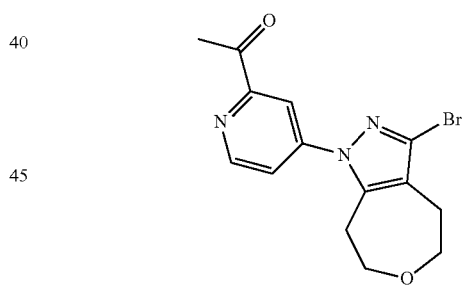

A microwave vial was charged with 3-bromo-4,5,7,8-tetrahydro-1H-oxepino[4,5-c]pyrazole (1 g, 4.61 mmol), 1-(4-chloropyridin-2-yl)ethan-1-one (0.986 g, 5.07 mmol), cesium carbonate (2.55 g, 7.83 mmol) and NMP (5 ml) and the mixture was put under an atmosphere of nitrogen then heated at 100° C. for 2 h in a microwave. The reaction mixture was partitioned between water (100 mL) and EtOAc (100 mL) and the organic phase was isolated. The aqueous phase was extracted with EtOAc (2×100 mL) and the combined organic extracts were dried by passing through a hydrophobic frit then concentrated under reduced pressure. The crude material was purified by reverse phase column chromatography using a C18 column, eluting with a 0 to 40% gradient of MeCN(+0.1% formic acid) in water(+0.1% formic acid) to give the title compound (220 mg).

LCMS (Method A): Rt=1.01 min, MH⁺ 336/338.

Intermediate 145. 3-bromo-1-(2-(1-(4-methylpiperazin-1-yl)ethyl)pyridin-4-yl)-4,5,7,8-tetrahydro-1H-oxepino[4,5-c]pyrazole

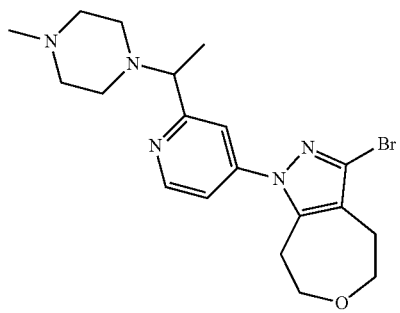 [SMILES: CC(c1cc(-n2nc(Br)c3c2CCOCC3)ccn1)N1CCN(C)CC1]

A stirred solution of 1-(4-(3-bromo-4,5,7,8-tetrahydro-1H-oxepino[4,5-c]pyrazol-1-yl)pyridin-2-yl)ethan-1-one (220 mg, 0.524 mmol), titanium(IV) isopropoxide (0.184 mL, 0.628 mmol), acetic acid (0.060 mL, 1.047 mmol) and 1-methylpiperazine (0.087 mL, 0.785 mmol) in 2-MeTHF (5 mL) in a microwave vial was sealed and stirred under nitrogen for 4 h. Sodium triacetoxyborohydride (222 mg, 1.047 mmol) was added to the reaction mixture and the vial was sealed, evacuated and refilled with nitrogen and heated for 1 hour at 100° C. in a microwave. Water (2.5 mL) was added and the mixture was left to stand overnight. The reaction mixture was filtered through a 10 g Celite® cartridge that had been preconditioned with EtOAc. The column was eluted with EtOAc (~200 mL) and the eluent was concentrated under reduced pressure. The residue was partitioned with EtOAc (50 mL) and water (50 mL), then treated with saturated aqueous NaHCO$_3$ solution (5 mL). The organic phase was isolated and the aqueous phase was extracted with EtOAc (2×50 mL). The combined organic extracts were dried by passing through a hydrophobic frit and concentrated under reduced pressure to give the crude title compound (326 mg). The material was used directly in the next step.

Example 1. 1-(1-(((2R,4r,6S)-2,6-Dimethylpiperidin-4-yl)methyl)-1H-pyrazol-4-yl)-3-(5-fluoro-6-methoxypyridin-3-yl)-4,5,7,8-tetrahydro-1H-oxepino[4,5-c]pyrazole

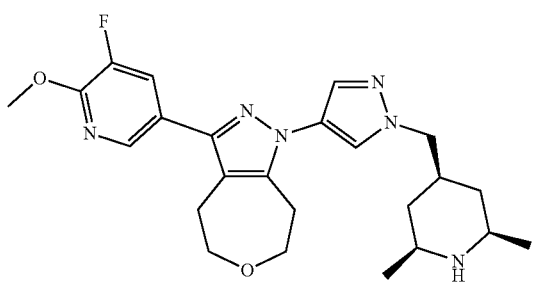

Prepared using the general Boc-deprotection procedure from (2R,4r,6S)-tert-butyl 4-((4-(3-(5-fluoro-6-methoxypyridin-3-yl)-4,5,7,8-tetrahydro-1H-oxepino[4,5-c]pyrazol-1-yl)-1H-pyrazol-1-yl)methyl)-2,6-dimethylpiperidine-1-carboxylate (85 mg, 0.153 mmol), DCM (1 mL) and TFA (0.472 mL), except the reaction was complete after stirring at room temperature for 2 h. The title compound was isolated as a pale yellow oil (76 mg).

LCMS (Method C): Rt=1.02 min, MH$^+$ 455.

Example 2. 3-(1-(((2R,4r,6S)-2,6-Dimethylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole

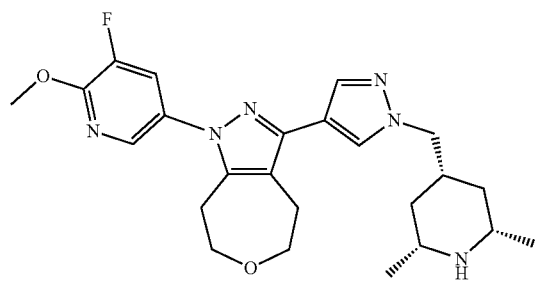

Prepared using the general Boc deprotection procedure from (2R,4r,6S)-tert-butyl 4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)-2,6-dimethylpiperidine-1-carboxylate (280 mg, 0.505 mol), DCM (3 mL) and TFA (1.556 mL) to give the title compound (57 mg) as a yellow oil after purification by MDAP (Method A).

LCMS (Method C): Rt=1.00 min, MH$^+$=455.

Example 3. N-(2-methoxy-5-(3-(1-methyl-1H-pyrazol-4-yl)-4,5,7,8-tetrahydro-1H-oxepino[4,5-c]pyrazol-1-yl)pyridin-3-yl)methanesulfonamide

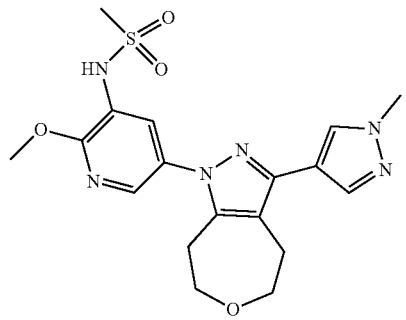

Copper (II) acetate (30 mg, 0.165 mmol) was added to a solution of 3-(1-methyl-1H-pyrazol-4-yl)-4,5,7,8-tetrahydro-1H-oxepino[4,5-c]pyrazole (36 mg, 0.165 mmol), N-(2-methoxy-5-(4,4,5,5-tetramethyl-1,3,2-dioxaborolan-2-yl)pyridin-3-yl)methanesulfonamide (81 mg, 0.248 mmol) and DMAP (40 mg, 0.330 mmol) in dry MeCN (1.5 ml). The reaction mixture was stirred at 50° C. for 15 h open to air. The reaction mixture was treated with a 5% by weight solution of EDTA in water (10 mL) and partitioned with EtOAc (25 ml). The organic layer was isolated and the aqueous layer reextacted with EtOAc (2×25 mL). The combined organic layer was dried, concentrated and purified by MDAP (Method B) to give the title compound (13 mg, 19%).

LCMS (Method A): Rt=0.74 min, MH$^+$ 419.

Example 4. 1-(6-Methoxy-5-methylpyridin-3-yl)-3-(1-methyl-1H-pyrazol-4-yl)-4,5,7,8-tetrahydro-1H-oxepino[4,5-c]pyrazole

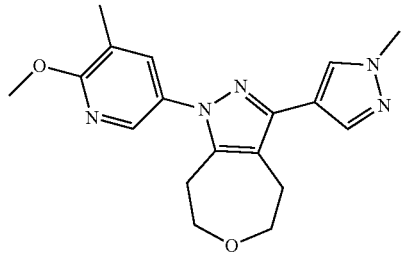

A mixture of 3-(1-methyl-1H-pyrazol-4-yl)-4,5,7,8-tetrahydro-1H-oxepino[4,5-c]pyrazole (50 mg, 0.229 mmol), (6-methoxy-5-methylpyridin-3-yl)boronic acid (38.3 mg, 0.229 mmol), CuOAc (41.6 mg, 0.229 mmol) and DMAP (56 mg, 0.458 mmol) in MeCN (1.5 mL) was heated with stirring at 50° C. for 15 h open to the air. The reaction mixture was treated with a 5% solution of EDTA in water (20 mL) then extracted with EtOAc (3×50 mL), concentrated and purified by MDAP (Method A) to give the title compound (22 mg, 28%).

LCMS (Method A): Rt=0.92 min, MH+ 340.

Example 5. N-(2-Methoxy-5-(1-(1-methyl-1H-pyrazol-4-yl)-4,5,7,8-tetrahydro-1H-oxepino[4,5-c]pyrazol-3-yl)pyridin-3-yl)methanesulfonamide

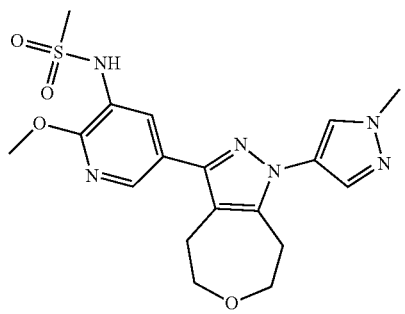

A mixture of N-(2-methoxy-5-(4,4,5,5-tetramethyl-1,3,2-dioxaborolan-2-yl)pyridin-3-yl)methanesulfonamide (13 mg, 0.040 mmol), 3-bromo-1-(1-methyl-1H-pyrazol-4-yl)-4,5,7,8-tetrahydro-1H-oxepino[4,5-c]pyrazole (10 mg, 0.034 mmol), chloro-[2'-(dimethylamino)-2-biphenylyl]-(dinorbornylphosphine)-palladium (2 mg, 3.57 µmol) and tripotassium phosphate (22 mg, 0.104 mmol) were combined in a mixture of dioxane (0.5 mL) and water (0.1 mL). The reaction mixture was heated using a microwave at 100° C. for 60 min.

The reaction mixture was passed through a silica cartridge (1 g), eluting with MeOH, and then purified by MDAP (Method A) to give the title compound (8 mg, 57%).

LCMS (Method A): Rt=0.57 min, MH+ 419.

Example 6. 1-(2-Methoxypyrimidin-5-yl)-3-(1-((1-methylpiperidin-4-yl)methyl)-1H-pyrazol-4-yl)-4,5,7,8-tetrahydro-1H-oxepino[4,5-c]pyrazole. Formate Salt

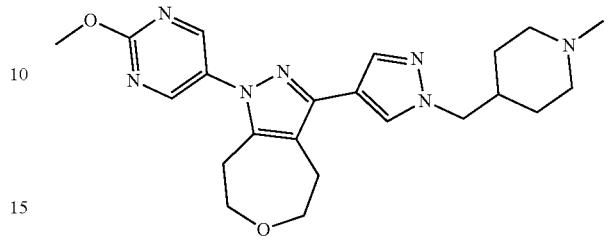

A mixture of 1-(2-methoxypyrimidin-5-yl)-3-(1-(piperidin-4-ylmethyl)-1H-pyrazol-4-yl)-4,5,7,8-tetrahydro-1H-oxepino[4,5-c]pyrazole compound and 2-(2-methoxypyrimidin-5-yl)-3-(1-(piperidin-4-ylmethyl)-1H-pyrazol-4-yl)-4,5,7,8-tetrahydro-2H-oxepino[4,5-c]pyrazole (82 mg) was dissolved in DMF (1 mL) and treated with a 37% by weight aqueous solution of formaldehyde (0.075 mL, 1.001 mmol). The reaction mixture was stirred at room temperature for 1 h under an atmosphere of nitrogen then treated with sodium triacetoxyborohydride (42.4 mg, 0.200 mmol). The reaction mixture was stirred under nitrogen for 3 h.

The reaction mixture was treated with a saturated aqueous solution of sodium bicarbonate (5 mL), water (5 mL) and EtOAc (5 mL). The organic layer was isolated and the aqueous layer re-extracted with EtOAc (2×5 mL). The organic layer was isolated and the combined organic layer was washed with brine (5 mL) then a 5% by weight aqueous solution of LiCl (2×5 mL) and passed through a hydrophobic frit. The organic layer was concentrated under reduced pressure to give crude product which was purified by MDAP (Method B) to give the title compound (32 mg, 68%).

LCMS (Method C): Rt=0.46 min, MH+ 424.

$^1$H NMR (400 MHz, CDCl$_3$) δ-ppm 8.45 (s, 2H), 8.39 (br. s, 1H), 7.35 (s, 1H), 7.22 (s, 1H), 4.09-3.97 (m, 5H), 3.93 (t, J=5 Hz, 2H), 3.84 (t, J=5 Hz, 2H), 3.47-3.33 (m, 2H), 3.05 (t, J=5 Hz, 2H), 2.71 (t, J=5 Hz, 2H), 2.62 (s, 3H), 2.47 (t, J=11 Hz, 2H), 2.21-2.05 (m, 1H), 1.81-1.55 (m, 4H).

Example 7. 3-(1-((1-Isopropylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole

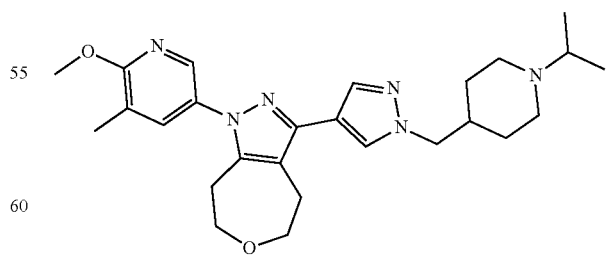

An oven dried round-bottomed flask was charged with 1-(6-methoxy-5-methylpyridin-3-yl)-3-(1-(piperidin-4-ylmethyl)-1H-pyrazol-4-yl)-4,5,7,8-tetrahydro-1H-oxepino[4,5-c]pyrazole (263 mg, 0.498 mmol) in DMF (1.5 mL). The reaction mixture was treated with acetone (2 mL) and stirred under an atmosphere of nitrogen for 45 min. The reaction mixture was treated with STAB (211 mg, 0.996 mmol) and stirred overnight. The reaction mixture was partitioned between a saturated solution of aqueous sodium bicarbonate (5 mL) and extracted with EtOAc (3×10 mL). The combined organic layer was washed with an aqueous solution of LiCl. The organic layer was concentrated under reduced pressure and crude product purified by MDAP (Method A) to give the title compound (107 mg, 45%).

LCMS (Method C): Rt=1.07 min, MH$^+$ 465.

$^1$H NMR (400 MHz, CDCl$_3$) 8.00 (d, J=2 Hz, 1H), 7.75 (s, 1H), 7.64 (s, 1H), 7.52 (d, J=2 Hz, 1H), 4.03-3.96 (m, 5H), 3.91 (t, J=5 Hz, 2H), 3.84 (t, J=5 Hz, 2H), 2.97-2.82 (m, 6H), 2.75-2.65 (m, 1H), 2.24 (s, 3H), 2.10 (t, J=10 Hz, 2H), 2.01-1.85 (m, 1H), 1.67-1.58 (m, 2H), 1.41-1.21 (m, 2H), 1.03 (s, 3H), 1.01 (s, 3H).

Example 8. 3-(1-((1-Isopropylpiperidin-3-yl)methyl)-1H-pyrazol-4-yl)-1-(6-methoxy-5-methylpyridin-3-yl)-4,5,7,8-tetrahydro-1H-oxepino[4,5-c]pyrazole

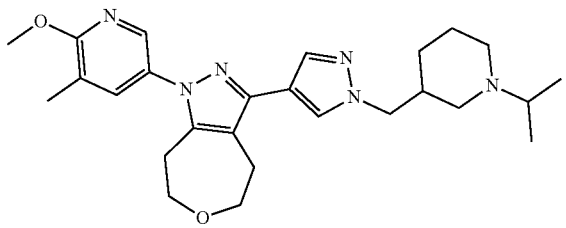 [SMILES: COc1ncc(-n2nc(-c3cnn(CC4CCCN(C(C)C)C4)c3)c3c2CCOCC3)cc1C]

A solution of 1-(6-methoxy-5-methylpyridin-3-yl)-3-(1-(piperidin-3-ylmethyl)-1H-pyrazol-4-yl)-4,5,7,8-tetrahydro-1H-oxepino[4,5-c]pyrazole (72 mg, 0.102 mmol) was dissolved in acetone (0.5 ml) and stirred at room temperature under an atmosphere of nitrogen for 1 h. The reaction mixture was carefully treated with sodium triacetoxyborohydride (43 mg, 0.204 mmol) and stirred overnight.

The reaction mixture was treated with an aqueous solution of sodium bicarbonate (1 mL) and stirred vigorously for 30 min. The reaction mixture was partitioned with sodium bicarbonate (5 mL) and EtOAc (10 mL). The organic layer was isolated and the aqueous layer re-extracted with EtOAc (2×10 mL). The combined organic layer was washed with a 5% by weight solution of LiCl then passed through a hydrophobic frit and concentrated under reduced pressure. An initial attempt to purify the crude product by MDAP led to the product being collected in the MDAP waste. The waste was evaporated to dryness then purified by MDAP (Method A) to give the title compound (17 mg, 34%).

LCMS (Method C): Rt=1.18 min, MH$^+$ 465.

$^1$H NMR (400 MHz, CDCl$_3$) δ-ppm 8.00 (d, J=2 Hz, 1H), 7.78 (s, 1H), 7.74 (br. s, 1H), 7.52 (d, J=2 Hz, 1H), 4.29-4.19 (m, 2H), 4.00 (s, 3H), 3.91 (t, J=5 Hz, 2H), 3.84 (t, J=5 Hz, 2H), 3.44-3.33 (m, 1H), 3.33-3.22 (m, 1H), 3.10-2.97 (m, 1H), 2.92 (t, J=5 Hz, 4H), 2.66 (t, J=12 Hz, 1H), 2.62-2.32 (m, 4H), 2.24 (s, 3H), 1.98-1.83 (m, 2H), 1.40 (d, J=7 Hz, 3H), 1.37 (d, J=7 Hz, 3H).

Example 9. 1-(6-Methoxy-5-methylpyridin-3-yl)-3-(1-((1-methylpiperidin-4-yl)methyl)-1H-pyrazol-4-yl)-4,5,7,8-tetrahydro-1H-oxepino[4,5-c]pyrazole

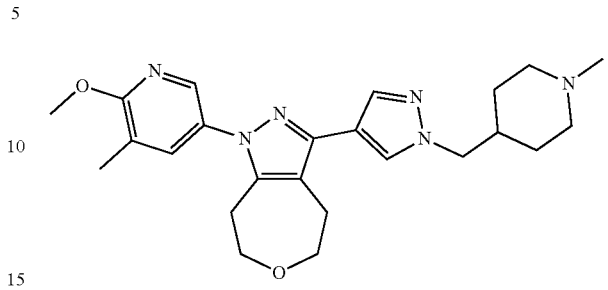

A solution of 1-(6-methoxy-5-methylpyridin-3-yl)-3-(1-(piperidin-4-ylmethyl)-1H-pyrazol-4-yl)-4,5,7,8-tetrahydro-1H-oxepino[4,5-c]pyrazole (200 mg, 0.284 mmol) in DMF (2 mL) was treated with a 37% by weight aqueous solution of formaldehyde (0.211 mL, 2.84 mmol). The reaction mixture was stirred at room temperature for 1 h under an atmosphere of nitrogen. The reaction mixture was treated with STAB (120 mg, 0.568 mmol) and stirred for 3 h. The reaction was quenched with an aqueous solution of sodium bicarbonate (1 mL) and left to stir for 30 min. The reaction mixture was partioned with more sodium bicarbonate solution (5 mL) and EtOAc (15 mL). The mixture was extracted with EtOAc (2×15 mL) and the combined organic layer was washed with a 5% solution of LiCl (3×15 mL). The organic layer was passed through a hydrophobic frit and concentrated under reduced pressure to give the crude product. The crude product was purified by MDAP (Method A) to give the title compound (39.8 mg, 32%).

LCMS (Method C): Rt=1.08 min, MH$^+$ 437.

$^1$H NMR (400 MHz, CDCl$_3$) δ-ppm 8.00 (d, J=2 Hz, 1H), 7.75 (s, 1H), 7.65 (s, 1H), 7.52 (d, J=2 Hz, 1H), 4.08-3.96 (m, 5H), 3.91 (t, J=5 Hz, 2H), 3.84 (t, J=5 Hz, 2H), 2.98-2.88 (m, 4H), 2.84 (d, J=12 Hz, 2H), 2.25 (s, 3H), 2.24 (s, 3H), 2.00-1.83 (m, 3H), 1.67-1.56 (m, 2H, partially obscured by residual water peak), 1.43-1.27 (1 m, 2H).

Example 10. 1-(5-Fluoro-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole

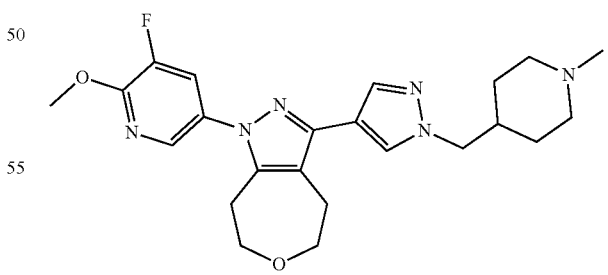

A solution of 1-(5-fluoro-6-methoxypyridin-3-yl)-3-(1-(piperidin-4-ylmethyl)-1H-pyrazol-4-yl)-4,5,7,8-tetrahydro-1H-oxepino[4,5-c]pyrazole (45 mg, 0.106 mmol) in DMF (1 mL) was treated with a 37% by weight aqueous solution of formaldehyde (0.15 mL, 2.015 mmol) and stirred at room temperature for 30 min. The reaction mixture was treated with STAB (90 mg, 0.425 mmol) and stirred at room temperature overnight. The reaction mixture was treated with a saturated aqueous solution of sodium bicarbonate (10 mL) and extracted with EtOAc (3×10 mL). The organic layer was extracted with a solution of LiCl (2×15 mL). The organic layer was concentrated under reduced pressure to give the crude product (46 mg). The crude product was purified by MDAP (Method A) to give the title compound as a white solid (26 mg, 53%).

LCMS (Method C): Rt=0.96 min, MH+ 441.

$^1$H NMR (400 MHz, CDCl$_3$) δ-ppm 7.99 (d, J=2 Hz, 1H), 7.76 (s, 1H), 7.66 (s, 1H), 7.53 (dd, J=10, 2 Hz, 1H), 4.08 (s, 3H), 4.04 (d, J=7 Hz, 2H), 3.92 (t, J=5 Hz, 2H), 3.87 (t, J=5 Hz, 2H), 3.00-2.84 (m, 6H), 2.38-2.27 (m, 2H), 2.07-1.89 (m, 4H), 1.69-1.60 (m, 2H), 1.55-1.34 (m, 2H).

Example 11. 1-(5-Fluoro-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole

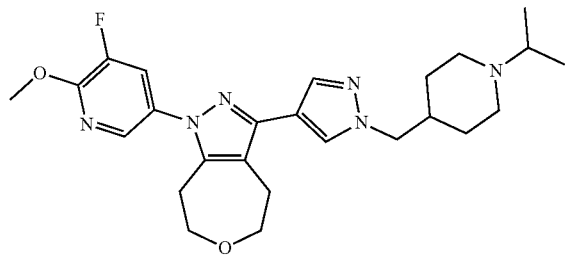 [SMILES: COc1ncc(-n2nc(-c3cnn(CC4CCN(C(C)C)CC4)c3)c3c2CCOCC3)cc1F]

A solution of 1-(5-fluoro-6-methoxypyridin-3-yl)-3-(1-(piperidin-4-ylmethyl)-1H-pyrazol-4-yl)-4,5,7,8-tetrahydro-1H-oxepino[4,5-c]pyrazole (86 mg, 0.201 mmol) and DIPEA (35 µL) in DMF (0.5 mL) was treated with acetone (1.5 mL). The reaction mixture was stirred at room temperature for 1 h then treated with STAB (0.210 g, 0.991 mmol) and stirred at room temperature for 14 h. The reaction mixture was treated with a saturated aqueous solution of sodium bicarbonate (10 mL).

Separately a solution of 1-(5-fluoro-6-methoxypyridin-3-yl)-3-(1-(piperidin-4-ylmethyl)-1H-pyrazol-4-yl)-4,5,7,8-tetrahydro-1H-oxepino[4,5-c]pyrazole (86 mg, 0.201 mmol) in DMF (0.5 mL) was treated with acetone (1.6 mL). The reaction mixture was stirred at room temperature for 1 h then treated with STAB (0.210 g, 0.991 mmol) and stirred at room temperature for 15 h. The reaction mixture was treated with a saturated aqueous solution of sodium bicarbonate (10 mL).

The two batches of quenched reaction mixtures were combined and extracted with EtOAc (3×25 mL). The combined organic layer was washed with a 5% solution of LiCl (3×25 mL), passed through a hydrophobic frit and concentrated under reduced pressure to give crude product (160 mg). The crude product was purified by MDAP (Method A) to give the title compound as a white solid (51 mg, 52%).

LCMS (Method C): Rt=1.07 min, MH+ 469.

$^1$H NMR (400 MHz, CDCl$_3$) δ-ppm 7.98 (d, J=2 Hz, 1H), 7.77 (s, 1H), 7.65 (s, 1H), 7.53 (dd, J=10, 2 Hz, 1H), 4.08 (s, 3H), 4.04 (d, J=7 Hz, 2H), 3.92 (t, J=5 Hz, 2H), 3.86 (t, J=5 Hz, 2H), 3.20-2.88 (m, 7H), 2.49-2.24 (m, 3H), 2.16-1.99 (m, 1H), 1.79-1.42 (m, 4H), 1.15 (d, J=6 Hz, 6H).

Example 12. N-(2-Methoxy-5-(3-(1-((1-methylpiperidin-4-yl)methyl)-1H-pyrazol-4-yl)-4,5,7,8-tetrahydro-1H-oxepino[4,5-c]pyrazol-1-yl)pyridin-3-yl)methanesulfonamide

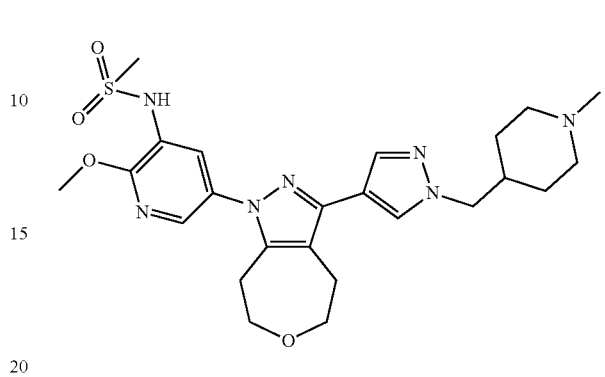

A solution of N-(2-methoxy-5-(3-(1-(piperidin-4-ylmethyl)-1H-pyrazol-4-yl)-4,5,7,8-tetrahydro-1H-oxepino[4,5-c]pyrazol-1-yl)pyridin-3-yl)methanesulfonamide (84 mg, 0.167 mmol) in DMF (1.5 mL) was treated with formaldehyde (37% by weight aqueous solution 0.250 mL, 0.167 mmol) and stirred under an atmosphere of nitrogen at room temperature for 30 min. The reaction mixture was treated with STAB (150 mg, 0.708 mmol) and stirred at room temperature for 2 h. The reaction mixture was quenched with a saturated aqueous solution of sodium bicarbonate (5 mL) and extracted with EtOAc (3×20 mL). The aqueous layer was passed through an Isolute 103 cartridge which was washed with water then MeOH. The MeOH washings were combined with the EtOAc layer and concentrated under reduced pressure to give crude product as a brown gum (50 mg). The crude product was purified by MDAP (Method B) to give the title compound as a colourless gum (9.5 mg, 10%).

LCMS (Method C): Rt=0.55 min, MH+ 516.

$^1$H NMR (400 MHz, CDCl$_3$) δ-ppm 8.38 (br. s, 1H), 7.98 (d, J=2 Hz, 1H), 7.87 (d, J=2 Hz, 1H), 7.78 (s, 1H), 7.67 (s, 1H), 4.12-4.02 (m, 5H), 3.91 (t, J=5 Hz, 2H), 3.85 (t, J=5 Hz, 2H), 3.48 (d, J=12 Hz, 2H), 3.09 (s, 3H), 2.98-2.88 (m, 4H), 2.68 (s, 3H), 2.63-2.52 (m, 2H), 2.30-2.16 (m, 1H), 1.93-1.70 (m, 4H).

Example 13. 2-Methoxy-5-(3-(1-((1-methylpiperidin-4-yl)methyl)-1H-pyrazol-4-yl)-4,5,7,8-tetrahydro-1H-oxepino[4,5-c]pyrazol-1-yl)nicotinonitrile

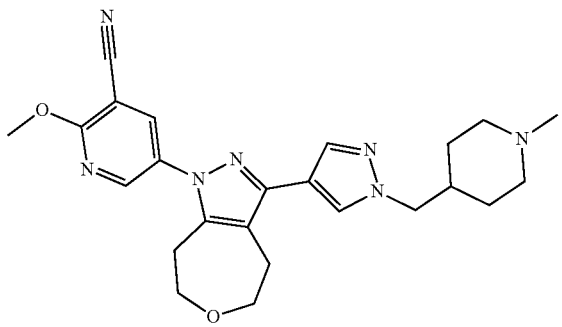

A solution of 2-methoxy-5-(3-(1-(piperidin-4-ylmethyl)-1H-pyrazol-4-yl)-4,5,7,8-tetrahydro-1H-oxepino[4,5-c]pyrazol-1-yl)nicotinonitrile (47 mg, 0.108 mmol) in DMF (1 mL) was treated with a 37% by weight aqueous solution of formaldehyde (0.18 mL, 2.287 mmol) and stirred under an atmosphere of nitrogen at room temperature for 30 min. The reaction mixture was treated with STAB (92 mg, 0.434 mmol) and stirred at room temperature for 3 h. The reaction mixture was quenched with a saturated aqueous solution of sodium bicarbonate (10 mL) and extracted with EtOAc (3×15 mL). The organic layer was washed with a solution of LiCl (20 mL), passed through a hydrophobic frit then concentrated under reduced pressure. The aqueous phase was passed through an Isolute 103 cartridge (5 g), which was washed with water then MeOH. The residue from the MeOH wash was combined with that obtained from the organic layer and purified by MDAP (Method A) to give the title compound as a white solid (16 mg, 31%).

LCMS (Method C): Rt=0.96 min, MH$^+$ 448.

$^1$H NMR (400 MHz, CDCl$_3$) δ-ppm 8.45 (d, J=2 Hz, 1H), 8.02 (d, J=2 Hz, 1H), 7.75 (s, 1H), 7.62 (s, 1H), 4.12 (s, 3H), 4.05 (d, J=7 Hz, 2H), 3.92 (t, J=5 Hz, 2H), 3.87 (t, J=5 Hz, 2H), 2.98-2.86 (m, 6H), 2.29 (s, 3H), 1.96 (td, J=12, 3 Hz, 3H), 1.67-1.59 (m, 2H), 1.47-1.34 (m, 2H).

Example 14. 5-(3-(1-((1-Isopropylpiperidin-4-yl)methyl)-1H-pyrazol-4-yl)-4,5,7,8-tetrahydro-1H-oxepino[4,5-c]pyrazol-1-yl)-2-methoxynicotinonitrile

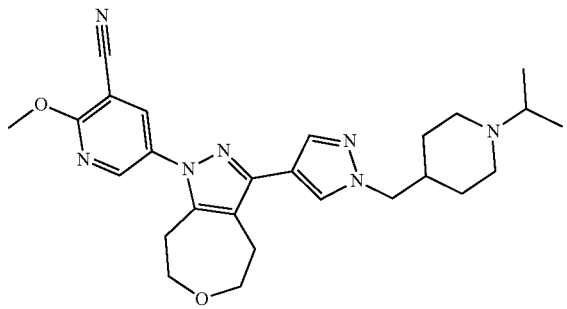 [SMILES: COc1ncc(-n2nc(-c3cnn(CC4CCN(C(C)C)CC4)c3)c3c2CCOCC3)cc1C#N]

A mixture of CuOAc (308 mg, 1.696 mmol), 3-(1-(4-methoxybenzyl)-1H-pyrazol-4-yl)-4,5,7,8-tetrahydro-1H-oxepino[4,5-c]pyrazole (550 mg, 1.696 mmol), 2-methoxy-5-(4,4,5,5-tetramethyl-1,3,2-dioxaborolan-2-yl)nicotinonitrile (463 mg, 1.780 mmol) and DMAP (414 mg, 3.39 mmol) in MeCN (14 mL) was stirred at room temperature overnight. The reaction mixture was heated open to the air at 40° C. for 7 h then overnight. A small amount of solvent was added, followed by EtOH (2 mL). The reaction was heated for 5 h then overnight. The reaction mixture was left over the weekend at room temperature. The reaction mixture was treated with 2-methoxy-5-(4,4,5,5-tetramethyl-1,3,2-dioxaborolan-2-yl)nicotinonitrile (463 mg, 1.780 mmol) and heated at 40° C. overnight and then for an additional 7 h. The reaction mixture was concentrated under reduced pressure and partitioned between water (25 mL) and extracted with EtOAc (3×25 mL), having added 5% DMEDA to the mixture. The combined organic phase was passed through a hydrophobic frit and concentrated under reduced pressure. The mixture was treated with DMAP (414 mg, 3.39 mmol), CuOAc (308 mg, 1.696 mmol) and 2-methoxy-5-(4,4,5,5-tetramethyl-1,3,2-dioxaborolan-2-yl)nicotinonitrile (463 mg, 1.780 mmol) in MeCN (14 mL) and heated at 40° C. for 7 h, then at room temperature overnight. The reaction mixture was concentrated under reduced pressure and partitioned between water (25 mL) and extracted with EtOAc (4×25 mL), with added 5% DMEDA. The combined organic layer was passed through a hydrophobic frit and concentrated under reduced pressure. The crude product was partially purified by reverse phase chromatography using a C18 silica column, eluting with a 30 to 85% gradient of MeCN+0.1% formic acid in water, plus 0.1% formic acid to give 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (347 mg).

Example 15. 1-(5-(Fluoromethyl)-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole

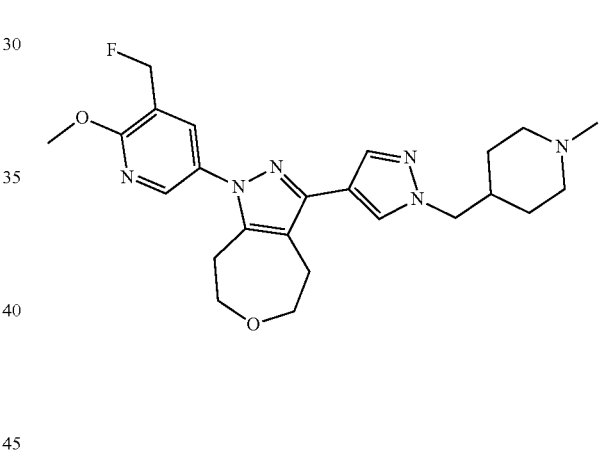

A solution of 1-(5-(fluoromethyl)-6-methoxypyridin-3-yl)-3-(1-(piperidin-4-ylmethyl)-1H-pyrazol-4-yl)-4,5,7,8-tetrahydro-1H-oxepino[4,5-c]pyrazole (125 mg, 0.284 mmol) in DMF (2 mL) was treated with a 37% by weight aqueous solution of formaldehyde (0.400 mL, 5.37 mmol) and stirred at room temperature under an atmosphere of nitrogen for 30 min. The reaction mixture was quenched with an aqueous solution of sodium bicarbonate (25 mL) and extracted with EtOAc (3×25 mL). The combined organic layer was washed with a 5% aqueous solution of LiCl (2×25 mL) then passed through a hydrophobic frit and concentrated under reduced pressure to give crude product. The crude product was purified by MDAP (Method A) to give the title compound as a colourless gum (7 mg, 5%).

LCMS (Method C): Rt=0.99 min, MH$^+$ 455.

$^1$H NMR (400 MHz, CDCl$_3$) δ-ppm 8.16 (d, J=2 Hz, 1H), 7.79 (d, J=2 Hz, 1H), 7.76 (s, 1H), 7.65 (s, 1H), 5.44 (d, $^2$J$_{H-F}$=47 Hz, 2H), 4.07-3.99 (m, 5H), 3.91 (t, J=5 Hz, 2H), 3.85 (t, J=5 Hz, 2H), 3.09-2.96 (m, 2H), 2.93 (t, J=5 Hz, 4H), 2.38 (s, 3H), 2.16-1.92 (m, 3H), 1.65 (d, J=12 Hz, 2H), 1.54-1.39 (m, 2H).

Example 16. 1-(5-(Fluoromethyl)-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole

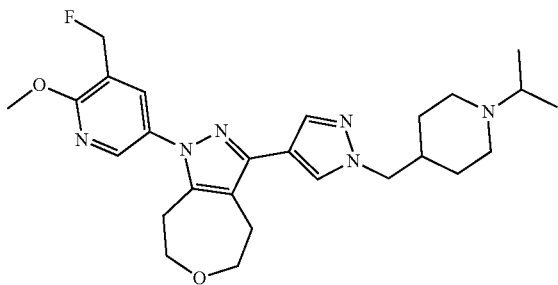 [SMILES: COc1ncc(-n2nc(-c3cnn(CC4CCN(C(C)C)CC4)c3)c3c2CCOCC3)cc1CF]

A solution of 1-(5-(fluoromethyl)-6-methoxypyridin-3-yl)-3-(1-(piperidin-4-ylmethyl)-1H-pyrazol-4-yl)-4,5,7,8-tetrahydro-1H-oxepino[4,5-c]pyrazole (125 mg, 0.284 mmol) and DIPEA (0.050 mL, 0.284 mmol) in DMF (2 mL) was treated with acetone (1.5 mL). The reaction mixture was stirred at room temperature under an atmosphere of nitrogen for 1 h. The reaction mixture was treated with STAB (241 mg, 1.135 mmol) and stirred for 15 h. The reaction mixture was quenched with a saturated aqueous solution of sodium bicarbonate (25 mL) and extracted with EtOAc (3×25 mL). The combined organic layer was washed with a 5% solution of LiCl (2×25 mL), passed through a hydrophobic frit and concentrated under reduced pressure to give crude product (105 mg). The crude product was purified by MDAP (Method A) to give the title compound as a colourless gum (19 mg, 13%).

LCMS (Method A): Rt=0.65 min, MH+ 483.

$^1$H NMR (400 MHz, CDCl$_3$) δ-ppm 8.16 (d, J=2 Hz, 1H), 7.79 (d, J=2 Hz, 1H), 7.76 (s, 1H), 7.65 (s, 1H), 5.44 (d, $^2J_{H-F}$=47 Hz, 2H), 4.07-3.98 (m, 5H), 3.91 (t, J=5 Hz, 2H), 3.85 (t, J=5 Hz, 2H), 3.10-2.96 (m, 2H), 2.96-2.88 (m, 4H), 2.32-2.16 (m, 2H), 2.11-1.92 (m, 2H), 1.68 (d, J=12 Hz, 2H), 1.57-1.37 (m, 2H), 1.10 (d, J=6 Hz, 6H).

Example 17. N-(5-(3-(1-((1-Isopropylpiperidin-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide

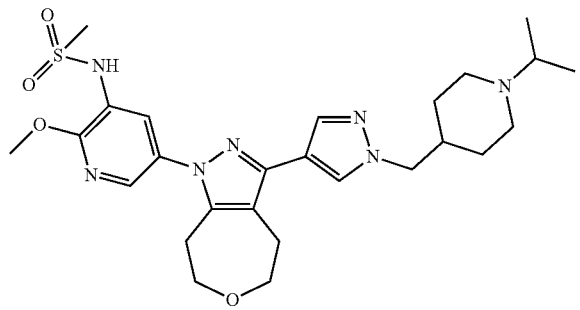 [SMILES: COc1ncc(-n2nc(-c3cnn(CC4CCN(C(C)C)CC4)c3)c3c2CCOCC3)cc1NS(C)(=O)=O]

A mixture of N-(2-methoxy-5-(3-(1-(piperidin-4-ylmethyl)-1H-pyrazol-4-yl)-4,5,7,8-tetrahydro-1H-oxepino[4,5-c]pyrazol-1-yl)pyridin-3-yl)methanesulfonamide (183 mg, 0.365 mmol), DMF (0.5 mL), acetone (1.5 mL) and DIPEA (0.064 mL, 0.365 mmol) was stirred at room temperature under an atmosphere of nitrogen for 18 h. The reaction mixture was quenched with a saturated aqueous solution of sodium bicarbonate (10 mL) and diluted with water (10 mL). The mixture was extracted with EtOAc (3×25 mL). The combined organic layer was washed with three equivalents of a 5% solution of LiCl, passed through a hydrophobic frit and concentrated under reduced pressure. A substantial amount of crude title compound remained in the aqueous layer so the aqueous layer was passed through an Isolute 103 cartridge which was washed with water then a solution of ammonia in MeOH. The MeOH-based wash was concentrated under reduced pressure and combined with the EtOAc extract to give 190 mg of crude product. The crude product was purified by MDAP (Method A) to give the title compound as a brown gum (28 mg).

LCMS (Method A): Rt=0.53 min, MH+ 544.

$^1$H NMR (400 MHz, CDCl$_3$) δ-ppm 7.98 (d, J=2 Hz, 1H), 7.87 (d, J=2 Hz, 1H), 7.75 (s, 1H), 7.65 (s, 1H), 4.06 (s, 3H), 4.02 (d, J=7 Hz, 2H), 3.91 (t, J=5 Hz, 2H), 3.85 (t, J=5 Hz, 2H), 3.08 (s, 3H), 3.00-2.80 (m, 6H), 2.77-2.67 (m, 1H), 2.13 (t, J=12 Hz, 2H), 2.00-1.86 (m, 1H), 1.64 (d, J=12 Hz, 2H), 1.41-1.28 (m, 2H), 1.03 (d, J=7 Hz, 6H).

Example 18. 3-(5-((4-Isopropylpiperazin-1-yl)methyl)oxazol-2-yl)-1-(6-methoxy-5-methylpyridin-3-yl)-4,5,7,8-tetrahydro-1H-oxepino[4,5-c]pyrazole. Formate Salt

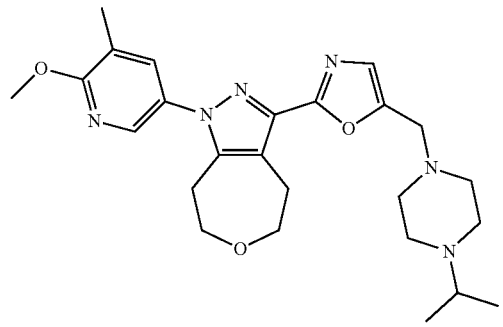 [SMILES: COc1ncc(-n2nc(-c3ncc(CN4CCN(C(C)C)CC4)o3)c3c2CCOCC3)cc1C]

A solution of (4-isopropylpiperazin-1-yl)(2-(1-(6-methoxy-5-methylpyridin-3-yl)-4,5,7,8-tetrahydro-1H-oxepino[4,5-c]pyrazol-3-yl)oxazol-5-yl)methanone (10 mg, 0.021 mmol) in THF (0.5 mL) was treated with a 1 M solution of DIBAL-H in THF (0.042 mL, 0.042 mmol). The reaction mixture was stirred overnight. The reaction mixture was treated with IPA (2 mL), concentrated under reduced pressure and purified by MDAP (Method A) to give the title compound as a colourless oil (2 mg, 21%).

LCMS (Method C): Rt=1.02 min, MH+ 467.

Example 19. 1-(6-Methoxy-5-methylpyridin-3-yl)-4,5,7,8-tetrahydro-1H-oxepino[4,5-c]pyrazole-3-carboxamide and Intermediate 146. 1-(6-methoxy-5-methylpyridin-3-yl)-4,5,7,8-tetrahydro-1H-oxepino[4,5-c]pyrazole-3-carboxylic acid

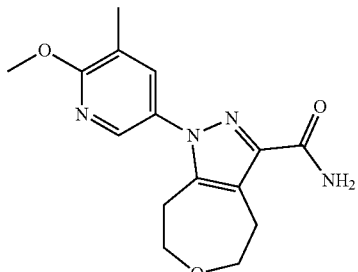

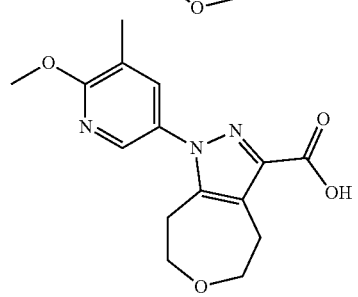

A mixture of a 0.6 M solution of sodium bis(trimethylsilyl) amide in toluene (0.2 mL, 0.120 mmol) and (1-methylpiperidin-3-yl)methanamine (7 mg, 0.055 mmol) was treated with THF (0.5 mL) and heated to 70° C. The reaction mixture was treated with ethyl 1-(6-methoxy-5-methylpyridin-3-yl)-4,5,7,8-tetrahydro-1H-oxepino[4,5-c]pyrazole-3-carboxylate (11 mg, 0.033 mmol) and heated for 16 h then concentrated under reduced pressure and purified by MDAP (Method A) to give 1-(6-methoxy-5-methylpyridin-3-yl)-4,5,7,8-tetrahydro-1H-oxepino[4,5-c]pyrazole-3-carboxylic acid (Intermediate 146, 4.6 mg, 46%), LCMS (Method A): Rt=0.85 min, MH+ 304, and the title compound (2 mg, 20%). LCMS (Method A): Rt=0.84 min, MH+ 303;

Example 20. 1-(6-Methoxy-5-methylpyridin-3-yl)-N-((1-methylpiperidin-3-yl)methyl)-4,5,7,8-tetrahydro-1H-oxepino[4,5-c]pyrazole-3-carboxamide, Formate Salt

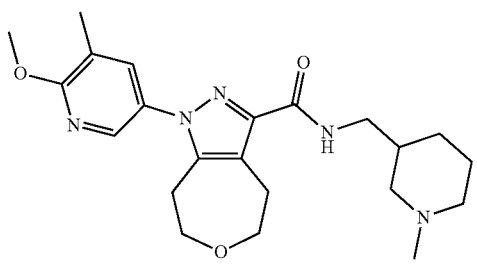 [SMILES: COc1ncc(-n2nc(C(=O)NCC3CCCN(C)C3)c3c2CCOCC3)cc1C]

A mixture of 1-(6-methoxy-5-methylpyridin-3-yl)-4,5,7,8-tetrahydro-1H-oxepino[4,5-c]pyrazole-3-carboxylic acid (4.6 mg, 0.015 mmol), DIPEA (7.95 µl, 0.045 mmol), and HATU (7 mg, 0.018 mmol) were dissolved in DMF (0.5 mL) and stirred for 30 min. The reaction mixture was treated with (1-methylpiperidin-3-yl)methanamine (2 mg, 0.016 mmol) and stirred for 16 h then concentrated under a stream of nitrogen. The crude product was purified by MDAP (Method B) to give the title compound as a colourless gum (2.4 mg, 34%).

LCMS (Method A): Rt=0.61 min, MH+ 414.

$^1$H NMR (400 MHz, MeOD) δ-ppm 8.54 (s, 1H), 8.05 (d, J=2 Hz, 1H), 7.61 (d, J=2 Hz, 1H), 4.01 (s, 3H), 3.85 (t, J=5 Hz, 2H), 3.80 (t, J=5 Hz, 2H), 3.27-3.14 (m, 4H), 2.90 (t, J=5 Hz, 2H), 2.68-2.49 (m, 4H), 2.47-2.34 (m, 1H), 2.25 (s, 3H), 2.10-1.95 (m, 1H), 1.94-1.82 (m, 2H), 1.80-1.54 (m, 2H), 1.37-1.10 (m, 2H).

General Alkylation by Epoxide Ring Opening Procedure

Example 21. 1-(3-((4-(1-(6-Methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol

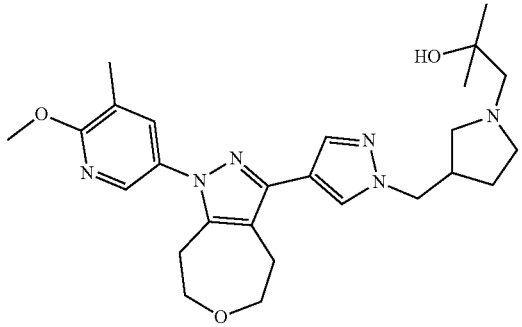 [SMILES: COc1ncc(-n2nc(-c3cnn(CC4CCN(CC(C)(C)O)C4)c3)c3c2CCOCC3)cc1C]

A mixture of 1-(6-methoxy-5-methylpyridin-3-yl)-3-(1-(pyrrolidin-3-ylmethyl)-1H-pyrazol-4-yl)-4,5,7,8-tetrahydro-1H-oxepino[4,5-c]pyrazole (118 mg, 0.289 mmol), EtOH (2 mL), DIPEA (0.101 mL, 0.578 mmol) and 2,2-dimethyloxirane (0.07 mL, 0.788 mmol) was heated using a microwave at 90° C. for 3 h and concentrated under reduced pressure. The material was purified by MDAP (Method A) to give the title compound as a colourless gum (60 mg, 41%).

LCMS (Method C): Rt=1.02 min, MH+ 481.

$^1$H NMR (400 MHz, CDCl$_3$) δ-ppm 8.00 (d, J=2 Hz, 1H), 7.75 (s, 1H), 7.68 (s, 1H), 7.52 (d, J=2 Hz, 1H), 4.13 (d, J=7 Hz, 1H), 4.00 (s, 3H), 3.91 (t, J=5 Hz, 2H), 3.84 (t, J=5 Hz, 2H), 2.98-2.83 (m, 5H), 2.82-2.60 (m, 5H), 2.47 (s, 2H), 2.24 (s, 3H), 2.04-1.90 (m, 1H), 1.63-1.51 (m, 1H), 1.17 (s, 6H).

Examples 22. and 23. (R)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol and (S)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol

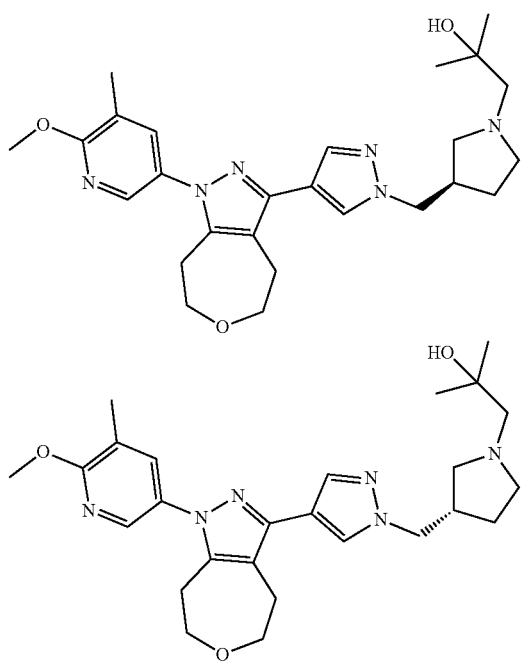

The two title compounds were isolated from a mixture of 1-(3-((4-(1-(6-Methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol (Example 21, 53 mg) by chiral, using a 30 mm×25 cm Chiralcel AD-H column, eluting with 30% EtOH (+0.2% isopropylamine)/heptane(+0.2% isopropylamine), using a flow rate of 30 mL/min.

Example 22

Isolated as a colourless gum (19 mg).
LCMS (Method C) Rt=1.03 min, MH+=481.
$^1$H NMR (400 MHz, CDCl$_3$) δ-ppm 8.00 (d, J=2 Hz, 1H), 7.75 (s, 1H), 7.68 (s, 1H), 7.52 (d, J=2 Hz, 1H), 4.14 (d, J=7 Hz, 2H), 4.00 (s, 3H), 3.91 (t, J=5 Hz, 2H), 3.84 (t, J=5 Hz, 2H), 3.05-2.58 (m, 10H), 2.49 (s, 2H), 2.24 (s, 3H), 2.06-1.91 (m, 1H), 1.66-1.50 (m, 1H), 1.18 (s, 6H). Enantiomeric purity by chiral HPLC=>99.0% e.e.

Example 23

Isolated as a colourless gum (20 mg).
LCMS (Method C) Rt=1.03 min, MH+=481.
$^1$H NMR (400 MHz, CDCl$_3$) δ-ppm 8.00 (d, J=2 Hz, 1H), 7.75 (s, 1H), 7.68 (s, 1H), 7.52 (d, J=2 Hz, 1H), 4.14 (d, J=7 Hz, 2H), 4.00 (s, 3H), 3.91 (t, J=5 Hz, 2H), 3.84 (t, J=5 Hz, 2H), 3.03-2.58 (m, 10H), 2.49 (s, 2H), 2.24 (s, 3H), 2.06-1.89 (m, 1H), 1.66-1.52 (m, 1H), 1.18 (s, 6H). Enantiomeric purity by chiral HPLC=>91.8% e.e.

Absolute stereochemistry was not assigned.

Example 24. 3-(1-Ethyl-5-methyl-1H-pyrazol-4-yl)-1-(1-methyl-1H-pyrazol-4-yl)-4,5,7,8-tetrahydro-1H-oxepino[4,5-c]pyrazole

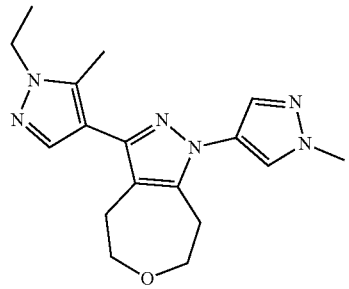 [SMILES: CCn1ncc(-c2nn(-c3cnn(C)c3)c3c2CCOCC3)c1C]

A microwave vial was charged with 4-bromo-1-ethyl-5-methyl-1H-pyrazole (99 mg, 0.525 mmol) and sealed. THF (1 mL) was added and the vial purged with nitrogen and cooled to −78° C. The reaction mixture was treated with a solution of nBuLi in hexanes (2.5 M, 0.210 mL, 0.525 mmol) and stirred for 30 min then allowed to warm to room temperature. The reaction mixture was treated with a 0.5 M solution of ZnCl$_2$ in THF (1.050 mL, 0.525 mmol) and stirred for 30 min. The reaction mixture was treated with PdCl$_2$(PPh$_3$)$_2$ (28.3 mg, 0.040 mmol) and a solution of 3-bromo-1-(1-methyl-1H-pyrazol-4-yl)-4,5,7,8-tetrahydro-1H-oxepino[4,5-c]pyrazole (60 mg, 0.202 mmol) in THF (1 mL), then heated at 80° C. for 7.5 h and allowed to cool to room temperature.
The reaction mixture was treated with EtOAc (10 mL) and a 1 M aqueous solution of NaOH (10 mL).
Further EtOAc (10 mL) was added and the organic layer isolated. The aqueous layer was re-extracted with EtOAc (2×10 mL) and the combined organic layer passed through a hydrophobic frit and concentrated under reduced pressure to give the crude product as an orange oil. The material was purified by MDAP (Method B) to give the title compound (2.0 mg, 3%).
LCMS (Method C): Rt=0.75 min, MH+ 327.

Example 25. 1-(6-Methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole

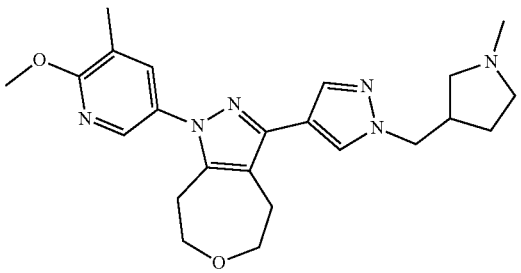 [SMILES: COc1ncc(-n2nc(-c3cnn(CC4CCN(C)C4)c3)c3c2CCOCC3)cc1C]

A mixture of 1-(6-methoxy-5-methylpyridin-3-yl)-3-(1-(pyrrolidin-3-ylmethyl)-1H-pyrazol-4-yl)-4,5,7,8-tetrahydro-1H-oxepino[4,5-c]pyrazole (118 mg, 0.289 mmol) and DMF (2 mL) and a 37% aqueous solution of formaldehyde (0.35 mL, 4.70 mmol) was stirred at room temperature under an atmosphere of nitrogen for 30 min. The reaction mixture was treated with STAB (250 mg, 1.180 mmol) and stirred for 15 h.

The reaction mixture was treated with a saturated aqueous solution of sodium bicarbonate (20 mL) and partitioned with EtOAc (20 mL). The organic layer was isolated and the aqueous layer was re-extracted with EtOAc (2×20 mL). The combined organic layer was washed with a 5% by weight solution of LiCl solution (3×30 mL) and passed through a hydrophobic frit and concentrated under reduced pressure to give the crude product as a brown oil (136 mg). The crude material was purified by MDAP (Method A) to give the title compound as a colourless gum (30 mg).

Example 26. and 27. (R)-1-(6-Methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole and (S)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole

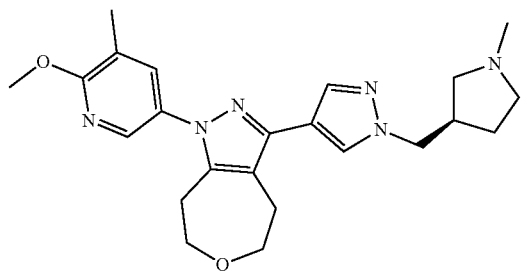

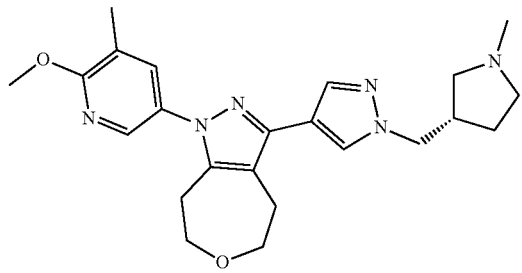

1-(6-Methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole (Example 25) was separated into its two component enantiomers by preparative chiral HPLC using a 30 mm×25 cm Chiralpak AD-H column. The column was eluted with 30% EtOH (+0.2% isopropylamine)/heptane(+0.2% isopropylamine), using a flow rate of 30 mL/min. Appropriate fractions were combined and evaporated to give the two enantiomers:

Example 26.: 10 mg, colourless oil. LCMS (Method C) Rt=0.97 min, MH+=423. Enantiomeric purity by chiral HPLC=>99.0% e.e.

Example 27.: 7 mg, colourless oil. LCMS (Method C) Rt=1.00 min, MH+=485. Enantiomeric purity by chiral HPLC=>97.4% e.e.

Absolute stereochemistry was not assigned.

Example 28. 3-(6-Methoxy-5-methylpyridin-3-yl)-1-(1-((1-methylpiperidin-4-yl)methyl)-1H-pyrazol-4-yl)-4,5,7,8-tetrahydro-1H-oxepino[4,5-c]pyrazole

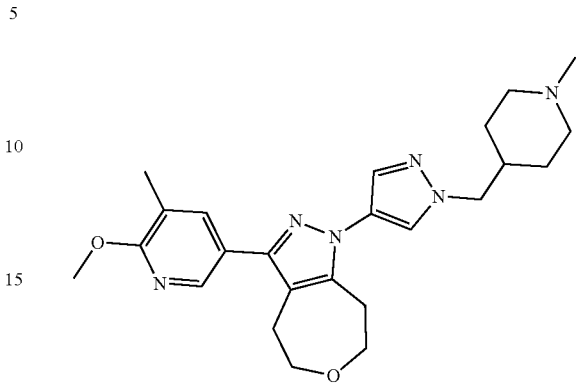

A solution of 3-(6-methoxy-5-methylpyridin-3-yl)-1-(1-(piperidin-4-ylmethyl)-1H-pyrazol-4-yl)-4,5,7,8-tetrahydro-1H-oxepino[4,5-c]pyrazole (40 mg, 0.095 mmol) in DMF (1 mL) was treated with a 37% aqueous solution of formaldehyde (0.141 mL, 1.893 mmol) and stirred at room temperature for 30 min. The reaction mixture was treated with STAB (85 mg, 0.401 mmol) and stirred for 2 h. The reaction was quenched with a saturated aqueous solution of sodium bicarbonate (5 mL) then partitioned with EtOAc (10 mL). The aqueous layer was re-extracted with EtOAc (3×10 mL). The combined organic layer was washed with a solution of LiCl (2×20 mL) and passed through a hydrophobic frit then concentrated under reduced pressure to give crude product. The crude product was purified by MDAP (Method A) to give the title compound (6 mg, 14%).

LCMS (Method C) Rt=1.01 min, MH+=437.

Example 29. 2-(4-((4-(1-(6-Methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol

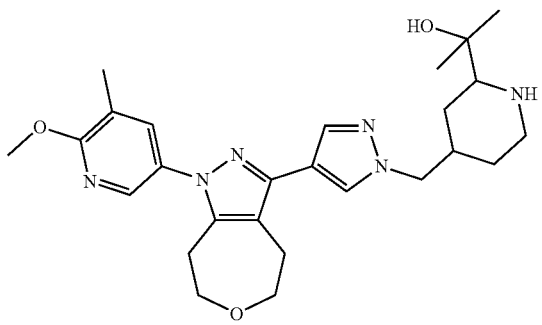 [SMILES: COc1ncc(-n2nc(-c3cnn(CC4CCNC(C(C)(C)O)C4)c3)c3c2CCOCC3)cc1C]

A solution of 2-(1-benzyl-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol (18 mg, 0.019 mmol) in MeOH (1 mL) and EtOAc (0.5 mL), was passed through a CatCart™ (palladium hydroxide on carbon) using an H-Cube® continuous-flow hydrogenation reactor at 25° C. and 50 bar and concentrated under reduced pressure. The crude product was purified by MDAP (Method A) to give the title compound (6 mg, 66%).

LCMS (Method C) Rt=0.91 min, MH+=481.

¹H NMR (400 MHz, CDCl₃) δ-ppm 8.00 (d, J=2 Hz, 1H), 7.76 (s, 1H), 7.65 (s, 1H), 7.52 (d, J=2 Hz, 1H), 4.06-3.96 (m, 5H), 3.91 (t, J=5 Hz, 2H), 3.84 (t, J=5 Hz, 2H), 3.22-3.12 (m, 1H), 2.98-2.87 (m, 4H), 2.68-2.55 (m, 3H), 2.39 (d, J=11 Hz, 1H), 2.24 (s, 3H), 2.17-2.00 (m, 1H), 1.73-1.53 (m, 4H), 1.17 (s, 3H), 1.11 (s, 3H).

Example 30. 5-(3-(1-((1-Isopropylpiperidin-3-yl) methyl)-1H-pyrazol-4-yl)-4,5,7,8-tetrahydro-1H-oxepino[4,5-c]pyrazol-1-yl)-2-methoxynicotinonitrile

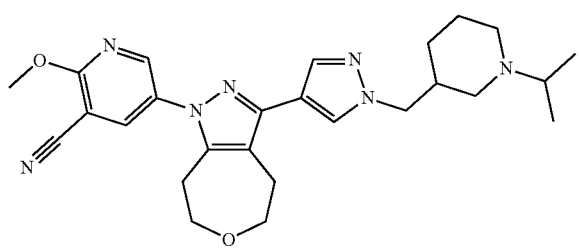 [SMILES: COc1ncc(-n2nc(-c3cnn(CC4CCCN(C(C)C)C4)c3)c3c2CCOCC3)cc1C#N]

A mixture of copper acetate (349 mg, 1.921 mmol), 3-(1-(4-methoxybenzyl)-1H-pyrazol-4-yl)-4,5,7,8-tetrahydro-1H-oxepino[4,5-c]pyrazole (623 mg, 1.921 mmol), 2-methoxy-5-(4,4,5,5-tetramethyl-1,3,2-dioxaborolan-2-yl) nicotinonitrile (500 mg, 1.921 mmol) and DMAP (469 mg, 3.84 mmol) in MeCN (16 mL) was stirred at 40° C. overnight open to air. The reaction was heated for 5 h then left to stand over a weekend. The reaction was diluted with water (25 mL) and reduced in volume by concentrating under reduced pressure. The resulting solution was extracted with EtOAc (3×25 mL) in the presence of a 5% solution of DMEDA. The combined organic layer was passed through a hydrophobic frit and concentrated under reduced pressure. The crude product was treated with DMAP (469 mg, 3.84 mmol), CuOAc (349 mg, 1.921 mmol), 2-methoxy-5-(4,4,5,5-tetramethyl-1,3,2-dioxaborolan-2-yl)nicotinonitrile (500 mg, 1.921 mmol) in MeCN (16 mL). The reaction mixture was heated at 40° C. for 7 h then at room temperature overnight. The reaction mixture was concentrated under reduced pressure and partitioned between water (25 mL) and EtOAc (4×25 mL), in the presence of 5% DMEDA in the aqueous phase. The combined organic layer was passed through a hydrophobic frit and concentrated under reduced pressure. The crude material was partially purified by reverse phase chromatography using a C18 column, eluting with a 30 to 85% gradient of a solution of MeCN (+0.1% formic acid in water) and 0.1% formic acid to give partially purified 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (633 mg). The material was used directly in the next step.

Crude 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (20 mg) was treated with DCM (0.1 mL) and TFA (0.1 mL, 1.298 mmol). The reaction mixture was heated 70° C. using a microwave for 2 h. The reaction mixture was treated with more crude 2-methoxy-5-(3-(1-(4-methoxybenzyl)-1H-pyrazol-4-yl)-4,5,7,8-tetrahydro-1H-oxepino[4,5-c]pyrazol-1-yl)nicotinonitrile (183 mg) in DCM (0.5 mL) followed by TFA (0.62 mL) and heated at 70° C. using a microwave for 5 h.

The reaction mixture was diluted with DCM (10 mL) and treated with a saturated aqueous solution of sodium bicarbonate in a dropwise manner until the reaction mixture was pH 9. The reaction mixture was stirred for 30 min then partitioned with DCM (20 mL). The organic layer was isolated and the aqueous layer re-extracted with DCM (2×20 mL). The combined organic layer was passed through a hydrophobic frit and concentrated under reduced pressure, to give crude 5-(3-(1H-pyrazol-4-yl)-4,5,7,8-tetrahydro-1H-oxepino[4,5-c]pyrazol-1-yl)-2-methoxynicotinonitrile as a light brown gum (240 mg).

The crude material was taken forward into the next reaction step without further purification.

5-(3-(1H-pyrazol-4-yl)-4,5,7,8-tetrahydro-1H-oxepino[4,5-c]pyrazol-1-yl)-2-methoxynicotinonitrile (100 mg) in DMF (1.4 mL) at 0° C. was treated with a 60% by weight suspension of sodium hydride in mineral oils (14.3 mg, 0.357 mmol) and stirred under an atmosphere of nitrogen for 1 h. The reaction mixture was treated with tert-butyl 3-(bromomethyl)piperidine-1-carboxylate (124 mg, 0.446 mmol) and stirred at room temperature under an atmosphere of nitrogen over the weekend.

The reaction mixture was treated with saturated ammonium chloride solution (5 mL), and extracted into ethyl acetate (3×10 mL). The organic layer was isolated and washed with a 5% by weight solution of LiCl. The solvent was passed through a hydrophobic frit and concentrated to give crude tert-Butyl 3-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate (193 mg).

LCMS (Method C) Rt=1.21 min, MH+=534.

The crude material was taken forward into the next reaction step without further purification.

A solution of tert-butyl 3-((4-(1-(5-cyano-6-methoxypyridin-3-yl)-4,5,7,8-tetrahydro-1H-oxepino[4,5-c]pyrazol-3-yl)-1H-pyrazol-1-yl)methyl)piperidine-1-carboxylate in DCM (3 mL) was treated with TFA (0.294 mL, 3.82 mmol). The reaction mixture was stirred at room temperature for 5 h and then overnight.

The reaction mixture was treated with a saturated aqueous solution of sodium bicarbonate (2 mL) and was stirred vigorously for 2 h. An additional 1 mL of a saturated aqueous solution of sodium bicarbonate was added and the mixture was diluted with DCM (15 mL) and more of a saturated aqueous solution of sodium bicarbonate was added to bring the total to 15 mL. The organic layer was isolated and the aqueous layer re-extracted with DCM (2×15 mL). The combined organic layer was passed through a hydrophobic frit and concentrated under reduced pressure to afford a crude product. The crude product was purified by MDAP (Method A) to give 2-methoxy-5-(3-(1-(piperidin-3-ylmethyl)-1H-pyrazol-4-yl)-4,5,7,8-tetrahydro-1H-oxepino [4,5-c]pyrazol-1-yl)nicotinonitrile (73 mg).

A solution of 2-methoxy-5-(3-(1-(piperidin-3-ylmethyl)-1H-pyrazol-4-yl)-4,5,7,8-tetrahydro-1H-oxepino[4,5-c] pyrazol-1-yl)nicotinonitrile (73 mg, 0.168 mmol) in DMF (0.75 mL) and acetone (1 mL) was stirred under an atmosphere of nitrogen in a sealed vial overnight. The reaction mixture was treated with STAB (71.4 mg, 0.337 mmol) and stirred for 3 h. The reaction was quenched with an aqueous solution of sodium bicarbonate (2 mL) and stirred vigorously over a weekend. The mixture was partitioned with sodium bicarbonate in water (10 mL) and EtOAc (10 mL), and extracted with further EtOAc (2×10 mL). The combined organic layer was passed through a hydrophobic frit and concentrated under reduced pressure to give crude product (47 mg). The crude product was placed in a vacuum oven for 3 h then placed under a stream of nitrogen overnight to remove residual DMF. The crude title compound was isolated (47 mg).

LCMS (Method A) Rt=0.65 min, MH⁺=476.

¹H NMR (400 MHz, CDCl₃) δ-ppm 8.40 (d, J=3 Hz, 1H), 8.01 (d, J=3 Hz, 1H), 7.74 (s, 1H), 7.66 (s, 1H), 4.15-4.02 (m, 5H), 3.97-3.79 (m, 4H), 2.98-2.90 (m, 4H), 2.32-2.11 (m, 2H), 2.08-1.96 (m, 1H), 1.81-1.47 (m, 7H), 1.13-0.79 (m, 6H).

Example 31. 3-(5-Fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole

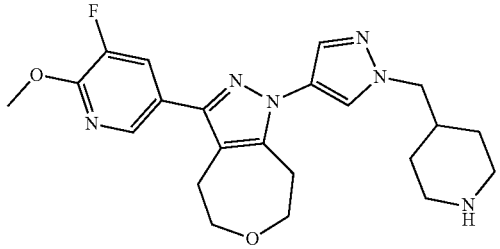 [SMILES: COc1ncc(-c2nn(-c3cnn(CC4CCNCC4)c3)c3c2CCOCC3)cc1F]

Prepared using the general Boc deprotection method from tert-butyl 4-((4-(3-(5-fluoro-6-methoxypyridin-3-yl)-4,5,7,8-tetrahydro-1H-oxepino[4,5-c]pyrazol-1-yl)-1H-pyrazol-1-yl)methyl)piperidine-1-carboxylate (304 mg, 0.577 mmol), DCM (3 mL) and TFA (1.677 mL) except the reaction mixture was heated at 70° C. for 15 min using a microwave. The title compound was isolated as a brown solid (254 mg, >99%).

LCMS (Method C) Rt=0.99 min, MH⁺=427.

Example 32. 3-(5-Fluoro-6-methoxypyridin-3-yl)-1-(1-((1-isopropylpiperidin-4-yl)methyl)-1H-pyrazol-4-yl)-4,5,7,8-tetrahydro-1H-oxepino[4,5-c]pyrazole

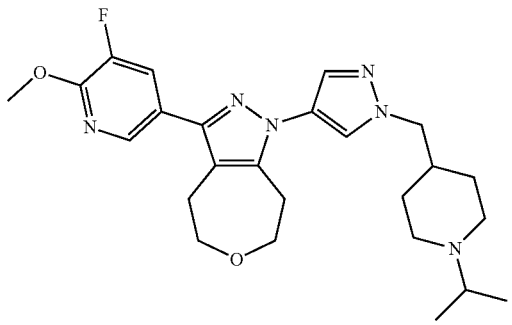 [SMILES: COc1ncc(-c2nn(-c3cnn(CC4CCN(C(C)C)CC4)c3)c3c2CCOCC3)cc1F]

An oven dried microwave vial was charged with 3-(5-fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole (65 mg, 0.142 mmol), acetone (0.7 mL) and DMF (0.60 mL). The reaction mixture was stirred under an atmosphere of nitrogen for 1 h then treated with STAB (120 mg, 0.567 mmol). The reaction mixture was stirred for 3 h. The reaction was quenched using a saturated aqueous solution of sodium bicarbonate (5 mL) and extracted with EtOAc (3×10 mL). The combined organic layer was washed with a 5% by weight aqueous solution of LiCl (2×15 mL), passed through a hydrophobic frit and concentrated under reduced pressure to give a yellow oil. The crude product was purified by MDAP (Method A) to give the title compound (16 mg, 23%) as an off white solid.

LCMS (Method C) Rt=1.15 min, MH⁺=469.

¹H NMR (400 MHz, CDCl₃) δ-ppm 8.10 (d, J=2 Hz, 1H), 7.64-7.56 (m, 3H), 4.06 (s, 3H), 4.01 (d, J=7 Hz, 2H), 3.87 (t, J=5 Hz, 4H), 2.98 (t, J=5 Hz, 2H), 2.90 (t, J=5 Hz, 4H), 2.73 (sep, J=7 Hz, 1H), 2.13 (t, J=10 Hz, 2H), 2.02-1.87 (m, 1H), 1.65 (d, J=12 Hz, 2H), 1.45-1.29 (m, 2H), 1.04 (d, J=6 Hz, 6H).

Example 33. 1-(1-((1-Isopropylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole

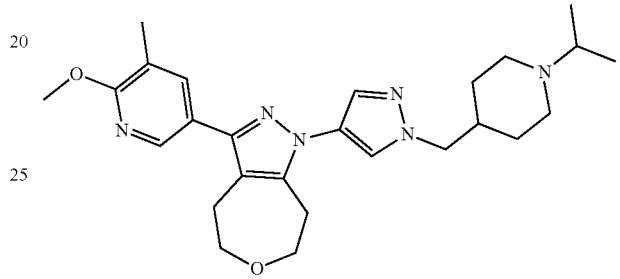

A solution of 3-(6-methoxy-5-methylpyridin-3-yl)-1-(1-(piperidin-4-ylmethyl)-1H-pyrazol-4-yl)-4,5,7,8-tetrahydro-1H-oxepino[4,5-c]pyrazole (116 mg, 0.275 mmol) in acetone (5 mL) was stirred under an atmosphere of nitrogen for 30 min at room temperature. The reaction mixture was treated with STAB (243 mg, 1.147 mmol) and stirred overnight. The reaction was quenched with a saturated aqueous solution of sodium bicarbonate (5 mL) and partitioned with EtOAc (10 mL). The aqueous layer was re-extracted with EtOAc (3×10 mL). The combined organic layer was passed through a hydrophobic frit and concentrated under reduced pressure to give crude product. The crude product was purified by MDAP (Method A) to give the title compound (20 mg, 15%).

LCMS (Method C) Rt=1.10 min, MH⁺=465.

¹H NMR (400 MHz, CDCl₃) δ-ppm 8.14 (d, J=2 Hz, 1H), 7.66 (d, J=1 Hz, 1H), 7.62 (s, 1H), 7.61 (s, 1H), 4.07-3.94 (m, 5H), 3.94-3.80 (m, 4H), 3.10-2.82 (m, 7H), 2.30-2.16 (m, 5H), 2.08-1.93 (m, 1H), 1.69 (d, J=12 Hz, 2H), 1.60-1.42 (m, 2H), 1.10 (d, J=7 Hz, 6H).

Example 34. 1-(5-Fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole

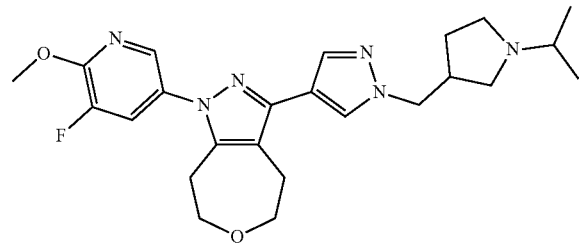 [SMILES: COc1ncc(-n2nc(-c3cnn(CC4CCN(C(C)C)C4)c3)c3c2CCOCC3)cc1F]

A mixture of 1-(5-fluoro-6-methoxypyridin-3-yl)-3-(1H-pyrazol-4-yl)-4,5,7,8-tetrahydro-1H-oxepino[4,5-c]pyrazole and 2-(5-fluoro-6-methoxypyridin-3-yl)-3-(1H-pyrazol-4-yl)-4,5,7,8-tetrahydro-2H-oxepino[4,5-c]pyrazole (50 mg) and a 60% by weight suspension of sodium hydride in mineral oils (14.57 mg, 0.364 mmol) in DMF (1.25 mL) at 0° C. was stirred under an atmosphere of nitrogen and was allowed to warm to room temperature over 3 h.

3-(Bromomethyl)-1-isopropylpyrrolidine hydrobromide (131 mg, 0.455 mmol) was dissolved in MeOH and loaded onto a silica aminopropyl SPE cartridge and eluted with MeOH and concentrated under a stream of nitrogen to afford 3-(bromomethyl)-1-isopropylpyrrolidine (94 mg, 0.455 mmol) as a clear liquid. 3-(Bromomethyl)-1-isopropylpyrrolidine (94 mg, 0.455 mmol) was added to the first reaction mixture and the reaction mixture was stirred overnight at room temperature under an atmosphere of nitrogen.

The reaction mixture was treated with a saturated solution of ammonium chloride solution (2 mL) and partitioned with EtOAc (7 mL). The organic layer was isolated and the aqueous layer re-extracted with EtOAc (5×7 mL). The combined organic layer was passed through a hydrophobic frit and concentrated under reduced pressure and crude material was purified by MDAP (Method A) to give the title compound (35 mg).

LCMS (Method C) Rt=1.04 min, MH+=455.

$^1$H NMR (400 MHz, MeCN-d$_3$) δ-ppm 8.03 (d, J=2 Hz, 1H), 7.82 (s, 1H), 7.69 (s, 1H), 7.62 (dd, J=11, 2 Hz, 1H), 4.18-4.07 (m, 2H), 4.04 (s, 3H), 3.88-3.74 (m, 4H), 2.97-2.83 (m, 4H), 2.81-2.60 (m, 5H), 2.59-2.36 (m, 2H), 1.63-1.50 (m, 1H), 1.10 (d, J=7 Hz, 6H).

Example 35. and Example 36. (S)-1-(5-Fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole and (R)-1-(5-Fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole

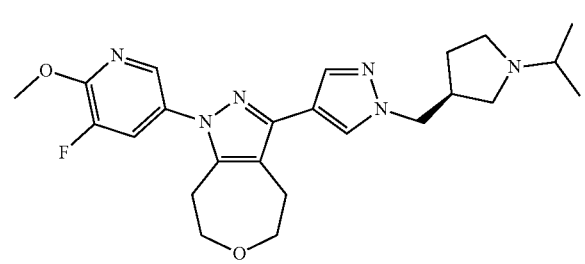

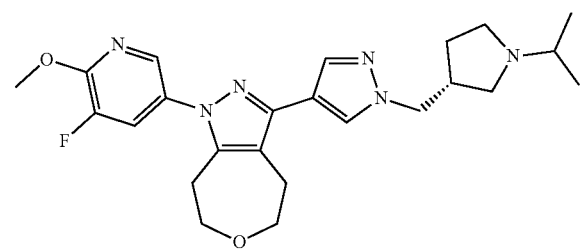

1-(5-Fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole (Example 34, 30 mg) was separated into its two component enantiomers by preparative chiral HPLC using a 30 mm×25 cm Chiralpak AD-H. The column was eluted with 10% EtOH (+0.2% isopropylamine)/heptane(+0.2% isopropylamine), using a flow rate of 42.5 mL/min. Appropriate fractions were combined and evaporated to give the two enantiomers:

Example 35.: 8 mg, clear gum. LCMS (Method C) Rt=1.00 min, MH+=455. Enantiomeric purity by chiral HPLC=>96.2% e.e.

Example 36.: 10 mg, clear gum. LCMS (Method C) Rt=1.00 min, MH+=455. Enantiomeric purity by chiral HPLC=>88.5% e.e.

Absolute stereochemistry was not assigned.

Example 37. 1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol

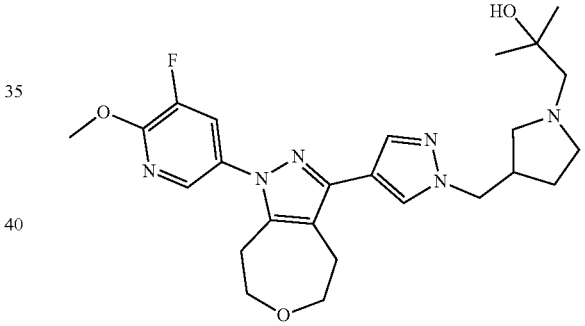

A solution of a mixture of 1-(5-fluoro-6-methoxypyridin-3-yl)-3-(1-(pyrrolidin-3-ylmethyl)-1H-pyrazol-4-yl)-4,5,7,8-tetrahydro-1H-oxepino[4,5-c]pyrazole and 2-(5-fluoro-6-methoxypyridin-3-yl)-3-(1-(pyrrolidin-3-ylmethyl)-1H-pyrazol-4-yl)-4,5,7,8-tetrahydro-2H-oxepino[4,5-c]pyrazole (100 mg), 2,2-dimethyloxirane (0.065 mL, 0.727 mmol), DIPEA (0.085 mL, 0.485 mmol) in EtOH (2 mL) was heated using a microwave at 70° C. for 1 h. The reaction mixture was treated with MeOH (1 m), concentrated under reduced pressure, then purified by MDAP (Method A) to give the title compound as a brown oil (39 mg, 33%).

LCMS (Method C) Rt=1.00 min, MH+=485.

Example 38. and Example 39. (R)-1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol and (S)-1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol Example 40. 3-(1-((1-Isopropylpyrrolidin-3-yl)methyl)-1H-pyrazol-4-yl)-1-(6-methoxy-5-methylpyridin-3-yl)-4,5,7,8-tetrahydro-1H-oxepino[4,5-c]pyrazole

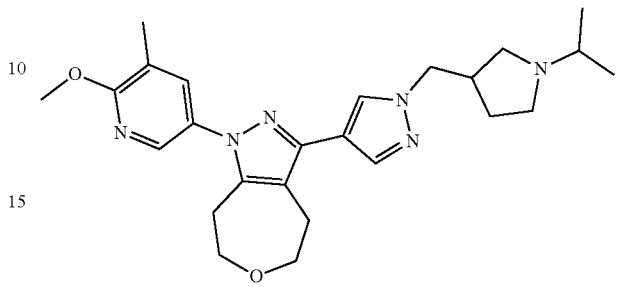

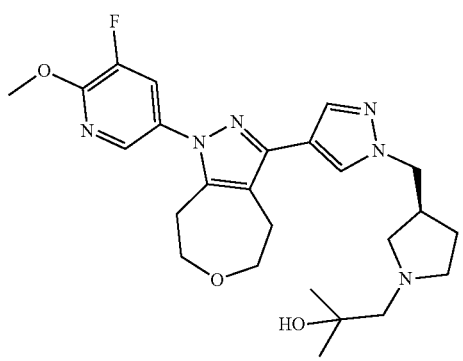

Prepared using the general alkylation procedure using 1-(6-methoxy-5-methylpyridin-3-yl)-3-(1H-pyrazol-4-yl)-4,5,7,8-tetrahydro-1H-oxepino[4,5-c]pyrazole (52 mg, 0.160 mmol), NaH (16 mg, 60% by weight suspension on mineral oils), DMF (2 mL) and 3-(bromomethyl)-1-isopropylpyrrolidine (99 mg, 0.479 mmol), except the reaction was quenched with a saturated aqueous solution of ammonium chloride (4 mL) instead of a saturated aqueous solution of sodium bicarbonate. Crude title compound was purified by MDAP (Method A) to give the title compound as a colourless oil (37 mg, 49%).

LCMS (Method C): Rt=1.08 min, MH$^+$ 451.

$^1$H NMR (400 MHz, CDCl$_3$) δ-ppm 8.00 (d, J=2 Hz, 1H), 7.75 (s, 1H), 7.67 (s, 1H), 7.52 (d, J=2 Hz, 1H), 4.13 (d, J=8 Hz, 1H), 4.00 (s, 3H), 3.91 (t, J=5 Hz, 2H), 3.84 (t, J=5 Hz, 2H), 2.97-2.87 (m, 4H), 2.87-2.68 (m, 2H), 2.63 (t, J=7 Hz, 2H), 2.43-2.28 (m, 2H), 2.24 (s, 3H), 2.05-1.92 (m, 1H), 1.71-1.50 (m, 2H), 1.08 (d, J=9 Hz, 6H).

Example 41. 4-((4-(1-(6-Methoxy-5-methylpyridin-3-yl)-4,5,7,8-tetrahydro-1H-oxepino[4,5-c]pyrazol-3-yl)-1H-pyrazol-1-yl)methyl)-1-methylpiperidin-4-ol

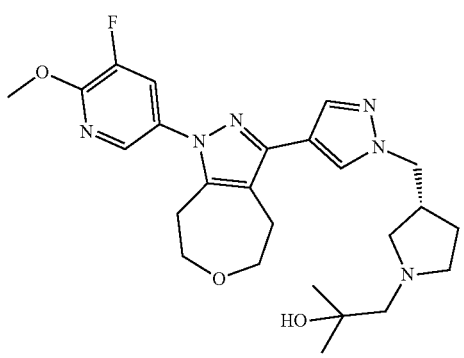

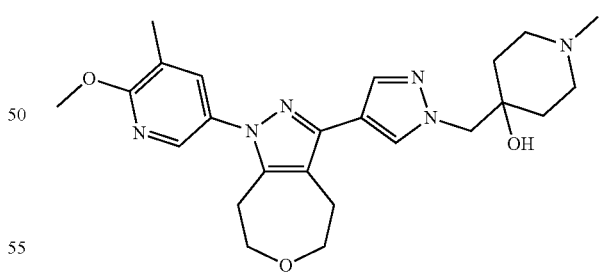

1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol (Example 37, 36 mg) was separated into its two component enantiomers by preparative chiral HPLC using a 30 mm×25 cm Chiralpak IC column. The column was eluted with 30% EtOH (+0.2% isopropylamine)/heptane(+0.2% isopropylamine), using a flow rate of 30 mL/min. Appropriate fractions were combined and evaporated to give the two enantiomers:

Example 38.: 15 mg, colourless glass. LCMS (Method C) Rt=1.00 min, MH$^+$=485. Enantiomeric purity by chiral HPLC=>99.0% e.e.

Example 39.: 14 mg, colourless glass. LCMS (Method C) Rt=1.00 min, MH$^+$=485. Enantiomeric purity by chiral HPLC=>93.0% e.e.

Absolute stereochemistry was not assigned.

A solution of 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-4-ol (245 mg, 0.559 mmol) in DMF (3 mL) was treated with a 37% by weight aqueous solution of formaldehyde (0.624 mL, 8.38 mmol) and stirred at room temperature for 1 h. The reaction mixture was treated with STAB (300 mg, 1.415 mmol) and stirred overnight. The reaction was quenched with a saturated aqueous solution of sodium bicarbonate (10 mL) and stirred for 20 min. The mixture was diluted with water (10 mL) and extracted with EtOAc (4×20 mL). The combined organic layer was passed through a hydrophobic frit and concentrated under reduced pressure to give crude product (234 mg). The crude product was purified by MDAP (Method A) to give the title compound as a colourless gum (93 mg, 35%).

LCMS (Method C): Rt=0.89 min, MH+ 453.

Example 42. 3-(5-Fluoro-6-methoxypyridin-3-yl)-1-(1-((1-methylpiperidin-4-yl)methyl)-1H-pyrazol-4-yl)-4,5,7,8-tetrahydro-1H-oxepino[4,5-c]pyrazole Example 43. 3-(1-((4-Fluoro-1-methylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole

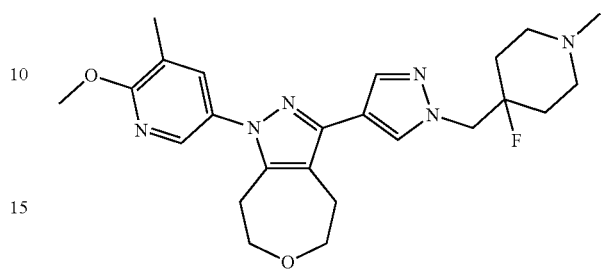

A mixture of 3-(1-((4-fluoropiperidin-4-yl)methyl)-1H-pyrazol-4-yl)-1-(6-methoxy-5-methylpyridin-3-yl)-4,5,7,8-tetrahydro-1H-oxepino[4,5-c]pyrazole (113 mg), DMF (2 mL), and a 37% by weight aqueous solution of formaldehyde (0.3 mL, 4.03 mmol) were stirred under an atmosphere of nitrogen for 30 min. The reaction was quenched using a saturated aqueous solution of sodium bicarbonate (5 mL), diluted with water (10 mL), then extracted with EtOAc (4×20 mL). The combined organic layer was passed through a hydrophobic frit and concentrated under reduced pressure to give the crude product (150 mg). Half of the crude product was purified by MDAP (Method A) to give the title compound as a red gum (24.9 mg).

LCMS (Method C): Rt=1.01 min, MH+ 455.

1H NMR (400 MHz, CDCl3) δ-ppm 8.00 (s, 1H), 7.81-7.71 (s, 2H), 7.52 (s, 1H), 4.31 (d, J=21 Hz, 2H), 4.00 (s, 3H), 3.91 (t, J=5 Hz, 2H), 3.84 (t, J=5 Hz, 2H), 3.00-2.83 (m, 4H), 2.71-2.62 (m, 2H), 2.38-2.18 (m, 8H), 2.02-1.63 (m, 4H).

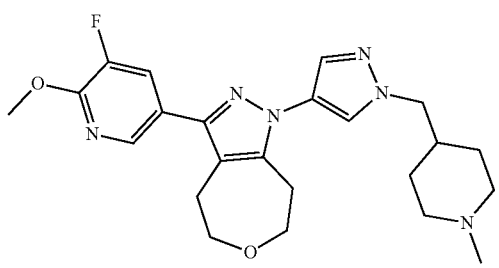 [SMILES: COc1ncc(-c2nn(-c3cnn(CC4CCN(C)CC4)c3)c3c2CCOCC3)cc1F]

A mixture of 3-(5-fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole (65 mg, 0.152 mmol) and a 37% by weight aqueous solution of formaldehyde (0.170 mL, 2.286 mmol) were combined in DMF (2 mL) and stirred under an atmosphere of nitrogen for 1 h. The reaction mixture was treated with STAB (81 mg, 0.381 mmol) and stirred overnight. The reaction was quenched using a saturated aqueous solution of sodium bicarbonate (5 mL), diluted with water (5 mL), then extracted with EtOAc (3×10 mL). The combined organic layer was washed with a 5% by weight aqueous solution of LiCl (2×15 mL), passed through a hydrophobic frit and concentrated under reduced pressure to give the crude product as a yellow oil. The crude product was purified by MDAP (Method A) to give the title compound as a white solid (16.9 mg, 24%).

LCMS (Method C): Rt=1.03 min, MH+ 441.

1H NMR (400 MHz, CDCl3) δ-ppm 8.09 (d, J=2 Hz, 1H), 7.65-7.57 (m, 3H), 4.06 (s, 3H), 4.02 (d, J=7 Hz, 2H), 3.87 (t, J=5 Hz, 4H), 2.98 (t, J=5 Hz, 2H), 2.94-2.82 (m, 4H), 2.28 (s, 3H), 1.93 (t, J=11 Hz, 3H), 1.64 (d, J=13 Hz, 2H), 1.46-1.32 (m, 2H).

1H NMR (400 MHz, CDCl3) δ-ppm 8.09 (d, J=2 Hz, 1H), 7.86 (s, 1H), 7.66-7.55 (m, 2H), 4.99-4.84 (m, 1H), 4.06 (s, 3H), 3.97 (t, J=5 Hz, 4H), 3.11-2.86 (m, 7H), 2.63-2.45 (m, 2H), 2.43 (s, 3H), 2.30-2.15 (m, 1H).

Example 44. (2R)-1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol

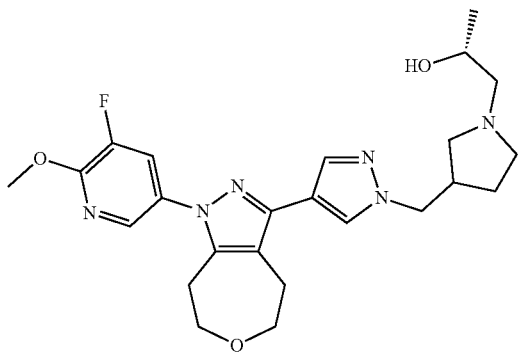 [SMILES: COc1ncc(-n2nc(-c3cnn(CC4CCN(C[C@@H](C)O)C4)c3)c3c2CCOCC3)cc1F]

A mixture of 1-(5-fluoro-6-methoxypyridin-3-yl)-3-(1-(pyrrolidin-3-ylmethyl)-1H-pyrazol-4-yl)-4,5,7,8-tetrahydro-1H-oxepino[4,5-c]pyrazole and 2-(5-fluoro-6-methoxypyridin-3-yl)-3-(1-(pyrrolidin-3-ylmethyl)-1H-pyrazol-4-yl)-4,5,7,8-tetrahydro-2H-oxepino[4,5-c]pyrazole (100 mg), (R)-2-methyloxirane (42.2 mg, 0.727 mmol), DIPEA (0.085 mL, 0.485 mmol) in EtOH (2 mL)

was heated at 70° C. for 1 h using a microwave. The reaction mixture was treated with MeOH (1 mL), concentrated under reduced pressure and purified by MDAP (Method A) to give the title compound as a colourless oil (36 mg).

LCMS (Method C): Rt=0.94 min, MH+ 471.

1H NMR (400 MHz, CDCl3) δ-ppm 7.98 (d, J=2 Hz, 1H), 7.75 (s, 1H), 7.68 (s, 1H), 7.53 (dd, J=10, 2 Hz, 1H), 4.13 (d, J=8 Hz, 2H), 4.08 (s, 3H), 3.91 (t, J=5 Hz, 2H), 3.86 (t, J=5 Hz, 2H), 3.82-3.70 (m, 1H), 2.99-2.89 (m, 5H), 2.89-2.57 (m, 4H), 2.57-2.38 (m, 3H), 2.25 (d, J=12 Hz, 1H), 2.08-1.91 (m, 1H), 1.13 (d, J=6 Hz, 3H).

Examples 45. and 46. (R)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol and (R)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol

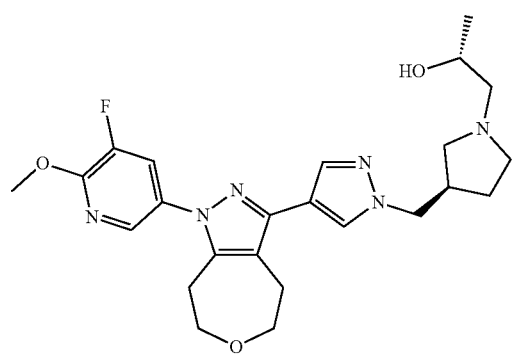

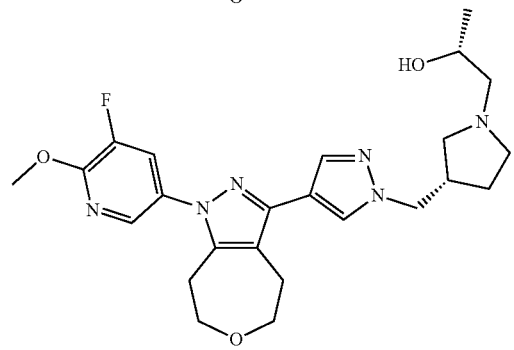

(2R)-1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol (Example 44, 36 mg) was separated into its two component enantiomers by preparative chiral HPLC using a 30 mm×25 cm Chiralpak AD-H column. The column was eluted with 40% EtOH (+0.2% isopropylamine)/heptane(+0.2% isopropylamine), using a flow rate of 30 mL/min. Appropriate fractions were combined and evaporated to give the two enantiomers:

Example 45.: 13 mg, clear glass. LCMS (Method C) Rt=0.94 min, MH+=471. Enantiomeric purity by chiral HPLC=>99.0% e.e.

Example 46.: 12 mg, clear glass. LCMS (Method C) Rt=0.94 min, MH+=471. Enantiomeric purity by chiral HPLC=>90.8% e.e.

Absolute stereochemistry was not assigned.

Example 47. (2S)-1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol

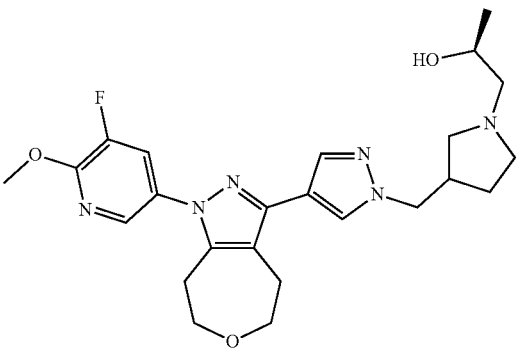 [SMILES: COc1ncc(-n2nc(-c3cnn(CC4CCN(C[C@H](C)O)C4)c3)c3c2CCOCC3)cc1F]

A mixture of 1-(5-fluoro-6-methoxypyridin-3-yl)-3-(1-(pyrrolidin-3-ylmethyl)-1H-pyrazol-4-yl)-4,5,7,8-tetrahydro-1H-oxepino[4,5-c]pyrazole and 2-(5-fluoro-6-methoxypyridin-3-yl)-3-(1-(pyrrolidin-3-ylmethyl)-1H-pyrazol-4-yl)-4,5,7,8-tetrahydro-2H-oxepino[4,5-c]pyrazole (100 mg), (S)-2-methyloxirane (42.2 mg, 0.727 mmol), DIPEA (0.085 mL, 0.485 mmol) in EtOH (2 mL) was heated at 70° C. for 1 h using a microwave. The reaction mixture was treated with MeOH (1 mL), concentrated under a stream of nitrogen and purified by MDAP (Method A) to give the title compound as a colourless, glassy oil (36 mg).

LCMS (Method C): Rt=0.94 min, MH+ 471.

1H NMR (400 MHz, CDCl3) δ-ppm 7.98 (d, J=2 Hz, 1H), 7.75 (s, 1H), 7.68 (s, 1H), 7.53 (dd, J=9, 2 Hz, 1H), 4.13 (d, J=8 Hz, 2H), 4.08 (s, 3H), 3.91 (t, J=5 Hz, 2H), 3.86 (t, J=5 Hz, 2H), 3.82-3.70 (m, 1H), 2.99-2.90 (m, 4H), 2.89-2.57 (m, 4H), 2.57-2.38 (m, 4H), 2.25 (d, J=14 Hz, 1H), 2.06-1.91 (m, 1H), 1.13 (d, J=6 Hz, 3H).

Example 48. and 49. (S)-1-((R)-3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol and (S)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol

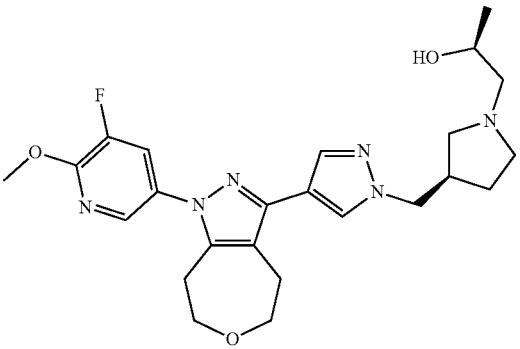

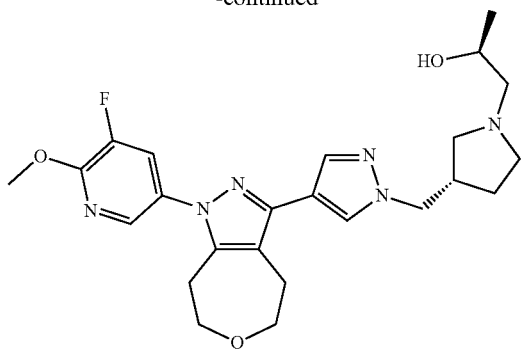

(2S)-1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol (Example 47, 34 mg) was separated into its two component enantiomers by preparative chiral HPLC using a 20 mm×25 cm Chiralpak IC column. The column was eluted with 40% EtOH (+0.2% isopropylamine)/heptane(+0.2% isopropylamine), using a flow rate of 20 mL/min. Appropriate fractions were combined and evaporated to give the two enantiomers:

Example 48.: 9 mg, clear glass. LCMS (Method C) Rt=0.94 min, MH⁺=471. Enantiomeric purity by chiral HPLC=>99.0% e.e.

Example 49.: 10 mg, clear glass. LCMS (Method C) Rt=0.94 min, MH⁺=471. Enantiomeric purity by chiral HPLC=>99.0% e.e.

Absolute stereochemistry was not assigned.

Example 50. 1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one

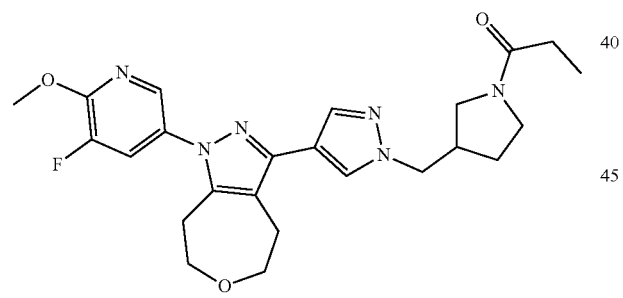

A solution of propionic acid (19.76 mg, 0.267 mmol) in DMF (1.25 mL) was treated with HATU (101 mg, 0.267 mmol) and DIPEA (0.085 mL, 0.485 mmol). The reaction mixture was stirred under an atmosphere of nitrogen at room temperature for 30 min. The reaction mixture was treated with a mixture of 1-(5-fluoro-6-methoxypyridin-3-yl)-3-(1-(pyrrolidin-3-ylmethyl)-1H-pyrazol-4-yl)-4,5,7,8-tetrahydro-1H-oxepino[4,5-c]pyrazole and 2-(5-fluoro-6-methoxypyridin-3-yl)-3-(1-(pyrrolidin-3-ylmethyl)-1H-pyrazol-4-yl)-4,5,7,8-tetrahydro-2H-oxepino[4,5-c]pyrazole (100 mg, 0.242 mmol) and DIPEA (0.085 mL, 0.485 mmol) in DMF (1.25 mL) and stirred for a further 2 h.

The reaction mixture was treated with MeOH (1 mL) and concentrated under reduced pressure. The residue was purified by MDAP (Method A) to give the title compound as a colourless oil (34 mg).

LCMS (Method C): Rt=0.93 min, MH⁺ 469.
¹H NMR (400 MHz, CDCl₃) δ-ppm 7.98 (d, J=2 Hz, 1H), 7.77 (d, J=6 Hz, 1H), 7.67 (s, 1H), 7.53 (dt, J=10, 2 Hz, 1H), 4.27-4.04 (m, 5H), 3.91 (t, J=5 Hz, 2H), 3.86 (t, J=5 Hz, 2H), 3.74-3.62 (m, 1H), 3.59-3.37 (m, 2H), 3.30-3.20 (m, 1H), 3.01-2.71 (m, 5H), 2.32-2.20 (m, 2H), 2.14-1.97 (m, 1H), 1.88-1.58 (m, 1H), 1.19-1.08 (m, 3H).

Example 51. and 52. (R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one and (S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one

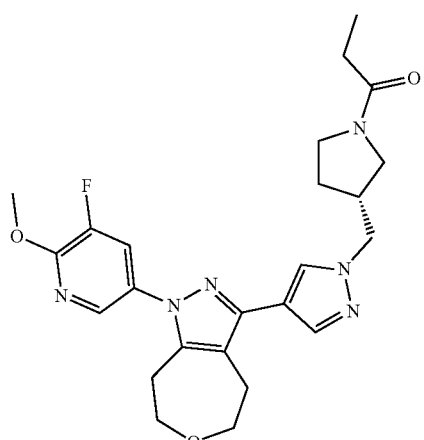

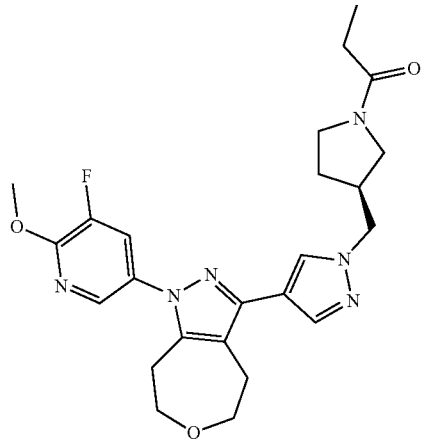

1-(3-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one (Example 50, 31 mg) was separated into its two component enantiomers by preparative chiral HPLC using a 30 mm×25 cm Chiralpak AS-H column. The column was eluted with 30% EtOH (+0.2% isopropylamine)/heptane(+0.2% isopropylamine), using a flow rate of 30 mL/min. Appropriate fractions were combined and evaporated to give the two enantiomers:

Example 51.: 11 mg, clear glass. LCMS (Method C) Rt=0.93 min, MH⁺=469. Enantiomeric purity by chiral HPLC=>99.0% e.e.

Example 52.: 12 mg, clear glass. LCMS (Method C) Rt=0.93 min, MH⁺=469. Enantiomeric purity by chiral HPLC=>92.8% e.e.

Absolute stereochemistry was not assigned.

Example 53. 7-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)-1,1-dimethyltetrahydro-1H-oxazolo[3,4-a]pyridin-3(5H)-one

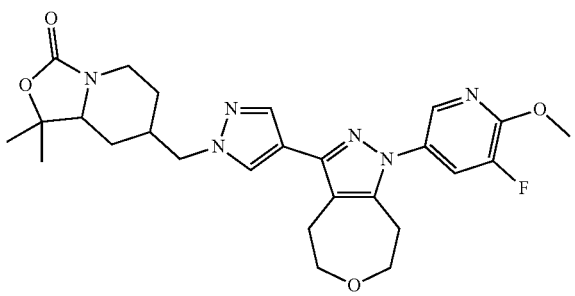

A solution of tert-butyl 4-(((tert-butyldiphenylsilyl)oxy)methyl)-2-(2-hydroxypropan-2-yl)piperidine-1-carboxylate (1786 mg, 3.49 mmol) in THF (30 mL) was treated with a 1 M solution of TBAF (3.80 mL, 3.8 mmol). The reaction mixture was stirred at room temperature for 2 h and quenched with a saturated solution of sodium hydrogen carbonate and extracted with EtOAc (3×30 ml). The reaction mixture was concentrated and purified by silica column chromatography using a 0 to 100% gradient of EtOAc in cyclohexane to give tert-butyl 4-(hydroxymethyl)-2-(2-hydroxypropan-2-yl)piperidine-1-carboxylate (785 mg, 95%).

A solution of tert-butyl 4-(hydroxymethyl)-2-(2-hydroxypropan-2-yl)piperidine-1-carboxylate (55 mg, 0.201 mmol) and pyridine (0.033 mL, 0.402 mmol) in DCM (1 mL) was treated with methanesulfonyl chloride (34.6 mg, 0.302 mmol). The reaction mixture was stirred at room temperature for 8 h and concentrated to give crude tert-butyl 2-(2-hydroxypropan-2-yl)-4-(((methylsulfonyl)oxy)methyl)piperidine-1-carboxylate (78 mg, >99%).

Sodium hydride (60% by weight suspension in mineral oils, 4.7 mg, 0.118 mmol) was added to a solution of 1-(5-fluoro-6-methoxypyridin-3-yl)-3-(1H-pyrazol-4-yl)-4,5,7,8-tetrahydro-1H-oxepino[4,5-c]pyrazole (30 mg, 0.091 mmol) in DMF (0.5 ml). The reaction mixture was stirred for 30 min and treated with a solution of crude tert-butyl 2-(2-hydroxypropan-2-yl)-4-(((methylsulfonyl)oxy)methyl)piperidine-1-carboxylate (50 mg, 0.142 mmol) in DMF (0.5 ml). The solution was stirred at room temperature for 3 h and at 60° C. for 1 h. The reaction mixture was concentrated and purified by MDAP (Method B) to give the title compound (3.6 mg, 8%).

LCMS (Method A): Rt=1.00 min, MH$^+$ 511.

Example 54. 1-(5-fluoro-6-methoxypyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole

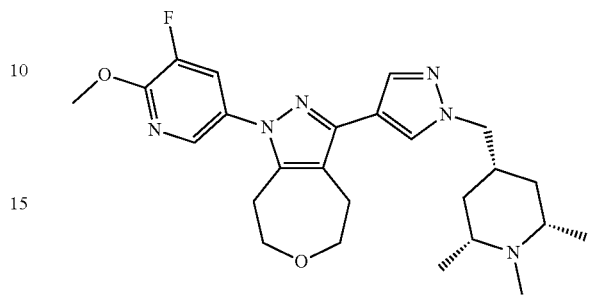

A mixture of 3-(1-(((2R,4r,6S)-2,6-dimethylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole (59 mg, 0.130 mmol) and a solution of formaldehyde (37% by weight, aqueous, 0.145 mL, 1.947 mmol) in DMF (2 mL) was stirred under an atmosphere of nitrogen for 2 h. The reaction mixture was treated with STAB (68.8 mg, 0.324 mmol) and stirred over the weekend.

The reaction mixture was treated with a saturated aqueous solution of sodium hydrogen carbonate (2 mL) in a dropwise manner, and stirred for 20 min. The reaction mixture was diluted further saturated aqueous sodium hydrogen carbonate solution (25 mL) and brine (25 mL) and partitioned with EtOAc (2×50 mL). The combined organic layer was passed through a hydrophobic frit, concentrated under reduced pressure and purified by MDAP (Method A) to give the title compound as an orange oil (20 mg, 33%).

LCMS (Method C): Rt=1.07 min, [M+H]$^+$=469.

$^1$H NMR (400 MHz, CDCl$_3$) 7.98 (d, J=2 Hz, 1H), 7.75 (s, 1H), 7.64 (s, 1H), 7.52 (dd, J=10, 2 Hz, 1H), 4.07 (s, 3H), 3.96 (d, J=7 Hz, 2H), 3.91 (t, J=5 Hz, 2H), 3.86 (t, J=5 Hz, 2H), 3.00-2.88 (m, 4H), 2.24 (s, 3H), 2.17-1.99 (m, 3H), 1.60-1.50 (m, 4H), 1.12 (d, J=6 Hz, 6H).

Example 55. 1-(6-Methoxy-5-methylpyridin-3-yl)-3-(3-methyl-1H-pyrazol-5-yl)-4,5,7,8-tetrahydro-1H-oxepino[4,5-c]pyrazole

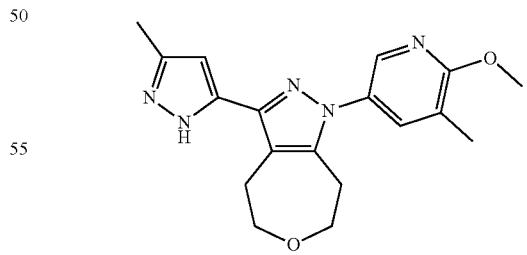

A mixture of 3-bromo-1-(6-methoxy-5-methylpyridin-3-yl)-4,5,7,8-tetrahydro-1H-oxepino[4,5-c]pyrazole (22 mg, 0.052 mmol) and (1-(tert-butoxycarbonyl)-3-methyl-1H-pyrazol-5-yl)boronic acid (25 mg, 0.111 mmol) in 1,4-dioxane (0.5 mL) and water (0.215 mL) was treated with PdCl$_2$(dtbpf) (3 mg, 4.60 μmol) and heated at 80° C. using a microwave for 60 min. The reaction mixture was treated with a solution of (1-(tert-butoxycarbonyl)-3-methyl-1H-pyrazol-5-yl)boronic acid (25 mg, 0.111 mmol) in 1,4-dioxane (0.05 mL) and a solution of potassium phosphate (21 mg, 0.099 mmol) in in water (0.02 mL). The reaction mixture was heated at 80° C. using a microwave for 120 min.

Separately a mixture of 3-bromo-1-(6-methoxy-5-methylpyridin-3-yl)-4,5,7,8-tetrahydro-1H-oxepino[4,5-c]pyrazole (22 mg, 0.052 mmol) and (1-(tert-butoxycarbonyl)-3-methyl-1H-pyrazol-5-yl)boronic acid (25 mg, 0.111 mmol) in 1,4-dioxane (0.550 mL) and water (0.215 mL) was treated with [1,3-bis(2,6-diisopropylphenyl)imidazole-2-ylidene](3-chloropyridyl)dichloropalladium (3.5 mg, 5.20 µmol). The mixture was heated at 80° C. using a microwave for 60 min. The reaction mixture was treated with a solution of potassium phosphate (21 mg, 0.099 mmol) in water (0.02 mL) and heated at 80° C. using a microwave 120 min.

Separately a mixture of 3-bromo-1-(6-methoxy-5-methylpyridin-3-yl)-4,5,7,8-tetrahydro-1H-oxepino[4,5-c]pyrazole (22 mg, 0.052 mmol) and (1-(tert-butoxycarbonyl)-3-methyl-1H-pyrazol-5-yl)boronic acid (25 mg, 0.111 mmol) in 1,4-dioxane (0.5 mL) and water (0.215 mL) was treated with XPhos Pd G2 (4.09 mg, 5.20 µmol). The mixture was heated at 80° C. using a microwave 60 min. The reaction mixture was treated with a solution of (1-(tert-butoxycarbonyl)-3-methyl-1H-pyrazol-5-yl)boronic acid (25 mg, 0.111 mmol) dissolved in 1,4-dioxane (0.05 mL) and a solution of potassium phosphate (21 mg, 0.099 mmol) in water (0.02 mL) and heated at 80° C. using a microwave for 120 min.

The three reaction mixtures were combined and partitioned with DCM (10 mL) and water (10 mL). The organic layer was isolated and the aqueous layer was extracted with further DCM (3×10 mL). The combined organic layers were passed through a hydrophobic frit and concentrated under reduced pressure to give the crude product (123 mg). The crude product was purified using MDAP (Method A) to give the title compound (9 mg).

LCMS (Method C): Rt=0.96 min, MH+ 340.

Example 56. 1-(5-Fluoro-6-methoxypyridin-3-yl)-3-(5-methyl-1H-pyrazol-4-yl)-4,5,7,8-tetrahydro-1H-oxepino[4,5-c]pyrazole

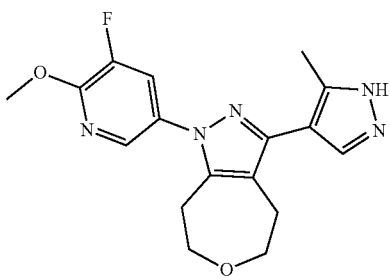 [SMILES: COc1ncc(-n2nc(-c3cn[nH]c3C)c3c2CCOCC3)cc1F]

A mixture of 3-bromo-1-(5-fluoro-6-methoxypyridin-3-yl)-4,5,7,8-tetrahydro-1H-oxepino[4,5-c]pyrazole (50 mg, 0.146 mmol), 3-methyl-4-(4,4,5,5-tetramethyl-1,3,2-dioxaborolan-2-yl)-1H-pyrazole (68 mg, 0.327 mmol), potassium phosphate (70 mg, 0.330 mmol), dicyclohexyl(2',4',6'-triisopropyl-[1,1'-biphenyl]-2-yl)phosphine (6 mg, 0.013 mmol) and XPhos Pd G2 (10 mg, 0.013 mmol) were added to a microwave vial. The vial was capped and purged with nitrogen. The reaction mixture was treated with EtOH (0.250 ml) and water (0.250 ml) were added and vial was purged again. The reaction mixture was heated at 100° C. for 1 h, then overnight at 100° C.

Separately a mixture of 3-bromo-1-(5-fluoro-6-methoxypyridin-3-yl)-4,5,7,8-tetrahydro-1H-oxepino[4,5-c]pyrazole (20 mg, 0.058 mmol), 3-methyl-4-(4,4,5,5-tetramethyl-1,3,2-dioxaborolan-2-yl)-1H-pyrazole (12 mg, 0.058 mmol), potassium phosphate (27 mg, 0.127 mmol) and XPhos Pd G2 (6 mg, 7.63 µmol) were added to a microwave vial. The vial was capped and purged with nitrogen. The reaction mixture was treated with 1,4-dioxane (0.5 mL) and water (0.125 ml) and heated at 80° C. overnight. The reaction mixture was treated with a solution of 3-methyl-4-(4,4,5,5-tetramethyl-1,3,2-dioxaborolan-2-yl)-1H-pyrazole (12 mg, 0.058 mmol) in 0.05 mL of 1,4-dioxane under nitrogen. The reaction mixture was heated at 80° C. for 2 h, then at 100° C. degrees for further 4 h. The reaction mixture was treated with XPhos Pd G2 (3 mg, 3.81 µmol) and dicyclohexyl(2',4',6'-triisopropyl-[1,1'-biphenyl]-2-yl)phosphine (3 mg, 6.29 µmol) and heated at 100° C. overnight.

The two batches of reaction mixtures were combined and passed through Celite®, washing with MeOH. Then the filtrate was concentrated under reduced pressure and the residue partitioned with EtOAc (10 mL) and water (10 mL). The organic layer was isolated and the aqueous layer extracted with further EtOAc (3×10 mL). The combined organic layer was passed through a hydrophobic frit and concentrated under reduced pressure to give the crude product (144 mg). The crude product was purified by MDAP (Method A) to give the title compound (15 mg).

LCMS (Method C): Rt=0.88 min, MH+ 344.

Example 57. 3-(1,3-Dimethyl-1H-pyrazol-5-yl)-1-(6-methoxy-5-methylpyridin-3-yl)-4,5,7,8-tetrahydro-1H-oxepino[4,5-c]pyrazole

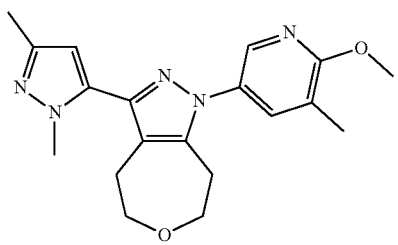

A solution of 1-(6-methoxy-5-methylpyridin-3-yl)-3-(3-methyl-1H-pyrazol-5-yl)-4,5,7,8-tetrahydro-1H-oxepino[4,5-c]pyrazole (34 mg, 0.100 mmol) in THF (1 mL) at room temperature under an atmosphere of nitrogen was treated with sodium hydride (60% by weight suspension in mineral oils, 4.81 mg, 0.120 mmol). The resulting mixture was stirred for 1 h and treated with iodomethane (7 µl, 0.112 mmol). The reaction mixture was stirred at room temperature for 1 h and treated with water (10 mL) in a dropwise fashion.

The reaction mixture was partitioned with EtOAc (10 mL) and the organic layer was isolated. The aqueous layer was extracted with EtOAc (3×10 mL) and the combined organic layer concentrated under reduced pressure to give crude product (33 mg). The crude product was purified by MDAP (Method A) to give the title compound (16 mg).

LCMS (Method C): Rt=1.03 min, MH+ 354.

Example 58. 1-(Dimethylamino)-3-(4-(1-(5-fluoro-6-methoxypyridin-3-yl)-4,5,7,8-tetrahydro-1H-oxepino[4,5-c]pyrazol-3-yl)-1H-pyrazol-1-yl)propan-2-ol

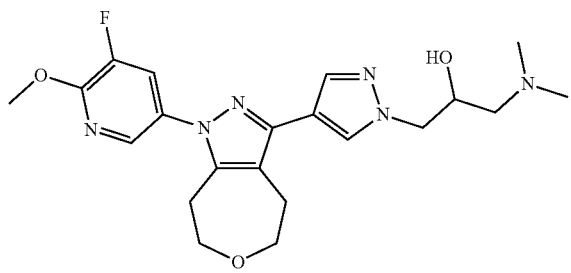

A microwave vial was charged with 1-(5-fluoro-6-methoxypyridin-3-yl)-3-(1H-pyrazol-4-yl)-4,5,7,8-tetrahydro-1H-oxepino[4,5-c]pyrazole (50 mg, 0.152 mmol), $Cs_2CO_3$ (77 mg, 0.236 mmol), 2-(chloromethyl)oxirane (0.024 mL, 0.304 mmol) and DMF (5 mL). The vial was sealed and heated using a microwave at 60° C. for 1 h 45 min. The reaction mixture was treated with a 2 M solution of dimethylamine in THF (0.190 mL, 0.380 mmol) and heated using a microwave at 70° C. 7 h. The reaction mixture was diluted with water (15 mL) and extracted with EtOAc (3×20 mL). The combined organic layer was passed through a hydrophobic frit and concentrated under reduced pressure. The material was purified by MDAP (Method B) to give the title compound as a white solid (15 mg, 22%).

LCMS (Method C): Rt=0.87 min, MH+ 431.

Example 59. 3-(1-((3-Fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole

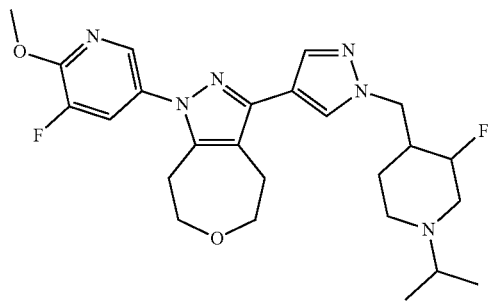 [SMILES: COc1ncc(-n2nc(-c3cnn(CC4CCN(C(C)C)CC4F)c3)c3c2CCOCC3)cc1F]

A mixture of 1-(5-fluoro-6-methoxypyridin-3-yl)-3-(1-((3-fluoropiperidin-4-yl)methyl)-1H-pyrazol-4-yl)-4,5,7,8-tetrahydro-1H-oxepino[4,5-c]pyrazole (52 mg, 0.117 mmol), DMF (0.6 mL) and acetone (0.5 mL) was stirred under an atmosphere of nitrogen for 1 h. The reaction mixture was treated with STAB (99 mg, 0.468 mmol) and stirred for 3 h. The reaction was quenched with a saturated aqueous solution of sodium bicarbonate (5 mL), and extracted with EtOAc (3×15 mL). The combined organic layer was washed with an aqueous solution of LiCl (2×50 mL) and concentrated under reduced pressure. The crude material was purified by MDAP (Method B) to give the title compound (37 mg, 64%).

LCMS (Method C): Rt=1.09 min, MH+ 487.

Example 60. 3-(1-(((3R,4S)-3-Fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole

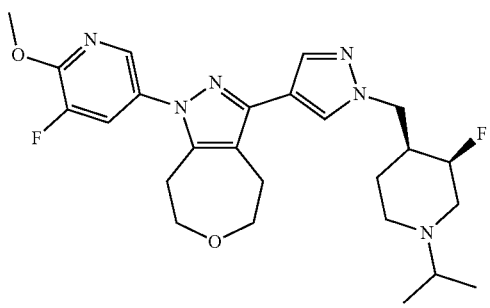 [SMILES: COc1ncc(-n2nc(-c3cnn(C[C@@H]4CCN(C(C)C)C[C@@H]4F)c3)c3c2CCOCC3)cc1F]

A mixture of 1-(5-fluoro-6-methoxypyridin-3-yl)-3-(1-(((3R,4S)-3-fluoropiperidin-4-yl)methyl)-1H-pyrazol-4-yl)-4,5,7,8-tetrahydro-1H-oxepino[4,5-c]pyrazole (57 mg, 0.128 mmol), acetone (0.5 mL) and DMF (0.6 mL) was stirred at room temperature under an atmosphere of nitrogen for 1 h. The reaction mixture was treated with STAB (109 mg, 0.513 mmol) and stirred for 3 h. The reaction was quenched with a saturated aqueous solution of sodium bicarbonate (5 mL), and extracted with EtOAc (3×15 mL). The combined organic layer was washed with an aqueous solution of LiCl (2×50 mL) and concentrated under reduced pressure. The crude material was purified by MDAP (Method B) to give the title compound (35 mg, 55%).

LCMS (Method C): Rt=1.15 min, MH+ 487.

Example 61. 5-(3-(1-((1-Isopropylpyrrolidin-3-yl)methyl)-1H-pyrazol-4-yl-4,5,7,8-tetrahydro-1H-oxepino[4,5-c]pyrazol-1-yl)-2-methoxynicotinonitrile

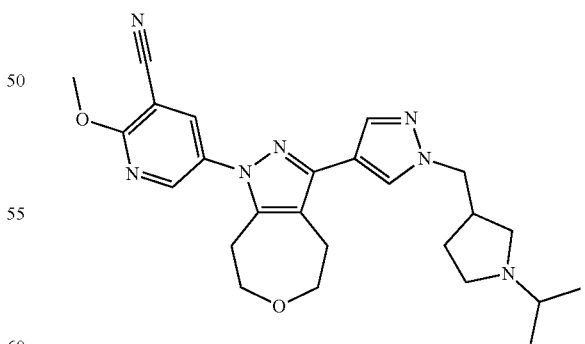

A mixture of 2-methoxy-5-(3-(1-(pyrrolidin-3-ylmethyl)-1H-pyrazol-4-yl)-4,5,7,8-tetrahydro-1H-oxepino[4,5-c]pyrazol-1-yl)nicotinonitrile (35 mg, 0.050 mmol) and acetone (1 mL) was stirred under an atmosphere of nitrogen for 30 min at room temperature. The reaction mixture was treated with STAB (42.4 mg, 0.200 mmol) and stirred overnight. The reaction was quenched with a saturated aqueous solution of sodium bicarbonate (5 mL), and partitioned with EtOAc (10 mL). The aqueous layer was extracted with EtOAc (3×15 mL). The combined organic layer was passed through a hydrophobic frit and concentrated under reduced pressure to give crude product (56 mg). The crude product was purified by MDAP (Method A) to give the title compound (4 mg, 16%).

LCMS (Method C): Rt=1.05 min, MH+ 462.

Example 62. 1-(4-((4-(1-(5-Fluoro-6-methoxypyridin-3-yl)-4,5,7,8-tetrahydro-1H-oxepino[4,5-c]pyrazol-3-yl)-1H-pyrazol-1-yl)methyl)piperidin-1-yl)propan-1-one

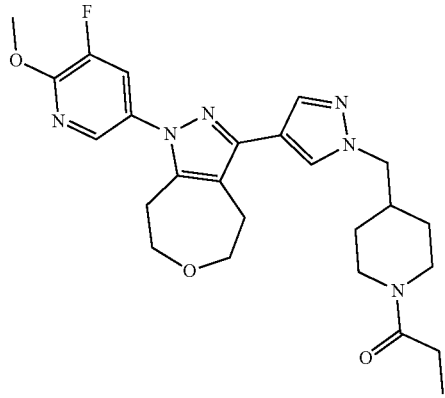 [SMILES: CCC(=O)N1CCC(Cn2cc(-c3nn(-c4cnc(OC)c(F)c4)c4c3CCOCC4)cn2)CC1]

A solution of 1-(5-fluoro-6-methoxypyridin-3-yl)-3-(1-(piperidin-4-ylmethyl)-1H-pyrazol-4-yl)-4,5,7,8-tetrahydro-1H-oxepino[4,5-c]pyrazole (97 mg, 0.227 mmol) in DCM (2.5 mL) under an atmosphere of nitrogen was treated with triethylamine (0.063 mL, 0.455 mmol) and propionyl chloride (0.030 mL, 0.341 mmol). The reaction mixture was stirred at room temperature overnight then quenched with sodium bicarbonate (10 mL) and extracted with DCM (3×10 mL). The combined organic layer was passed through a hydrophobic frit and concentrated under reduced pressure to give crude product (102 mg). The crude product was purified by MDAP (Method A) to give the title compound (37 mg, 32%).

LCMS (Method C): Rt=0.96 min, MH+ 483.

Example 63. 1-(1-(((2R,4r,6S)-2,6-Dimethylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole

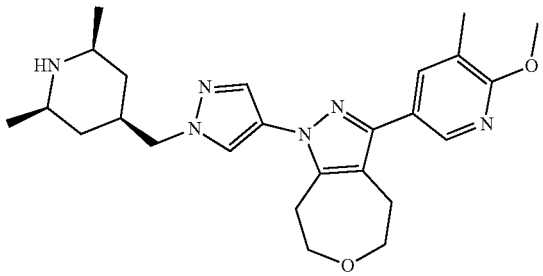

Prepared using the general Boc-deprotection procedure from (2R,4r,6S)-tert-butyl 4-((4-(3-(6-methoxy-5-methylpyridin-3-yl)-4,5,7,8-tetrahydro-1H-oxepino[4,5-c]pyrazol-1-yl)-1H-pyrazol-1-yl)methyl)-2,6-dimethylpiperidine-1-carboxylate (33 mg, 0.060 mmol), DCM (0.5 mL) and TFA (0.185 mL), to give the title compound as a brown solid (27 mg).

LCMS (Method C): Rt=1.03 min, MH+=451.

Example 64. N-(5-(3-(1-(((2R,6S)-2,6-Dimethyltetrahydro-2H-pyran-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide

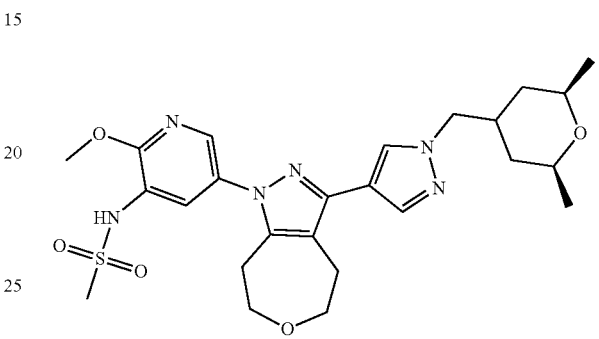

A mixture of $K_2CO_3$ (36.4 mg, 0.264 mmol), 1-(((2R,6S)-2,6-dimethyltetrahydro-2H-pyran-4-yl)methyl)-4-(4,4,5,5-tetramethyl-1,3,2-dioxaborolan-2-yl)-1H-pyrazole (84 mg, 0.264 mmol) and N-(5-(3-bromo-4,5,7,8-tetrahydro-1H-oxepino[4,5-c]pyrazol-1-yl)-2-methoxypyridin-3-yl)methanesulfonamide (110 mg, 0.264 mmol) in 1,4-dioxane (5 mL) and water (1.000 mL) at room temperature and under an atmosphere of argon was treated with $PdCl_2$(dppf)-DCM (21.53 mg, 0.026 mmol) and heated in a sealed tube with stirring at 100° C. for 16 h.

The reaction mixture was diluted with water (10 mL) and extracted with EtOAc (30 mL×3). The combined organic layer was washed with saturated brine (25 mL), dried over sodium sulphate and concentrated under reduced pressure to give the crude product as a yellow liquid (150 mg). The crude product was purified by silica column chromatography, eluting with a 2% solution of MeOH in DCM to give crude product as a yellow solid (20 mg).

Separately a mixture of $K_2CO_3$ (159 mg, 1.150 mmol), 1-(((2R,6S)-2,6-dimethyltetrahydro-2H-pyran-4-yl)methyl)-4-(4,4,5,5-tetramethyl-1,3,2-dioxaborolan-2-yl)-1H-pyrazole (123 mg, 0.383 mmol) and N-(5-(3-bromo-4,5,7,8-tetrahydro-1H-oxepino[4,5-c]pyrazol-1-yl)-2-methoxypyridin-3-yl)methanesulfonamide (160 mg, 0.383 mmol) in 1,4-dioxane (5 mL) and water (1.000 mL) at room temperature and under an atmosphere of argon was treated with $PdCl_2$(dppf)-DCM (31.3 mg, 0.038 mmol) and heated in a sealed tube with stirring at 100° C. for 16 h. The reaction mixture was diluted with water (10 mL) and extracted with EtOAc (30 mL×3). The combined organic layer was washed with saturated brine (25 mL), dried over sodium sulphate and concentrated under reduced pressure to give the crude product as a yellow liquid (210 mg). The crude product was purified by silica column chromatography, eluting with a 2% solution of MeOH in DCM to give crude product as a brown solid (35 mg).

The two batches of crude product were purified by preparative TLC using silica (GF254) and a 50% solution of EtOAc in hexane. The silica with desired product absorbed to it was scratched off and dissolved in a 10% solution of MeOH in DCM (20 mL) then filtered using Celite® and washed with a 10% solution of MeOH in DCM (10 mL×2). The filtrate was evaporated under reduced pressure to give the title compound as a brown solid (40 mg).

LCMS (Method A): Rt=0.95 min, MH$^+$=531.

Example 65. 3-(1-(((2R,4r,6S)-2,6-Dimethylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole

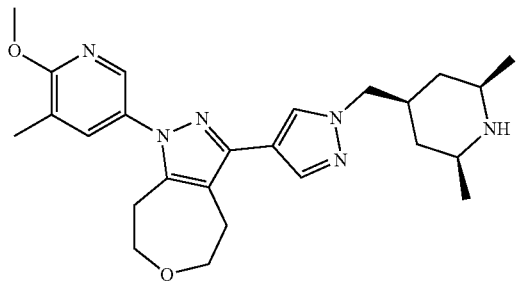 [SMILES: COc1ncc(-n2nc(-c3cnn(C[C@H]4C[C@@H](C)N[C@@H](C)C4)c3)c3c2CCOCC3)cc1C]

Prepared using the general Boc deprotection procedure from (2R,4r,6S)-tert-butyl 4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)-2,6-dimethylpiperidine-1-carboxylate (447 mg, 0.649 mmol), DCM (4 mL), and TFA (1.00 mL). A portion of the crude product (135 mg) was purified by MDAP (Method A) to give the title compound as a clear oil (8 mg).

LCMS (Method C): Rt=1.02 min, MH$^+$=451.

Example 66. 3-(6-Methoxy-5-methylpyridin-3-yl)-1-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole

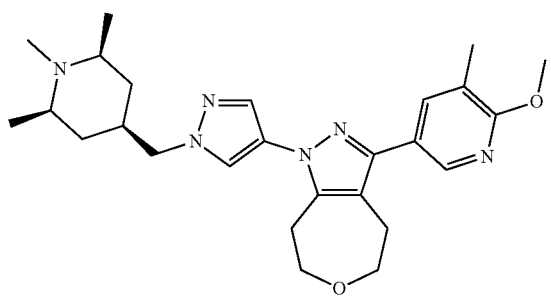

A mixture of 1-(1-(((2R,4r,6S)-2,6-dimethylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole (20 mg, 0.044 mmol), a 37% by weight aqueous solution of formaldehyde (0.264 mL, 3.55 mmol), DMF (0.2 mL) was stirred under an atmosphere of nitrogen for 1 h. The reaction mixture was treated with STAB (23.5 mg, 0.111 mmol) and stirred for 48 h. The reaction mixture was treated with a 37% by weight aqueous solution of formaldehyde (0.132 mL, 1.775 mmol) and STAB (23.5 mg, 0.111 mmol) and the reaction was stirred for 8 h. The reaction mixture was treated with AcOH (2.54 µL, 0.044 mmol) and stirred overnight at 50° C. The reaction mixture was concentrated under reduced pressure and purified by MDAP (Method A) to give the title compound as a colourless glassy oil (9 mg, 44%).

LCMS (Method C): Rt=1.11 min, MH$^+$=465.

$^1$H NMR (400 MHz, MeOD) δ ppm 8.14 (d, J=2 Hz, 1H), 7.68-7.64 (m, 1H), 7.82 (s, 1H), 7.81 (s, 1H), 3.99 (s, 3H), 3.96 (d, J=7 Hz, 2H), 3.91-3.82 (m, 4H), 2.98 (t, J=5 Hz, 2H), 2.91 (t, J=5 Hz, 2H), 2.26 (s, 3H), 2.22 (s, 3H), 2.15-2.02 (m, 3H), 1.63-1.54 (m, 2H), 1.19-1.07 (m, 8H).

Example 67. 1-(1-((1-Isopropylpiperidin-4-yl)methyl)-1H-pyrazol-4-yl)-3-(6-methoxypyridin-3-yl)-4,5,7,8-tetrahydro-1H-oxepino[4,5-c]pyrazole

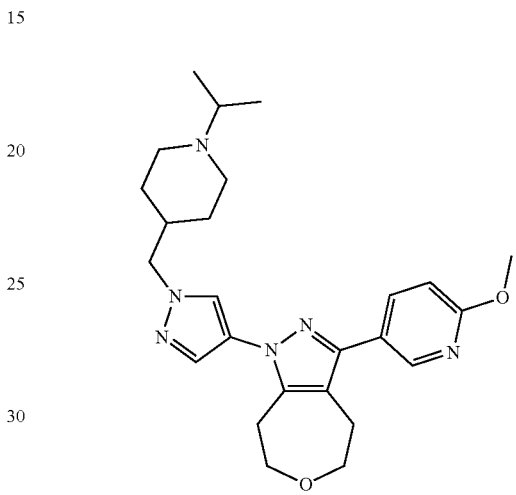

Prepared using the general Suzuki coupling procedure using 3-bromo-1-(1-(((1-isopropylpiperidin-4-yl)methyl)-1H-pyrazol-4-yl)-4,5,7,8-tetrahydro-1H-oxepino[4,5-c]pyrazole (20 mg, 0.047 mmol), (6-methoxypyridin-3-yl)boronic acid (14.48 mg, 0.095 mmol), tripotassium phosphate (20.10 mg, 0.095 mmol), XPhos Pd G2 (2.61 mg, 3.31 µmol), 1,4-dioxane (0.4 ml) and water (0.100 ml), to give the title compound as an oil (4.4 mg, 21%).

LCMS (Method C): Rt=1.00 min, MH$^+$=451.

Example 68. 1-(6-Methoxy-5-methylpyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole

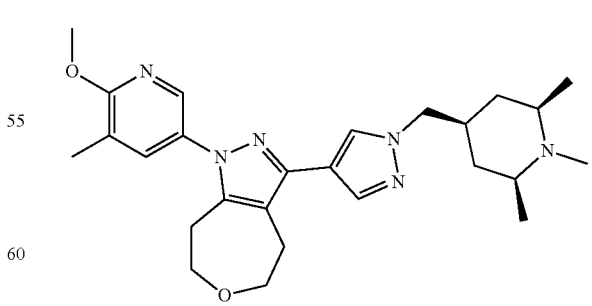

A solution of 3-(1-(((2R,4r,6S)-2,6-dimethylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole (186 mg, 0.413 mmol) in MeOH (2 mL) was treated with formic acid (0.055 mL, 1.445 mmol) and an aqueous solution of formaldehyde (36% by weight, 0.063 mL, 0.826 mmol). The reaction mixture was heated in the microwave 100° C. for 2 h, then treated with a further portion of formaldehyde (0.063 mL, 0.826 mmol) and formic acid (0.055 mL, 1.445 mmol) and heated for 1 h. The mixture was transferred to a microwave vial and further portions of both formaldehyde (0.063 mL, 0.826 mmol) and formic acid (0.055 mL, 1.445 mmol) were added. The mixture was heated in a microwave to 100° C. for 1 h. The reaction mixture was treated with a further portion of aqueous solution of formaldehyde (36% by weight, 0.063 mL, 0.826 mmol) and formic acid (0.055 mL, 1.445 mmol) and heated in a microwave at 110° C. for 1 h. The reaction mixture was treated dropwise with an aqueous solution of sodium hydrogen carbonate (3 mL) and stirred for 20 min. The reaction mixture was treated with further aqueous sodium hydrogen carbonate solution and extracted with EtOAc (2×20 mL). The combined organic layer was passed through a hydrophobic frit, and concentrated under reduced pressure to give crude product (167 mg). The crude product was purified by reverse phase chromatography using a 19 mm×25 cm Xterra® Prep RP$_{18}$ OBD™ column, eluting with a 30 to 90% gradient of MeCN and 10 mM ammonium bicarbonate in water to give the title compound as a white, oily precipitate (19.8 mg, 82% purity).

LCMS (Method C): Rt=1.09 min, MH$^+$=465.

$^1$H NMR (400 MHz, CDCl$_3$) δ-ppm 8.00 (d, J=2 Hz, 1H), 7.76 (s, 1H), 7.65 (s, 1H), 7.52 (d, J=2 Hz, 1H), 4.01 (s, 3H), 4.00-3.89 (m, 5H), 3.85 (t, J=5 Hz, 2H), 2.98-2.90 (m, 4H), 2.37-1.96 (m, 10H), 1.26-1.03 (m, 8H).

Example 69. N-(5-(3-(2-(4-(2-Hydroxypropan-2-yl)piperidin-1-yl)ethoxy)-4,5,7,8-tetrahydro-1H-oxepino[4,5-c]pyrazol-1-yl)-2-methoxypyridin-3-yl)methanesulfonamide

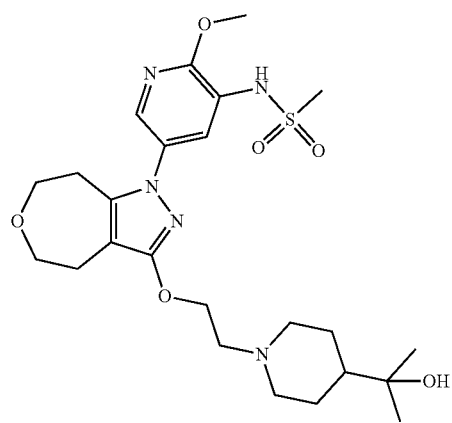 [SMILES: COc1ncc(-n2nc(OCCN3CCC(C(C)(C)O)CC3)c3c2CCOCC3)cc1NS(C)(=O)=O]

To a microwave vial was added N-(5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxypyridin-3-yl)-N-(4-methoxybenzyl)methanesulfonamide (80 mg, 0.087 mmol) dissolved in DCM (1 mL), followed by TFA (0.5 mL, 6.49 mmol). The reaction mixture was heated at 50° C. for 105 min in a microwave reactor. NaHCO$_3$ (1 mL) was added to quench the reaction mixture. The reaction mixture was transferred to a separating funnel, partitioned with DCM (5 mL) and the aqueous layer was extracted with further DCM (3×5 mL). The combined organic layer was passed through a hydrophobic frit and concentrated under reduced pressure. The crude product was purified by MDAP (Method A) to give the title compound. (5 mg, 10%).

LCMS (Method C): Rt=0.69 min, MH$^+$=524.

$^1$H NMR (400 MHz, MeOD) δ ppm 7.91 (d, J=3 Hz, 1H), 7.74 (d, J=3 Hz, 1H), 4.36 (t, J=6 Hz, 2H), 4.05 (s, 3H), 3.84 (dt, J=11, 5 Hz, 4H), 3.15 (d, J=11 Hz, 2H), 3.03 (s, 3H), 2.85 (dt, J=19, 5 Hz, 4H), 2.70 (t, J=5. Hz, 2H), 2.19-2.09 (m, 2H), 1.79 (d, J=12 Hz, 2H), 1.53-1.40 (m, 2H), 1.35 (d, J=12 Hz, 1H), 1.16 (s, 6H).

Example 70. 2-(1-(2-((1-(6-Methoxy-5-methylpyridin-3-yl)-4,5,7,8-tetrahydro-1H-oxepino[4,5-c]pyrazol-3-yl)oxy)ethyl)piperidin-4-yl)propan-2-ol. Formate Salt

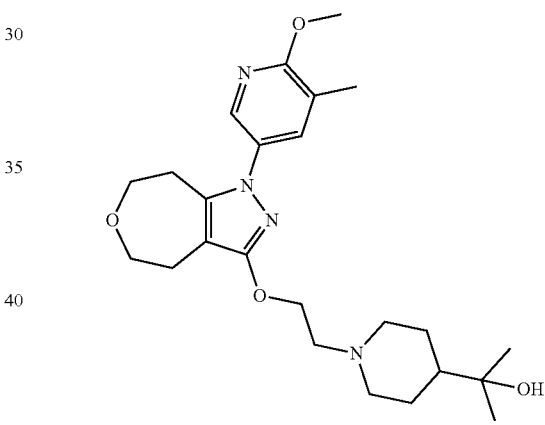

2-(tributylphosphoranylidene)acetonitrile (263 mg, 1.090 mmol) was added to a solution of 1-(6-methoxy-5-methylpyridin-3-yl)-4,5,7,8-tetrahydro-1H-oxepino[4,5-c]pyrazol-3-ol (100 mg, 0.363 mmol) and 2-(1-(2-hydroxyethyl)piperidin-4-yl)propan-2-ol (68.0 mg, 0.363 mmol) in toluene (3 mL). The reaction mixture was stirred at 100° C. for 12 h, then purified by MDAP (Method B) to give the title compound (110 mg, 62%).

LCMS (Method A): Rt=0.62 min, MH$^+$=445.

$^1$H NMR (400 MHz, CDCl$_3$) δ ppm 8.40 (s, 1H), 7.94 (d, J=2 Hz, 1H), 7.45 (d, J=2 Hz, 1H), 4.63-4.52 (m, 2H), 4.00 (s, 3H), 3.84 (dt, J=20, 5 Hz, 4H), 3.64 (d, J=12 Hz, 2H), 3.38-3.29 (m, 2H), 2.91-2.81 (m, 2H), 2.74-2.60 (m, 4H), 2.25 (s, 3H), 1.96-1.78 (m, 4H), 1.54-1.43 (m, 1H), 1.22 (s, 6H)

Example 71. 2-(1-(2-((1-(5-(Fluoromethyl)-6-methoxypyridin-3-yl)-4,5,7,8-tetrahydro-1H-oxepino[4,5-c]pyrazol-3-yl)oxy)ethyl)piperidin-4-yl)propan-2-ol

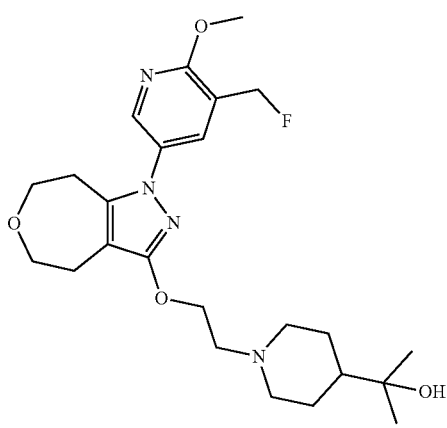 [SMILES: COc1ncc(-n2nc(OCCN3CCC(C(C)(C)O)CC3)c3c2CCOCC3)cc1CF]

A microwave vial was charged with 2-(tributylphosphoranylidene)acetonitrile (0.081 mL, 0.307 mmol) and 2-(1-(2-hydroxyethyl)piperidin-4-yl)propan-2-ol (59 mg, 0.315 mmol). The vial was sealed and purged with nitrogen. The reaction mixture was treated with a solution of 1-(5-(fluoromethyl)-6-methoxypyridin-3-yl)-4,5,7,8-tetrahydro-1H-oxepino[4,5-c]pyrazol-3-ol (60 mg, 0.153 mmol) in toluene (1.5 mL). The reaction mixture was repurged and heated at 100° C. for 2 h. The reaction mixture was concentrated under a stream of nitrogen and the residue was taken up in water (10 mL) and partitioned with EtOAc (10 mL). The aqueous layer was extracted with further EtOAc (3×10 mL) and the combined organic layer was passed through a hydrophobic frit and concentrated under reduced pressure. The crude product was purified by MDAP (Method B) to give the title compound (6.5 mg, 9%).

LCMS (Method A): Rt=0.62 min, MH$^+$=463.

$^1$H NMR (400 MHz, CDCl$_3$) δ ppm 8.46 (br. s., 1H), 8.10 (d, J=2 Hz, 1H), 7.73 (d, J=2 Hz, 1H), 5.51 (s, 1H), 5.39 (s, 1H), 4.51 (t, J=5 Hz, 2H), 4.02 (s, 3H), 3.85 (dt, J=17, 5 Hz, 4H), 3.43 (d, J=11 Hz, 2H), 3.13 (t, J=5 Hz, 2H), 2.92-2.81 (m, 2H), 2.76-2.66 (m, 2H), 2.52-2.37 (m, 2H), 1.92-1.78 (m, 2H), 1.70 (qd, J=13, 4 Hz, 2H), 1.48-1.34 (m, 1H), 1.21 (s, 6H)

Example 72. 2-(1-(2-((1-(5-Fluoro-6-methoxypyridin-3-yl)-4,5,7,8-tetrahydro-1H-oxepino[4,5-c]pyrazol-3-yl)oxy)ethyl)piperidin-4-yl)propan-2-ol. Formate Salt

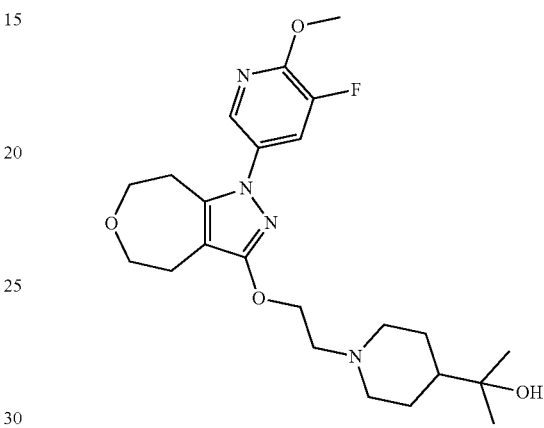

A microwave vial was charged with 2-(tributylphosphoranylidene)acetonitrile (0.23 mL, 0.877 mmol) and 2-(1-(2-hydroxyethyl)piperidin-4-yl)propan-2-ol (167 mg, 0.892 mmol). The vial was sealed and purged with nitrogen and the reaction mixture treated with a solution of 1-(5-fluoro-6-methoxypyridin-3-yl)-4,5,7,8-tetrahydro-1H-oxepino[4,5-c]pyrazol-3-ol (165 mg, 0.443 mmol) in toluene (4 mL). The vial was repurged and the mixture was heated at 100° C. for 2 h then concentrated under a stream of nitrogen. The residue was taken up in water (5 mL) and partitioned with EtOAc (5 mL). The aqueous layer was extracted with further EtOAc (4×5 mL) and the combined organic layer was passed through a hydrophobic frit and concentrated under reduced pressure. The crude product was purified by MDAP (Method B) to give the title compound (33 mg, 14%).

LCMS (Method A): Rt=0.62 min, MH$^+$=449.

$^1$H NMR (400 MHz, CDCl$_3$) δ ppm 8.36 (s, 1H), 7.89 (d, J=2 Hz, 1H), 7.45 (dd, J=10, 2 Hz, 1H), 4.50 (t, J=5 Hz, 2H), 4.06 (s, 3H), 3.88-3.76 (m, 4H), 3.47-3.38 (m, 2H), 3.13 (t, J=5 Hz, 2H), 2.88 (t, J=5 Hz, 2H), 2.67 (t, J=5 Hz, 2H), 2.50-2.39 (m, 2H), 1.89-1.78 (m, 2H), 1.77-1.62 (m, 2H), 1.46-1.35 (m, 1H), 1.20 (s, 6H).

Example 73. 5-(3-(2-(4-(2-Hydroxypropan-2-yl)piperidin-1-yl)ethoxy)-4,5,7,8-tetrahydro-1H-oxepino[4,5-c]pyrazol-1-yl)-2-methoxynicotinonitrile

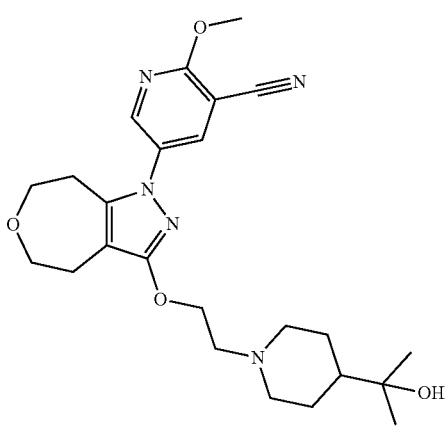 [SMILES: COc1ncc(-n2nc(OCCN3CCC(C(C)(C)O)CC3)c3c2CCOCC3)cc1C#N]

A microwave vial was charged with 2-(tributylphosphoranylidene)acetonitrile (0.050 mL, 0.190 mmol) and 2-(1-(2-hydroxyethyl)piperidin-4-yl)propan-2-ol (44 mg, 0.235 mmol). The vial was sealed and purged with nitrogen. The reaction mixture was treated with a solution of 5-(3-hydroxy-4,5,7,8-tetrahydro-1H-oxepino[4,5-c]pyrazol-1-yl)-2-methoxynicotinonitrile (32 mg, 0.095 mmol) in toluene (1 mL) and the vial was repurged and heated at 100° C. for two h. The reaction mixture was concentrated under a stream of nitrogen. The residue was taken up in water (5 mL) and partitioned with EtOAc (5 mL). The aqueous layer was extracted with further EtOAc (6×10 mL) and the combined organic layer was passed through a hydrophobic frit and concentrated under reduced pressure. The crude product was purified by MDAP (Method B) to give the title compound (14 mg, 31%).

LCMS (Method C): Rt=0.60 min, MH+=456.

$^1$H NMR (400 MHz, CDCl$_3$) δ ppm 8.33 (d, J=2.5 Hz, 1H), 7.94 (d, J=3 Hz, 1H), 4.65-4.48 (m, 2H), 4.11 (s, 3H), 3.85 (dt, J=10, 5. Hz, 4H), 3.71 (d, J=12 Hz, 2H), 3.44-3.30 (m, 2H), 2.91-2.80 (m, 2H), 2.77-2.60 (m, 5H), 2.00-1.72 (m, 4H), 1.58-1.43 (m, 1H), 1.26-1.20 (m, 6H)

Example 74. 2-(1-(2-((1-(2-Methoxypyrimidin-5-yl)-4,5,7,8-tetrahydro-1H-oxepino[4,5-c]pyrazol-3-yl)oxy)ethyl)piperidin-4-yl)propan-2-ol

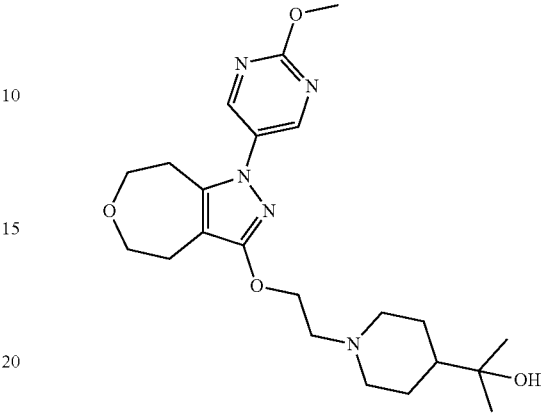

1-(2-methoxypyrimidin-5-yl)-4,5,7,8-tetrahydro-1H-oxepino[4,5-c]pyrazol-3-ol (20 mg, 0.076 mmol), 2-(1-(2-hydroxyethyl)piperidin-4-yl)propan-2-ol (20 mg, 0.107 mmol) and 2-(tributylphosphoranylidene)acetonitrile (0.043 mL, 0.166 mmol) were combined in a microwave vial in toluene (0.5 mL). The reaction mixture was heated in the microwave at 120° C. for 4 h and concentrated under reduced pressure and purified by MDAP (Method B) give the title compound (5 mg, 15%).

LCMS (Method A): Rt=0.50 min, MH+=432.

$^1$H NMR (400 MHz, CDCl$_3$) δ ppm 8.55 (s, 2H), 4.43 (t, J=5 Hz, 2H), 4.08 (s, 3H), 3.86 (dt, J=12, 5 Hz, 4H), 3.24 (d, J=12 Hz, 2H), 2.94 (t, J=5 Hz, 2H), 2.90-2.81 (m, 2H), 2.66-2.76 (m, 2H), 2.24 (t, J=12 Hz, 2H), 1.80 (d, J=13 Hz, 2H), 1.54 (dd, J=12, 3 Hz, 2H), 1.37-1.32 (m, 1H), 1.21 (s, 6H)

Example 75. tert-Butyl 4-(((1-(6-methoxy-5-methylpyridin-3-yl)-4,5,7,8-tetrahydro-1H-oxepino[4,5-c]pyrazol-3-yl)oxy)methyl)piperidine-1-carboxylate

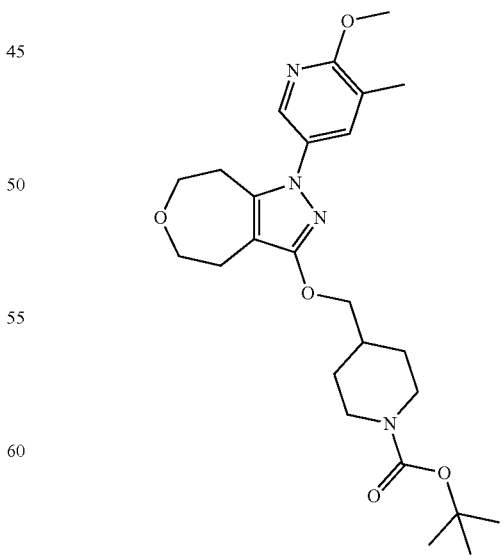

A microwave vial was charged with 1-(6-methoxy-5-methylpyridin-3-yl)-4,5,7,8-tetrahydro-1H-oxepino[4,5-c]

pyrazol-3-ol (51 mg, 0.185 mmol), tert-butyl 4-(hydroxymethyl)piperidine-1-carboxylate (80 mg, 0.372 mmol) and 2-(tributylphosphoranylidene)acetonitrile (0.143 mL, 0.547 mmol). The vial was sealed and degassed with nitrogen. Anhydrous toluene (2.5 mL) was added to the reaction mixture which was then heated in microwave at 120° C. for 1 h. The reaction mixture was concentrated under a stream of nitrogen. The residue was taken up in water (5 mL) and partitioned with EtOAc (5 mL). The aqueous layer was extracted with further EtOAc (3×5 mL) and the combined organic layer was passed through a hydrophobic frit and concentrated under reduced pressure. The crude product was purified by MDAP (Method A) to give the title compound (62 mg, 67%).

LCMS (Method C): Rt=1.47 min, MH+=473.

$^1$H NMR (400 MHz, MeOD) δ ppm 8.16 (s, 1H), 7.72 (s, 1H), 4.31 (d, J=13 Hz, 2H), 4.26-4.12 (m, 5H), 4.08-3.93 (m, 4H), 3.10-2.93 (m, 4H), 2.87 (t, J=5 Hz, 2H), 2.44 (s, 3H), 2.25-2.14 (m, 1H), 2.00 (d, J=12 Hz, 2H), 1.67 (s, 9H), 1.53-1.36 (m, 2H)

Example 76. 1-(6-Methoxy-5-methylpyridin-3-yl)-3-(piperidin-4-ylmethoxy)-4,5,7,8-tetrahydro-1H-oxepino[4,5-c]pyrazole

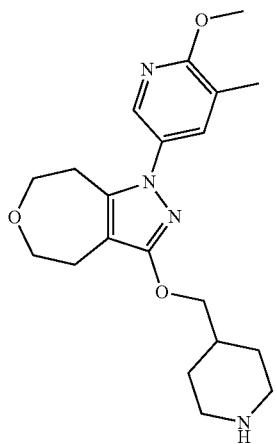 [SMILES: COc1ncc(-n2nc(OCC3CCNCC3)c3c2CCOCC3)cc1C]

To round-bottomed flask containing tert-butyl 4-(((1-(6-methoxy-5-methylpyridin-3-yl)-4,5,7,8-tetrahydro-1H-oxepino[4,5-c]pyrazol-3-yl)oxy)methyl)piperidine-1-carboxylate (57 mg, 0.115 mmol) was added DCM (4 mL), followed by TFA (0.5 ml, 6.49 mmol). After 30 min of stirring at room temperature, NaHCO$_3$ (10 mL) was added to quench the reaction. The reaction mixture was partitioned with DCM (10 mL) and the aqueous layer was washed with further DCM (3×10 mL). The combined organics layer was passed through a hydrophobic frit, concentrated under reduced pressure, and dried overnight on the high vacuum line. The crude product was purified by MDAP (Method A) to give the title compound (30 mg, 67%).

LCMS (Method C): Rt=1.07 min, MH+=373.

$^1$H NMR (400 MHz, MeOD) δ ppm 7.97 (d, J=2 Hz, 1H), 7.55-7.41 (m, 1H), 3.95-4.07 (m, 5H), 3.83 (dt, J=15, 5 Hz, 4H), 3.14 (d, J=12 Hz, 2H), 2.87-2.77 (m, 2H), 2.75-2.63 (m, 4H), 2.25 (s, 3H), 2.05-1.91 (m, 1H), 1.86 (d, J=12 Hz, 2H), 1.37 (qd, J=12, 4 Hz, 2H)

Example 77. 3-((1-Isopropylpiperidin-4-yl)methoxy)-1-(6-methoxy-5-methylpyridin-3-yl)-4,5,7,8-tetrahydro-1H-oxepino[4,5-c]pyrazole. Formate Salt

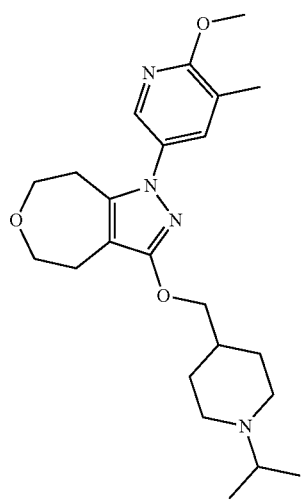 [SMILES: COc1ncc(-n2nc(OCC3CCN(C(C)C)CC3)c3c2CCOCC3)cc1C]

A microwave vial was charged with 1-(6-methoxy-5-methylpyridin-3-yl)-4,5,7,8-tetrahydro-1H-oxepino[4,5-c]pyrazol-3-ol (51 mg, 0.185 mmol), (1-isopropylpiperidin-4-yl)methanol (68 mg, 0.411 mmol) and 2-(tributylphosphoranylidene)acetonitrile (0.143 mL, 0.547 mmol). The vial was sealed and degassed with nitrogen. Anhydrous toluene (2.5 mL) was added to the reaction mixture which was then heated in a microwave at 120° C. for 1 h. The reaction mixture was treated with further (1-isopropylpiperidin-4-yl)methanol (50 mg, 0.302 mmol) and 2-(tributylphosphoranylidene)acetonitrile (0.143 mL, 0.547 mmol) and the reaction mixture was heated at 120° C. for 1 h.

The reaction mixture was concentrated under a stream of nitrogen and the residue was taken up in water (5 mL) and partitioned with EtOAc (5 mL). The aqueous layer was extracted with further EtOAc (3×5 mL) and the combined organic layer was passed through a hydrophobic frit and concentrated under reduced pressure. The crude product was purified by MDAP (Method A) to give the title compound (15 mg, 17%).

LCMS (Method A): Rt=0.66 min, MH+=415.

$^1$H NMR (400 MHz, MeOD) δ ppm 8.56 (br. s., 1H), 7.95 (br. s., 1H), 7.51 (br. s., 1H), 4.09 (d, J=5 Hz, 2H), 3.99 (s, 3H), 3.80 (dt, J=15, 5 Hz, 4H), 3.50-3.32 (m, 3H), 2.98 (t, J=12 Hz, 2H), 2.81 (t, J=4 Hz, 2H), 2.74-2.60 (m, 3H), 2.23 (s, 3H), 2.07 (d, J=14 Hz, 2H), 1.81-1.59 (m, 2H), 1.33 (d, J=6 Hz, 6H)

Example 78. tert-Butyl 3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate

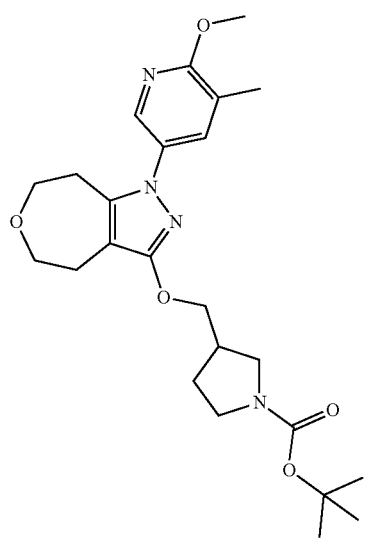 [SMILES: COc1ncc(-n2nc(OCC3CCN(C(=O)OC(C)(C)C)C3)c3c2CCOCC3)cc1C]

A microwave vial was charged with 1-(6-methoxy-5-methylpyridin-3-yl)-4,5,7,8-tetrahydro-1H-oxepino[4,5-c]pyrazol-3-ol (52 mg, 0.189 mmol), tert-butyl 3-(hydroxymethyl)pyrrolidine-1-carboxylate (74 mg, 0.368 mmol) and (tributylphosphoranylidene)Acetonitrile (0.143 mL, 0.547 mmol). The vial was sealed and degassed with nitrogen. Anhydrous toluene (2.5 mL) was added to the degassed solids. The reaction mixture was heated at 120° C. for 1 h and concentrated under a stream of nitrogen. The residue was taken up in water (5 mL) and partitioned with EtOAc (5 mL). The aqueous layer was extracted with further EtOAc (3×5 mL) and the combined organic layer was passed through a hydrophobic frit and concentrated under reduced pressure. The crude product was purified by MDAP (Method A) to give the title compound (51 mg, 58%).

LCMS (Method C): Rt=1.36 min, MH$^+$=459.

$^1$H NMR (400 MHz, MeOD) δ ppm 8.17 (s, 1H), 7.73 (s, 1H), 4.38 (br. s., 1H), 4.34-4.27 (m, 1H), 4.20 (s, 3H), 4.03 (dt, J=16, 5 Hz, 4H), 3.79-3.69 (m, 1H), 3.69-3.61 (m, 1H), 3.56-3.51 (m, 1H), 3.42 (dd, J=11, 7 Hz, 1H), 3.02 (t, J=5 Hz, 2H), 2.93-2.81 (m, 3H), 2.44 (s, 3H), 2.23-2.34 (m, 1H), 2.00 (br. s., 1H), 1.67 (s, 9H)

Example 79. tert-Butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate

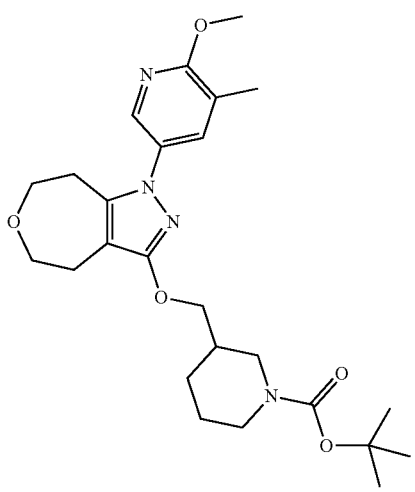 [SMILES: COc1ncc(-n2nc(OCC3CCCN(C(=O)OC(C)(C)C)C3)c3c2CCOCC3)cc1C]

A microwave vial was charged with 1-(6-methoxy-5-methylpyridin-3-yl)-4,5,7,8-tetrahydro-1H-oxepino[4,5-c]pyrazol-3-ol (51 mg, 0.185 mmol), tert-butyl 3-(hydroxymethyl)piperidine-1-carboxylate (82 mg, 0.381 mmol) and (tributylphosphoranylidene)Acetonitrile (0.143 mL, 0.545 mmol). The vial was sealed and degassed with nitrogen. Anhydrous toluene (2.5 mL) was added to the degassed solids. The reaction mixture was heated in a microwave at 120° C. for 1 h. The reaction mixture was concentrated under a stream of nitrogen and the residue was taken up in water (5 mL) and partitioned with EtOAc (5 mL). The aqueous layer was extracted with further EtOAc (3×5 mL) and the combined organic layer was passed through a hydrophobic frit and concentrated under reduced pressure. The crude product was purified by MDAP (Method A) to give the title compound (60 mg, 65%).

LCMS (Method C): Rt=1.43 min, MH$^+$=473.

$^1$H NMR (400 MHz, MeOD) δ ppm 8.14 (d, J=2 Hz, 1H), 7.75-7.63 (m, 1H), 4.30-4.23 (m, 1H), 4.23-4.13 (m, 5H), 4.00 (dt, J=17, 5 Hz, 5H), 3.53-3.45 (m, 1H), 3.13 (br. s., 1H), 3.03-2.94 (m, 2H), 2.87 (t, J=5 Hz, 2H), 2.41 (s, 3H), 2.16 (dd, J=8, 5 Hz, 1H), 2.10-1.98 (m, 1H), 1.69-1.58 (m, 11H), 1.88 (dt, J=13, 4 Hz, 1H)

Example 80. 1-(6-Methoxy-5-methylpyridin-3-yl)-3-(piperidin-3-ylmethoxy)-4,5,7,8-tetrahydro-1H-oxepino[4,5-c]pyrazole

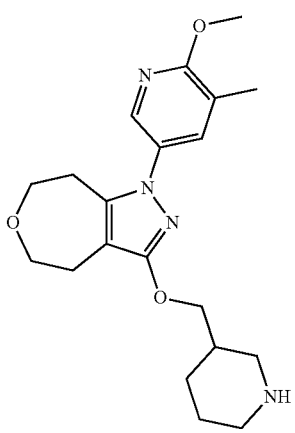 [SMILES: COc1ncc(-n2nc(OCC3CCCNC3)c3c2CCOCC3)cc1C]

To a round bottom flask containing tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate (53 mg, 0.112 mmol) was added DCM (4 mL), followed by TFA (0.5 mL, 6.49 mmol). After 20 min of stirring at room temperature, NaHCO$_3$ (10 mL) was added to quench the reaction. The reaction mixture was partitioned with DCM (10 mL) and the aqueous layer was extracted with further DCM (3×10 mL). The combined organics layer was passed through a hydrophobic frit, concentrated under reduced pressure, and then dried overnight on the high vacuum line. The crude product was purified by MDAP (Method A) to give the title compound (29 mg, 68%).

LCMS (Method C): Rt=1.01 min, MH$^+$=373.

$^1$H NMR (400 MHz, MeOD) δ ppm 7.97 (d, J=2 Hz, 1H), 7.55-7.49 (m, 1H), 3.93-4.12 (m, 5H), 3.83 (dt, J=16, 5 Hz, 4H), 3.21 (d, J=11 Hz, 1H), 3.05 (d, J=7 Hz, 1H), 2.80 (t, J=5 Hz, 2H), 2.66 (t, J=5 Hz, 2H), 2.61 (t, J=11 Hz, 1H), 2.52-2.38 (m, 1H), 2.23 (s, 3H), 2.10-1.96 (s, 1H), 1.89 (d, J=11 Hz, 1H), 1.81-1.69 (qd, J=12, 4 Hz, 1H), 1.64-1.47 (m, 1H), 1.34-1.18 (m, 1H).

Example 81. (g)-tert-Butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate

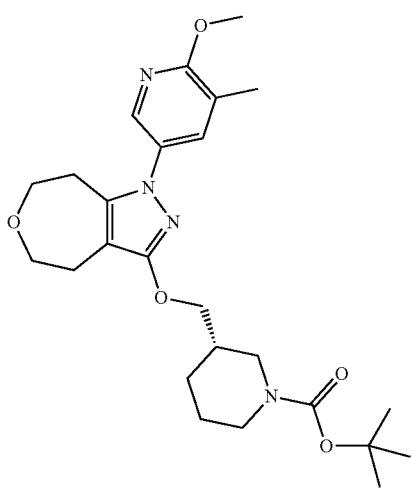 [SMILES: COc1ncc(-n2nc(OC[C@H]3CCCN(C(=O)OC(C)(C)C)C3)c3c2CCOCC3)cc1C]

A microwave vial was charged with 1-(6-methoxy-5-methylpyridin-3-yl)-4,5,7,8-tetrahydro-1H-oxepino[4,5-c]pyrazol-3-ol (203 mg, 0.737 mmol), (S)-tert-butyl 3-(hydroxymethyl)piperidine-1-carboxylate (181 mg, 0.841 mmol) and (tributylphosphoranylidene)Acetonitrile (0.3 mL, 1.144 mmol). The vial was sealed and degassed with nitrogen. Anhydrous toluene (8 mL) was added to the degassed solids. After 2 hours of stirring at 110° C., the reaction mixture was concentrated under a stream of nitrogen. The residue was taken up in water (10 mL) and partitioned with EtOAc (10 mL). The aqueous layer was extracted with further EtOAc (3×10 mL) and the combined organic layer was passed through a hydrophobic frit and concentrated under reduced pressure. The crude product was purified by silica column chromatography, eluting with a 0 to 50% gradient of cyclohexane/EtOAc to give the title compound (293 mg, 80%).

LCMS (Method A acid): Rt=1.45 min, MH$^+$=473.

$^1$H NMR (400 MHz, CDCl$_3$) δ ppm 7.95 (d, J=2 Hz, 1H), 7.51-7.43 (m, 1H), 4.17-3.92 (m, 7H), 3.92-3.76 (m, 4H), 3.51 (s, 3H), 2.89-2.78 (m, 2H), 2.77-2.64 (m, 2H), 2.24 (s, 3H), 2.09-1.95 (m, 1H), 1.94-1.84 (m, 1H), 1.70 (dt, J=13, 4 Hz, 1H), 1.52-1.42 (m, 10H)

Example 82. (S)-1-(6-Methoxy-5-methylpyridin-3-yl)-3-(piperidin-3-ylmethoxy)-4,5,7,8-tetrahydro-1H-oxepino[4,5-c]pyrazole

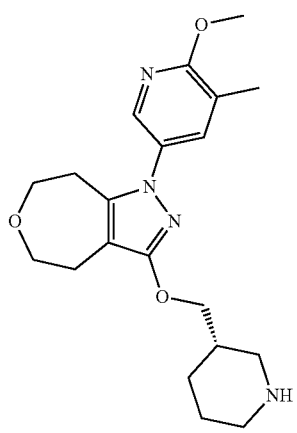 [SMILES: COc1ncc(-n2nc(OC[C@H]3CCCNC3)c3c2CCOCC3)cc1C]

To a round bottom flask containing (S)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate (293 mg, 0.620 mmol) was added DCM (6 mL), followed by TFA (1 mL, 12.98 mmol). After 1 h of stirring at room temperature under an atmosphere of nitrogen, NaHCO$_3$ (10 mL) was added to quench the reaction. The reaction mixture was partitioned with DCM (10 mL) and the aqueous layer was extracted with further DCM (3×10 mL). The combined organic layer was passed through a hydrophobic frit and concentrated under reduced pressure. The compound was passed through a 10 g aminopropyl column using methanol to give the title compound (211 mg, 82%).

LCMS (Method C): Rt=1.04 min, MH$^+$=373.

$^1$H NMR (400 MHz, CDCl$_3$) δ ppm 7.95 (d, J=3 Hz, 1H), 7.46 (dd, J=3, 1 Hz, 1H), 4.14-3.99 (m, 5H), 3.92-3.75 (m, 4H), 3.25 (d, J=9 Hz, 1H), 3.05 (d, J=12 Hz, 1H), 2.90-2.80 (m, 2H), 2.75-2.67 (m, 2H), 2.61 (td, J=12, 3 Hz, 1H), 2.48 (dd, J=12, 10 Hz, 1H), 2.24 (s, 3H), 2.09-1.97 (m, 1H), 1.96-1.84 (m, 1H), 1.76-1.67 (m, 1H), 1.65-1.45 (m, 2H), 1.31-1.16 (m, 1H)

Example 83. (S)-1-(3-(((1-(6-Methoxy-5-methylpyridin-3-yl)-4,5,7,8-tetrahydro-1H-oxepino[4,5-c]pyrazol-3-yl)oxy)methyl)piperidin-1-yl)-2-methylpropan-2-ol

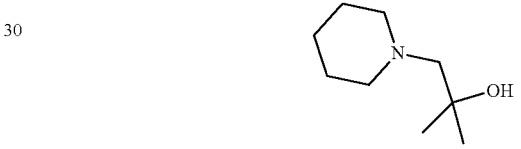

DIPEA (0.061 mL, 0.348 mmol) and 1-chloro-2-methylpropan-2-ol (0.018 mL, 0.174 mmol) were added to (S)-1-(6-methoxy-5-methylpyridin-3-yl)-3-(piperidin-3-ylmethoxy)-4,5,7,8-tetrahydro-1H-oxepino[4,5-c]pyrazole (48 mg, 0.116 mmol) in EtOH (1 mL). The reaction mixture was heated to 90° C. for 1 h in a microwave. 1-Chloro-2-methylpropan-2-ol (0.018 mL, 0.174 mmol) was added to the reaction mixture which was heated in a microwave for a further 2 h at 90° C. 1-Chloro-2-methylpropan-2-ol (0.018 mL, 0.174 mmol) was added to the reaction mixture which was heated in a microwave for a further 5 h. The reaction mixture was concentrated under a stream of nitrogen and purified using MDAP (Method A) to give the title compound (44.5 mg, 86%).

LCMS (Method C): Rt=1.31 min, MH$^+$=445.

$^1$H NMR (400 MHz, CDCl$_3$) δ ppm 7.92 (d, J=2 Hz, 1H), 7.46-7.40 (m, 1H), 4.17 (dd, J=10, 3 Hz, 1H), 4.06 (dd, J=10, 6 Hz, 1H), 3.98 (s, 3H), 3.85 (t, J=5 Hz, 2H), 3.79 (t, J=5 Hz, 2H), 3.70-3.19 (m, 2H), 2.91-2.71 (m, 4H), 2.72-2.44 (m, 5H), 2.22 (s, 3H), 1.97-1.76 (m, 3H), 1.41-1.20 (m, 7H)

Example 84. (R)-1-((S)-3-(((1-(6-Methoxy-5-methylpyridin-3-yl)-4,5,7,8-tetrahydro-1H-oxepino[4,5-c]pyrazol-3-yl)oxy)methyl)piperidin-1-yl)propan-2-ol

Example 85. (S)-1-((S)-3-(((1-(6-Methoxy-5-methylpyridin-3-yl)-4,5,7,8-tetrahydro-1H-oxepino[4,5-c]pyrazol-3-yl)oxy)methyl)piperidin-1-yl)propan-2-ol

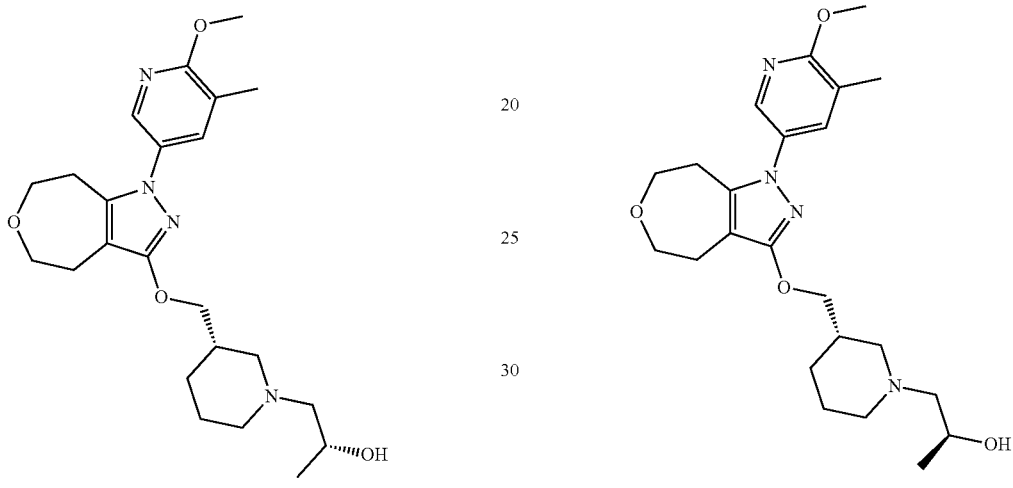

DIPEA (0.041 mL, 0.232 mmol) and (S)-2-methyloxirane (0.012 mL, 0.174 mmol) were added to (5)-1-(6-methoxy-5-methylpyridin-3-yl)-3-(piperidin-3-ylmethoxy)-4,5,7,8-tetrahydro-1H-oxepino[4,5-c]pyrazole (48 mg, 0.116 mmol) in EtOH (1 mL). The reaction mixture was heated at 90° C. for 1 h in a microwave. (S)-2-Methyloxirane (0.012 mL, 0.174 mmol) was added to the reaction mixture which was heated in a microwave for a further 1 h at 90° C. The reaction mixture was concentrated under reduced pressure and purified by MDAP (Method A) to give the title compound (36 mg, 69%).

LCMS (Method C): Rt=1.18 min, MH$^+$=431.

$^1$H NMR (400 MHz, CDCl$_3$) δ ppm 7.94 (d, J=2 Hz, 1H), 7.47 (d, J=2 Hz, 1H), 4.14-4.07 (m, 1H), 4.07-3.93 (m, 4H), 3.92-3.83 (m, 3H), 3.83-3.77 (m, 2H), 3.14 (d, J=10 Hz, 1H), 2.90-2.79 (m, 2H), 2.79-2.66 (m, 3H), 2.32 (dd, J=12, 3 Hz, 2H), 2.27-2.17 (m, 4H), 2.09 (br. s., 1H), 1.89-1.75 (m, 2H), 1.75-1.57 (m, 2H), 1.18-1.07 (m, 4H)

DIPEA (0.041 mL, 0.232 mmol) and (R)-2-methyloxirane (0.012 mL, 0.174 mmol) were added to (5)-1-(6-methoxy-5-methylpyridin-3-yl)-3-(piperidin-3-ylmethoxy)-4,5,7,8-tetrahydro-1H-oxepino[4,5-c]pyrazole (48 mg, 0.116 mmol) in EtOH (1 mL). The reaction mixture was heated at 90° C. for 2 h in a microwave. Further (R)-2-methyloxirane (0.012 mL, 0.174 mmol) was added to the reaction mixture which was heated at 90° C. for a further 45 min. The reaction mixture was concentrated under reduced pressure and purified by MDAP (Method A) to give the title compound (32 mg, 61%).

LCMS (Method C): Rt=1.19 min, MH$^+$=431.

$^1$H NMR (400 MHz, CDCl$_3$) δ ppm 7.94 (d, J=2 Hz, 1H), 7.45 (dd, J=2, 1.01 Hz, 1H), 4.13-4.07 (m, 1H), 4.07-4.00 (m, 1H), 3.98 (s, 3H), 3.89-3.84 (m, 3H), 3.84-3.76 (m, 3H), 2.98-2.87 (m, 2H), 2.87-2.78 (m, 2H), 2.75-2.66 (m, 2H), 2.33-2.27 (m, 1H), 2.25-2.21 (m, 4H), 2.21-2.10 (m, 2H), 2.00-1.90 (m, 1H), 1.84-1.76 (m, 1H), 1.76-1.66 (m, 1H), 1.64-1.50 (m, 1H), 1.18-1.04 (m, 4H)

Example 86. (R)-tert-Butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate

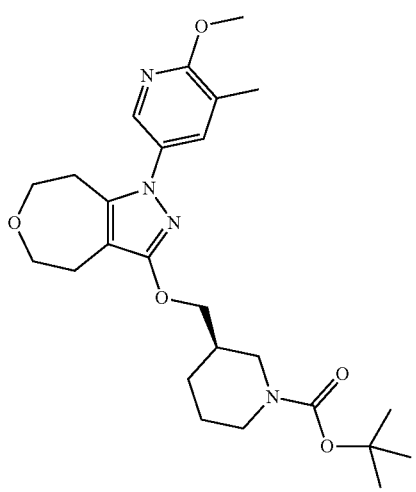 [SMILES: COc1ncc(-n2nc(OC[C@@H]3CCCN(C(=O)OC(C)(C)C)C3)c3c2CCOCC3)cc1C]

A microwave vial was charged with 1-(6-methoxy-5-methylpyridin-3-yl)-4,5,7,8-tetrahydro-1H-oxepino[4,5-c]pyrazol-3-ol (100 mg, 0.363 mmol), (R)-tert-butyl 3-(hydroxymethyl)piperidine-1-carboxylate (78 mg, 0.363 mmol) and (tributylphosphoranylidene)Acetonitrile (0.143 mL, 0.547 mmol). The vial was sealed and degassed with nitrogen. Anhydrous toluene (3.5 mL) was added to the degassed solids. The reaction mixture was heated at 110° C. for 6 h and concentrated under a stream of nitrogen. The residue was taken up in water (5 mL) and partitioned with EtOAc (5 mL). The aqueous layer was extracted with further EtOAc (3×5 mL) and the combined organic layer was passed through a hydrophobic frit and concentrated under reduced pressure. The crude product was purified by MDAP (Method A) to give the title compound (96 mg, 55%).

LCMS (Method C): Rt=1.44 min, MH$^+$=473.

$^1$H NMR (400 MHz, MeOD) δ ppm 7.93 (d, J=2 Hz, 1H), 7.45 (d, J=2 Hz, 1H), 4.16-4.08 (m, 1H), 4.04 (d, J=8 Hz, 1H), 4.01-3.91 (m, 4H), 3.85 (t, J=5 Hz, 2H), 3.83-3.73 (m, 2H), 2.91-2.75 (m, 3H), 2.75-2.65 (m, 3H), 2.23 (s, 3H), 2.03 (d, J=18 Hz, 1H), 1.92-1.80 (m, 1H), 1.69 (dt, J=13, 3 Hz, 1H), 1.58-1.49 (m, 1H), 1.46 (s, 9H), 1.36-1.19 (m, 1H)

Example 87. (S)-1-(2-(((1-(6-Methoxy-5-methylpyridin-3-yl)-4,5,7,8-tetrahydro-1H-oxepino[4,5-c]pyrazol-3-yl)oxy)methyl)morpholino)-2-methylpropan-2-ol

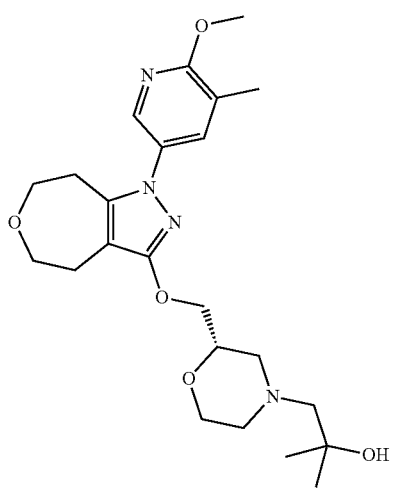 [SMILES: COc1ncc(-n2nc(OC[C@@H]3CN(CC(C)(C)O)CCO3)c3c2CCOCC3)cc1C]

DIPEA (0.112 mL, 0.642 mmol) and 1-chloro-2-methylpropan-2-ol (0.033 mL, 0.321 mmol) were added to a solution of (S)-1-(6-methoxy-5-methylpyridin-3-yl)-3-(morpholin-2-ylmethoxy)-4,5,7,8-tetrahydro-1H-oxepino[4,5-c]pyrazole (89 mg, 0.214 mmol) in EtOH (1.5 mL). The reaction mixture was heated at 90° C. for 2 h using a microwave. 1-Chloro-2-methylpropan-2-ol (0.033 mL, 0.321 mmol) was added to the reaction mixture which was heated using a microwave for 8 h. The reaction mixture was concentrated under a stream of nitrogen then purified using MDAP (Method A) to give the title compound (23 mg, 22%).

LCMS (Method C): Rt=1.08 min, MH$^+$=447.

$^1$H NMR (400 MHz, MeOD) δ ppm 7.91 (d, J=2 Hz, 1H), 7.43 (d, J=2 Hz, 1H), 4.22 (dd, J=11, 6 Hz, 1H), 4.22 (dd, J=11, 4 Hz, 1H), 3.98 (s, 4H), 3.91 (d, J=11 Hz, 1H), 3.84 (t, J=5 Hz, 2H), 3.82-3.71 (m, 2H), 2.90 (br. s., 1H), 2.87-2.81 (m, 2H), 2.78 (br. s., 1H), 2.76-2.68 (m, 2H), 2.54 (br. s., 1H), 2.37 (br. s., 2H), 2.22 (s, 3H), 1.72-1.61 (m, 1H), 1.61-1.51 (m, 1H), 1.48-1.34 (m, 1H), 1.19 (s, 6H)

Example 88. 3-((1-Isopropylpyrrolidin-3-yl)methoxy)-1-(6-methoxy-5-methylpyridin-3-yl)-4,5,7,8-tetrahydro-1H-oxepino[4,5-c]pyrazole. Formate Salt

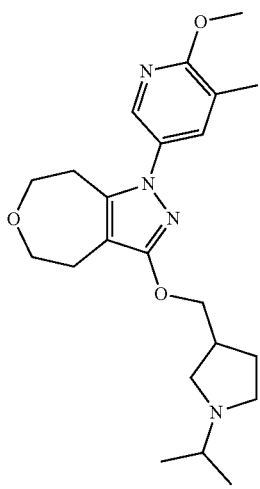 [SMILES: COc1ncc(-n2nc(OCC3CCN(C(C)C)C3)c3c2CCOCC3)cc1C]

1-(6-Methoxy-5-methylpyridin-3-yl)-4,5,7,8-tetrahydro-1H-oxepino[4,5-c]pyrazol-3-ol (50 mg, 0.182 mmol), (1-isopropylpyrrolidin-3-yl)methanol (38 mg, 0.272 mmol) and 2-(tributylphosphoranylidene)acetonitrile (0.545 mL, 0.545 mmol) were combined in toluene (1 mL). The sealed reaction vessel was heated with stirring at 110° C. for 18 h. The reaction mixture was treated with further 2-(tributylphosphoranylidene)acetonitrile (0.273 mL, 0.273 mmol) and (1-isopropylpyrrolidin-3-yl)methanol (25 mg, 0.181 mmol) and heated at 110° C. with stirring in a sealed reaction vessel for 18 h. The reaction mixture was diluted with $CHCl_3$ and passed down a silica SPE column (1 g) that had been, pre-conditioned with $CHCl_3$ (3 ml). The SPE column was eluted with ether then a 5% solution of MeCN in ether, and then EtOAc. Product eluted in the EtOAc which was concentrated under a stream of nitrogen. Crude product was purified by MDAP (Method D) to give the title compound (2.9 mg, 4+).

LCMS (Method C): Rt=1.29 min, $MH^+$=401.

$^1$H NMR (600 MHz, d6-DMSO): δ ppm 8.01 (d, J=3 Hz, 1H), 7.62 (dq, J=3, 1 Hz, 1H), 4.04-3.97 (m, 2H), 3.92-3.91 (m, 3H), 3.76-3.72 (m, 2H), 3.71 (dd, J=6, 4 Hz, 2H), 2.80 (dd, J=6, 4 Hz, 2H), 2.69 (dd, J=9, 8 Hz, 1H), 2.56-2.51 (m, 5H), 2.40-2.36 (m, 1H), 2.37-2.32 (m, 1H), 2.21-2.16 (m, 3H), 1.88 (dddd, J=13, 10, 7, 6 Hz, 1H), 1.50-1.41 (m, 1H), 1.02 (d, J=6 Hz, 3H), 1.01 (d, J=6 Hz, 3H).

The examples in the following table, Examples 89-95 were prepared in manner similar to that described for the previous example, Example 88.

| Example No. | Structure | Name | LCMS method | Rt min | $MH^+$ |
|---|---|---|---|---|---|
| 89 | 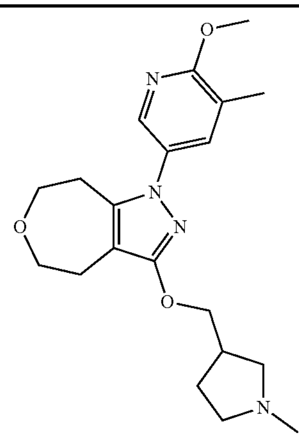 | 1-(6-Methoxy-5-methylpyridin-3-yl)-3-((1-methylpyrrolidin-3-yl)methoxy)-4,5,7,8-tetrahydro-1H-oxepino[4,5-c]pyrazole. Formate salt. | C | 1.20 | 373 |
| 90 | 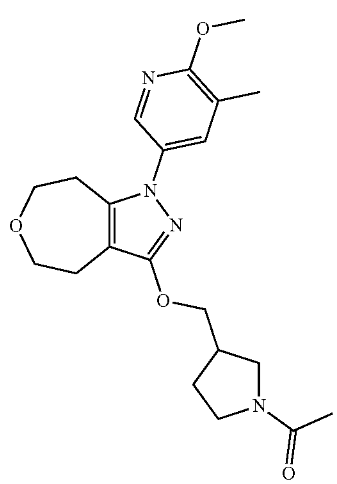 [SMILES: COc1ncc(-n2nc(OCC3CCN(C(C)=O)C3)c3c2CCOCC3)cc1C] | 1-(3-(((1-(6-Methoxy-5-methylpyridin-3-yl)-4,5,7,8-tetrahydro-1H-oxepino[4,5-c]pyrazol-3-yl)oxy)methyl)pyrrolidin-1-yl)ethanone. Formate salt. | C | 0.97 | 401 |

| Example No. | Structure | Name | LCMS method | Rt min | MH+ |
|---|---|---|---|---|---|
| 91 | 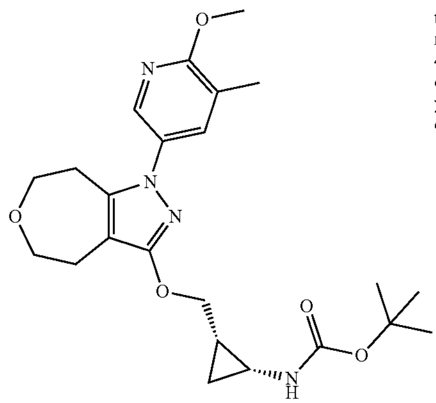 [SMILES: COc1ncc(-n2nc(OC[C@H]3C[C@H]3NC(=O)OC(C)(C)C)c3c2CCOCC3)cc1C] | tert-Butyl ((1R,2S)-2-(((1-(6-methoxy-5-methylpyridin-3-yl)-4,5,7,8-tetrahydro-1H-oxepino[4,5-c]pyrazol-3-yl)oxy)methyl)cyclopropyl)carbamate. Formate salt. | C | 1.26 | 445 |
| 92 | 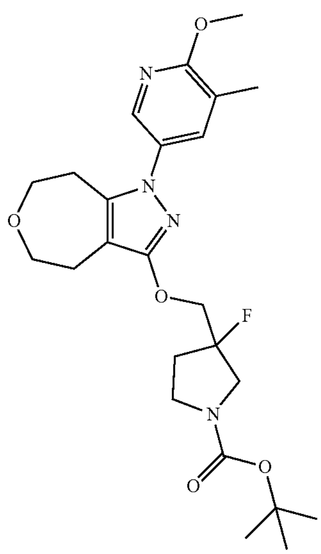 [SMILES: COc1ncc(-n2nc(OCC3(F)CCN(C(=O)OC(C)(C)C)C3)c3c2CCOCC3)cc1C] | tert-Butyl 3-fluoro-3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate. Formate salt. | C | 1.33 | 477 |
| 93 | 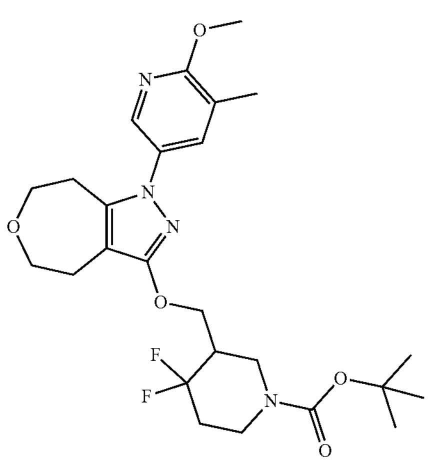 [SMILES: COc1ncc(-n2nc(OCC3CN(C(=O)OC(C)(C)C)CCC3(F)F)c3c2CCOCC3)cc1C] | tert-Butyl 4,4-difluoro-3-(((1-(6-methoxy-5-methylpyridin-3-yl)-4,5,7,8-tetrahydro-1H-oxepino[4,5-c]pyrazol-3-yl)oxy)methyl)piperidine-1-carboxylate. Formate salt. | C | 1.42 | 509 |

-continued
| Example No. | Structure | Name | LCMS method | Rt min | MH+ |
|---|---|---|---|---|---|
| 94 | 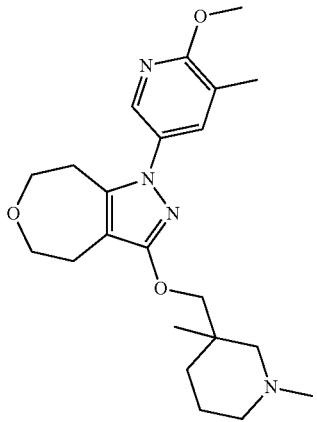 [SMILES: COc1ncc(-n2nc(OCC3(C)CCCN(C)C3)c3c2CCOCC3)cc1C] | 3-((1,3-Dimethylpiperidin-3-yl)methoxy)-1-(6-methoxy-5-methylpyridin-3-yl)-4,5,7,8-tetrahydro-1H-oxepino[4,5-c]pyrazole. Formate salt. | C | 1.34 | 401 |
| 95 | 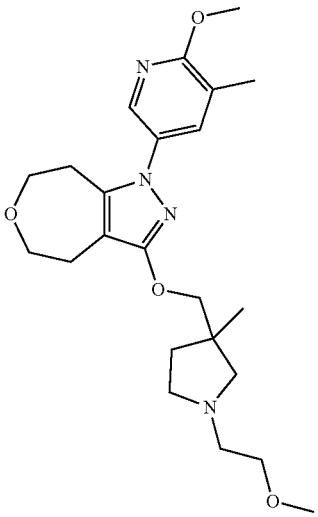 [SMILES: COCCN1CCC(C)(COc2nn(-c3cnc(OC)c(C)c3)c3c2CCOCC3)C1] | 1-(6-methoxy-5-methylpyridin-3-yl)-3-((1-(2-methmethyl)-3-methylpyrrolidin-3-yl)methoxy)-4,5,7,8-tetrahydro-1H-oxepino[4,5-c]pyrazole. Formate salt. | C | 1.22 | 431 |

Example 96. 1-(6-Methoxy-5-methylpyridin-3-yl)-3-((pyrrolidin-3-yl)methoxy)-4,5,7,8-tetrahydro-1H-oxepino[4,5-c]pyrazole

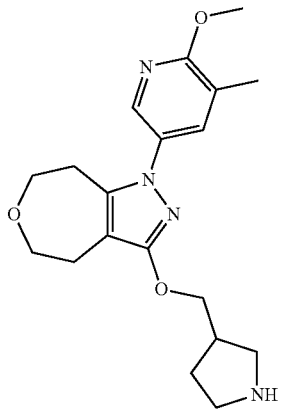 [SMILES: COc1ncc(-n2nc(OCC3CCNC3)c3c2CCOCC3)cc1C]

To a round bottom flask containing tert-butyl 3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate (50 mg, 0.104 mmol) was added DCM (4 mL), followed by the addition of the TFA (0.5 ml, 6.49 mmol). After 1 h of stirring at room temperature, NaHCO$_3$ (10 mL) was added to quench the reaction. The reaction mixture was partitioned with DCM (10 mL) and the aqueous layer was extracted with further DCM (3×10 mL). The combined organic extracts were dried by passing through a hydrophobic frit and concentrated under reduced pressure. The crude product was purified by MDAP (Method A) to give the title compound (23 mg).

LCMS (Method C): Rt=1.02 min, MH$^+$=359.

Example 97. 1-(6-Methoxypyridin-3-yl)-3-(2-(1-(4-methylpiperazin-1-yl)ethyl)pyridin-4-yl)-4,5,7,8-tetrahydro-1H-oxepino[4,5-c]pyrazole

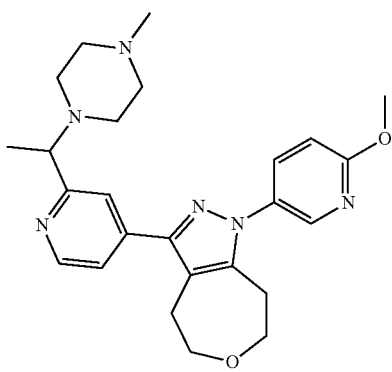 [SMILES: COc1ccc(-n2nc(-c3ccnc(C(C)N4CCN(C)CC4)c3)c3c2CCOCC3)cn1]

A mixture of 1-(4-(1-(6-methoxypyridin-3-yl)-4,5,7,8-tetrahydro-1H-oxepino[4,5-c]pyrazol-3-yl)pyridin-2-yl)ethanone (100 mg, 0.274 mmol), titanium(IV) isopropoxide (0.096 mL, 0.329 mmol), acetic acid (0.031 mL, 0.549 mmol) and 1-methylpiperazine (0.046 mL, 0.412 mmol) in THF (1 mL) was stirred under nitrogen for 1 h at room temperature. The reaction mixture was treated with sodium triacetoxyborohydride (116 mg, 0.549 mmol) and the reaction mixture was placed under an atmosphere of nitrogen by evacuation/re-fill then heated using a microwave at 100° C. for 1 h. The reaction mixture was treated with water (5 mL) and filtered through a Celite® pad, washing with EtOAc (200 mL). The solvent was removed under reduced pressure. The residue was taken up in EtOAc (50 mL) and water (50 mL) and the layers were separated. The aqueous phase was basified to pH 10 by the addition of saturated NaHCO$_3$ (10 mL) and extracted with EtOAc (3×40 mL). The combined organic extracts were dried by passing through a hydrophobic frit and concentrated under reduced pressure to give the title compound (48 mg, 39%).

LCMS (Method C): Rt=0.91 min, MH$^+$=449.

$^1$H NMR (400 MHz, CDCl$_3$) δ-ppm 8.63 (d, J=5 Hz, 1H), 8.25 (d, J=3 Hz, 1H), 7.72 (dd, J=9, 3 Hz, 1H), 7.61 (s, 1H), 7.39 (dd, J=5, 2 Hz, 1H), 6.90 (d, J=9 Hz, 1H), 4.02 (s, 3H), 3.94-3.87 (m, 4H), 3.70-3.62 (m, 1H), 3.03-2.98 (m, 4H), 2.78-2.60 (br. s, 2H), 2.58-2.46 (br. s, 5H), 2.44-2.37 (m, 1H), 2.31 (s, 3H), 1.47 (d, J=7 Hz, 3H).

Example 98. 1-(5-Fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole

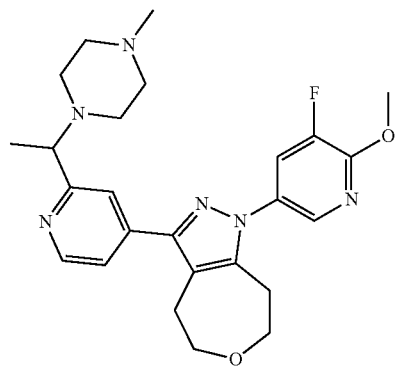

A mixture of 1-(4-(1-(5-fluoro-6-methoxypyridin-3-yl)-4,5,7,8-tetrahydro-1H-oxepino[4,5-c]pyrazol-3-yl)pyridin-2-yl)ethan-1-one (87 mg, 0.228 mmol), titanium(IV) isopropoxide (0.08 mL, 0.273 mmol), acetic acid (0.026 mL, 0.455 mmol) and 1-methylpiperazine (0.038 mL, 0.314 mmol) in THF (0.5 mL) was stirred under nitrogen for 30 min at room temperature. The reaction mixture was treated with sodium triacetoxyborohydride (96 mg, 0.455 mmol) and placed under an atmosphere of nitrogen by evacuation/re-fill then heated using a microwave at 100° C. for 1 h. The reaction mixture was filtered through a Celite® pad, washing with EtOAc (20 mL). The organic phase was extracted with water (30 mL) and the aqueous phase was basified with a 2 M aqueous solution of NaOH (20 mL) then extracted with EtOAc (50 mL). The organic extract was passed through a hydrophobic frit and concentrated under reduced pressure to give the title compound (39 mg) as a pale brown solid.

LCMS (Method C): Rt=0.98 min, MH$^+$=467.

$^1$H NMR (400 MHz, CDCl$_3$) δ-ppm 8.61 (d, J=5 Hz, 1H), 8.02 (d, J=2 Hz, 1H), 7.57 (s, 1H), 7.55 (d, J=2 Hz, 1H), 7.36 (dd, J=5, 2 Hz, 1H), 4.09 (s, 3H), 3.91-3.86 (m, 4H), 3.64 (q, J=7 Hz, 1H), 3.01-2.95 (m, 4H), 2.72-2.57 (br. s, 2H), 2.56-2.34 (m, 6H), 2.27 (s, 3H), 1.44 (d, J=7 Hz, 3H).

Example 99. 1-(5-Fluoro-6-methoxypyridin-3-yl-3-(2-(1-(4-isopropylpiperazin-1-yl)ethyl)pyridin-4-yl)-4,5,7,8-tetrahydro-1H-oxepino[4,5-c]pyrazole

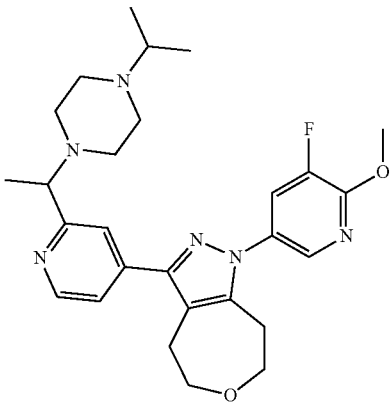 [SMILES: COc1ncc(-n2nc(-c3ccnc(C(C)N4CCN(C(C)C)CC4)c3)c3c2CCOCC3)cc1F]

A mixture of 1-(4-(1-(5-fluoro-6-methoxypyridin-3-yl)-4,5,7,8-tetrahydro-1H-oxepino[4,5-c]pyrazol-3-yl)pyridin-2-yl)ethan-1-one (150 mg, 0.392 mmol), titanium(IV) isopropoxide (0.138 mL, 0.471 mmol), acetic acid (0.045 mL, 0.785 mmol) and 1-isopropylpiperazine (75 mg, 0.588 mmol) in THF (0.5 mL) was stirred under nitrogen for 30 min at room temperature. The reaction mixture was treated with sodium triacetoxyborohydride (166 mg, 0.785 mmol) and placed under an atmosphere of nitrogen by evacuation/re-fill then heated using a microwave at 100° C. for 1 h. The reaction mixture was filtered through a Celite® pad, washing with EtOAc (20 mL). The organic phase was extracted with water (30 mL) and the aqueous phase was basified with a 2 M aqueous solution of NaOH (20 mL) then extracted with EtOAc (50 mL). The organic extract was passed through a hydrophobic frit and concentrated under reduced pressure to give the title compound (114 mg) as a brown oil.

LCMS (Method C): Rt=1.10 min, MH$^+$=495.
$^1$H NMR (400 MHz, CDCl$_3$) δ-ppm 8.61 (d, J=5 Hz, 1H), 8.01 (d, J=2 Hz, 1H), 7.57 (s, 1H), 7.54 (d, J=2 Hz, 1H), 7.35 (dd, J=5, 2 Hz, 1H), 4.09 (s, 3H), 3.91-3.86 (m, 4H), 3.65 (q, J=7 Hz, 1H), 3.01-2.99 (m, 4H), 2.70-2.45 (m, 9H), 1.44 (d, J=7 Hz, 3H), 1.06-1.02 (m, 6H).

Example 100. 1-(6-Methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole

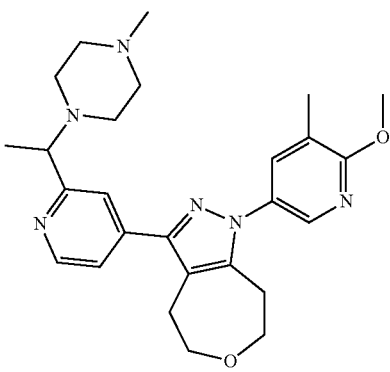 [SMILES: COc1ncc(-n2nc(-c3ccnc(C(C)N4CCN(C)CC4)c3)c3c2CCOCC3)cc1C]

A mixture of 1-(4-(1-(6-methoxy-5-methylpyridin-3-yl)-4,5,7,8-tetrahydro-1H-oxepino[4,5-c]pyrazol-3-yl)pyridin-2-yl)ethanone (50 mg, 0.132 mmol), titanium(IV) isopropoxide (0.046 mL, 0.159 mmol), acetic acid (0.015 mL, 0.264 mmol) and 1-methylpiperazine (0.022 mL, 0.198 mmol) in THF (1 mL) was stirred under nitrogen for 30 min at room temperature. The reaction mixture was treated with sodium triacetoxyborohydride (56 mg, 0.264 mmol) and placed under an atmosphere of nitrogen by evacuation/re-fill then heated using a microwave at 100° C. for 1 h. The reaction mixture was filtered through a Celite® pad, washing with EtOAc (20 mL). The organic phase was extracted into water (30 mL) and the aqueous phase was basified with saturated NaHCO$_3$ (20 mL) then extracted with EtOAc (50 mL). The organic extract was dried by passing through a hydrophobic frit and concentrated under reduced pressure to give the title compound (26 mg) as a white solid.

LCMS (Method C): Rt=1.03 min, MH$^+$=463.
$^1$H NMR (400 MHz, CDCl$_3$) δ-ppm 8.60 (d, J=5 Hz, 1H), 8.04 (d, J=2 Hz, 1H), 7.58 (s, 1H), 7.55 (dd, J=2, 1 Hz, 1H), 7.37 (dd, J=5, 2 Hz, 1H), 4.01 (s, 3H), 3.91-3.84 (m, 4H), 3.63 (q, J=7 Hz, 1H), 3.00-2.96 (m, 4H), 2.71-2.57 (br. s, 2H), 2.55-2.35 (m, 6H), 2.26-2.25 (m, 6H), 1.44 (d, J=7 Hz, 3H).

Example 101. 3-(2-(1-(4-Isopropylpiperazin-1-yl)ethyl)pyridin-4-yl)-1-(6-methoxy-5-methylpyridin-3-yl)-4,5,7,8-tetrahydro-1H-oxepino[4,5-c]pyrazole

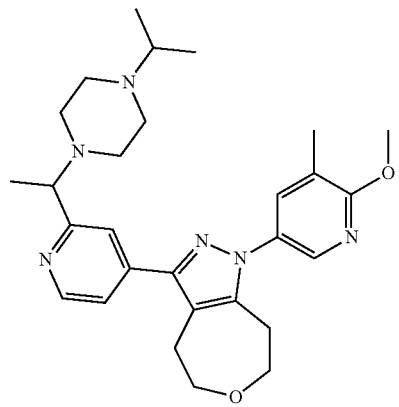 [SMILES: COc1ncc(-n2nc(-c3ccnc(C(C)N4CCN(C(C)C)CC4)c3)c3c2CCOCC3)cc1C]

A mixture of 1-(4-(1-(6-methoxy-5-methylpyridin-3-yl)-4,5,7,8-tetrahydro-1H-oxepino[4,5-c]pyrazol-3-yl)pyridin-2-yl)ethan one (100 mg, 0.264 mmol), titanium(IV) isopropoxide (0.093 mL, 0.317 mmol), acetic acid (0.030 mL, 0.528 mmol) and 1-isopropylpiperazine (50.8 mg, 0.396 mmol) in THF (0.5 mL) was stirred under nitrogen for 30 min at room temperature. The reaction mixture was treated with sodium triacetoxyborohydride (112 mg, 0.528 mmol) and placed under an atmosphere of nitrogen by evacuation/re-fill then heated using a microwave at 100° C. for 1 h. The reaction mixture was filtered through a Celite® pad, washing with EtOAc (20 mL). The organic phase was extracted into water (30 mL) and the aqueous phase was basified with a 2 M aqueous solution of NaOH (20 mL) then extracted with EtOAc (50 mL). The organic extract was passed through a hydrophobic frit and concentrated under reduced pressure to give the title compound (39 mg) as a pale brown solid.

LCMS (Method C): Rt=1.15 min, MH$^+$=491.

¹H NMR (400 MHz, CDCl₃) δ-ppm 8.60 (d, J=5 Hz, 1H), 8.04 (d, J=2 Hz, 1H), 7.58-7.54 (m, 2H), 7.36 (dd, J=5, 2 Hz, 1H), 4.01 (s, 3H), 3.91-3.84 (m, 4H), 3.64 (q, J=7 Hz, 1H), 3.00-2.96 (m, 4H), 2.74-2.42 (m, 9H), 2.26 (s, 3H), 1.44 (d, J=7 Hz, 3H), 1.10-1.01 (m, 6H).

Example 102. 1-(6-methoxy-5-methylpyridin-3-yl)-3-(2-(1-((3S,5R)-3,4,5-trimethylpiperazin-1-yl)ethyl)pyridin-4-yl)-4,5,7,8-tetrahydro-1H-oxepino[4,5-c]pyrazole

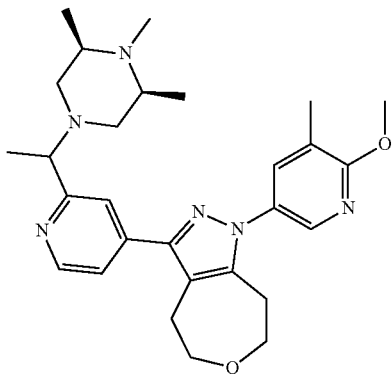 [SMILES: COc1ncc(-n2nc(-c3ccnc(C(C)N4C[C@@H](C)N(C)[C@@H](C)C4)c3)c3c2CCOCC3)cc1C]

A mixture of 1-(4-(1-(6-methoxy-5-methylpyridin-3-yl)-4,5,7,8-tetrahydro-1H-oxepino[4,5-c]pyrazol-3-yl)pyridin-2-yl)ethanone (100 mg, 0.264 mmol), titanium(IV) isopropoxide (0.093 mL, 0.317 mmol), acetic acid (0.030 mL, 0.528 mmol) and (2S,6R)-1,2,6-trimethylpiperazine (44 mg, 0.343 mmol) in THF (0.5 mL) was stirred under nitrogen for 1.5 h at room temperature. Sodium triacetoxyborohydride (112 mg, 0.528 mmol) was added and the reaction mixture was placed under an atmosphere of nitrogen by evacuation/re-fill then heated using a microwave at 100° C. for 1 h. The reaction mixture was filtered through a Celite® pad, washing with EtOAc (20 mL). The organic phase was extracted with water (10 mL) and the aqueous phase was basified with saturated NaHCO₃ (10 mL) then extracted with EtOAc (2×10 mL). The organic extract was dried by passing through a hydrophobic frit and concentrated under reduced pressure. The residue was taken up in MeOH, concentrated under a stream of nitrogen and dried in a vacuum oven at 40° C. for 1.5 h to give the title compound (70 mg) as a pale orange foam.

LCMS (Method A): Rt=0.60 min, MH⁺=491.

¹H NMR (400 MHz, CDCl₃) δ-ppm 8.60 (d, J=5 Hz, 1H), 8.04 (d, J=2 Hz, 1H), 7.56-7.54 (m, 2H), 7.38 (d, J=5 Hz, 1H), 4.01 (s, 3H), 3.91-3.84 (m, 4H), 3.57 (q, J=7 Hz, 1H), 3.00-2.93 (m, 5H), 2.65-2.62 (m, 1H), 2.37-2.21 (m, 8H), 2.05-1.93 (s, 2H), 1.42 (d, J=7 Hz, 3H), 1.13-1.05 (m, 3H), 1.03-0.96 (m, 3H).

Example 103. 1-(5-Fluoro-6-methoxypyridin-3-yl)-3-(1-((3-fluoropiperidin-4-yl)methyl)-1H-pyrazol-4-yl)-4,5,7,8-tetrahydro-1H-oxepino[4,5-c]pyrazole

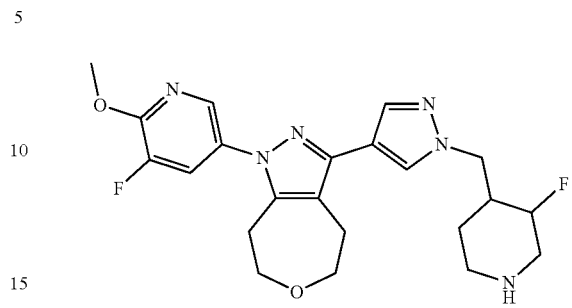

Prepared using the general Boc-deprotection procedure from tert-butyl 3-fluoro-4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidine-1-carboxylate (75 mg, 0.138 mmol), DCM (2 mL) and TFA (0.637 mL), except the reaction mixture was heated at 70° C. for 15 min using a microwave, to give the title compound (52 mg).

LCMS (Method C): Rt=0.90 min, MH⁺ 445.

The crude compound was taken forward into the next reaction step without further purification.

Example 104. 1-(5-Fluoro-6-methoxypyridin-3-yl)-3-(1-(((3R,4S)-3-fluoropiperidin-4-yl)methyl)-1H-pyrazol-4-yl)-4,5,7,8-tetrahydro-1H-oxepino[4,5-c]pyrazole

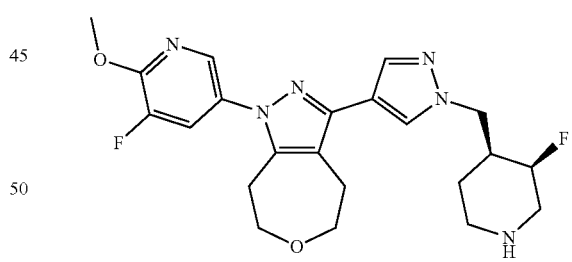

Prepared using the general Boc-deprotection procedure from tert-butyl (3R,4S)-3-fluoro-4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidine-1-carboxylate (102 mg, 0.187 mmol), DCM (2 mL) and TFA (0.866 mL), except the reaction mixture was heated at 70° C. for 15 min using a microwave, to give the title compound (57 mg, 55%).

LCMS (Method C): Rt=0.91 min, MH⁺ 445.

Example 105. (S)-tert-Butyl 2-(((1-(6-methoxy-5-methylpyridin-3-yl)-4,5,7,8-tetrahydro-1H-oxepino[4,5-c]pyrazol-3-yl)oxy)methyl)morpholine-4-carboxylate

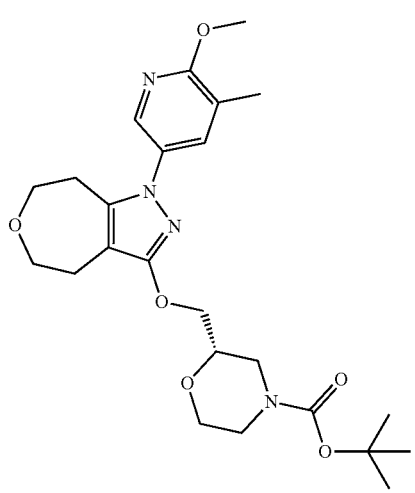 [SMILES: COc1ncc(-n2nc(OC[C@@H]3CN(C(=O)OC(C)(C)C)CCO3)c3c2CCOCC3)cc1C]

A microwave vial was charged with 1-(6-methoxy-5-methylpyridin-3-yl)-4,5,7,8-tetrahydro-1H-oxepino[4,5-c]pyrazol-3-ol (50 mg, 0.182 mmol), (tributylphosphoranylidene)Acetonitrile (0.143 mL, 0.545 mmol) and (S)-tert-butyl 2-(hydroxymethyl)morpholine-4-carboxylate (79 mg, 0.363 mmol). The vial was sealed and degassed with nitrogen. Anhydrous toluene (1 mL) was added to the degassed solids. The reaction mixture was heated at 120° C. for 4 h and concentrated under a stream of nitrogen. The residue was taken up in water (10 mL) and partitioned with EtOAc (10 mL). The aqueous layer was extracted with further EtOAc (2×5 mL). The combined organic layer was passed through a hydrophobic frit and concentrated under reduced pressure. The crude product was purified using reverse phase chromatography using a C18 silica column and a 50 to 99% gradient of MeCN and 0.1% NH$_3$ in water, plus 10 mM ammonium bicarbonate to afford the title compound (109 mg, >99%).

LCMS (Method C): Rt=1.30 min, MH$^+$=475.

The crude compound was used for the next step without further purification.

Example 106. (S)-1-(6-Methoxy-5-methylpyridin-3-yl)-3-(morpholin-2-ylmethoxy)-4,5,7,8-tetrahydro-1H-oxepino[4,5-c]pyrazole

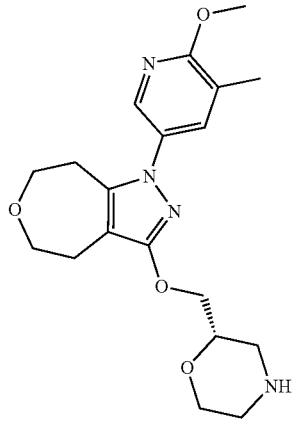 [SMILES: COc1ncc(-n2nc(OC[C@@H]3CNCCO3)c3c2CCOCC3)cc1C]

A solution of (S)-tert-butyl 2-(((1-(6-methoxy-5-methylpyridin-3-yl)-4,5,7,8-tetrahydro-1H-oxepino[4,5-c]pyrazol-3-yl)oxy)methyl)morpholine-4-carboxylate (109 mg, 0.207 mmol) in DCM (1 mL) and treated with TFA (0.159 mL, 2.067 mmol). The reaction mixture was stirred at room temperature over the weekend then quenched with saturated sodium bicarbonate (2 mL) and stirred for 30 min. The reaction mixture was treated with sodium bicarbonate (4 mL) and extracted with DCM (3×10 mL). The combined organic layer was through a hydrophobic frit and concentrated under reduced pressure to afford the title compound (89 mg, >99%).

LCMS (Method C): Rt=0.87 min, MH$^+$=375.

The crude material was used in the next step without further purification.

Example 107. (4-Isopropylpiperazin-1-yl)(2-(1-(6-methoxy-5-methylpyridin-3-yl)-4,5,7,8-tetrahydro-1H-oxepino[4,5-c]pyrazol-3-yl)oxazol-5-yl)methanone

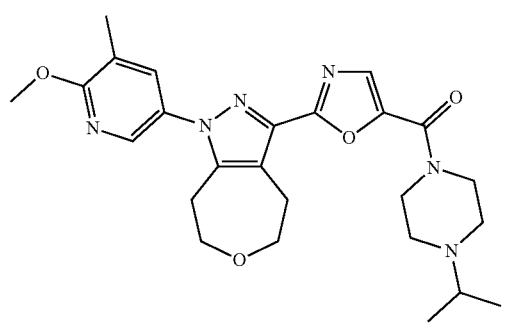 [SMILES: COc1ncc(-n2nc(-c3ncc(C(=O)N4CCN(C(C)C)CC4)o3)c3c2CCOCC3)cc1C]

A mixture of 3-bromo-1-(6-methoxy-5-methylpyridin-3-yl)-4,5,7,8-tetrahydro-1H-oxepino[4,5-c]pyrazole and 3-bromo-2-(6-methoxy-5-methylpyridin-3-yl)-4,5,7,8-tetrahydro-2H-oxepino[4,5-c]pyrazole (220 mg, 0.651 mmol) in a microwave vial was treated with (4-isopropylpiperazin-1-yl)(oxazol-5-yl)methanone (145 mg, 0.651 mmol), palladium(II) chloride (24 mg, 0.135 mmol), pivalic acid (40 mg, 0.392 mmol), XPhos (62 mg, 0.130 mmol) and potassium carbonate (180 mg, 1.302 mmol). The microwave vial was sealed and purged with nitrogen. The reaction mixture was treated with toluene (2.5 mL) and heated at 110° C. for 96 hours.

The reaction mixture was filtered through Celite®, washed with MeOH (two column volumes) and the solvent concentrated under reduced pressure. The crude material was treated with saturated solution of sodium carbonate in water (20 mL) and partitioned with EtOAc (20 mL). The organic layer was isolated and the aqueous layer extracted with EtOAc (2×20 mL). The combined organic layer was passed through a hydrophobic frit and concentrated under reduced pressure to give crude product as a brown gum (400 mg). The crude product was purified by MDAP (Method B) to give the title compound (91 mg, 28%).

LCMS (Method A): Rt=0.64 min, MH$^+$ 481.

$^1$H NMR (400 MHz, CDCl$_3$) δ-ppm 8.03 (d, J=3 Hz, 1H), 7.71 (s, 1H), 7.53 (d, J=2 Hz, 1H), 4.09-3.88 (m, 11H), 3.84 (t, J=5 Hz, 2H), 3.34 (t, J=5 Hz, 2H), 3.03-2.89 (m, 3H), 2.76 (t, J=5 Hz, 2H), 2.26 (s, 3H), 1.14 (d, J=7 Hz, 6H).

Example 108. 4-((4-(1-(6-Methoxy-5-methylpyridin-3-yl)-4,5,7,8-tetrahydro-1H-oxepino[4,5-c]pyrazol-3-yl)-1H-pyrazol-1-yl)methyl)piperidin-4-ol

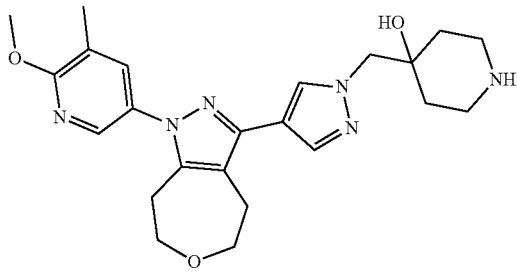 [SMILES: COc1ncc(-n2nc(-c3cnn(CC4(O)CCNCC4)c3)c3c2CCOCC3)cc1C]

Prepared using the general Boc-deprotection procedure from tert-butyl 4-hydroxy-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate (155 mg, 0.288 mmol), DCM (2.5 mL) and TFA (0.67 mL) to give the title compound as an off-white gum (245 mg, >99%).

LCMS (Method C): Rt=0.86 min, MH$^+$=439.

The crude product was taken forward to the next synthetic step without further purification.

Example 109. 3-(1-((4-Fluoropiperidin-4-yl)methyl)-1H-pyrazol-4-yl)-1-(6-methoxy-5-methylpyridin-3-yl)-4,5,7,8-tetrahydro-1H-oxepino[4,5-c]pyrazole

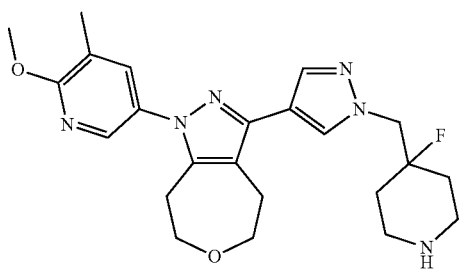 [SMILES: COc1ncc(-n2nc(-c3cnn(CC4(F)CCNCC4)c3)c3c2CCOCC3)cc1C]

Prepared using the general Boc deprotection procedure from tert-butyl 4-fluoro-4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidine-1-carboxylate (153 mg), DCM (2 mL) and TFA (0.6 mL) to give the title compound as a brown gum (113 mg).

LCMS (Method C): Rt=0.98 min, MH$^+$=441.

Example 110. 1-(6-methoxypyridin-3-yl)-3-(2-((S)-1-((3S,5R)-3,4,5-trimethylpiperazin-1-yl)ethyl)pyridin-4-yl)-4,5,7,8-tetrahydro-1H-oxepino[4,5-c]pyrazole

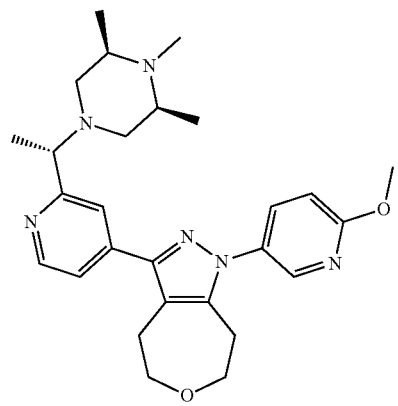 [SMILES: COc1ccc(-n2nc(-c3ccnc([C@H](C)N4C[C@@H](C)N(C)[C@@H](C)C4)c3)c3c2CCOCC3)cn1]

3-bromo-1-(6-methoxypyridin-3-yl)-4,5,7,8-tetrahydro-1H-oxepino[4,5-c]pyrazole (4.31 g, 13.30 mmol), potassium phosphate (8.47 g, 39.9 mmol), XPhos Pd G2 (0.262 g, 0.332 mmol) and XPhos (0.158 g, 0.332 mmol) were split across three microwave vials. (2S,6R)-1,2,6-trimethyl-4-((S)-1-(4-(4,4,5,5-tetramethyl-1,3,2-dioxaborolan-2-yl)pyridin-2-yl)ethyl)piperazine (4.78 g, 13.30 mmol) was dissolved in ethanol (21 mL) and was also split across the three microwave vials. Water (21 mL) was split across the three microwave vials then the reaction mixtures were degassed with nitrogen and heated at 100° C. for 3 h using a microwave. The reaction mixtures were combined and filtered through Celite®, washing with EtOAc and the filtrate was concentrated under reduced pressure. The crude product was taken up in EtOAc (150 mL) and water (150 mL) and the layers were separated. The aqueous phase was extracted with EtOAc (2×150 mL) and the combined organic extracts were dried by passing through a hydrophobic frit and concentrated under reduced pressure. The crude product was purified by chromatography on KP-NH silica, eluting with a 40% solution of EtOAc containing 1% NEt$_3$ in cyclohexane. The residue obtained was purified further by chromatography on KP-NH silica, eluting with 0-40% MeOH containing 1% NEt$_3$ in EtOAc. The residue obtained was taken up in EtOAc (30 mL) and QuadraPure® TU metal scavenger (4 g) was added and the mixture was heated at 75° C. for 5 h. The QuadraPure® TU was removed by vacuum filtration, washing with EtOAc, and the filtrate was concentrated under reduced pressure and dried on a high vacuum line to give the title compound (3.58 g, 54%).

LCMS (Method C): Rt=1.00 min, MH$^+$ 477. Enantiomeric purity by chiral HPLC=>99.0% e.e.

$^1$H NMR (400 MHz, CDCl$_3$) δ-ppm 8.62 (d, J=5 Hz, 1H), 8.25 (d, J=2 Hz, 1H), 7.72 (dd, J=9 Hz, 3 Hz, 1H), 7.59 (s, 1H), 7.40 (dd, J=5 Hz, 2 Hz, 1H), 6.89 (d, J=9 Hz, 1H), 4.02

(s, 3H), 3.93-3.87 (m, 4H), 3.59 (q, J=7 Hz, 1H), 3.03-2.95 (m, 5H), 2.69-2.63 (m, 1H), 2.39-2.22 (m, 5H), 2.05-1.96 (s, 2H), 1.68 (br. s., 1H), 1.44 (d, J=7 Hz, 3H), 1.12 (d, J=6 Hz, 3H), 1.01 (d, J=6 Hz, 3H).

The examples in the following table, Examples 111-114 were prepared in manner similar to that described for the previous example, Example 110, using the aryl halide intermediates specified and the following boronic acids:

(2S,6R)-1,2,6-trimethyl-4-((S)-1-(4-(4,4,5,5-tetramethyl-1,3,2-dioxaborolan-2-yl)pyridin-2-yl)ethyl)piperazine (S)-1-methyl-4-(1-(4-(4,4,5,5-tetramethyl-1,3,2-dioxaborolan-2-yl)pyridin-2-yl)ethyl)piperazine

| Example No. | Intermediate | Structure | Name | Purification Method | LCMS method | Rt min | MH+ |
|---|---|---|---|---|---|---|---|
| 111 | 18 | 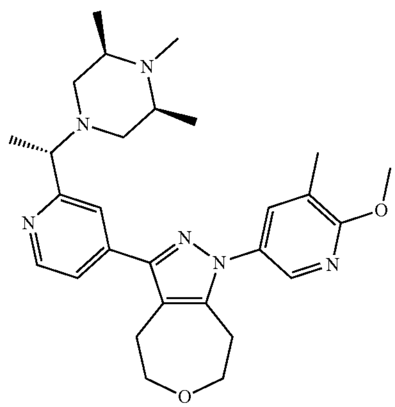 [SMILES: COc1ncc(-n2nc(-c3ccnc([C@H](C)N4C[C@@H](C)N(C)[C@@H](C)C4)c3)c3c2CCOCC3)cc1C] | 1-(6-methoxy-5-methylpyridin-3-yl)-3-(2-((S)-1-((3S,5R)-3,4,5-trimethylpiperazin-1-yl)ethyl)pyridin-4-yl)-4,5,7,8-tetrahydro-1H-oxepino[4,5-c]pyrazole | MDAP (Method A) | C | 1.07 | 491 |
| 112 | 110 | 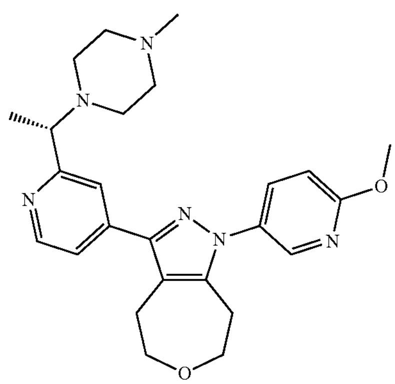 [SMILES: COc1ccc(-n2nc(-c3ccnc([C@H](C)N4CCN(C)CC4)c3)c3c2CCOCC3)cn1] | (S)-1-(6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole | Normal phase silica, eluting with 0-40% MeOH (+1% NEt$_3$)/ EtOAc | C | 0.92 | 449 |
| 113 | 67 | 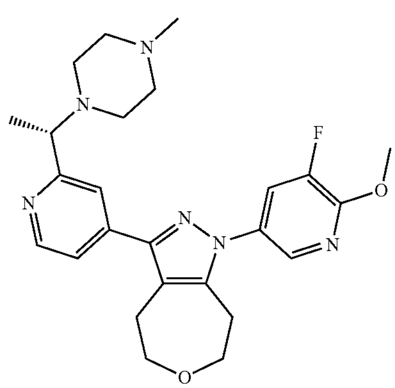 [SMILES: COc1ncc(-n2nc(-c3ccnc([C@H](C)N4CCN(C)CC4)c3)c3c2CCOCC3)cc1F] | (S)-1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole | MDAP (Method A) | C | 0.99 | 467 |

Example 114. (g)-1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole

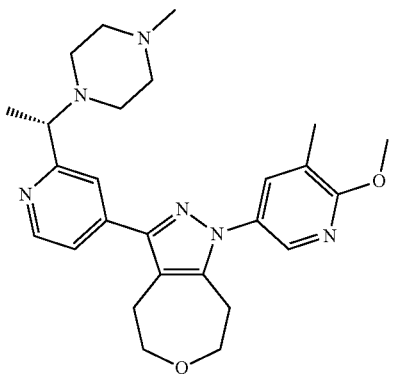

To a stirred solution of (R)-1-(4-(1-(6-methoxy-5-methylpyridin-3-yl)-4,5,7,8-tetrahydro-1H-oxepino[4,5-c]pyrazol-3-yl)pyridin-2-yl)ethyl methanesulfonate (3.3 g, 7.20 mmol) in DMF (30 mL) was added DIPEA (2.51 mL, 14.39 mmol) followed by 1-methylpiperazine (0.721 g, 7.20 mmol). The reaction mixture was stirred at 50° C. under nitrogen for 6 h. The reaction mixture was quenched with water (50 ml-) extracted with 10% MeOH in DCM (3×100 mL). The combined organic extracts were washed with brine (100 mL), dried over $Na_2SO_4$, filtered and concentrated under reduced pressure. The crude material was pre-absorbed on silicagel (100-200 mesh, 15 g) and purified by normal phase column chromatography, eluting with 0-20% MeOH/DCM. The appropriate fractions were combined and concentrated under reduced pressure and the residue purified by chiral SFC (Method A) to afford the title compound (1.8 g).

LCMS (Method B): Rt=1.46 min, MH+ 463.

Example 115. 1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole

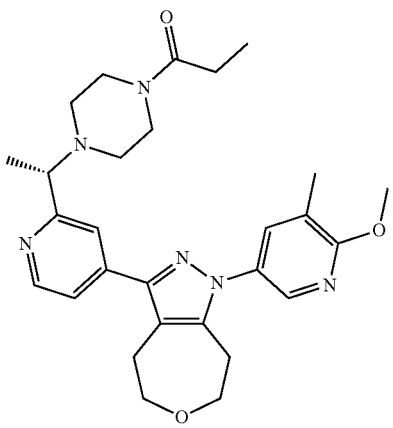 [SMILES: CCC(=O)N1CCN([C@@H](C)c2cc(-c3nn(-c4cnc(OC)c(C)c4)c4c3CCOCC4)ccn2)CC1]

A mixture of 1-(4-(1-(6-methoxy-5-methylpyridin-3-yl)-4,5,7,8-tetrahydro-1H-oxepino[4,5-c]pyrazol-3-yl)pyridin-2-yl)ethanone (1 g, 2.64 mmol), 1-(piperazin-1-yl)propan-1-one (0.564 g, 3.96 mmol)tetraisopropoxytitanium (0.962 mL, 3.17 mmol), acetic acid (0.303 mL, 5.29 mmol) and 1,4-Dioxane (10 mL) was stirred at room temperature for 30 min under an atmosphere of nitrogen. Sodium triacetoxyborohydride (1.120 g, 5.29 mmol) was added and the mixture was heated to 120° C. for 16 h. The reaction mixture was filtered through Celite®, washing with EtOAc. The product was extracted into water (50 mL), then the aqueous phase was basified with saturated $NaHCO_3$ solution (50 mL). The aqueous phase was extracted with EtOAc (100 mL). The organic layer was dried over $Na_2SO_4$, filtered and concentrated under reduced pressure. The crude material was purified by preparative HPLC (Method C) to afford the racemic compound (450 mg), which was further purified by chiral SFC (Method B) to afford the title compound (155 mg).

LCMS (Method B): Rt=1.65 min, MH+ 505.

Absolute configuration was assigned by comparing the experimental solution VCD spectrum with the calculated VCD spectrum of the modeled structure.

Example 116. (S)-1-(1-(4-(1-(5-fluoro-6-methoxypyridin-3-yl)-4,5,7,8-tetrahydro-1H-oxepino[4,5-c]pyrazol-3-yl)pyridin-2-yl)ethyl)-3-methylimidazolidin-2-one

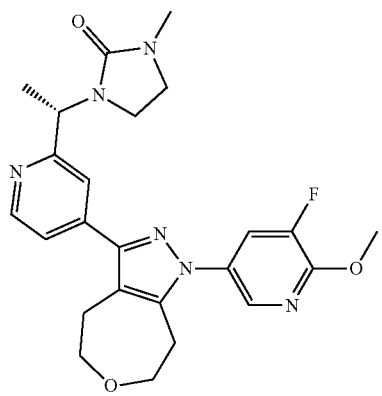 [SMILES: COc1ncc(-n2nc(-c3ccnc([C@H](C)N4CCN(C)C4=O)c3)c3c2CCOCC3)cc1F]

In one reaction vessel, lithium bis(trimethylsilyl)amide solution (1 M in THF, 5.9 mL, 5.9 mmol) was added dropwise to a solution of 1-methyl-2-imidazolidinone (0.626 g, 6.28 mmol) in 2-MeTHF (9 mL) and the mixture was stirred for 17 min. 1-(4-(1-(5-fluoro-6-methoxypyridin-3-yl)-4,5,7,8-tetrahydro-1H-oxepino[4,5-c]pyrazol-3-yl)pyridin-2-yl)ethyl methanesulfonate (0.91 g, 1.97 mmol) in 2-MeTHF (9 mL) was added dropwise and the mixture heated to 80° C. overnight. In a second reaction vessel, lithium bis(trimethylsilyl)amide solution (1 M in THF, 5.9 mL, 5.9 mmol) was added dropwise to a solution of 1-methyl-2-imidazolidinone (0.626 g, 6.28 mmol) in 2-MeTHF (9 mL) and the mixture was stirred for 17 min. 1-(4-(1-(5-fluoro-6-methoxypyridin-3-yl)-4,5,7,8-tetrahydro-1H-oxepino[4,5-c]pyrazol-3-yl)pyridin-2-yl)ethyl methanesulfonate (0.91 g, 1.97 mmol) in 2-MeTHF (9 mL) was added dropwise and the mixture heated to 80° C. overnight. The crude reaction mixtures were combined, followed by the addition of MeOH to get a solution. The solvent was removed under reduced pressure and the crude material was purified by normal phase column chromatography on silica, eluting with 0-20% MeOH/DCM. The reaction was repeated on 0.19 g and 0.91 g scale and all the Example 117. 3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole

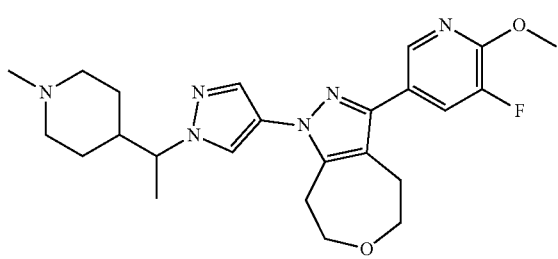

A solution of 3-(5-fluoro-6-methoxypyridin-3-yl)-1-(1-(1-(piperidin-4-yl)ethyl)-1H-pyrazol-4-yl)-4,5,7,8-tetrahydro-1H-oxepino[4,5-c]pyrazole (150 mg, 0.341 mmol), formaldehyde (36.5% aqueous solution, 0.103 mL, 1.362 mmol) and formic acid (0.091 mL, 2.384 mmol in Methanol (1.5 mL) was sealed and placed under an atmosphere of nitrogen. The mixture was heated at 80° C. in the microwave for 1.5 h. Saturated aqueous NaHCO₃ solution was added dropwise to the reaction mixture until the solution reached pH 8, then more was added to give an aqueous phase of approx 50 mL. The MeOH was removed under reduced pressure and the aqueous phase was extracted with EtOAc (2×50 mL). The combined organic extracts were washed with saturated aqueous NaHCO₃ solution (50 mL) and the aqueous phase was extracted with further EtOAc (20 mL). The combined organic extracts were dried by passing through a hydrophobic frit and the solvent was removed under reduced pressure to afford the title compound (142 mg).

LCMS (Method C): Rt=1.03 min, MH⁺ 455.

Example 118 and 119. (S)-3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole and (R)-3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole

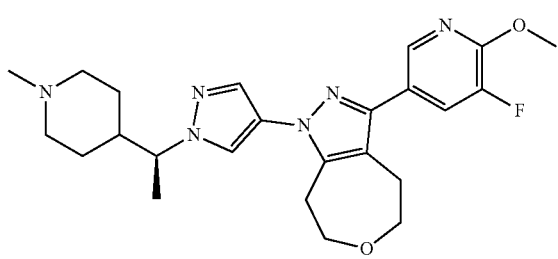

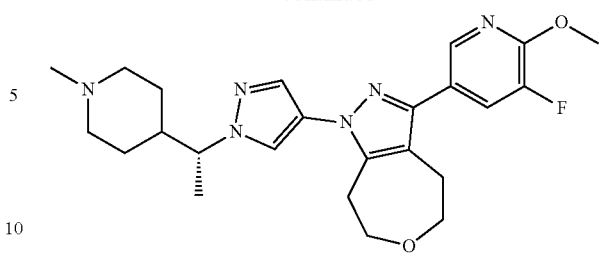

3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole (Example 117) was separated into its two component enantiomers by preparative chiral HPLC using a 30 mm×25 cm Chiralpak AD-H column. The column was eluted with 30% EtOH(+0.2% isopropylamine)/Heptane(+0.2% isopropylamine), using a flow rate of 30 mL/min. Appropriate fractions were combined and evaporated to give the two enantiomers:

Example 118: 39 mg, colourless oil. LCMS (Method C) Rt=1.04 min, MH⁺=455. Enantiomeric purity by chiral HPLC=>99.0% e.e.

Example 119: 42 mg, colourless oil. LCMS (Method C) Rt=1.04 min, MH⁺=455. Enantiomeric purity by chiral HPLC=>99.0% e.e.

Absolute stereochemistry was not assigned.

Example 120. 1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole

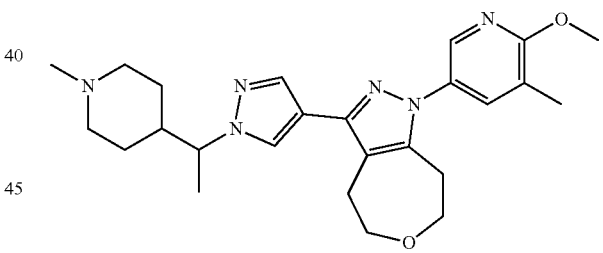

1-(6-methoxy-5-methylpyridin-3-yl)-3-(1-(1-(piperidin-4-yl)ethyl)-1H-pyrazol-4-yl)-4,5,7,8-tetrahydro-1H-oxepino[4,5-c]pyrazole (65 mg, 0.149 mmol), formaldehyde (0.017 mL, 0.234 mmol), formic acid (0.033 mL, 0.869 mmol) and anhydrous MeOH (1 mL) were added to a microwave vial. The reaction mixture was placed under with nitrogen then heated at 80° C. for 2 h using a microwave. The reaction mixture was quenched with dropwise addition of saturated aqueous NaHCO₃ solution (2 mL) and stirred for 5 mins, then diluted further with saturated aqueous NaHCO₃ solution (5 mL) and extracted with ethyl acetate (3×20 mL). The combined organic extracts were passed through a hydrophobic frit and concentrated under reduced pressure. The crude product was purified by MDAP (Method A) to give the title compound (18 mg).

LCMS (Method C): Rt=1.07 min, MH⁺ 451.

Example 121 and 122. (S)-1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole and (R)-1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole

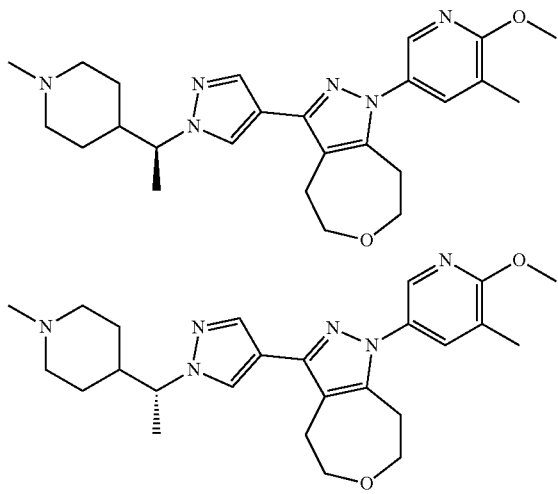

1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole (Example 120) was separated into its two component enantiomers by preparative chiral HPLC using a 30 mm×25 cm Chiralpak IF column. The column was eluted with 100% MeCN(+0.2% isopropylamine), using a flow rate of 30 mL/min. Appropriate fractions were combined and evaporated to give the two enantiomers:

Example 121: 4 mg. LCMS (Method C) Rt=1.03 min, MH$^+$=451. Enantiomeric purity by chiral HPLC=>99.0% e.e.

Example 122: 4 mg. LCMS (Method C) Rt=1.03 min, MH$^+$=451. Enantiomeric purity by chiral HPLC==>94.9% e.e.

Absolute stereochemistry was not assigned.

Example 123. (R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole

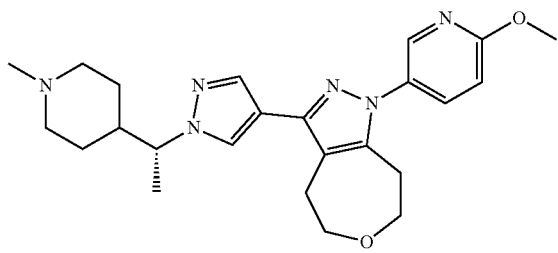

(R)-1-(6-methoxypyridin-3-yl)-3-(1-(1-(piperidin-4-yl)ethyl)-1H-pyrazol-4-yl)-4,5,7,8-tetrahydro-1H-oxepino[4,5-c]pyrazole (3.49 g, 8.26 mmol), formic acid (1.1 mL, 28.7 mmol), formaldehyde (1 mL, 13.43 mmol) and MeOH (20 mL) were split between two microwave vials. The vials were sealed, flushed with nitrogen and heated at 80° C. for 3 h using a microwave. The reaction mixtures were combined, quenched with saturated aqueous NaHCO$_3$ solution (40 mL) and left to stir for 10 mins. More sat. aq. NaHCO$_3$ (20 mL) was added and the aqueous phase was extracted with EtOAc (2×80 mL then 3×50 mL). The combined organic extracts were dried by passing through a hydrophobic frit and the solvent removed under reduced pressure. The crude material was purified by preparative chiral HPLC using a 30 mm×25 cm Chiralpak AD-H (5 μm) column. The column was eluted with 50% EtOH(+0.2% isopropylamine)/Heptane(+0.2% isopropylamine) using a flow rate of 30 mL/min. Appropriate fractions were combined and evaporated and the residue was taken up in MeCN/water (1:1, 20 mL), frozen in cardice for 2 h and placed on a freeze drier over the weekend. The resulting solid was purified further by preparative HPLC (Method B). The appropriate fractions were combined and the pH adjusted to pH 10 with aqueous ammonia solution. The organic solvent was removed under a stream of nitrogen and more aqueous ammonia solution was added to ensure pH 10. Brine (200 mL) was added and the aqueous phase was extracted with DCM (3×600 mL). The combined organic extracts were dried over Na$_2$SO$_4$, filtered and concentrated under reduced pressure. The material was taken up in a minimum amount of MeCN/water and placed on a freeze drier. The resulting solid was dried further in a vacuum oven to afford the title compound (2.1 g).

LCMS (Method F): Rt=3.29 min, MH$^+$ 437. Enantiomeric purity by chiral HPLC=>99.0% e.e.

$^1$H NMR (400 MHz, d6-DMSO) δ-ppm 8.28 (d, J=3 Hz, 1H), 7.99 (s, 1H), 7.84 (dd, J=9 Hz, 3 Hz, 1H), 7.68 (s, 1H), 6.97 (d, J=9 Hz, 1H), 4.17-4.10 (m, 1H), 3.92 (s, 3H), 3.84-3.80 (m, 2H), 3.79-3.74 (m, 2H), 2.89-2.82 (m, 4H), 2.78 (br. d, J=11 Hz, 1H), 2.67 (br. d, J=11 Hz, 1H), 2.10 (s, 3H), 1.83-1.76 (m, 1H), 1.71-1.61 (m, 3H), 1.44 (d, J=7 Hz, 3H), 1.26-1.09 (m, 2H), 1.03-0.97 (m, 1H).

Example 124. 3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole

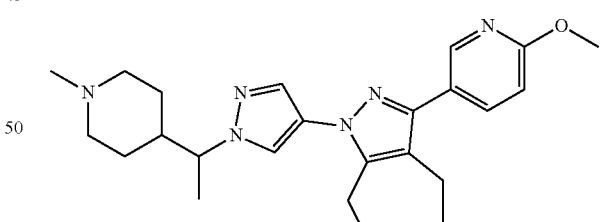

To a solution of 3-(6-methoxypyridin-3-yl)-1-(1-(1-(piperidin-4-yl)ethyl)-1H-pyrazol-4-yl)-4,5,7,8-tetrahydro-1H-oxepino[4,5-c]pyrazole (183 mg, 0.433 mmol) in MeOH (2 mL) was added formaldehyde (36.5% aqueous solution, 0.064 mL, 0.866 mmol) and formic acid (0.058 mL, 1.516 mmol). The vial was sealed and placed under an atmosphere of nitrogen. The mixture was heated at 80° C. in the microwave for 1 h. Saturated aqueous NaHCO$_3$ solution (2 mL) was added dropwise to the reaction mixture, then the solution was diluted with more saturated aqueous NaHCO$_3$ solution (8 mL). The aqueous phase was extracted with EtOAc (3×20 mL). The combined organic extracts were dried by passing through a hydrophobic frit and the solvent was removed under reduced pressure. The crude material was purified by MDAP (Method A) to afford the title compound (80 mg).

LCMS (Method C): Rt=0.95 min, MH+ 437.

Example 125 and 126. (S)-3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole and (R)-3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole

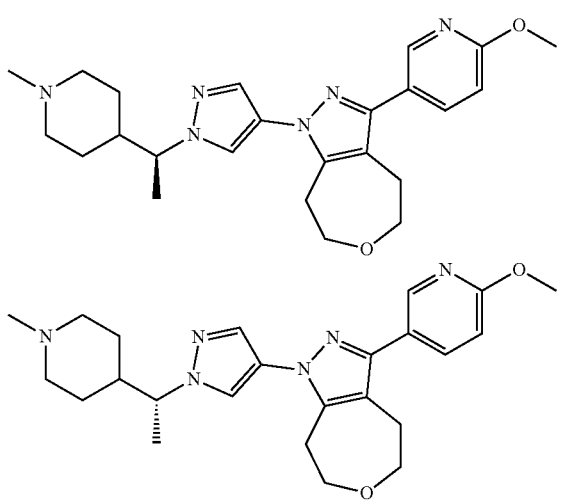

3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole (Example 124) was separated into its two component enantiomers by preparative chiral HPLC using a 30 mm×25 cm Chiralpak AD-H column. The column was eluted with 50% EtOH(+0.2% isopropylamine)/Heptane(+0.2% isopropylamine), using a flow rate of 30 mL/min.

Appropriate fractions were combined and evaporated to give the two enantiomers:

Example 125: 25 mg. LCMS (Method C) Rt=0.95 min, MH+=437. Enantiomeric purity by chiral HPLC=>99.0% e.e.

Example 126: 24 mg. LCMS (Method C) Rt=0.96 min, MH+=437. Enantiomeric purity by chiral HPLC=>99.0% e.e.

Absolute stereochemistry was not assigned.

Example 127. 1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole

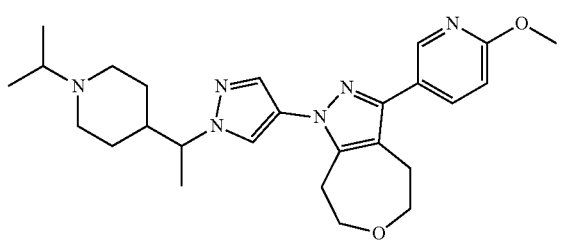 [SMILES: COc1ccc(-c2nn(-c3cnn(C(C)C4CCN(C(C)C)CC4)c3)c3c2CCOCC3)cn1]

To a solution of 3-(6-methoxypyridin-3-yl)-1-(1-(1-(piperidin-4-yl)ethyl)-1H-pyrazol-4-yl)-4,5,7,8-tetrahydro-1H-oxepino[4,5-c]pyrazole (42 mg, 0.099 mmol) in MeCN (1 mL) were added NEt$_3$ (0.042 mL, 0.298 mmol) and 2-iodopropane (0.016 mL, 0.159 mmol). The reaction mixture was stirred at 50° C. for 72 h. 2-Iodopropane (0.008 mL, 0.08 mmol) and NEt$_3$ (0.021 mL, 0.149 mmol) were added to the reaction mixture and stirring was continued at 50° C. for 48 h. 2-Iodopropane (0.008 mL, 0.08 mmol) and NEt$_3$ (0.021 mL, 0.149 mmol) were added to the reaction mixture and stirring was continued at 50° C. for 6 h. The solvent was removed under reduced pressure and the residue was taken up in EtOAc (10 mL) and washed with saturated aqueous NaHCO$_3$ solution. The organic phase was dried by passing through a hydrophobic frit and the solvent removed under reduced pressure. The crude material was purified by MDAP (Method A) to afford the title compound (23 mg).

LCMS (Method C): Rt=1.06 min, MH+ 465.

Example 128. and 129. (S)-1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole and (R)-1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole

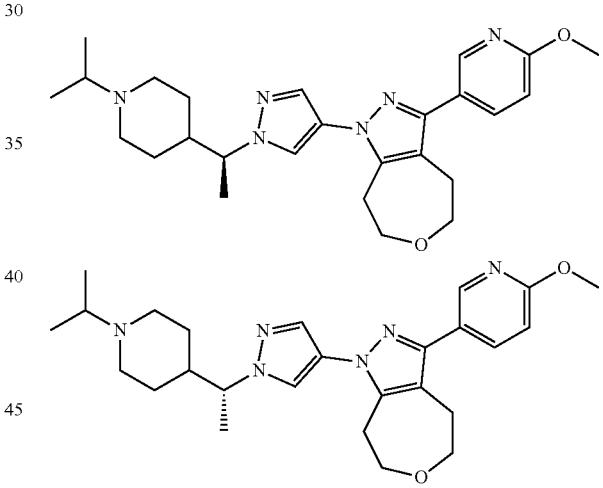

1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole (Example 127) was separated into its two component enantiomers by preparative chiral HPLC using a 30 mm×25 cm Chiralpak AD-H column. The column was eluted with 10% EtOH(+0.2% isopropylamine)/Heptane(+0.2% isopropylamine), using a flow rate of 30 mL/min. Appropriate fractions were combined and evaporated to give the two enantiomers:

Example 129: 9 mg. LCMS (Method C) Rt=1.08 min, MH+=465. Enantiomeric purity by chiral HPLC=>99.0% e.e.

Example 130: 10 mg. LCMS (Method C) Rt=1.09 min, MH+=465. Enantiomeric purity by chiral HPLC=>90.0% e.e.

Absolute stereochemistry was not assigned.

Example 130. 3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole Example 131. and 132. (S)-3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole and (R)-3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole

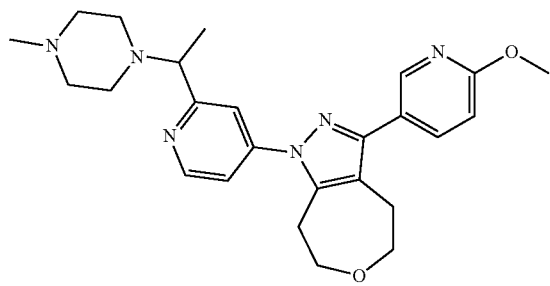

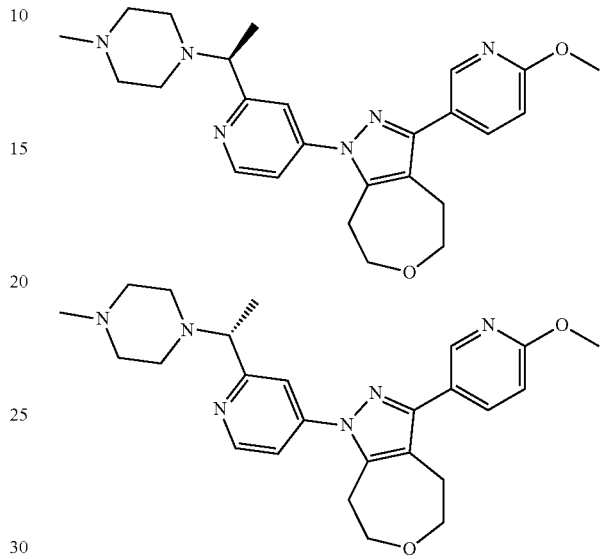

A microwave vial was charged with XPhos Pd G2 (25.6 mg, 0.033 mmol), (6-methoxypyridin-3-yl)boronic acid (142 mg, 0.931 mmol) and a solution of 3-bromo-1-(2-(1-(4-methylpiperazin-1-yl)ethyl)pyridin-4-yl)-4,5,7,8-tetrahydro-1H-oxepino[4,5-c]pyrazole (326 mg, 0.465 mmol) in 1,4-Dioxane (0.5 mL). The reaction mixture was treated with a solution of tripotassium phosphate (198 mg, 0.931 mmol) in Water (2 mL) and the reaction mixture was flushed with nitrogen then heated for 1 h at 100° C. in a microwave. The reaction mixture was transferred to a round bottomed flask using EtOAc and the solvent was removed under reduced pressure. The mixture was partitioned between EtOAc (50 mL) and water (50 mL). The organic phase was isolated and the aqueous phase was extracted with EtOAc (2×50 mL). The combined organic extracts were dried by passing through a hydrophobic frit and concentrated under reduced pressure. The crude material was purified by reverse phase column chromatography using a C18 column, eluting with a 0 to 50% gradient of MeCN(+0.1% ammonia) in 10 mM ammonium bicarbonate in water, then by MDAP (Method A) to give the title compound (62 mg).

LCMS (Method C): Rt=0.94 min, MH+ 449.

3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole (Example 130) was separated into its two component enantiomers by preparative chiral HPLC using a 30 mm×25 cm Chiralpak AD-H column. The column was eluted with 10% EtOH(+0.2% isopropylamine)/Heptane(+0.2% isopropylamine), using a flow rate of 30 mL/min.

Appropriate fractions were combined and evaporated to give the two enantiomers:

Example 131: 26 mg. LCMS (Method C) Rt=0.94 min, MH+=449. Enantiomeric purity by chiral HPLC=>99.0% e.e.

Example 132: 23 mg. LCMS (Method C) Rt=0.94 min, MH+=449. Enantiomeric purity by chiral HPLC=>97.0% e.e.

Absolute stereochemistry was not assigned.

The following compounds were also prepared by similar methods:

| Example | Structure | LCMS method | Rt min | MH+ |
|---------|-----------|-------------|--------|-----|
| 133 | 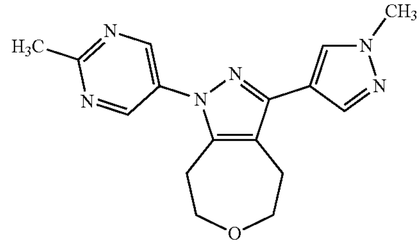 | A | 0.67 | 311 |

-continued
| Example | Structure | LCMS method | Rt min | MH+ |
|---|---|---|---|---|
| 134 | 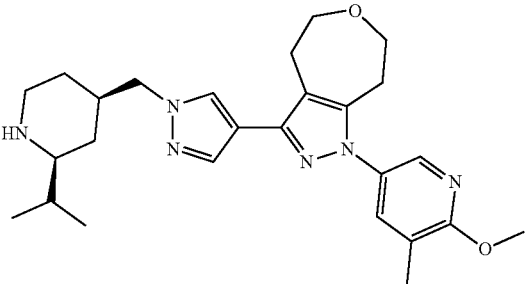 [SMILES: COc1ncc(-n2nc(-c3cnn(C[C@@H]4CCN[C@H](C(C)C)C4)c3)c3c2CCOCC3)cc1C] UNKNOWN ISOMER 1 | C | 1.21 | 465 |
| 135 | 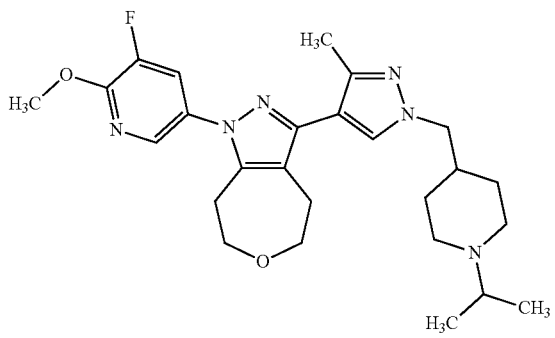 [SMILES: COc1ncc(-n2nc(-c3cn(CC4CCN(C(C)C)CC4)nc3C)c3c2CCOCC3)cc1F] | C | 1.10 | 483 |
| 136 | 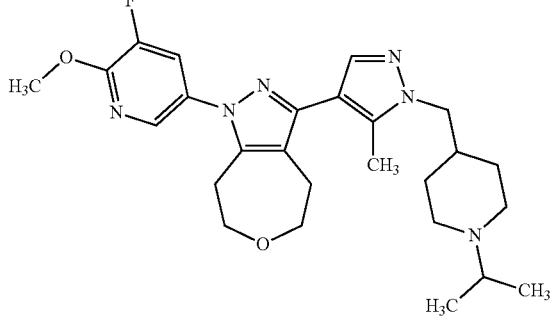 | C | 1.13 | 483 |
| 137 | 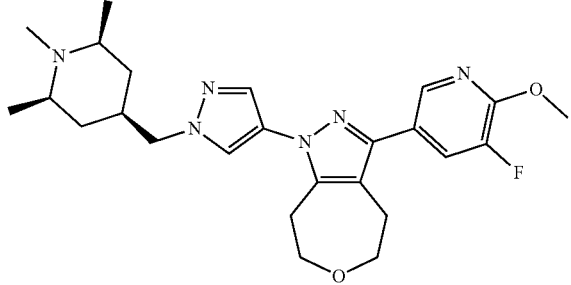 | C | 1.09 | 469 |
| 138 | 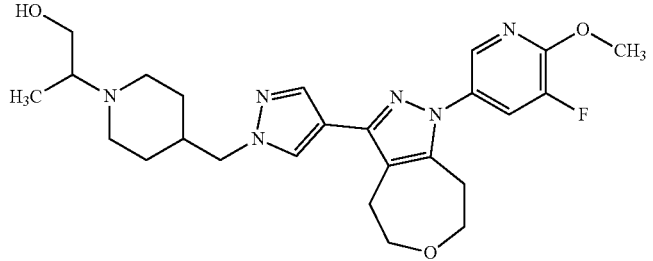 [SMILES: COc1ncc(-n2nc(-c3cnn(CC4CCN(C(C)CO)CC4)c3)c3c2CCOCC3)cc1F] | C | 0.93 | 485 |

| Example | Structure | LCMS method | Rt min | MH+ |
|---|---|---|---|---|
| 139 | 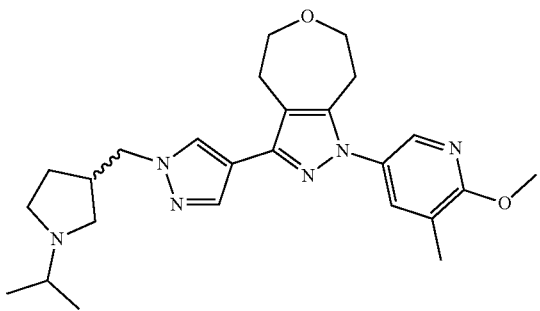 [SMILES: COc1ncc(-n2nc(-c3cnn(CC4CCN(C(C)C)C4)c3)c3c2CCOCC3)cc1C]<br>SINGLE UNKNOWN ISOMER 1 | C | 1.11 | 451 |
| 140 | 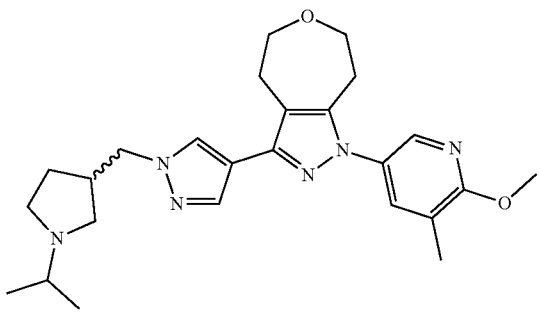 [SMILES: COc1ncc(-n2nc(-c3cnn(CC4CCN(C(C)C)C4)c3)c3c2CCOCC3)cc1C]<br>SINGLE UNKNOWN ISOMER 2 | C | 1.11 | 451 |
| 141 | 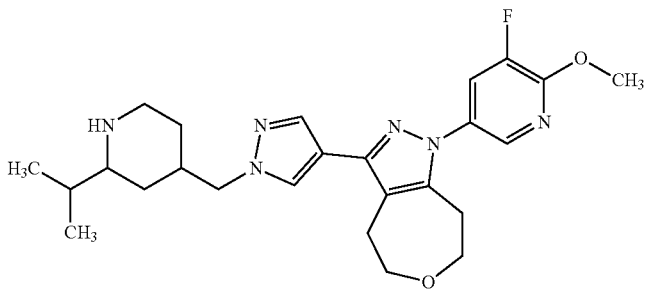 [SMILES: COc1ncc(-n2nc(-c3cnn(CC4CCNC(C(C)C)C4)c3)c3c2CCOCC3)cc1F] | C | 1.13 | 469 |
| 142 | 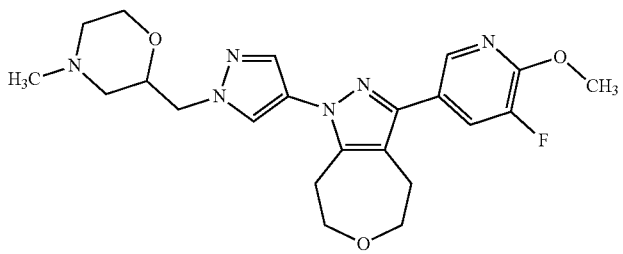 | C | 0.91 | 443 |

-continued

| Example | Structure | LCMS method | Rt min | MH+ |
|---|---|---|---|---|
| 143 | 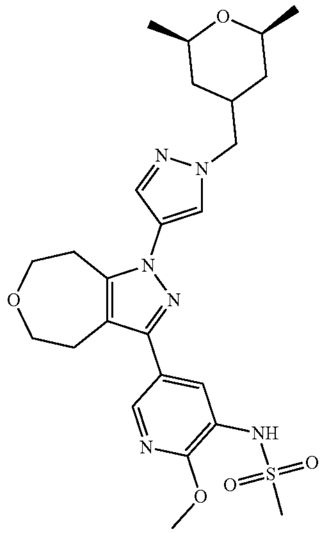 [SMILES: COc1ncc(-c2nn(-c3cnn(CC4C[C@@H](C)O[C@@H](C)C4)c3)c3c2CCOCC3)cc1NS(C)(=O)=O] | B | 1.95 | 531 |
| 144 | 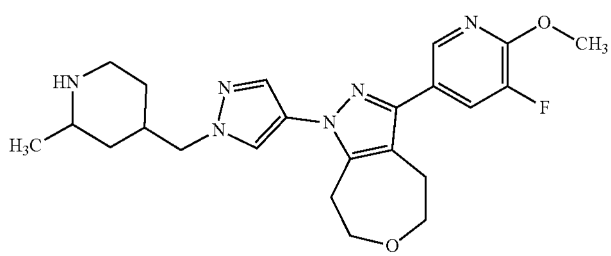 | C | 1.05 | 441 |
| 145 | 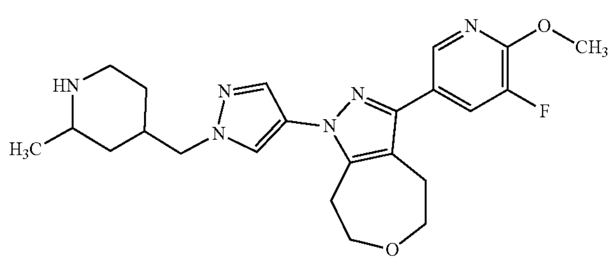 | C | 1.07 | 455 |
| 146 | 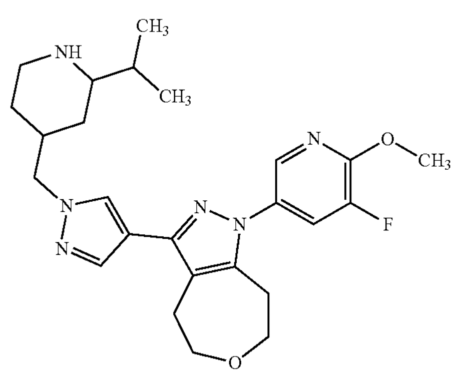 [SMILES: COc1ncc(-n2nc(-c3cnn(CC4CCNC(C(C)C)C4)c3)c3c2CCOCC3)cc1F] | C | 1.07 | 469 |

-continued

| Example | Structure | LCMS method | Rt min | MH+ |
|---|---|---|---|---|
| 147 | 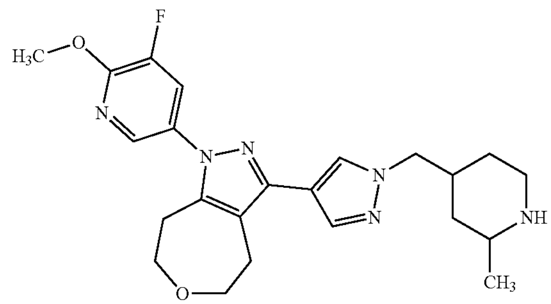 [SMILES: COc1ncc(-n2nc(-c3cnn(CC4CCNC(C)C4)c3)c3c2CCOCC3)cc1F] | C | 0.89 | 441 |
| 148 | 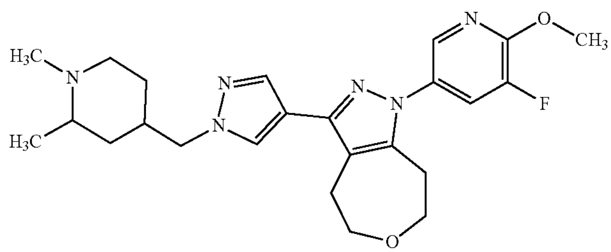 | C | 0.99 | 455 |
| 149 | 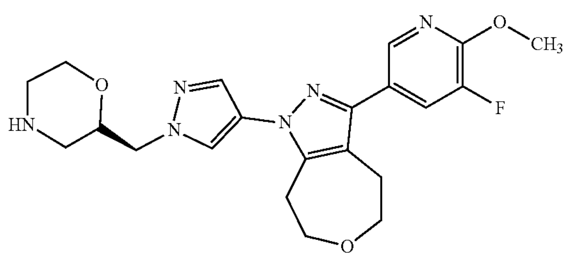 | C | 0.88 | 429 |
| 150 | 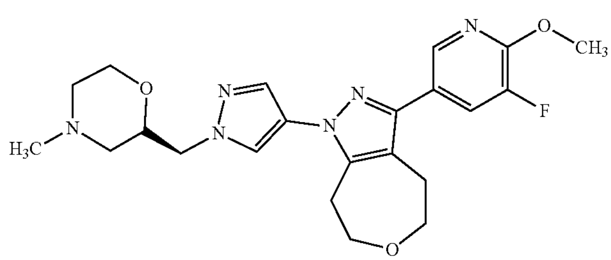 | C | 0.93 | 443 |
| 151 | 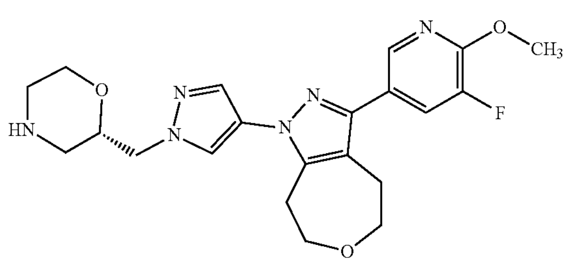 [SMILES: COc1ncc(-c2nn(-c3cnn(C[C@@H]4CNCCO4)c3)c3c2CCOCC3)cc1F] | C | 0.85 | 429 |

-continued

| Example | Structure | LCMS method | Rt min | MH+ |
|---------|-----------|-------------|--------|-----|
| 152 | 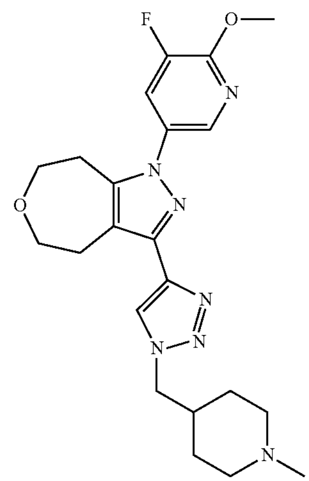 [SMILES: COc1ncc(-n2nc(-c3cn(CC4CCN(C)CC4)nn3)c3c2CCOCC3)cc1F] | C | 0.99 | 442 |
| 153 | 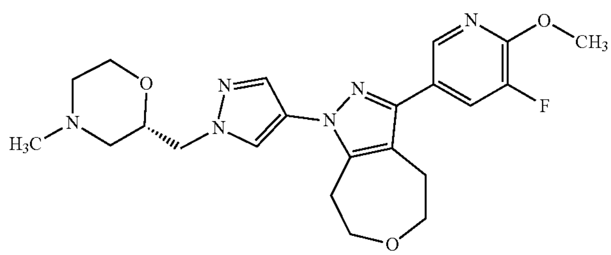 | C | 0.93 | 443 |
| 154 | 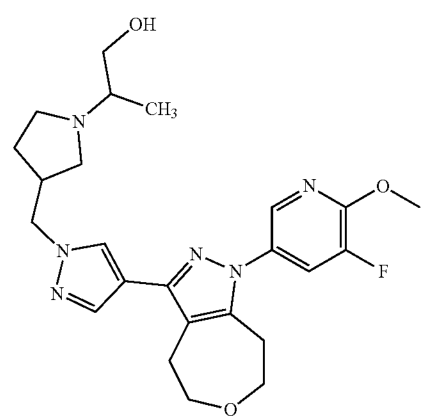 [SMILES: COc1ncc(-n2nc(-c3cnn(CC4CCN(C(C)CO)C4)c3)c3c2CCOCC3)cc1F] | C | 0.89 | 471 |
| 155 | 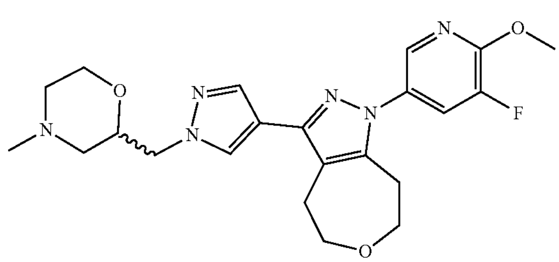 | C | 0.90 | 443 |

SINGLE UNKNOWN ISOMER 1

-continued

| Example | Structure | LCMS method | Rt min | MH+ |
|---|---|---|---|---|
| 156 | SINGLE UNKNOWN ISOMER 2 | C | 0.90 | 443 |
| 157 | 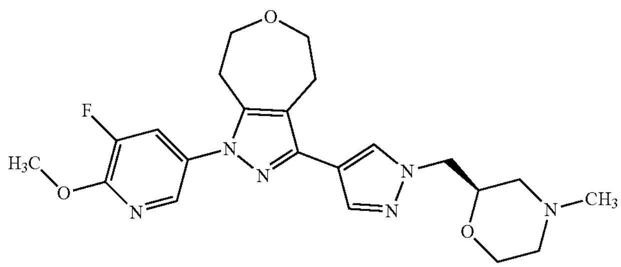 | C | 0.90 | 443 |
| 158 | 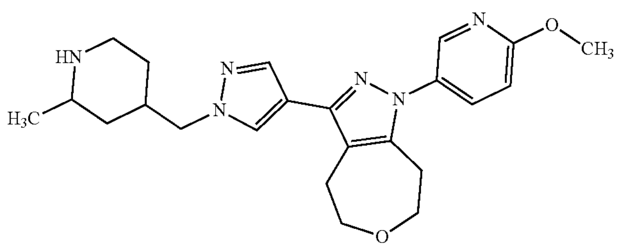 | C | 0.84 | 423 |
| 159 | 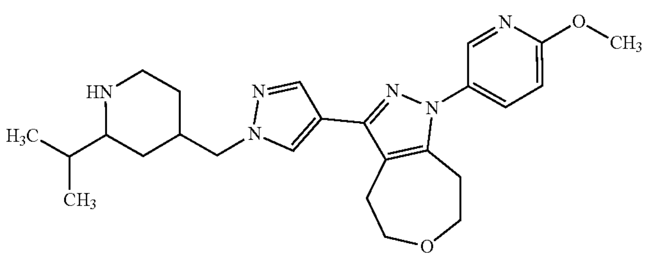 [SMILES: COc1ccc(-n2nc(-c3cnn(CC4CCNC(C(C)C)C4)c3)c3c2CCOCC3)cn1] | C | 1.00 | 451 |
| 160 | 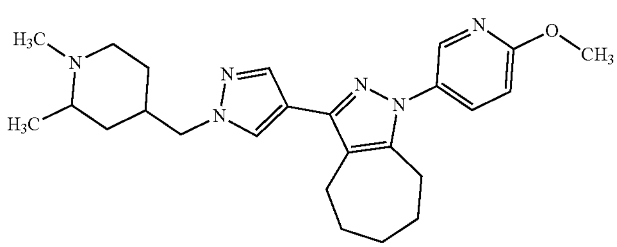 | C | 0.97 | 437 |
| 161 | 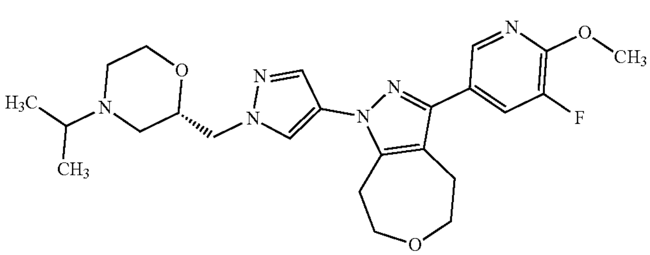 [SMILES: COc1ncc(-c2nn(-c3cnn(C[C@@H]4CN(C(C)C)CCO4)c3)c3c2CCOCC3)cc1F] | C | 1.08 | 471 |

| Example | Structure | LCMS method | Rt min | MH+ |
|---------|-----------|-------------|--------|-----|
| 162 | 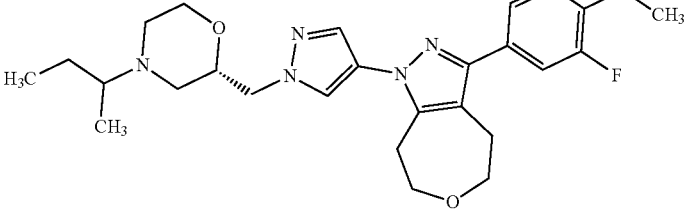 | C | 1.21 | 485 |
| 163 | 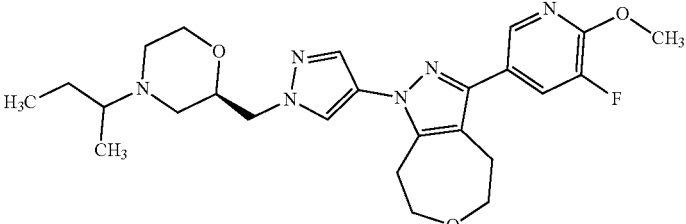 | C | 1.21 | 485 |
| 164 | 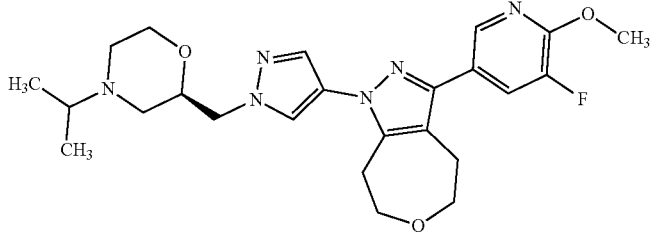 [SMILES: COc1ncc(-c2nn(-c3cnn(C[C@H]4CN(C(C)C)CCO4)c3)c3c2CCOCC3)cc1F] | C | 1.09 | 471 |
| 165 | 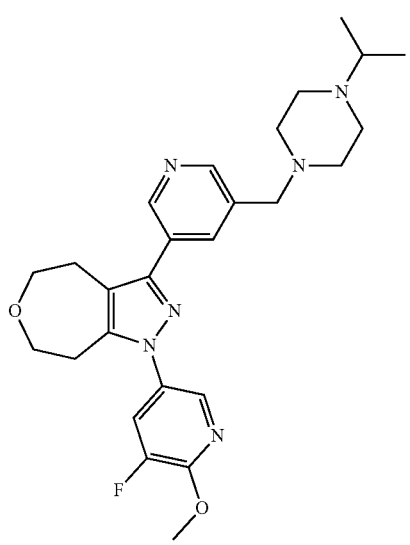 [SMILES: COc1ncc(-n2nc(-c3cncc(CN4CCN(C(C)C)CC4)c3)c3c2CCOCC3)cc1F] | C | 1.02 | 481 |

-continued

| Example | Structure | LCMS method | Rt min | MH+ |
|---|---|---|---|---|
| 166 | 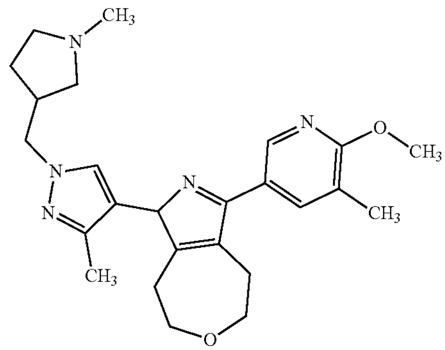 [SMILES: COc1ncc(C2=NC(c3cn(CC4CCN(C)C4)nc3C)C3=C2CCOCC3)cc1C] | C | 1.04 | 437 |
| 167 | 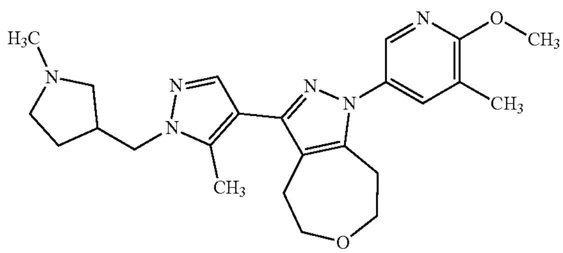 [SMILES: COc1ncc(-n2nc(-c3cnn(CC4CCN(C)C4)c3C)c3c2CCOCC3)cc1C] | C | 1.05 | 437 |
| 168 | 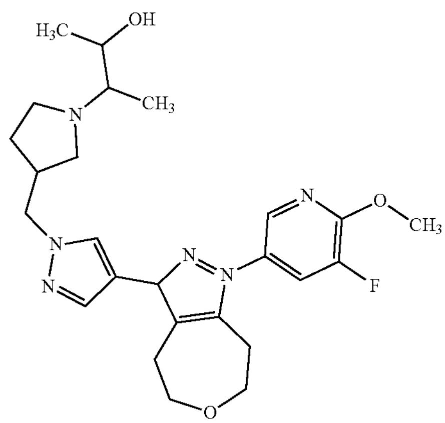 | C | 0.99 | 485 |
| 169 | 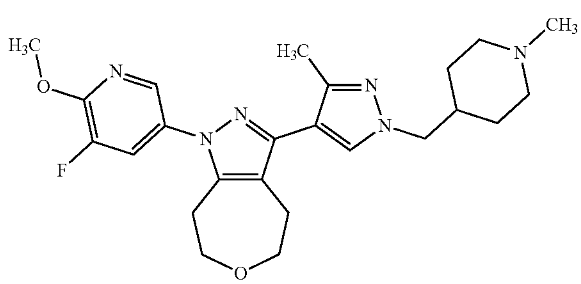 | C | 1.04 | 455 |
| 170 | 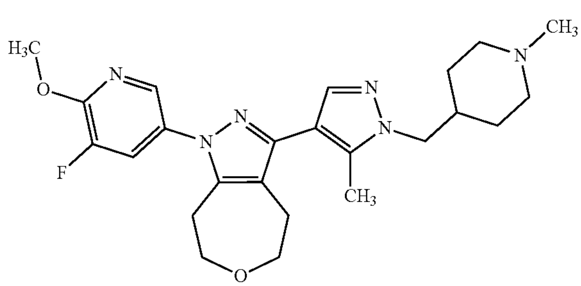 | C | 1.05 | 455 |

| Example | Structure | LCMS method | Rt min | MH+ |
|---|---|---|---|---|
| 171 | 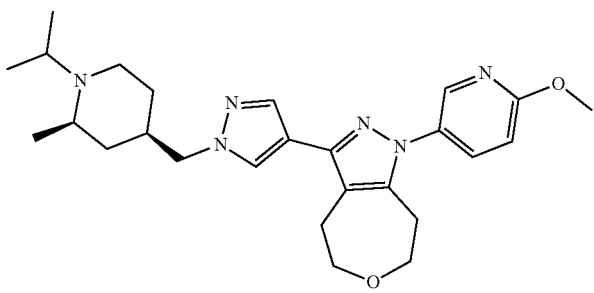 [SMILES: COc1ccc(-n2nc(-c3cnn(C[C@@H]4CCN(C(C)C)[C@H](C)C4)c3)c3c2CCOCC3)cn1] RACEMIC DIASTEREOMER WITH KNOWN RELATIVE STEREOCHEMISTRY | C | 0.97 | 465 |
| 172 | 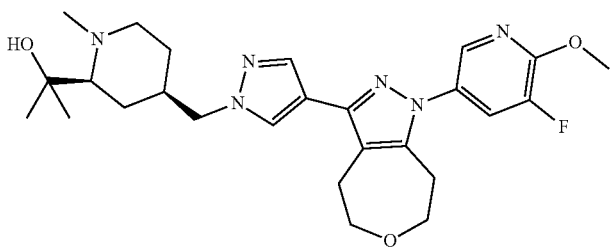 [SMILES: COc1ncc(-n2nc(-c3cnn(C[C@@H]4CCN(C)[C@H](C(C)(C)O)C4)c3)c3c2CCOCC3)cc1F] SINGLE UNKNOWN ISOMER 1 WITH KNOWN RELATIVE STEREOCHEMISTRY | C | 0.91 | 499 |
| 173 | 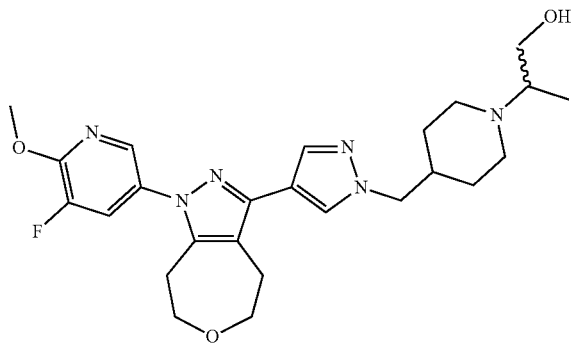 [SMILES: COc1ncc(-n2nc(-c3cnn(CC4CCN(C(C)CO)CC4)c3)c3c2CCOCC3)cc1F] SINGLE UNKNOWN ISOMER 1 | C | 0.93 | 485 |
| 174 | 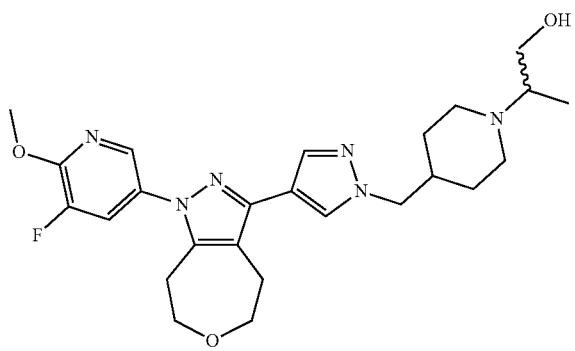 [SMILES: COc1ncc(-n2nc(-c3cnn(CC4CCN(C(C)CO)CC4)c3)c3c2CCOCC3)cc1F] SINGLE UNKNOWN ISOMER 2 | C | 0.94 | 485 |

-continued
| Example | Structure | LCMS method | Rt min | MH+ |
|---|---|---|---|---|
| 175 | 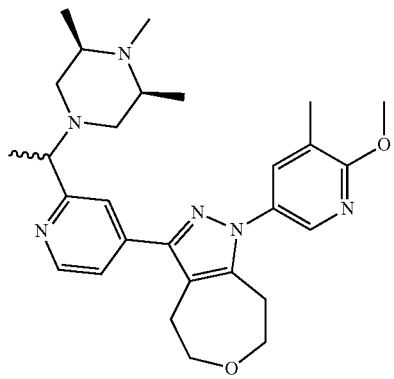 [SMILES: COc1ncc(-n2nc(-c3ccnc(C(C)N4C[C@@H](C)N(C)[C@@H](C)C4)c3)c3c2CCOCC3)cc1C]<br>SINGLE UNKNOWN ISOMER 1 | C | 1.12 | 491 |
| 176 | 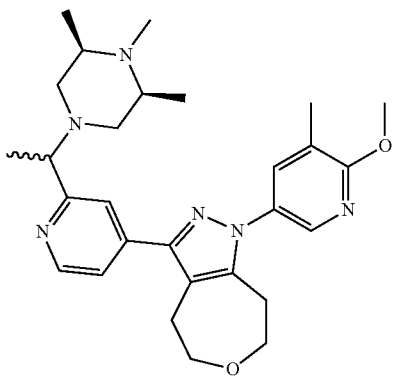 [SMILES: COc1ncc(-n2nc(-c3ccnc(C(C)N4C[C@@H](C)N(C)[C@@H](C)C4)c3)c3c2CCOCC3)cc1C]<br>SINGLE UNKNOWN ISOMER 2 | C | 1.12 | 491 |
| 177 | 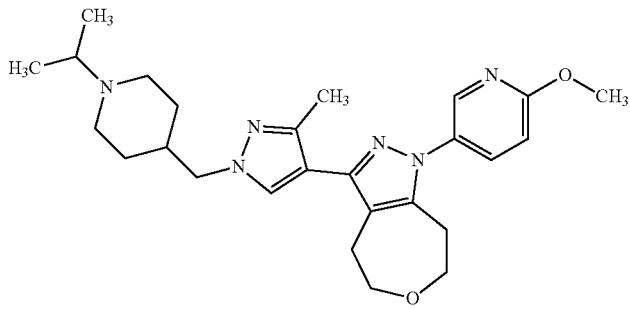 [SMILES: COc1ccc(-n2nc(-c3cn(CC4CCN(C(C)C)CC4)nc3C)c3c2CCOCC3)cn1] | C | 1.02 | 465 |

| Example | Structure | LCMS method | Rt min | MH+ |
|---|---|---|---|---|
| 178 | 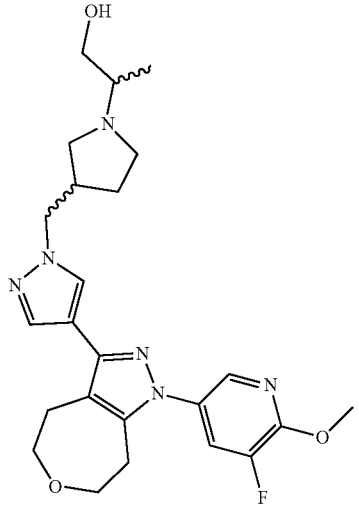 [SMILES: COc1ncc(-n2nc(-c3cnn(CC4CCN(C(C)CO)C4)c3)c3c2CCOCC3)cc1F]<br>SINGLE UNKNOWN ISOMER 1 | C | 0.90 | 471 |
| 179 | 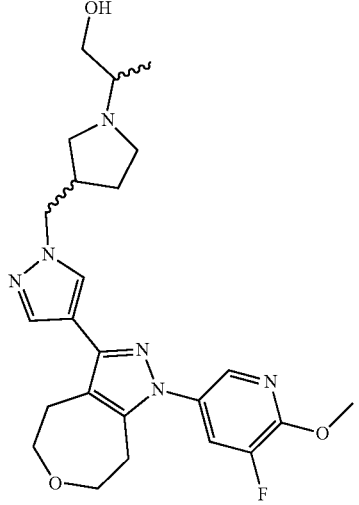 [SMILES: COc1ncc(-n2nc(-c3cnn(CC4CCN(C(C)CO)C4)c3)c3c2CCOCC3)cc1F]<br>SINGLE UNKNOWN ISOMER 2 | C | 0.91 | 471 |

| Example | Structure | LCMS method | Rt min | MH+ |
|---|---|---|---|---|
| 180 | SINGLE UNKNOWN ISOMER 3 | C | 0.90 | 471 |
| 181 | SINGLE UNKNOWN ISOMER 4 | C | 0.91 | 471 |
| 182 | SINGLE UNKNOWN CIS ISOMER 1 | C | 1.06 | 469 |

-continued

| Example | Structure | LCMS method | Rt min | MH+ |
|---|---|---|---|---|
| 183 | SINGLE UNKNOWN CIS ISOMER 2 | C | 1.07 | 469 |
| 184 | 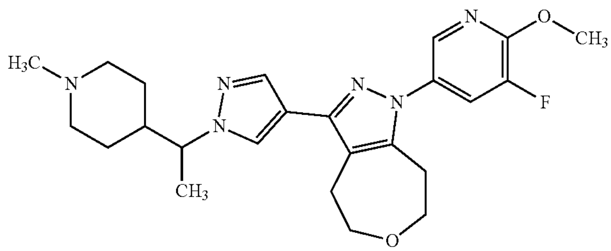 | C | 0.96 | 437 |
| 185 | 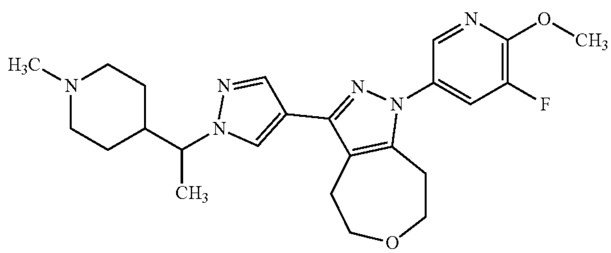 | C | 1.08 | 455 |
| 186 | SINGLE UNKNOWN ISOMER 1 | C | 1.02 | 463 |
| 187 | SINGLE UNKNOWN ISOMER 2 | C | 1.03 | 463 |

-continued
| Example | Structure | LCMS method | Rt min | MH+ |
|---|---|---|---|---|
| 188 | 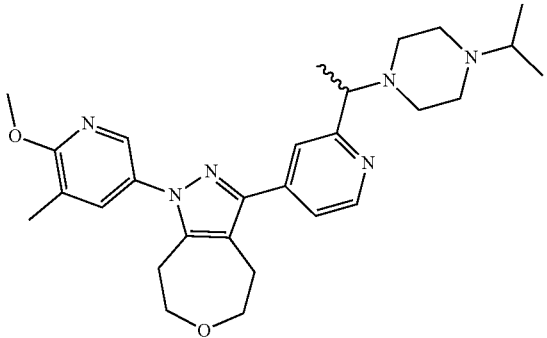 [SMILES: COc1ncc(-n2nc(-c3ccnc(C(C)N4CCN(C(C)C)CC4)c3)c3c2CCOCC3)cc1C]<br>SINGLE UNKNOWN ISOMER 1 | C | 1.17 | 491 |
| 189 | 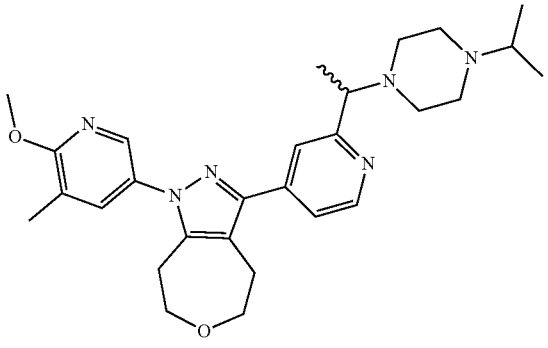 [SMILES: COc1ncc(-n2nc(-c3ccnc(C(C)N4CCN(C(C)C)CC4)c3)c3c2CCOCC3)cc1C]<br>SINGLE UNKNOWN ISOMER 2 | C | 1.17 | 491 |
| 190 | 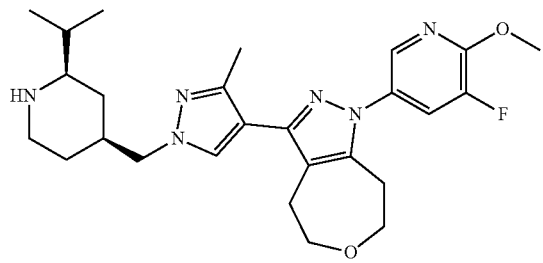 [SMILES: COc1ncc(-n2nc(-c3cn(C[C@H]4CCN[C@@H](C(C)C)C4)nc3C)c3c2CCOCC3)cc1F]<br>SINGLE UNKNOWN ISOMER 1 WITH KNOWN RELATIVE STEREOCHEMISTRY | C | 1.12 | 483 |
| 191 | 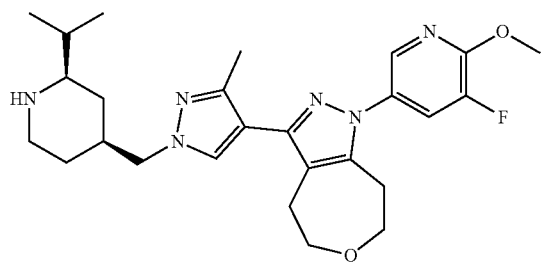 [SMILES: COc1ncc(-n2nc(-c3cn(C[C@H]4CCN[C@@H](C(C)C)C4)nc3C)c3c2CCOCC3)cc1F]<br>SINGLE UNKNOWN ISOMER 2 WITH KNOWN RELATIVE STEREOCHEMISTRY | C | 1.13 | 483 |

| Example | Structure | LCMS method | Rt min | MH+ |
|---|---|---|---|---|
| 192 | *SINGLE UNKNOWN ISOMER 1 WITH KNOWN RELATIVE STEREOCHEMISTRY* | C | 1.14 | 483 |
| 193 | *SINGLE UNKNOWN ISOMER 2 WITH KNOWN RELATIVE STEREOCHEMISTRY* | C | 1.14 | 483 |
| 194 | 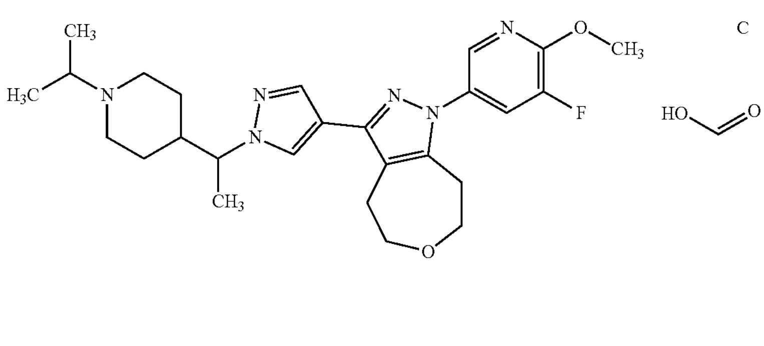 [SMILES: COc1ncc(-n2nc(-c3cnn(C(C)C4CCN(C(C)C)CC4)c3)c3c2CCOCC3)cc1F ; O=CO] | C | 1.06 | 483 |

| Example | Structure | LCMS method | Rt min | MH+ |
|---|---|---|---|---|
| 195 | 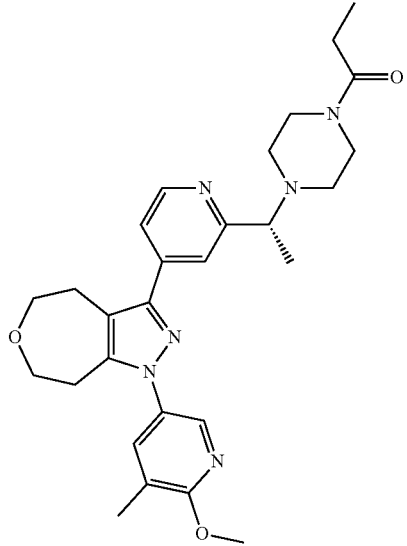 [SMILES: CCC(=O)N1CCN([C@H](C)c2cc(-c3nn(-c4cnc(OC)c(C)c4)c4c3CCOCC4)ccn2)CC1] | B | 1.66 | 505 |
| 196 | 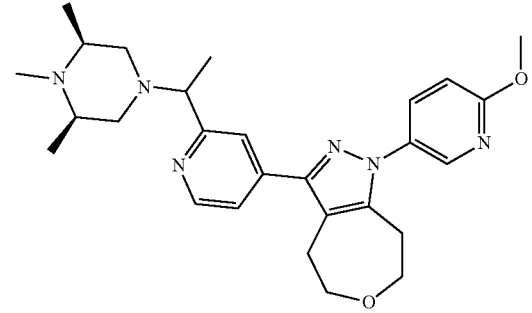 | C | 0.97 | 477 |
| 197 | 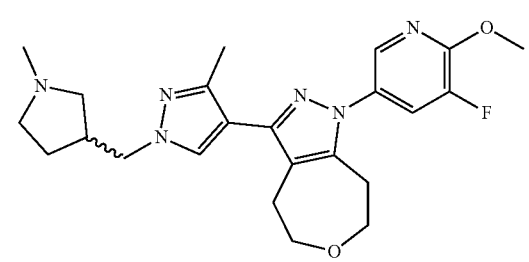 [SMILES: COc1ncc(-n2nc(-c3cn(CC4CCN(C)C4)nc3C)c3c2CCOCC3)cc1F]<br>SINGLE UNKNOWN ISOMER 1 | A | 1.10 | 441 |
| 198 | 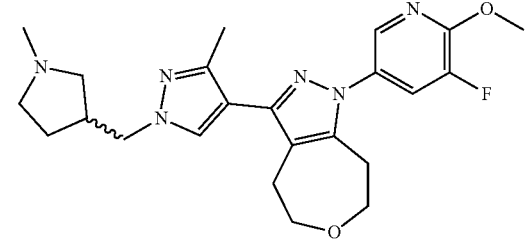 [SMILES: COc1ncc(-n2nc(-c3cn(CC4CCN(C)C4)nc3C)c3c2CCOCC3)cc1F]<br>SINGLE UNKNOWN ISOMER 2 | C | 1.09 | 441 |

-continued

| Example | Structure | LCMS method | Rt min | MH+ |
|---|---|---|---|---|
| 199 | SINGLE UNKNOWN ISOMER 1 | A | 1.10 | 441 |
| 200 | SINGLE UNKNOWN ISOMER 2 | C | 0.98 | 441 |
| 201 | SINGLE UNKNOWN ISOMER 1 | C | 1.00 | 455 |
| 202 | SINGLE UNKNOWN ISOMER 2 | C | 0.99 | 455 |

-continued

| Example | Structure | LCMS method | Rt min | MH+ |
|---|---|---|---|---|
| 203 | 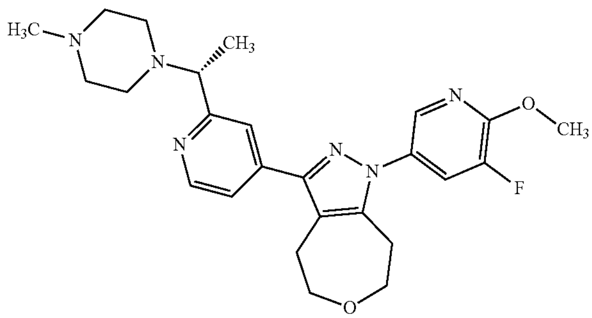 | C | 0.97 | 467 |
| 204 | 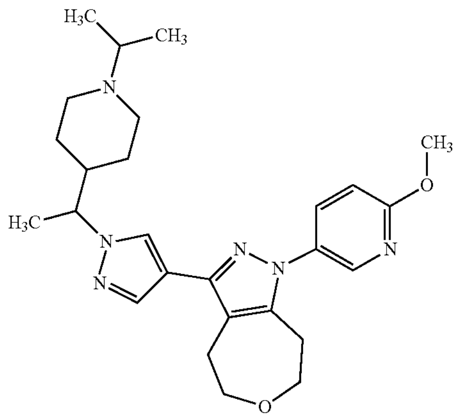 [SMILES: COc1ccc(-n2nc(-c3cnn(C(C)C4CCN(C(C)C)CC4)c3)c3c2CCOCC3)cn1] | C | 1.02 | 465 |
| 205 | SINGLE UNKNOWN ISOMER 1 | C | 1.09 | 495 |
| 206 | SINGLE UNKNOWN ISOMER 2 | C | 1.09 | 495 |

| Example | Structure | LCMS method | Rt min | MH+ |
|---|---|---|---|---|
| 207 | 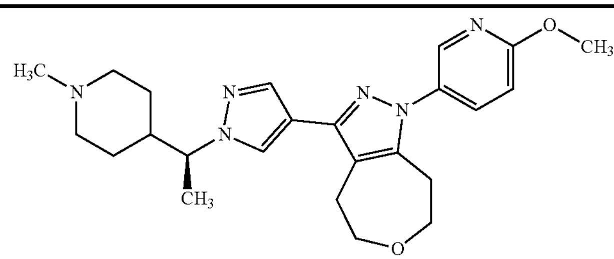 | C | 0.96 | 437 |
| 208 | UNKNOWN ISOMER 1 | C | 0.98 | 477 |
| 209 | UNKNOWN ISOMER 2 | C | 0.98 | 477 |
| 210 | SINGLE UNKNOWN ISOMER 1 | C | 1.00 | 465 |
| 211 | SINGLE UNKNOWN ISOMER 2 | C | 1.03 | 465 |

-continued
| Example | Structure | LCMS method | Rt min | MH+ |
|---|---|---|---|---|
| 212 | 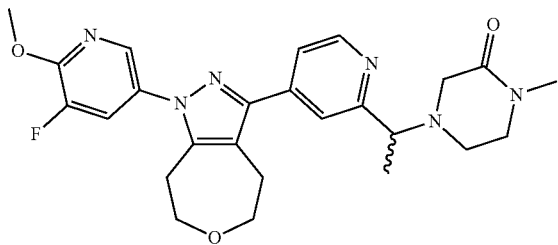<br>SINGLE UNKNOWN ISOMER 1 | E | 0.65 | 481 |
| 213 | 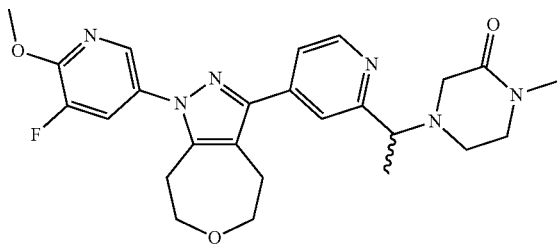<br>SINGLE UNKNOWN ISOMER 2 | E | 0.68 | 481 |
| 214 | 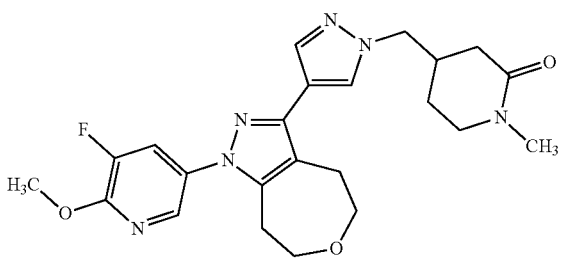 [SMILES: COc1ncc(-n2nc(-c3cnn(CC4CCN(C)C(=O)C4)c3)c3c2CCOCC3)cc1F] | E | 0.81 | 455 |
| 215 | 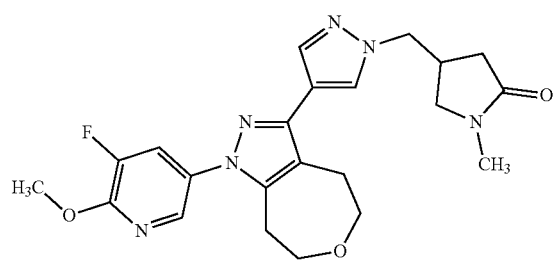 [SMILES: COc1ncc(-n2nc(-c3cnn(CC4CC(=O)N(C)C4)c3)c3c2CCOCC3)cc1F] | E | 0.80 | 441 |

-continued
| Example | Structure | LCMS method | Rt min | MH+ |
|---|---|---|---|---|
| 216 | 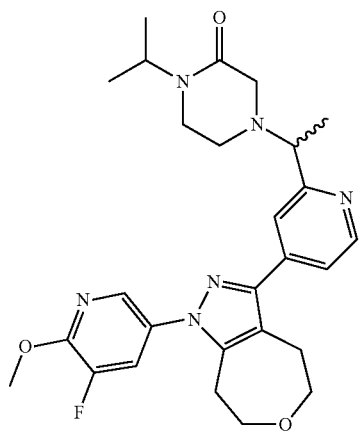 [SMILES: COc1ncc(-n2nc(-c3ccnc(C(C)N4CCN(C(C)C)C(=O)C4)c3)c3c2CCOCC3)cc1F]<br>SINGLE UNKNOWN ISOMER 1 | E | 0.73 | 509 |
| 217 | 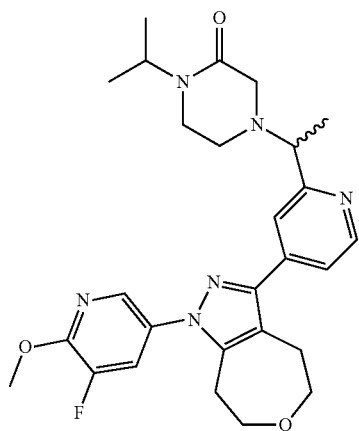 [SMILES: COc1ncc(-n2nc(-c3ccnc(C(C)N4CCN(C(C)C)C(=O)C4)c3)c3c2CCOCC3)cc1F]<br>SINGLE UNKNOWN ISOMER 2 | E | 0.73 | 509 |
| 218 | 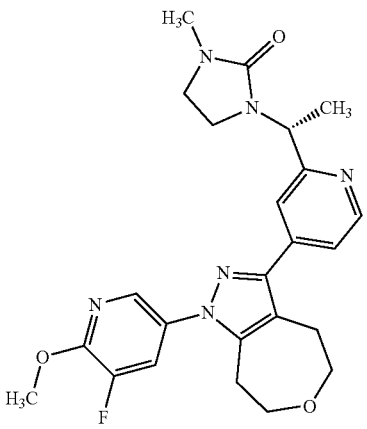 [SMILES: COc1ncc(-n2nc(-c3ccnc([C@@H](C)N4CCN(C)C4=O)c3)c3c2CCOCC3)cc1F] | E | 0.68 | 467 |

-continued
| Example | Structure | LCMS method | Rt min | MH+ |
|---|---|---|---|---|
| 219 | 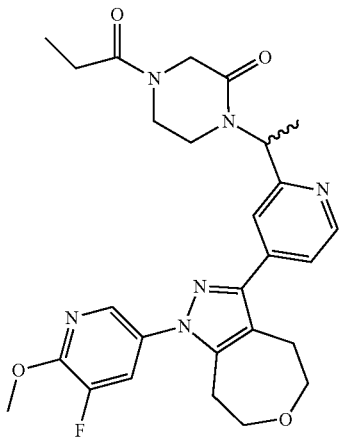 [SMILES: CCC(=O)N1CCN(C(C)c2cc(-c3nn(-c4cnc(OC)c(F)c4)c4c3CCOCC4)ccn2)C(=O)C1]<br>SINGLE UNKNOWN ISOMER 1 | E | 0.72 | 523 |
| 220 | 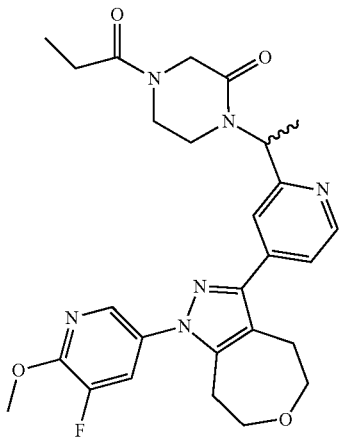 [SMILES: CCC(=O)N1CCN(C(C)c2cc(-c3nn(-c4cnc(OC)c(F)c4)c4c3CCOCC4)ccn2)C(=O)C1]<br>SINGLE UNKNOWN ISOMER 2 | E | 0.71 | 523 |
| 221 | 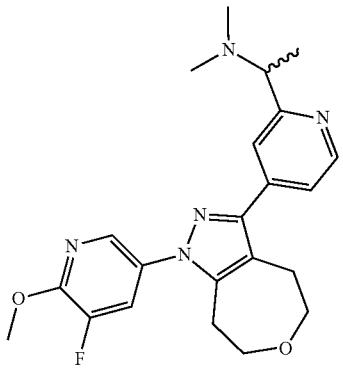 [SMILES: COc1ncc(-n2nc(-c3ccnc(C(C)N(C)C)c3)c3c2CCOCC3)cc1F]<br>SINGLE UNKNOWN ISOMER 1 | E | 0.67 | 412 |

| Example | Structure | LCMS method | Rt min | MH+ |
|---|---|---|---|---|
| 222 | 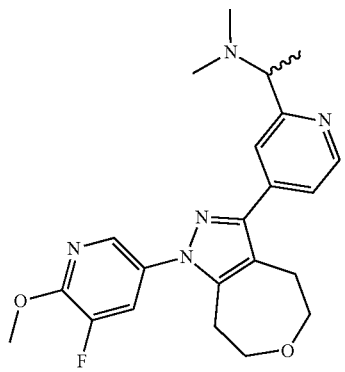 [SMILES: COc1ncc(-n2nc(-c3ccnc(C(C)N(C)C)c3)c3c2CCOCC3)cc1F]<br>SINGLE UNKNOWN ISOMER 2 | E | 0.67 | 412 |
| 223 | 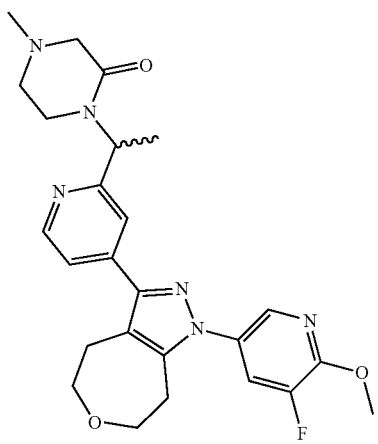<br>SINGLE UNKNOWN ISOMER 1 | E | 0.61 | 481 |
| 224 | 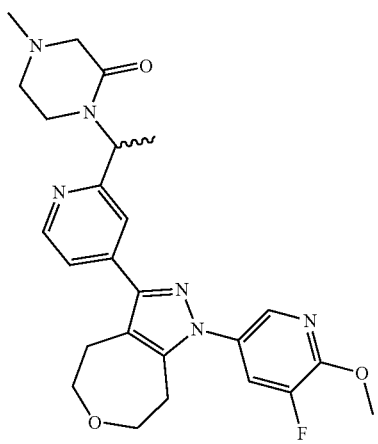<br>SINGLE UNKNOWN ISOMER 2 | E | 0.61 | 481 |

-continued
| Example | Structure | LCMS method | Rt min | MH+ |
|---|---|---|---|---|
| 225 | 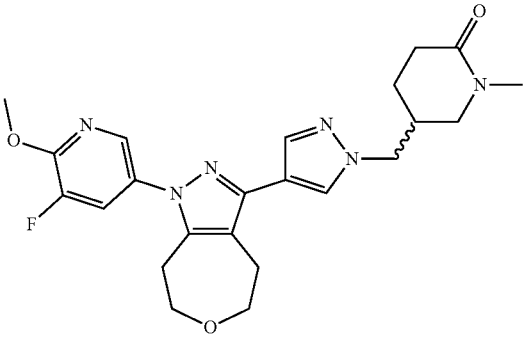<br>SINGLE UNKNOWN ISOMER 1 | E | 0.82 | 455 |
| 226 | 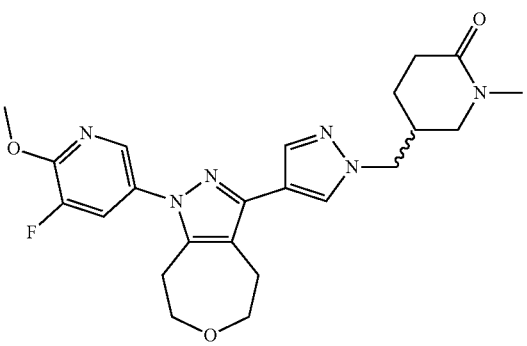<br>SINGLE UNKNOWN ISOMER 2 | — | — | — |
| 227 | 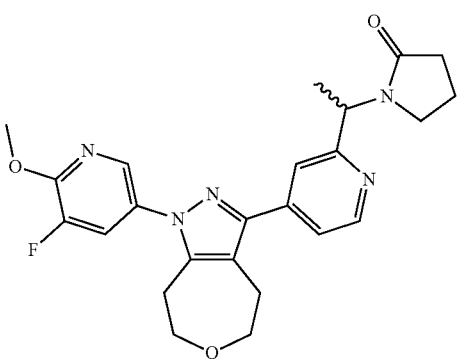 [SMILES: COc1ncc(-n2nc(-c3ccnc(C(C)N4CCCC4=O)c3)c3c2CCOCC3)cc1F]<br>SINGLE UNKNOWN ISOMER 1 | E | 0.73 | 452 |
| 228 | 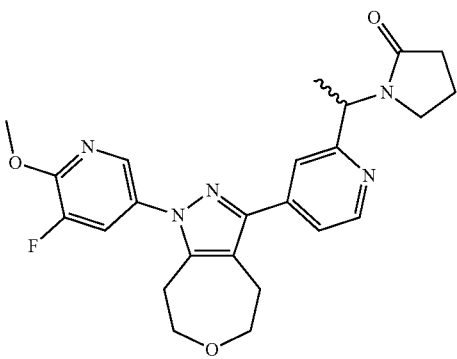 [SMILES: COc1ncc(-n2nc(-c3ccnc(C(C)N4CCCC4=O)c3)c3c2CCOCC3)cc1F]<br>SINGLE UNKNOWN ISOMER 2 | E | 0.71 | 452 |

-continued
| Example | Structure | LCMS method | Rt min | MH+ |
|---|---|---|---|---|
| 229 | 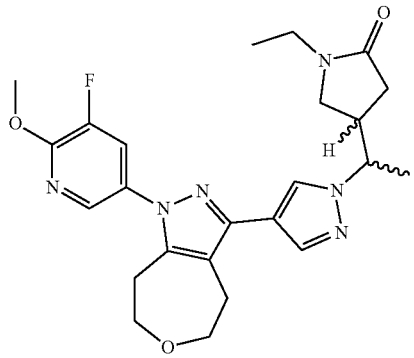 [SMILES: CCN1CC(C(C)n2cc(-c3nn(-c4cnc(OC)c(F)c4)c4c3CCOCC4)cn2)CC1=O]<br>SINGLE UNKNOWN ISOMER 1 | E | 0.89 | 469 |
| 230 | 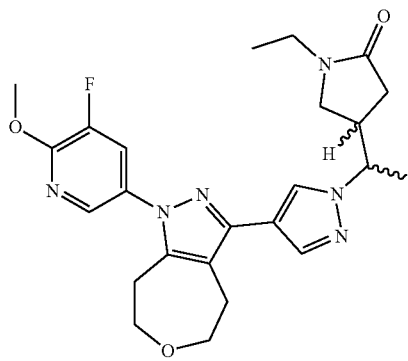 [SMILES: CCN1CC(C(C)n2cc(-c3nn(-c4cnc(OC)c(F)c4)c4c3CCOCC4)cn2)CC1=O]<br>SINGLE UNKNOWN ISOMER 2 | E | 0.89 | 469 |
| 231 | 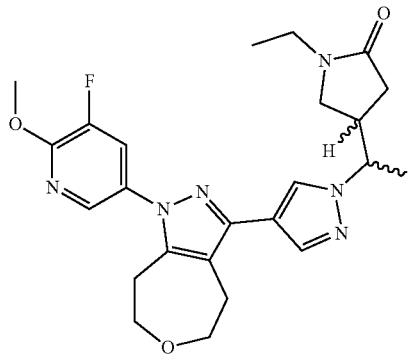 [SMILES: CCN1CC(C(C)n2cc(-c3nn(-c4cnc(OC)c(F)c4)c4c3CCOCC4)cn2)CC1=O]<br>SINGLE UNKNOWN ISOMER 3 | E | 0.90 | 469 |

-continued

| Example | Structure | LCMS method | Rt min | MH+ |
|---------|-----------|-------------|--------|-----|
| 232 | SINGLE UNKNOWN ISOMER 4 | E | 0.89 | 469 |
| 233 | 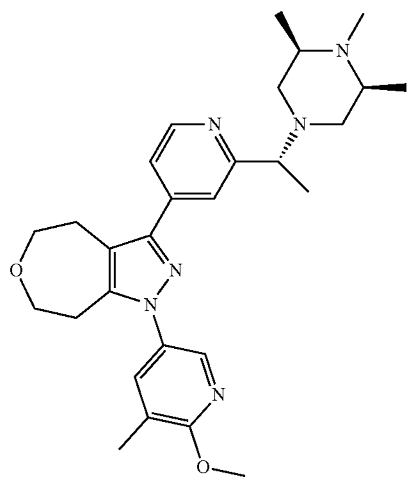 [SMILES: COc1ncc(-n2nc(-c3ccnc([C@@H](C)N4C[C@@H](C)N(C)[C@@H](C)C4)c3)c3c2CCOCC3)cc1C] | B | 1.55 | 491 |
| 234 | 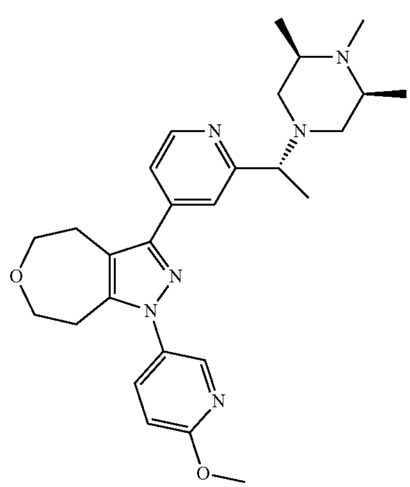 [SMILES: COc1ccc(-n2nc(-c3ccnc([C@@H](C)N4C[C@@H](C)N(C)[C@@H](C)C4)c3)c3c2CCOCC3)cn1] | B | 1.41 | 477 |

-continued

| Example | Structure | LCMS method | Rt min | MH+ |
|---|---|---|---|---|
| 235 | 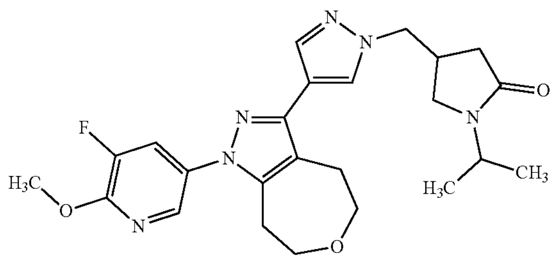 [SMILES: COc1ncc(-n2nc(-c3cnn(CC4CC(=O)N(C(C)C)C4)c3)c3c2CCOCC3)cc1F] | E | 0.90 | 469 |
| 236 | SINGLE UNKNOWN ISOMER 1 | E | 0.85 | 455 |
| 237 | SINGLE UNKNOWN ISOMER 2 | E | 0.85 | 455 |
| 238 | SINGLE UNKNOWN ISOMER 1 | E | 0.74 | 466 |

| Example | Structure | LCMS method | Rt min | MH+ |
|---|---|---|---|---|
| 239 | 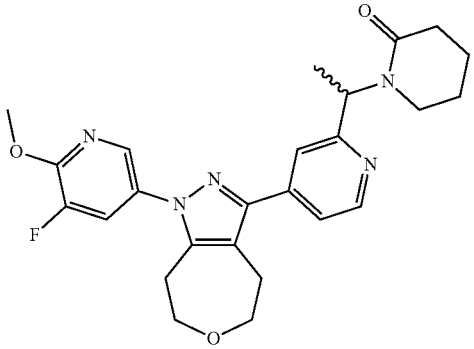 [SMILES: COc1ncc(-n2nc(-c3ccnc(C(C)N4CCCCC4=O)c3)c3c2CCOCC3)cc1F]  SINGLE UNKNOWN ISOMER 2 | E | 0.74 | 466 |
| 240 | 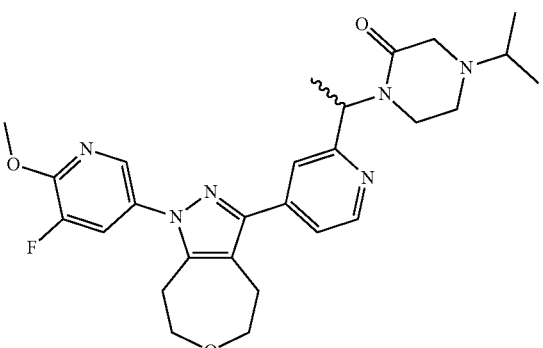  SINGLE UNKNOWN ISOMER 1 | E | 0.64 | 509 |
| 241 | 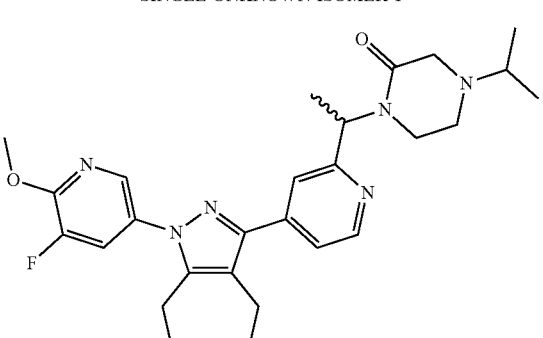  SINGLE UNKNOWN ISOMER 2 | E | 0.65 | 509 |
| 242 | 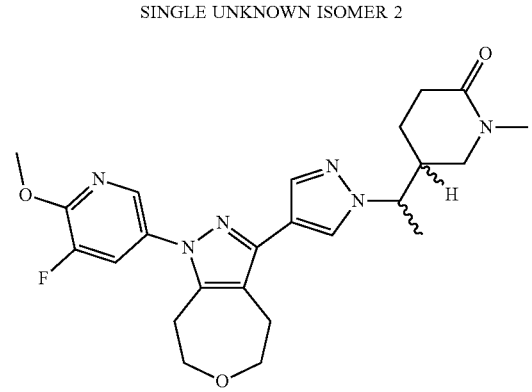  SINGLE UNKNOWN ISOMER 1 | E | 0.88 | 469 |

-continued
| Example | Structure | LCMS method | Rt min | MH+ |
|---|---|---|---|---|
| 243 | 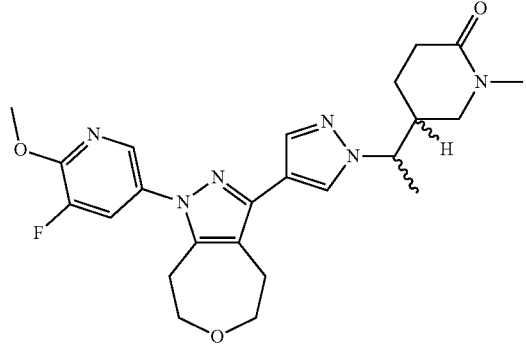  SINGLE UNKNOWN ISOMER 2 | E | 0.88 | 469 |
| 244 | 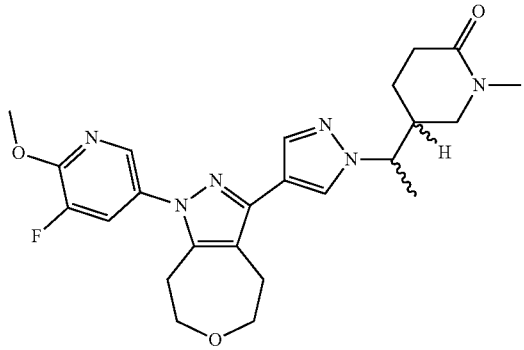  SINGLE UNKNOWN ISOMER 3 | E | 0.88 | 469 |
| 245 | 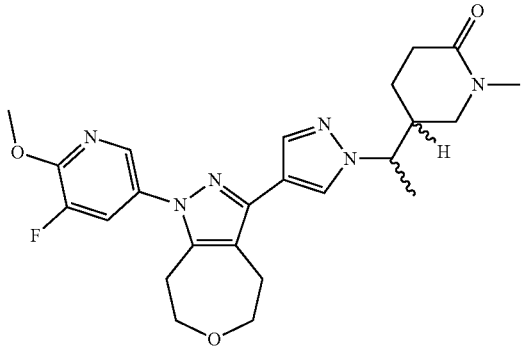  SINGLE UNKNOWN ISOMER 4 | E | 0.88 | 469 |
| 246 | 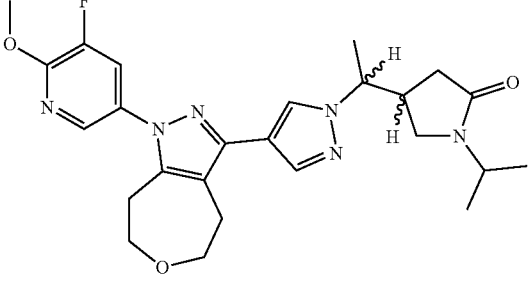  SINGLE UNKNOWN ISOMER 1 | E | 0.97 | 483 |

-continued
| Example | Structure | LCMS method | Rt min | MH+ |
|---|---|---|---|---|
| 247 | 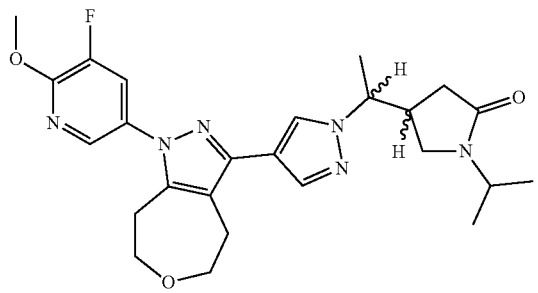 [SMILES: COc1ncc(-n2nc(-c3cnn(C(C)C4CC(=O)N(C(C)C)C4)c3)c3c2CCOCC3)cc1F]<br>SINGLE UNKNOWN ISOMER 2 | E | 0.98 | 483 |
| 248 | 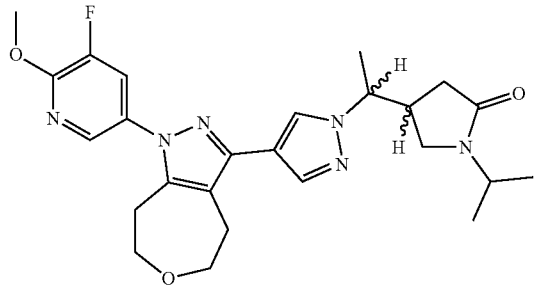 [SMILES: COc1ncc(-n2nc(-c3cnn(C(C)C4CC(=O)N(C(C)C)C4)c3)c3c2CCOCC3)cc1F]<br>SINGLE UNKNOWN ISOMER 3 | E | 0.97 | 483 |
| 249 | 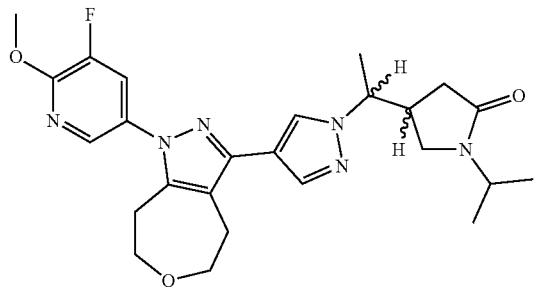 [SMILES: COc1ncc(-n2nc(-c3cnn(C(C)C4CC(=O)N(C(C)C)C4)c3)c3c2CCOCC3)cc1F]<br>SINGLE UNKNOWN ISOMER 4 | E | 0.97 | 483 |
| 250 | 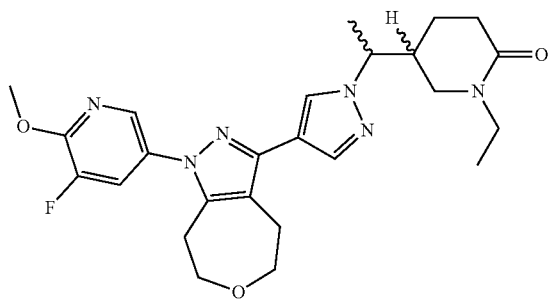 [SMILES: CCN1CC(C(C)n2cc(-c3nn(-c4cnc(OC)c(F)c4)c4c3CCOCC4)cn2)CCC1=O]<br>SINGLE UNKNOWN ISOMER 1 | E | 0.95 | 483 |

-continued

| Example | Structure | LCMS method | Rt min | MH+ |
|---|---|---|---|---|
| 251 | SINGLE UNKNOWN ISOMER 2 | E | 0.94 | 483 |
| 252 | SINGLE UNKNOWN ISOMER 3 | E | 0.95 | 483 |
| 253 | SINGLE UNKNOWN ISOMER 4 | E | 0.95 | 483 |
| 254 | SINGLE UNKNOWN ISOMER 1 | E | 0.94 | 469 |

| Example | Structure | LCMS method | Rt min | MH+ |
|---|---|---|---|---|
| 255 | 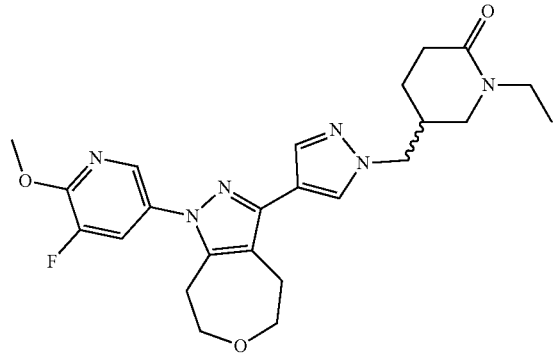 [SMILES: CCN1CC(Cn2cc(-c3nn(-c4cnc(OC)c(F)c4)c4c3CCOCC4)cn2)CCC1=O]<br>SINGLE UNKNOWN ISOMER 2 | E | 0.92 | 469 |
| 256 | 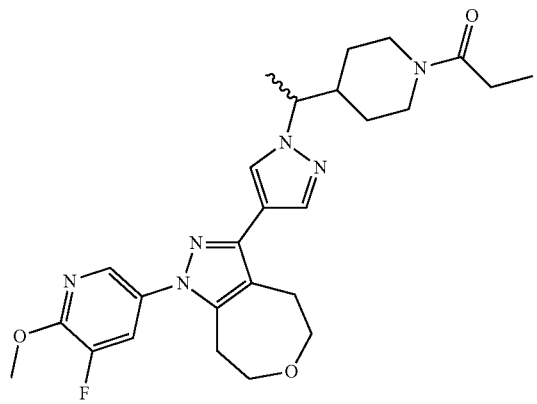 [SMILES: CCC(=O)N1CCC(C(C)n2cc(-c3nn(-c4cnc(OC)c(F)c4)c4c3CCOCC4)cn2)CC1]<br>SINGLE UNKNOWN ISOMER 1 | E | 0.96 | 497 |
| 257 | 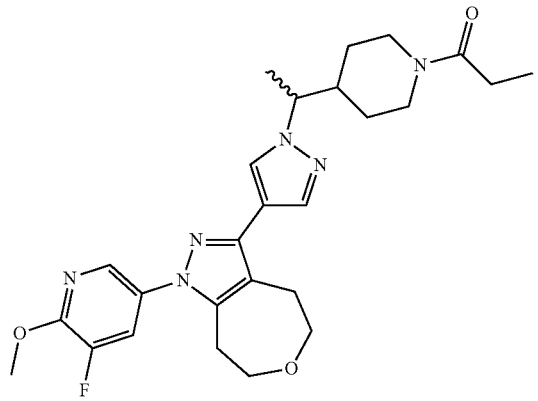 [SMILES: CCC(=O)N1CCC(C(C)n2cc(-c3nn(-c4cnc(OC)c(F)c4)c4c3CCOCC4)cn2)CC1]<br>SINGLE UNKNOWN ISOMER 2 | E | 0.96 | 497 |

-continued

| Example | Structure | LCMS method | Rt min | MH+ |
|---|---|---|---|---|
| 258 | SINGLE UNKNOWN ISOMER 1 | E | 0.94 | 497 |
| 259 | SINGLE UNKNOWN ISOMER 2 | E | 0.94 | 497 |
| 260 | SINGLE UNKNOWN ISOMER 1 | E | 0.91 | 483 |
| 261 | SINGLE UNKNOWN ISOMER 2 | E | 0.91 | 483 |

| Example | Structure | LCMS method | Rt min | MH+ |
|---|---|---|---|---|
| 262 | 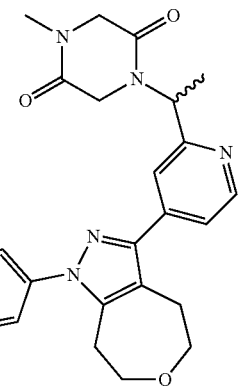<br>SINGLE UNKNOWN ISOMER 1 | E | 0.68 | 495 |
| 263 | 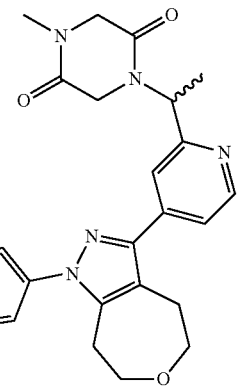<br>SINGLE UNKNOWN ISOMER 2 | E | 0.67 | 495 |
| 264 | 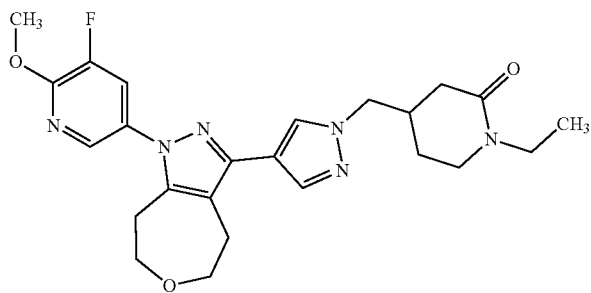 [SMILES: CCN1CCC(Cn2cc(-c3nn(-c4cnc(OC)c(F)c4)c4c3CCOCC4)cn2)CC1=O] | E | 0.87 | 469 |

-continued
| Example | Structure | LCMS method | Rt min | MH+ |
|---|---|---|---|---|
| 265 | 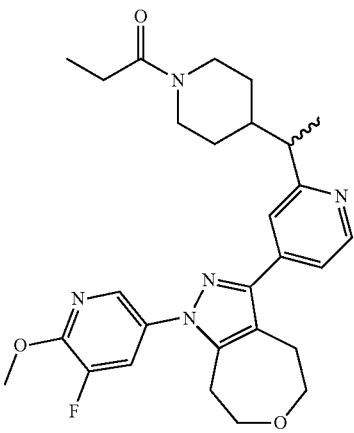 [SMILES: CCC(=O)N1CCC(C(C)c2cc(-c3nn(-c4cnc(OC)c(F)c4)c4c3CCOCC4)ccn2)CC1]<br>SINGLE UNKNOWN ISOMER 1 | E | 0.75 | 508 |
| 266 | 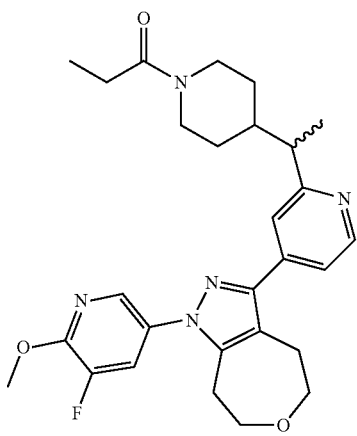 [SMILES: CCC(=O)N1CCC(C(C)c2cc(-c3nn(-c4cnc(OC)c(F)c4)c4c3CCOCC4)ccn2)CC1]<br>SINGLE UNKNOWN ISOMER 2 | E | 0.75 | 508 |
| 267 | 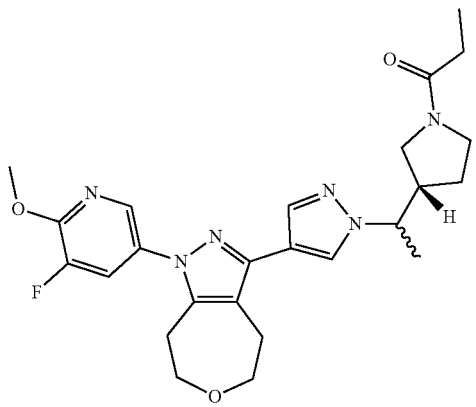 [SMILES: CCC(=O)N1CC[C@H](C(C)n2cc(-c3nn(-c4cnc(OC)c(F)c4)c4c3CCOCC4)cn2)C1]<br>SINGLE UNKNOWN ISOMER 1 | E | 0.92 | 483 |

| Example | Structure | LCMS method | Rt min | MH+ |
|---|---|---|---|---|
| 268 | 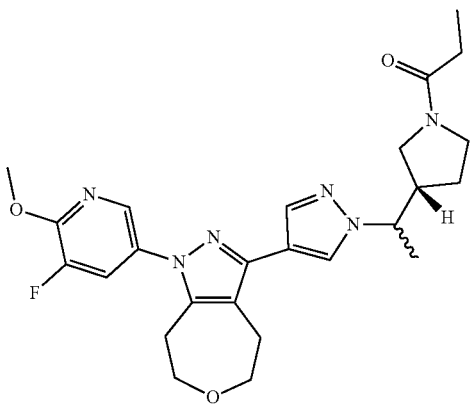 [SMILES: CCC(=O)N1CC[C@H](C(C)n2cc(-c3nn(-c4cnc(OC)c(F)c4)c4c3CCOCC4)cn2)C1]<br>SINGLE UNKNOWN ISOMER 2 | E | 0.93 | 483 |
| 269 | 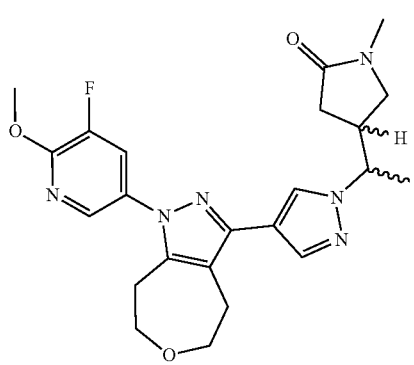 [SMILES: COc1ncc(-n2nc(-c3cnn(C(C)C4CC(=O)N(C)C4)c3)c3c2CCOCC3)cc1F]<br>SINGLE UNKNOWN ISOMER 1 | E | 0.84 | 455 |
| 270 | 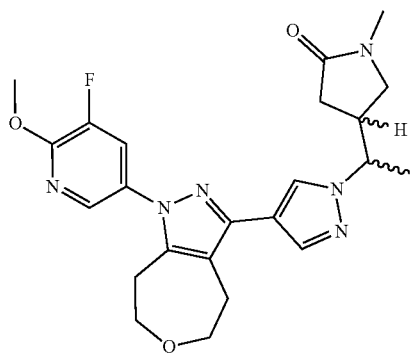 [SMILES: COc1ncc(-n2nc(-c3cnn(C(C)C4CC(=O)N(C)C4)c3)c3c2CCOCC3)cc1F]<br>SINGLE UNKNOWN ISOMER 2 | E | 0.84 | 455 |

-continued
| Example | Structure | LCMS method | Rt min | MH+ |
|---|---|---|---|---|
| 271 | 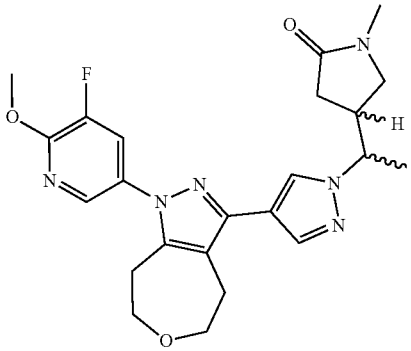 [SMILES: COc1ncc(-n2nc(-c3cnn(C(C)C4CC(=O)N(C)C4)c3)c3c2CCOCC3)cc1F]<br>SINGLE UNKNOWN ISOMER 3 | E | 0.83 | 455 |
| 272 | 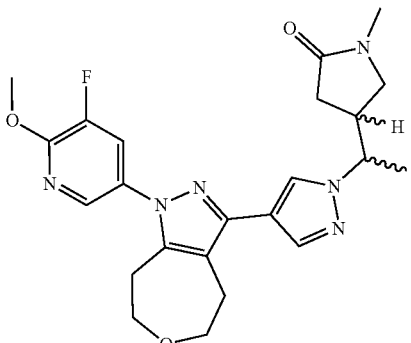<br>SINGLE UNKNOWN ISOMER 4 | E | 0.83 | 455 |
| 273 | 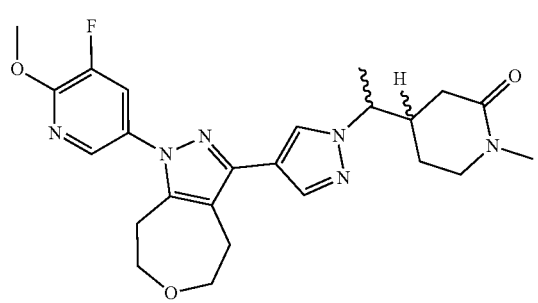<br>SINGLE UNKNOWN ISOMER 1 | E | 0.85 | 469 |
| 274 | 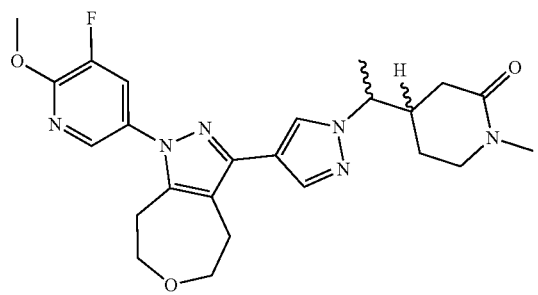<br>SINGLE UNKNOWN ISOMER 2 | E | 0.85 | 469 |

| Example | Structure | LCMS method | Rt min | MH+ |
|---------|-----------|-------------|--------|-----|
| 275 | SINGLE UNKNOWN ISOMER 3 | E | 0.85 | 469 |
| 276 | SINGLE UNKNOWN ISOMER 4 | E | 0.86 | 469 |
| 277 | 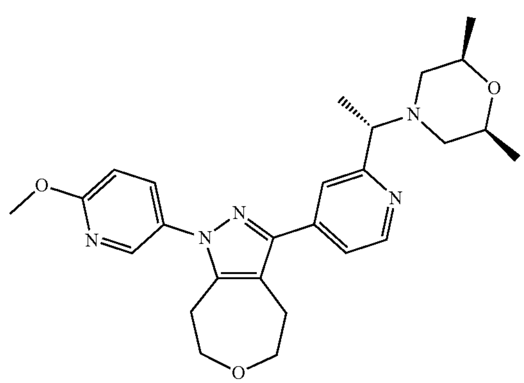 | C | 1.04 | 464 |
| 278 | 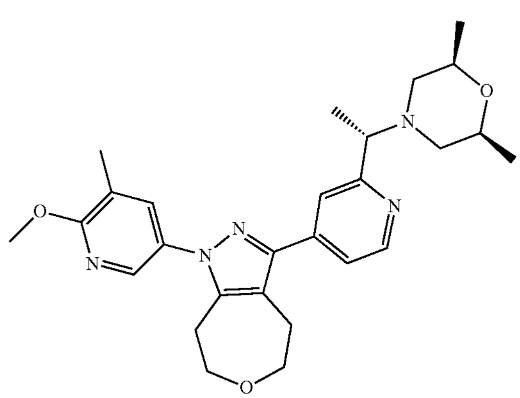 | C | 1.16 | 478 |

-continued
| Example | Structure | LCMS method | Rt min | MH+ |
|---|---|---|---|---|
| 279 | 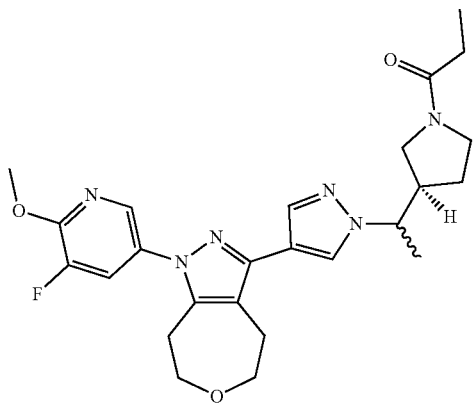 [SMILES: CCC(=O)N1CC[C@@H](C(C)n2cc(-c3nn(-c4cnc(OC)c(F)c4)c4c3CCOCC4)cn2)C1]<br>SINGLE UNKNOWN ISOMER 1 | E | 0.92 | 483 |
| 280 | 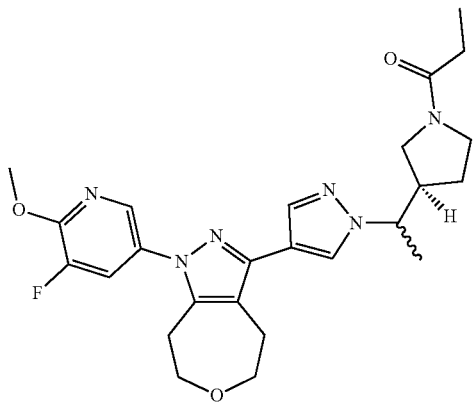 [SMILES: CCC(=O)N1CC[C@@H](C(C)n2cc(-c3nn(-c4cnc(OC)c(F)c4)c4c3CCOCC4)cn2)C1]<br>SINGLE UNKNOWN ISOMER 2 | E | 0.92 | 483 |
| 281 | 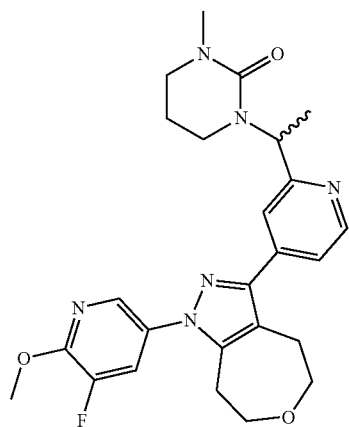 [SMILES: COc1ncc(-n2nc(-c3ccnc(C(C)N4CCCN(C)C4=O)c3)c3c2CCOCC3)cc1F]<br>SINGLE UNKNOWN ISOMER 1 | E | 0.70 | 481 |

| Example | Structure | LCMS method | Rt min | MH+ |
|---|---|---|---|---|
| 282 | 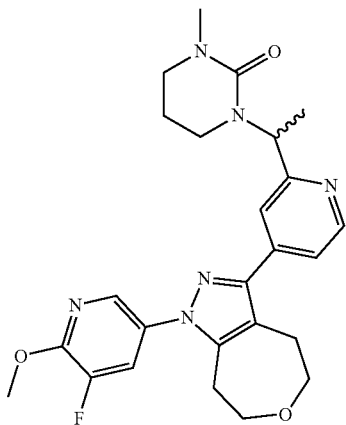 [SMILES: COc1ncc(-n2nc(-c3ccnc(C(C)N4CCCN(C)C4=O)c3)c3c2CCOCC3)cc1F]<br>SINGLE UNKNOWN ISOMER 2 | E | 0.70 | 481 |
| 283 | 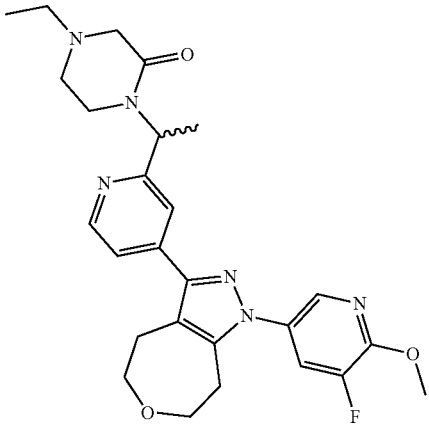 [SMILES: CCN1CCN(C(C)c2cc(-c3nn(-c4cnc(OC)c(F)c4)c4c3CCOCC4)ccn2)C(=O)C1]<br>SINGLE UNKNOWN ISOMER 1 | E | 0.61 | 495 |
| 284 | 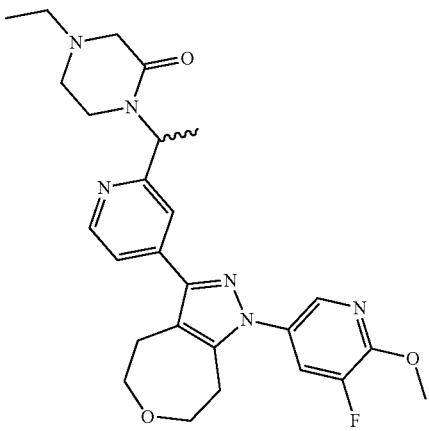 [SMILES: CCN1CCN(C(C)c2cc(-c3nn(-c4cnc(OC)c(F)c4)c4c3CCOCC4)ccn2)C(=O)C1]<br>SINGLE UNKNOWN ISOMER 2 | E | 0.61 | 495 |

-continued
| Example | Structure | LCMS method | Rt min | MH+ |
|---|---|---|---|---|
| 285 | 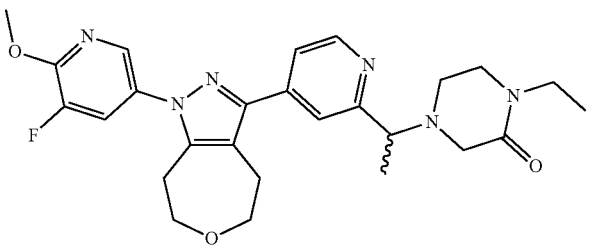 [SMILES: CCN1CCN(C(C)c2cc(-c3nn(-c4cnc(OC)c(F)c4)c4c3CCOCC4)ccn2)CC1=O]<br>SINGLE UNKNOWN ISOMER 1 | E | 0.68 | 495 |
| 286 | 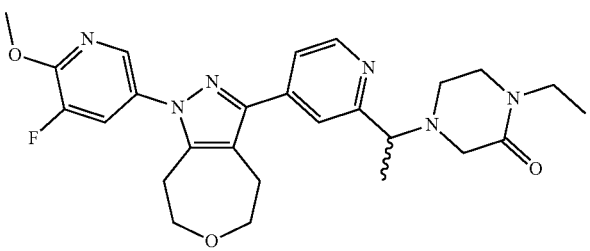 [SMILES: CCN1CCN(C(C)c2cc(-c3nn(-c4cnc(OC)c(F)c4)c4c3CCOCC4)ccn2)CC1=O]<br>SINGLE UNKNOWN ISOMER 2 | E | 0.69 | 495 |
| 287 | 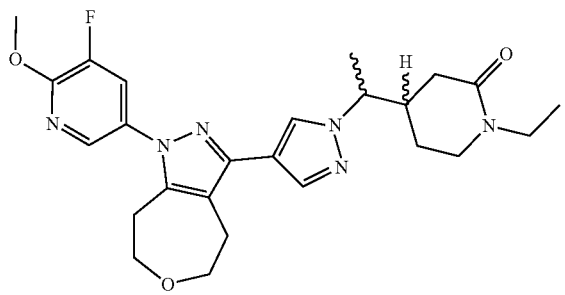 [SMILES: CCN1CCC(C(C)n2cc(-c3nn(-c4cnc(OC)c(F)c4)c4c3CCOCC4)cn2)CC1=O]<br>SINGLE UNKNOWN ISOMER 1 | E | 0.89 | 483 |
| 288 | 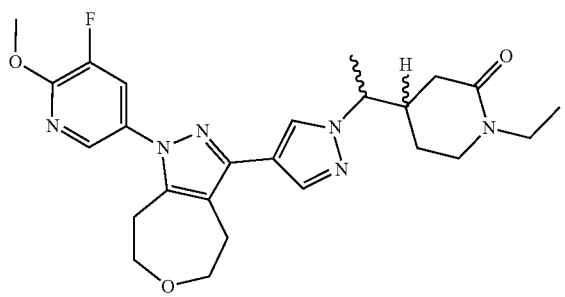 [SMILES: CCN1CCC(C(C)n2cc(-c3nn(-c4cnc(OC)c(F)c4)c4c3CCOCC4)cn2)CC1=O]<br>SINGLE UNKNOWN ISOMER 2 | E | 0.91 | 483 |

-continued

| Example | Structure | LCMS method | Rt min | MH+ |
|---|---|---|---|---|
| 289 | SINGLE UNKNOWN ISOMER 3 | E | 0.90 | 483 |
| 290 | SINGLE UNKNOWN ISOMER 4 | E | 0.91 | 483 |
| 291 | 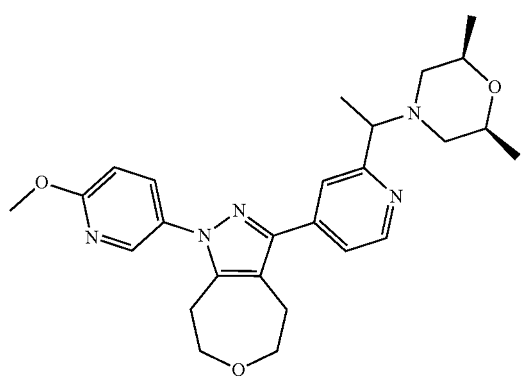 | C | 1.04 | 464 |
| 292 | 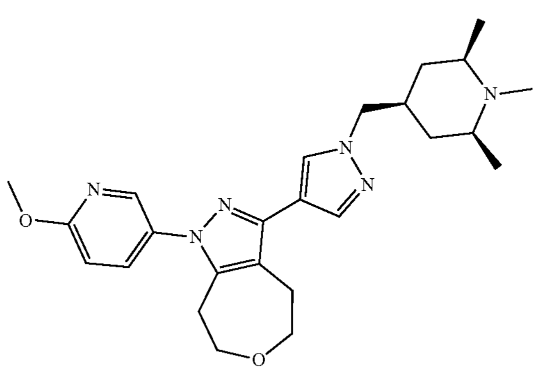 | C | 0.94 | 451 |

Example 293. (R)-1-(4-(1-(6-methoxy-5-methylpyridin-3-yl)-4,5,7,8-tetrahydro-1H-oxepino[4,5-c]pyrazol-3-yl)pyridin-2-yl)ethanol

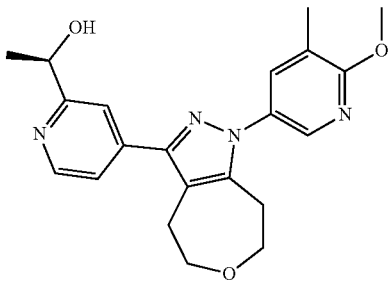 [SMILES: COc1ncc(-n2nc(-c3ccnc([C@@H](C)O)c3)c3c2CCOCC3)cc1C]

Triethylamine (2.005 g, 19.82 mmol) was added dropwise to neat formic acid (1.581 g, 34.4 mmol) in a MeOH-ice bath. 1-(4-(1-(6-methoxy-5-methylpyridin-3-yl)-4,5,7,8-tetrahydro-1H-oxepino[4,5-c]pyrazol-3-yl)pyridin-2-yl)ethanone (3 g, 7.93 mmol) was added rapidly to the above reaction mixture. To this, RuCl[(R,R)-Tsdpen](p-cymene) (0.025 g, 0.039 mmol) was added and the mixture was stirred under vacuum for 10 min and then under nitrogen for 16 h. 10% aqueous Na₂CO₃ solution was added dropwise with cooling and mixture was stirred for 1 h then extracted with EtOAc (3×10 mL). The combined organic extracts were dried over sodium sulphate, filtered then concentrated under reduced pressure. The crude product was pre-adsorbed on silicagel (60-120 mesh, 30 g) and purified by normal phase column chromatography on silica, eluting with 0-100% EtOAc in petroleum ether to give the title compound (2.2 g).

LCMS (Method D): Rt=1.87 min, MH⁺ 381.

Example 294. 1-(4-(1-(5-fluoro-6-methoxypyridin-3-yl)-4,5,7,8-tetrahydro-1H-oxepino[4,5-c]pyrazol-3-yl)pyridin-2-yl)ethanol

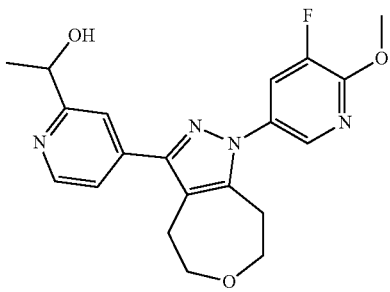 [SMILES: COc1ncc(-n2nc(-c3ccnc(C(C)O)c3)c3c2CCOCC3)cc1F]

A mixture of 1-(4-(1-(5-fluoro-6-methoxypyridin-3-yl)-4,5,7,8-tetrahydro-1H-oxepino[4,5-c]pyrazol-3-yl)pyridin-2-yl)ethan-1-one (1.82 g, 4.82 mmol) and sodium borohydride (0.21 g, 5.79 mmol) in THF (19 mL) was cooled with an ice/water bath. MeOH (4.8 mL) was added portionwise and the mixture was stirred for 11 min. The reaction mixture was quenched by the addition of 20 mL 2M aqueous NaOH solution, by slow addition over 13 min. Brine solution was added and the mixture was allowed to warm to room temperature and stirred for 5 min. The phases were separated and the aqueous phase was extracted with 10% MeOH/CHCl₃ (3×20 mL). The THF solution and the combined MeOH/CHCl₃ organic extracts were washed separately with brine (5 and 10 mL respectively) then combined and dried over sodium sulphate and concentrated under reduced pressure to afford crude title compound (1.97 g). The material was used directly in the next step.

Example 295. 3-(5-fluoro-6-methoxypyridin-3-yl)-1-(1-(1-(piperidin-4-yl)ethyl)-1H-pyrazol-4-yl)-4,5,7,8-tetrahydro-1H-oxepino[4,5-c]pyrazole

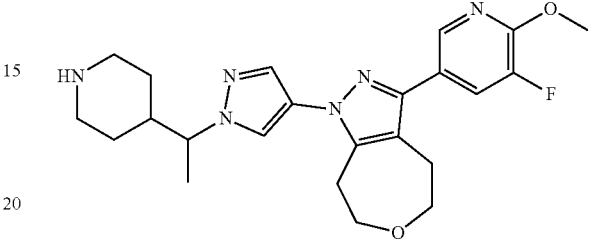

tert-Butyl 4-(1-(4-(3-(5-fluoro-6-methoxypyridin-3-yl)-4,5,7,8-tetrahydro-1H-oxepino[4,5-c]pyrazol-1-yl)-1H-pyrazol-1-yl)ethyl)piperidine-1-carboxylate (374 mg, 0.692 mmol) was dissolved in DCM (3 mL) and trifluoroacetic acid (1.066 mL, 13.84 mmol) was added. The reaction mixture was placed under an atmosphere of nitrogen and stirred at room temperature for 4 h. Saturated aqueous NaHCO₃ solution was added dropwise to the reaction mixture until the solution had reached pH 8, then more saturated aqueous NaHCO₃ solution was added to give an aqueous phase of approx. 50 mL. The organic phase was separated and the aqueous phase extracted with further DCM (50 mL). The combined organic extracts were washed with saturated aqueous NaHCO₃ solution (50 mL) and the aqueous phase was extracted with further DCM (20 mL). The combined organic extracts were dried by passing through a hydrophobic frit and the solvent was removed under reduced pressure to afford the title compound (298 mg).

LCMS (Method C): Rt=0.92 min, MH⁺ 441.

Example 296. 3-(6-methoxypyridin-3-yl)-1-(1-(1-(piperidin-4-yl)ethyl)-1H-pyrazol-4-yl)-4,5,7,8-tetrahydro-1H-oxepino[4,5-c]pyrazole

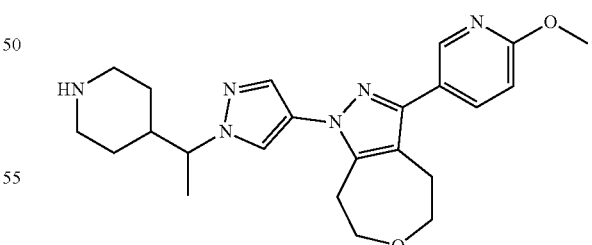

tert-Butyl 4-(1-(4-(3-(6-methoxypyridin-3-yl)-4,5,7,8-tetrahydro-1H-oxepino[4,5-c]pyrazol-1-yl)-1H-pyrazol-1-yl)ethyl)piperidine-1-carboxylate (248 mg, 0.475 mmol) was dissolved in DCM (3 mL) and trifluoroacetic acid (0.531 mL, 6.89 mmol) was added. The reaction mixture was placed under an atmosphere of nitrogen and stirred at room temperature for 1 h. Saturated aqueous NaHCO₃ solution and EtOAc was added. The organic phase was separated and the aqueous phase extracted with DCM (3×20 mL). The combined organic extracts were dried by passing through a hydrophobic frit and the solvent was removed under reduced pressure to afford the crude title compound (298 mg). The material was used directly in the next step.

Biological Data

PI3K HTRF Assays

The binding of compounds to PI3K-alpha/beta/delta/gamma was determined by homogeneous time resolved fluorescence (HTRF) assays as follows;

Briefly, solid compound was dissolved in 100% DMSO at a concentration of 2 mM. Dilutions were prepared in 100% DMSO using a 1 in 4 serial step dilution. The dilutions were transferred to black low volume Greiner assay plates ensuring that the DMSO concentration was constant across the plate at 1% (0.1 μl/well).

PI3K Reaction Buffer (contained 50 mM HEPES pH7.0 (NaOH), 150 mM NaCl, 10 mM $MgCl_2$, 2.3 mM sodium cholate, 10 μM CHAPS made up in milliQ water). Fresh DTT was added at a final concentration of 1 mM on the day of use. Wortmannin at a concentration sufficient to produce 100% inhibition (8.33e-6 M) was added to column 18 of compound plates.

Enzyme solutions: 1×PI3K assay Buffer typically contained:
  550 pM PI3K-Alpha enzyme (275 pM final assay concentration)
  800 pM PI3K-Beta enzyme (400 pM final assay concentration)
  3 nM PI3K-Delta enzyme (1.5 nM final assay concentration)
  10 nM PI3K-Gamma enzyme (5 nM final assay concentration)

These concentrations were optimal to achieve a signal:background of between 1.5-4.5. The enzyme solution was added to columns 1-24 (3 ul/well) and plates were incubated for 15 minutes at room temperature.

Substrate solution: 1×PI3K assay buffer typically contained:
  PI3K-Alpha: 500 μM ATP, 20 μM PIP2 and 120 nM biotin-PIP3. (Final assay concentrations are 250 μM ATP, 10 μM PIP2 (both at $K_m$) and 40 nM biotin-PIP3)
  PI3K-Beta: 800 μM ATP, 20 μM PIP2 and 120 nM biotin-PIP3. (Final assay concentrations are 400 μM ATP, 10 μM PIP2 (both at $K_m$) and 40 nM biotin-PIP3)
  PI3K-Delta: 160 μM ATP, 20 μM PIP2 and 120 nM biotin-PIP3. (Final assay concentrations are 80 μM ATP, 10 μM PIP2 (both at $K_m$) and 40 nM biotin-PIP3)
  PI3K-Gamma: 30 μM ATP, 20 μM PIP2 and 120 nM biotin-PIP3. (Final assay concentrations are 15 μM ATP, 10 μM PIP2 (both at $K_m$) and 40 nM biotin-PIP3)

This is added to all wells and plates were incubated for 1 hour at room temperature.

Detection solution: PI3K Detection Buffer (contained 50 mM HEPES pH 7.0 (HCl), 150 mM NaCl, 2.3 mM sodium cholate, 10 μM CHAPS, 240 mM potassium fluoride) containing 2 mM DTT (2× final concentration), 90 nM GRP-1 PH domain, 300 nM Streptavidin-APC and 24 nM Europium-anti-GST (6× final concentrations)

This mixture was left at room temperature (protected from light).

STOP solution: PI3K STOP Buffer (contained 50 mM HEPES pH 7.0 (HCl), 150 mM NaCl, 2.3 mM sodium cholate, 10 μM CHAPS, 150 mM EDTA).

Detection solution was diluted 1:1 with STOP solution and added to all wells (3 μl/well). Plates were covered and incubated on the bench for 45-60 minutes.

Plates were read on a PerkinElmer Envision, measuring TR-FRET between the complex formed between the GST-tagged PH domain and biotinylated PIP3 which both recruit fluorophores (Europium-labelled anti-GST & Strep-APC respectively). In the absence of an inhibitor, this complex is disrupted by the competitive action of non-biotinylated PIP3 (formed in the assay by the phosphorylation of PIP2 by the kinase & ATP). From this, the ratio of acceptor/donor was calculated (λex=317 nm, λem donor=615 nm, em acceptor=665 nm) and used for data analysis.

The compounds and salts of Examples 1 to 42, 44 to 95, 97 to 101, 109 to 133 and 134 to 292 were tested in the PI3K Alpha, Beta, Delta and/or Gamma assays above or similar assays and were found to have a mean $pIC_{50}$ in the PI3K Delta assay of at least 5 or greater. Examples 1, 2, 7 to 11, 16, 21 to 23, 27 to 29, 32 to 36, 39, 40, 42, 43, 49, 50 to 54, 60, 62, 63, 65, 66, 68, 78, 96, 97 to 102, 104, 105, 107, 109 to 120 and 122, 123, 126, 127, 129, 130, 132, 134, 137-148, 150, 153, 154, 157, 159, 161-165, 168, 171 to 176, 178 to 180, 182, 183, 185 to 191, 194 to 196, 202, 203, 205, 206, 208 to 210, 212, 213 to 218, 223 to 227, 229 to 238, 240 to 292 were found to have a mean $pIC_{50}$ in the PI3K Delta assay of at least 8.5 or greater. For example, Examples 29 and 53 were found to have mean $pIC_{50}$s in the PI3K Delta assay of 9.6 and 9.5 respectively, and Examples 110 and 123 were found to have mean $pIC_{50}$s in the PI3K Delta assay of 9.3 and 8.6.

What is claimed is:

1. A compound of formula (I):

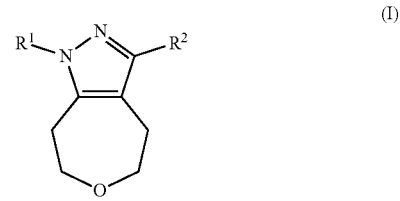

wherein $R^1$ is 5- or 6-membered heteroaryl wherein the heteroaryl contains from one to three heteroatoms independently selected from oxygen and nitrogen and is substituted by one or two substituents independently selected from halo, cyano, $C_{1-6}$alkoxy, —$NHSO_2C_{1-6}$alkyl, —$XR^3$ and $C_{1-6}$alkyl wherein the $C_{1-6}$alkyl is optionally substituted by halo;

$R^2$ is —$OR^4$, —$CONHR^5$, or 5- or 6-membered heteroaryl wherein the heteroaryl contains from one to three heteroatoms independently selected from oxygen and nitrogen and is substituted by one or two substituents independently selected from halo, cyano, $C_{1-6}$alkoxy, —$NHSO_2C_{1-6}$alkyl, —$CONR^6R^7$, —$YR^8$ and $C_{1-6}$alkyl wherein the $C_{1-6}$alkyl is optionally substituted by one or two substituents independently selected from hydroxy and —$NR^9R^{10}$;

$R^3$ is 5- or 6-membered heterocyclyl wherein the heterocyclyl contains one or two heteroatoms independently selected from oxygen and nitrogen and is optionally substituted by from one to three substituents independently selected from $C_{1-6}$alkyl;

$R^4$ is $C_{1-6}$alkyl optionally substituted by $C_{3-6}$cycloalkyl or 5- or 6-membered heterocyclyl containing one or two heteroatoms selected from oxygen and nitrogen wherein the $C_{3-6}$cycloalkyl is optionally substituted by —$NHCO_2C_{1-6}$alkyl and the heterocyclyl is optionally substituted by from one to three substituents independently selected from halo, —COC$_{1-6}$alkyl, —CO$_2$C$_{1-6}$alkyl and C$_{1-6}$alkyl optionally substituted by —OR$^{11}$;

R$^5$ is hydrogen or C$_{1-6}$alkyl optionally substituted by 6-membered heterocyclyl wherein the heterocyclyl contains an oxygen atom or a nitrogen atom and is optionally substituted by C$_{1-6}$alkyl;

R$^6$ and R$^7$, together with the nitrogen atom to which they are attached, are linked to form a 5- or 6-membered heterocyclyl wherein the heterocyclyl optionally contains an oxygen atom or a further nitrogen atom and is optionally substituted by C$_{1-6}$alkyl;

R$^8$ is 5- to 9-membered heterocyclyl wherein the heterocyclyl contains one or two heteroatoms independently selected from oxygen and nitrogen and is substituted by from one to three substituents independently selected from oxo, hydroxy, halo, —COC$_{1-6}$alkyl and C$_{1-6}$alkyl optionally substituted by —OR$^{12}$;

R$^9$, R$^{10}$, R$^{11}$ and R$^{12}$ are each independently hydrogen or C$_{1-6}$alkyl;

X and Y are each independently —CH$_2$— or —CH(CH$_3$)—;

or a salt thereof.

2. A compound according to claim 1, or a salt thereof wherein R$^1$ is 5- or 6-membered heteroaryl wherein the heteroaryl contains one or two nitrogen atoms and is substituted by one or two substituents independently selected from halo, C$_{1-6}$alkoxy, —XR$^3$ and C$_{1-6}$alkyl wherein the C$_{1-6}$alkyl is optionally substituted by halo.

3. A compound according to claim 1, or a salt thereof, wherein R$^2$ is 5- or 6-membered heteroaryl wherein the heteroaryl contains one or two nitrogen atoms and is substituted by one or two substituents independently selected from halo, C$_{1-6}$alkoxy, —YR$^8$ and C$_{1-6}$alkyl.

4. A compound according to claim 1, or a salt thereof, wherein R$^3$ is 6-membered heterocyclyl wherein the heterocyclyl contains one or two nitrogen atoms and is optionally substituted by from one to three substituents independently selected from C$_{1-6}$alkyl.

5. A compound according to claim 1, or a salt thereof, wherein R$^8$ is 5- or 6-membered heterocyclyl wherein the heterocyclyl contains one or two heteroatoms independently selected from oxygen and nitrogen and is substituted by from one to three substituents independently selected from oxo, hydroxy, halo, —COC$_{1-6}$alkyl and C$_{1-6}$alkyl optionally substituted by —OR$^2$.

6. A compound which is:

1-(1-(((2R,4r,6S)-2,6-dimethylpiperidin-4-yl)methyl)-1H-pyrazol-4-yl)-3-(5-fluoro-6-methoxypyridin-3-yl)-4,5,7,8-tetrahydro-1H-oxepino[4,5-c]pyrazole;

3-(1-(((2R,4r,6S)-2,6-dimethylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

N-(2-methoxy-5-(3-(1-methyl-1H-pyrazol-4-yl)-4,5,7,8-tetrahydro-1H-oxepino[4,5-c]pyrazol-1-yl)pyridin-3-yl)methanesulfonamide;

1-(6-methoxy-5-methylpyridin-3-yl)-3-(1-methyl-1H-pyrazol-4-yl)-4,5,7,8-tetrahydro-1H-oxepino[4,5-c]pyrazole;

N-(2-methoxy-5-(1-(1-methyl-1H-pyrazol-4-yl)-4,5,7,8-tetrahydro-1H-oxepino[4,5-c]pyrazol-3-yl)pyridin-3-yl)methanesulfonamide;

1-(2-methoxypyrimidin-5-yl)-3-(1-((1-methylpiperidin-4-yl)methyl)-1H-pyrazol-4-yl)-4,5,7,8-tetrahydro-1H-oxepino[4,5-c]pyrazole;

3-(1-((1-isopropylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

3-(1-((1-isopropylpiperidin-3-yl)methyl)-1H-pyrazol-4-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;

N-(2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)pyridin-3-yl)methanesulfonamide;

2-methoxy-5-(3-(1-((1-methylpiperidin-4-yl)methyl)-1H-pyrazol-4-yl)-4,5,7,8-tetrahydro-1H-oxepino[4,5-c]pyrazol-1-yl)nicotinonitrile;

5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxynicotinonitrile;

1-(5-(fluoromethyl)-6-methoxypyridin-3-yl)-3-(1-((1-methylpiperidin-4-yl)methyl)-1H-pyrazol-4-yl)-4,5,7,8-tetrahydro-1H-oxepino[4,5-c]pyrazole;

1-(5-(fluoromethyl)-6-methoxypyridin-3-yl)-3-(1-((1-isopropylpiperidin-4-yl)methyl)-1H-pyrazol-4-yl)-4,5,7,8-tetrahydro-1H-oxepino[4,5-c]pyrazole;

N-(5-(3-(1-((1-isopropylpiperidin-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(5-((4-isopropylpiperazin-1-yl)methyl)oxazol-2-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-4,5,7,8-tetrahydro-1H-oxepino[4,5-c]pyrazole-3-carboxamide;

1-(6-methoxy-5-methylpyridin-3-yl)-N-((1-methylpiperidin-3-yl)methyl)-4,5,7,8-tetrahydro-1H-oxepino[4,5-c]pyrazole-3-carboxamide;

1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(R)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(S)-1-(3-((4-(1-(6-methoxy-5-methylpyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

3-(1-ethyl-5-methyl-1H-pyrazol-4-yl)-1-(1-methyl-1H-pyrazol-4-yl)-4,5,7,8-tetrahydro-1H-oxepino[4,5-c]pyrazole;

1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

(R)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

(S)-1-(6-methoxy-5-methylpyridin-3-yl)-3-(1-((1-methylpyrrolidin-3-yl)methyl)-1H-pyrazol-4-yl)-4,5,7,8-tetrahydro-1H-oxepino[4,5-c]pyrazole;

3-(6-methoxy-5-methylpyridin-3-yl)-1-(1-((1-methylpiperidin-4-yl)methyl)-1H-pyrazol-4-yl)-4,5,7,8-tetrahydro-1H-oxepino[4,5-c]pyrazole;

2-(4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-2-yl)propan-2-ol;

5-(3-(1-((1-isopropylpiperidin-3-yl)methyl)-1H-pyrazol-4-yl)-4,5,7,8-tetrahydro-1H-oxepino[4,5-c]pyrazol-1-yl)-2-methoxynicotinonitrile;

3-(5-fluoro-6-methoxypyridin-3-yl)-1-(1-(piperidin-4-ylmethyl)-1H-pyrazol-4-yl)-4,5,7,8-tetrahydro-1H-oxepino[4,5-c]pyrazole;

3-(5-fluoro-6-methoxypyridin-3-yl)-1-(1-((1-isopropylpiperidin-4-yl)methyl)-1H-pyrazol-4-yl)-4,5,7,8-tetrahydro-1H-oxepino[4,5-c]pyrazole;

1-(1-((1-isopropylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;

1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

(S)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

(R)-1-(5-fluoro-6-methoxypyridin-3-yl)-3-(1-((1-isopropylpyrrolidin-3-yl)methyl)-1H-pyrazol-4-yl)-4,5,7,8-tetrahydro-1H-oxepino[4,5-c]pyrazole;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)-2-methylpropan-2-ol;

3-(1-((1-isopropylpyrrolidin-3-yl)methyl)-1H-pyrazol-4-yl)-1-(6-methoxy-5-methylpyridin-3-yl)-4,5,7,8-tetrahydro-1H-oxepino[4,5-c]pyrazole;

4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)-1-methylpiperidin-4-ol;

3-(5-fluoro-6-methoxypyridin-3-yl)-1-(1-((1-methylpiperidin-4-yl)methyl)-1H-pyrazol-4-yl)-4,5,7,8-tetrahydro-1H-oxepino[4,5-c]pyrazole;

3-(1-((4-fluoro-1-methylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

(2R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(R)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(2S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((R)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

(S)-1-((S)-3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-2-ol;

1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(R)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

(S)-1-(3-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)pyrrolidin-1-yl)propan-1-one;

7-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)-1,1-dimethyltetrahydro-1H-oxazolo[3,4-a]pyridin-3(5 h)-one;

1-(5-fluoro-6-methoxypyridin-3-yl)-3-(1-(((2R,4r,6S)-1,2,6-trimethylpiperidin-4-yl)methyl)-1H pyrazol-4-yl)-4,5,7,8-tetrahydro-1H-oxepino[4,5-c]pyrazole;

1-(6-methoxy-5-methylpyridin-3-yl)-3-(3-methyl-1H-pyrazol-5-yl)-4,5,7,8-tetrahydro-1H-oxepino[4,5-c]pyrazole;

1-(5-fluoro-6-methoxypyridin-3-yl)-3-(5-methyl-1H-pyrazol-4-yl)-4,5,7,8-tetrahydro-1H-oxepino[4,5-c]pyrazole;

3-(1,3-dimethyl-1H-pyrazol-5-yl)-1-(6-methoxy-5-methylpyridin-3-yl)-4,5,7,8-tetrahydro-1H-oxepino[4,5-c]pyrazole;

1-(dimethylamino)-3-(4-(1-(5-fluoro-6-methoxypyridin-3-yl)-4,5,7,8-tetrahydro-1H-oxepino[4,5-c]pyrazol-3-yl)-1H-pyrazol-1-yl)propan-2-ol;

3-(1-((3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

3-(1-(((3R,4S)-3-fluoro-1-isopropylpiperidin-4-yl)methyl)-1H-pyrazol-4-yl)-1-(5-fluoro-6-methoxypyridin-3-yl)-4,5,7,8-tetrahydro-1H-oxepino[4,5-c]pyrazole;

5-(3-(1-((1-isopropylpyrrolidin-3-yl)methyl)-1H-pyrazol-4-yl)-4,5,7,8-tetrahydro-1H-oxepino[4,5-c]pyrazol-1-yl)-2-methoxynicotinonitrile;

1-(4-((4-(1-(5-fluoro-6-methoxypyridin-3-yl)-4,5,7,8-tetrahydro-1H-oxepino[4,5-c]pyrazol-3-yl)-1H-pyrazol-1-yl)methyl)piperidin-1-yl)propan-1-one;

1-(1-(((2R,4r,6S)-2,6-dimethylpiperidin-4-yl)methyl)-1H-pyrazol-4-yl)-3-(6-methoxy-5-methylpyridin-3-yl)-4,5,7,8-tetrahydro-1H-oxepino[4,5-c]pyrazole;

N-(5-(3-(1-(((2R,6S)-2,6-dimethyltetrahydro-2H-pyran-4-yl)methyl)-1H-pyrazol-4-yl)-4,5,7,8-tetrahydro-1H-oxepino[4,5-c]pyrazol-1-yl)-2-methoxypyridin-3-yl)methanesulfonamide;

3-(1-(((2R,4r,6S)-2,6-dimethylpiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

3-(6-methoxy-5-methylpyridin-3-yl)-1-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

1-(1-((1-isopropylpiperidin-4-yl)methyl)-1H-pyrazol-4-yl)-3-(6-methoxypyridin-3-yl)-4,5,7,8-tetrahydro-1H-oxepino[4,5-c]pyrazole;

1-(6-methoxy-5-methylpyridin-3-yl)-3-(1-(((2R,4r,6S)-1,2,6-trimethylpiperidin-4-yl)methyl)-1H-pyrazol-4-yl)-4,5,7,8-tetrahydro-1H-oxepino[4,5-c]pyrazole;

N-(5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxypyridin-3-yl)methanesulfonamide;

2-(1-(2-((1-(6-methoxy-5-methylpyridin-3-yl)-4,5,7,8-tetrahydro-1H-oxepino[4,5-c]pyrazol-3-yl)oxy)ethyl)piperidin-4-yl)propan-2-ol;

2-(1-(2-((1-(5-(fluoromethyl)-6-methoxypyridin-3-yl)-4,5,7,8-tetrahydro-1H-oxepino[4,5-c]pyrazol-3-yl)oxy)ethyl)piperidin-4-yl)propan-2-ol;

2-(1-(2-((1-(5-fluoro-6-methoxypyridin-3-yl)-4,5,7,8-tetrahydro-1H-oxepino[4,5-c]pyrazol-3-yl)oxy)ethyl)piperidin-4-yl)propan-2-ol;

5-(3-(2-(4-(2-hydroxypropan-2-yl)piperidin-1-yl)ethoxy)-4,5,7,8-tetrahydro-1H-oxepino[4,5-c]pyrazol-1-yl)-2-methoxynicotinonitrile;

2-(1-(2-((1-(2-methoxypyrimidin-5-yl)-4,5,7,8-tetrahydro-1H-oxepino[4,5-c]pyrazol-3-yl)oxy)ethyl)piperidin-4-yl)propan-2-ol;

tert-butyl 4-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

1-(6-methoxy-5-methylpyridin-3-yl)-3-(piperidin-4-ylmethoxy)-4,5,7,8-tetrahydro-1H-oxepino[4,5-c]pyrazole;

3-((1-isopropylpiperidin-4-yl)methoxy)-1-(6-methoxy-5-methylpyridin-3-yl)-4,5,7,8-tetrahydro-1H-oxepino[4,5-c]pyrazole;

tert-butyl 3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;

tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

1-(6-methoxy-5-methylpyridin-3-yl)-3-(piperidin-3-ylmethoxy)-4,5,7,8-tetrahydro-1H-oxepino[4,5-c]pyrazole;

(S)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

(S)-1-(6-methoxy-5-methylpyridin-3-yl)-3-(piperidin-3-ylmethoxy)-4,5,7,8-tetrahydro-1H-oxepino[4,5-c]pyrazole;

(S)-1-(3-(((1-(6-methoxy-5-methylpyridin-3-yl)-4,5,7,8-tetrahydro-1H-oxepino[4,5-c]pyrazol-3-yl)oxy)methyl)piperidin-1-yl)-2-methylpropan-2-ol;

(R)-1-((S)-3-(((1-(6-methoxy-5-methylpyridin-3-yl)-4,5,7,8-tetrahydro-1H-oxepino[4,5-c]pyrazol-3-yl)oxy)methyl)piperidin-1-yl)propan-2-ol;

(S)-1-((S)-3-(((1-(6-methoxy-5-methylpyridin-3-yl)-4,5,7,8-tetrahydro-1H-oxepino[4,5-c]pyrazol-3-yl)oxy)methyl)piperidin-1-yl)propan-2-ol;

(R)-tert-butyl 3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

(S)-1-(2-(((1-(6-methoxy-5-methylpyridin-3-yl)-4,5,7,8-tetrahydro-1H-oxepino[4,5-c]pyrazol-3-yl)oxy)methyl)morpholino)-2-methylpropan-2-ol;

3-((1-isopropylpyrrolidin-3-yl)methoxy)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-((1-methylpyrrolidin-3-yl)methoxy)-4,5,7,8-tetrahydro-1H-oxepino[4,5-c]pyrazole;

1-(3-(((1-(6-methoxy-5-methylpyridin-3-yl)-4,5,7,8-tetrahydro-1H-oxepino[4,5-c]pyrazol-3-yl)oxy)methyl)pyrrolidin-1-yl)ethanone;

tert-butyl ((1R,2S)-2-(((1-(6-methoxy-5-methylpyridin-3-yl)-4,5,7,8-tetrahydro-1H-oxepino[4,5-c]pyrazol-3-yl)oxy)methyl)cyclopropyl)carbamate;

tert-butyl 3-fluoro-3-(((1-(6-methoxy-5-methylpyridin-3-yl)-4,5,7,8-tetrahydro-1H-oxepino[4,5-c]pyrazol-3-yl)oxy)methyl)pyrrolidine-1-carboxylate;

tert-butyl 4,4-difluoro-3-(((1-(6-methoxy-5-methylpyridin-3-yl)-4,5,7,8-tetrahydro-1H-oxepino[4,5-c]pyrazol-3-yl)oxy)methyl)piperidine-1-carboxylate;

3-((1,3-dimethylpiperidin-3-yl)methoxy)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-((1-(2-methoxyethyl)-3-methylpyrrolidin-3-yl)methoxy)-4,5,7,8-tetrahydro-1H-oxepino[4,5-c]pyrazole;

1-(6-methoxy-5-methylpyridin-3-yl)-3-((pyrrolidin-3-yl)methoxy)-4,5,7,8-tetrahydro-1H-oxepino[4,5-c]pyrazole;

1-(6-methoxypyridin-3-yl)-3-(2-(1-(4-methylpiperazin-1-yl)ethyl)pyridin-4-yl)-4,5,7,8-tetrahydro-1H oxepino[4,5-c]pyrazole;

1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(2-(1-(4-isopropylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole;

3-(2-(1-(4-isopropylpiperazin-1-yl)ethyl)pyridin-4-yl)-1-(6-methoxy-5-methylpyridin-3-yl)-4,5,7,8-tetrahydro-1H-oxepino[4,5-c]pyrazole;

1-(6-methoxy-5-methylpyridin-3-yl)-3-(2-(1-((3S,5R)-3,4,5-trimethylpiperazin-1-yl)ethyl)pyridin-4-yl)-4,5,7,8-tetrahydro-1H-oxepino[4,5-c]pyrazole;

1-(5-fluoro-6-methoxypyridin-3-yl)-3-(1-(((3-fluoropiperidin-4-yl)methyl)-1H-pyrazol-4-yl)-4,5,7,8-tetrahydro-1H-oxepino[4,5-c]pyrazole;

1-(5-fluoro-6-methoxypyridin-3-yl)-3-(1-(((3R,4S)-3-fluoropiperidin-4-yl)methyl)-1H-pyrazol-4-yl)-4,5,7,8-tetrahydro-1H-oxepino[4,5-c]pyrazole;

(S)-tert-butyl 2-(((1-(6-methoxy-5-methylpyridin-3-yl)-4,5,7,8-tetrahydro-1H-oxepino[4,5-c]pyrazol-3-yl)oxy)methyl)morpholine-4-carboxylate;

(S)-1-(6-methoxy-5-methylpyridin-3-yl)-3-(morpholin-2-ylmethoxy)-4,5,7,8-tetrahydro-1H-oxepino[4,5-c]pyrazole;

(4-isopropylpiperazin-1-yl)(2-(1-(6-methoxy-5-methylpyridin-3-yl)-4,5,7,8-tetrahydro-1H-oxepino[4,5-c]pyrazol-3-yl)oxazol-5-yl)methanone;

4-((4-(1-(6-methoxy-5-methylpyridin-3-yl)-4,5,7,8-tetrahydro-1H-oxepino[4,5-c]pyrazol-3-yl)-1H-pyrazol-1-yl)methyl)piperidin-4-ol;

3-(1-((4-fluoropiperidin-4-yl)methyl)-1H-pyrazol-4-yl)-1-(6-methoxy-5-methylpyridin-3-yl)-4,5,7,8-tetrahydro-1H-oxepino[4,5-c]pyrazole;

1-(6-methoxypyridin-3-yl)-3-(2-((S)-1-((3S,5R)-3,4,5-trimethylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(2-((S)-1-((3S,5R)-3,4,5-trimethylpiperazin-1-yl)ethyl)pyridin-4-yl)-4,5,7,8-tetrahydro-1H-oxepino[4,5-c]pyrazole;

(S)-1-(6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

(S)-1-(5-fluoro-6-methoxypyridin-3-yl)-3-(2-(1-(4-methylpiperazin-1-yl)ethyl)pyridin-4-yl)-4,5,7,8-tetrahydro-1H-oxepino[4,5-c]pyrazole;

(S)-1-(6-methoxy-5-methylpyridin-3-yl)-3-(2-(1-(4-methylpiperazin-1-yl)ethyl)pyridin-4-yl)-4,5,7,8-tetrahydro-1H-oxepino[4,5-c]pyrazole;

1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;
(S)-1-(1-(4-(1-(5-fluoro-6-methoxypyridin-3-yl)-4,5,7,8-tetrahydro-1H-oxepino[4,5-c]pyrazol-3-yl)pyridin-2-yl)ethyl)-3-methylimidazolidin-2-one;
3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;
(S)-3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;
(R)-3-(5-fluoro-6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;
1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;
(S)-1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;
(R)-1-(6-methoxy-5-methylpyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;
(R)-1-(6-methoxypyridin-3-yl)-3-(1-(1-(1-methylpiperidin-4-yl)ethyl)-1H-pyrazol-4-yl)-4,5,7,8-tetrahydro-1H-oxepino[4,5-c]pyrazole;
3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;
(S)-3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;
(R)-3-(6-methoxypyridin-3-yl)-1-(1-(1-(1-methylpiperidin-4-yl)ethyl)-1H-pyrazol-4-yl)-4,5,7,8-tetrahydro-1H-oxepino[4,5-c]pyrazole;
1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole;
(S)-1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole
(R)-1-(1-(1-(1-isopropylpiperidin-4-yl)ethyl)-1H-pyrazol-4-yl)-3-(6-methoxypyridin-3-yl)-4,5,7,8-tetrahydro-1H-oxepino[4,5-c]pyrazole;
3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole;
(S)-3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole; or
(R)-3-(6-methoxypyridin-3-yl)-1-(2-(1-(4-methylpiperazin-1-yl)ethyl)pyridin-4-yl)-4,5,7,8-tetrahydro-1H-oxepino[4,5-c]pyrazole;
or a salt thereof.

7. A compound which is:

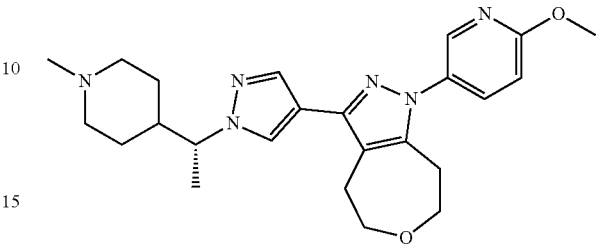

or a salt thereof.

8. A compound according to claim 1 in the form of a pharmaceutically acceptable salt.

9. A pharmaceutical composition comprising a compound as defined in claim 1, or a pharmaceutically acceptable salt thereof, and one or more pharmaceutically acceptable excipients.

10. A method of alleviating one or more symptoms associated with or slowing the progression of a disorder mediated by inappropriate PI3-kinase activity comprising administering a safe and effective amount of a compound as defined in claim 1, or a pharmaceutically acceptable salt thereof, to a patient in need thereof.

11. A method according to claim 10 wherein the disorder mediated by inappropriate PI3-kinase activity is a respiratory disease, a ciliopathy, a bacterial infection or bacterial exacerbation of a respiratory condition or lung damage, a viral infection or viral exacerbation of a respiratory condition or lung damage, a non-viral respiratory infection, an allergic disease, an autoimmune disease, an inflammatory disorder, diabetes, a cardiovascular disease, a hematologic malignancy, a neurodegenerative disease, pancreatitis, multiorgan failure, kidney disease, platelet aggregation, cancer, sperm motility, transplantation rejection, graft rejection, lung injury, pain, fibrotic disease, depression, a psychotic disorder, bronchiectasis or activated PI3Kδ syndrome (APDS).

12. A method according to claim 10 wherein the disorder mediated by inappropriate PI3-kinase activity is asthma.

13. A method according to claim 10 wherein the disorder mediated by inappropriate PI3-kinase activity is COPD.

* * * * *